US007148226B2

(12) United States Patent
Borchardt et al.

(10) Patent No.: US 7,148,226 B2
(45) Date of Patent: Dec. 12, 2006

(54) INHIBITORS OF HEPATITIS C VIRUS RNA-DEPENDENT RNA POLYMERASE, AND COMPOSITIONS AND TREATMENTS USING THE SAME

(75) Inventors: Allen Borchardt, San Diego, CA (US); Javier Gonzalez, Oceanside, CA (US); Hui Li, Carlsbad, CA (US); Maria Angelica Linton, Linton, CA (US); John Howard Tatlock, San Diego, CA (US)

(73) Assignee: Agouron Pharmaceuticals, Inc., San Diego, CA (US)

( * ) Notice: Subject to any disclaimer, the term of this patent is extended or adjusted under 35 U.S.C. 154(b) by 49 days.

(21) Appl. No.: 10/718,337

(22) Filed: Nov. 19, 2003

(65) Prior Publication Data

US 2005/0176701 A1 Aug. 11, 2005

Related U.S. Application Data

(60) Provisional application No. 60/472,355, filed on May 20, 2003, provisional application No. 60/449,088, filed on Feb. 21, 2003.

(51) Int. Cl.
*A61K 31/519* (2006.01)
(52) U.S. Cl. ............... 514/259.1; 514/397; 514/378; 514/394; 514/263.1; 514/263.23; 514/406; 514/414; 514/383; 544/264; 544/278; 548/263.2; 548/264.2; 548/304.7; 548/365.7
(58) Field of Classification Search ............. 514/259.1, 514/397, 378, 394, 263.1, 263.23, 406, 383, 514/414; 544/278, 264; 548/304.7, 263.2, 548/264.2, 365.7
See application file for complete search history.

(56) References Cited

U.S. PATENT DOCUMENTS

| | | | |
|---|---|---|---|
| 3,786,063 A | 1/1974 | Arnold | |
| 4,326,058 A | 4/1982 | Okabe et al. | |
| 4,489,077 A | 12/1984 | Sircar et al. | |
| 4,591,583 A | 5/1986 | Helgstrand et al. | |
| 5,504,104 A | 4/1996 | Ellsworth et al. | |
| 5,789,440 A | 8/1998 | Ellsworth et al. | |
| 5,808,062 A | 9/1998 | Domagala et al. | |
| 5,834,506 A | 11/1998 | Boyer, Jr. et al. | |
| 5,840,751 A | 11/1998 | Ellsworth et al. | |
| 5,846,964 A | 12/1998 | Ozeki | |
| 5,936,128 A | 8/1999 | Ellsworth et al. | |
| 6,046,355 A | 4/2000 | Boyer, Jr. et al. | |
| 6,174,868 B1 | 1/2001 | Anderson et al. | |
| 6,512,006 B1 | 1/2003 | Boyer, Jr. et al. | |
| 6,528,510 B1 | 3/2003 | Boyer, Jr. et al. | |
| 2003/0171425 A1 | 9/2003 | Boyer, Jr. et al. | |

FOREIGN PATENT DOCUMENTS

| | | |
|---|---|---|
| EP | 1 256 628 | 11/2002 |
| WO | WO 95 14011 A | 5/1995 |
| WO | WO 95 14012 A | 5/1995 |
| WO | WO 98 19997 | 5/1998 |
| WO | WO 015634 | 3/2000 |
| WO | WO 03/095441 | 11/2003 |

OTHER PUBLICATIONS

Borchardt, AJ et al 'preparation of tetrahydopyranones as hepatitis C virus RNA-dependent RNA polymerase inhibitors' CA 141:243338 (2004).*
Tan et al Hepatitis C therapeutics: Current Status and Emerging Strategies, Nature Reviews, Drug Discover, vol. 1, Nov. 2002, 867-881.*
Crotty, Ribavirin's antiviral mechanism of action: lethal mutagenesis?, J Mol Med (2002) 80:86-95.*
Allen, C.F.H., et al. "The Structure of Certain Polyazaindenes. III. 1,2,3a,7- and 1,3,3a,7-Tetrazaindenes," *J. Org. Chem*, 1959, pp. 793-796, vol. 24.
Baginski S., et al. "Mechanism of Action Of A Pestivirus Antiviral Compound," *Proc. Natl. Acad. Sci. USA*, 2000, pp. 7981-7986, vol. 97.
Bagshawe, K., "Antibody-Directed Enzyme Prodrug Therapy: A Review," *Drug. Development Research*, 1995, pp. 220-230, vol. 34.
Bartenschlager, R., et al., "Molecular Targets In Inhibition Of Hepatitis C Virus Replication" *Anitviral Chemistry & Chemotherapy*, 1997, pp. 281-301, vol. 8, No. 4.
Bartenschlager, R., et al., "Nonstructural Protein 3 Of The Hepatitis C Virus Encodes A Serine-Type Proteinase Required For Cleavage At The NS3/4 And NS4/5 Junctions," *Journal of Virology*, Jul. 1993, pp. 3835-3844, vol. 67, No. 7.

(Continued)

*Primary Examiner*—Amelia A. Owens
(74) *Attorney, Agent, or Firm*—Jeffrey H. Tidwell; Bryan C. Zielinski

(57) ABSTRACT

The invention relates to compounds of the formula 1 and to pharmaceutically acceptable salts, solvates, prodrugs and metabolites thereof, wherein W, Z, $R^1$ and $R^2$, are as defined herein. The invention also relates to methods of treating Hepatitis C virus in mammals by administering the compounds of formula 1, and to pharmaceutical compositions for treating such disorders, which contain the compounds of formula 1. The invention also relates to methods of preparing the compounds of formula 1.

28 Claims, No Drawings

OTHER PUBLICATIONS

Bergman, J., et al, "Synethesis if Chrysogine, a Metabolite of Penicillium chrysogenum and some related 1-substituted 4-(3H)-Quinazolinones," *Tetrahedron*, 1990, pp. 1295-1310, vol. 46.

Bertolini, et al., "A New Rational Hypothesis for the Pharmacophore of the Active Metabolite of Leflunomide, a Potent Immunosuppressive Drug," *J. Med. Chem.*, 1997, pp. 2011-2016, vol. 40, issue 13.

Bodor, N, "Novel Approaches to the Design of Safer Drugs: Soft Drugs and Site-Specific Chemical Delivery Systems," *Advances in Drug Research*, 1984, pp. 255-331, vol. 13.

Boyer, F.E., et al., 5,6-Dihydropyran-2-ones Possessing Various Sulfonyl Functionalities: Potent Nonpeptidic Inhibitors of HIV Protease, *J. Med. Chem.*, 2000, pp. 843-858, vol. 43, no.

Brown, E.A., et al., "Secondary Structure Of The 5'Nontranslated Regions of Hepatitis C Virus And Pestivirus Genomic RNAs," *Nucleic Acids Research* 1992, pp. 5041-5045, vol. 20, No. 19.

Bukh, J., et. al., "Sequence Analysis of the 5' Noncoding Region of Hepatitis C Virus," *Proc. National Academy of Science USA*, 1992, pp. 4942-4946, vol. 89.

Bundgaard, H., et al., *Design and Application of Prodrugs, Drug Design and Development*, 1991, Krogsgaard-Larsen, et al., editors, Harwood Academic Publishers.

Burke, T.R., et al., "Conformationally Constrained Phosphotyrosyl Mimetics Designed As Monomeric Src Homology 2 Domain Inhibitors," *J. Med. Chem.* 1995, pp. 1386-1396, vol. 38.

Carvalho, C.F., et al., "Naturally Occurring Dibenzofurans. Part 6. Synthesis Of Didymic Acid," *J. Chem Soc. Perkin Trans 1*, 1984, pp. 1621-1626.

Chavignon, O., et al., "Pyrrolozation Processes Of Vinyl Substitued Imidazo[1,2-α]pyridine, Pyrimidine And 1,8-Naphthyridine," *J. Heterocyclic Chem.*, 1992, pp. 691-697, vol. 29.

Choo, Q.-L., et al., "Isolation of a cDNA Clone Derived From A Blood-Borne Non-A, Non-B Viral Hepatitis Genome," *Science*, Apr. 21, 1989, pp. 359-362, vol. 244.

Cuthbert, J., "Hepatitis C: Progress and Problems" *Clinical Microbiology Reviews*, Oct. 1994, pp. 505-532, vol. 7, No. 4.

Doria, G., et al, "7-Trans-(2-Pyridylethenyl)-5H-Thiazolo[3,2-a]Pyrimidine-5-Ones: Synthesis And Pharmacological Activity," *Farmaco Ed. Sci.*, 1985, pp. 885-895.

Doyle, M., et al., "Macrocycle Formation By Catalytic Intramolecular Cyclopropanation. A New General Methodology For The Synthesis Of Macrolides" *Journal of the American Chemical Society*, 1997, pp. 8826-8837.

Earl, R A., et al., The preparation of 2(1H)-pyridinones and 2,3-dihydro-5(1H)-indolizinones via transition metal mediated cocyclization of alkynes and isocyanates. A novel construction of the antitumor agent camptothecin, *Journal of Organic Chemistry*, 1984, pp. 4786-4800, vol. 149.

Ellsworth, E.L., et al., "4 Hydroxy -5,6-Dihydro-2H-Pyran-2-ones. 3.Bicyclic and Hetero-Aromatic Ring Systems as 3-Position Scaffolds to Bind to $S_1$'nd $S_2$' of the HIV-1 Protease Enzyme," *Bioorg. Med. Chem. Lett.*, 1999, pp. 2019-2024, vol. 9, issue 14.

Ferrari, E., et al., "Characterization of Soluble Hepatitis C Virus RNA-Dependent RNA Polymerase Expressed in *Escherichia Coli*," *Journal of Virology*, 1999, pp. 1649-1654, vol. 73, No. 2.

Francki, et al., "Some observations on the Binding Properties of Alfalfa Mosaic Virus to Polystyrene and its significance to indirect ELISA," *Arch. Virol.*, 1991, pp. 219-235, vol. 2.

Gerecke, M., et al, "New Tetracyclic Derivatives of Imidazo-[1,5-a][1,4]Benzodiazepines and of Imidazo [1,5-a]Thieno[3,2-f][1,4]Diazepines," *Heterocycles*, 1994, pp. 693-721, vol. 39, No. 2.

Grakoui, A., et al., "Expression And Identification Of Hepatitis C Virus Polyprotein Cleavage Products" *Journal Of Virology*, Mar. 1993, pp. 1385-1395, vol. 67, No. 3.

Hagen, et al., "4-Hydroxy-5,6-dihydropyrones as Inhibitors of HIV Protease: The Effect of Heterocyclic Substituents at C-6 on Antiviral Potency and Pharmacokinetic Parameters" *J Med*.

Hagen, S., et al., "Synthesis of 5,6-Dihydro-4-hydroxy-2-pyrones as HIV-1 Protease Inhibitors: The Profound Effect of Polarity on Antiviral Activity," *J. Med Chem.*, 1997, pp. 3707-3711, vol. 40, issue 23.

Hénichart, J., et al., "A Convenient Method For The Preparation Of ω-Di-Alkylaminoalkyl Isothiocyanates," *Synthesis*, 1980, pp. 311-312.

Hijikata, M., et al., "Gene Mapping Of The Putative Structural Region Of The Hepatitis C Virus Genome By In Vitro Processing Analysis" *Proc. Natl. Acad. Sci. USA*, Jul. 1991, pp. 5547-5551, vol. 88.

Hwang, S.B., et al., "Hepatitis C Virus NS5B Protein Is A Membrane-Associated Phosphoprotein With A Predominantly Perinuclear Localization," *Virology*, 1997, pp. 439-446, vol. 227.

Ishii, et al., "Expression of Hepatitis C Virus NS5B Protein: Characterization of Its RNA Polymerase Activity and RNA Bindint", *Hepatology*, 1999, pp. 1227-1235, vol. 29.

Ishizumi, K., et al. "Synthesis And Anxiolytic Activity of N-Substituted Cyclic Imides (1R*, 2S*, 3R*, 4S*)-N-[4[4-(2-Pyrimidinyl)-1-Piperazinyl]butyl]-2,3-Bicyclo[2.2.1]Heptanedicarboximide (Tandospirone) And Related Compounds," *Chem. Pharm Bull.*, 1991, pp. 2288-2300, vol. 39, No. 9.

Kim, et al., "Hepatitis C Virus NS3 RNA Helicase Domain With A Bound Oligonucleotide: The Crystal Structure Provides Insights Into The Mode Of Unwinding" *Structure*, 1998, pp. 89-100, vol. 6, No. 1.

Kim, et al., "Crystal Structure Of The Hepatitis C Virus NS3 Protease Domain Complexed With A Synthetic NS4A Cofactor Peptide," *Cell*, Oct. 18, 1996, pp. 343-355, vol. 87.

Kolykhalov, A.A., et. al., "Identification of a Highly Conserved Sequence Element at the 3' Terminus of Hepatitis C Virus Genome RNA," *Journal of Virology*, 1996, pp. 3363-3371, vol. 70, No. 9.

Kuchar, M., et al., "The Synthesis Of Arylpropionic Acids And The Quantitative Relationship Between The Structure And The Activation Of Fibrinolysis," *Collect. Czech. Chem. Commun*, 1981, pp. 1173-1187, vol. 46.

Lee, Y.R., et al., "A New Route For The Synthesis of Furanoflavone And Furanochalcone Natural Products," *Tetrahedron*, 1995, pp. 4909-4922, vol. 51.

Lin, C., et al., "Processing In The Hepatitis C Virus E2-NS2 Region: Identification of p7 and Two Distinct E2-Specific Products With Different C Termini," *Journal of Virology*, Aug. 1994, pp. 5063-5073, vol. 68, No. 8.

Lohmann, V., et al., Biochemical Properties of Hepatitis C Virus NS5B RNA-Dependant RNA Polymerase and Identification of Amino Acid Sequence Motifs Essential for Enzymatic Activity, *J. Virol.*, 1997, pp. 8416-8428, vol. 71.

Lohmann, V., et al., "Biochemical And Kinetic Analyses Of NS5B RNA-Dependent RNA Polymerase Of The Hepatitis C Virus" *Virology*, 1998, pp. 108-118.

Lorentzen, R. et al., "Application Of The Benzene Sector And The Benzene Chirality Rules To Perhydrobenzocycloalkenes And Related Compounds," *Journal Amer. Chem. Soc.*, 1992, pp. 2181-2187, vol. 114.

Love, et al., "The Crystal Structure Of Hepatitis C Virus NS3 Proteinase Reveals A Trypsin-Like Fold And A Structural Zinc Binding Site" *Cell*, 1996, pp. 331-342, vol. 87.

Marcellin, P., et al., "Long-Term Histologic Improvement And Loss Of Detectable Intrahepatic HCV RNA In Patients With Chronic Hepatitis C And Sustained Response To Interferon-alpha Therapy," *Ann. Inter. Med.*, Nov. 15, 1997, pp. 875-881, vol. 127.

Miller, R.H., et al., "Hepatitis C Virus Shares Amino Acid Sequence Similarity With Pestiviruses And Flaviviruses As Well As Members Of Two Plant Virus Supergroups," *Proc. Natl. Acad. Sci. USA*, Mar. 1990, pp. 2057-2061, vol. 87.

Moloney, G.P, et al., "Synthesis and Serotonergic Activity of 2-oxadiazolyl-5-substituted-N,N-dimethyltryptamines: novel antagonists for the vascular 5-HT $_{1b}$-like receptor" *J. Chem. Soc Perkin*, 1999, pp. 2725-2733, vol. 19.

Mylari, B.L., et al., "Potent, orally active aldose reductase inhibitors related to zopolrestat: surrogates for benzothiazole side chain," *J. Med. Chem.*, 1992, pp. 457-465, vol. 35, issue 3.

Palazzo, G, et al., "1,2,4-Oxadiazoles—IV. Synthesis and Pharmacological Properties of a Series of Substituted Aminoalkyl-1,2,4-oxadiazoles," *J. Med. Pharm. Chem.*, 1961, pp. 351-367, vol. 4, issue 2.

Poch, O., et al., "Identification Of Four Conserved Motifs Among The RNA-Dependent Polymerase Encoding Elements" *The EMBO Journal*, 1989, pp. 3867-3874, vol. 8, No. 12.

Powell, M.T., et al., "Optically active $C^3$-symmetric triarylphosphines in asymmetric allylations," *Tetrahedron*, 2001, pp. 5027-5038, vol. 57.

Prox, A., et al., "Rapid Structure Elucidation of Drug Metabolites by Use of Stable Isotopes," *Xenobiotica*, 1973, pp. 103-112, vol. 3 No. 2.

Ren, R., et al., "Total Synthesis Of The Ocular Age Pigment A2-E: A Convergent Pathway," *J. Am. Chem. Soc.*, 1997, pp. 3619-3620, vol. 119.

Rink, H., "Solid-Phase Synthesis Of Protected Peptide Fragments Using A Trialkoxy-Diphenyl-Methylester Resin," *Tetrahedron Letters*, 1987, pp. 3787-3790, vol. 28, No. 33.

Selassie, C., et al., "QSAR For The Cytotoxicity Of 2-Alkyl Or 2,6-Fislkyl, 4-X-Phenols: The Nature Of The Radical Reaction," *J. Chem. Soc. Perkin Trans 2*, 2002, pp. 1112-1117.

Shan, D., et al., "Prodrug Strategies Based On Intramolecular Cyclization Reactions" *J. Pharm. Sci.*, 1997, pp. 765-767, vol. 86, No. 7.

Shishoo, C. J., et al., "Reaction of Nitriles Under Acidic Conditions. Part III. A Facile Synthesis of Thienopyrimidin-4(3H)-ones," *J. Heterocyclic Chem.*, 1984, pp. 375-380, vol. 21.

Simmonds, et al., "Classification Of Hepatitis C Virus Into Six Major Genotypes And A Series Of Subtypes By Phylogenetic Analysis Of The NS-5 Region" *Journal of General Virology*, 1993, pp. 2391-2399, vol. 74.

Smith, A. et al., "Photochemical Reactions of 1-Cyclopentenyl And 1-Cyclohexenyl Ketones" *Journal of American Chem. Soc.*, 1973, pp. 1961-1968.

Spraul, M., et al., "Liquid Chromatography Coupled with High-Field Proton NMR for Profiling Human Urine for Endogenous Compounds and Drug Metabolites", *J. Pharmaceutical & Biomedical Analysis*, 1992, pp. 601-605, vol. 10, issue 8.

Szmuszkovicz, J., et al., "A Study Of The Inhibitory Effect Of Various Hydrazides On Monoamine Oxidase *in vitro* and *in vivo*," *Journal Of Medicinal And Pharmaceutical Chemistry*, 1961, pp. 259-296, vol. 4, No. 2.

Tanaka, T., et al., "Structure Of The 3' Terminus Of The Hepatitis C Virus Genome," *Journal of Virology*, May 1996, pp. 3307-3312, vol. 70, No. 5.

Tee, et al., "Kinetics and Mechanism of Bromination of 2-Pyridone and Related Derivatives in Aqueous Solution", J. Am. Chem. Soc., 1982, pp. 4142-4246.

Vara Prasad, J.V.N., et al., "Nonpeptidic HIV Protease Inhibitors: 6-Alkyl-5,6-Dihydropyran-2-Ones Possessing Achiral 3-(4-Amino/Carboxaminde-2-t-Butyl, 5-Methylphenyl Thio) Moiety: Antiviral Activities and Pharmacokinetic Properties," *Bioorg. Med. Chem. Lett.*, (Jul. 6, 1999), pp. 1481-1486, vol. 9, issue 11.

Vara Prasad, et al., "Nonpeptidic HIV Protease Inhibitors Processing Excellent Antiviral Activities and Therapeutic Indices. PD 178390: A Lead HIV Protease Inhibitor", *Bioorganic Medicinal Chemistry Letters*, 1999, pp. 2775-2800.

Wang, et al., "Recent Advances In Prevention And Treatment Of Hepatitis C Virus Infections," *Progress in Drug Research*, 2000, pp. 1-32, vol. 55.

Weiner, A.J., et al., "Evidence for Immune Selection of Hepatitis C Virus (HCV) Putative Envelope Glycoprotein Variants: Potential Role in Chronic HCV Infections", *Proc. Natl. Acad. Sci. USA*, 1992, pp. 3468-3472, vol. 89.

Weiner, A.J., et al., "Variable And Hypervariable Domains Are Found In The Regions Of HCV Corresponding To The Flavivirus Envelope And NS1 Proteins And The Pestivirus Envelope Glycoproteins," *Virology*, 1991, pp. 842-848, vol. 180.

Wyatt, C.A., et al., "Immunity In Chimpanzees Chronically Infected With Hepatitis C Virus: Role Of Minor Quasispecies In Reinfection" *Journal Of Virology*, Mar. 1998, pp. 1725-1730, vol. 72, No. 3.

Yamashita, T., et al., RNA-Dependant RNA Polymerase Activity of the Souable Recombinant Hepatitis Cvirus NS5B Protein Truncated at the C-Termainal Region, *J. Biol. Chem.*, 1998, pp. 15479-15486, vol. 273 (25).

Zeuzem, et al., "Hepatitis C Virus Dynamics In Vivo: Effect Of Ribavirin And Interferon Alfa On Viral Turnover" *Hepatology*, 1998, pp. 245-252.

Gadja, C., et al. "An Efficient Asymmetric Synthesis of Lead Dihydropyrone HIV Protease Inhibitors," *Abstracts of Papers, 37th Interscience Conference on Antimicrobial Agents and Chemotherapy*, Toronto, Canada, Sep. 1997, Abstr. I-199b.

Künstlinger, M., "Triazolo[1,5-α]- und -[4,3-α]pyrimidine aus 3-Alkoxyacroleinen und 3 Amino-1,2,4-triazolen," *Communications, Synthesis*, Jan. 1983, p. 44-47.

Tait, B.D., "4-Hydroxy-5, 6-dihydropyrones. 2. Potent Non-Peptide Inhibitors of HIV Protease," *J. Med. Chem.*, 1997, 3781-3792, vol. 40.

* cited by examiner

INHIBITORS OF HEPATITIS C VIRUS RNA-DEPENDENT RNA POLYMERASE, AND COMPOSITIONS AND TREATMENTS USING THE SAME

BACKGROUND OF THE INVENTION

This application claims priority under 35 U.S.C. § 119(e) to U.S. Provisional Application No. 60/472,355, filed May 20, 2003, and U.S. Provisional Application No. 60/449,088, filed Feb. 21, 2003, both of which are hereby incorporated by reference.

The invention relates to agents that inhibit hepatitis C virus (HCV) RNA-dependent RNA polymerase (RdRp). The invention also relates to the use of such compounds in pharmaceutical compositions and therapeutic treatments useful for inhibition of HCV replication.

HCV is an enveloped RNA virus containing a single-stranded positive-sense RNA genome approximately 9.5 kb in length (Choo et al., *Science* 244:359–362 (1989)). The RNA genome contains a 5'-nontranslated region (5' NTR) of 341 nucleotides (Brown et al., *Nucl. Acids Res.* 20:5041–5045 (1992); Bukh et al., *Proc. Natl. Acad. Sci. USA* 89:4942–4946 (1992)), a large open reading frame (ORF) encoding a single polypeptide of 3,010 to 3,040 amino acids (Choo et al. (1989), supra;), and a 3'-nontranslated region (3'-NTR) of variable length of about 230 nucleotides (Kolykhalov et al., *J. Virol.* 70:3363–3371 (1996); Tanaka et al., *J. Virol.* 70:3307–3312 (1996)).

The 5' NTR is one of the most conserved regions of the viral genome and plays a pivotal role in the initiation of translation of the viral polyprotein (Bartenschlager (1997), supra). A single ORF encodes a polyprotein that is co- or post-translationally processed into structural (core, E1, and E2) and nonstructural (NS2, NS3, NS4A, NS4B, NS5A, and NS5B) viral proteins by either cellular or viral proteinases (Bartenschlager (1997), supra). The 3' NTR consists of three distinct regions: a variable region of about 38 nucleotides following the stop codon of the polyprotein, a polyuridine tract of variable length with interspersed substitutions of cystines, and 98 nucleotides (nt) at the very 3' end which are highly conserved among various HCV isolates. The order of the genes within the genome is: $NH_2$—C-E1-E2-p7-NS2-NS3-NS4A-NS4B-NS5A-NS5B-COOH (Grakoui et al., *J. Virol.* 67:1385–1395 (1993)).

Hepatitis C virus (HCV) is a member of the hepacivirus genus in the family Flaviviridae. It is the major causative agent of non-A, non-B viral hepatitis and is the major cause of transfusion-associated hepatitis and accounts for a significant proportion of hepatitis cases worldwide. Although acute HCV infection is often asymptomatic, nearly 80% of cases resolve to chronic hepatitis. The persistent property of the HCV infection has been explained by its ability to escape from the host immune surveillance through hypermutability of the exposed regions in the envelope protein E2 (Weiner et al., *Virology* 180:842–848 (1991); Weiner et al. *Proc. Natl. Acad. Sci. USA* 89:3468–3472 (1992).

Processing of the structural proteins core (C), envelope protein 1 and (E1, E2), and the p7 region is mediated by host signal peptidases. In contrast, maturation of the nonstructural (NS) region is accomplished by two viral enzymes. The HCV polyprotein is first cleaved by a host signal peptidase generating the structural proteins C/E1, E1/E2, E2/p7, and p7/NS2 (Hijikata et al., *Proc. Natl. Acad. Sci. USA* 88:5547–5551 (1991); Lin et al., *J. Virol.* 68:5063–5073 (1994)). The NS2–3 proteinase, which is a metalloprotease, then cleaves at the NS2/NS3 junction. The NS3/4A protein-ase complex (NS3 serine protease/NS4A cofactor), then at all the remaining cleavage sites (Bartenschlager et al., *J. Virol.* 67:3835–3844 (1993); Bartenschlager (1997), supra). RNA helicase and NTPase activities have also been identified in the NS3 protein. The N-terminal one-third of the NS3 protein functions as a protease, and the remaining two-thirds of the molecule acts as a helicase/ATPase, which is thought to be involved in HCV replication (Bartenschlager (1997), supra). NS5A may be phosphorylated and act as a putative cofactor of NS5B. The fourth viral enzyme, NS5B, is an RNA-dependent RNA polymerase (RdRp) and a key component responsible for replication of the viral RNA genome (Lohmann et al., *J. Virol.* 71:8416–8428 (1997)).

Replication of HCV is thought to occur in membrane-associated replication complexes. Within these, the genomic plus-strand RNA is transcribed into minus-strand RNA, which in turn can be used as a template for synthesis of progeny genomic plus strands. Two viral proteins appear to be involved in this reaction: the NS3 protein, which carries in the carboxy terminal two-thirds a nucleoside triphosphatase/RNA helicase, and the NS5B protein, which is a membrane-associated phosphoprotein with an RNA-dependent RNA polymerase activity (RdRp) (Hwang et al., *J. Virol.* 227:439–446 (1997)). While the role of NS3 in RNA replication is less clear, NS5B apparently is the key enzyme responsible for synthesis of progeny RNA strands. Using recombinant baculoviruses to express NS5B in insect cells and a synthetic nonviral RNA as a substrate, two enzymatic activities have been identified as being associated with NS5B. The two activities include a primer-dependent RdRp and a terminal transferase (TNTase) activity. NS5B's activity was confirmed and further characterized through the use of the HCV RNA genome as a substrate (Lohmann et al., *Virology* 249:108–118 (1998)). Recent studies have shown that NS5B with a C-terminal 21 amino-acid truncation expressed in *Escherichia coli* is also active for in vitro RNA synthesis (Ferrari et al., *J. Virol.* 73:1649–1654 (1999); Yamashita et al., *J. Biol. Chem.* 273:15479–15486 (1998)).

Since persistent infection of HCV is related to chronic hepatitis and eventually to hepatocarcinogenesis, HCV replication is one of the targets to eliminate HCV reproduction and to prevent hepatocellular carcinoma. Unfortunately, present treatment approaches for HCV infection are characterized by relatively poor efficacy and an unfavorable side-effect profile. Therefore, intensive effort is directed at the discovery of molecules to treat this disease, including the discovery of drugs designed to inhibit HC replication, as there is a persistent need for non-peptide, small-molecule compounds that are HCV RdRp inhibitors having desirable or improved physical and chemical properties appropriate for pharmaceutical applications.

SUMMARY OF THE INVENTION

The present invention relates to compounds of the formula 1

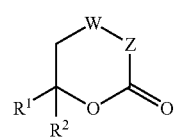

and to pharmaceutically acceptable salts, hydrates, metabolites, prodrugs and solvates thereof, wherein:

W-Z is —C(=O)—C(—R$^3$)(H)— or —C(—OR$^6$)=C(—R$^{3'}$)—, wherein when W-Z is —C(—OR$^6$)=C(—R$^{3'}$)—;

each R$^1$ is independently selected from hydrogen, C$_1$–C$_6$ alkyl, C$_2$–C$_6$ alkenyl, C$_2$–C$_6$ alkynyl, (C$_3$–C$_{10}$) cycloalkyl, 4- to 10-membered heterocyclic, and C$_6$–C$_{10}$ aryl, wherein the foregoing R$^1$ groups, except H, are optionally substituted by 1 to 4 substituents selected from R$^4$;

R$^2$ is selected from the group of R$^1$ substituents, —(CR$^8$R$^9$)$_t$(C$_6$–C$_{10}$ aryl), —(CR$^8$R$^9$)$_t$(4–10 membered heterocyclic), —(CR$^8$R$^9$)$_q$C(O)(CR$^8$R$^9$)$_t$(C$_6$–C$_{10}$ aryl), —(CR$^8$R$^9$)$_q$C(O)(CR$^8$R$^9$)$_t$(4–10 membered heterocyclic), —(CR$^8$R$^9$)$_t$O(CR$^8$R$^9$)$_q$(C$_6$–C$_{10}$ aryl), —(CR$^8$R$^9$)$_t$O(CR$^8$R$^9$)$_q$(4–10 membered heterocyclic), —(CR$^8$R$^9$)$_q$SO$_n$(CR$^8$R$^9$)$_t$(C$_6$–C$_{10}$ aryl), and —(CR$^8$R$^9$)$_q$SO$_n$(CR$^8$R$^9$)$_t$(4–10 membered heterocyclic), wherein q and t are each independently an integer from 0 to 5, n is an integer from 0 to 2, the alkyl, aryl and heterocyclic moieties of said R$^2$ groups are optionally substituted by 1 to 5 R$^4$ groups, and with the proviso that R$^2$ is not H;

R$^3$ is hydrogen, —OR$^6$, —SR$^6$, —NR$^6$R$^7$, and the group of R$^2$ substituents;

R$^{3'}$ is selected from the group of R$^3$ substituents except R$^{3'}$ is not H;

each R$^4$ is independently selected from halo, cyano, nitro, trifluoromethoxy, trifluoromethyl, azido, C$_1$–C$_{10}$ alkyl, C$_2$–C$_6$ alkenyl, C$_2$–C$_6$ alkynyl, —C(O)R$^6$, —C(O)OR$^6$, —OC(O)R$^6$, —NR$^6$C(O)R$^7$, —NR$^6$C(O)NR$^7$, —C(O)NR$^6$R$^7$, —NR$^6$R$^7$, —NR$^6$OR$^7$, —SO$_2$NR$^6$R$^7$, —NR$^6$SO$_2$R$^7$, —(CR$^8$R$^9$)$_t$(C$_6$–C$_{10}$ aryl)(wherein t is an integer from 0 to 5), —(CR$^8$R$^9$)$_t$(4–10 membered heterocyclic)(wherein t is an integer from 0 to 5), C$_3$–C$_{10}$ cycloalkyl, R$^6$—O—, R$^6$—SO$_n$— (wherein n is an integer from 0 to 2), and oxo (=O), and wherein the alkyl, aryl, and heterocyclic moieties of said R$^4$ groups are optionally substituted by 1 to 4 substituents selected from R$^5$;

each R$^5$ is independently selected from halo, trifluoromethyl, trifluoromethoxy, cyano, C$_1$–C$_6$ alkyl, C$_2$–C$_6$ alkenyl, C$_2$–C$_6$ alkynyl, —OR$^8$, C$_3$–C$_{10}$ cycloalkyl, C$_6$–C$_{10}$ aryl, 4- to 10-membered heterocyclic, oxo (=O), —C(O)R$^6$, —C(O)OR$^6$, —OC(O)R$^6$, —NR$^6$C(O)R$^6$, —NR$^6$C(O)NR$^7$, —C(O)NR$^6$R$^7$, —NR$^6$R$^7$, —NR$^6$OR$^7$, —NR$^6$SO$_2$R$^7$ and —SO$_2$NR$^6$R$^7$, wherein the alkyl, aryl and heterocyclic moieties of the foregoing R$^5$ groups are optionally substituted by 1 to 3 R$^{10}$;

each R$^6$ and R$^7$ is independently selected from H, C$_1$–C$_6$ alkyl, C$_3$–C$_{10}$ cycloalkyl, —(CR$^8$R$^9$)$_t$(C$_6$–C$_{10}$ aryl), and —(CR$^8$R$^9$)$_t$(4–10 membered heterocyclic), wherein t is an integer from 0 to 5, 1 or 2 ring carbon atoms of the heterocyclic group are optionally substituted with an oxo (=O) moiety, and the alkyl, aryl and heterocyclic moieties of the foregoing R$^6$ and R$^7$ groups are optionally substituted with 1 to 3 halo, cyano, trifluoromethyl, trifluoromethoxy, C$_1$–C$_6$ alkyl, C$_1$–C$_6$ alkoxy, C$_2$–C$_6$ alkenyl, C$_2$–C$_6$ alkynyl, —(CR$^8$R$^9$)$_t$(C$_6$–C$_{10}$ aryl), and —(CR$^8$R$^9$)$_t$(4–10 membered heterocyclic), wherein t is an integer from 0 to 5;

each R$^8$ and R$^9$ is independently selected from H and C$_1$–C$_4$ alkyl; and each R$^{10}$ is independently selected from halo, cyano, trifluoromethyl, trifluoromethoxy, —C(O)O—R$^6$, —OR$^6$, —C(O)(CR$^8$R$^9$)$_p$C(O)OR$^6$, wherein p is an integer from 1 to 5, C$_1$–C$_6$ alkyl, C$_2$–C$_6$ alkenyl, C$_2$–C$_6$ alkynyl, and —NR$^6$R$^7$.

The present invention also relates to compounds of formula (1), wherein:

W-Z is —C(=O)—C(—R$^3$)(H)— or —C(—OR$^6$)=C(—R$^{3'}$)—;

each R$^1$ is independently selected from hydrogen, C$_1$–C$_6$ alkyl, C$_2$–C$_6$ alkenyl, C$_2$–C$_6$ alkynyl, (C$_3$–C$_{10}$) cycloalkyl, 4- to 10-membered heterocyclic, and C$_6$–C$_{10}$ aryl, wherein the foregoing R$^1$ groups, except H, are optionally substituted by 1 to 4 substituents selected from R$^4$;

R$^2$ is selected from the group of R$^1$ substituents, —(CR$^8$R$^9$)$_t$(C$_3$–C$_{10}$ cycloalkyl), —(CR$^8$R$^9$)$_t$(C$_6$–C$_{10}$ aryl), —(CR$^8$R$^9$)$_t$(4–10 membered heterocyclic), —(CR$^8$R$^9$)$_q$C(O)(CR$^8$R$^9$)$_t$(C$_6$–C$_{10}$ aryl), —(CR$^8$R$^9$)$_q$C(O)(CR$^8$R$^9$)$_t$(4–10 membered heterocyclic), —(CR$^8$R$^9$)$_t$O(CR$^8$R$^9$)$_q$(C$_6$–C$_{10}$ aryl), —(CR$^8$R$^9$)$_t$O(CR$^8$R$^9$)$_q$(4–10 membered heterocyclic), —(CR$^8$R$^9$)$_q$SO$_n$(CR$^8$R$^9$)$_t$(C$_6$–C$_{10}$ aryl), and —(CR$^8$R$^9$)$_q$SO$_n$(CR$^8$R$^9$)$_t$(4–10 membered heterocyclic), wherein q and t are each independently an integer from 0 to 5, n is an integer from 0 to 2, the alkyl, cycloalkyl, aryl and heterocyclic moieties of said R$^2$ groups are optionally substituted by 1 to 5 R$^4$ groups, and with the proviso that R$^2$ is not H;

R$^3$ is hydrogen, —OR$^6$, —SR$^6$, —NR$^6$R$^7$, and the group of R$^2$ substituents;

R$^{3'}$ is selected from the group of R$^3$ substituents;

each R$^4$ is independently selected from halo, cyano, nitro, trifluoromethoxy, trifluoromethyl, azido, C$_1$–C$_{10}$ alkyl, C$_2$–C$_6$ alkenyl, C$_2$–C$_6$ alkynyl, C$_3$–C$_{10}$ cycloalkyl, —(CR$^8$R$^9$)$_t$N(R$^5$)$_2$, —(CR$^8$R$^9$)$_t$NR$^6$C(O)R$^6$, —(CR$^8$R$^9$)$_t$OR$^6$, —(CR$^8$R$^9$)$_t$C(O)R$^6$, —(CR$^8$R$^9$)$_t$ C(O)OR$^6$, —(CR$^8$R$^9$)$_t$C(O)R$^6$, —(CR$^8$R$^9$)$_t$ NR$^6$C(O)R$^7$, —(CR$^8$R$^9$)$_t$ NR$^6$C(O)OR$^6$—(CR$^8$R$^9$)$_t$NR$^6$C(O)NR$^7$, —(CR$^8$R$^9$)$_t$C(O) NR$^6$R$^7$, —(CR$^8$R$^9$)$_t$NR$^6$R$^7$, —(CR$^8$R$^9$)$_t$NR$^6$OR$^7$, —(CR$^8$R$^9$)$_t$SO$_2$NR$^6$R$^7$, —(CR$^8$R$^9$)$_t$NR$^6$SO$_2$R$^7$, —(CR$^8$R$^9$)$_t$(C$_6$–C$_{10}$ aryl)(wherein t is an integer from 0 to 5), —(CR$^8$R$^9$)$_t$(4–10 membered heterocyclic)(wherein t is an integer from 0 to 5), C$_3$–C$_{10}$ cycloalkyl, R$^6$—O—, R$^6$—SO$_n$—(CR$^8$R$^9$)$_t$— (wherein n is an integer from 0 to 2), and oxo (=O), and wherein the alkyl, aryl, and heterocyclic moieties of said R$^4$ groups are optionally substituted by 1 to 4 substituents selected from R$^5$;

each R$^5$ is independently selected from halo, trifluoromethyl, trifluoromethoxy, cyano, C$_1$–C$_6$ alkyl, C$_2$–C$_6$ alkenyl, C$_2$–C$_6$ alkynyl, —OR$^8$, C$_3$–C$_{10}$ cycloalkyl, C$_6$–C$_{10}$ aryl, 4- to 10-membered heterocyclic, oxo (=O), —C(O)R$^6$, —C(O)OR$^6$, —OC(O)R$^6$, —NR$^6$C(O)R$^6$, —NR$^6$C(O)NR$^7$—C(O)NR$^6$R$^7$—NR$^6$R$^7$, —NR$^6$OR$^7$, —NR$^6$SO$_2$R$^7$ and —SO$_2$NR$^6$R$^7$, wherein the alkyl, aryl and heterocyclic moieties of the foregoing R$^5$ groups are optionally substituted by 1 to 3 R$^{10}$;

each R$^6$ and R$^7$ is independently selected from H, cyano, C$_1$–C$_6$ alkyl, C$_3$–C$_{10}$ cycloalkyl, —(CR$^8$R$^9$)$_t$(C$_6$–C$_{10}$ aryl), and —(CR$^8$R$^9$)$_t$(4–10 membered heterocyclic), —(CR$^8$R$^9$)$_t$ C(O)R$^8$ wherein t is an integer from 0 to 5, 1 or 2 ring carbon atoms of the heterocyclic group are optionally substituted with an oxo (=O) moiety, and the alkyl, aryl, and heterocyclic moieties of the foregoing R$^6$ and R$^7$ groups are optionally substituted with 1 to 3 halo, cyano, C$_3$–C$_{10}$ cycloalkyl, —C(O)OR$^8$—NR$^8$C(O)R$^9$, —(CR$^8$R$^9$)$_t$NR$^8$R$^9$, —OR$^8$, —NC(O)R$^9$, trifluoromethyl, trifluoromethoxy, C$_1$–C$_6$ alkyl, C$_1$–C$_6$ alkoxy, C$_2$–C$_6$ alkenyl, C$_2$–C$_6$ alkynyl, —(CR$^8$R$^9$)$_t$(C$_6$–C$_{10}$ aryl), and —(CR$^8$R$^9$)$_t$(4–10 membered heterocyclic), wherein t is an integer from 0 to 5;

each R$^8$ and R$^9$ is independently selected from H and C$_1$–C$_4$ alkyl; and each R$^{10}$ is independently selected from halo, cyano, trifluoromethyl, trifluoromethoxy, —C(O)OR$^6$, —C(O)O—R$^6$, —OR$^6$, —C(O)(CR$^8$R$^9$)$_p$C(O)OR$^6$, wherein p is an integer from 1 to 5, C$_1$–C$_6$ alkyl, C$_2$–C$_6$ alkenyl, C$_2$–C$_6$ alkynyl, and —NR$^6$R$^7$.

The present futher relates to a comound of the formula 2

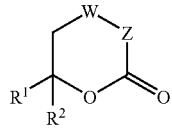

and pharmaceutically acceptable salts, solvates, metabolites, prodrugs and solvates thereof, wherein:

W-Z is —C(—OR$^6$)=C(—R$^{3'}$)—;

R$^1$ is cyclopentyl;

R$^2$ is —(CR$^8$R$^9$)$_t$(C$_6$–C$_{10}$ aryl) or —(CR$^8$R$^9$)$_t$(4–10 membered heterocyclic), wherein t is an integer from 0 to 5, and the aryl and heterocyclic moieties of said R$^2$ groups are optionally substituted by 1 to 5 R$^4$ groups, and with the proviso that R$^2$ is not H;

R$^3$ is hydrogen, —OR$^6$, —SR$^6$, —NR$^6$R$^7$, and the group of R$^2$ substituents;

each R$^4$ is independently selected from halo, cyano, nitro, trifluoromethoxy, trifluoromethyl, azido, C$_1$–C$_{10}$ alkyl, C$_2$–C$_6$ alkenyl, C$_2$–C$_6$ alkynyl, —C(O)R$^6$, —C(O)OR$^6$, —OC(O)R$^6$, —NR$^6$C(O)R$^7$, —NR$^6$C(O)NR$^7$, —C(O)NR$^6$R$^7$, —NR$^6$R$^7$, —NR$^6$OR$^7$, —SO$_2$NR$^6$R$^7$, —NR$_6$SO$_2$R$^7$—(CR$^8$R$^9$)$_t$(C$_6$–C$_{10}$ aryl)(wherein t is an integer from 0 to 5), —(CR$^8$R$^9$)$_t$(4–10 membered heterocyclic) (wherein t is an integer from 0 to 5), C$_3$–C$_{10}$ cycloalkyl, R$^6$—O—, R$^6$—SO$_n$—(wherein n is an integer from 0 to 2), and oxo (=O), and wherein the alkyl, aryl, and heterocyclic moieties of said R$^4$ groups are optionally substituted by 1 to 4 substituents selected from R$^5$;

each R$^5$ is independently selected from halo, trifluoromethyl, trifluoromethoxy, cyano, C$_1$–C$_6$ alkyl, C$_2$–C$_6$ alkenyl, C$_2$–C$_6$ alkynyl, —OR$^8$, C$_3$–C$_{10}$ cycloalkyl, C$_6$–C$_{10}$ aryl, 4- to 10-membered heterocyclic, oxo (=O), —C(O)R$^6$, —C(O)OR$^6$, —OC(O)R$^6$, —NR$^6$C(O)R$^6$, —NR$^6$C(O)NR$^7$, —C(O)NR$^6$R$^7$, —NR$^6$R$^7$, —NR$^6$OR$^7$, —NR$^6$SO$_2$R$^7$ and —SO$_2$NR$^6$R$^7$, wherein the alkyl, aryl and heterocyclic moieties of the foregoing R$^5$ groups are optionally substituted by 1 to 3 R$^{10}$;

each R$^6$ and R$^7$ is independently selected from H, C$_1$–C$_6$ alkyl, C$_3$–C$_{10}$ cycloalkyl, —(CR$^8$R$^9$)$_t$(C$_6$–C$_{10}$ aryl), and —(CR$^8$R$^9$)$_t$(4–10 membered heterocyclic), wherein t is an integer from 0 to 5, 1 or 2 ring carbon atoms of the heterocyclic group are optionally substituted with an oxo (=O) moiety, and the alkyl, aryl and heterocyclic moieties of the foregoing R$^6$ and R$^7$ groups are optionally substituted with 1 to 3 halo, cyano, trifluoromethyl, trifluoromethoxy, C$_1$–C$_6$ alkyl, C$_1$–C$_6$ alkoxy, C$_2$–C$_6$ alkenyl, C$_2$–C$_6$ alkynyl, (CR$^8$R$^9$)$_t$(C$_6$–C$_{10}$ aryl), and —(CR$^8$R$^9$)$_t$(4–10 membered heterocyclic), wherein t is an integer from 0 to 5;

each R$^8$ and R$^9$ is independently selected from H and C$_1$–C$_4$ alkyl; and each R$^{10}$ is independently selected from halo, cyano, trifluoromethyl, trifluoromethoxy, —C(O)O—R$^6$, —OR$^6$, —C(O)(CR$^8$R$^9$)pC(O)OR wherein p is an integer from 1 to 5, C$_1$–C$_6$ alkyl, C$_2$–C$_6$ alkenyl, C$_2$–C$_6$ alkynyl, and NR$^6$R$^7$.

The present invention further relates to a compound of the formula (3)

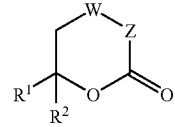

and to pharmaceutically acceptable salts, solvates, prodrugs, and metabolites thereof, wherein:

W-Z is —C(=O)—C(—R$^3$)(H)—;

R$^1$ is cyclopentyl;

R$^2$ is —(CR$^8$R$^9$)$_t$(C$_6$–C$_{10}$ aryl) or —(CR$^8$R$^9$)$_t$(4–10 membered heterocyclic), wherein t is an integer from 0 to 5, and the aryl and heterocyclic moieties of said R$^2$ groups are optionally substituted by 1 to 5 R$^4$ groups, and with the proviso that R$^2$ is not H;

R$^3$ is hydrogen;

each R$^4$ is independently selected from halo, cyano, nitro, trifluoromethoxy, trifluoromethyl, azido, C$_1$–C$_{10}$ alkyl, C$_2$–C$_6$ alkenyl, C$_2$–C$_6$ alkynyl, —C(O)R$^6$, —C(O)OR$^6$, —OC(O)R$^6$, —NR$^6$C(O)R$^7$, —NR$^6$C(O)NR$^7$, —C(O)NR$^6$R$^7$, —NR$^6$R$^7$, —NR$^6$OR$^7$, —SO$_2$NR$^6$R$^7$, —NR$^6$SO$_2$R$^7$, —(CR$^8$R$^9$)$_t$(C$_6$–C$_{10}$ aryl)(wherein t is an integer from 0 to 5), —(CR$^8$R$^9$)$_t$(4–10 membered heterocyclic)(wherein t is an integer from 0 to 5), C$_3$–C$_{10}$ cycloalkyl, R$^6$—O—, R$^6$—SO$_n$— (wherein n is an integer from 0 to 2), and oxo (=O), and wherein the alkyl, aryl, and heterocyclic moieties of said R$^4$ groups are optionally substituted by 1 to 4 substituents selected from R$^5$;

each R$^5$ is independently selected from halo, trifluoromethyl, trifluoromethoxy, cyano, C$_1$–C$_6$ alkyl, C$_2$–C$_6$ alkenyl, C$_2$–C$_6$ alkynyl, —OR$^8$, C$_3$–C$_{10}$ cycloalkyl, C$_6$–C$_{10}$ aryl, 4- to 10-membered heterocyclic, oxo (=O), —C(O)R$^6$, —C(O)OR$^6$, —OC(O)R$^6$, —NR$^6$C(O)R$^6$, —NR$^6$C(O)NR$^7$, —C(O)NR$^6$R$^7$, —NR$^6$R$^7$, —NR$^6$OR$^7$, —NR$^6$SO$_2$R$^7$ and —SO$_2$NR$^6$R$^7$, wherein the alkyl, aryl and heterocyclic moieties of the foregoing R$^5$ groups are optionally substituted by 1 to 3 R$^{10}$;

each R$^6$ and R$^7$ is independently selected from H, C$_1$–C$_6$ alkyl, C$_3$–C$_{10}$ cycloalkyl, —(CR$^8$R$^9$)$_t$(C$_6$–C$_{10}$ aryl), and —(CR$^8$R$^9$)$_t$(4–10 membered heterocyclic), wherein t is an integer from 0 to 5, 1 or 2 ring carbon atoms of the heterocyclic group are optionally substituted with an oxo (=O) moiety, and the alkyl, aryl and heterocyclic moieties of the foregoing R$^6$ and R$^7$ groups are optionally substituted with 1 to 3 halo, cyano, trifluoromethyl, trifluoromethoxy, C$_1$–C$_6$ alkyl, C$_1$–C$_6$ alkoxy, C$_2$–C$_6$ alkenyl, C$_2$–C$_6$ alkynyl, (CR$^8$R$^9$)$_t$(C$_6$–C$_{10}$ aryl), and —(CR$^8$R$^9$)$_t$(4–10 membered heterocyclic), wherein t is an integer from 0 to 5;

each R$^8$ and R$^9$ is independently selected from H and C$_1$–C$_4$ alkyl; and each R$^{10}$ is independently selected from halo, cyano, trifluoromethyl, trifluoromethoxy, —C(O)O—R$^6$, —OR$^6$, —C(O)(CR$^8$R$^9$)pC(O)OR$^6$, wherein p is an integer from 1 to 5, C$_1$–C$_6$ alkyl, C$_2$–C$_6$ alkenyl, C$_2$–C$_6$ alkynyl, and NR$^6$R$^7$.

In a specific embodiment of the present invention, according to formula 1, R$^2$ is —(CR$^8$R$^9$)$_t$(C$_6$–C$_{10}$ aryl), wherein t is an integer from 2 to 5, and the aryl moiety of said R$^2$ group is optionally substituted by 1 to 5 R$^4$ groups, and with the proviso that R$^2$ is not H; optionally each R$^4$ is independently selected from halo, nitro, C$_1$–C$_{10}$ alkyl, —C(O)R$^6$, —C(O)OR$^6$, —OC(O)R$^6$, —C(O)NR$^6$R$^7$, —(CR$^8$R$^9$)$_t$(4–10 membered heterocyclic)(wherein t is an integer from 0 to 5), C$_3$–C$_{10}$ cycloalkyl, R$^6$—O—, and wherein the alkyl, aryl, and heterocyclic moieties of said R$^4$ groups are optionally substituted by 1 to 4 substituents selected from R$^5$, optionally each R$^5$ is independently selected from halo, trifluoromethyl, C$_1$–C$_6$ alkyl, —OR$^8$, C$_3$–C$_{10}$ cycloalkyl, C$_6$–C$_{10}$ aryl, oxo (=O), —C(O)R$^6$, —C(O)OR$^6$, —OC(O)R$^6$, —NR$^6$C(O)R$^6$, —NR$^6$C(O)NR$^7$, —C(O)NR$^6$R$^7$, —NR$^6$R$^7$, —NR$^6$OR$^7$, —NR$^6$SO$_2$R$^7$ and —SO$_2$NR$^6$R$^7$, wherein the alkyl and aryl moieties of the foregoing R$^5$ groups are optionally substituted by 1 to 3 R$^{10}$; optionally each R$^{10}$ is independently selected from halo, trifluoromethyl, —C(O)O—R$^6$, —OR$^6$, C$_1$–C$_6$ alkyl and NR$^6$R$^7$; optionally R$^3$ is —OR$^6$, —SR$^6$, —NR$^6$R$^7$, and —(CR$^8$R$^9$)$_t$(C$_6$–C$_{10}$ aryl), wherein t is an integer from 2 to 5, and the aryl moiety of said R$^2$ group is optionally substituted by 1 to 5 R$^4$ groups.

In yet another aspect of the present invention are provided compounds of formula (4),

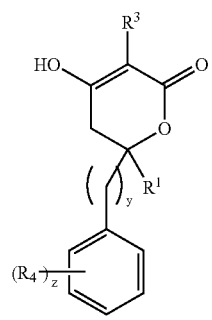

(4)

wherein:

R$^1$ is cyclopentyl;

R$^3$ is —(CR$^8$R$^9$)$_t$(C$_6$–C$_{10}$ aryl) or —(CR$^8$R$^9$)$_t$(4–10 membered heterocyclic), wherein t is an integer from 0 to 5, and the aryl and heterocyclic moieties of said R$^3$ groups are optionally substituted by 1 to 5 R$^4$ groups;

each R$^4$ is independently chosen from halo, C$_1$–C$_{10}$ alkyl, and R$^6$—O—, and each C$_1$–C$_{10}$ alkyl may be optionally substituted by at least one substituent chosen from halo, trifluoromethyl, trifluoromethoxy, C$_1$–C$_{10}$ alkyl, and cyano; or when two adjacent R$^4$ groups are both C$_1$–C$_{10}$ alkyl, they, together with the atoms to which they are attached, form a 3- to 7-membered ring, wherein in said ring any carbon atom may be replaced by a heteroatom chosen from N, O, and S, provided that two adjacent carbons are not both replaced by heteroatoms;

R$^6$ is hydrogen or C$_1$–C$_{10}$ alkyl;

R$^8$ and R$^9$ are independently chosen from hydrogen and C$_1$–C$_{10}$ alkyl;

z is an integer from 1 to 5; and y is an integer from 0 to 5.

In a further aspect of the present invention are provided compounds of formula (4), wherein:

R$^1$ is cyclopentyl;

R$^3$ is —(CR$^8$R$^9$)$_t$(4–10 membered heterocyclic), wherein t is an integer from 0 to 5, and the heterocyclic moiety is optionally substituted by 1 to 5 R$^4$ groups;

each R$^4$ is independently chosen from halo, C$_1$–C$_{10}$ alkyl, and R$^6$—O—, and each C$_1$–C$_{10}$ alkyl may be optionally substituted by at least one substituent chosen from halo, trifluoromethyl, trifluoromethoxy, C$_1$–C$_{10}$ alkyl, and cyano; or when two adjacent R$^4$ groups are both C$_1$–C$_{10}$ alkyl, they, together with the atoms to which they are attached, form a 3- to 7-membered ring, wherein in said ring any carbon atom may be replaced by a heteroatom chosen from N, O, and S, provided that two adjacent carbons are not both replaced by heteroatoms;

R$^6$ is hydrogen or C$_1$–C$_{10}$ alkyl;

R$^8$ and R$^9$ are hydrogen;

z is an integer from 1 to 5; and y is an integer from 0 to 5.

In yet another aspect of the present invention are provided compounds of formula (4), wherein:

R$^1$ is cyclopentyl;

R$^3$ is —(CH$_2$)$_t$([1,2,4]triazolo[1,5-a]pyrimidinyl), optionally substituted by 1 to 3 R$^4$ groups;

t is an integer from 1–3;

each R$^4$ is independently chosen from halo, C$_1$–C$_{10}$ alkyl, and R$^6$—O—, and each C$_1$–C$_{10}$ alkyl may be optionally substituted by at least one substituent chosen from halo, trifluoromethyl, trifluoromethoxy, C$_1$–C$_{10}$ alkyl, and cyano; or when two adjacent R$^4$ groups are both C$_1$–C$_{10}$ alkyl, they, together with the atoms to which they are attached, form a 3- to 7-membered ring, wherein in said ring any carbon atom may be replaced by a heteroatom chosen from N, O, and S, provided that two adjacent carbons are not both replaced by heteroatoms;

R$^6$ is hydrogen or C$_1$–C$_{10}$ alkyl;

z is an integer from 1 to 5; and y is an integer from 1 to 3.

In still a further aspect of the present invention are provided compounds of formula (4), wherein:

R$^1$ is cyclopentyl;

R$^3$ is —(CH$_2$)([1,2,4]triazolo[1,5-a]pyrimidinyl), substituted by 1 to 3 R$^4$ groups;

each R$^4$ is independently chosen from halo and C$_1$–C$_{10}$ alkyl optionally substituted with cyano; or two adjacent R$^4$ groups are both C$_1$–C$_{10}$ alkyl and, together with the atoms to which they are attached, form a 3- to 7-membered ring, wherein a carbon atom is replaced by a heteroatom chosen from N, O, and S;

z is an integer from 2 to 3; and y is 2.

In yet another aspect of the present invention are provided compounds of formula (4), wherein:

R$^1$ is cyclopentyl;

R$^3$ is —(CH$_2$)([1,2,4]triazolo[1,5-a]pyrimidinyl), substituted by 2 R$^4$ groups;

each R$^4$ is independently chosen from halo, —CH$_3$, and —C(CH$_3$)$_2$CN; and y is 2.

In still a further aspect of the present invention are provided compounds of formula (4), wherein:

R$^1$ is cyclopentyl;

R$^3$ is —(CH$_2$)([1,2,4]triazolo[1,5-a]pyrimidinyl), substituted by at least one substituent chosen from halo and methyl;

two adjacent R$^4$ groups, together with the atoms to which they are attached form a 5-membered ring, wherein in said ring one carbon atom is replaced by O;

z is an integer from 2 to 3; and y is 2.

In yet another aspect of the present invention are provided compounds of formula (4b),

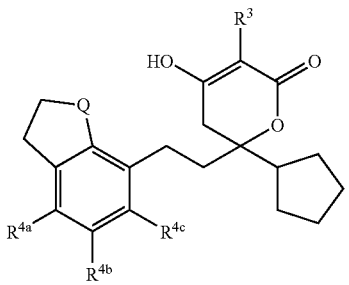

(4b)

wherein:

R$^3$ is —(CH$_2$)([1,2,4]triazolo[1,5-a]pyrimidinyl), substituted by at least one substituent chosen from halo and methyl;

Q is chosen from N, O, and S;

R$^{4a}$, R$^{4b}$, and R$^{4c}$ are independently chosen from hydrogen, halo, C$_1$–C$_{10}$ alkyl, and R$^6$—O—; and R$^6$ is chosen from hydrogen and C$_1$–C$_{10}$ alkyl.

Another aspect of the present invention provides compounds of formula (5),

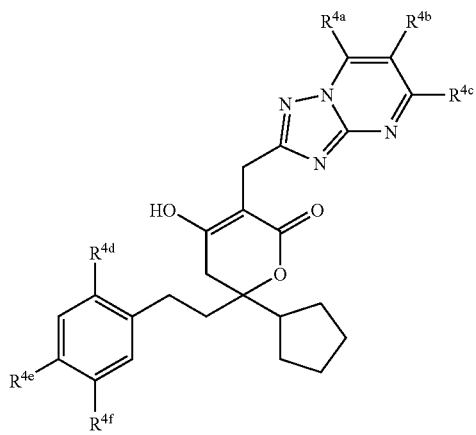

(5)

wherein:

R$^{4a}$, R$^{4b}$, and R$^{4c}$ are independently chosen from halo and C$_1$–C$_{10}$ alkyl;

R$^{4d}$, R$^{4e}$, and R$^{4f}$ are independently chosen from halo, R$^6$—O—, and C$_1$–C$_{10}$ alkyl, wherein said C$_1$–C$_{10}$ alkyl is optionally substituted with at least one substituent chosen from halo and cyano; and R$^6$ is C$_1$–C$_{10}$ alkyl or hydrogen.

Another aspect of the present invention provides compounds of formula (6),

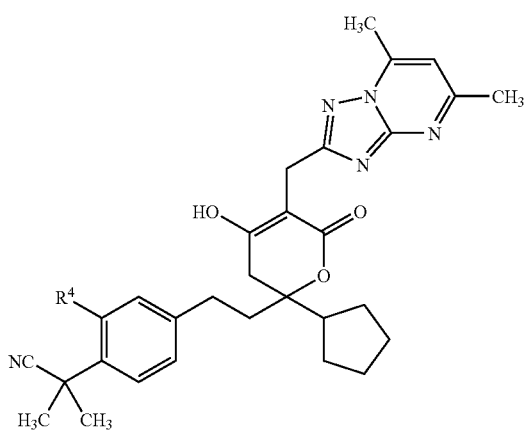

(6)

wherein R$^4$ is halo.

In still a further aspect of the present invention provides compounds of formula (7),

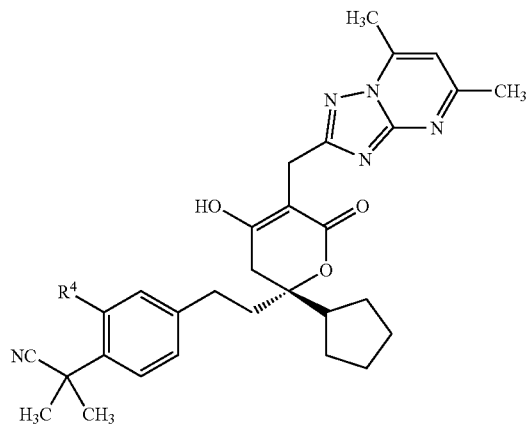

(7)

wherein R$^4$ is halo.

Another aspect of the present invention provides compounds of formula (8),

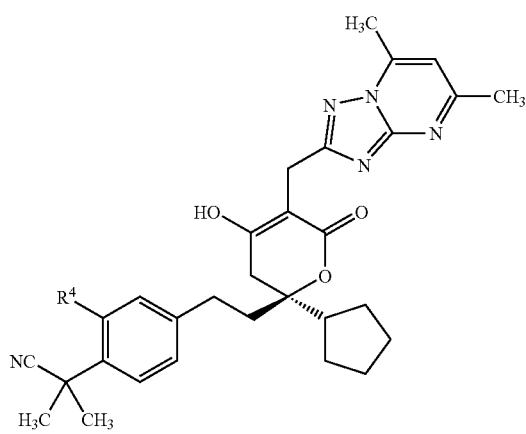

(8)

wherein R$^4$ is halo.

Still a further aspect of the present invention provides compounds of formulas (6), (7), and (8), wherein R$^4$ is chosen from fluorine and chlorine. In yet another aspect of the present invention are provided compounds of formulas (6), (7), and (8), wherein R$^4$ is fluorine. In still a further aspect are provided those compounds of formula (6), (7), and (8), wherein R$^4$ is chlorine.

Another aspect of the present invention provides compounds of formula (4), wherein:

R$^1$ is cyclopentyl;

R$^3$ is —(CH$_2$)([1,2,4]triazolo[1,5-a]pyrimidinyl), optionally substituted by 1 to 3 R$^4$ groups;

each R$^4$ is independently chosen from halo, C$_1$–C$_{10}$ alkyl, and R$^6$—O—, and each C$_1$–C$_{10}$ alkyl may be optionally substituted by at least one substituent chosen from halo, trifluoromethyl, trifluoromethoxy, C$_1$–C$_{10}$ alkyl, and cyano;

R$^6$ is hydrogen or C$_1$–C$_{10}$ alkyl;

z is an integer from 1 to 3; and y is 2.

In still a further aspect of the present invention are provided compounds of formula (4), wherein:

$R^1$ is cyclopentyl;

$R^3$ is —(CH$_2$)([1,2,4]triazolo[1,5-a]pyrimidinyl), optionally substituted by 1 to 3 $R^4$ groups;

each $R^4$ is independently chosen from halo, $C_1$–$C_{10}$ alkyl, and $R^6$—O—, and each $C_1$–$C_{10}$ alkyl may be optionally substituted by at least one substituent chosen from halo, trifluoromethyl, trifluoromethoxy, $C_1$–$C_{10}$ alkyl, and cyano;

$R^6$ is hydrogen or methyl;

z is an integer from 2–3; and y is 2.

In still a further aspect of the present invention are provided compounds of formula (9),

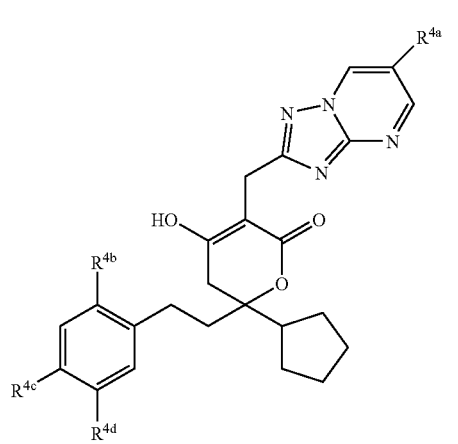

(9)

wherein:

$R^{4a}$ is halo or $C_1$–$C_{10}$ alkyl;

$R^{4b}$, $R^{4c}$, and $R^{4d}$ are independently chosen from $C_1$–$C_{10}$ alkyl and $R^6$—O—; and $R^6$ is hydrogen or methyl.

Also provided in the present invention are compounds of formula (9), wherein:

$R^{4a}$ is halo;

$R^{4b}$ and $R^{4c}$ are each $R^6$—O—;

$R^{4d}$ is $C_1$–$C_{10}$ alkyl; and $R^6$ is hydrogen or methyl.

In another aspect of the present invention are provided compounds of formula (9), wherein:

$R^{4a}$ is fluorine or chlorine;

$R^{4b}$ is —OCH$_3$;

$R^{4c}$ is —OH; and $R^{4d}$ is —CH$_2$CH$_3$.

Another aspect provides compounds of formula (9), wherein:

$R^{4a}$ is chlorine;

$R^{4b}$ is —OCH$_3$;

$R^{4c}$ is —OH; and $R^{4d}$ is —CH$_2$CH$_3$.

Another aspect of the present invention provides compounds of formula (10),

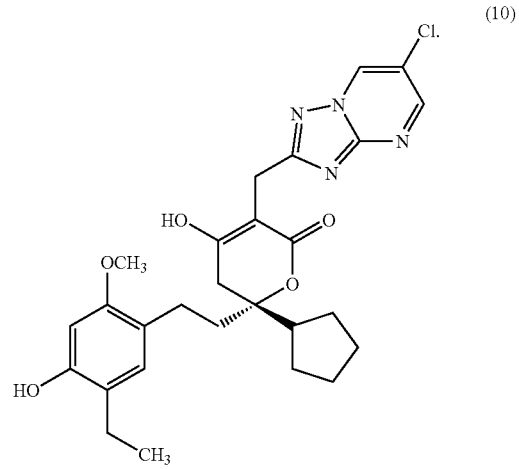

(10)

Still a further aspect of the present invention provides compounds of formula (11),

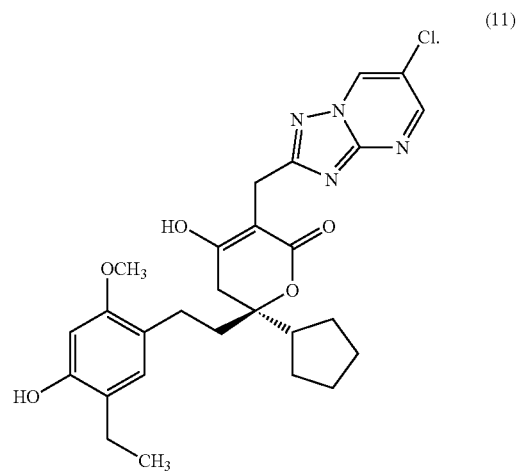

(11)

In another embodiment of the present invention, the invention relates to a compound selected from the group consisting of:

6-Cyclopentyl-3-(5,7-dimethyl-[1,2,4]triazolo[1,5-a-pyrimidin-2-ylmethyl)-6-[2-(3-fluoro-4-methoxy-phenyl)-ethyl]-4-hydroxy-5,6-dihydro-pyran-2-one;

6-[2-(3-tert-Butyl-phenyl)-ethyl]-6-cyclopentyl-3-(5,7-dimethyl-[1,2,4]triazolo[1,5-a]pyrimidin-2-ylmethyl)-4-hydroxy-5,6-dihydro-pyran-2-one;

6-Cyclopentyl-3-(5,7-dimethyl-[1,2,4]triazolo[1,5-a]pyrimidin-2-ylmethyl)-6-[2-(3-ethyl-4-hydroxy-phenyl)-ethyl]4-hydroxy-5,6-dihydro-pyran-2-one;

6-[2-(3-tert-Butyl-4-hydroxy-phenyl)-ethyl]-6-cyclopentyl-3-(5,7-dimethyl-[1,2,4]triazolo[1,5-a]pyrimidin-2-ylmethyl)-4-hydroxy-5,6-dihydro-pyran-2-one;

6-[2-(3-Chloro-4-isopropoxy-phenyl)-ethyl]-6-cyclopentyl-3-(5,7-dimethyl-[1,2,4]triazolo[1,5-a]pyrimidin-2-ylmethyl)-4-hydroxy-5,6-dihydro-pyran-2-one;

6-Cyclopentyl-6-[2-(3,5-dichloro-4-ethoxy-phenyl)-ethyl]-3-(5,7-dimethyl-[1,2,4]triazolo[1,5-a]pyrimidin-2-ylmethyl)-4-hydroxy-5,6-dihydro-pyran-2-one;

6-cyclopentyl-3-[(5,7-dimethyl [1,2,4]triazolo[1,5-a]pyrimidin-2-yl)methyl]-6-[2-(3-isopropylphenyl)ethyl]dihydro-2H-pyran-2,4(3H)-dione;

7-({6-[2-(5-Chloro-2,4-dimethoxyphenyl)ethyl]-6-cyclopentyl-4-hydroxy-2-oxo-5,6-dihydro-2H-pyran-3-yl}methyl)-3-methyl-5H-[1,3]thiazolo[3,2-a]pyrimidin-5-one;

2-(4-{2-[2-Cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-2-fluoro-phenyl)-2-methyl-propionitrile;

1-(4-{2-[2-Cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-2-fluoro-phenyl)-cyclopropanecarbonitrile;

6-[2-(5-chloro-2,4-dimethoxyphenyl)ethyl]-6-cyclopentyl-4-hydroxy-3-(imidazo[1,2-a]pyrimidin-2-ylmethyl)-5,6-dihydro-2H-pyran-2-one;

6 N-[4-(2-{2-cyclopentyl-5-[(5,7-dimethyl[1,2,4]triazolo[1,5-a]pyrimidin-2-yl)methyl]4,6-dioxotetrahydro-2H-pyran-2-yl}ethyl)-2-ethylphenyl]-N-methylmethanesulfonamide;

2-[4-(2-{2-cyclopentyl-4-hydroxy-5-[(1-methyl-1H-indol-5-yl)methyl]-6-oxo-3,6-dihydro-2H-pyran-2-yl}ethyl)-2-fluorophenyl]-2-methylpropanenitrile;

6-[2-(3-Chloro-4-hydroxy-phenyl)-ethyl]-6-cyclopentyl-3-(5,7-dimethyl-[1,2,4]triazolo[1,5-a]pyrimidin-2-ylmethyl)-4-hydroxy-5,6-dihydro-pyran-2-one;

6-Cyclopentyl-3-(5,7-dimethyl-[1,2,4]triazolo[1,5-a]pyrimidin-2-ylmethyl)-6-[2-(3-ethyl-4-methoxy-phenyl)-ethyl]-4-hydroxy-5,6-dihydro-pyran-2-one;

3-(5-Chloro-1-isopropyl-1-benzoimidazol-2-ylsulfanyl)-6-cyclopentyl-6-[2-(3-fluoro-4-isopropoxy-phenyl)-ethyl]-4-hydroxy-5,6-dihydro-pyran-2-one;

5-{6-Cyclopentyl-6-[2-(3-fluoro-4-isopropoxy-phenyl)-ethyl]-4-hydroxy-2-oxo-5,6-dihydro-2H-pyran-3-ylsulfanyl}4-methyl-4H-[1,2,4]triazole-3-carboxylic acid methyl ester;

3-(5-Chloro-1-methyl-1H-benzoimidazol-2-ylsulfanyl)-6-cyclopentyl-6-{2-[4-(3,5-dimethyl-isoxazol-4-yl)-phenyl]-ethyl}-4-hydroxy-5,6-dihydro-pyran-2-one;

6-[2-(3-chloro-4-methoxyphenyl)ethyl]-6-cyclopentyl-3-{[5-(2-furyl)-4-methyl-4H-1,2,4-triazol-3-yl]thio}4-hydroxy-5,6-dihydro-2H-pyran-2-one;

6-[2-(3-chloro-4-methoxyphenyl)ethyl]-6-cyclopentyl-4-hydroxy-3-[(5-pyridin-4-yl-4H-1,2,4-triazol-3-yl)thio]-5,6-dihydro-2H-pyran-2-one;

6-[2-(3-chloro-4-methoxyphenyl)ethyl]-3-[(5-chloro-1-methyl-1H-benzimidazol-2-yl)thio]-6-cyclopentyl-4-hydroxy-5,6-dihydro-2H-pyran-2-one;

6-[2-(5-chloro-2,4-dimethoxyphenyl)ethyl]-3-[(5-chloro-1-methyl-1H-benzimidazol-2-yl)thio]-6-cyclopentyl-4-hydroxy-5,6-dihydro-2H-pyran-2-one;

6-[2-(3-chloro-4-isopropoxyphenyl)ethyl]-3-[(5-chloro-1-methyl-1H-benzimidazol-2-yl)thio]-6-cyclopentyl-4-hydroxy-5,6-dihydro-2H-pyran-2-one;

8-({6-[2-(5-chloro-2,4-dimethoxyphenyl)ethyl]-6-cyclopentyl-4-hydroxy-2-oxo-5,6-dihydro-2H-pyran-3-yl}thio)-1,7-dihydro-6H-purin-6-one;

6-[2-(5-chloro-2,4-dimethoxyphenyl)ethyl]-6-cyclopentyl-4-hydroxy-3-{[5-(4-hydroxyphenyl)-4H-1,2,4-triazol-3-yl]thio}-5,6-dihydro-2H-pyran-2-one;

ethyl 2-({6-[2-(5-chloro-2,4-dimethoxyphenyl)ethyl]-6-cyclopentyl-4-hydroxy-2-oxo-5,6-dihydro-2H-pyran-3-yl}thio)(1,2,4)triazolo[1,5-a]pyrimidine-6-carboxylate;

6-cyclopentyl-3-[(5,7-dimethyl[1,2,4]triazolo[1,5-a]pyrimidin-2-yl)methyl]-6-[2-(3-fluoro-4-isopropoxyphenyl)ethyl]-4-hydroxy-5,6-dihydro-2H-pyran-2-one;

6-Cyclopentyl-3-(5,7-dimethyl-[1,2,4]triazolo[1,5-a]pyrimidin-2-ylmethyl)-6-[2-(3-ethyl-phenyl)-ethyl]-4-hydroxy-5,6-dihydro-pyran-2-one;

6-Cyclopentyl-3-(5,7-dimethyl-[1,2,4]triazolo[1,5-a]pyrimidin-2-ylmethyl)-6-[2-(3-ethyl-phenyl)-ethyl]-4-hydroxy-5,6-dihydro-pyran-2-one;

2-[4-(2-{5-[(4-chloro-1-methyl-1H-pyrazol-3-yl)methyl]-2-cyclopentyl-4-hydroxy-6-oxo-3,6-dihydro-2H-pyran-2-yl}ethyl)-2-fluorophenyl]-2-methylpropanenitrile;

2-{4-[2-(2-Cyclopentyl-4,6-dioxo-5-[1,2,4]triazolo[1,5-a]pyrimidin-2-ylmethyl-tetrahydro-pyran-2-yl)-ethyl]-2-fluoro-phenyl}-2-methyl-propionitrile;

2-(4-{2-[2-Cyclopentyl-5-(6-methyl-[1,2,4]triazolo[1,5-a]pyrimidin-2-ylmethyl)-4,6-dioxo-tetrahydro-pyran-2-yl]-ethyl}-2-fluoro-phenyl)-2-methyl-propionitrile;

(+)-2-(4-{2-[2-Cyclopentyl-5-(6-methyl-[1,2,4]triazolo[1,5-a]pyrimidin-2-ylmethyl)-4,6-dioxo-tetrahydro-pyran-2-yl]-ethyl}-2-fluoro-phenyl)-2-methyl-propionitrile;

(−)-2-(4-{2-[2-Cyclopentyl-5-(6-methyl-[1,2,4]triazolo[1,5-a]pyrimidin-2-ylmethyl)-4,6-dioxo-tetrahydro-pyran-2-yl]-ethyl}-2-fluoro-phenyl)-2-methyl-propionitrile;

2-(4-{2-[5-(6-Chloro-[1,2,4]triazolo[1,5-a]pyrimidin-2-ylmethyl)-2-cyclopentyl-4,6-dioxo-tetrahydro-pyran-2-yl]-ethyl}-2-fluoro-phenyl)-2-methyl-propionitrile;

2-(4-{2-[2-Cyclopentyl-5-(5,7-dimethyl-[1,2,4]triazolo[1,5-a]pyrimidin-2-ylmethyl)-4,6-dioxo-tetrahydro-pyran-2-yl]-ethyl}-2-fluoro-phenyl)-2-ethyl-butyronitrile;

1-(4-{2-[2-Cyclopentyl-5-(6-methyl-[1,2,4]triazolo[1,5-a]pyrimidin-2-ylmethyl)-4,6-dioxo-tetrahydro-pyran-2-yl]-ethyl}-2-fluoro-phenyl)-cyclopropanecarbonitrile;

1-(4-{2-[5-(6-Chloro-[1,2,4]triazolo[1,5-a]pyrimidin-2-ylmethyl)-2-cyclopentyl-4, 6-dioxo-tetrahydro-pyran-2-yl]-ethyl}-2-fluoro-phenyl)-cyclopropanecarbonitrile;

6-Cyclopentyl-6-[2-(3-ethyl-4-hydroxy-phenyl)-ethyl]-4-hydroxy-3-(6-methyl-[2,4]triazolo[1,5-a]pyrimidin-2-ylmethyl)-5,6-dihydro-pyran-2-one;

3-(6-Chloro-[1,2,4]triazolo[1,5-a]pyrimidin-2-ylmethyl)-6-cyclopentyl-6-[2-(3-ethyl-4-hydroxy-phenyl)-ethyl]-4-hydroxy-5,6-dihydro-pyran-2-one;

6-cyclopentyl-3-[(5,7-diethyl[1,2,4]triazolo[1,5-a]pyrimidin-2-yl)methyl]-4-hydroxy-6-[2-(4-hydroxy-3-propylphenyl)ethyl]-5,6-dihydro-2H-pyran-2-one;

6-cyclopentyl-3-[(5,7-diethyl[1,2,4]triazolo[1,5-a]pyrimidin-2-yl)methyl]-6-[2-(3-ethyl-4-hydroxyphenyl)ethyl]-4-hydroxy-5,6-dihydro-2H-pyran-2-one;

N-{2-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylphenoxy]ethyl}acetamide;

2-(4-{2-[2-Cyclopentyl-5-5,7-dimethyl-[1,2,4]triazolo[1,5-a]pyrimidin-2-ylmethyl]-4-hydroxy-6-oxo-3,6-dihydro-2H-pyran-2-yl]-ethyl)-2,6-difluoro-phenyl)-2-methyl-propionitrile;

2-(4-{2-[2-Cyclopentyl-4-hydroxy-5-(6-methyl-[1,2,4]triazolo[1,5-a]pyrimidin-2-ylmethyl)-6-oxo-3,6-dihydro-2H-pyran-2-yl]-ethyl}-2,6-difluoro-phenyl)-2-methyl-propionitrile;

2-(2-Chloro-4-{2-[2-cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-phenyl)-2-methyl-propionitrile;

1-(2-Chloro-4-{2-[2-cyclopentyl-5-(5,7-dimethyl-[1,2,4]
triazolo[1,5-a]pyrimidin-2-ylmethyl)-4-hydroxy-6-oxo-3,
6-dihydro-2H-pyran-2-yl]-ethyl}-phenyl)-cyclopropan-
ecarbonitrile;

6-Cyclopentyl-3-(5,7-dimethyl-[1,2,4]triazolo[1,5-a]pyri-
midin-2-ylmethyl)-6-[2-(5-ethyl-4-hydroxy-2-methoxy-
phenyl)-ethyl]-4-hydroxy-5,6-dihydro-pyran-2-one;

(+)-2-(2-chloro-4-{2-[2-cyclopentyl-5-(5,7-dimethyl-[1,2,
4]triazolo[1,5-a]pyrimidin-2-ylmethyl)-4-hydroxy-6-
oxo-3,6-dihydro-2H-pyran-2-yl]-ethyl}-phenyl)-2-me-
thyl-propionitrile;

(−)-2-(2-chloro-4-{2-[2-cyclopentyl-5-(5,7-dimethyl-[1,2,
4]triazolo[1,5-a]pyrimidin-2-ylmethyl)-4-hydroxy-6-
oxo-3,6-dihydro-2H-pyran-2-yl]-ethyl}-phenyl)-2-me-
thyl-propionitrile (+)-2-(2-fluoro-4-{2-[2-cyclopentyl-5-(5,7-dimethyl-[1,2,4]
triazolo[1,5-a]pyrimidin-2-ylmethyl)-4-hydroxy-6-oxo-3,
6-dihydro-2H-pyran-2-yl]-ethyl}-phenyl)-2-methyl-pro-
pionitrile;

(−)-2-(2-fluoro-4-{2-[2-cyclopentyl-5-(5,7-dimethyl-[1,2,4]
triazolo[1,5-a]pyrimidin-2-ylmethyl)-4-hydroxy-6-oxo-3,
6-dihydro-2H-pyran-2-yl]-ethyl}-phenyl)-2-methyl-pro-
pionitrile;

(+)-3-[(6-chloro[1,2,4]triazolo[1,5-a]pyrimidin-2-yl)me-
thyl]-6-cyclopentyl-6-[2-(5-ethyl-4-hydroxy-2-methox-
yphenyl)ethyl]-4-hydroxy-5,6-dihydro-2H-pyran-2-one (−)-3-[(6-chloro[1,2,4]triazolo[1,5-a]pyrimidin-2-yl)me-
thyl]-6-cyclopentyl-6-[2-(5-ethyl-4-hydroxy-2-methox-
yphenyl)ethyl]-4-hydroxy-5,6-dihydro-2H-pyran-2-one 6-Cyclopentyl-3-(5,7-dimethyl-[1,2,4]triazolo[1,5-a]pyri-
midin-2-ylmethyl)-6-[2-(5-ethyl-4-hydroxy-2-methoxy-
phenyl)-ethyl]-4-hydroxy-5,6-dihydro-pyran-2-one;

(−)-6-Cyclopentyl-3-(5,7-dimethyl-[1,2,4]triazolo[1,5-a]py-
rimidin-2-ylmethyl)-6-[2-(5-ethyl-4-hydroxy-2-methoxy-
phenyl)-ethyl]-4-hydroxy-5,6-dihydro-pyran-2-one;

6-[2-(3-Chloro-5-ethyl-4-methoxy-phenyl)-ethyl]-6-cyclo-
pentyl-3-(5,7-dimethyl-[1,2,4]triazolo[1,5-a]pyrimidin-2-
ylmethyl)-4-hydroxy-5,6-dihydro-pyran-2-one;

6-Cyclopentyl-3-(5,7-dimethyl-[1,2,4]triazolo[1,5-a]pyri-
midin-2-ylmethyl)-6-[2-(5-ethyl-2-methoxy-phenyl)-
ethyl]4-hydroxy-5,6-dihydro-pyran-2-one;

6-[2-(3-Chloro-5-ethyl-4-hydroxy-phenyl)-ethyl]-6-cyclo-
pentyl-3-(5,7-dimethyl-[1,2,4]triazolo[1,5-a]pyrimidin-2-
ylmethyl)-4-hydroxy-5,6-dihydro-pyran-2-one;

6-Cyclopentyl-3-(5,7-dimethyl-[1,2,4]triazolo[1,5-a]pyri-
midin-2-ylmethyl)-6-{2-[3-ethyl-4-(2-hydroxy-ethoxy)-
phenyl]-ethyl}-4-hydroxy-5,6-dihydro-pyran-2-one;

6-Cyclopentyl-6-[2-(3-cyclopropyl-4-methoxy-phenyl)-
ethyl]-3-(5,7-dimethyl-[1,2,4]triazolo[1,5-a]pyrimidin-2-
ylmethyl)-4-hydroxy-5,6-dihydro-pyran-2-one;

6-Cyclopentyl-3-(5,7-dimethyl-[1,2,4]triazolo[1,5-a]pyri-
midin-2-ylmethyl)-6-[2-(5-ethyl-4-hydroxy-2,3-dihydro-
benzofuran-7-yl)-ethyl]-4-hydroxy-5,6-dihydro-pyran-2-
one;

(+)-6-Cyclopentyl-3-(5,7-dimethyl-[1,2,4]triazolo[1,5-a]py-
rimidin-2-ylmethyl)-6-[2-(5-ethyl-4-hydroxy-2,3-dihy-
dro-benzofuran-7-yl)-ethyl]-4-hydroxy-5,6-dihydro-py-
ran-2-one;

(−)-6-Cyclopentyl-3-(5,7-dimethyl-[1,2,4]triazolo[1,5-a]py-
rimidin-2-ylmethyl)-6-[2-(5-ethyl-4-hydroxy-2,3-dihy-
dro-benzofuran-7-yl)-ethyl]-4-hydroxy-5,6-dihydro-py-
ran-2-one;

6-Cyclopentyl-3-(5,7-dimethyl-[1,2,4]triazolo[1,5-a]pyri-
midin-2-ylmethyl)-6-[2-(5-ethyl-pyridin-3-yl)-ethyl]4-
hydroxy-5,6-dihydro-pyran-2-one; and pharmaceutically acceptable salts, solvates and prodrugs of
the foregoing compounds.

The present invention also provides compounds chosen
from:

2-[4-(2-{5-[(4-chloro-1-methyl-1H-pyrazol-3-yl)methyl]-2-
cyclopentyl-4-hydroxy-6-oxo-3,6-dihydro-2H-pyran-2-
yl}ethyl)-2-fluorophenyl]-2-methylpropanenitrile;

2-(4-{2-[2-Cyclopentyl-5-(6-methyl-[1,2,4]triazolo[1,5-a]
pyrimidin-2-ylmethyl)-4,6-dioxo-tetrahydro-pyran-2-yl]-
ethyl}-2-fluoro-phenyl)-2-methyl-propionitrile;

(+)-2-(4-{2-[2-Cyclopentyl-5-(6-methyl-[1,2,4]triazolo[1,5-
a]pyrimidin-2-ylmethyl)-4,6-dioxo-tetrahydro-pyran-2-
yl]-ethyl}-2-fluoro-phenyl)-2-methyl-propionitrile;

(−)-2-(4-{2-[2-Cyclopentyl-5-(6-methyl-[1,2,4]triazolo[1,5-
a]pyrimidin-2-ylmethyl)-4,6-dioxo-tetrahydro-pyran-2-
yl]-ethyl}-2-fluoro-phenyl)-2-methyl-propionitrile;

2-(4-{2-[5-(6-Chloro-[1,2,4]triazolo[1,5-a]pyrimidin-2-yl-
methyl)-2-cyclopentyl-4,6-dioxo-tetrahydro-pyran-2-yl]-
ethyl}-2-fluoro-phenyl)-2-methyl-propionitrile;

3-(6-Chloro-[1,2,4]triazolo[1,5-a]pyrimidin-2-ylmethyl)-6-
cyclopentyl-6-[2-(3-ethyl-4-hydroxy-phenyl)-ethyl]4-hy-
droxy-5,6-dihydro-pyran-2-one;

N-{2-[4-(2-{2-cyclopentyl-5-[(5,7-dimethyl[1,2,4]triazolo
[1,5-a]pyrimidin-2-yl)methyl]-4-hydroxy-6-oxo-3,6-di-
hydro-2H-pyran-2-yl}ethyl)-2-ethylphenoxy]
ethyl}acetamide;

2-(4-{2-[2-Cyclopentyl-5-5,7-dimethyl-[1,2,4]triazolo[1,5-
a]pyrimidin-2-ylmethyl]-4-hydroxy-6-oxo-3,6-dihydro-
2H-pyran-2-yl]-ethyl}-2,6-difluoro-phenyl)-2-methyl-
propionitrile;

(+)-2-(2-chloro-4-{2-[2-cyclopentyl-5-(5,7-dimethyl-[1,2,
4]triazolo[1,5-a]pyrimidin-2-ylmethyl)-4-hydroxy-6-
oxo-3,6-dihydro-2H-pyran-2-yl]-ethyl}-phenyl)-2-me-
thyl-propionitrile;

(−)-2-(2-chloro-4-{2-[2-cyclopentyl-5-(5,7-dimethyl-[1,2,
4]triazolo[1,5-a]pyrimidin-2-ylmethyl)-4-hydroxy-6-
oxo-3,6-dihydro-2H-pyran-2-yl]-ethyl}-phenyl)-2-me-
thyl-propionitrile;

(+)-2-(2-fluoro-4-{2-[2-cyclopentyl-5-(5,7-dimethyl-[1,2,4]
triazolo[1,5-a]pyrimidin-2-ylmethyl)-4-hydroxy-6-oxo-3,
6-dihydro-2H-pyran-2-yl]-ethyl}-phenyl)-2-methyl-pro-
pionitrile;

(−)-2-(2-fluoro-4-{2-[2-cyclopentyl-5-(5,7-dimethyl-[1,2,4]
triazolo[1,5-a]pyrimidin-2-ylmethyl)-4-hydroxy-6-oxo-3,
6-dihydro-2H-pyran-2-yl]-ethyl}-phenyl)-2-methyl-pro-
pionitrile;

(+)-3-[(6-chloro[1,2,4]triazolo[1,5-a]pyrimidin-2-yl)me-
thyl]-6-cyclopentyl-6-[2-(5-ethyl-4-hydroxy-2-methox-
yphenyl)ethyl]-4-hydroxy-5,6-dihydro-2H-pyran-2-one (−)-3-[(6-chloro[1,2,4]triazolo[1,5-a]pyrimidin-2-yl)me-
thyl]-6-cyclopentyl-6-[2-(5-ethyl-4-hydroxy-2-methox-
yphenyl)ethyl]-4-hydroxy-5,6-dihydro-2H-pyran-2-one 1-(2-Chloro-4-{2-[2-cyclopentyl-5-(5,7-dimethyl-[1,2,4]
triazolo[1,5-a]pyrimidin-2-ylmethyl)-4-hydroxy-6-oxo-3,
6-dihydro-2H-pyran-2-yl]-ethyl}-phenyl)-cyclopropan-
ecarbonitrile;

6-Cyclopentyl-3-(5,7-dimethyl-[1,2,4]triazolo[1,5-a]pyri-
midin-2-ylmethyl)-6-[2-(5-ethyl-4-hydroxy-2-methoxy-
phenyl)-ethyl]-4-hydroxy-5,6-dihydro-pyran-2-one;

(−)-6-Cyclopentyl-3-(5,7-dimethyl-[1,2,4]triazolo[1,5-a]py-
rimidin-2-ylmethyl)-6-[2-(5-ethyl-4-hydroxy-2-methoxy-
phenyl)-ethyl]-4-hydroxy-5,6-dihydro-pyran-2-one;

6-[2-(3-Chloro-5-ethyl-4-hydroxy-phenyl)-ethyl]-6-cyclo-
pentyl-3-(5,7-dimethyl-[1,2,4]triazolo[1,5-a]pyrimidin-2-
ylmethyl)-4-hydroxy-5,6-dihydro-pyran-2-one;

6-Cyclopentyl-3-(5,7-dimethyl-[1,2,4]triazolo[1,5-a]pyrimidin-2-ylmethyl)-6-{2-[3-ethyl-4-(2-hydroxy-ethoxy)-phenyl]-ethyl}4-hydroxy-5,6-dihydro-pyran-2-one;

6-Cyclopentyl-3-(5,7-dimethyl-[1,2,4]triazolo[1,5-a]pyrimidin-2-ylmethyl)-6-[2-(5-ethyl-4-hydroxy-2,3-dihydro-benzofuran-7-yl)-ethyl]-4-hydroxy-5,6-dihydro-pyran-2-one;

(+)-6-Cyclopentyl-3-(5,7-dimethyl-[1,2,4]triazolo[1,5-a]pyrimidin-2-ylmethyl)-6-[2-(5-ethyl-4-hydroxy-2,3-dihydro-benzofuran-7-yl)-ethyl]-4-hydroxy-5,6-dihydro-pyran-2-one;

(−)-6-Cyclopentyl-3-(5,7-dimethyl-[1,2,4]triazolo[1,5-a]pyrimidin-2-ylmethyl)-6-[2-(5-ethyl-4-hydroxy-2,3-dihydro-benzofuran-7-yl)-ethyl]-4-hydroxy-5,6-dihydro-pyran-2-one;

6-Cyclopentyl-3-(5,7-dimethyl-[1,2,4]triazolo[1,5-a]pyrimidin-2-ylmethyl)-6-[2-(5-ethyl-pyridin-3-yl)-ethyl]-4-hydroxy-5,6-dihydro-pyran-2-one; and the pharmaceutically acceptable salts, solvates and prodrugs of the foregoing compounds.

In a further aspect, the invention relates to compounds chosen from:

6-[2-(3-tert-Butyl-phenyl)-ethyl]-6-cyclopentyl-3-(5,7-dimethyl-[1,2,4]triazolo[1,5-a]pyrimidin-2-ylmethyl)-4-hydroxy-5,6-dihydro-pyran-2-one;

6-Cyclopentyl-3-(5,7-dimethyl-[1,2,4]triazolo[1,5-a]pyrimidin-2-ylmethyl)-6-[2-(3-ethyl-4-hydroxy-phenyl)-ethyl]-4-hydroxy-5,6-dihydro-pyran-2-one;

6-[2-(3-Chloro-4-isopropoxy-phenyl)-ethyl]-6-cyclopentyl-3-(5,7-dimethyl-[1,2,4]triazolo[1,5-a]pyrimidin-2-ylmethyl)-4-hydroxy-5,6-dihydro-pyran-2-one;

6-Cyclopentyl-6-[2-(3,5-dichloro-4-ethoxy-phenyl)-ethyl]-3-(5,7-dimethyl-[1,2,4]triazolo[1,5-a]pyrimidin-2-ylmethyl)-4-hydroxy-5,6-dihydro-pyran-2-one;

7-({6-[2-(5-Chloro-2,4-dimethoxyphenyl)ethyl]-6-cyclopentyl-4-hydroxy-2-oxo-5,6-dihydro-2H-pyran-3-yl}methyl)-3-methyl-5H-[1,3]thiazolo[3,2-a]pyrimidin-5-one;

2-(4-{2-[2-Cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-2-fluoro-phenyl)-2-methyl-propionitrile;

1-(4-{2-[2-Cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-2-fluoro-phenyl)-cyclopropanecarbonitrile;

6-[2-(5-chloro-2,4-dimethoxyphenyl)ethyl]-6-cyclopentyl-4-hydroxy-3-(imidazo[1,2-a]pyrimidin-2-ylmethyl)-5,6-dihydro-2H-pyran-2-one;

2-[4-(2-{2-cyclopentyl-4-hydroxy-5-[(1-methyl-1H-indol-5-yl)methyl]-6-oxo-3,6-dihydro-2H-pyran-2-yl}ethyl)-2-fluorophenyl]-2-methylpropanenitrile;

6-Cyclopentyl-3-(5,7-dimethyl-[1,2,4]triazolo[1,5-a]pyrimidin-2-ylmethyl)-6-[2-(3-ethyl-4-methoxy-phenyl)-ethyl]-4-hydroxy-5,6-dihydro-pyran-2-one;

6-[2-(5-chloro-2,4-dimethoxyphenyl)ethyl]-3-[(5-chloro-1-methyl-1H-benzimidazol-2-yl)thio]-6-cyclopentyl-4-hydroxy-5,6-dihydro-2H-pyran-2-one;

6-cyclopentyl-3-[(5,7-dimethyl-[1,2,4]triazolo[1,5-a]pyrimidin-2-yl)methyl]-6-[2-(3-fluoro-4-isopropoxyphenyl)ethyl]-4-hydroxy-5,6-dihydro-2H-pyran-2-one;

(+)-2-(2-fluoro-4-{2-[2-cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-phenyl)-2-methyl-propionitrile;

(−)-2-(2-fluoro-4-{2-[2-cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-phenyl)-2-methyl-propionitrile;

(+)-2-(2-chloro-4-{2-[2-cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-phenyl)-2-methyl-propionitrile;

(−)-2-(2-chloro-4-{2-[2-cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-phenyl)-2-methyl-propionitrile;

(+)-3-[(6-chloro[1,2,4]triazolo[1,5-a]pyrimidin-2-yl)methyl]-6-cyclopentyl-6-[2-(5-ethyl-4-hydroxy-2-methoxyphenyl)ethyl]-4-hydroxy-5,6-dihydro-2H-pyran-2-one;

(−)-3-[(6-chloro[1,2,4]triazolo[1,5-a]pyrimidin-2-yl)methyl]-6-cyclopentyl-6-[2-(5-ethyl-4-hydroxy-2-methoxyphenyl)ethyl]-4-hydroxy-5,6-dihydro-2H-pyran-2-one;

6-Cyclopentyl-3-(5,7-dimethyl-[1,2,4]triazolo[1,5-a]pyrimidin-2-ylmethyl)-6-[2-(5-ethyl-4-hydroxy-2,3-dihydro-benzofuran-7-yl)-ethyl]4-hydroxy-5,6-dihydro-pyran-2-one;

(+)-6-Cyclopentyl-3-(5,7-dimethyl-[1,2,4]triazolo[1,5-a]pyrimidin-2-ylmethyl)-6-[2-(5-ethyl-4-hydroxy-2,3-dihydro-benzofuran-7-yl)-ethyl]-4-hydroxy-5,6-dihydro-pyran-2-one;

(−)-6-Cyclopentyl-3-(5,7-dimethyl-[1,2,4]triazolo[1,5-a]pyrimidin-2-ylmethyl)-6-[2-(5-ethyl-4-hydroxy-2,3-dihydro-benzofuran-7-yl)-ethyl]-4-hydroxy-5,6-dihydro-pyran-2-one;

6-Cyclopentyl-3-(5,7-dimethyl-[1,2,4]triazolo[1,5-a]pyrimidin-2-ylmethyl)-6-[2-(5-ethyl-pyridin-3-yl)-ethyl]4-hydroxy-5,6-dihydro-pyran-2-one; and pharmaceutically acceptable salts, solvates and prodrugs of the foregoing compounds.

In yet another aspect of the present invention are provided compounds chosen from:

(+)-2-(2-fluoro-4-{2-[2-cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-phenyl)-2-methyl-propionitrile;

(−)-2-(2-fluoro-4-{2-[2-cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-phenyl)-2-methyl-propionitrile;

(+)-2-(2-chloro-4-{2-[2-cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-phenyl)-2-methyl-propionitrile;

(−)-2-(2-chloro-4-{2-[2-cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-phenyl)-2-methyl-propionitrile;

(+)-3-[(6-chloro[1,2,4]triazolo[1,5-a]pyrimidin-2-yl)methyl]-6-cyclopentyl-6-[2-(5-ethyl-4-hydroxy-2-methoxyphenyl)ethyl]-4-hydroxy-5,6-dihydro-2H-pyran-2-one;

(−)-3-[(6-chloro[1,2,4]triazolo[1,5-a]pyrimidin-2-yl)methyl]-6-cyclopentyl-6-[2-(5-ethyl-4-hydroxy-2-methoxyphenyl)ethyl]-4-hydroxy-5,6-dihydro-2H-pyran-2-one;

6-Cyclopentyl-3-(5,7-dimethyl-[1,2,4]triazolo[1,5-a]pyrimidin-2-ylmethyl)-6-[2-(5-ethyl-4-hydroxy-2,3-dihydro-benzofuran-7-yl)-ethyl]-4-hydroxy-5,6-dihydro-pyran-2-one;

(+)-6-Cyclopentyl-3-(5,7-dimethyl-[1,2,4]triazolo[1,5-a]pyrimidin-2-ylmethyl)-6-[2-(5-ethyl-4-hydroxy-2,3-dihydro-benzofuran-7-yl)-ethyl]-4-hydroxy-5,6-dihydro-pyran-2-one;

(−)-6-Cyclopentyl-3-(5,7-dimethyl-[1,2,4]triazolo[1,5-a]pyrimidin-2-ylmethyl)-6-[2-(5-ethyl-4-hydroxy-2,3-dihydro-benzofuran-7-yl)-ethyl]-4-hydroxy-5,6-dihydro-pyran-2-one;

6-Cyclopentyl-3-(5,7-dimethyl-[1,2,4]triazolo[1,5-a]pyrimidin-2-ylmethyl)-6-[2-(5-ethyl-pyridin-3-yl)-ethyl]4-hydroxy-5,6-dihydro-pyran-2-one; and pharmaceutically acceptable salts, solvates and prodrugs of the foregoing compounds.

The invention also relates to a method for the treatment of Hepatitis C virus (HCV) in a mammal, such as a human, comprising administering to said mammal an amount of a compound of the present invention or a salt or solvate thereof that is effective in treating HCV.

In a further aspect of the present invention are provided methods for the treatment of a mammal, such as a human, suffering from infection with Hepatitis C virus, comprising administering to said mammal a Hepatitis C virus-inhibiting amount of a compound of the present invention, or a pharmaceutically acceptable salt, prodrug, pharmaceutically active metabolite, or solvate thereof.

The present invention also relates to a method of inhibiting Hepatitis C polymerase, comprising contacting said polymerase with a polymerase-inhibiting amount of a compound of the present invention, or a pharmaceutically acceptable salt, prodrug, pharmaceutically active metabolite, or solvate thereof.

The present invention is also directed to a pharmaceutical composition for the treatment of Hepatitis C virus (HCV) in a mammal, such as a human, comprising an amount of a compound the present invention, or a pharmaceutically acceptable salt, prodrug, pharmaceutically active metabolite, or solvate thereof, that is effective in treating HCV, and a pharmaceutically acceptable carrier.

The present invention is also directed to inhibition of Hepatitis C virus replication in a mammal, such as a human, comprising administering to said mammal a Hepatitis C virus replication-inhibiting amount of a compound of the present invention.

The present invention is further directed to a method of inhibiting HCV RdRp activity, comprising contacting the protein with an effective amount of a compound of the present invention, or a pharmaceutically acceptable salt, prodrug, pharmaceutically active metabolite, or solvate thereof. For Example, HCV activity may be inhibited in mammalian tissue by administering an HCV-inhibiting agent according to the invention.

The present invention also relates to the use of the compounds of the invention in the preparation of a medicament for the treatment of a mammal suffering from infection with Hepatitis C virus. The medicament may comprise a Hepatitis C virus-inhibiting amount of a compound or compounds of the invention and a pharmaceutically acceptable carrier or carriers.

As used herein, the terms "comprising" and "including" are used in their open, non-limiting sense.

In accordance with a convention used in the art, the symbol

is used in structural formulas herein to depict the bond that is the point of attachment of the moiety or substituent to the core or backbone structure. In accordance with another convention, in some structural formulae herein the carbon atoms and their bound hydrogen atoms are not explicitly depicted, e.g.,

represents a methyl group,

represents an ethyl group,

represents a cyclopentyl group, etc.

The compounds of the present invention may exist in several tautomeric forms. For example, a compound of the invention may exist in a form in which two ketones are present on a ring of the compound, as shown in (A) below. Alternatively, the compounds of the present invention may exist in at least two different enol forms, as shown in compounds (B) and (C) below. These three forms may be in equilibrium and the compounds of the invention may exist in more than one of these forms at the same time. For example, in a particular compound of the invention, a certain percentage of the molecules may be present in form (A) while the remainder are present in form (B) or form (C). Which form predominates in a particular compound of the invention depends on several factors that include, but are not limited to, whether the compound is in solid, liquid, or crystalline form, whether the compound is dissolved in a solvent and the identity of the solvent, the environmental temperature, and the relative humidity. It is specifically contemplated that when the compounds of the present invention are drawn in a particular form, form (A) for example, all the tautomeric forms, forms (B) and (C) for example, are included as well.

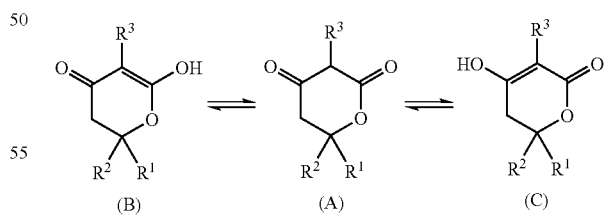

The term "$C_1$–$C_6$ alkyl", as used herein, unless otherwise indicated, includes saturated monovalent hydrocarbon radicals having straight, branched, or cyclic moieties (including fused and bridged bicyclic and spirocyclic moieties), or a combination of the foregoing moieties, and containing from 1–6 carbon atoms. For an alkyl group to have cyclic moieties, the group must have at least three carbon atoms.

A "lower alkyl" is intended to mean an alkyl group having from 1 to 4 carbon atoms in its chain. The term "heteroalkyl"

refers to a straight- or branched-chain alkyl group having from 2 to 12 atoms in the chain, one or more of which is a heteroatom selected from S, O, and N. Exemplary heteroalkyls include alkyl ethers, secondary and tertiary amines, alkyl sulfides and the like.

The term "$C_2$–$C_6$ alkenyl", as used herein, unless otherwise indicated, includes alkyl moieties having at least one carbon-carbon double bond wherein alkyl is as defined above and including E and Z isomers of said alkenyl moiety, and having from 2 to 6 carbon atoms.

The term "$C_2$–$C_6$ alkynyl", as used herein, unless otherwise indicated, includes alkyl moieties having at least one carbon-carbon triple bond wherein alkyl is as defined above, and containing from 2–6 carbon atoms.

The term "carbocycle" refers to a saturated, partially saturated, unsaturated, or aromatic, monocyclic or fused or non-fused polycyclic, ring structure having only carbon ring atoms (no heteroatoms, i.e., non-carbon ring atoms). Exemplary carbocycles include cycloalkyl, aryl, and cycloalkyl-aryl groups.

A "$C_3$–$C_{10}$ cycloalkyl group" is intended to mean a saturated or partially saturated, monocyclic, or fused or spiro polycyclic, ring structure having a total of from 3 to 10 carbon ring atoms (but no heteroatoms). Exemplary cycloalkyls include cyclopropyl, cyclobutyl, cyclopentyl, cyclopentenyl, cyclohexyl, cycloheptyl, adamantyl, and like groups.

A "heterocycloalkyl group" is intended to mean a monocyclic, or fused or spiro polycyclic, ring structure that is saturated or partially saturated, and has a total of from 3 to 18 ring atoms, including 1 to 5 heteroatoms selected from nitrogen, oxygen, and sulfur. Illustrative Examples of heterocycloalkyl groups include pyrrolidinyl, tetrahydrofuryl, piperidinyl, piperazinyl, morpholinyl, thiomorpholinyl, aziridinyl, and like groups.

The term "$C_6$–$C_{10}$ aryl", as used herein, unless otherwise indicated, includes an organic radical derived from an aromatic hydrocarbon by removal of one hydrogen, such as phenyl or naphthyl.

The term "4–10 membered heterocyclic", as used herein, unless otherwise indicated, includes aromatic and non-aromatic heterocyclic groups containing one to four heteroatoms each selected from O, S and N, wherein each heterocyclic group has from 4–10 atoms in its ring system, and with the proviso that the ring of said group does not contain two adjacent O or S atoms. Furthermore, the sulfur atoms contained in such heterocyclic groups may be oxidized with one or two sulfur atoms. Non-aromatic heterocyclic groups include groups having only 4 atoms in their ring system, but aromatic heterocyclic groups must have at least 5 atoms in their ring system. The heterocyclic groups include benzo-fused ring systems. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl.

Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). An example of a heterocyclic group wherein 2 ring carbon atoms are substituted with oxo (=O) moieties is 1,1-dioxo-thiomorpholinyl.

A "heteroaryl group" is intended to mean a monocyclic or fused or spiro polycyclic, aromatic ring structure having from 4 to 18 ring atoms, including from 1 to 5 heteroatoms selected from nitrogen, oxygen, and sulfur. Illustrative Examples of heteroaryl groups include pyrrolyl, thienyl, oxazolyl, pyrazolyl, thiazolyl, furyl, pyridinyl, pyrazinyl, triazolyl, tetrazolyl, indolyl, quinolinyl, quinoxalinyl, benzthiazolyl, benzodioxinyl, benzodioxolyl, benzooxazolyl, and the like.

The term "alkoxy", as used herein, unless otherwise indicated, includes O-alkyl groups wherein alkyl is as defined above.

The term "amino" is intended to mean the —$NH_2$ radical.

The terms "halogen" and "halo," as used herein represent chlorine, fluorine, bromine or iodine.

The term "trifluoromethyl," as used herein, is meant to represent a group —$CF_3$.

The term "trifluoromethoxy," as used herein, is meant to represent a group —$OCF_3$.

The term "cyano," as used herein, is meant to represent a group —CN.

The term "substituted" means that the specified group or moiety bears one or more substituents. The term "unsubstituted" means that the specified group bears no substituents. The term "optionally substituted" means that the specified group is unsubstituted or substituted by one or more substituents.

The term "HCV," as used herein, refers to Hepatitis C virus.

The term "inhibiting Hepatitis C virus" means inhibiting Hepatitis C virus replication in a mammal, such as a human, by administering to the mammal a Hepatitis C virus-inhibiting amount of a compound of the invention. The amount of inhibition of Hepatitis C virus replication in a mammal can be measured using methods known to those of ordinary skill in the art. For example, an amount of a compound of the invention may be administered to a mammal, either alone or as part of a pharmaceutically acceptable formulation. Blood samples may then be withdrawn from the mammal and the amount of Hepatitis C virus in the sample may be quantified using methods known to those of ordinary skill in the art. A reduction in the amount of Hepatitis C virus in the sample compared to the amount found in the blood before administration of a compound of the invention would represent inhibition of the replication of Hepatitis C virus in the mammal. The administration of a compound of the invention to the mammal may be in the form of single dose or a series of doses over successive days.

An "HCV-inhibiting agent" means a compound of the present invention or a pharmaceutically acceptable salt, hydrate, prodrug, active metabolite or solvate thereof.

The term "HCV-inhibiting amount," as used herein, refers to an amount of a compound of the present invention that is sufficient to inhibit the replication of the Hepatitis C virus when administered to a mammal, such as a human.

The term "HCV polymerase-inhibiting amount," as used herein, means an amount of a compound of the present invention that is sufficient to inhibit the function of the Hepatitis C virus polymerase enzyme when the compound is placed in contact with the enzyme.

A "prodrug" is a compound that may be converted under physiological conditions or by solvolysis to the specified compound or to a pharmaceutically acceptable salt of such compound. A prodrug may be a derivative of one of the compounds of the present invention that contains a moiety, such as for example —$CO_2R$, —$PO(OR)_2$ or —C=NR, that may be cleaved under physiological conditions or by solvolysis. Any suitable R substituent may be used that provides a pharmaceutically acceptable solvolysis or cleavage product. A prodrug containing such a moiety may be prepared according to conventional procedures by treatment of a hydroxamate derivative of this invention containing, for example, an amido, carboxylic acid, or hydroxyl moiety with a suitable reagent. An "active metabolite" is a pharmacologically active product produced through metabolism in the body of a specified hydroxamate derivative or salt thereof. Prodrugs and active metabolites of the hydroxamate derivative may be identified using routine techniques known in the art. See, e.g., Bertolini et al., *J. Med. Chem.*, 40:2011–2016 (1997); Shan et al., *J. Pharm. Sci.*, 86 (7): 765–767 (1997); Bagshawe, *Drug Dev. Res.*, 34:220–230 (1995); Bodor, *Advances in Drug Res.*, 13:224–331 (1984); Bundgaard, "Design of Prodrugs" (Elsevier Press, 1985); Larsen, *Design and Application of Prodrugs*, Drug Design and Development (Krogsgaard-Larsen et al. eds., Harwood Academic Publishers, 1991); Dear et al., *Chromatogr. B*, 748:281–293 (2000); Spraul et al., *J. Pharmaceutical & Biomedical Analysis*, 10 (8):601–605 (1992); and Prox et al., *Xenobiol*, 3(2):103–112 (1992).

A "solvate" is intended to mean a pharmaceutically acceptable solvate form of a specified compound that retains the biological effectiveness of such compound. Examples of solvates include compounds of the invention in combination with solvents such as, but not limited to, water, isopropanol, ethanol, methanol, DMSO, ethyl acetate, acetic acid, or ethanolamine. A "pharmaceutically acceptable salt" is intended to mean a salt that retains the biological effectiveness of the free acids and bases of the specified derivative and that is not biologically or otherwise undesirable. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methane-sulfonates, propane-sulfonates, naphthalene-1-sulfonates, naphthalene-2-sulfonates, and mandelates.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

The phrase "pharmaceutically acceptable salt(s)", as used herein, unless otherwise indicated, includes salts of acidic or basic groups, which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds of the present invention are those that form non-toxic acid addition salts, i.e., salts containing pharmacologically acceptable anions, such as the acetate, benzenesulfonate, benzoate, bicarbonate, bisulfate, bitartrate, borate, bromide, calcium edetate, camsylate, carbonate, chloride, clavulanate, citrate, dihydrochloride, edetate, edislyate, estolate, esylate, ethylsuccinate, fumarate, gluceptate, gluconate, glutamate, glycollylarsanilate, hexylresorcinate, hydrabamine, hydrobromide, hydrochloride, iodide, isothionate, lactate, lactobionate, laurate, malate, maleate, mandelate, mesylate, methylsulfate, mucate, napsylate, nitrate, oleate, oxalate, pamoate (embonate), palmitate, pantothenate, phospate/diphosphate, polygalacturonate, salicylate, stearate, subacetate, succinate, tannate, tartrate, teoclate, tosylate, triethiodode, and valerate salts.

The phrases "therapeutically effective amount," "effective amount," and "HCV-inhibiting amount," are intended to mean the amount of an inventive agent that, when administered to a mammal in need of treatment, is sufficient to effect treatment for injury or disease conditions alleviated by the inhibition of HCV RNA replication such as for potentiation of anti-cancer therapies or inhibition of neurotoxicity consequent to stroke, head trauma, and neurodegenerative diseases. The amount of a given HCV-inhibiting agent used in the method of the invention that will be therapeutically effective will vary depending upon factors such as the particular HCV-inhibiting agent, the disease condition and the severity thereof, the identity and characteristics of the mammal in need thereof, which amount may be routinely determined by artisans.

DETAILED DESCRIPTION OF THE INVENTION

The compounds of the present invention may have asymmetric carbon atoms. The carbon-carbon bonds of the compounds of the present invention may be depicted herein using a solid line (———), a solid wedge (———▶), or a dotted wedge (·······ɪɪɪ).

The use of a solid line to depict bonds to asymmetric carbon atoms is meant to indicate that all possible stereoisomers at that carbon atom are included. The use of either a solid or dotted wedge to depict bonds to asymmetric carbon atoms is meant to indicate that only the stereoisomer shown is meant to be included. It is possible that compounds of the invention may contain more than one asymmetric carbon atom. In those compounds, the use of a solid line to depict bonds to asymmetric carbon atoms is meant to indicate that all possible stereoisomers are meant to be included. The use of a solid line to depict bonds to one or more asymmetric carbon atoms in a compound of the invention and the use of a solid or dotted wedge to depict bonds to other asymmetric carbon atoms in the same compound is meant to indicate that a mixture of diastereomers is present.

Solutions of individual stereoisomeric compounds of the present invention may rotate plane-polarized light. The use of either a "(+)" or "(−)" symbol in the name of a compound of the invention indicates that a solution of a particular stereoisomer rotates plane-polarized light in the (+) or (−) direction, as measured using techniques known to those of ordinary skill in the art.

Diastereomeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomeric mixtures and pure enantiomers are considered as part of the invention.

Alternatively, individual stereoisomeric compounds of the present invention may be prepared in enantiomerically enriched form by asymmetric synthesis. Asymmetric synthesis may be performed using techniques known to those of skill in the art, such as the use of asymmetric starting materials that are commercially available or readily prepared using methods known to those of ordinary skill in the art, the use of asymmetric auxiliaries that may be removed at the completion of the synthesis, or the resolution of intermediate compounds using enzymatic methods. The choice of such a method will depend on factors that include, but are not limited to, the availability of starting materials, the relative efficiency of a method, and whether such methods are useful for the compounds of the invention containing particular functional groups. Such choices are within the knowledge of one of ordinary skill in the art.

When the compounds of the present invention contain asymmetric carbon atoms, the derivative salts, prodrugs and solvates may exist as single stereoisomers, racemates, and/or mixtures of enantiomers and/or diastereomers. All such single stereoisomers, racemates, and mixtures thereof are intended to be within the scope of the present invention.

As generally understood by those skilled in the art, an optically pure compound is one that is enantiomerically pure. As used herein, the term "optically pure" is intended to mean a compound comprising at least a sufficient activity. Preferably, an optically pure amount of a single enantiomer to yield a compound having the desired pharmacological pure compound of the invention comprises at least 90% of a single isomer (80% enantiomeric excess), more preferably at least 95% (90% e.e.), even more preferably at least 97.5% (95% e.e.), and most preferably at least 99% (98% e.e.).

If a derivative used in the method of the invention is a base, a desired salt may be prepared by any suitable method known to the art, including treatment of the free base with an inorganic acid, such as hydrochloric acid; hydrobromic acid; sulfuric acid; nitric acid; phosphoric acid; and the like, or with an organic acid, such as acetic acid; maleic acid; succinic acid; mandelic acid; fumaric acid; malonic acid; pyruvic acid; oxalic acid; glycolic acid; salicylic acid; pyranosidyl acid, such as glucuronic acid or galacturonic acid; alpha-hydroxy acid, such as citric acid or tartaric acid; amino acid, such as aspartic acid or glutamic acid; aromatic acid, such as benzoic acid or cinnamic acid; sulfonic acid, such as p-toluenesulfonic acid or ethanesulfonic acid; and the like.

If a derivative used in the method of the invention is an acid, a desired salt may be prepared by any suitable method known to the art, including treatment of the free acid with an inorganic or organic base, such as an amine (primary, secondary, or tertiary); an alkali metal or alkaline earth metal hydroxide; or the like. Illustrative Examples of suitable salts include organic salts derived from amino acids such as glycine and arginine; ammonia; primary, secondary, and tertiary amines; and cyclic amines, such as piperidine, morpholine, and piperazine; as well as inorganic salts derived from sodium, calcium, potassium, magnesium, manganese, iron, copper, zinc, aluminum, and lithium.

In the case of derivatives, prodrugs, salts, or solvates that are solids, it is understood by those skilled in the art that the derivatives, prodrugs, salts, and solvates used in the method of the invention, may exist in different polymorph or crystal forms, all of which are intended to be within the scope of the present invention and specified formulas. In addition, the derivative, salts, prodrugs and solvates used in the method of the invention may exist as tautomers, all of which are intended to be within the broad scope of the present invention.

The compounds of the present invention that are basic in nature are capable of forming a wide variety of different salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of the present invention that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The activity of the compounds as inhibitors of HCV activity may be measured by any of the suitable methods available in the art, including in vivo and in vitro assays. An Example of a suitable assay for activity measurements is the HCV replicon assay described herein.

Administration of the compounds and their pharmaceutically acceptable prodrugs, salts, active metabolites, and solvates may be performed according to any of the accepted modes of administration available to those skilled in the art. Illustrative Examples of suitable modes of administration include oral, nasal, parenteral, topical, transdermal, and rectal. Oral and intravenous deliveries are preferred.

An HCV-inhibiting agent of the present invention may be administered as a pharmaceutical composition in any suitable pharmaceutical form. Suitable pharmaceutical forms include solid, semisolid, liquid, or lyopholized formulations, such as tablets, powders, capsules, suppositories, suspensions, liposomes, and aerosols. The HCV-inhibiting agent may be prepared as a solution using any of a variety of methodologies. For Example, the HCV-inhibiting agent can be dissolved with acid (e.g., 1 M HCl) and diluted with a sufficient volume of a solution of 5% dextrose in water (D5W) to yield the desired final concentration of HCV-inhibiting agent (e.g., about 15 mM). Alternatively, a solution of D5W containing about 15 mM HCl can be used to provide a solution of the HCV-inhibiting agent at the appropriate concentration. Further, the HCV-inhibiting agent can be prepared as a suspension using, for example, a 1% solution of carboxymethylcellulose (CMC).

Acceptable methods of preparing suitable pharmaceutical forms of the pharmaceutical compositions are known or may be routinely determined by those skilled in the art. For Example, pharmaceutical preparations may be prepared following conventional techniques of the pharmaceutical chemist involving steps such as mixing, granulating, and compressing when necessary for tablet forms, or mixing, filling, and dissolving the ingredients as appropriate, to give the desired products for oral, parenteral, topical, intravaginal, intranasal, intrabronchial, intraocular, intraaural, and/or rectal administration.

Pharmaceutical compositions of the invention may also include suitable excipients, diluents, vehicles, and carriers, as well as other pharmaceutically active agents, depending upon the intended use. Solid or liquid pharmaceutically acceptable carriers, diluents, vehicles, or excipients may be employed in the pharmaceutical compositions. Illustrative solid carriers include starch, lactose, calcium sulfate dihydrate, terra alba, sucrose, talc, gelatin, pectin, acacia, magnesium stearate, and stearic acid. Illustrative liquid carriers include syrup, peanut oil, olive oil, saline solution, and water. The carrier or diluent may include a suitable prolonged-release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g., solution), or a nonaqueous or aqueous liquid suspension.

A dose of the pharmaceutical composition may contain at least a therapeutically effective amount of an HCV-inhibiting agent and preferably is made up of one or more pharmaceutical dosage units. The selected dose may be administered to a mammal, for example, a human, in need of treatment mediated by inhibition of HCV activity, by any known or suitable method of administering the dose, including topically, for example, as an ointment or cream; orally; rectally, for example, as a suppository; parenterally by injection; intravenously; or continuously by intravaginal, intranasal, intrabronchial, intraaural, or intraocular infusion. When the composition is administered in conjunction with a cytotoxic drug, the composition can be administered before, with, and/or after introduction of the cytotoxic drug. However, when the composition is administered in conjunction with radiotherapy, the composition is preferably introduced before radiotherapy is commenced.

Methods of preparing various pharmaceutical compositions with a specific amount of active compound are known, or will be apparent, to those skilled in this art. For examples, see *Remington's Pharmaceutical Sciences*, Mack Publishing Company, Easter, Pa., 15$^{th}$ Edition (1975).

It will be appreciated that the actual dosages of the HCV-inhibiting agents used in the pharmaceutical compositions of this invention will be selected according to the properties of the particular agent being used, the particular composition formulated, the mode of administration and the particular site, and the host and condition being treated. Optimal dosages for a given set of conditions can be ascertained by those skilled in the art using conventional dosage-determination tests. For oral administration, e.g., a dose that may be employed is from about 0.001 to about 1000 mg/kg body weight, preferably from about 0.1 to about 100 mg/kg body weight, and even more preferably from about 1 to about 50 mg/kg body weight, with courses of treatment repeated at appropriate intervals.

The subject invention also includes isotopically-labelled compounds, which are identical to those recited in the compounds of the present invention, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures disclosed in the Schemes and/or in the Examples and Preparations below, by substituting a readily available isotopically labelled reagent for a non-isotopically labelled reagent.

EXAMPLES

Specific Examples of various compounds according to the invention may be advantageously prepared as set out in the Examples above. These examples and the compounds contained therein are not meant to limit the scope of the present invention in any way.

The structures of the compounds of the following Examples were confirmed by one or more of the following: proton magnetic resonance spectroscopy, infrared spectroscopy, elemental microanalysis, mass spectrometry, thin layer chromatography, melting point, boiling point, and HPLC.

Proton magnetic resonance ($^1$H NMR) spectra were determined using a 300 megahertz Tech-Mag, Bruker Avance 300DPX, or Bruker Avance 500 DRX spectrometer operating at a field strength of 300 or 500 megahertz (MHz). Chemical shifts are reported in parts per million (ppm, δ) downfield from an internal tetramethylsilane standard. Alternatively, $^1$H NMR spectra were referenced to residual protic solvent signals as follows: $CHCl_3$=7.26 ppm; DMSO=2.49 ppm; $C_6HD_5$=7.15 ppm. Peak multiplicities are designated as follows: s=singlet; d=doublet; dd=doublet of doublets; t=triplet; q=quartet; br=broad resonance; and m=multiplet. Coupling constants are given in Hertz. Infrared absorption (IR) spectra were obtained using a Perkin-Elmer 1600 series FTIR spectrometer. Elemental microanalyses were performed by Atlantic Microlab Inc. (Norcross, Ga.) and gave results for the elements stated within ±0.4% of the theoretical values. Flash column chromatography was performed using Silica gel 60 (Merck Art 9385). Analytical thin layer chromatography (TLC) was performed using precoated sheets of Silica 60 $F_{254}$ (Merck Art 5719). HPLC chromatographs were run on a Hewlett Packard Model 1100 system fitted with a Zorbax SB-C18 4.6 mm×150 mm column having 3.5 micron packing material. Unless otherwise stated, a ramp of 5% $CH_3CN/H_2O$ to 95% $CH_3CN/H_2O$ over 7.5 minutes then holding at 95% $CH_3CN/H_2O$ for 2.5 minutes (both solvents contained 0.1% v/v TFA) at a flow of 1 mL/min was used. Retention times (Rt) are given in minutes. Semi-preparative HPLC samples were run on a Gilson LC3D system fitted with a 21.2 mm×250 mm C8 column. Ramps were optimized for each compound with a $CH_3CN/H_2O$ solvent system. Melting points were determined on a Mel-Temp apparatus and are uncorrected. All reactions were performed in septum-sealed flasks under a slight positive pressure of argon, unless otherwise noted. All commercial reagents were used as received from their respective suppliers with the following exceptions: tetrahydrofuran (THF) was distilled from sodium-benzophenone ketyl prior to use; dichloromethane ($CH_2Cl_2$) was distilled from calcium hydride prior to use; anhydrous lithium chloride was prepared by heating at 110° C. under vacuum overnight. Mass spectra, both low and high resolution, were measured using either electrospray (EI) or fast atom bombardment (FAB) ionization techniques.

The following abbreviations are used herein: $Et_2O$ (diethyl ether); DMF (N,N-dimethylformamide); DMSO (dimethylsulfoxide); MeOH (methanol); EtOH (ethanol); EtOAc (ethyl acetate); Ac (acetyl); Hex (hexane); Me (methyl); Et (ethyl); Ph (phenyl); DIEA (diisopropylethylamine); TFA (trifluoroacetic acid); DTT (dithiothreitol); and THF (tetrahydrofuran); and (precipitate); min. or min (minutes); h (hours).

Solid-phase syntheses were performed by immobilizing reagents with Rink amide linkers (Rink, *Tetrahedron Letters* (1987) 28:3787), which are standard acid-cleavable linkers that upon cleavage generate a free carboxamide group. Small-scale solid-phase syntheses, e.g., about 2–5 μmole, were performed using Chiron SynPhase® polystyrene O-series crowns (pins) derivatized with Fmoc-protected Rink amide linkers. For larger scale (e.g., greater than about 100 μmole) syntheses, the Rink amide linkages were formed to Argonaut Technologies Argogel® resin, a grafted polystyrene-poly(ethylene glycol) copolymer. Any suitable resin may be used as the solid phase, selected from resins that are physically resilient and that, other than with regard to the linking and cleavage reactions, are inert to the synthetic reaction conditions.

Example A(1)

6-Cyclopentyl-6-[2-(1-ethyl-6-oxo-1,6-dihydro-pyridin-3-yl)-ethyl]-dihydro-pyran-2,4-dione

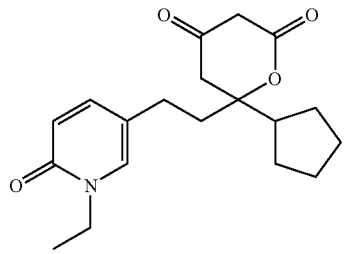

The title compound was prepared analogously to Example A(82), where 5-Bromo-1-ethyl-1H-pyridin-2-one was substituted in place of 2-Bromopyridine in Step 1 of that example.

$^1$H NMR (CDCl$_3$): δ 1.35 (t, J=7.2 Hz, 3H), 1.52–1.81 (brm, 8H), 1.87 (m, 2H), 2.28 (m, 1H), 2.45 (t, J=8.5 Hz, 2H), 2.72 (d, J=16 Hz, 1H), 2.80 (d, J=16 Hz, 1H), 3.43 (s, 2H), 3.96 (q, J=7.2 Hz, 2H), 6.54 (d, J=9.2 Hz, 1H), 7.06 (s, 1H), 7.14 (d, J=9.2 Hz, 1H). Anal. Calcd. For $C_{19}H_{25}N_1O_4$: C, 68.86; H, 7.60; N, 4.23. Found: C, 68.74; H, 7.42; N, 4.34.

Example A(2)

6-[2-(3-tert-Butyl-4-hydroxy-phenyl)-ethyl]-6-cyclopentyl-dihydro-pyran-2,4-dione

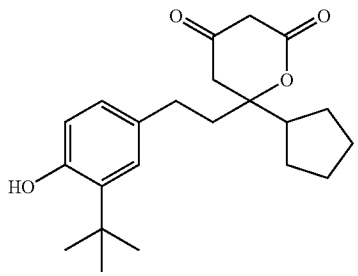

The title compound was prepared analogously to Example A(22), where 4-Bromo-2-tert-butyl-phenol from Step 1, was used in place of 4-Bromo-2-ethyl-phenol in Step 2 of that example.

$^1$H NMR (CDCl$_3$): δ 1.39 (s, 9H,), 1.43–1.85 (br m, 8H), 1.87–2.01 (m, 2H), 2.27 (m, 1H), 2.60 (t, J=8.4 Hz, 2H), 2.77 (s, 2H), 3.42 (s, 2H), 4.74 (s, 1H), 6.60 (d, J=8.1 Hz 1H)), 6.84 (d, J=8.1 Hz, 1H), 7.00 (s, 1H).

Step 1

4-Bromo-2-tert-butyl-phenol

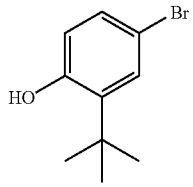

2-tert-Butyl-phenol (5 g, 0.033 mol) was dissolved in CHCl$_3$ (100 mL) and magnetically stirred at room temperature. To this solution was added a solution of Tetrabutyl ammonium tribromide (16.05 g, 0.033 mol) in CHCl$_3$ (100 mL). The resulting yellow solution was allowed to stir at room temperature for 1 hour. The reaction was quenched with a 5% solution of sodium thiosulfate (200 mL). The biphasic mixture was stirred for 15 min. The organics were separated and concentrated. The residue was dissolved in EtOAc (100 mL) and washed with water (2×100 mL) and brine (1×100 mL). The organics were dried over Na2SO4, filtered and concentrated. The residue was purified by flash chromatography (silica gel) eluting with 3% EtOAc in Hexanes. The result was a clear oil (6.8 g, 89%).

$^1$H NMR (CDCl$_3$): δ 1.39 (s, 9H), 4.95 (s, 1H), 6.59 (d, J=8.5 Hz 1H), 7.19 (d, J=8.5 Hz, 1H), 7.24 (s, 1H).

Example A(3)

6-Cyclopentyl-6-[2-(4-eth xy-3-methyl-phenyl)-ethyl]-dihydro-pyran-2,4-dione

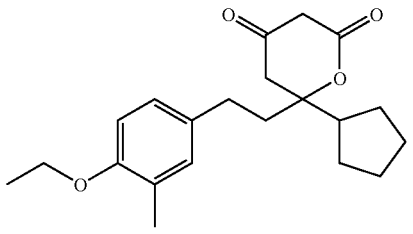

The title compound was prepared analogously to Example A(82), where 4-Bromo-1-ethoxy-2-methyl-benzene was substituted in place of 2-Bromopyridine in Step 1 of that example.

$^1$H NMR (CDCl$_3$): δ 1.40 (t, J=7 Hz, 3H), 1.52–1.81 (brm, 8H), 1.99 (m, 2H), 2.19 (s, 3H), 2.30 (m, 1H), 2.58 (t, J=8.6 Hz, 2H), 2.76 (s, 2H), 3.41 (s, 2H), 4.00 (q, J=7 Hz, 2H), 6.71 (d, J=8.8 Hz, 1H), 6.89 (m, 2H). Anal. Calcd. For C$_{21}$H$_{28}$O$_4$: C, 73.23; H, 8.19. Found: C, 73.12; H, 8.22.

Example A(4)

6-Cyclopentyl-6-[2-(4-isopropoxy-3-methyl-phenyl)-ethyl]-dihydro-pyran-2,4-dione

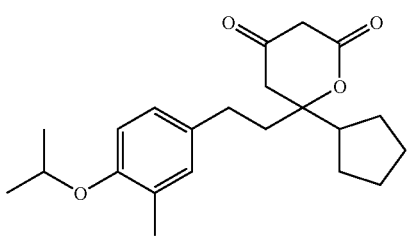

The title compound was prepared analogously to Example A(82), where 4-Bromo-1-isopropoxy-2-methyl-benzene was substituted in place of 2-Bromopyridine in Step 1 of that example.

$^1$H NMR (CDCl$_3$): δ 1.30 (d, J=6.2 Hz, 6H), 1.52–1.81 (brm, 8H), 1.99 (m, 2H), 2.15 (s, 3H), 2.37 (m, 1H), 2.58 (t, J=8.6 Hz, 2H), 2.74 (s, 2H), 3.42 (s, 2H), 4.43 (m, 1H), 6.71 (d, J=8.2 Hz, 1H), 6.88 (m, 2H). Anal. Calcd. For C$_{22}$H$_{30}$O$_4$: C, 73.71; H, 8.44. Found: C, 73.64; H, 8.22.

Example A(5)

6-{2-[3-Chloro-4-(2,2,2-trifluoro-ethoxy)-phenyl]-ethyl}-6-cyclopentyl-dihydro-pyran-2,4-dione

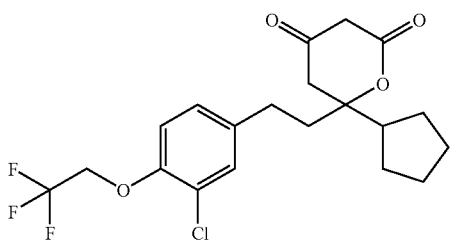

The title compound was prepared analogously to Example A(82), where was 4-Bromo-2-chloro-1-(2,2,2-trifluoro-ethoxy)-benzene substituted in place of 2-Bromopyridine in Step 1 of that example.

$^1$H NMR (CDCl$_3$): δ 1.44–1.77 (brm, 8H), 1.92 (m, 2H), 2.27 (m, 1H), 2.63 (m, 2H), 2.74 (d, J=15.8 Hz, 1H), 2.79 (d, J=15.8 Hz, 1H), 3.43 (s, 2H), 4.35 (d, J=8.1 Hz, 1H), 4.40 (d, J=8.1 Hz, 1H), 6.90 (d, J=8.5 Hz, 1H), 7.02 (d, J=8.5 Hz, 1H), 7.19 (s, 1H). Anal. Calcd. For C$_{20}$H$_{22}$ClF$_3$O$_4$: C, 57.35; H, 5.29. Found: C, 57.55; H, 5.12.

Example A(6)

6-Cyclopentyl-6-(4-methoxy-phenylsulfanylmethyl)-dihydro-pyran-2,4-dione

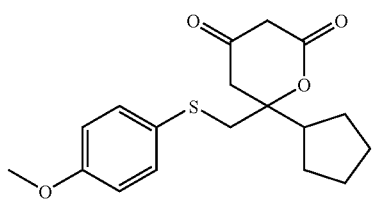

1-Cyclopentyl-2-(4-methoxy-phenylsulfanyl)-ethanone (from Step 2 below) was subjected to the methyl acetoacetate dianion addition reaction described in the synthesis of Example A(82), to yield the title compound as a white solid.

$^1$H NMR (CDCl$_3$): δ 1.35–1.86 (brm, 8H), 2.35 (m, 1H), 2.61–3.62 (m, 6H), 3.85 (s, 3H), 6.82 (d, J=8.2 Hz, 2H), 7.44 (d, J=8.2 Hz, 2H).

Step 1

2-Chloro-1-cyclopentyl-ethanone

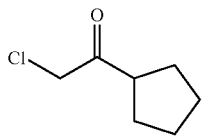

Cyclopentanecarbonyl chloride (5.0 g, 0.038 mol) was dissolved in THF (100 mL) and cooled to 0° C. The solution was treated with a 2M solution of TMS-Diazomethane in hexanes (56.56 mL, 0.113 mol) over 10 min. The resulting yellow solution was allowed to stand at room temperature for 12 hours. The solution was then concentrated and the residue was dissolved in THF (100 mL) and treated slowly with a 4N HCl in Dioxane solution (28.28 mL, 0.113 mol). The result was allowed to stir at 24° C. for 2 hours. The solution was concentrated to an oil which was chromatographed on silica gel eluting with 5% EtOAc in Hexanes to give the intermediate depicted below (4.9 g, 88%).

$^1$H NMR (CDCl$_3$): δ 1.62–1.98 (m, 8H), 3.12–3.25 (m, 1H), 4.21 (s, 2H).

Step 2

1-Cyclopentyl-2-(4-methoxy-phenylsulfanyl)-ethanone

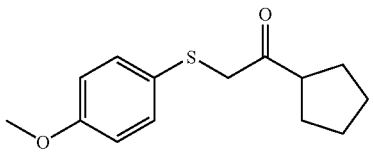

The intermediate 2-Chloro-1-cyclopentyl-ethanone from Step 1 (1 g, 6.81 mmol), was combined with 4-methoxybenzenethiol (1.05 g, 7.50 mmol), in THF (20 mL) and treated with Triethylamine (1.05 mL, 7.50 mmol). The mixture was stirred for 1 hour at room temperature then poured into water (50 mL) and extracted with EtOAc (2×50 mL). The organics were then washed with 0.5N HCl (2×50 mL), 2N NaOH (2×50 mL), water (2×50 mL) and brine (1×50 mL) the organics were dried over Na$_2$SO$_4$, filtered and concentrated. The residue was used without further purification (1.65 g, 97%).

Example A(7)

N-{4-[2-(2-Cyclopentyl-4,6-dioxo-tetrahydro-pyran-2-yl)-ethyl]-2-fluoro-phenyl}-acetamide

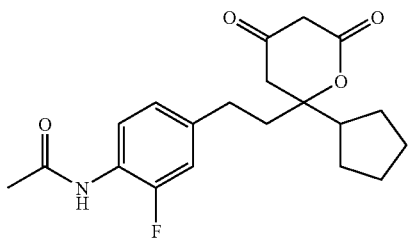

The title compound was prepared analogously to Example A(64), where N-(4-Bromo-2-fluoro-phenyl)-acetamide was substituted in place of 4-bromo-2-fluoro-1-isopropylbenzene of that example.

$^1$H NMR (CDCl$_3$): δ 1.55–1.77 (br m, 8H), 1.94 (m, 2H), 2.21 (s, 3H), 2.26 (m, 1H), 2.65 (m, 2H), 2.76 (s, 2H), 3.43 (s, 2H), 6.90 (m, 2H), 8.19 (t, 1H, J=8.3 Hz). ESIMS: (M+H)$^+$384.05.

Example A(8)

6-Cyclopentyl-6-[2-(3-fluoro-4-methoxymethyl-phenyl)-ethyl]-dihydro-pyran-2,4-dione

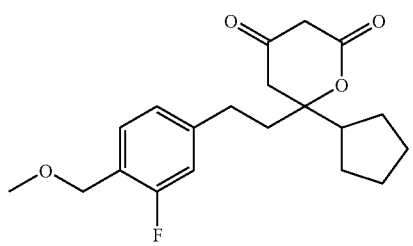

The title compound was prepared analogously to Example A(64), where 4-Bromo-2-fluoro-1-methoxymethyl-benzene was substituted in place of 4-bromo-2-fluoro-1-isopropyl-benzene of that example.

$^1$H NMR (CDCl$_3$): δ 1.55–1.80 (br m, 8H), 1.95 (m, 2H), 2.27 (m, 1H), 2.68 (m, 2H), 2.76 (s, 2H), 3.40 (s, 3H), 3.43 (s, 2H), 4.48 (s, 2H), 6.85 (d, 1H, J=9.6 Hz), 6.93 (d, 1H, J=6.2 Hz), 7.32 (t, 1H, J=7.7 Hz). Anal. Calcd. For C$_{20}$H$_{25}$O$_4$F: C, 68.77; H, 7.11. Found: C, 68.90; H, 7.23.

Example A(9)

6-Cyclopentyl-6-[2-(2-fluoro-biphenyl-4-yl)-ethyl]-dihydro-pyran-2,4-dione

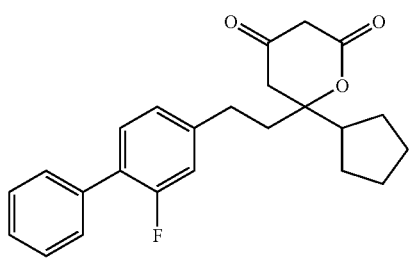

The title compound was prepared analogously to Example A(64), where 4-Bromo-2-fluoro-biphenyl was substituted in place of 4-bromo-2-fluoro-1-isopropylbenzene of that example.

$^1$H NMR (CDCl$_3$): δ 1.55–1.83 (br m, 8H), 2.0 (m, 2H), 2.30 (m, 1H), 2.72 (m, 2H), 2.79 (s, 2H), 3.45 (s, 2H), 6.96 (d, 1H, J=11.7 Hz), 7.0 (d, 1H, J=7.9 Hz), 7.36 (m, 2H), 7.44 (m, 2H), 7.52 (m, 2H). Anal. Calcd. For C$_{24}$H$_{25}$O$_3$F: C, 75.76; H, 6.62. Found: C, 75.56; H, 6.66.

Example A(10)

6-[2-(4-Benzo[b]thiophen-2-yl-3-fluoro-phenyl)-ethyl]-6-cyclopentyl-dihydro-pyran-2,4-dione

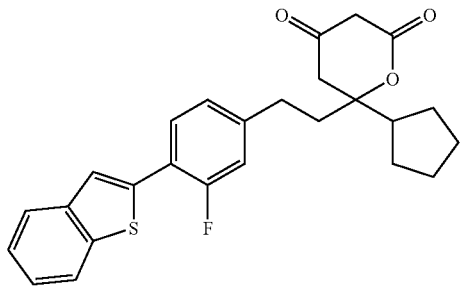

The title compound was prepared analogously to Example A(64), where 2-(4-Bromo-2-fluoro-phenyl)-benzo[b]thiophene (described below) was substituted in place of 4-bromo-2-fluoro-1-isopropylbenzene of that example.

$^1$H NMR (CDCl$_3$): δ 1.55–1.83 (br m, 8H), 2.0 (m, 2H), 2.29 (m, 1H), 2.73 (m, 2H), 2.79 (s, 2H), 3.45 (s, 2H), 6.98 (d, 1H, J=6.0 Hz), 7.0 (s, 1H), 7.34 (m, 2H), 7.62 (t, 1H, J=10.5 Hz), 7.70 (s, 1H), 7.82 (m, 2H). ESIMS: MH⁻435.05.

Step 1

2-(4-Bromo-2-fluoro-phenyl)-benzo[b]thiophene

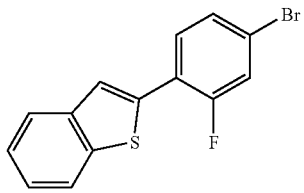

A mixture of Benzo[b]thiophene-2-boronic acid (0.71 g, 4 mmol), 1-bromo-3-fluoro-4-iodobenzene (1 g, 3.3 mmol), bis(triphenylphospine)palladium(II) chloride (46 mg, 2 mol %), NaHCO$_3$ (0.83 g, 9.9 mmol) in DME (4 mL) and H$_2$O (4 mL) was heated to 80° C. under N$_2$ for 72 h. The reaction mixture was partitioned between 1N HCl and EtOAc. The organic layer was washed with saturated NaHCO$_3$, brine, dried over Na$_2$SO$_4$ and concentrated. The residue was purified by silica gel chromatography (hexanes) to give the title compound as a white solid (0.13 g, 13%).

$^1$H NMR (CDCl$_3$): δ 7.33–7.41 (m, 4H), 7.57 (m, 1H), 7.72 (s, 1H), 1.80–7.86 (m, 2H).

Example A(11)

4-[2-(2-Cyclopentyl-4,6-dioxo-tetrahydro-pyran-2-yl)-ethyl]-2-fluoro-N-methyl-benzamide

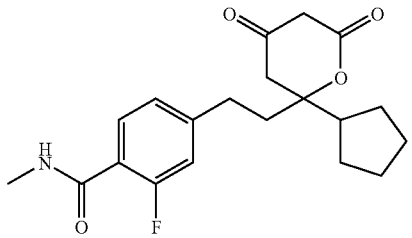

The title compound was prepared analogously to Example A(64), where 4-Bromo-2-fluoro-N-methyl-benzamide (described below), was substituted in place of 4-bromo-2-fluoro-1-isopropylbenzene of that example.

$^1$H NMR (CDCl$_3$): δ 1.46–1.80 (br m, 8H), 1.96 (m, 2H), 2.27 (m, 1H), 2.73 (m, 2H), 2.77 (d, 2H, J=5.3 Hz), 3.03 (d, 3H, J=4.5 Hz), 3.44 (s, 2H), 6.71 (br s, 1H), 6.91 (d, 1H, J=12.8 Hz), 7.05 (d, 1H, J=9.2 Hz), 8.10 (t, 1H, J=8.0 Hz). Anal. Calcd. For C$_{20}$H$_{24}$NO$_4$F.0.3H$_2$O: C, 65.48; H, 6.76; N, 3.82. Found: C, 65.29; H, 6.48; N, 3.56.

Step 1

4-Bromo-2-fluoro-N-methyl-benzamide

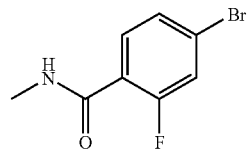

A solution of 4-bromo-2-fluorobenzoic acid (0.8 g, 3.7 mmol), methylamine (3.65 mL, 7.3 mmol), EDC (1.4 g, 7.3 mmol), triethylamine (1.0 mL, 7.3 mmol) dissolved in CH$_2$Cl$_2$(15 mL) was stirred under N$_2$ for 24 h. The reaction mixture was partitioned between 1N HCl and EtOAc. The organic layers were washed with saturated NaHCO$_3$, brine, dried over dried over Na$_2$SO$_4$ and concentrated. The residue was purified by silica gel chromatography (40% EtOAc in hexanes) to give the title compound as a white solid (0.27 g, 32%).

$^1$H NMR (CDCl$_3$): δ 3.03 (d, 3H, J=6.0 Hz), 6.68 (br s, 1H), 7.32 (d, 1H, J=11.3 Hz), 7.42 (d, 1H, J=10.2 Hz), 8.01 (t, 1H, J=8.5 Hz).

Example A(12)

6-cyclopentyl-6-{2-[3-fluoro-4-(5-methyl-thiophen-2-yl)-phenyl]-ethyl}-dihydro-pyran-2,4-dione

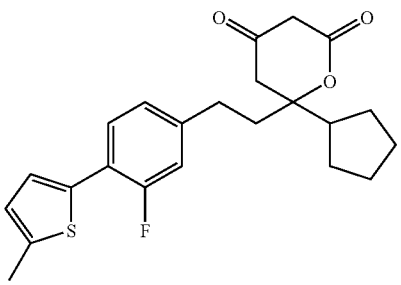

The title compound was prepared analogously to Example A(64), where 2-(4-Bromo-2-fluoro-phenyl)-5-methyl-thiophene (described below) was substituted in place of 4-bromo-2-fluoro-1-isopropylbenzene of that example.

$^1$H NMR (CDCl$_3$): δ 1.55–1.80 (br m, 8H), 1.97 (m, 2H), 2.28 (m, 1H), 2.51 (s, 3H), 2.68 (m, 2H), 2.78 (s, 2H), 3.44 (s, 2H), 6.75 (d, 1H, J=4.5 Hz), 6.90 (d, 1H, J=2.6 Hz), 6.93 (s, 1H), 7.22 (d, 1H, J=2.5 Hz), 7.48 (t, 1H, J=8.3 Hz). Anal. Calcd. For C$_{23}$H$_{25}$O$_3$SF: C, 68.97; H, 6.29. Found: C, 69.29; H, 6.24.

Step 1

2-(4-Bromo-2-fluoro-phenyl)-5-methyl-thiophene

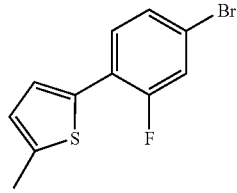

A mixture of 5-methyl-2-thiophene-boronic acid (1 g, 7.0 mmol), 1-bromo-3-fluoro-4-iodobenzene (1.77 g, 5.9 mmol), tetrakis(triphenylphosphine)palladium(0) (0.34 g, 0.3 mmol), 2M $Na_2CO_3$(10 mL) in DME (10 mL) was heated to 75° C. under $N_2$ for 15 h. The reaction mixture was partitioned between 1 N HCl and EtOAc. The organic layer was washed with saturated $NaHCO_3$, brine, dried over $Na_2SO_4$ and concentrated. The residue was purified by silica gel chromatography (hexanes) to give the title compound (1.2 g, 75%).

$^1$H NMR (CDCl$_3$): δ 2.52 (s, 3H), 6.76 (s, 1H), 7.25–7.32 (m, 3H), 7.43 (t, 1H, J=8.5 Hz).

Example A(13)

6-(2-Cyclohex-1-enyl-ethyl)-6-cyclopentyl-dihydro-pyran-2,4-dione

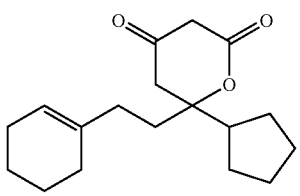

Methyl acetoacetate (0.66 g, 5.7 mmol) was added to a cooled 0° C. suspension of NaH (0.23 g, 5.7 mmol, 60% dispersion in mineral oil) in THF (10 ml). After 30 min n-BuLi (2.3 mL, 5.7 mmol, 2.5M in hexanes) was added. The resulting dianion was stirred for an additional 30 min and then treated with a solution 3-Cyclohex-1-enyl-1-cyclopentyl-propan-1-one (0.39 g, 1.9 mmol, Step 4 below) in THF (3 ml). After stirring for 4 h at 0° C., the reaction mixture was quenched with 1N HCl and extracted with EtOAc. The organic layers were washed with brine, dried over $Na_2SO_4$ and concentrated to an orange oil that was used without further purification. The oil was dissolved in methanol (8 mL), treated with potassium carbonate (0.79 g, 5.7 mmol), and refluxed under $N_2$ for 90 min. The reaction mixture was partitioned between 1N HCl and EtOAc. The organic layers were washed with brine, dried over $Na_2SO_4$ and concentrated to an orange oil that was purified by silica gel chromatography (0% to 20% EtOAc in hexanes). to give the title compound as a white solid. (0.22 g, 40% yield).

$^1$H NMR (CDCl$_3$): δ 1.42–1.98 (br m, 20H), 2.22 (m, 1H), 2.71 (s, 2H), 3.40 (s, 2H), 5.40 (s, 1H). Anal. Calcd. For $C_{18}H_{26}O_3$.0.2$H_2O$: C, 75.53; H, 9.05. Found: C, 73.74; H, 9.01.

Step 1

3-Cyclohex-1-enyl-propionic acid ethyl ester

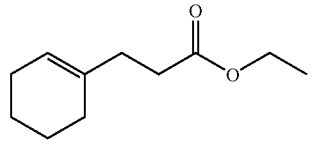

The title compound was prepared as described in the following reference: JOC, 1998, 63, 2755–57.

Step 2

3-Cyclohex-1-enyl-propionic acid

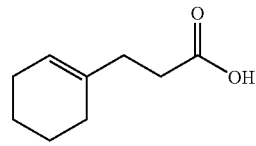

2N LiOH (3.5 mL) was added to a solution of 3-Cyclohex-1-enyl-propionic acid ethyl ester (0.6 g, 3.4 mmol, from Step 1) dissolved in THF (12 mL) and MeOH (3 mL). The mixture was stirred for 2 h under $N_2$ and then partitioned between 1N HCl and EtOAc. The organic layer was washed with brine, dried over $Na_2SO_4$ and concentrated to a clear oil.

$^1$H NMR (CDCl$_3$): δ 1.54 (m, 2H), 1.62 (m, 2H), 1.92 (m, 2H), 1.97 (m, 2H), 2.26 (m, 2H), 2.46 (t, 2H, J=8.3 Hz), 5.44 (s, 1H).

Step 3

3-Cyclohex-1-enyl-thiopropionic acid S-pyridin-2-yl ester

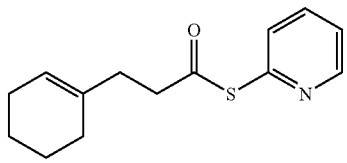

A solution of 3-Cyclohex-1-enyl-propionic acid (0.47 g, 3.04 mmol, from Step 2), triphenylphosphine (1.04 g, 3.95 mmol) and 2,2'-dipyridyl disulfide (0.87 g, 3.95 mmol) dissolved in $CH_2Cl_2$ (12 mL) was stirred under $N_2$ for 3 h. The reaction mixture was concentrated to a yellow oil and purified by silica gel chromatography (5% to 20% EtOAc in hexanes) to give the title compound as a yellow oil (0.7 g, 93%).

$^1$H NMR (CDCl$_3$): δ 1.55 (m, 2H), 1.63 (m, 2H), 1.94 (m, 2H), 1.99 (m, 2H), 2.35 (t, 2H, J=7.3 Hz), 2.81 (t, 2H, J=8.0 Hz), 5.47 (s, 1H), 7.28 (dd, 1H, J=7.8, 4.8 Hz), 7.61 (d, 1H, J=7.8 Hz), 7.74 (td, 1H, J=7.8 Hz), 8.61 (d, 1H, J=4.8 Hz).

Step 4

3-cyclohex-1-enyl-1-cyclopentyl-propan-1-one. {TB-4059-095}

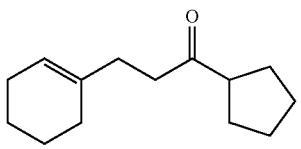

Cyclopentylmagnesium bromide (1.6 mL, 3.15 mmol, 2M soln in ether) was added to a cooled −78° C. solution of 3-Cyclohex-1-enyl-thiopropionic acid S-pyridin-2-yl ester (0.65 g, 2.63 mmol, from Step 3) dissolved in THF (10 mL). The reaction mixture was stirred for 45 min at −78° C. and then warmed up to rt. The reaction was quenched with 1 N HCl and extracted with EtOAc. The organic layer was washed with saturated $NaHCO_3$, brine, dried over $Na_2SO_4$ and concentrated. The residue was purified by silica gel chromatography (0% to 5% EtOAc in hexanes) to give the title compound as a clear oil (0.39 g, 72%).

$^1$H NMR ($CDCl_3$): δ 1.51–1.83 (br m, 12H), 1.91 (m, 2H), 1.97 (m, 2H), 2.20 (t, 2H, J=7.6 Hz), 2.54 (t, 2H, J=7.8 Hz), 2.87 (m, 1H), 5.39 (s, 1H).

Example A(14)

6-Cyclopentyl-6-[2-(2-oxo-pyrrolidin-1-yl)-ethyl]-dihydro-pyran-2,4-dione

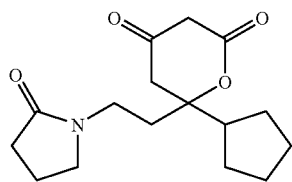

The title compound was prepared as described in Example A(13), where 1-(3-Cyclopentyl-3-oxo-propyl)-pyrrolidin-2-one (described in Step 2 below) was substituted in place of 3-Cyclohex-1-enyl-1-cyclopentyl-propan-1-one.

$^1$H NMR ($CDCl_3$): δ 1.41–1.84 (br m, 9H), 1.98–2.21 (m, 4H), 2.37 (m, 2H), 2.67 (d, 1H, J=15.8 Hz), 3.08 (d, 1H, J=15.8 Hz), 3.28–3.51 (m, 5H), 3.61 (m, 1H). Anal. Calcd. For $C_{16}H_{23}NO_4$: C, 63.55; H, 8.00; N, 4.63. Found: C, 63.41; H, 8.04; N, 4.52.

Step 1

3-(2-Oxo-pyrrolidin-1-yl)-propionic acid

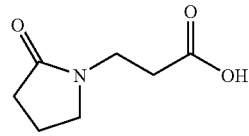

A solution of 2-oxo-1-pyrrolidinepropionitrile (22.4 g, 16.2 mmol), 15% NaOH solution (40 mL) and dioxane (40 mL) was heated under reflux for 5 h under $N_2$. The reaction mixture was extracted with EtOAc. The aqueous layer was made acidic with 6N HCl amd extracted with $CH_2Cl_2$ (5×50 mL). The organic layers were dried over $Na_2SO_4$ and concentrated to give the title compound as a cream solid (12.4 g, 49%).

$^1$H NMR ($CDCl_3$): δ 2.04 (m, 2H), 2.42 (t, 2H, J=7.9 Hz), 2.60 (t, 2H, J=6.8 Hz), 3.48 (t, 2H, J=7.2 Hz), 3.59 (t, 2H, J=6.8 Hz), 10.29 (br s, 1H).

Step 2

1-(3-Cyclopentyl-3-oxo-propyl)-pyrrolidin-2-one

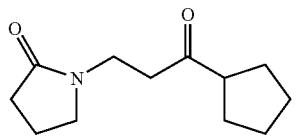

2-Chloro-4-6-dimethoxy-1,3,5-triazine (2.68 g, 15.2 mmol) and N-methylmorpholine (4.2 mL, 38.1 mmol) were added to a solution of 3-(2-Oxo-pyrrolidin-1-yl)-propionic acid (2 g, 12.7 mmol, from Step 1) in THF (35 mL). After 1 h the reaction mixture was filtered through a glass frit to remove a white precipitate. The filtrate was treated with copper iodide (2.4 g, 12.7 mmol), cooled to 0° C. and then cyclopentyl magnesium bromide (6.35 mL, 12.7 mmol, 2M in ether) was added. After 4 h the resulting black mixture was quenched with saturated $NH_4Cl$ and extracted with $CH_2Cl_2$. The organic layers were washed with 1 N HCl, saturated $NaHCO_3$, brine, dried over $Na_2SO_4$ and concentrated. The residue was purified by silica gel chromatography (75% EtOAc in hexanes then 5% MeOH in $CH_2Cl_2$) to give the title compound as a yellow oil. (0.4 g, 15% yield).

$^1$H NMR ($CDCl_3$): δ 1.55–1.83 (br m, 8H), 1.99 (m, 3H), 2.35 (t, 2H, J=8.3 Hz), 2.74 (t, 2H, J=6.8 Hz), 3.41 (d, 2H, J=7.2 Hz), 3.53 (t, 2H, J=6.6 Hz).

Example A(15)

6-Cyclopentyl-6-{2-[3-fluoro-4-(5-methyl-[1,2,4]oxadiazol-3-yl)-phenyl]-ethyl}-dihydro-pyran-2,4-dione

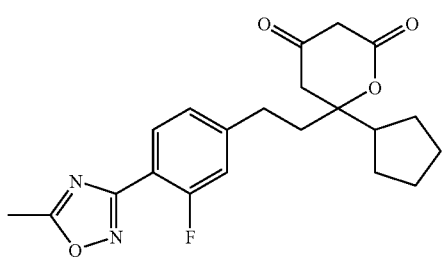

The title compound was prepared analogously to Example A(64), where 3-(4-Bromo-2-fluoro-phenyl)-5-methyl-[1,2,4]oxadiazole (described below), was substituted in place of 4-bromo-2-fluoro-1-isopropylbenzene of that example.

¹H NMR (CDCl₃): δ 1.55–1.82 (br m, 8H), 1.99 (m, 2H), 2.29 (m, 1H), 2.68 (s, 3H), 2.73–2.79 (m, 4H), 3.45 (s, 2H), 7.06 (m, 2H), 7.96 (t 1H, J=7.5 Hz). ESIMS: MH⁺387.20, MH⁻385.20.

Step 1

3-(4-Bromo-2-fluoro-phenyl)-5-methyl-[1,2,4]oxadiazole

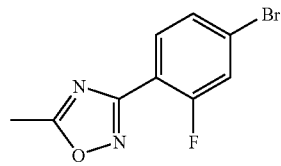

A mixture of 4-bromo-2-fluorobenzonitrile (3 g, 15 mmol), hydroxylamine hydrochloride (5.21 g, 75 mmol), potassium carbonate (10.4 g, 75 mmol) in EtOH (50 mL) was refluxed under N₂. After 24 hrs the reaction mixture was flitered through a glass frit washing with hot EtOH. The filtrate was concentrated to give a white solid.

The solid was suspended in pyridine (20 mL) and treated with acetic anhydride (4.24 mL, 45 mmol). The mixture was refluxed for 2 h and then stirred at rt for 15 h. The reaction mixture was partitioned between 2N HCl and EtOAc. The organic layer was washed with 1 N HCl, saturated NaHCO₃, brine, dried over Na₂SO₄ and concentrated. The residue was purifed by silica gel chromatography (5% hexanes in EtOAc), to give the title compound as a white solid, (1.1 g, 29% yield).

¹H NMR (CDCl₃): δ 2.68 (s, 3H), 7.43 (m, 2H), 7.92 (t, 1H, J=7.7 Hz).

Example A(16)

4-[2-(2-Cyclopentyl-4,6-dioxo-tetrahydro-pyran-2-yl)-ethyl]-2-fluoro-N,N-dimethyl-benzamide

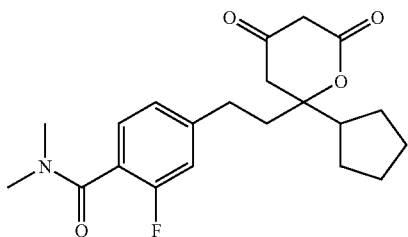

The title compound was prepared analogously to Example A(64), where 4-Bromo-2-fluoro-N,N-dimethyl-benzamide (described below), was substituted in place of 4-bromo-2-fluoro-1-isopropylbenzene.

¹H NMR (CDCl₃): δ 1.42–1.79 (br m, 8H), 1.95 (m, 2H), 2.28 (m, 1H), 2.71 (m, 2H), 2.79 (m, 2H), 2.94 (s, 3H), 3.12 (s, 3H), 3.44 (s, 2H), 6.88 (d, 1H, J=10.5 Hz), 6.99 (d, 1H, J=7.7 Hz), 7.32 (t, 1H, J=7.3 Hz). Anal. Calcd. For C₂₁H₂₆NO₄F.0.4H₂O: C, 65.91; H, 7.06; N, 3.66. Found: C, 65.84; H, 6.79; N, 3.59.

Step 1

4-Bromo-2-fluoro-N,N-dimethyl-benzamide

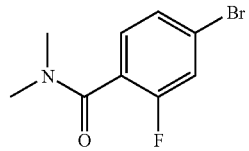

The title compound was prepared as described in Step 1 of Example A(11), where dimethylamine hydrochloride was substituted in place of methylamine.

¹H NMR (CDCl₃): δ 2.93 (s, 3H), 3.12 (s, 3H), 7.28 (m, 2H), 7.36 (d, 1H, J=6.4 Hz).

Example A(17)

4-[2-(2-Cyclopentyl-4,6-dioxo-tetrahydro-pyran-2-yl)-ethyl]-N-ethyl-2-fluoro-benzamide

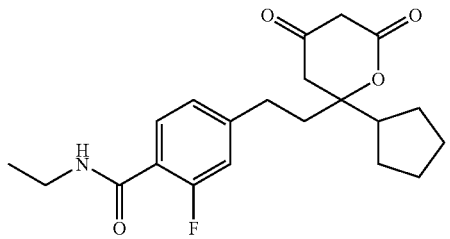

The title compound was prepared analogously to Example A(64), where 4-Bromo-N-ethyl-2-fluoro-benzamide (described below), was substituted in place of 4-bromo-2-fluoro-1-isopropylbenzene of that example.

¹H NMR (CDCl₃): δ 1.25 (t, 3H, J=7.1 Hz), 1.45–1.80 (br m, 8H), 1.96 (m, 2H), 2.27 (m, 1H), 2.70–2.82 (m, 4H), 3.44 (s, 2H), 3.51 (m, 2H), 6.70 (br s, 1H), 6.90 (d, 1H, J=14.1 Hz), 7.05 (d, 1H, J=9.6 Hz), 8.03 (t, 1H, J=8.1 Hz). Anal. Calcd. For C₂₁H₂₆NO₄F.0.5H₂O: C, 65.61; H, 7.08; N, 3.64. Found: C, 65.76; H, 6.89; N, 3.58.

Step 1

4-Bromo-N-ethyl-2-fluoro-benzamide

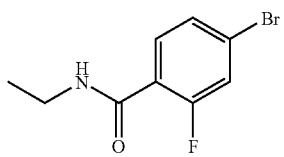

The title compound was prepared as described in Step 1 of Example A(11), where ethylamine hydrochloride was substituted in place of methylamine.

¹H NMR (CDCl₃): δ 1.26 (t, 3H, J=7.4 Hz), 3.65 (m, 2H), 6.63 (br s 1H), 7.32 (d, 1H, J=11.3 Hz), 7.42 (d, 1H, J=10.2 Hz), 8.48 (t, 1H, J=8.5 Hz).

Example A(18)

6-Cyclopentyl-6-{2-[4-(3,5-dimethyl-isoxazol-4-yl)-phenyl]-ethyl}-dihydro-pyran-2,4-dione

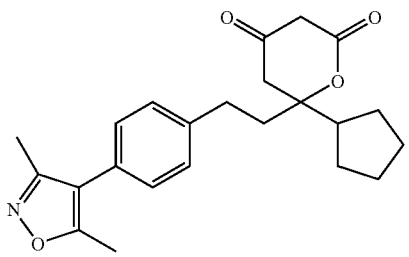

The title compound was prepared analogously to Example A(64), where 4-(4-Bromo-phenyl)-3,5-dimethyl-isoxazole (described below) was substituted in place of 4-bromo-2-fluoro-1-isopropylbenzene of that example.

$^1$H NMR (CDCl$_3$): δ 1.48–1.82 (br m, 8H), 2.02 (m, 2H), 2.26 (s, 3H), 2.32 (m, 1H), 2.40 (s, 3H), 2.73 (m, 2H), 2.80 (s, 2H), 3.44 (s, 2H), 7.18 (d, 2H, J=8.3 Hz), 7.05 (d, 2H, J=8.3 Hz) Anal. Calcd. For C$_{23}$H$_{27}$NO$_4$·0.2H$_2$O: C, 71.74; H, 7.17; N, 3.64. Found: C, 71.77; H, 7.14; N, 3.47.

Step 1

4-(4-Bromo-phenyl)-3,5-dimethyl-isoxazole

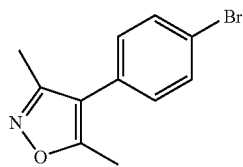

A mixture of 4-bromophenylboronic acid (1 g, 5 mmol), 3,5-dimethyl-4-iodoisoxazole (0.93 g, 4.2 mmol), bis(triphenylphospine)palladium(II) chloride (59 mg, 2 mol %), NaHCO$_3$ (1.06 g, 12.6 mmol) in DME (5 mL) and H$_2$O (5 mL) was heated to 80° C. under N$_2$ for 18 h. The reaction mixture was partitioned between 1 N HCl and EtOAc. The organic layer was washed with saturated NaHCO$_3$, brine, dried over Na$_2$SO$_4$ and concentrated. The residue was purified by silica gel chromatography (5% EtOAc in hexanes) to give the title compound as a white solid (0.9 g, 86%).

$^1$H NMR (CDCl$_3$): δ 2.26 (s, 3H), 2.40 (s, 3H), 7.13 (d, 2H, J=8.3 Hz), 7.58 (d, 2H, J=8.3 Hz).

Example A(19)

6-[2-(1-Acetyl-3,5-dimethyl-1H-pyrazol-4-yl)-ethyl]-6-cyclopentyl-dihydro-pyran-2,4-dione

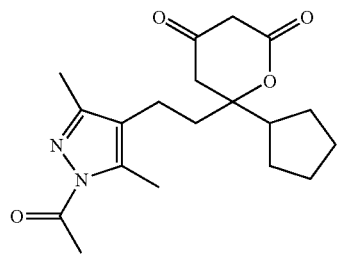

The title compound was prepared analogously to Example A(64), where 1-(4-Iodo-3,5-dimethyl-pyrazol-1-yl)-ethanone (described below) was substituted in place of 4-bromo-2-fluoro-1-isopropylbenzene of that example.

$^1$H NMR (CDCl$_3$): δ 1.46–1.83 (br m, 9H), 2.18 (s, 3H), 2.28–2.44 (m, 4H), 2.45 (s, 3H), 2.63 (s, 3H), 2.75 (d, 1H, J=16.0 Hz), 2.83 (d, 1H, J=16.0 Hz), 3.37 (d, 1H, J=21.3 Hz), 3.47 (d, 1H, J=21.3 Hz) Anal. Calcd. For C$_{19}$H$_{26}$N$_2$O$_4$·0.5H$_2$O: C, 64.20; H, 7.66; N, 7.88. Found: C, 64.35; H, 7.61; N, 7.56.

Step 1

1-(4-Iodo-3,5-dimethyl-pyrazol-1-yl)-ethanone

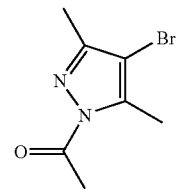

Acetic anhydride (0.51 mL, 5.4 mmol) and triethylamine (0.75 mL, 5.4 mmol) were added to a solution of 3,5-dimethyl-4-iodopyrazole (1 g, 4.5 mmol) in CH$_2$Cl$_2$. After 1 h the reaction mixture was partitioned between 1 N HCl and EtOAc. The organic layer was washed with 1 N HCl, saturated NaHCO$_3$, brine, dried over Na2SO4, and concentrated to give the title compound as a white solid (1 g, 85%).

$^1$H NMR (CDCl$_3$): δ 2.27 (s, 3H), 2.60 (s, 3H), 2.66 (s, 3H).

Example A(20)

6-Cyclopentyl-6-(5-methoxy-indan-1-ylmethyl)-dihydro-pyran-2,4-dione

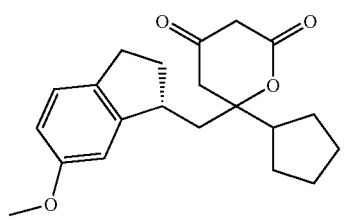

The title compound was prepared as described in Example A(13), where 1-Cyclopentyl-2-(5-methoxy-indan-1-yl)-ethanone (described in Step 4 below), was substituted in place of 3-Cyclohex-1-enyl-1-cyclopentyl-propan-1-one.

$^1$H NMR (CDCl$_3$): δ 1.24–1.87 (br m, 10H), 2.24–2.56 (m 3H), 2.75–2.93 (m, 4H), 3.15–3.31 (m, 1H), 3.42 (s, 2H), 3.78 (s, 3H), 6.73 (d, 1H, J=8.3 Hz), 6.78 (s, 1H), 7.02 (d, 1H, J=8.3 Hz).

ESIMS: MH$^+$343.10, MH$^-$341.10.

Step 1

[3(1"R), 4 R]-3-[2'-(5"-Methoxy-1"-indanyl)acetyl]-4-(phenylmethyl)-2-oxazolidinone (A) and [3(1"S), 4 R]-3-[2'-(5"-Methoxy-1"-indanyl)acetyl]-4-(phenylmethyl)-2-oxazolidinone (B):

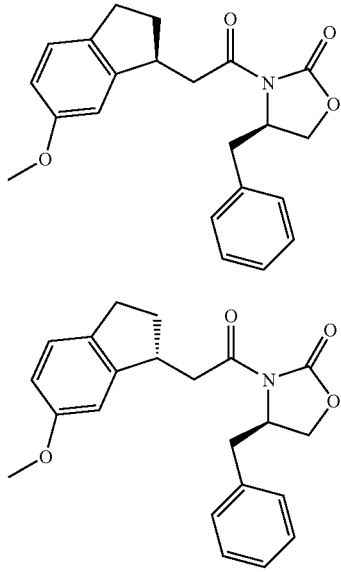

The diastereomers were prepared and separated as described in the following reference: *J. Med Chem.* 1995, 38, 1386–1396.

Step 2

(5-Methoxy-indan-1-yl)-acetic acid

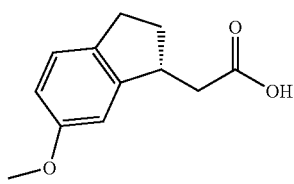

2N LiOH (0.82 mL) was added to a solution of [3(1"S), 4R]-3-[2'-(5"-Methoxy-1"-indanyl)acetyl]-4-(phenylmethyl)-2-oxazolidinone (0.3 g, 1.64 mmol, from Step 1) dissolved in THF (3 mL). The mixture was stirred for 2 h under $N_2$ and then partitioned between 1 N HCl and EtOAc. The organic layer was extracted with 1 N NaOH (×2). The aqueous layers were made acidic with 2N HCl and extracted with EtOAc (×3). The organic layers were washed with brine, dried over $Na_2SO_4$ and concentrated to an clear oil (0.14 g, 83%).

$^1$H NMR (CDCl$_3$): δ 1.78 (m, 1H), 2.38–2.50 (m, 2H), 2.77–2.95 (m, 3H), 3.54 (m, 1H), 3.79 (s, 3H), 6.72 (d, 1H, J=10.6 Hz), 6.78 (s, 1H), 7.10 (d, 1H, J=10.6 Hz).

Step 3

(5-Methoxy-indan-1-yl)-thioacetic acid S-pyridin-2-yl ester

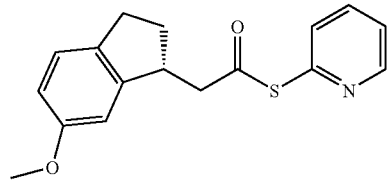

The title compound was prepared as described in Step 3 of Example A(13), where (5-Methoxy-indan-1-yl)-acetic acid (from Step 2 below) was substituted in place of 3-Cyclohex-1-enyl-propionic acid.

$^1$H NMR (CDCl$_3$): δ 1.85 (m, 1H), 2.41 (m, 1H), 2.78–2.95 (m, 3H), 3.13 (dd, 1H, J=15.6, 5.7 Hz), 3.64 (m, 1H), 3.79 (s, 3H), 6.72 (d, 1H, J=8.3 Hz), 6.78 (s, 1H), 7.10 (d, 1H, J=8.3 Hz), 7.31 (m, 1H), 7.65 (m, 1H), 7.76 (t, 1H, J=7.8 Hz), 8.63 (d, 1H, J=5.05 Hz).

Step 4

1-Cyclopentyl-2-(5-methoxy-indan-1-yl)-ethanone

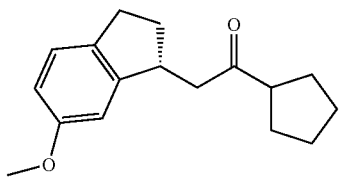

The title compound was prepared as described in Step 4 of Example A(13), where (5-Methoxy-indan-1-yl)-thioacetic acid S-pyridin-2-yl ester (from Step 3) was substituted in place of 3-Cyclohex-1-enyl-thiopropionic acid S-pyridin-2-yl ester.

$^1$H NMR (CDCl$_3$): δ 1.55–1.85 (br m, 9H), 2.39 (m, 1H), 2.60 (dd, 1H, J=17.2, 8.6 Hz), 2.80–2.92 (m, 4H), 3.59 (m, 1H), 3.78 (s, 3H), 6.70 (d, 1H, J=8.3 Hz), 6.77 (s, 1H), 7.02 (d, 1H, J=8.3 Hz).

Example A(21)

6-Cyclopentyl-6-(5-methoxy-indan-1-ylmethyl)-dihydro-pyran-2,4-dione

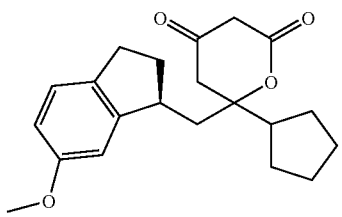

The title compound was prepared analogously to Example A(20), where [3(1"R), 4R]-3-[2'-(5"-Methoxy-1"-indanyl)

acetyl]-4-(phenylmethyl)-2-oxazolidinone (A) (from Step 1 of that example) was substituted in place of [3(1"S), 4R]-3-[2'-(5"-Methoxy-1"-indanyl)acetyl]-4-(phenylmethyl)-2-oxazolidinone (B) in Step 2 of that Example.

$^1$H NMR (CDCl$_3$): δ 1.24–1.87 (br m, 10H), 2.24–2.41 (m, 2H), 2.51 (m 1H), 2.73–2.93 (m, 4H), 3.15–3.31 (m, 1H), 3.42 (s, 2H), 3.78 (s, 3H), 6.73 (d, 1H, J=8.3 Hz), 6.78 (s, 1H), 7.02 (d, 1H, J=8.3 Hz). ESIMS: MH$^+$343.10, MH$^-$341.10.

Example A(22)

6-Cyclopentyl-6-[2-(3-ethyl-4-hydroxy-phenyl)-ethyl]-dihydro-pyran-2,4-dione

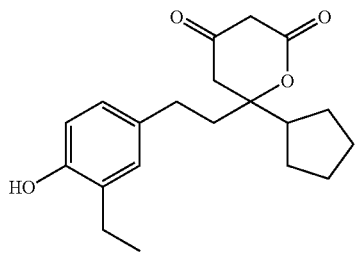

A mixture of acetic acid 4-[2-(2-cyclopentyl-4,6-dioxo-tetrahydro-pyran-2-yl)-ethyl]-2-ethyl-phenyl ester (0.92 g, 2.47 mmol, from Step 3), potassium carbonate (0.68 g, 4.9 mmol) in MeOH (10 mL) was stirred at rt for 1 h. The reaction mixture was partitioned between 1 N HCl and EtOAc. The organic layer was washed with brine, dried over Na$_2$SO$_4$ and concentrated to a yellow oil. The oil was purified by silica gel chromatography (20% to 40% EtOAc in hexanes) to give the title compound (2.44 g, 59%).

$^1$H NMR (CDCl$_3$): δ 1.22 (t, 3H, J=7.6 Hz), 1.43–1.78 (br m, 8H), 1.87–2.01 (m, 2H), 2.28 (m, 1H), 2.57–2.63 (m, 4H), 2.76 (s, 2H), 3.42 (s, 2H), 4.63 (s, 1H), 6.68 (d, 1H, J=8.1 Hz), 6.84 (d, 1H, J=8.1 Hz), 6.90 (s, 1H). Anal. Calcd. For C$_{20}$H$_{26}$O$_4$.0.25H$_2$O: C, 71.72; H, 7.98. Found: C, 71.10; H, 7.99.

Step 1

4-Bromo-2-ethyl-phenol

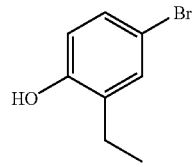

Sodium hydroxide (1.4 g, 35 mmol) and hydrazine monohydrate (2.04 mL, 42 mmol) were added to a solution of 5'-bromo-2'-hydroxyacetophenone (3 g, 14 mmol) dissolved in triethylene glycol (17 mL). The reaction mixture was heated to 170° C. for 24 h and then partitioned between 1 N HCl and EtOAc. The organic layer was washed with saturated NaHCO$_3$, brine, dried over Na$_2$SO$_4$ and concentrated. The residue was purified by flash silica gel chromatography (0% to 10% EtOAc in hexanes) to give the title compound (2.52 g, 90%).

$^1$H NMR (CDCl$_3$): δ 1.22 (t, 3H, J=7.5 Hz), 2.60 (q, 2H, J=7.5 Hz), 6.64 (d, 1H, J=8.5 Hz), 7.17 (dd, 1H, J=8.5, 2.5 Hz), 7.24 (d, 1H, J=2.5 Hz).

Step 2

Acetic acid 4-bromo-2-ethyl-phenyl ester

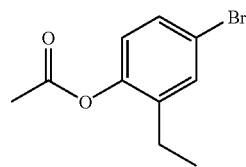

Acetyl chloride (1.06 mL, 14.9 mmol) followed by triethylamine (2.08 mL, 14.9 mmol) were added to a cooled 0° C. solution of 4-Bromo-2-ethyl-phenol (2.5 g, 12.4 mmol, from Step 1) dissolved in CH$_2$Cl$_2$. The reaction was stirred for 2 hrs and then partitioned between 1 N HCl and EtOAc. The organic layer was washed with saturated NaHCO$_3$, brine, dried over Na$_2$SO$_4$ and concentrated to a brown oil. The oil was purified by silica gel chromatography (0% to 10% EtOAc in hexanes) to give the title compound as a clear oil (2.44 g, 81%).

$^1$H NMR (CDCl$_3$): δ 1.19 (t, 3H, J=7.7 Hz), 2.32 (s, 3H), 2.52 (q, 2H, J=7.7 Hz), 6.89 (d, 1H, J=8.5 Hz), 7.32 (dd, 1H, J=8.5, 2.2 Hz), 7.38 (d, 1H, J=2.2 Hz).

Step 3

Acetic acid 4-[2-(2-cyclopentyl-4,6-dioxo-tetrahydro-pyran-2-yl)-ethyl]-2-ethyl-phenyl ester.

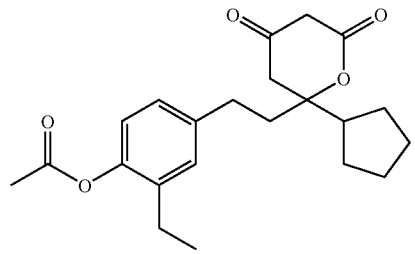

The title compound was prepared analogously to Example A(64), where Acetic acid 4-bromo-2-ethyl-phenyl ester (from Step 2) was substituted in place of 4-bromo-2-fluoro-1-isopropylbenzene of that example.

ESIMS: MH$^+$373.20, MH$^-$371.20.

Example A(23)

6-Ethyl-6-[2-(4-methoxy-phenyl)-ethyl]-dihydro-pyran-2,4-dione

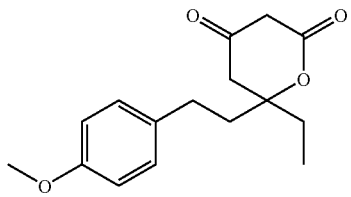

The title compound was prepared as described in Example A(13), where 1-(4-Methoxy-phenyl)-pentan-3-one (described Step 2 below) was substituted in place of 3-Cyclohex-1-enyl-1-cyclopentyl-propan-1-one.

$^1$H NMR (CDCl$_3$): δ 1.01 (t, 3H, J=7.5 Hz), 1.80 (m, 2H), 1.95 (m, 2H), 2.66 (m, 2H), 2.72 (s, 2H), 3.42 (s, 2H), 3.79 (s, 3H), 6.83 (d, 2H, J=8.5 Hz), 7.08 (d, 2H, J=8.5 Hz) Anal. Calcd. For C$_{16}$H$_{20}$O$_4$: C, 69.70; H, 7.52. Found: C, 69.54; H, 7.30.

Step 1

N-Methoxy-3-(4-methoxy-phenyl)-N-methyl-propionamide

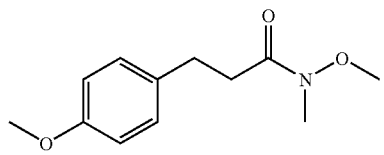

N,O-dimethylhydroxylamine hydrochloride (5.41 g, 55.5 mmol), EDC (12.77 g, 66.6 mmol), followed by triethylamine (17 mL, 122 mmol) were added to a cooled 0° C. solution of 3-(4-methoxyphenyl)propionic acid (10 g, 55.5 mmol). The reaction mixture was stirred for 15 h under $N_2$ and then concentrated. The residue was partitioned between 1 N HCl and EtOAc. The organic layers were washed with saturated $NaHCO_3$, brine, dried over $Na_2SO_4$ and concentrated to an oil. The oil was purified by silica gel chromatography (40% EtOAc in hexanes) to give a clear oil (10.6 g, 85%).

$^1$H NMR (CDCl$_3$): δ 2.70 (t, 2H, J=7.5 Hz), 2.91 (t, 2H, J=7.5 Hz), 3.18 (s, 3H), 3.61 (s, 3H), 3.79 (s, 3H), 6.83 (d, 2H, J=8.7 Hz), 7.15 (d, 2H, J=8.7 Hz).

Step 2

1-(4-Methoxy-phenyl)-pentan-3-one

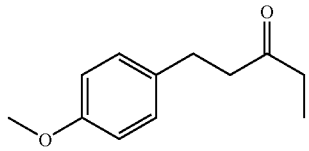

Ethylmagnesium bromide (10.8 mL, 10.8 mmol, 1M soln in THF) was added to a cooled −78° C. solution of N-Methoxy-3-(4-methoxy-phenyl)-N-methyl-propionamide (2 g, 8.96 mmol, from Step 1) dissolved in THF (20 mL). The reaction mixture was stirred for 60 min. The reaction was quenched with saturated NH$_4$Cl and extracted with EtOAc. The organic layer was washed brine, dried over Na$_2$SO$_4$ and concentrated to a clear oil. The residue was purified by silica gel chromatography (5% EtOAc in hexanes) to give the title compound as a clear oil (0.87 g, 50%).

$^1$H NMR (CDCl$_3$): δ 1.04 (t, 3H, J=7.4 Hz), 2.39 (q, 2H, J=7.4 Hz), 7.54 (m, 2H), 2.84 (m, 2H), 3.78 (s, 3H), 6.82 (d, 2H, J=8.7 Hz), 7.09 (d, 2H, J=8.7 Hz).

Example A(24)

6-Isobutyl-6-[2-(4-methoxy-phenyl)-ethyl]-dihydropyran-2,4-dione

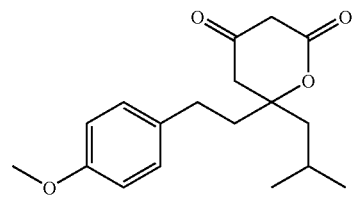

The title compound was prepared as described in Example A(13), where 1-(4-Methoxy-phenyl)-5-methyl-hexan-3-one (described in Step 2 below) was substituted in place of 3-Cyclohex-1-enyl-1-cyclopentyl-propan-1-one.

$^1$H NMR (CDCl$_3$): δ 0.99 (d, 3H, J=6.6 Hz), 1.02 (d, 3H, J=6.6 Hz), 1.65 (m 2H), 1.88 (m, 1H), 2.01 (m, 2H), 2.64 (m, 2H), 2.74 (s, 2H), 3.24 (s, 2H), 3.79 (s, 3H), 6.85 (d, 2H, J=8.5 Hz), 7.08 (d, 2H, J=8.5 Hz). ESIMS: MH$^+$305.20, MH$^-$303.20.

Step 1

3-(4-Methoxy-phenyl)-thiopropionic acid S-pyridin-2-yl ester

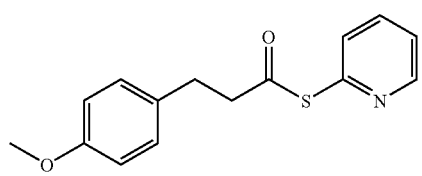

The title compound was prepared as described in Step 3 of Example A(13), where 3-(4-methoxyphenyl)propionic acid was substituted in place of 3-Cyclohex-1-enyl-propionic acid.

$^1$H NMR (CDCl$_3$): δ 2.98 (s, 4H), 3.76 (s, 3H), 6.83 (d, 2H, J=8.7 Hz), 7.13 (d, 2H, J=8.7 Hz), 7.28 (dd, 1H, J=7.5, 5.8 Hz), 7.60 (m, 1H), 7.74 (td, 1H, J=7.7, 1.9 Hz), 8.63 (d, 1H, J=5.8 Hz).

Step 2

1-(4-Methoxy-phenyl)-5-methyl-hexan-3-one

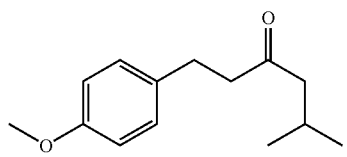

Isobutylmagnesium bromide (0.88 mL, 1.75 mmol, 2M soln in THF) was added to a cooled −78° C. solution of 3-(4-Methoxy-phenyl)-thiopropionic acid S-pyridin-2-yl ester (0.4 g, 1.46 mmol, from Step 1) dissolved in THF (6 mL). The reaction mixture was stirred for 60 min. The reaction was quenched with saturated NH$_4$Cl and extracted with EtOAc. The organic layer was washed with brine, dried over Na$_2$SO$_4$ and concentrated to a yellow oil. The residue was purified by silica gel chromatography (5% EtOAc in hexanes) to give the title compound as a clear oil (0.24 g, 75%).

$^1$H NMR (CDCl$_3$): δ 0.89 (d, 6H, J=6.6 Hz), 2.12 (m, 1H), 2.26 (d, 2H, J=7.0 Hz), 2.60–2.69 (m, 2H), 2.81–2.90 (m, 2H), 3.78 (s, 3H), 6.82 (d, 2H, J=8.7 Hz), 7.09 (d, 2H, J=8.7 Hz).

Example A(25)

6-[2-(4-Methoxy-phenyl)-ethyl]-6-propyl-dihydro-pyran-2,4-dione

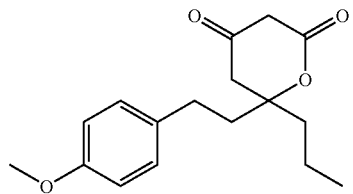

The title compound was prepared analogously to Example A(13), where propylmagnesium chloride was substituted in place of Cyclopentylmagnesium bromide in Step 4 of that Example.

$^1$H NMR (CDCl$_3$): δ 0.96 (t, 3H, J=7.2 Hz), 1.44 (m, 2H), 1.70 (m, 2H), 1.95 (m, 2H), 2.66 (m, 2H), 2.72 (s, 2H), 3.42 (s, 2H), 3.79 (s, 3H), 6.83 (d, 2H, J=8.5 Hz), 7.08 (d, 2H, J=8.5 Hz) Anal. Calcd. For C$_{17}$H$_{22}$O$_4$.0.2H$_2$O: C, 69.46; H, 7.68. Found: C, 69.40; H, 7.75.

Example A(26)

6-Allyl-6-[2-(4-methoxy-phenyl)-ethyl]-dihydro-pyran-2,4-dione

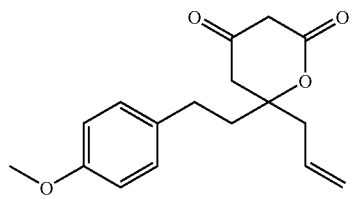

The title compound was prepared analogously to Example A(23), where allyl magnesium chloride was substituted in place of ethylmagnesium bromide in Step 2 of that Example.

$^1$H NMR (CDCl$_3$): δ 1.95 (m, 2H), 2.53 (d, 2H, J=7.2 Hz), 2.66–2.74 (m, 4H), 3.43 (s, 2H), 3.79 (s, 3H), 5.23 (d, 1H, J=18.5 Hz), 5.27 (d, 1H, J=10.2 Hz), 5.79 (m, 1H), 6.83 (d, 2H, J=8.5 Hz), 7.08 (d, 2H, J=8.5 Hz) Anal. Calcd. For C$_{17}$H$_{20}$O$_4$: C, 70.56; H, 7.07. Found: C, 70.81; H, 6.99.

Example A(27)

6-[2-(3-Chloro-4-(6-Methyl-dihydro-pyran-2,4-dione)-phenyl)-ethyl]-6-cyclopentyl-dihydro-pyran-2,4-dione

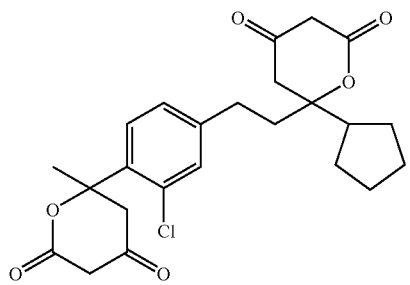

NaH (60% in mineral oil, 0.14 g, 3.42 mmol) was suspended in THF (5 mL) and cooled to 0° C. Methylacetoacetate (0.19 mL, 1.72 mmol) was slowly added via syringe and the reaction mixture stirred 20 min. A solution of n-BuLi in hexanes (1.6 M, 2.13 mL, 3.42 mmol) was added dropwise and the resulting mixture was stirred an additional 20 min. A solution of 3-(4-Acetyl-3-chloro-phenyl)-1-cyclopentyl-propan-1-one (0.16 g, 0.57 mmol) from Step 3 below in THF (2 mL) was added dropwise. After stirring 1 h, the reaction mixture was quenched with 1 N HCl (10 mL) and extracted with EtOAc (10 mL). The organic phase was dried over Na$_2$SO$_4$ and evaporated. The crude organic product was then dissolved in 5 mL of MeOH, and 0.47 grams of finely powdered K$_2$CO$_3$ (anhydrous) was added. The slurry was stirred at 60° C. for 1.5 h, and then concentrated by rotary evaporation. The residue was dissolved in 10 mL of water and 10 mL of EtOAc, and acidified with 2N HCl. The aqueous solution was extracted 3 times with 5 mL of EtOAc. The organics were combined, and dried with Na$_2$SO$_4$. After filtering the residue was purified by flash column chromatography (40% EtOAc in hexanes) to give the product (0.035 g, 45%) as a white foam.

$^1$H NMR (CDCl$_3$): δ 1.44–1.69 (m, 8H), 1.85 (s, 3H), 1.86–1.90 (m, 2H), 2.17–2.22 (m, 1H), 2.57–2.63 (m, 2H), 2.69 (d, J=8.1 Hz, 2H), 2.88 (d, J=17.3 Hz, 1H), 3.06 (dd, J=20.5, 3.4 Hz, 1H), 3.29 (d, J=20.5 Hz, 1H), 3.36 (s, 2H), 3.86 (dd, J=17.3, 1.7 Hz, 1H), 7.02 (dd, J=8.3, 1.7 Hz, 1H), 7.15 (d, J=1.7 Hz, 1H), 7.86 (d, J=8.1 Hz, 1H). Anal. Calcd. For C$_{24}$H$_{27}$ClO$_6$.0.5H$_2$O: C, 63.22; H, 6.19. Found: C, 63.45; H, 6.3. ESIMS (MH+): 447.1.

Step 1

4-Bromo-2-chloro-thiobenzoic acid S-pyridin-2-yl ester

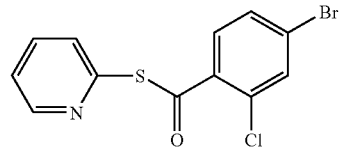

4-Bromo-2-chlorobenzoic acid (15 g, 63.70 mmol), triphenylphosphine (21.72 g, 82.81 mmol) and 2,2'-dipyridyl disulfide (18.24 g, 82.81 mmol) were combined successively in CH$_2$Cl$_2$ (200 mL). The reaction mixture was stirred 1 h and then loaded directly onto a column for purification by flash chromatography (10% EtOAc in hexanes) to give the product (13.34 g, 67%) as a white solid.

$^1$H NMR (CDCl$_3$) δ 7.34–7.38 (m, 1H), 7.53 (dd, J=8.3, 1.7 Hz, 1H), 7.67–7.85 (m, 4H), 8.68 (d, J=5.6 Hz, 1H). ESIMS (MH+): 329.

Step 2

1-(4-Bromo-2-chloro-phenyl)-ethanone

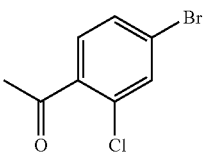

4-Bromo-2-chloro-thiobenzoic acid S-pyridin-2-yl ester (1.86 g, 5.66 mmol) from Step 1 above was dissolved in dry THF (30 mL) and cooled to –78° C. A solution of methyl magnesium bromide in 75:25 toluene/THF (1.4 M, 4.45 mL, 6.23 mmol) was added dropwise. After stirring 35 min, the cooling bath was removed. The reaction mixture was quenched with saturated 1N HCl and extracted with EtOAc (30 mL). The organic phase was washed with brine (50 mL), dried over Na$_2$SO$_4$ and evaporated. The residue was purified by flash column chromatography (10% EtOAc in hexanes) to give the product (1.05 g, 80%) as a colorless oil.

$^1$H NMR (CDCl$_3$) δ 2.64 (s, 3H), 7.46–7.48 (m, 2H), 7.61 (s, 1H).

Step 3

3-(4-Acetyl-3-chloro-phenyl)-1-cyclopentyl-propan-1-one

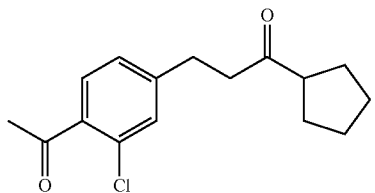

To a magnetically stirring solution of 1-(4-Bromo-2-chloro-phenyl)-ethanone (0.92 g, 3.96 mmol) from Step 2 above and 1-Cyclopentyl-2-propen-1-ol (0.60 g, 4.75 mmol) in anhydrous N-methylpyrrolidinone (3.0 mL), under argon at room temperature, was added sodium bicarbonate (0.40 g, 4.75 mmol) followed by dichlorobis (triphenylphosphine) palladium (II) (84 mg, 0.12 mmol). The resulting mixture was heated to 140° C. in an oil bath and maintained for 4 hours. The resulting dark reaction mixture was cooled to room temperature and poured into water (50 mL) and extracted with EtOAc (2×25 mL). The organics were washed with water (50 mL) and brine (50 mL) then dried over Na$_2$SO$_4$, filtered and concentrated. The crude residue was purified by flash chromatography (1% through 10% EtOAc in Hexanes) to yield the intermediate ketone as a yellow oil (0.16 g, 16%).

$^1$H NMR (CDCl$_3$): δ ?1.55–1.8 (m, 8H), 2.64 (s, 3H), 2.78–2.93 (m, 5H), 7.14 (dd, J=8.0, 1.7 Hz, 1H), 7.25 (d, J=1.7 Hz, 1H), 7.51 (d, J=8.0 Hz, 1H).

Example A(28)

6-Cyclopentyl-6-[2-(3-(6-Methyl-dihydro-pyran-2,4-dione)-phenyl)-ethyl]-dihydro-pyran-2,4-dione

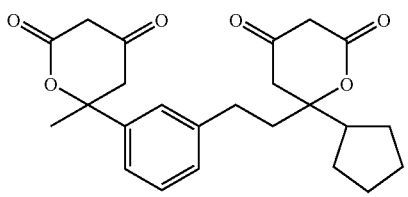

The title compound was prepared analogously to Example A(27), where 3-Bromo acetophenone was substituted in place of 1-(4-Bromo-2-chloro-phenyl)-ethanone in Step 3 of that example.

$^1$H NMR (CDCl$_3$): δ 1.17–1.70 (m, 11H), 1.86–1.89 (m, 2H), 2.35–2.45 (m, 1H), 2.53–3.35 (m, 10H), 7.05–7.256 (m, 4H). ESIMS (MH+) C$_{24}$H$_{28}$O$_6$: 413.

Example A(29)

6-Cyclopentyl-6-{2-[4-(2-methyl-5-oxo-tetrahydro-furan-2-yl)-phenyl]-ethyl}-dihydro-pyran-2,4-dione

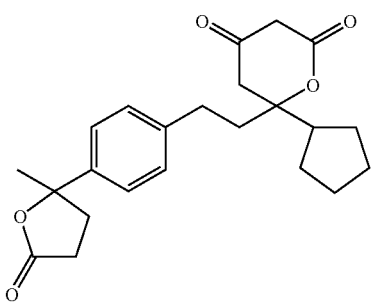

The title compound was prepared analogously to Example A(27), where 5-(3-Bromo-phenyl)-5-methyl-dihydro-furan-2-one (described in Step 1 below) was substituted in place of 1-(4-Bromo-2-chloro-phenyl)-ethanone in Step 3 of that example.

$^1$H NMR (CDCl$_3$): δ 1.58–1.83 (m, 11H), 1.90–2.0 (m, 2H), 2.26–2.33 (m, 1H), 2.26–2.27 (m, 6H), 2.78 (s, 2H), 3.42 (s, 2H), 7.14 (d, J=8.2 Hz, 2H), 7.29 (d, J=8.2 Hz, 2H). ESIMS (MH+) C$_{23}$H$_{28}$O$_5$: 385

Step 1

5-(3-Bromo-phenyl)-5-methyl-dihydro-furan-2-one

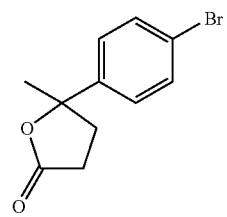

To a magnetically stirring solution of 3-(4-Bromobenzoyl)propionic acid (1.0 g, 3.89 mmol) in anhydrous THF (20 mL), under argon at room temperature, was added a solution of methyl magnesium bromide in 75:25 toluene/THF (1.4 M, 5.8 mL, 8.17 mmol) over a period of 1 h. The resulting solution was stirred at room temperature for 18 hours. Ice and conc HCl (2 mL) were carefully added and the resulting reaction mixture was stirred at 80° C. for 8 h. The resultant reaction was cooled to room temperature and extracted with EtOAc (2×25 mL). The organics were washed with water (50 mL) and brine (50 mL) then dried over Na$_2$SO$_4$, filtered and concentrated. The crude residue was purified by flash chromatography (40% EtOAc in Hexanes) to yield the intermediate bromide as a clear oil (0.49 g, 50%).

$^1$H NMR (CDCl$_3$): δ ?1.70 (m, 3H), 2.39–2.71 (m, 4H), 7.23–7.28 (m, 2H), 7.48–7.53 (m, 2H).

Example A(30)

6-[2-(3-Chloro-4-(6-Ethyl-dihydro-pyran-2,4-dione)-phenyl)-ethyl]-6-cyclopentyl-dihydro-pyran-2,4-dione

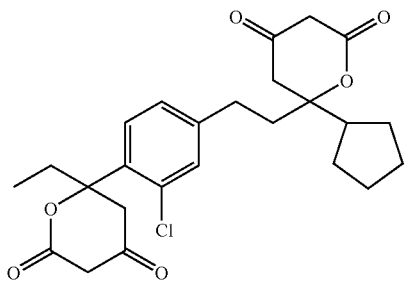

The title compound was prepared analogously to Example A(27), where 1-(4-Bromo-2-chloro-phenyl)-propan-1-one (described in Step 1 below) was substituted in place of 1-(4-Bromo-2-chloro-phenyl)-ethanone in Step 3 of that example.

$^1$H NMR (CDCl$_3$): δ 0.87 (t, J=7.3 Hz, 3H), 1.4–1.7 (m, 8H), 1.92–1.98 (m, 2H), 2.09–2.17 (m, 1H), 2.18 (s, 2H), 2.22–2.33 (m, 1H), 2.37–2.47 (m, 1H), 2.62–2.78 (m, 2H), 2.95 (d, J=17 Hz, 1H), 3.09 (dd, J=20, 4.7 Hz, 1H), 3.33 (d, J=20 Hz, 1H), 3.43 (s, 2H), 3.93 (d, J=17 Hz, 1H), 7.09(d, J=8.1, 1H), 7.22 (s, 1H), 7.88 (d, J=8.1 Hz, 1H). ESIMS (MH−) C$_{25}$H$_{29}$ClO$_6$: 459.

Step 1

1-(4-Bromo-2-chloro-phenyl)-propan-1-one

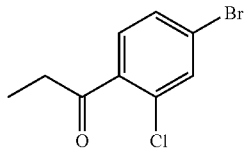

The title compound was prepared as described in Step 2 of Example A(27), where ethyl magnesium bromide was substituted for methyl magnesium bromide. Yield 84%.

$^1$H NMR (CDCl$_3$) δ 1.2 (t, J=7.3 Hz, 3H), 2.93 (q, J=7.3 Hz, 2H), 7.44–7.64 (m, 3H).

Example A(31)

6-[2-(3-Chloro-4-(6-Cyclopropyl-dihydro-pyran-2,4-dione)-phenyl)-ethyl]-6-cyclopentyl-dihydro-pyran-2,4-dione

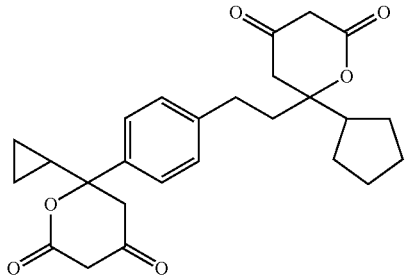

The title compound was prepared analogously to Example A(27), where (4-Bromo-phenyl)-cyclopropyl-methanone was substituted in place of 1-(4-Bromo-2-chloro-phenyl)-ethanone in Step 3 of that example.

$^1$H NMR (CDCl$_3$): δ 0.46–0.61 (m, 2H), 0.83–1.01 (m, 2H), 1.20–1.79 (m, 8H), 1.88–2.10 (m, 2H), 2.23–2.42 (m, 2H), 2.62–3.43 (m, 10H), 7.17–7.24 (m, 4H). ESIMS (MH−) C$_{26}$H$_{30}$O$_6$: 437.

Example A(32)

6-Cyclopentyl-6-[2-(4-cyclopropanecarbonyl-phenyl)-ethyl]-dihydro-pyran-2,4-dione

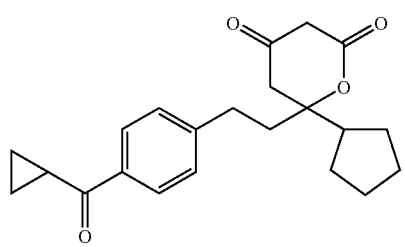

The title compound was prepared analogously to Example A(27), where (4-Bromo-phenyl)-cyclopropyl-methanone was substituted in place of 1-(4-Bromo-2-chloro-phenyl)-ethanone in Step 3 of that example. The title compound was obtained side product previously described Example A(31).

$^1$H NMR (CDCl$_3$): δ 1.02–1.06 (m, 2H), 1.21–1.25 (m, 2H), 1.28–1.75 (m, 9H), 1.97–2.05 (m, 2H), 2.24–2.30 (m, 1H), 2.64–2.73 (m, 2H), 2.79 (s, 2H), 3.44 (s, 2H), 7.25 (d, J=8.3 Hz, 2H), 7.95 (d, J=8.3 Hz, 2H). Anal. Calcd. For C$_{22}$H$_{26}$O$_4$·0.5H$_2$O: C, 72.70; H, 7.49. Found: C, 72.87; H, 7.38. ESIMS (MH−): 353.

Example A(33)

2-{4-[2-(2-Cyclopentyl-4,6-dioxo-tetrahydro-pyran-2-yl)-ethyl]-phenyl}-2-methyl-propionic acid methyl ester

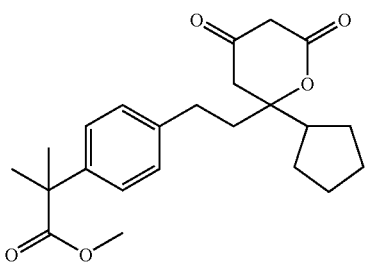

The title compound was prepared analogously to Example A(64), where 2-(4-Bromo-phenyl)-2-methyl-propionic acid methyl ester was substituted in place of 4-bromo-2-fluoro-1-isopropylbenzene in Step 3 of that example.

$^1$H NMR (CDCl$_3$): 1.53–1.68 (m, 14H), 1.93–1.98 (m, 2H), 2.25–2.38 (m, 1H), 2.63–2.68 (m, 2H) 2.77 (s, 2H), 3.42 (s, 2H), 3.65 (s, 3H), 7.09–7.12 (m, 2H), 7.22–7.24 (m, 2H) Anal. Calcd. For C$_{23}$H$_{30}$O$_5$·0.25H$_2$O: C, 70.65, H, 7.86. Found: C, 70.88, H, 7.82. ESIMS (MH+): 345.2.

Example A(34)

6-{2-[4-(2-tert-Butyl-[1,3]dioxolan-2-yl)-phenyl]-ethyl}-6-cyclopentyl-dihydro-pyran-2,4-dione

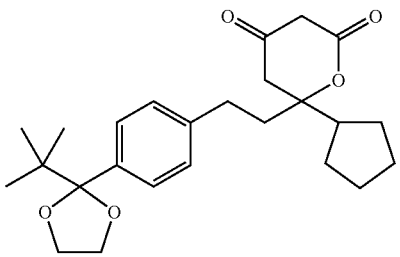

The title compound was prepared analogously to Example A(64), where 2-(4-Bromo-phenyl)-2-tert-butyl-[1,3]dioxolane was substituted in place of 4-bromo-2-fluoro-1-isopropylbenzene in Step 3 of that example.

$^1$H NMR (CDCl$_3$): δ 0.94 (s, 9H), 1.5–1.8 (m, 8H), 1.91–2.05 (m, 2H), 2.27–2.32 (m, 1H), 2.64–2.70 (m, 2H) 2.77 (s, 2H), 3.42 (s, 2H), 3.64–3.68 (m, 2H), 3.92–3.95 (m, 2H), 7.07 (d, J=8.3 Hz, 2H), 7.35 (d, J=8.3 Hz, 2H). Anal. Calcd. For C$_{25}$H$_{34}$O$_5$: C, 72.44; H, 8.27. Found: C, 72.65; H, 8.43. ESIMS (MH+): 415.

Example A(35)

6-Cyclopentyl-6-{2-[4-(1-hydroxy-ethyl)-phenyl]-ethyl}-dihydro-pyran-2,4-dione

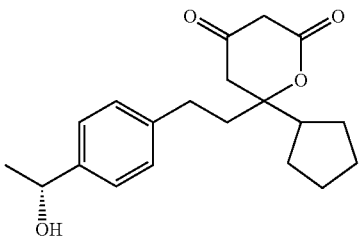

The title compound was prepared analogously to Example A(27), where (R)1-(4-Bromo-phenyl)-ethanol (described in Step 1 below) was substituted in place of 1-(4-Bromo-2-chloro-phenyl)-ethanone in Step 3 of that example.

$^1$H NMR (CDCl$_3$): δ 1.48 (d, J=6.4 Hz, 3H), 1.52–1.79 (m, 8H), 1.95 (q, J=17, 8.5 Hz, 2H), 2.26–2.32 (m, 1H), 2.68 (t, J=8.5 Hz, 2H), 2.78 (s, 2H), 3.42 (s, 2H), 4.88 (q, J=13, 6.4 Hz, 1H), 7.13 (d, J=8.1 Hz, 2H), 7.31 (d, J=8.1 Hz, 2H). Anal. Calcd. For C$_{20}$H$_{26}$O$_4$·0.5H$_2$O: C, 70.77; H, 8.02. Found: C, 70.37; H, 7.95. ESIMS (MH−): 329.

Step 1

(R)1-(4-Bromo-phenyl)-ethanol

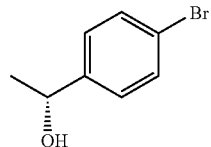

This compound was prepared as described in the following reference: *Tetrahedron* 2001, 57, 5027–5038.

Example A(36)

6-Cyclopentyl-6-{2-[4-(1-hydroxy-ethyl)-phenyl]-ethyl}-dihydro-pyran-2,4-dione

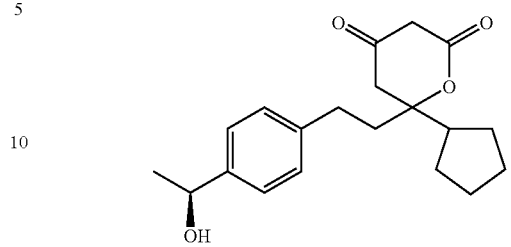

The title compound was prepared analogously to Example A(27), where (S)1-(4-Bromo-phenyl)-ethanol (described below) was substituted in place of 1-(4-Bromo-2-chloro-phenyl)-ethanone in Step 3 of that example.

$^1$H NMR (CDCl$_3$): δ 1.48 (d, J=6.4 Hz, 3H), 1.55–1.80 (m, 8H), 1.95 (q, J=17, 8.5 Hz, 2H), 2.23–2.35 (m, 1H), 2.68 (t, J=8.5 Hz, 2H), 2.78 (s, 2H), 3.42 (s, 2H), 4.88 (q, J=13, 6.4 Hz, 1H), 7.13 (d, J=8.1 Hz, 2H), 7.31 (d, J=8.1 Hz, 2H). Anal. Calcd. For C$_{20}$H$_{26}$O$_4$·0.25H$_2$O: C, 71.72; H, 7.97. Found: C, 71.4; H, 7.95. ESIMS (MH−): 329.

Step 1

(S)1-(4-Bromo-phenyl)-ethanol

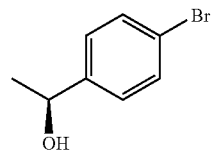

This compound was prepared as described in the following reference: *Tetrahedron* 2001, 57, 5027–5038.

Example A(37)

6-Cyclopentyl-6-{2-[4-(2,2-dimethyl-propionyl)-phenyl]-ethyl}-dihydro-pyran-2,4-dione.

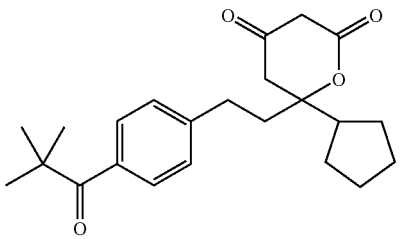

To a solution of 6-{2-[4-(2-tert-Butyl-[1,3]dioxolan-2-yl)-phenyl]-ethyl}-6-cyclopentyl-dihydro-pyran-2,4-dione from Example A(34), . (0.173 g) in acetone (1 mL) was added Amberlyst 15 (0.05 g). The reaction mixture was stirred at room temperature overnight, and then filtrated. The solvent was removed under reduced pressure. The residue was purified by flash chromatography (40% EtOAc in Hexanes) to yield the product as a white foam (0.04 g, 95%).

$^1$H NMR (CDCl$_3$): δ 1.35 (s, 9H), 1.47–1.84 (m, 8H), 1.91–2.03 (m, 2H), 2.25–2.34 (m, 1H), 2.72 (t, J=8.0 Hz,

2H), 2.78 (s, 2H), 3.44 (s, 2H), 7.18 (d, J=8.2 Hz, 2H), 7.67 (d, J=8.2 Hz, 2H). Anal. Calcd. For C₂₃H₃₀O₄: C, 74.56; H, 8.16. Found: C, 74.86; H, 8.43. ESIMS (MH+): 371.

Example A(38)

N-(1-{4-[2-(2-Cyclopentyl-4,6-dioxo-tetrahydro-pyran-2-yl)-ethyl]-phenyl}-ethyl)-acetamide

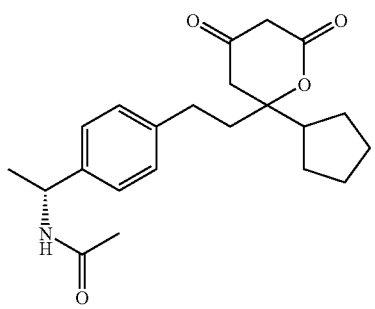

The title compound was prepared analogously to Example A(64), where (R)N-[1-(4-Bromo-phenyl)-ethyl]-acetamide (described in Step 1 below) was substituted in place of 4-bromo-2-fluoro-1-isopropylbenzene in Step 3 of that example.

¹H NMR (CDCl₃): δ 1.47 (d, J=6.8 Hz, 3H), 1.53–1.82 (m, 8H), 1.91–1.96 (m, 2H), 1.98 (s, 3H), 2.24–2.33 (m, 1H), 2.62–2.70 (m, 2H), 2.77 (s, 2H), 3.41 (d, J=2.0 Hz, 2H), 5.05–5.13 (m, 1H), 5.66 (d, J=7.5 Hz, 1H), 7.11 (d, J=8.1 Hz, 2H), 7.24 (d, J=8.1 Hz, 2H). Anal. Calcd. For C₂₂H₂₉NO₄·0.25AcOH: C, 69.92; H, 7.82; N, 3.62; Found: C, 69.66; H, 7.66; N, 3.75. ESIMS (MH+): 372.

Step 1

(R)N-[1-(4-Bromo-phenyl)-ethyl]-acetamide

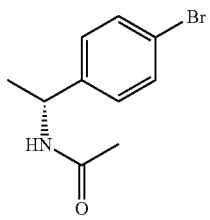

To a stirred solution of (R)-(+)-1-(4-bromophenyl)ethylamine (0.52 g, 2.59 mmol) in anhydrous CH₂Cl₂ (5 mL) under argon were added acetic anhydride (0.37 mL, 3.89 mmol) and Pyridine (0.31 mL, 3.89 mmol). The resulting solution was stirred at 25° C. for 3 hrs. The reaction mixture was quenched with saturated 1 N HCl and extracted with EtOAc (30 mL). The organic phase was washed with brine (50 mL), dried over Na₂SO₄ and evaporated. The residue was purified by flash column chromatography (80% EtOAc in hexanes) to give the product (0.62 g, 100%) as a white solid.

¹H NMR (CDCl₃) δ: 1.46 (d, J=7.0 Hz, 3H), 1.99 (s, 3H), 5.03–5.12 (m, 1H), 5.68 (brs, 1H), 7.18 (d, J=8.4 Hz, 2H), 7.47 (d, J=8.4 Hz, 2H). ESIMS (MNa+): 264.

Example A(39)

N-(1-{4-[2-(2-Cyclopentyl-4,6-dioxo-tetrahydro-pyran-2-yl)-ethyl]-phenyl}-ethyl)-malonamic acid ethyl ester

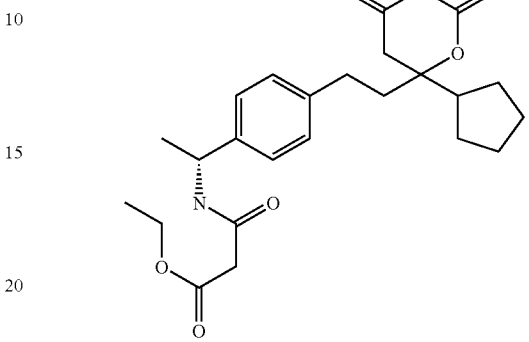

The title compound was prepared analogously to Example A(64), where (R)N-[1-(4-Bromo-phenyl)-ethyl]-malonamic acid ethyl ester (described in Step 1 below) was substituted in place of 4-bromo-2-fluoro-1-isopropylbenzene in Step 3 of that example.

¹H NMR (CDCl₃): δ 1.29 (t, J=7.7 Hz, 3H), 1.48 (d, J=7.1 Hz, 3H), 1.59–1.78 (m, 8H), 1.89–2.05 (m, 2H), 2.25–2.30 (m, 1H), 2.64–2.68 (m, 2H), 2.77 (s, 2H), 3.31 (d, J=3.4 Hz, 2H), 3.42 (s, 2H), 4.19 (q, J=7.1 Hz, 2H), 5.09–5.14 (m, 1H), 7.11 (d, J=8.1 Hz, 2H), 7.25 (d, J=8.1 Hz, 2H), 7.49 (d, J=7.3 Hz, 1H). Anal. Calcd. For C₂₅H₃₃NO₆·1.0AcOH·0.5H₂O: C, 63.27; H, 7.47; N, 2.73. Found: C, 63.30; H, 7.19; N, 2.91. ESIMS (MH+): 444.

Step 1

(R)N-[1-(4-Bromo-phenyl)-ethyl]-malonamic acid ethyl ester

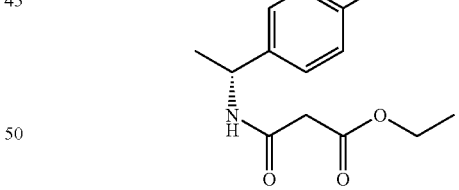

To a magnetically stirred solution of (R)-(+)-1-(4-bromophenyl)ethylamine (0.51 g, 2.55 mmol) in anhydrous CH₂Cl₂ under argon and cooled to 0° C., were added ethyl hydrogen malonate (0.4 g, 3.06 mmol) EDC·HCl (0.58 g, 3.06 mmol) and HOBt (0.41 g, 3.06 mmol). The resulting solution was stirred at 25° C. overnight. CH₂Cl₂ was evaporate and residue partitioned between EtOAC and 1 N HCl. The organic layer was washed with H₂O, brine and dried over Na₂SO₄. The solvent was removed in vacuo and the residue was purified by flash column chromatography (40% EtOAc in hexanes) to provide the desired product (0.57 g, 71%) as a white solid.

¹H NMR (CDCl₃): δ 1.29 (t, J=7.2 Hz, 3H), 1.48 (d, J=7.0 Hz, 3H), 3.31 (d, J=1.9 Hz, 2H), 4.2 (q, J=7.2 Hz, 2H), 5.06–5.14 (m, 1H), 7.20 (d, J=8.3 Hz, 2H), 7.45 (d, J=8.3 Hz, 2H), 7.48 (brs, 1H). ESIMS (MH+): 315.

Example A(40)

1-{4-[2-(2-Cyclopentyl-4,6-dioxo-tetrahydro-pyran-2-yl)-ethyl]-phenyl}-cyclopropanecarbonitrile

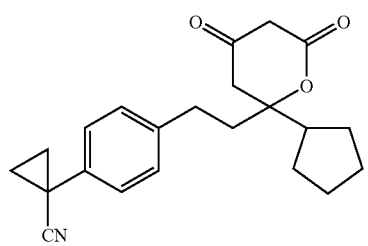

The title compound was prepared analogously to Example A(64), where 1-(4-Bromophenyl)cyclopropane carbonitrile was substituted in place of 4-bromo-2-fluoro-1-isopropylbenzene in Step 3 of that example.

$^1$H NMR (CDCl$_3$): δ 1.35–1.39 (m, 2H), 1.5–1.87 (m, 10H), 1.87–2.00 (m, 2H), 2.22–2.33 (m, 1H), 2.67 (t, J=8.4 Hz, 2H), 2.77 (s, 2H), 3.42 (d, J=1.5 Hz, 2H), 7.12 (d, J=8.3 Hz, 2H), 7.22 (d, J=8.3 Hz, 2H). Anal. Calcd. For C$_{22}$H$_{25}$NO$_3$: C, 75.19; H, 7.17; N, 3.99. Found: C, 75.38; H, 7.40; N, 4.04. ESIMS (MH−): 352.

Example A(41)

1-(1-{4-[2-(2-Cyclopentyl-4,6-dioxo-tetrahydro-pyran-2-yl)-ethyl]-phenyl}-ethyl)-3-methyl-urea

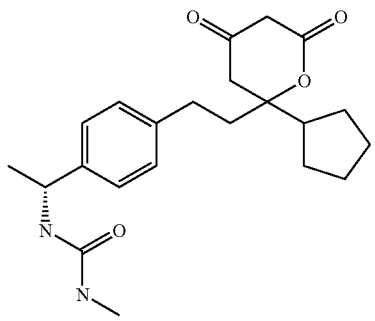

The title compound was prepared analogously to Example A(64), where (R) 1-[1-(4-Bromo-phenyl)-ethyl]-3-methyl-urea (described in Step 1 below) was substituted in place of 4-bromo-2-fluoro-1-isopropylbenzene in Step 3 of that example.

$^1$H NMR (DMSO-d$_6$): δ 1.09 (d, J=6.8 Hz, 3H), 1.32–1.47 (m, 8H), 1.69–1.73 (m, 2H), 1.91 (s, 3H), 2.12–2.18 (m, 1H), 2.33–2.42 (m, 2H), 3.16 (s, 2H), 4.45–4.57 (m, 1H), 4.80 (s, 1H), 5.4 (q, J=4.3 Hz, 1H), 6.10 (d, J=8.3 Hz, 1H), 6.93 (d, J=8.1 Hz, 2H), 7.00 (d, J=8.1 Hz, 2H), 11.17 (s, 1H). ESIMS (MH−) C$_{22}$H$_{30}$N$_2$O$_4$: 385.

Step 1

(R) 1-[1-(4-Bromo-phenyl)ethyl]-3-methyl-urea

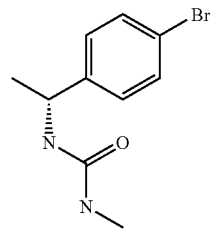

To a stirred solution of (R)-(+)-1-(4-bromophenyl)ethylamine (0.5 g, 2.49 mmol) in anhydrous CH$_2$Cl$_2$ was added methyl isocyanate (0.15 mL, 2.49 mmol). The resulting solution was stirred at 25° C. overnight. CH$_2$Cl$_2$ was evaporate and residue partitioned between EtOAC and 1 N HCl. The organic layer was washed with H$_2$O, brine and dried over Na$_2$SO$_4$. The solvent was removed in vacuo and the residue was purified by flash column chromatography (80% EtOAc in hexanes) to provide the desired product (0.60 g, 94%) as a white solid.

$^1$H NMR (CDCl$_3$) δ: 1.42 (d, J=7.0 Hz, 3H), 2.72 (d, J=4.9 Hz, 3H), 4.25 (brs, 1H), 4.73 (brs, 1H), 4.74–4.81 (m, 1H), 7.20 (d, J=8.3 Hz, 2H), 7.45 (d, J=8.3 Hz, 2H). ESIMS (MNa+): 258.

Example A(42)

N-(1-{4-[2-(2-Cyclopentyl-4,6-dioxo-tetrahydro-pyran-2-yl)-ethyl]-phenyl}-ethyl)-methanesulfonamide

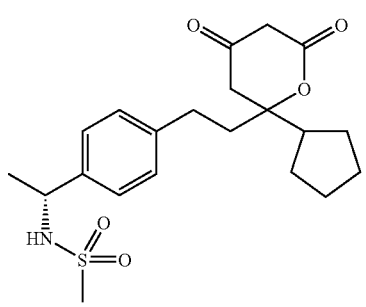

The title compound was prepared analogously to Example A(64), where (R)N-[1-(4-Bromo-phenyl)-ethyl]-methanesulfonamide (described in Step 1 below) was substituted in place of 4-bromo-2-fluoro-1-isopropylbenzene in Step 3 of that example.

$^1$H NMR (CDCl$_3$): δ 1.52 (d, J=7.2 Hz, 3H), 1.58–1.72 (m, 8H), 1.93–2.05 (m, 2H), 2.27–2.30 (m, 2H), 2.66 (s, 3H), 2.45–2.46 (m, 1H), 2.78 (s, 2H), 3.42 (d, J=2.7 Hz, 2H), 4.54 (d, J=3.0 Hz, 1H), 4.60–4.65 (m, 1H), 7.15 (d, J=8.3 Hz, 2H), 7.26 (d, J=8.3 Hz, 2H). Anal. Calcd. For C$_{21}$H$_{29}$NO$_5$S: C, 61.89; H, 7.17; N, 3.44. Found: C, 61.94; H, 7.40; N, 3.59. ESIMS (MH−): 406.

63

Step 1

(R)N-[1-(4-Bromo-phenyl)-ethyl]-methanesulfonamide

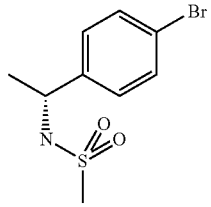

To a stirred solution of (R)-(+)-1-(4-bromophenyl)ethylamine (0.5 g, 2.49 mmol), in anhydrous $CH_2Cl_2$ (5 mL) under argon were added methane sulfonyl chloride (0.23 mL, 2.99 mmol) and Pyridine (0.30 mL, 3.73 mmol). The resulting solution was stirred at 25° C. for 3 hrs. The reaction mixture was quenched with 1 N HCl and extracted with EtOAc (30 mL). The organic phase was washed with brine (50 mL), dried over $Na_2SO_4$ and evaporated. The residue was purified by flash column chromatography (80% EtOAc in hexanes) to give the product (0.40 g, 58%) as a white solid.

$^1$H NMR ($CDCl_3$) δ: 1.52 (d, J=6.8 Hz, 3H), 2.67 (s, 3H), 4.61–4.72 (m, 2H), 7.24 (d, J=8.3 Hz, 2H), 7.51 (d, J=8.3 Hz, 2H). ESIMS (MNa+): 279.

Example A(43)

5-Methyl-isoxazole-3-carboxylic acid (1-{4-[2-(2-cyclopentyl-4,6-dioxo-tetrahydro-pyran-2-yl)-ethyl]-phenyl}-ethyl)-amide

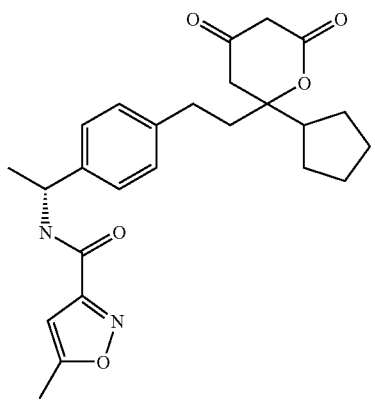

The title compound was prepared analogously to Example A(64), where (R)-5-Methyl-isoxazole-3-carboxylic acid [1-(4-bromo-phenyl)-ethyl]-amide (described in Step 1 below) was substituted in place of 4-bromo-2-fluoro-1-isopropyl-benzene in Step 3 of that example.

$^1$H NMR ($CDCl_3$): δ 1.56 (d, J=6.0 Hz, 3H), 1.58–1.89 (m, 8H), 1.91–2.05 (m, 2H), 2.25–2.29 (m, 1H), 2.47 (s, 3H), 2.64–2.67 (m, 2H), 2.77 (s, 2H), 3.42 (s, 2H), 5.19–5.25 (m, 1H), 6.42 (s, 1H), 6.99 (d, J=3.0 Hz, 1H), 7.13 (d, J=6.0 Hz, 2H), 7.29 (d, J=6.0 Hz, 2H). Anal. Calcd. For $C_{25}H_{30}N_2O_5$: C, 68.47; H, 6.90; N, 6.39. Found: C, 68.70; H, 7.10; N, 6.65. ESIMS (MH+): 439.

64

Step 1

(R)-5-Methyl-isoxazole-3-carboxylic acid [1-(4-bromo-phenyl)-ethyl]-amide

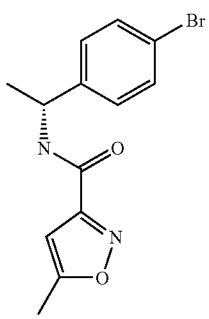

The title compound was prepared as described in Step 1 of Example A(39), where 5-methylisoxazole-3-carboxylic acid was substituted for ethyl hydrogen malonate. Yield 84%.

Example A(44)

6-(2-Cyclohexyl-ethyl)-6-cyclopentyl-dihydro-pyran-2,4-dione

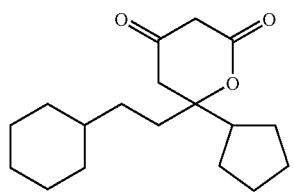

The title compound was prepared analogously to Example A(27), where 3-Cyclohexyl-1-cyclopentyl-propan-1-one (from Step 2 below), was substituted in place of 3-(4-Acetyl-3-chloro-phenyl)-1-cyclopentyl-propan-1-one of that example.

$^1$H NMR ($CDCl_3$): δ 1.17–2.17 (m, 24H), 2.69 (s, 2H), 3.39 (s, 2H) Anal. Calcd. For $C_{18}H_{28}O_3$: C, 73.93; H, 9.65. Found: C, 74.01; H, 9.80. ESIMS (MH+): 293.

Step 1

3-Cyclohexyl-thiopropionic acid S-pyridin-2-yl ester

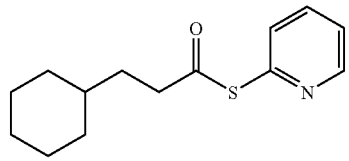

3-Cyclohexylpropionic acid (1 g, 6.40 mmol), triphenylphosphine (2.18 g, 8.32 mmol) and 2,2'-dipyridyl disulfide (1.83 g, 8.32 mmol) were combined successively in CH$_2$Cl$_2$ (20 mL). The reaction mixture was stirred 1 h and then loaded directly onto a column for purification by flash chromatography (20% EtOAc in hexanes) to give a residue. This residue was washed with hexanes (20 mL) and the solid, partially crystalline material was collected by filtration and air dried to give the product (1.43 g, 90%) as a white solid.

$^1$H NMR (CDCl$_3$): δ: 0.91–1.52 (m, 13 H), 2.1 (t, J=7.5 Hz, 2 H), 7.21–7.26 (m, 1 H), 7.53–7.56 (m, 1 H), 7.65–7.70 (m, 1 H), 8.54–8.56 (m, 1 H).

Step 2

3-Cyclohexyl-1-cyclopentyl-propan-1-one

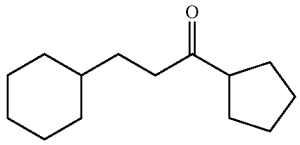

3-Cyclohexyl-thiopropionic acid S-pyridin-2-yl ester (1.43 g, 5.74 mmol) from Step 1 above was dissolved in dry THF (28 mL) and cooled to −78° C. A solution of cyclopentylmagnesium bromide in Et$_2$O (2.0 M, 3.01 mL, 6.02 mmol) was added dropwise. After stirring 1 h, the cooling bath was removed. The reaction mixture was quenched with 1 N HCl and extracted with EtOAc (100 mL). The organic phase was washed with brine (50 mL), dried over Na$_2$SO$_4$ and evaporated. The residue was purified by flash column chromatography (1% EtOAc in hexanes) to give the product (0.99 g, 83%) as clear oil.

$^1$H NMR (CDCl$_3$) δ: 0.82–1.84 (m, 21 H), 2.42–2.47 (m, 2H), 2.82–2.92 (m, 1 H).

Example A(45)

4'-[2-(2-Cyclopentyl-4,6-dioxo-tetrahydro-pyran-2-yl)-ethyl]-biphenyl-3-carbonitrile

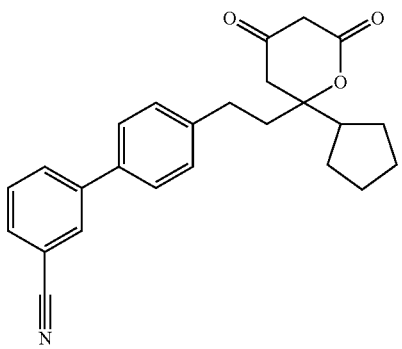

The title compound was prepared analogously to Example A(27), where 4'-Bromo-biphenyl-3-carbonitrile (described in Step 1 below), was substituted in place of 1-(4-Bromo-2-chloro-phenyl)-ethanone in Step 3 of that example.

$^1$H NMR (CDCl$_3$): δ 1.59–1.81 (m, 8H), 1.99–2.05 (m, 2H), 2.30–2.33 (m, 1H), 2.72–2.79 (m, 2H), 2.8 (s, 2H), 3.45 (s, 2H), 7.26 (d, J=7.4 Hz, 2H), 7.46–7.56 (s, 3H), 7.61–7.64 (m, 1H), 7.77–7.8 (m, 1H), 7.83–7.85 (m, 1H). Anal. Calcd. For C$_{25}$H$_{25}$O$_3$: C, 77.49; H, 6.50; N, 3.61. Found: C, 77.63; H, 6.75; N, 3.80. ESIMS (MH+): 388. IR (cm$^{-1}$): 3397, 2955, 2229, 1659, 1227.

Step 1

4'-Bromo-biphenyl-3-carbonitrile

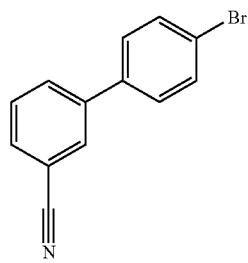

To a magnetically stirring solution of 3-cyanophenyl boronic acid (0.62 g, 4.24 mmol) and 1-bromo-4-iodobenzene (1.0 g, 3.53 mmol) in anhydrous DMF (7.0 mL), under argon at room temperature, was added 2M sodium carbonate solution (7.0 mL) followed by Pd(PPh$_3$)$_4$ (0.21 g, 0.18 mmol). The resulting mixture was heated to 75° C. overnight. The resulting dark reaction mixture was cooled to room temperature filtered to remove the solids and the resultant filtrate was poured into water (50 mL) and extracted with EtOAc (2×25 mL). The organics were washed with water (50 mL) and brine (50 mL) then dried over Na$_2$SO$_4$, filtered and concentrated. The crude residue was purified by flash chromatography (5% EtOAc in Hexanes) to yield the intermediate bromide as a white solid (0.36 g, 33%).

$^1$H NMR (CDCl$_3$): δ $^1$H NMR (CDCl$_3$) δ: 7.43 (d, J=7.4 Hz, 2H), 7.53–7.67 (m, 4H), 7.76–7.84 (m, 2H).

Example A(46)

2-[2-(2-Cyclopentyl-4,6-dioxo-tetrahydro-pyran-2-yl)-ethyl]-benzonitrile

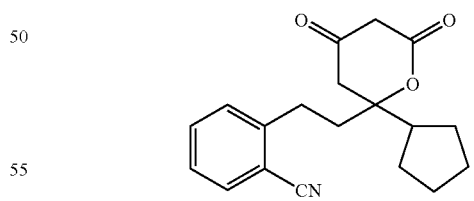

The title compound was prepared analogously to Example A(27), where 2-bromobenzonitrile was substituted in place of 1-(4-Bromo-2-chloro-phenyl)-ethanone in Step 3 of that example.

$^1$H NMR (CDCl$_3$): δ 1.59–1.81 (m, 8H), 1.99–2.05 (m, 2H), 2.30–2.33 (m, 1H), 2.72–2.77 (m, 2H), 2.81 (s, 2H), 3.48 (s, 2H), 7.26–7.85 (m, 4H) Anal. Calcd. For C$_{19}$H$_{21}$NO$_3$: C, 73.29; H, 6.80; N, 4.50. Found: C, 73.17; H, 6.84; N, 4.42. ESIMS (MH−): 310.

Example A(47)

6-Cyclopentyl-6-(2-naphthalen-2-yl-ethyl)-dihydro-pyran-2,4-dione

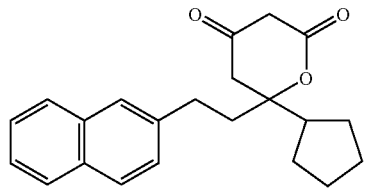

The title compound was prepared analogously to Example A(64), where 2-bromonaphatalene was substituted in place of 4-bromo-2-fluoro-1-isopropylbenzene in Step 3 of that example.

$^1$H NMR (CDCl$_3$): δ 1.5–1.9 (m, 8H), 1.93 (m, 2H), 2.24 (m, 1H), 2.9 (s, 2H), 2.90 (t, J=8.4 Hz, 2H), 3.5 (s, 2H), 7.2 (m, 1H), 7.4 (m, 2H), 7.6 (s, 1H), 7.8 (m 3H). Anal. Calcd. For C$_{22}$H$_{24}$O$_3$: C, 78.54; H, 7.19. Found: C, 78.70; H, 7.25. ESIMS (MH+): 337.

Example A(48)

6-Cyclopentyl-6{2-[4-(tetrahydro-pyran-2-yloxy)-phenyl]-ethyl}-dihydro-pyran-2,4-dione

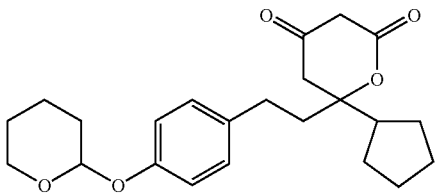

The title compound was prepared analogously to Example A(64), where 2-(4-bromophenoxyl) tetrahydro 2H-pyran was substituted in place of 4-bromo-2-fluoro-1-isopropylbenzene in Step 3 of that example.

$^1$H NMR (CDCl$_3$): δ 1.28–1.98 (m, 16H), 2.2–2.31 (m, 1H), 2.62 (t, J=8.6, 2H), 2.76 (s, 2H), 3.42 (s, 2H), 3.55–3.61 (m, 1H), 3.86–3.94 (m, 1H), 5.38 (t, J=3.1, 1H), 6.97 (d, J=8.7, 2H), 7.05 (d, J=8.7, 2H). Anal. Calcd. For C$_{23}$H$_{30}$O$_5$·0.5H$_2$O: C, 69.85; H, 7.90. Found: C, 70.19; H, 8.01. ESIMS (MNa+): 409.

Example A(49)

2{4-[2-(2-Cyclopentyl-4,6-dioxo-tetrahydro-pyran-2-yl)-ethyl]-phenyl}-N-methyl-isobutyramide

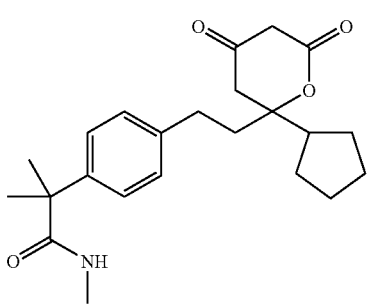

The title compound was prepared analogously to Example A(64), where 2-(4-Bromo-phenyl)-N-methyl-isobutyramide (described in Step 1 below), was substituted in place of 4-bromo-2-fluoro-1-isopropylbenzene in Step 3 of that example.

$^1$H NMR (CDCl$_3$): δ 1.55 (s, 6H); 1.59–1.73 (m, 8H), 1.94–2.05 (m, 2H), 2.28–2.35 (m, 1H), 2.67–2.69 (m, 2H), 2.76 (s, 3H), 2.76 (s, 2H), 3.40 (s, 2H), 5.2 (brs, 1H), 7.14 (d, J=8.3, 2H), 7.30 (d, J=8.3, 2H). Anal. Calcd. For C$_{23}$H$_{31}$NO$_4$: C, 71.66; H, 8.10; N, 3.63. Found: C, 71.80; H, 8.35; N, 3.77. ESIMS (MH+): 386.

Step 1

2-(4-Bromo-phenyl)-N-methyl-isobutyramide

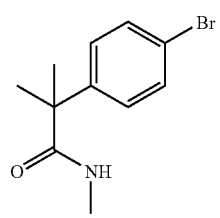

The title compound was prepared as described in Step 1 of Example A(39), where 2-(4-bromophenyl)-2-methyl propionic acid was substituted for ethyl hydrogen malonate and methyl amine was substituted instead of (R)-(+)-1-(4-bromophenyl)ethylamine on that example. Yield 84%.

$^1$H NMR (CDCl$_3$) δ: 1.55 (s, 6H), 2.72 (d, J=4.6 Hz, 3H), 5.15 (brs, 1H), 7.22–7.26 (m, 2H), 7.46–7.50 (m, 2H).

Example A(50)

6-Cyclopentyl-6-{2-[4-(5-phenyl-[1,3,4]oxadiazol-2-yl)-phenyl]-ethyl}-dihydro-pyran-2,4-dione

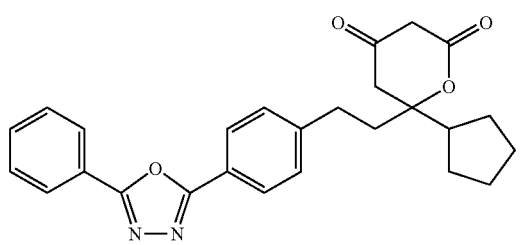

The title compound was prepared analogously to Example A(64), where 2-(4-bromophenyl)-5-phenyl-1,2,3-oxadiazole was substituted in place of 4-bromo-2-fluoro-1-isopropylbenzene in Step 3 of that example.

$^1$H NMR (CDCl$_3$): δ 1.44–1.82 (m, 8H), 1.99–2.05 (m, 2H), 2.30–2.34 (m, 1H), 2.76–2.79 (m, 2H), 2.81 (s, 2H), 3.46 (s, 2H), 7.32 (d, J=8.3, 2H), 7.51–7.58 (m, 3H), 8.07 (d, J=8.3, 2H), 8.13–8.16 (m, 2H). Anal. Calcd. For C$_{26}$H$_{26}$N$_2$O$_4$·0.5H$_2$O: C, 71.05; H, 6.19; N, 6.37. Found: C, 71.32; H, 6.06; N, 6.45. ESIMS (MH+): 431.

Example A(51)

2-{4-[2-(2-Cyclopentyl-4,6-dioxo-tetrahydro-pyran-2-yl)-ethyl]-phenyl)-N-ethyl-isobutyramide

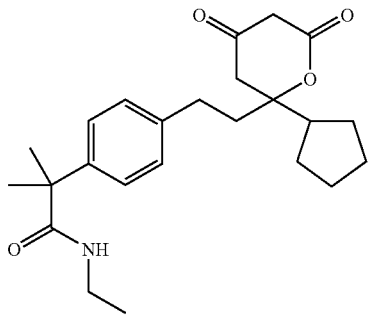

The title compound was prepared analogously to Example A(64), where 2-(4-Bromo-phenyl)-N-ethyl-isobutyramide (described in Step 1 below) was substituted in place of 4-bromo-2-fluoro-1-isopropylbenzene in Step 3 of that example.

$^1$H NMR (CDCl$_3$): δ 1.01 (t, J=7.2, 3H), 1.54 (s, 6H); 1.63–1.7 (m, 8H), 1.92–1.99 (m, 2H), 2.29–2.32 (m, 1H), 2.69 (t, J=8.3, 2H), 2.76 (s, 2H), 3.21 (q, J=7.2, 5.28, 2H), 3.40 (s, 2H), 5.4 (brs, 1H), 7.12 (d, J=8.3, 2H), 7.28 (d, J=8.3, 2H). Anal. Calcd. For C$_{24}$H$_{33}$NO$_4$: C, 72.15; H, 8.32; N, 3.51. Found: C, 72.40; H, 8.60; N, 3.77. ESIMS (MH+): 400.

Step 1

2-(4-Bromo-phenyl)-N-ethyl-isobutyramide

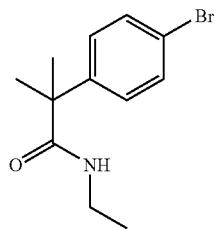

The title compound was prepared as described in Step 1 of Example A(39), where 2-(4-bromophenyl)-2-methyl propionic acid was substituted for ethyl hydrogen malonate and ethyl amine was substituted for (R)-(+)-1-(4-bromophenyl)ethylamine on that example. Yield 82%.

$^1$H NMR (CDCl$_3$) δ: 1.01 (t, J=5.3 Hz, 3H), 1.55 (s, 6H),), 3.2 (q, J=7.0, 5.3, 2H), 5.15 (brs, 11), 7.22–7.26 (m, 2H), 7.46–7.50 (m, 2H).

Example A(52)

6–4-[2-(2-Cyclopentyl-4,6-dioxo-tetrahydro-pyran-2-yl)-ethyl]-2-fluoro-phenoxy}-6-methyl-3,5-dioxo-heptanoic acid methyl ester

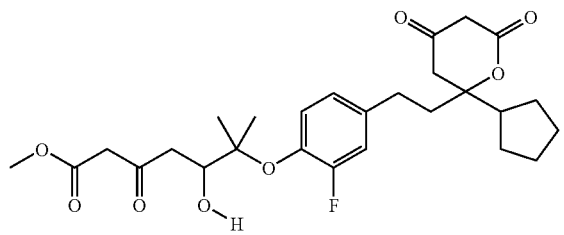

The title compound was prepared analogously to Example A(27), where 2-(4-Bromo-2-fluoro-phenoxy)-2-methyl-propionic acid methyl ester (described in Step 1 below) was substituted in place of 1-(4-Bromo-2-chloro-phenyl)-ethanone in Step 3 of that example.

$^1$H NMR (CDCl$_3$): δ 1.48 (s, 3H); 1.55 (s, 3H), 1.58–1.77 (m, 8H), 1.90–1.97 (m, 2H), 2.22–2.30 (m, 1H), 2.60–2.88 (m, 6H), 3.39 (s, 2H), 3.43 (s, 1H), 3.72 (s, 1H), 3.75 (s, 3H), 6.76–7.01 (m, 3H). ESIMS (MH+): 505.

Step 1

2-(4-Bromo-2-fluoro-phenoxy)-2-methyl-propionic acid methyl ester

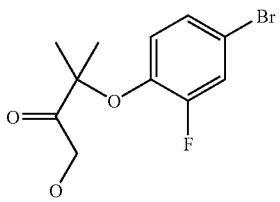

To a solution of 4-Bromo-2-fluorophenol (1 g, 5.24 mmol) and methyl □-bromobutyrate (1.89 g, 10.47 mmol) in DMF (20 mL) was added K$_2$CO$_3$ (3.6 g, 26 mmol). The resultant slurry was heated to 100° C. under argon for 12 h. DMF was evaporate and residue partitioned between EtOAC and 1 N HCl. The organic layer was washed with H$_2$O, and brine then dried over Na$_2$SO$_4$. The solvent was removed in vacuo and the residue was purified by flash column chromatography (10% EtOAc in hexanes) to provide the desired product (1.17 g, 77%) as a white solid.

$^1$H NMR (CDCl$_3$) δ: 1.57 (s, 6H), 3.79 (s, 3H),), 6.86 (t, J=8.7, 1H), 7.12–7.16 (m, 1H), 7.23–7.27 (m, 1H).

Example A(53)

2-{2-Chloro-4-[2-(2-cyclopentyl-4,6-dioxo-tetrahydro-pyran-2-yl)-ethyl]-phenoxy}-2-methyl-propionic acid methyl ester

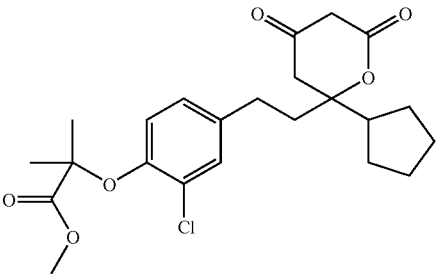

REVERSE ADDITION MODIFICATION: NaH (60% in mineral oil, 0.13 g, 3.13 mmol) was suspended in THF (10 mL) and cooled to 0° C. Methylacetoacetate (0.19 mL, 1.72 mmol) was slowly added via syringe and the reaction mixture stirred 20 min. A solution of n-BuLi in hexanes (1.6 M, 1.95 mL, 3.13 mmol) was added dropwise and the resulting mixture was stirred an additional 20 min. The resultant slurry was added via canula to a solution of 2-[2-Chloro-4-(3-cyclopentyl-3-oxo-propyl)-phenoxy]-2-methyl-propionic acid methyl ester (0.85 g, 2.41 mmol) from Step 1 below in THF (2 mL) pre-cooled to 0° C. After stirring 1 h, the reaction mixture was quenched with 1N HCl (10 mL) and extracted with EtOAc (10 mL). The organic phase was dried over Na$_2$SO$_4$ and evaporated. The crude organic product was then dissolved in 5 mL of MeOH, and 0.67 grams of finely powdered K$_2$CO$_3$ (anhydrous) was added. The slurry was stirred at 60° C. for 1.5 h, and then concentrated by rotary evaporation. The residue was dissolved in 10 mL of water and 10 mL of EtOAc, and acidified with 2N HCl. The aqueous solution was extracted 3 times with 5 mL of EtOAc. The organics were combined, and dried with Na$_2$SO$_4$. After filtering the residue was purified by flash column chromatography (50% EtOAc in hexanes) to give the product (0.22 g, 25%) as a white foam.

$^1$H NMR (CDCl$_3$): δ 1.60 (s, 6H); 1.55–1.81 (m, 8H), 1.88–1.96 (m, 2H), 2.23–2.26 (m, 1H), 2.60 (t, J=7.9, 2H), 2.75 (d, J=2.6, 2H), 3.43 (s, 2H), 3.80 (s, 3H), 6.79 (d, J=8.3, 1H), 6.90 (d, J=2, 1H), 7.15 (d, J=2, 1H). Anal. Calcd. For C$_{23}$H$_{29}$ClO$_6$: C, 63.23; H, 6.69. Found: C, 63.20; H, 6.95. ESIMS (MH+): 437.

Step 1

2-[2-Chloro-4-(3-cyclopentyl-3-oxo-propyl)-phenoxy]-2-methyl-propionic acid methyl ester

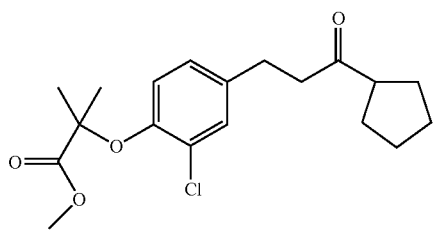

The title compound was prepared analogously to Step 1 from example A(52), where 3-(3-Chloro-4-hydroxy-phenyl)-1-cyclopentyl-propan-1-one was substituted for 4-Bromo-2-fluorophenol in Step 1 of that example. Yield 74%.

$^1$H NMR (CDCl$_3$) δ: 1.59 (s, 6H), 1.61–1.80 (m, 9H), 2.70–2.84 (m, 4H), 3.79 (s, 3H),), 6.78 (d, J=8.4, 1H), 6.93 (dd, J=8.4, 2.3, 1H), 7.18 (d, J=2.3, 1H).

Example A(54)

2-Chloro-4-[2-(2-cyclopentyl-4,6-dioxo-tetrahydropyran-2-yl)-ethyl]-phenoxy)-acetic acid

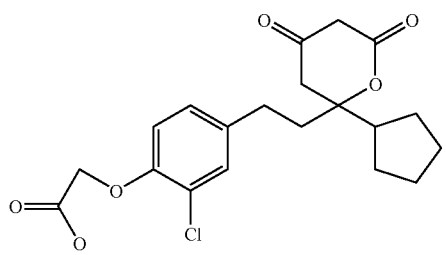

The title compound was prepared analogously to Example A(53), where [2-Chloro-4-(3-cyclopentyl-3-oxo-propyl)-phenoxy]-acetic acid methyl ester (described in Step 1 below) was substituted in place of 2-[2-Chloro-4-(3-cyclopentyl-3-oxo-propyl)-phenoxy]-2-methyl-propionic acid methyl ester) of that example.

$^1$H NMR (CDCl3): δ 1.47–1.74 (s, 8H); 1.89–1.96 (m, 2H), 2.23–2.29 (m, 1H), 2.62 (t, 1 J=8.3, 2H), 2.76 (s, 2H), 3.43 (s, 2H), 4.72 (s, 2H), 6.81 (d, J=8.3, 1H), 6.98 (dd, J=8.3, 2.3, 1H), 7.18 (d, J=2.3, 1H).
ESIMS (MH+): 395.

Step 1

[2-Chloro-4-(3-cyclopentyl-3-oxo-propyl)-phenoxy]-acetic acid methyl ester

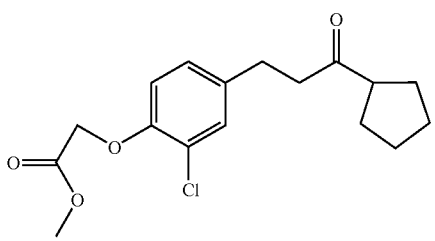

The title compound was prepared analogously to Step 1 from Example A(52), where 3-(3-Chloro-4-hydroxy-phenyl)-1-cyclopentyl-propan-1-one was substituted for 4-Bromo-2-fluorophenol and methyl bromo acetate was substituted for methyl □-bromobutyrate in Step 1 of that example. Yield 78%.

$^1$H NMR (CDCl$_3$) δ: 1.55–1.77 (m, 9H), 2.70–2.85 (m, 4H), 3.80 (s, 3H),), 4.68 (sm 2H), 6.75 (d, J=8.5, 1H), 7.0 (dd, J=8.5, 2.2, 1H), 7.21 (d, J=2.2, 1H).

Example A(55)

2-{4-[2-(2-Cyclopentyl-4,6-dioxo-tetrahydro-pyran-2-yl)-ethyl]-2-fluoro-phenoxy}-2-methyl-propionic acid methyl ester

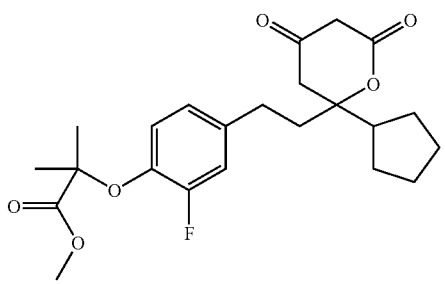

The title compound was prepared analogously to Example A(27), where 2-(4-Bromo-2-fluoro-phenoxy)-2-methyl-propionic acid methyl ester (described in Step 1 of Example A(52), was substituted in place of 1-(4-Bromo-2-chloro-phenyl)-ethanone in Step 3 of that example.

$^1$H NMR (CDCl3): δ 1.56 (s, 6H); 1.58–1.73 (m, 8H), 1.90–1.97 (m, 2H), 2.20–2.23 (m, 1H), 2.62 (t, J=8.1, 2H), 2.75 (s, 2H), 3.43 (s, 2H), 3.79 (s, 3H), 6.80–6.92 (m, 2H), 7.32–7.38 (m, 1H). Anal. Calcd. For C$_{23}$H$_{29}$FO$_6$.0.5H$_2$O: C, 65.00; H, 7.00. Found: C, 65.30; H, 7.32. ESIMS (MH+): 421.

Example A(56)

6-Cyclopentyl-6-(2-{4-[1-methyl-1-(5-methyl-[1,2,4]oxadiazol-3-yl)-ethyl]-phenyl}-ethyl)-dihydro-pyran-2,4-dione

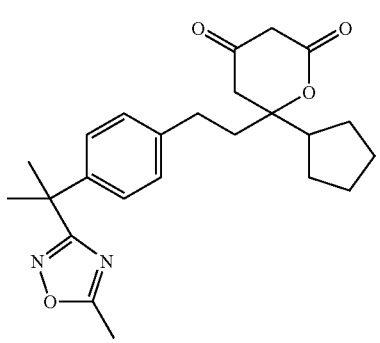

The title compound was prepared analogously to Example A(27), where 3-[1-(4-Bromo-phenyl)-1-methyl-ethyl]-5-methyl-[1,2,4]oxadiazole (described in Step 1 below) was substituted in place of 1-(4-Bromo-2-chloro-phenyl)-ethanone in Step 3 of that example.

$_1$H NMR (CDCl3): δ 1.59–1.78 (m 9H); 1.85–1.98 (m, 2H), 2.18 (s, 6H), 2.20–2.31 (m, 1H), 2.52 (s, 3H), 2.61–2.67 (m, 1H), 2.77 (s, 2H), 3.42 (s, 2H), 7.09 (d, J=8.3, 2H), 7.24 (d, J=8.3, 2H). ESIMS (MH+): 411.

Step 1

3-[1-(4-Bromo-phenyl)-1-methyl-ethyl]-5-methyl-[1,2,4]oxadiazole

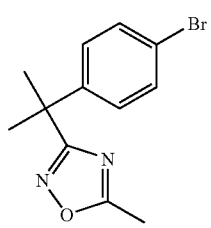

To a solution of 2-(4-bromophenyl)-2-methylpropionitrile (3 g, 13.38 mmol)) in EtOH (40 mL) was added hydroxylamine HCl (4.65 g, 66.93 mmol) and K$_2$CO$_3$ (9.25 g, 66.93 mmol). The reaction mixture was stirred at room temperature overnight. The resultant white precipitate was eliminated by filtration and the filtrate was concentrated to a yellow oil which was dissolved in pyridine (16 mL). Acetic anhydride (3.79 mL, 40.14 mol) was added and the reaction was stirred to reflux for 2 hours. The solution was quenched with 2N HCl (50 mL) and extracted 3 times with EtOAc (20 mL). The organics were combined, and dried with Na$_2$SO$_4$. The solvent was removed under reduced pressure and the residue was purified by flash chromatography (40% EtOAc in Hexanes) to yield the product as a white foam (0.88 g, 30%).

$^1$H NMR (CDCl3): δ 1.71 (s, 6H); 2.53 (s, 3H), 7.18–7.54 (m, 4H).

Example A(57)

6-(4-Cyclohexyl-butyl)-6-cyclopentyl-dihydro-pyran-2,4-dione

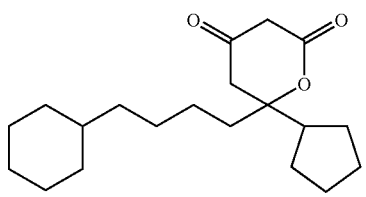

The title compound was prepared analogously to Example A(44), where 4-Cyclohexyl-butyric acid was substituted in place of 3-Cyclohexylpropionic acid in Step 1 of that example.

$^1$H NMR (CDCl$_3$): δ 0.75–1.9 (m, 26H), 2–2.25 (m, 2H), 2.69 (s, 2H), 3.40 (s, 2H). Anal. Calcd. For C$_{20}$H$_{32}$O$_3$: C, 74.96; H, 10.06. Found: C, 75.04; H, 10.34. ESIMS (MH+): 321.

Example A(58)

6-Cyclopentyl-6-[2-(4-difluoromethoxy-phenyl)-ethyl]-dihydro-pyran-2,4-dione

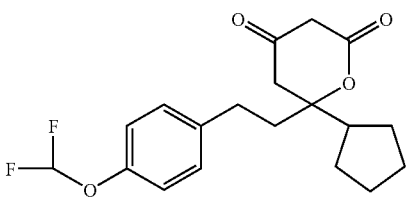

The title compound was prepared analogously to Example A(64), where 4-(difluoromethoxy) bromobenzene was substituted in place of 4-bromo-2-fluoro-1-isopropylbenzene in Step 3 of that example.

$^1$H NMR (CDCl3): δ 1.5–1.9 (m, 8H), 1.93 (m, 2H), 2.24 (m, 2H), 2.9 (s, 2H), 2.93 (t, J=8.4 Hz, 2H), 3.2 (s, 2H), 7.2 (d, J=8.3, 2H), 7.4 (d, J=8.3, 2H). ESIMS (MH+): 353.

Example A(59)

6-Cyclopentyl-6-[2-(2,2,3,3-tetrafluoro-2,3-dihydro-benzo[1,4]dioxin-6-yl)-ethyl]-dihydro-pyran-2,4-dione

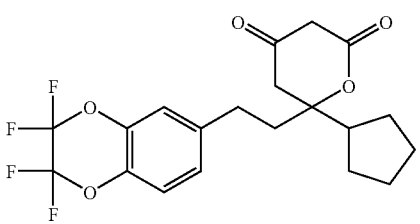

The title compound was prepared analogously to Example A(64), where 6-bromo-2,2,3,3-tetrafluoro-1,4-benzodioxene was substituted in place of 4-bromo-2-fluoro-1-isopropylbenzene in Step 3 of that example.

$^1$H NMR (CDCl3): δ 1.63–1.75 (m, 8H), 1.90–1.97 (m, 2H), 2.24–2.29 (m, 1H), 2.64–2.71 (m, 2H), 2.77 (d, J=4.9, 2H), 3.43 (d, J=2.4, 2H), 6.90–6.97 (m, 2H), 7.07 (d, J=7.5, 1H). Anal. Calcd. For $C_{20}H_{20}F_4O_5$: C, 57.69; H, 4.84. Found: C, 57.76; H, 4.90. ESIMS (MH+): 417.

Example A(60)

6-Cyclopentyl-6-[2-(4-propoxy-phenyl)-ethyl]-dihydro-pyran-2,4-dione

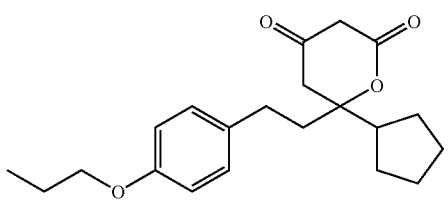

The title compound was prepared analogously to Example A(44), where 3-(4-Propoxy-phenyl)-propionic acid (described in Step 1 below) was substituted in place of 3-Cyclohexylpropionic acid in Step 3 of that example of that example.

$^1$H NMR (dmso-$d_6$): δ 0.96 (t, J=7.4, 3H), 1.34–1.73 (m, 10H), 1.87–1.90 (m, 2H), 2.25–2.35 (m, 1H), 2.46–2.55 (m, 2H), 3.33 (s, 2H), 3.87 (t, J=6.5, 2H), 4.98 (s, 2H), 6.82 (d, J=8.4, 2H), 7.07 (d, J=8.4, 2H). Anal. Calcd. For $C_{21}H_{28}O_4$: C, 73.23; H, 8.19. Found: C, 73.24; H, 8.30. ESIMS (MH+): 345.

Step 1

3-(4-Propoxy-phenyl)-propionic acid

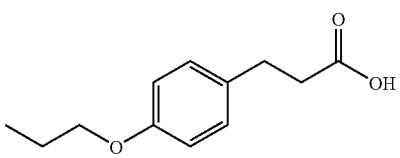

To a solution of methyl 3-(hydroxyphenyl)propionate (15 g, 83.24 mmol) and iodopropane (12.14 mL, 124.5 mmol) in DMF (80 mL) was added $K_2CO_3$ (34 g, 249.7 mmol). The resultant slurry was stirred vigorously and heated to 60° C. under argon for 12 h. DMF was evaporated and residue partitioned between EtOAC and 1N HCl. The organic layer was washed with $H_2O$, and brine then dried over $Na_2SO_4$. The solvent was removed in vacuo and the residue was purified by flash column chromatography (10% EtOAc in hexanes) to provide the desired product (17 g, 98%) as a clear oil. The resultat oil was dissolved in THF (150 mL), and 2M NaOH (68 mL) was added. The reaction was stirred overnight at room temperature. THF was evaporated and residue acidified with concentrated HCl and extracted 3 times with EtOAC, (100 mL). The organic layer was washed with $H_2O$, dried over $Na_2SO_4$ and concentrated to a white solid which was recrystalized from hexanes to provide the desired product (14.06 g 82%).

$^1$H NMR (CDCl$_3$) δ: 1.04 (t, J=7.2, 3H), 1.76–1.85 (m, 2H), 2.64 (t, J=8.1, 2H), 2.90 (t, J=8.1, 2H), 3.89 (t, J=6.6, 2H), 6.82 (d, J=8.6, 2H), 7.10 (d, J=8.6, 2H).

Example A(61)

6-[2-(2-acetyl-4-methoxyphenyl)ethyl]-6-cyclopentyldihydro-2H-pyran-2,4(3H)-dione

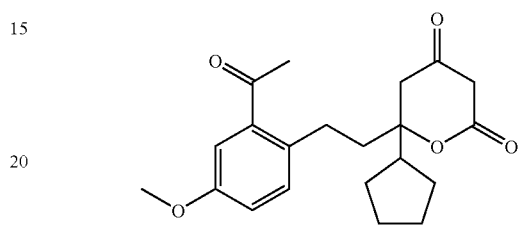

The title compound was prepared analogously to Example A(64), where 1-(2-bromo-5-methoxyphenyl)ethanone was substituted in place of 4-bromo-2-fluoro-1-isopropylbenzene.

$^1$H NMR (300 MHz, CDCL$_3$) δ ppm 1.41 (m, 1 H), 1.61 (m, 5 H), 1.78 (m, 2 H), 1.88 (ddd, J=14.0, 12.2, 5.0 Hz, 1 H), 2.02 (td, J=12.25 4.5 Hz, 1 H), 2.36 (m, 1 H), 2.56 (s, 3 H), 2.72 (td, J=12.2, 4.7 Hz, 1 H), 2.76 (d, J=16.4 Hz, 1 H), 2.84 (d, J=16.4 Hz, 1 H), 2.92 (td, J=12.2, 4.6 Hz, 1 H), 3.42 (d, J=21.2 Hz, 1 H), 3.62 (d, J=21.2 Hz, 1 H), 3.83 (s, 3 H), 6.97 (dd, J=8.5, 2.8 Hz, 1 H), 7.13 (d, J=8.5 Hz, 1 H), 7.24 (d, J=2.8 Hz, 1 H). HRMS calcd. For $C_{21}H_{26}O_5Na$ (M+Na): 381.1672. Found: 381.1666.

Example A(62)

6-cyclopentyl-6-[2-(4-methoxy-2-propionylphenyl) ethyl]dihydro-2H-pyran-2,4(3H)-dione

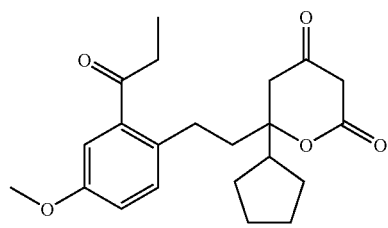

The title compound was prepared analogously to Example A(64), where 1-(2-bromo-5-ethoxyphenyl)ethanone was substituted in place of 4-bromo-2-fluoro-1-isopropylbenzene.

$^1$H NMR (300 MHz, CDCl$_3$) δ ppm 1.17 (t, J=7.2 Hz, 3 H), 1.40 (m, 1 H), 1.73 (m, 8 H), 2.03 (m, 1 H), 2.35 (m, 1 H), 2.68 (td, J=12.3, 4.8 Hz, 1 H), 2.79 (m, 2 H), 2.89 (m, 3 H), 3.42 (d, J=21.1 Hz, 1 H), 3.63 (d, J=21.1 Hz, 1 H), 3.82 (s, 3 H), 6.95 (dd, J=8.4, 2.7 Hz, 1 H), 7.13 (d, J=8.4 Hz, 1 H), 7.16 (d, J=2.7 Hz, 1 H). Anal. Calcd. For $C_{22}H_{28}O_5$: C, 70.94; H, 7.58; O, 21.48. Found: C, 70.72; H, 7.60; O, 21.33.

Example A(63)

6-[2-(3-chloro-4-isopropylphenyl)ethyl]-6-cyclopentyldihydro-2H-pyran-2,4(3H)-dione

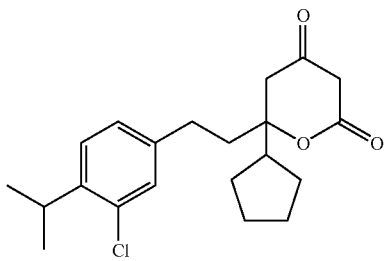

The title compound was prepared analogously to Example A(82), where 4-bromo-2-chloro-1-isopropylbenzene was substituted in place of 2-Bromopyridine.

$^1$H NMR (300 MHz, CDCl$_3$) δ: 1.22 (d, J=6.78 Hz, 6 H), 1.60–1.80 (m, 8 H), 1.91–1.98 (m, 2 H), 2.22–2.30 (m, 1 H), 2.59–2.66 (m, 2 H), 2.76 (s, 2 H), 3.31–3.38 (m, 1 H), 3.43 (s, 2 H), 7.01 (dd, J=8.01, 1.79 Hz, 1 H), 7.12 (d, J=1.88 Hz, 1 H), 7.20 (d, J=7.91 Hz, 1 H). HRMS calcd for C$_{21}$H$_{27}$ClO$_3$Na: 385.1541. Found: 385.1543.

Example A(64)

6-cyclopentyl-6-[2-(3-fluoro-4-isopropylphenyl)ethyl]dihydro-2H-pyran-2,4(3H)-dione

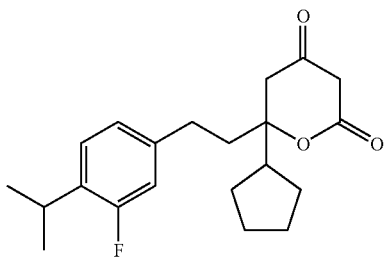

6-[2-cyclopentyl-4-(3-fluoro-4-isopropylphenyl)-2-hydroxybut-3-ynyl]-2,2-dimethyl-4H-1,3-dioxin-4-one (3.83 g, 9.6 mmol, described in Step 3 below) dissolved in anhydrous MeOH (45 mL) was added Pd(OH)$_2$ (1.26 g). The reaction was stirred under H$_2$ (1 atm) for 12 hours. The mixture was filtered through a pad of celite. The solvent was removed in vacuo and the residue was taken directly into next step without further purification.

The crude mixture from previous Step was dissolved in anhydrous MeOH (70 mL) and treated with K$_2$CO$_3$ (3.97 g, 28.8 mmol) at 45° C. for 1 hour before it was cooled down to 25° C. The mixture was diluted with EtOAc (200 mL) and the combined organic extracts were washed with aqueous NH$_4$Cl, brine, and dried over Na$_2$SO$_4$. The solvent was removed in vacuo and the residue was purified by flash column chromatography (0–40% EtOAc in hexanes) to give the desired product (2.2 g, 65% yield).

$^1$H NMR (CDCl$_3$, 300 MHz) δ: 1.23 (d, J=6.97 Hz, 4 H), 1.64–1.80 (m, 8 H), 1.91–1.98 (m, 2 H), 2.22–2.30 (m, 1 H), 2.61–2.67 (m, 2 H), 2.77 (s, 2 H), 3.14–3.23 (m, 1 H), 3.42 (s, 2 H), 6.79 (dd, J=11.21, 1.60 Hz, 1 H), 6.87 (dd, J=7.82, 1.60 Hz, 1 H), 7.15 (t, J=7.91 Hz, 1 H). HRMS calcd for C$_{21}$H$_{28}$FO$_3$ (M+H$^+$): 347.2017. Found: 347.2021.

Step 1

2-(4-bromo-2-fluorophenyl)propan-2-ol

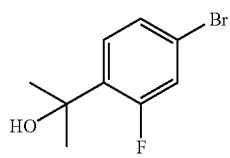

A solution of methyl 4-bromo-2-fluorobenzoate (8.0 g, 34.3 mmol) in anhydrous Et$_2$O (85 mL) was treated with MeMgBr (3.0 M in THF, 30 mL). The resulting solution was stirred at 25° C. for 3 hours before it was quenched by the addition of H$_2$O (10 mL). The mixture was extracted with EtOAc (50 mL) three times and the combined organic extracts were washed with aqueous NH$_4$Cl, brine, and dried over Na$_2$SO$_4$. The solvent was removed in vacuo and the residue was purified by flash column chromatography (0–25% EtOAc in hexanes) to give the desired product (7.2 g, 91% yield).

$^1$H NMR (CDCl$_3$, 300 MHz) δ: 1.62 (s, 6 H), 7.19–7.22 (m, 1 H), 7.27–7.29 (m, 1 H), 7.45–7.49 (m, 1 H).

Step 2

4-bromo-2-fluoro-1-isopropylbenzene

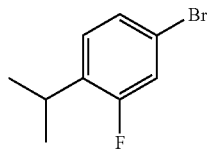

To a solution of 2-(4-bromo-2-fluorophenyl)propan-2-ol (7.6 g, 32.8 mmol) dissolved in anhydrous CH$_2$Cl$_2$ (300 mL) at 25° C. was added triethylsilane (7.8 mL, 49.1 mmol), followed by trifluoroacetic acid (25 mL, 328 mmol). The resulting solution was stirred at that temperature for 45 min. The solvent was removed in vacuo and the residue was purified by flash column chromatography (0–10% EtOAc in hexanes) to give the desired product (5.7 g, 80% yield).

$^1$H NMR (CDCl$_3$, 400 MHz) δ: 1.23 (d, J=6.82 Hz, 3 H), 3.15–3.22 (m, 1 H), 7.11 (t, J=8.08 Hz, 1 H), 7.17 (dd, J=9.85, 1.77 Hz, 1 H), 7.22 (d, J=8.34 Hz, 1 H).

Step 3

6-[2-cyclopentyl-4-(3-fluoro-4-isopropylphenyl)-2-hydroxybut-3-ynyl]-2,2-dimethyl-4H-1,3-dioxin-4-one

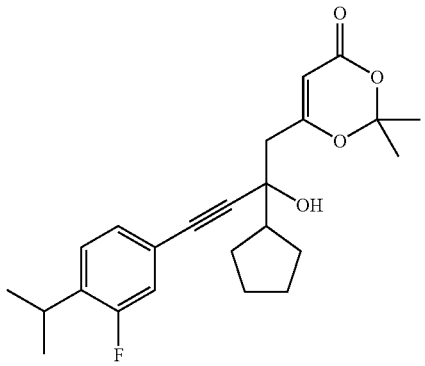

4-Bromo-2-fluoro-1-isopropylbenzene (5.0 g, 23.2 mmol), 6-(2-cyclopentyl-2-hydroxybut-3-ynyl)-2,2-dimethyl-4H-1,3-dioxin-4-one (5.56 g, 21.0 mmol) were dissolved in anhydrous DMF (30 mL). To this solution, CuI (120 mg, 0.63 mmol), Pd(PPh$_3$)$_2$Cl$_2$ (0.59 g, 0.84 mmol), and diisopropylamine (60 mL), were added sequentially. The mixture was then heated at 90° C. for 20 min before it was cooled down to 25° C. The reaction was diluted with EtOAc (150 mL) and washed with aqueous NH$_4$Cl, brine, and dried over Na$_2$SO$_4$. The solvent was removed in vacuo and the residue was purified by flash column chromatography (040% EtOAc in hexanes) to give the desired product (7.5 g, 81% yield).

$^1$H NMR (CDCl$_3$, 300 MHz) δ: 1.22–1.28 (m, 8 H), 1.69–1.74 (m, 10 H), 1.80–1.86 (m, 2 H), 2.19–2.26 (m, 1 H), 2.62–2.70 (m, 2 H), 3.18–3.25 (m, 1 H), 5.46 (s, 1 H), 7.00 (dd, J=10.61, 1.52 Hz, 1 H), 7.09–7.11 (m, 1 H), 7.18 (t, J=7.71 Hz, 1 H).

Example A(65)

6-cyclopentyl-6-[2-(3-ethyl-4-fluorophenyl)ethyl]dihydro-2H-pyran-2,4(3H)-dione

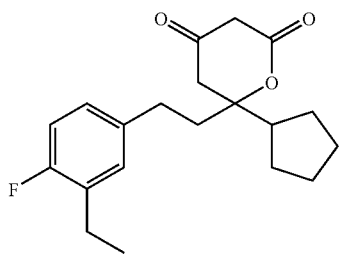

The title compound was prepared analogously to Example A(82), where 4-bromo-2-ethyl-1-fluorobenzene was substituted in place of 2-bromopyridine in Step 1 of that example. LCMS: 331-ve APCI. Anal. Calcd. For C$_{20}$H$_{25}$O$_3$F: C, 72.76; H, 7.58. Found: C, 72.87, H, 8.03.

Step 1

4-bromo-2-ethyl-1-fluorobenzene

Ethyl iodide (0.14 ml, 1.8 mmol) was added to a solution of (5-bromo-2-fluorophenyl)(iodo)zinc (0.5M in tetrahydrofuran) (5.4 ml, 2.7 mmol) in HMPA (10 ml). The reaction mixture was heated to 100° C. for 48 hrs. After which time the reaction mixture was cooled to room temperature and partitioned between ethyl acetate (100 ml) and water (100 ml). The organic layer was separated and dried over anhydrous sodium sulfate, filtered and the solvent was removed in vacuo. The crude oil was purified by column chromatography on silica gel eluting with 80:20 hexanes:ethyl acetate, to afford the title compound as a yellow oil (0.4 g).

$^1$H NMR (CDCl$_3$): δ 1.19 (t, J=7.06 Hz, 3H), 3.45 (q, J=7.03 Hz, 2H), 7.10 (m, 1H), 7.25 (m, 2H).

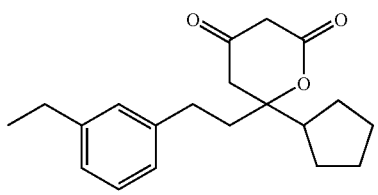

Example A(66)

6-Cyclopentyl-6-[2-(3-ethyl-phenyl)-ethyl]-dihydropyran-2,4-dione.

The title compound was prepared analogously to Example A(86), where 3-Bromo-ethylbenzene was substituted in place of 1-(4-Bromo-phenyl)-cyclopropanecarboxylic acid methyl ester in Step 3 of that example.

$^1$H NMR (CDCl$_3$): δ 1.81 (t, J=8.4 Hz, 1H), 1.30 to 1.80 (bm, 8H), 1.94 (m, 2H), 2.26 (m, 1H), 2.59 (m, 4H), 2.72 (s, 2H), 3.39 (s, 2H), 6.95 (m, 2H), 7.04 (d, J=5.2 Hz, 1H), 7.17 (m, 1H). ESIMS (M+H$^+$): 315.19.

Example A(67)

{3-[2-(2-Cyclopentyl-4,6-dioxo-tetrahydro-pyran-2-yl)-ethyl]-phenyl}-acetic acid methyl ester

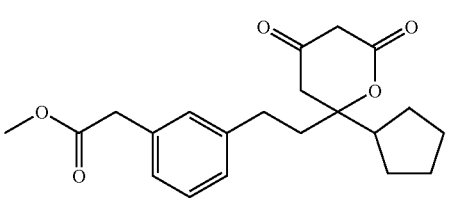

The title compound was prepared analogously to Example A(86), where (3-Bromo-phenyl)-acetic acid methyl ester was substituted in place of 1-(4-Bromo-phenyl)-cyclopropanecarboxylic acid methyl ester in Step 3 of that example.

¹H NMR (CDCl₃): δ 1.30 to 1.80 (bm, 8H), 1.90 (m, 2H), 2.23 (m, 1H), 2.64 (m, 2H), 2.70 (s, 2H), 3.36 (s, 2H), 3.65 (s, 2H), 6.95 (m, 2H), 7.00 (m, 2H), 7.09 (d, J=4.6 Hz, 1H) 7.22 (m, 1H). ESIMS (M+H⁺): 359.18.

Example A(68)

6-Cyclopentyl-6-[2-(3,3-dimethyl-2-oxo-2,3-dihydro-benzofuran-5-yl)-ethyl]-dihydro-pyran-2,4-dione

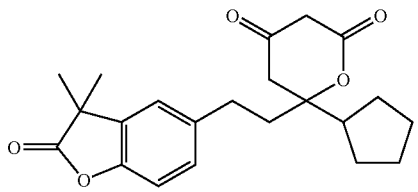

The title compound was prepared analogously to example A(86), where 5-Bromo-3,3-dimethyl-3H-benzofuran-2-one was substituted in place of 1-(4-Bromo-phenyl)-cyclopropanecarboxylic acid methyl ester in Step 3 of that example.

¹H NMR (CDCl₃): δ 1.55 (s, 6H), 1.59 to 1.89 (bm, 8H), 2.01 (m, 2H), 2.33 (m, 1H), 2.74 (m, 2H), 2.83 (m, 2H), 3.48 (m, 2H), 7.05 (s, 1H), 7.10 (s, 2H). ESIMS (M+H⁺): 371.18.

Step 1

3,3-Dimethyl-3H-benzofuran-2-one

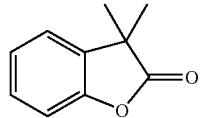

A solution of 3H-Benzofuran-2-one (4.02 g, 30 mmol) dissolved in THF (15 mL) was added cautiously to a suspension of NaH (95% dry, 1.58 g, 66 mmol) in DMF (60 mL) and THF (30 mL) under a nitrogen atmosphere, at 0° C. The mixture was stirred until gas evolution ceased, then MeI (5.6 mL, 90 mmol) was added slowly to avoid boiling over. After MeI addition was complete the reaction further stirred 1 h at room temperature then quenched by carefully pouring onto a mixture of HCl (1N) and ice. The resulting solution was extracted with ether, washed with brine, dried over MgSO4, and chromatographed on silica eluted with a gradient of 5–50% ethyl acetate/hexanes, yielding 3.16 g (65% yield) of the product.

Step 2

5-Bromo-3,3-dimethyl-3H-benzofuran-2-one

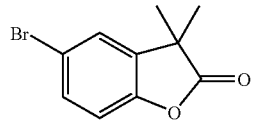

3,3-Dimethyl-3H-benzofuran-2-one (2.81 g, 17.3 mmol) was added to a solution of Bromine (1.51 mL, 29.5 mmoL) and Acetic acid (35 mL) at room temperature, then stirred overnight. The resulting mixture was stripped of solvent, then distilled under high vacuum. The product fraction (2.08 g, 50%) was collected between 65° C. and 79° C.

Example A(69)

1-{3-[2-(2-Cyclopentyl-4,6-dioxo-tetrahydro-pyran-2-yl)-ethyl]-phenyl}-cyclopropanecarboxylic acid methyl ester

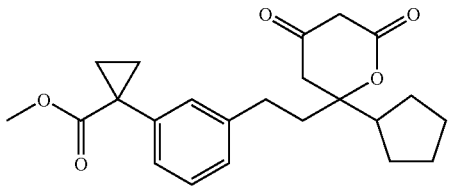

The title compound was prepared analogously to example A(86), where 1-(3-Bromo-phenyl)-cyclopropanecarboxylic acid methyl ester was substituted in place of 1-(4-Bromo-phenyl)-cyclopropanecarboxylic acid methyl ester in Step 3 of that example.

¹H NMR (CDCl₃): δ 1.19 (s, 2H), 1.39 to 1.86 (bm, 10H), 1.98 (m, 2H), 2.68 (m, 1H), 2.77 (s, 2H), 3.42 (s, 2H), 3.14 (s, 3H), 7.05 (d, J=2.7 Hz, 1H), 7.14 (s, 1H), 7.24 (m, 2H). ESIMS (M+H⁺): 385.19.

Step 1

1-(3-Bromo-phenyl)-cyclopropanecarboxylic acid methyl ester

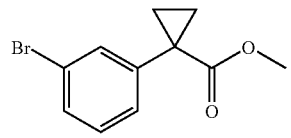

A solution of (3-Bromo-phenyl)-acetic acid methyl ester (4.54 g, 20 mmol) dissolved in dry THF (10 mL) was added dropwise to suspension of NaH (95% dry, 1.05 g, 44 mmol) in DMF (40 mL) and THF (10 mL), under a nitrogen atmosphere, at 0° C. After 30 min, gas evolution ceased, and 1,2-dibromoethane (3.79 mL, 44 mmol) was added dropwise over 20 min. The resulting mixture was stirred for 1 h, then quenched with 1N HCl, extracted with ether, washed with brine, dried over MgSO4, and stripped of solvent. The resulting oil was distilled under high vacuum. The product was collected between 95° C. and 105° C. Yield 2 g, 39%.

Example A(70)

{3-[2-(2-Cyclopentyl-4,6-dioxo-tetrahydro-pyran-2-yl)-ethyl]-phenyl}-acetonitrile

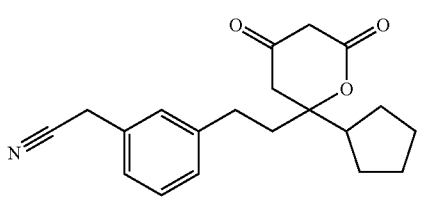

The title compound was prepared analogously to example A(86), where (3-Bromo-phenyl)-acetonitrile was substituted in place of 1-(4-Bromo-phenyl)-cyclopropanecarboxylic acid methyl ester in Step 3 of that example.

¹H NMR (CDCl₃): δ 1.40 to 1.85 (bm, 8H), 1.97 (m, 2H), 2.28 (m, 1H), 2.70 (t, J=7.1 Hz, 2H), 2.78 (s, 2H), 3.74 (s, 2H), 7.12 (m, 2H), 7.18 (m, 1H), 7.30 (m, 1H). ESIMS (M+H⁺): 326.17.

Example A(71)

1H-Pyrazole-3-carboxylic acid (2-{3-[2-(2-cyclopentyl-4,6-dioxo-tetrahydro-pyran-2-yl)-ethyl]-phenyl}-2-methyl-propyl)-amide

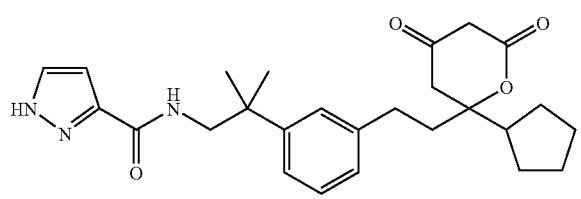

HATU (169.6 mg, 0.4464 mmol) was added to a solution of 6-{2-[3-(2-Amino-1,1-dimethyl-ethyl)-phenyl]-ethyl}-6-cyclopentyl-dihydro-pyran-2,4-dione trifluoroacetic acid salt (175 mg, 0.372 mmol), Et₃N (207 µL, 1.488 mmol), 1H-Pyrazole-3-carboxylic acid (50.0 mg, 0.4464 mmol), dissolved in DMF (2 mL). The reaction was stirred overnight, then purified directly by RPHPLC. Yield 55 mg, 33%.

¹H NMR (CDCl₃): δ 1.38 (s, 6H), 1.40 to 2.00 (bm, 10H), 2.36 (m, 1H), 2.64 (m, 2H), 2.81 (m, 2H), 3.46 (m, 2H), 3.63 (m, 2H), 6.63 to 6.79 (bm, 3H), 6.84 (s, 1H), 7.03 (s, 1H), 7.19 (s, 1H), 7.45 to 7.60 (bm, 3H). ESIMS (M+Na⁺): 474.25.

Step 1

[2-(3-Bromo-phenyl)-2-methyl-propyl]-carbamic acid tert-butyl ester

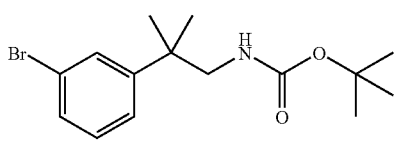

2-(3-Bromo-phenyl)-2-methyl-propionitrile was added to a solution of Lithium aluminum hydride (1M in THF, 37.4 ml, 37.4 mmol), in dry THF (70 mL), under a nitrogen atmosphere. The reaction was stirred for 5 h then quenched by cautiously adding water (1.51 ml), followed by 15% NaOH/water (1.51 mL), followed by water (4.53 ml). A white precipitate formed which was removed by filtration. The resulting solution was treated with di-tert butyl dicarbonate (1M in THF, 37.4 mL, 37.4 mmol), and stirred for an additional 30 minutes. The reaction was stripped of solvent and purified by column chromatography (5% to 25% ethyl acetate/hexanes). Yield 8.64 g, 87%.

Step 2

(2-{3-[2-(2-Cyclopentyl-4,6-dioxo-tetrahydro-pyran-2-yl)-ethyl]-phenyl}-2-methyl-propyl)-carbamic acid tert-butyl ester

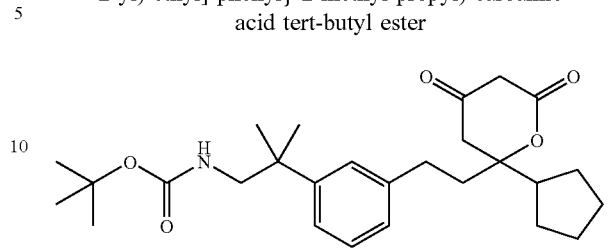

The above compound was prepared analogously to example A(86), where [2-(3-Bromo-phenyl)-2-methyl-propyl]-carbamic acid tert-butyl ester (from Step 1 above) was substituted in place of 1-(4-Bromo-phenyl)-cyclopropanecarboxylic acid methyl ester in Step 3 of that example.

Step 3

6-{2-[3-(2-Amino-1,1-dimethyl-ethyl)-phenyl]-ethyl}-6-cyclopentyl-dihydro-pyran-2,4-dione trifluoroacetic acid salt

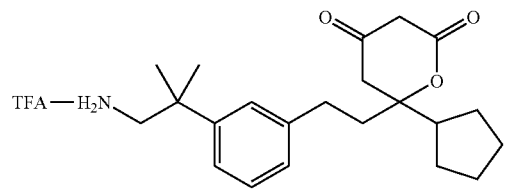

(2-{3-[2-(2-Cyclopentyl-4,6-dioxo-tetrahydro-pyran-2-yl)-ethyl]-phenyl}-2-methyl-propyl)-carbamic acid tert-butyl ester (1.80 g, 3.94 mmol), was stirred with 30% TFA/CH₂Cl₂ (30 mL), for 2 h. The reaction was diluted with Toluene (30 mL) and stripped of all solvents. The crude product was used without further purification. Yield 3.22 g.

Example A(72)

N-(2-{3-[2-(2-Cyclopentyl-4,6-dioxo-tetrahydropyran-2-yl)-ethyl]-phenyl}-2-methyl-propyl)-3-furan-2-yl-propionamide

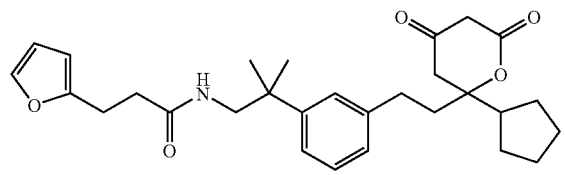

The title compound was prepared analogously to example A(71), where 3-Furan-2-yl-propionic acid was substituted in place of 1H-Pyrazole-3-carboxylic acid methyl ester in the final Step of that example. Yield 34 mg, 19%.

¹H NMR (CDCl₃): δ 1.34 (s, 6H), 1.40 to 2.05 (bm, 9H), 2.08 to 3.13 (bm, 12H), 3.44(bs, 2H), 6.93to 7.58 (bm, 8H). ESIMS (M+Na⁺): 502.27.

Example A(73)

4,5-Dimethyl-furan-2-carboxylic acid (2-{3-[2-(2-cyclopentyl-4,6-dioxo-tetrahydro-pyran-2-yl)-ethyl]-phenyl}-2-methyl-propyl)-amide

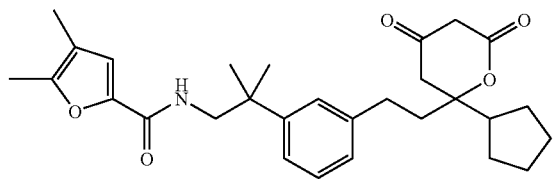

The title compound was prepared analogously to example A(71), where 4,5-Dimethyl-furan-2-carboxylic acid was substituted in place of 1H-Pyrazole-3-carboxylic acid methyl ester in the final Step of that example. Yield 23 mg, 13%.

$^1$H NMR (CDCl$_3$): δ 1.39 (bs, 6H), 1.43 to 1.84 (bm, 8H), 1.95 (s, 3H), 2.10 (s, 3H), 2.17 (s, 2H), 2.33 (m, 1H), 2.65 (m, 4H), 3.44 (m, 2H), 3.57 (m, 2H), 6.00 (bs, 1H), 6.83 (m, 1H), 7.19 (bm, 4H). ESIMS (M+Na$^+$): 502.27.

Example A(74)

5-Hydroxy-pyrazine-2-carboxylic acid (2-{3-[2-(2-cyclopentyl-4,6-dioxo-tetrahydro-pyran-2-yl)-ethyl]-phenyl}-2-methyl-propyl)-amide

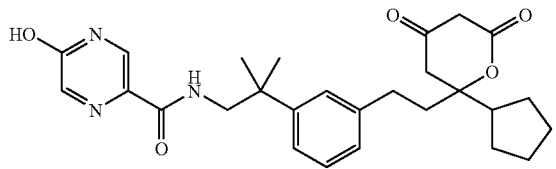

The title compound was prepared analogously to example A(71), where 5-Hydroxy-pyrazine-2-carboxylic acid was substituted in place of 1H-Pyrazole-3-carboxylic acid methyl ester in the final Step of that example. Yield 6.4 mg, 4%.

$^1$H NMR (CDCl$_3$): δ 1.35 (bs, 6H), 1.49 to 1.89 (bm, 8H), 2.00 (m, 2H), 2.23 (s, 1H), 2.66 (m, 2H), 2.78 (s, 2H), 3.45 (m, 2H), 3.59 (m, 2H), 7.00 (m, 1H), 7.03 to 7.58 (bm, 5H), 7.99 (m, 1H), 8.11 (m, 1H). ESIMS (M+Na$^+$): 502.24.

Example A(75)

3-{4-[2-(2-Cyclopentyl-4,6-dioxo-tetrahydro-pyran-2-yl)-ethyl]-phenyl)-3-oxo-propionitrile

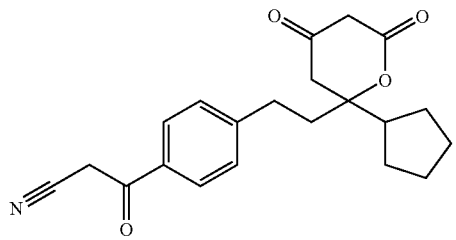

The title compound was prepared analogously to example A(86), where 5-(4-Iodo-phenyl)-isoxazole was substituted in place of 1-(4-Bromo-phenyl)-cyclopropanecarboxylic acid methyl ester in Step 3 of that example (Note that the isoxazole opens to the cyanomethyl ketone during the Sonogashira coupling Step). Yield 30 mg, 14%.

$^1$H NMR (CDCl$_3$): δ 1.18 to 1.70 (bm, 8H), 1.85 (m, 2H), 2.15 (m, 1H), 2.67 (m, 4H), 3.31 (m, 2H), 3.94 (s, 2H), 7.18 (d, J=8.1 Hz, 2H), 7.72 (d, J=8.3 Hz, 2H). ESIMS (M+Na$^+$): 376.16.

Example A(76)

6-Cyclopentyl-6-[2-(3,3-dimethyl-2,3-dihydro-benzofuran-5-yl)-ethyl]-dihydro-pyran-2,4-dione

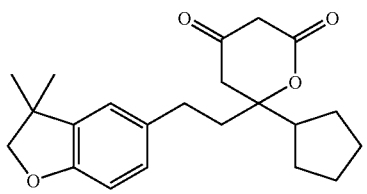

The title compound was prepared analogously to example A(86), where 5-Bromo-3,3-dimethyl-2,3-dihydro-benzofuran was substituted in place of 1-(4-Bromo-phenyl)-cyclopropanecarboxylic acid methyl ester in Step 3 of that example.

$^1$H NMR (CDCl$_3$): δ 1.34 (s, 6H), 1.971.4 to 1.88 (bm, 8H), 1.96 (m, 2H), 2.30 (s, 1H), 2.63 (t, J=8.2 Hz, 2H), 2.79 (s, 2H), 3.46 (s, 2H), 4.24 (s, 2H), 6.73 (d, J=6.5 Hz, 1H), 6.90 (m, 2H). ESIMS (M+H$^+$): 357.20.

Step 1

5-Bromo-3,3-dimethyl-2,3-dihydro-benzofuran-2-ol

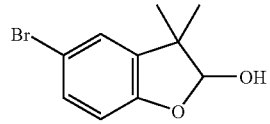

To a solution of 5-Bromo-3,3-dimethyl-3H-benzofuran-2-one (1.199 g, 5.0 mmol) (described in Step 2 of Example A(68), ), dissolved in anhydrous CH$_2$Cl$_2$ (20 ml), and cooled to −78° C., was added DIBAL (3.67 mL, 5.5 mmol, 1.5M in Toluene). The reaction was stirred for 1 h at this temperature then quenched with 1N HCl until acidic. The resulting mixture was extracted with ether, which was washed with brine, dried with MgSO4, concentrated and purified by silica gel chromatography (gradient elution 5–15% Ethylacetate/Hexanes). Yield 0.95 g, 79%.

Step 2

5-Bromo-3,3-dimethyl-2,3-dihydro-benzofuran

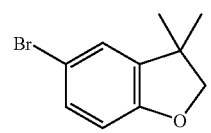

A solution of 5-Bromo-3,3-dimethyl-2,3-dihydro-benzofuran-2-ol (813 mg, 3.36 mmol), Triethylsilane (805 □L, 5.04 mmol), and 30% TFA/CH$_2$Cl$_2$ (15 mL), were stirred at room temperature for 1 h. The solution was then diluted with Toluene (15 mL), stripped of all solvents, and chromatographed on silica eluted with a gradient 5–25% Ethyl acetate/Hexanes. Yield 549 mg, 72%.

Example A(77)

6-Cyclopentyl-6-[2-(3-fluoro-4-thiazol-2-ylmethyl-phenyl)-ethyl]-dihydro-pyran-2,4-dione

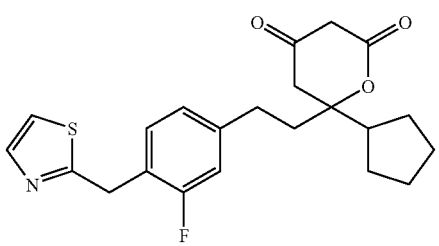

The title compound was prepared analogously to example A(86), where 2-(4-Bromo-3-fluoro-benzyl)-thiazole (prepared below), was substituted in place of 1-(4-Bromophenyl)-cyclopropanecarboxylic acid methyl ester in Step 3 of that example.

$^1$H NMR (CDCl$_3$): δ 1.40 to 1.85 (bm, 8H), 1.99 (m, 2H), 2.33 (m, 1H), 2.75 (m, 2H), 2.86 (s, 2H), 3.50 (s, 2H), 4.44 (s, 2H), 6.94 (m, 2H), 7.29 (m, 2H), 7.75 (d, J=3.5 Hz, 1H). ESIMS (M+H$^+$): 402.15.

Step 1

(4-Bromo-3-fluoro-phenyl)-thiazol-2-yl-methanol

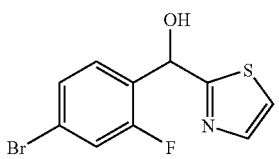

To a solution of Butyl lithium (9.6 mL, 24 mmol, 2.5 M in Hexane), in anhydrous Ether (80 ml), at −78° C., was added 2-Bromothiazole (2.0 mL, 22 mmol). After stirring for 20 min at this temperature, 4-Bromo-2-fluoro-benzaldehyde (20 mmol) was added, and stirring was continued an additional 30 min, then quenched with MeOH and Citric acid. The resulting mixture was extracted into ether, which was then washed with NaHCO$_3$ (sat. aq.), brine, dried over MgSO$_4$, and purified by silica gel chromatography (gradient elution 15–50% Ethyl acetate/Hexanes). Yield 4.55 g, 79%.

Step 2

2-(4-Bromo-3-fluoro-benzyl)-thiazole

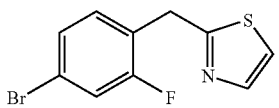

A solution of (4-Bromo-3-fluoro-phenyl)-thiazol-2-yl-methanol (3.4 g, 12.6 mmol), TFA (25 mL), and Triethylsilane (10 mL, 63 mmol), were refluxed overnight. The reaction was then concentrated under vacuum, and purified by silica gel chromatography (gradient elution 10–40% Ethylacetate/Hexanes). Yield 1.96 g, 61%.

Example A(78)

6-Cyclopentyl-6-[2-(3-thiazol-2-ylmethyl-phenyl)-ethyl]-dihydro-pyran-2,4-dione

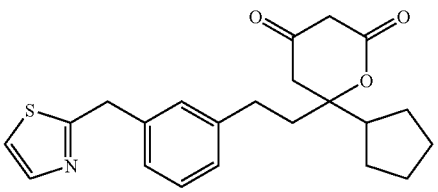

The title compound was prepared analogously to example A(77), where 3-Bromobenzaldehyde was substituted in place of 4-Bromo-2-fluoro-benzaldehyde in Step 1 of that example.

$^1$H NMR (CDCl$_3$): δ 1.40 to 1.85 (bm, 8H), 1.86 (m, 2H), 2.18 (m, 1H), 2.58 (m, 2H), 2.67 (s, 2H), 3.33 (s, 2H), 4.27 (s, 2H), 6.96 to 7.20 (m, 5H), 7.64 (d, J=3.3 Hz, 1H). ESIMS (M+H$^+$): 384.16.

Example A(79)

6-Cyclopentyl-6-{2-[4-(2-hydroxy-ethyl)-phenyl]-ethyl}-dihydro-pyran-2,4-dione

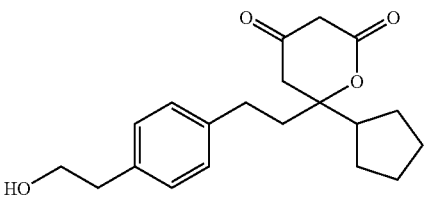

The title compound was prepared analogously to example A(86), where 2-(4-Bromo-phenyl)-ethanol was substituted in place of 1-(4-Bromo-phenyl)-cyclopropanecarboxylic acid methyl ester in Step 3 of that example.

$^1$H NMR (CDCl$_3$): δ 1.40 to 1.82 (bm, 8H), 1.96 (m, 2H), 2.29 (m, 1H), 2.66 (d, J=8.2 Hz, 2H), 2.76 (s, 2H), 2.84 (d, J=6.2 Hz, 1H), 3.41 (s, 2H), 3.84 (d, J=6.6 Hz, 1H), 7.10 (d, J=8.2 Hz, 2H), 7.16 (d, J=8.2 Hz, 2H). ESIMS (M+H$^+$): 331.18.

Example A(80)

6-Cyclopentyl-6-{2-[3-(2-hydroxy-ethyl)-phenyl]-ethyl}-dihydro-pyran-2,4-dione

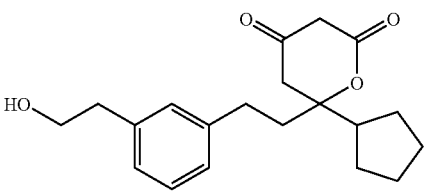

The title compound was prepared analogously to example A(86), where 2-(3-Bromo-phenyl)-ethanol was substituted in place of 1-(4-Bromo-phenyl)-cyclopropanecarboxylic acid methyl ester in Step 3 of that example.

$^1$H NMR (CDCl$_3$): δ 1.39 to 1.84 (bm, 8H), 1.99 (m, 2H), 2.30 (m, 1H), 2.68 (d, J=8.6 Hz, 2H), 2.76 (s, 2H), 2.84 (d, J=6.6 Hz, 1H), 3.40 (s, 2H), 3.86 (d, J=6.6 Hz, 1H), 7.02 (m, 2H), 7.08 (m, 1H), 7.23 (m, 1H). ESIMS (M+H$^+$): 331.18.

Example A(81)

2{4-[2-(2-Cyclopentyl-4,6-dioxo-tetrahydro-pyran-2-yl)-ethyl]-2-fluoro-phenyl}-2-methyl-propionitrile

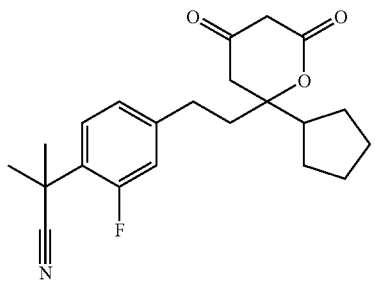

The desired product was prepared analogously to Step 5 of Example A(86), substituting 2-{4-[3-Cyclopentyl-4-(2,2-dimethyl-6-oxo-6H-[1,3]dioxin-4-yl)-3-hydroxy-butyl]-2-fluoro-phenyl}-2-methyl-propionitrile (1.23 g, 2.9 mmol) from Step 3 below in place of 1-{4-[3-Cyclopentyl-4-(2,2-dimethyl-6-oxo-6H-[1,3]dioxin-4-yl)-3-hydroxy-butyl]-2-fluoro-phenyl}-cyclopropanecarbonitrile. Yield: 0.614 g, 56%.

$^1$H NMR (CDCl$_3$) δ: 1.24–1.66 (m, 14H), 1.75–1.80 (m, 2H), 2.10 (p, J=9.35 Hz, 1H), 2.47–2.56 (m, 2H), 2.60 (d, J=5.56 Hz, 2H), 3.26 (d, J=3.28 Hz, 2H), 6.71–6.79 (m, 2H), 7.23 (t, J=8.24 Hz, 1H). MS (ESI): 370 (M–H).

Step 1

2-(4-Bromo-2-fluoro-phenyl)-2-methyl-propionitrile

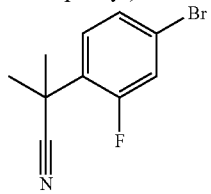

The desired product was prepared analogously to Example A(86), Step 2, substituting iodomethane (1.3 mL, 20.6 mmol) in place of 1,2-dibromoethane. Yield: 2.25 g, 99%.

$^1$H NMR (CDCl$_3$) δ: 2.81 (s, 3H), 2.88 (s, 3H), 7.20–7.25 (m, 3H).

Step 2

2-{4-[3-Cyclopentyl-4-(2,2-dimethyl-6-oxo-6H-[1,3]dioxin-4-yl)-3-hydroxy-but-1-ynyl]-2-fluoro-phenyl}-2-methyl-propionitrile

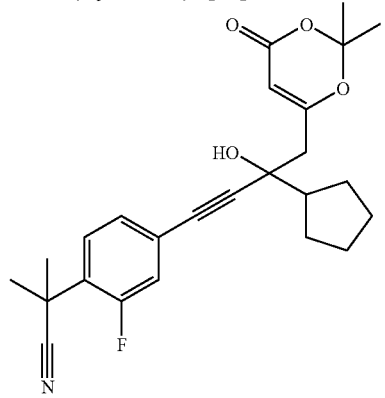

The desired product was prepared analogously to Example A(86), Step 5, substituting 2-(4-bromo-2-fluoro-phenyl)-2-methyl-propionitrile (1.1 g, 4.5 mmol) from Step 1 above in place of 1-(4-bromo-2-fluoro-phenyl)-cyclopropanecarbonitrile. Yield: 1.415 g, 74%.

MS (ESI): 424 (M–H).

Step 3

2-{4-[3-Cyclopentyl-4-(2,2-dimethyl-6-oxo-6H-[1,3]dioxin-4-yl)-3-hydroxy-butyl]-2-fluoro-phenyl}-2-methyl-propionitrile

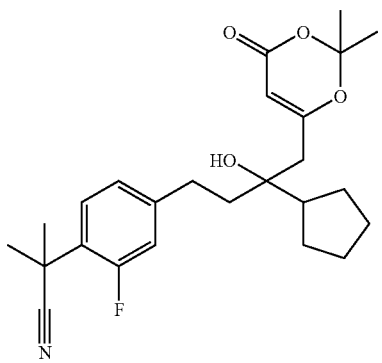

The desired product was prepared analogously to example A(86), Step 6, substituting 2-{4-[3-Cyclopentyl-4-(2,2-dimethyl-6-oxo-6H-[1,3]dioxin-4-yl)-3-hydroxy-but-1-ynyl]-2-fluoro-phenyl}-2-methyl-propionitrile (1.25 g, 2.9 mmol) from Step 2 above in place of 1-{4-[3-Cyclopentyl-4-(2,2-dimethyl-6-oxo-6H-[1,3]dioxin-4-yl)-3-hydroxy-but-1-ynyl]-2-fluoro-phenyl}-cyclopropanecarbonitrile. Yield: 1.23 g, 99%.

MS (ESI): 428 (M–H).

Example A(82)

6-Cyclopentyl-6-(2-pyridin-2-yl-ethyl)-dihydro-pyran-2,4-dione

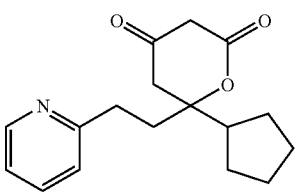

Sodium hydride (60%) (0.24 g, 5.90 mmol) was magnetically stirred in dry THF (12 mL) and cooled to 0° C. The mixture was then treated with Methyl acetoacetate (0.64 mL, 5.90 mmol) dropwise over 15 min. The reaction was allowed to stir for 30 min at 0° C. To the resulting clear solution was added nBuLi (1.6M in Hexanes) (3.68 mL, 5.90 mmol). The reaction was then allowed to stir for 30 min at 0° C. To the yellow solution was added the ketone from Step 1 below (0.4 g, 1.96 mmol) as a solution in dry THF (6 mL). The result was stirred at 0° C. for 15 min and then at room temperature for 90 min. The solution was next poured into 0.5N HCl (50 mL) and extracted with EtOAc (2×50 mL). The organics were concentrated and the residue dissolved in MeOH (12 mL) and treated with K$_2$CO$_3$ (0.6 g). The mixture was heated to 65° C. and maintained for 1 hr. The reaction was cooled and poured into 0.5N HCl (50 mL) and extracted with EtOAc (2×50 mL). The organics were dried over Na$_2$SO$_4$, filtered and concentrated. The residue was purified by flash chromatography (silica gel) eluting with $CH_2Cl_2$ through 1% MeOH in $CH_2Cl_2$ to yield the title compound as a white solid. (0.41 g, 73%).

$^1$H NMR (CDCl$_3$): δ 1.41–1.85 (brm, 8H), 1.95 (m, 2H), 2.29 (t, J=7.6 Hz, 1H), 2.65 (t, J=8.6 Hz, 2H), 2.80 (s, 2H), 3.40 (s, 2H), 7.10 (d, J=6.6 Hz, 1H), 7.24 (brs, 1H), 7.32 (m, 2H). ESIMS (MH+): 288.3.

Step 1

1-Cyclopentyl-3-pyridin-2-yl-propan-1-one

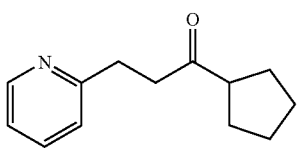

To a magnetically stirring solution of 2-Bromopyridine (0.4 g, 2.61 mmol) and 1-Cyclopentyl-2-propen-1-ol (1.5 eq, 0.49 g, 3.88 mmol) in anhydrous N-Methylpyrrolidinone (3.0 mL), under argon at room temperature, was added Sodium Bicarbonate (1.2 eq, 0.26 g, 3.10 mmol) followed by Dichlorobis (triphenylphosphine) palladium (II) (0.02 eq, 36.7 mg, 0.05 mmol). The resulting mixture was heated to 140° C. in an oil bath and maintained for 4 hours. The dark reaction mixture was cooled to room temperature and poured into water (50 mL) and extracted with EtOAc (2×25 mL). The organics were washed with water (50 mL) and brine (50 mL) then dried over Na$_2$SO$_4$, filtered and concentrated. The crude residue was purified by flash chromatography (1% through 10% EtOAc in Hexanes) to yield the intermediate ketone as a yellow oil (0.43 g, 81%).

$^1$H NM(CDCl$_3$): δ?1.45–1.87 (m, 8H), 2.70–2.95 (m, 5H), 7.10 (d, J=6.6 Hz, 1H), 7.24 (brs, 1H), 7.32 (m, 2H).

Example A(83)

6-{2-[3-Chloro-4-(1-ethyl-propoxy)-phenyl]-ethyl}-6-cyclopentyl-dihydro-pyran-2,4-dione

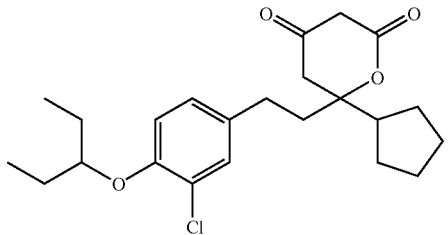

The title compound was prepared analogously to Example A(82), where 4-Bromo-2-chloro-1-(1-ethyl-propoxy)-benzene was substituted in place of 2-Bromopyridine in Step 1 of that example.

$^1$H NMR (CDCl$_3$): δ 1.04 (t, J=7.5 Hz, 6H), 1.52–1.86 (brm, 12H), 1.92 (m, 2H), 2.27 (m, 1H), 2.65 (t, J=7.9 Hz, 2H), 2.76 (s, 2H), 3.43 (s, 2H), 4.48 (m, 1H), 6.81–6.92 (m, 3H). Anal. Calcd. For $C_{23}H_{31}ClO_4$: C, 67.88; H, 7.68. Found: C, 67.63; H, 7.43.

Example A(84)

6-[2-(5-Acetyl-thiophen-2-yl)-ethyl]-6-cyclopentyl-dihydro-pyran-2,4-dione

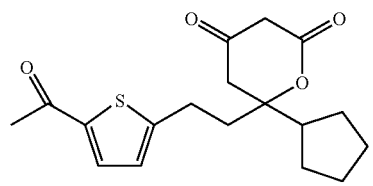

The title compound was prepared analogously to Example A(82), where 1-(5-Bromo-thiophen-2-yl)-ethanone was substituted in place of 2-Bromopyridine in Step 1 of that example.

$^1$H NMR (CDCl$_3$): δ 1.49–1.79 (brm, 8H), 2.05–2.25 (m, 2H), 2.27 (m, 1H), 2.55 (s, 3H), 2.71 (d, J=15.8 Hz, 1H), 2.79 (d, J=15.8 Hz, 1H), 2.96 (m, 2H), 3.45 (s, 2H), 6.83 (d, J=3.5 Hz, 1H), 7.52 (d, J=3.5 Hz, 1H). Anal. Calcd. For $C_{18}H_{22}O_4S$: C, 64.64; H, 6.63. Found: C, 64.34; H, 6.73.

Example A(85)

4-[2-(2-Cyclopentyl-4,6-dioxo-tetrahydro-pyran-2-yl)-ethyl]-2-fluoro-methyl-benzenesulfonamide

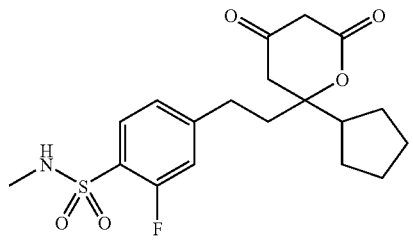

The title compound was prepared analogously to Example A(82), where 4-Bromo-2-fluoro-N-methyl-benzenesulfonamide was substituted in place of 2-Bromopyridine in Step 1 of that example.

$^1$H NMR (CDCl$_3$): δ 1.50–1.82 (brm, 8H), 1.92 (m, 2H), 2.27 (m, 1H), 2.63 ( s, 3H), 2.79 (m, 4H), 3.38 (s, 2H), 7.02–7.41 (m, 2H), 7.70 (s, 1H). Anal. Calcd. For $C_{19}H_{24}FNO_5S$: C, 57.42; H, 6.09; N, 3.52. Found: C, 57.60; H, 6.22; N, 3.25.

Example A(86)

1-{4-[2-(2-Cyclopentyl-4,6-dioxo-tetrahydro-pyran-2-yl)-ethyl]-2-fluoro-phenyl}-cyclopropanecarbonitrile

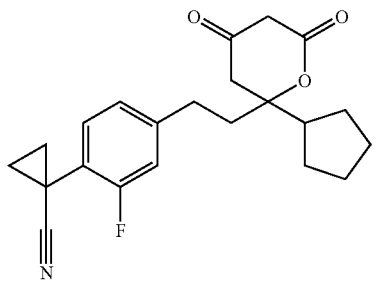

A solution of 1-{4-[3-Cyclopentyl-4-(2,2-dimethyl-6-oxo-6H-[1,3]dioxin-4-yl)-3-hydroxy-butyl]2-fluoro-phenyl}-cyclopropanecarbonitrile (0.9 g, 2.1 mmol) from Step 6 below in NaOH (0.3 M in MeOH, 21 mL, 6.3 mmol) was stirred at room temperature for 3 hours. The reaction was then quenched with 100 mL saturated NH₄Cl and 5 mL 1 N HCl. To this solution was added 100 mL CH₂Cl₂ and the layers were separated. The aqueous layer was extracted with 2×100 mL CH₂Cl₂ and the organic layers were combined. After drying the organic with MgSO₄, and filtering to remove the solids, the solvent was removed by rotary evaporation. The remaining oil was purified by flash chromatography to yield the desired product (0.367 g, 47%).

$^1$H NMR (CDCl₃) δ: 1.27–1.30 (m, 2H), 1.51–1.73 (m, 10H), 1.84–1.89 (m, 2H), 2.19 (p J=8.08 Hz, 1H), 2.58–2.71 (m, 4H), 3.36 (d, J=4.04 Hz, 2H), 6.81–6.86 (m, 2H), 7.16–7.18 (m, 1H). MS (ESI): 368 (M–H).

Step 1

(4-Bromo-2-fluoro-phenyl)-acetonitrile

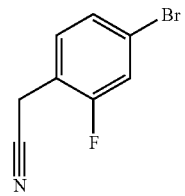

To a solution of 4-bromo-1-bromomethyl-2-fluoro-benzene (8.15 g, 30.4 mmol) dissolved in DMF (16 mL) were added sodium cyanide (2.24 g, 45.6 mmol) and water (2 mL). The reaction was stirred for one hour at 70° C. To the reaction was added 130 mL water; 120 mL saturated NaHCO₃, and 100 mL EtOAc. The layers were separated, and the aqueous layer was extracted with 3×100 mL EtOAc. The combined organics were washed with 100 mL water, and then dried over Na₂SO₄. After filtering off the solids, the mother liquor was concentrated to the desired product by rotary evaporation (6.5 g, 99% yield).

MS (APCI): 240 (M+H), 242 (M+2+H).

Step 2

1-(4-Bromo-2-fluoro-phenyl)-cyclopropanecarbonitrile

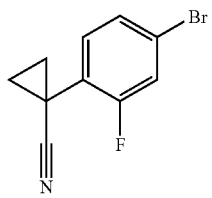

To a slurry of sodium hydride (60% dispersion in mineral oil, 0.82 g, 20.6 mmol) in DMF (20 mL) cooled to 0° C. was added a solution of (4-bromo-2-fluoro-phenyl)-acetonitrile (2.0 g, 9.35 mmol) from Step 1 above dissolved in THF (10 mL). The reaction was stirred till gas evolution ceased, and then 1,2-dibromoethane (1.8 mL, 20.6 mmol) was added slowly. The reaction was stirred for 30 minutes, and then diluted with 100 mL EtOAc. The solids were removed by filtration, and the organic layer was washed with 100 mL water. The organic layer was dried over MgSO₄, and then filtered. The mother liquor was concentrated by rotary evaporation, and the product was distilled under high vacuum (0.3 torr, 45° C.). Yield: 0.98 g, 44%.

$^1$H NMR (CDCl₃) δ: 1.15 (dd, J1=5.31 Hz, J2=2.27 Hz, 2H), 1.48 (dd, J1=5.05 Hz, J2=2.53 Hz, 2H), 6.97–7.12 (m, 3H).

Step 3

1-Cyclopentyl-3-trimethylsilanyl-propynone

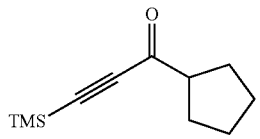

The title compound was prepared as described in the following reference: *Journal of Organic Chemistry* 1984, 106, 4786–4800.

$^1$H NMR (CDCl₃): δ 0.24 (s, 9H), 1.63 (m, 4H), 1.90 (m, 4H), 2.92 (pentet, 1H, J=8.2 Hz).

Step 4

6-(2-Cyclopentyl-2-hydroxy-4-trimethylsilanyl-but-3-ynyl)-2,2-dimethyl-[1,3]dioxin-4-one

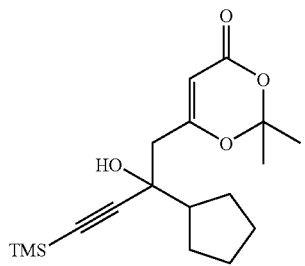

A solution of diisopropylamine (3.85 mL, 27.5 mmol) dissolved in THF (100 mL; dry), was cooled to –78° C., where BuLi (11 mL, 27.5 mmol; 2.5 M in hexanes) was added dropwise over 10 minutes. After stirring at this temperature for 5 minutes the mixture was warmed to room temperature for 5 minutes, then cooled back to –78° C., where commercially available 2,2,6-trimethyl-[1,3]dioxin-4-one (3.60 mL, 27.5 mmol) was added dropwise over 5 minutes, then stirred an additional 30 minutes at –78° C. To this solution was added 1-Cyclopentyl-3-trimethylsilanyl-propynone (4.85 g, 25 mmol; prepared as described in Step 3 above over 5 minutes. The resulting mixture was stirred at –78° C. for 1 hr, then slowly warmed to –30° C. and quenched with 0.5 N citric acid. The mixture was diluted with ether, extracted with 1 N NaHCO₃, brine, and then dried with MgSO₄. This material (9.38 g), which contained a unreacted 2,2,6-trimethyl-[1,3]dioxin-4-one, was used without further purification.

$^1$H NMR (CDCl₃) δ: 0.15 (s, 9H), 1.60 (m, 4H), 1.72 (s, 3H), 1.75 (s, 3H), 2.01 (s, 1H), 2.14 (pentet, 1H), 2.47 (s, 1H), 2.55 (s, 2H), 5.40 (s, 1H). ESIMS (M+Na⁺): 359.1.

95

Step 5

1-{4-[3-Cyclopentyl-4-(2,2-dimethyl-6-oxo-6H-[1,3]dioxin-4-yl)-3-hydroxy-but-1-ynyl]-2-fluoro-phenyl}-cyclopropanecarbonitrile

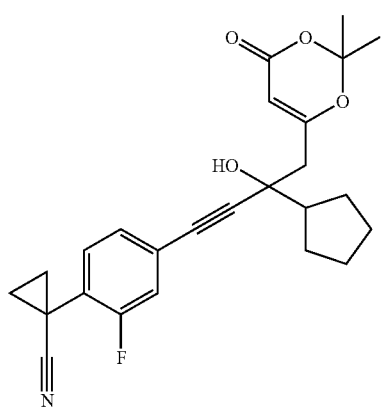

The desired product was prepared analogously to example F(7), Step 5, substituting 1-(4-bromo-2-fluoro-phenyl)-cyclopropanecarbonitrile (0.96 g, 4.0 mmol), from Step 2 above in place of 3-iodophenol, and 6-(2-cyclopentyl-2-hydroxy-but-3-ynyl)-2,2-dimethyl-[1,3]dioxin-4-one (1.06 g, 4.0 mmol; from Step 4 above) in place of 6-but-3-ynyl-3-chloro-6-cyclopentyl-dihydro-pyran-2,4-dione. Yield: 1.241 g, 73%.

MS (ESI): 422 (M–H).

Step 6

1-{4-[3-Cyclopentyl-4-(2,2-dimethyl-6-oxo-6H-[1,3]dioxin-4-yl)-3-hydroxy-butyl]-2-fluoro-phenyl}-cyclopropanecarbonitrile

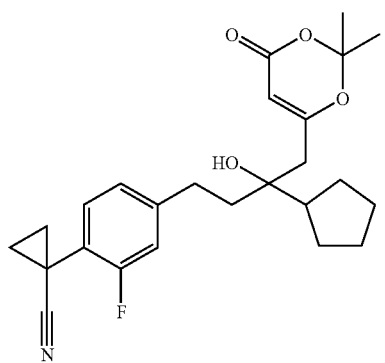

To a solution of 1-{4-[3-Cyclopentyl-4-(2,2-dimethyl-6-oxo-6H-[1,3]dioxin-4-yl)-3-hydroxy-but-1-ynyl]-2-fluoro-phenyl}-cyclopropanecarbonitrile (1.0 g, 2.4 mmol) from Step 5 above dissolved in EtOH (20 mL) was added Pd(OH)$_2$/C (20% wt dry basis, 100 mg) and the reaction was stirred under a hydrogen atmosphere for 6 hours. The palladium catalyst was removed by filtration, and the solvent removed by rotary evaporation. The resulting oil was used without further purification (1.02 g, 99% yield).

MS (ESI): 426 (M–H).

96

Example A(87)

N-{4-[2-(2-cyclopentyl-4,6-dioxotetrahydro-2H-pyran-2-yl)ethyl]-2-ethylphenyl}-N-methylmethanesulfonamide

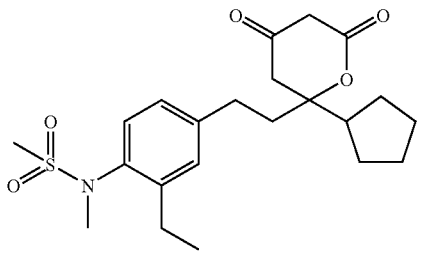

The title compound was prepared analogously to Example A(64) where N-(4-bromo-2-ethylphenyl)-N-methylmethanesulfonamide was substituted in place of 4-bromo-2-fluoro-1-isopropylbenzene in step 2 of that example.

$^1$H NMR (CDCl$_3$): δ 1.12 (t, J=7.54 Hz, 3H), 1.4–2.2 (brm, 11H), 2.60–2.80 (brm, 6H), 2.94s, 3), 3.02(s, 3H), 6.56 (d, J=4.90 Hz, 1H), 7.00, (d, J=4.90 Hz, 1H), 7.07 (s, 1H). Anal. Calcd. For C$_{22}$H$_{31}$NO$_5$S: C, 62.68; H, 7.41; N, 3.32. Found: C, 62.49; H, 6.98; N, 3.20.

Step 1

N-(4-bromo-2-ethylphenyl)methanesulfonamide

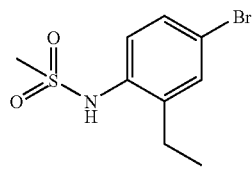

Methane sulfonyl chloride (1.93 ml, 0.025M) was added to a solution of 4-bromo-2-ethylaniline (5.0 g, 0.025M) and pyridine (2.02 ml, 0.025M) in dichloromethane (100 ml) at 0° C. The reaction mixture was stirred for 1 hr, after which time it was partitioned between dichloromethane (100 ml) and 1N hydrochloric acid (100 ml). The organics were separated and dried over magnesium sulfate, filtered and concentrated in vacuuo to afford the title compound as a clear oil (4.77 g).

$^1$H NMR (CDCl$_3$): δ 1.12 (t, J=8.60 Hz, 3H), 2.91 (q, 2H), 3.06 (s, 3H), 6.81 (d, J=7.54 Hz, 1H), 7.05 (d, J=7.54 Hz, 1H), 7.26 (s, 1H).

Step 2

N-(4-bromo-2-ethylphenyl)-N-methylmethanesulfonamide

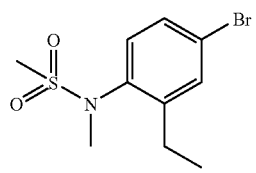

Methyl iodide (1.6 g, 0.0256M) was added to a mixture of N-(4-bromo-2-ethylphenyl)methanesulfonamide (4.77 g, 0.0171M) and potassium carbonate (3.5 g, 0.0256M) in dimethylformamide (50 ml) at room temperature under an atmosphere of nitrogen. The reaction mixture was stirred for a further 24 hrs after which time it was partitioned between diethylether (100 ml) and water (100 ml). The aqueous was extracted further with diethyl ether (2×100 ml). The combined organics were dried over magnesium sulfate, filtered and the solvent concentrated in vacuuo to afford the title compound as a brown oil (3.6 g).

$^1$H NMR (CDCl$_3$): δ 1.12 (t, J=8.60 Hz, 3H), 2.94 (m, 5H), 3.02 (s, 3H), 6.71 (d, J=8.5 Hz, 1H), 7.05 (d, J=8.5 Hz, 1H), 7.28 (s, 1H).

Example A(88)

N-{4-[2-(2-cyclopentyl-4,6-dioxotetrahydro-2H-pyran-2-yl)ethyl]phenyl}-N-methylmethanesulfonamide

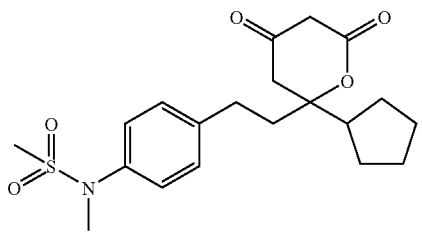

The title compound was prepared analogously to Example A(64) where N-(4-bromophenyl)-N-methylmethanesulfonamide was substituted in place of 4-bromo-2-fluoro-1-isopropylbenzene in step 2 of that example.

$^1$H NMR (CDCl$_3$): δ 1.4–2.24 (brm, 11H), 2.60–2.89 (brm, 4H), 2.94 (s, 3H), 3.04 (m, 5H), 6.96 (dd, J=4,96 Hz, 2H), 7.23 (dd, J=4.96 Hz, 2H). Anal. Calcd. For C$_{20}$H$_{27}$NO$_5$S: C, 61.04; H, 6.91; N, 3.56. Found: C, 61.35; H, 6.94; N, 3.20.

Step 1

N-(4-bromophenyl)methanesulfonamide

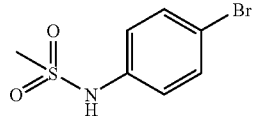

Methane sulfonyl chloride (2.4 ml, 0.031 M) was added to a solution of 4-bromo-aniline (5.28 g, 0.031 M) and pyridine (2.5 ml, 0.031 M) in dichloromethane (100 ml) at 0° C. The reaction mixture was stirred for 1 hr, after which time it was partitioned between dichloromethane (100 ml) and 1N hydrochloric acid (100 ml). The organics were separated and dried over magnesium sulfate, filtered and concentrated in vacuuo to afford the title compound as a white solid (6.37 g).

$^1$H NMR (CDCl$_3$): 2.97 (s, 3H), 6.81 (d, J=2.56 Hz, 2H), 7.25 (d, J=2.56 Hz, 2H),).

Step 2

N-(4-bromophenyl)-N-methylmethanesulfonamide

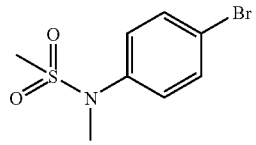

Methyl iodide (2.38 g, 0.0382M) was added to a mixture of N-(4-bromophenyl)methanesulfonamide (6.37 g, 0.0255M) and potassium carbonate (5.21 g, 0.0382M) in dimethylformamide (50 ml) at room temperature under an atmosphere of nitrogen. The reaction mixture was stirred for a further 24 hrs after which time it was partitioned between diethylether (100 ml) and water (100 ml). The aqueous was extracted further with diethyl ether (2×100 ml). The combined organics were dried over magnesium sulfate, filtered and the solvent concentrated in vacuuo to afford the title compound as a white solid (5.6 g).

$^1$H NMR (CDCl$_3$): 2.94 (s, 3H), 3.04 (s, 3H), 6.89 (d, J=2.56 Hz, 2H), 7.30 (d, J=2.56 Hz, 2H),).

Example A(89)

6-cyclopentyl-6-[2-(3-cyclopentyl-4-hydroxyphenyl)ethyl]dihydro-2H-pyran-2,4(3H)-dione

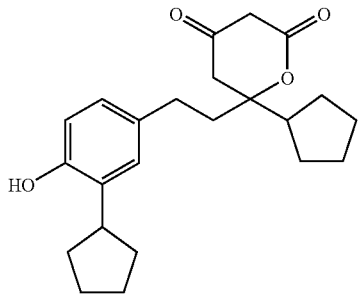

The title compound was prepared analogously to Example A(22): where 4-bromo-2-cyclopentylphenol, from step 1, was used in place of 4-Bromo-2-ethyl-phenol in step 2 of that example.

$^1$H NMR (CDCl$_3$): δ 1.43–1.85 (br m, 16H), 1.87–2.21, (m, 3H), 2.70–3.18 (brm, 7H), 4.95 (s, 1H), 6.60 (d, J=8.1 Hz 1H)), 6.84 (d, J=8.1 Hz, 1H), 7.12 (s, 1H). LCMS=369-ve APCI.

Step 1

4-bromo-2-cyclopentylphenol

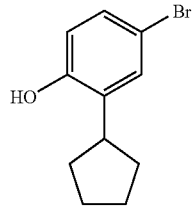

2-cyclopentyl phenol (3.0 g, 0.0185 mol) was dissolved in CHCl$_3$ (100 mL) and magnetically stirred at room temperature. To this solution was added a solution of Tetrabutyl ammonium tribromide (8.92 g, 0.0185 mol) in CHCl$_3$ (100 mL). The resulting yellow solution was allowed to stir at room temperature for 1 hour. The reaction was quenched with a 5% solution of sodium thiosulfate (200 mL). The biphasic mixture was stirred for 15 min. The organics were separated and concentrated. The residue was dissolved in EtOAc (100 mL) and washed with water (2×100 mL) and brine (1×100 mL). The organics were dried over Na$_2$SO$_4$, filtered and concentrated. The residue was purified by flash chromatography (silica gel) eluting with 3% EtOAc in Hexanes. The result was a yellow oil (3.70 g).

$^1$H NMR (CDCl$_3$): δ 1.39–1.73 (brm, 8H), 2.83 (m, 1H), 4.81 (s, 1H), 6.68 (d, J=7.10 Hz 1H), 7.19 (d, J=7.10 Hz, 1H), 7.26(s, 1H).

Example A(90)

6-cyclopentyl-6-[2-(4-hydroxy-3-propylphenyl) ethyl]dihydro-2H-pyran-2,4(3H)-dione

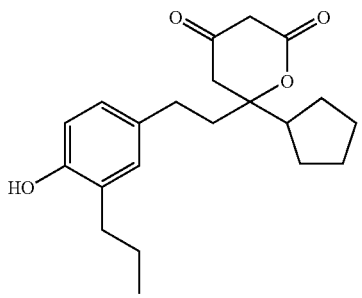

The title compound was prepared analogously to Example A(22): where 4-bromo-2-propylphenol, from step 1, was used in place of 4-Bromo-2-ethyl-phenol in step 2 of that example.

$^1$H NMR(CDCl$_3$): δ 1.00(t, J=8.1 Hz3H,), 1.33–1.85(brm, 8H), 1.87–2.01(m, 2H), 2.22 (m, 3H),2.30 (m, 2H), 2.60–3.10(brm, 6H), 5.78(s, 1H), 6.70(d, J=2.07 Hz1H)), 6.80(s, 1H), 6.85(d, J=2.07 Hz, 1H). LCMS=343-ve APCI.

Step 1

4-bromo-2-propylphenol

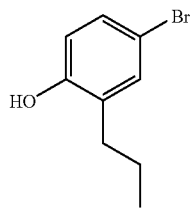

2-propylphenol (3.0 g, 0.022 mol) was dissolved in CHCl$_3$ (100 mL) and magnetically stirred at room temperature. To this solution was added a solution of Tetrabutyl ammonium tribromide (10.68 g, 0.022 mol) in CHCl$_3$ (100 mL). The resulting yellow solution was allowed to stir at room temperature for 1 hour. The reaction was quenched with a 5% solution of sodium thiosulfate (200 mL). The biphasic mixture was stirred for 15 min. The organics were separated and concentrated. The residue was dissolved in EtOAc (100 mL) and washed with water (2×100 mL) and brine (1×100 mL). The organics were dried over Na$_2$SO$_4$, filtered and concentrated. The residue was purified by flash chromatography (silica gel) eluting with 3% EtOAc in Hexanes. The result was a yellow oil (4.54 g).

$^1$H NM(CDCl$_3$): δ 1.00 (t, J=8.10 Hz, 3H), 1.52 (m, 2H), 2.50 (t, J=4.56 Hz 2H), 4.95 (s, 1H), 6.72 (d, J=2.07 Hz 1H)), 6.80 (s, 1H), 6.85 (d, J=2.07 Hz, 1H).

Example A(91)

2-{4-[2-(2-Cyclopentyl-4,6-dioxo-tetrahydro-pyran-2-yl)-ethyl]-2-fluoro-phenyl}-2-ethyl-butyronitrile

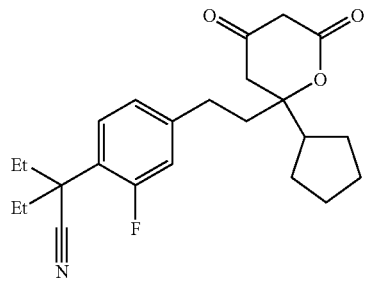

The desired product was prepared analogously to Example A(86) step 5, substituting 2-{4-[3-Cyclopentyl-4-(2,2-dimethyl-6-oxo-6H-[1,3]dioxin-4-yl)-3-hydroxy-butyl]-2-fluoro-phenyl}-2-ethyl-butyronitrile (0.84 g, 1.8 mmol) from step 3 below in place of 1-{4-[3-Cyclopentyl-4-(2,2-dimethyl-6-oxo-6H-[1, 3]dioxin-4-yl]-3-hydroxy-butyl]-2-fluoro-phenyl}-cyclopropanecarbonitrile. Yield: 0.393 g, 54%.

$^1$H NMR (CDCl$_3$) δ: 1.01 (t, J=7.45 Hz, 6H), 1.62–1.90 (br, 8H), 2.03–2.17 (br, 4H), 2.20–2.29 (br, 2H), 2.37 (p, J=9.35 Hz, 1H), 2.75–2.82 (m, 2H), 2.86 (d, J=7.58 Hz, 2H), 3.53 (d, J=2.02 Hz, 2H), 6.94 (dd, J1=13.01 Hz, J2=1.64 Hz, 1H), 7.04 (dd, J1=7.83 Hz, J2=1.77 Hz, 1H), 7.57 (t, J=8.21 Hz, 1H).

Step 1

2-(4-Bromo-2-fluoro-phenyl)-2-ethyl-butyronitrile

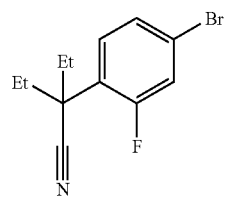

The desired product was prepared analogously to Example A(86) step 2, substituting bromoethane (1.94 mL, 20.6 mmol) in place of 1,2-dibromoethane. Yield: 2.1 g, 84%.

MS (APCI) 270 (M+H), 272 (M+2+H).

Step 2

2-{4-[3-Cyclopentyl-4-(2,2-dimethyl-6-oxo-6H-[1,3] dioxin-4-yl)-3-hydroxy-but-1-ynyl]-2-fluoro-phenyl}-2-ethyl-butyronitrile

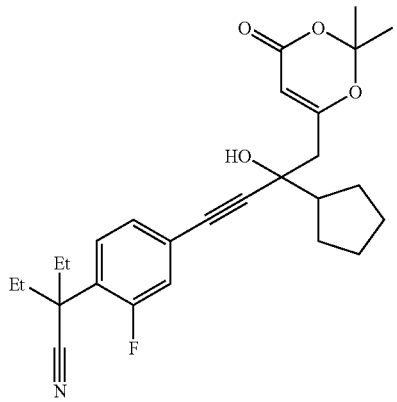

The desired product was prepared analogously to Example A(86) step 5, substituting 2-(4-Bromo-2-fluoro-phenyl)-2-ethyl-butyronitrile (1.01 g, 4.0 mmol) from step 1 above in place of 1-(4-bromo-2-fluoro-phenyl)-cyclopropanecarbonitrile. Yield: 0.953 g, 53%.

MS (ESI): 436 (M−H).

Step 3

2-{4-[3-Cyclopentyl-4-(2,2-dimethyl-6-x-6H-[1,3]dioxin-4-yl)-3-hydroxy-butyl]-2-fluoro-phenyl}-2-ethyl-butyronitrile

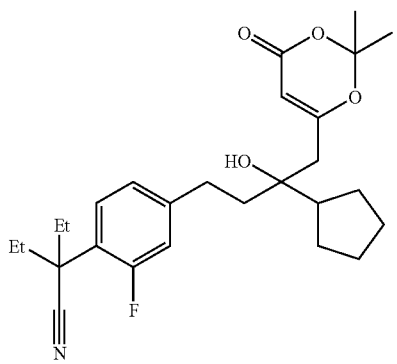

The desired product was prepared analogously to example A(86) step 6, substituting 1-{4-[3-Cyclopentyl-4-(2,2-dimethyl-6-oxo-6H-[1,3]dioxin-4-yl)-3-hydroxy-but-1-ynyl]-2-fluoro-phenyl}-2-ethyl-butyronitrile (0.900 g, 2.0 mmol) from step 2 above in place of 1-{4-[3-Cyclopentyl-4-(2,2-dimethyl-6-oxo-6H-[1,3]dioxin-4-yl)-3-hydroxy-but-1-ynyl]-2-fluoro-phenyl}-cyclopropanecarbonitrile. Yield: 0.841 g, 92%.

MS (ESI): 456 (M–H).

Example A(92)

1-{4-[2-(2-Cyclopentyl-4,6-dioxo-tetrahydro-pyran-2-yl)-ethyl]-2-fluoro-phenyl}-cyclobutanecarbonitrile

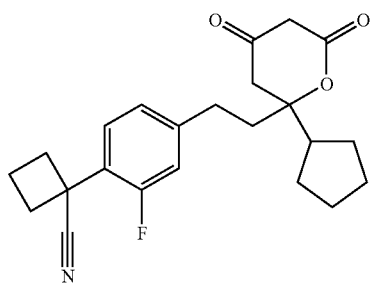

The desired product was prepared analogously to Example A(86) step 5 substituting 1-{4-[3-Cyclopentyl-4-(2,2-dimethyl-6-oxo-6H-[1,3]dioxin-4-yl)-3-hydroxy-butyl]-2-fluoro-phenyl}-cyclobutanecarbonitrile (1.00 g, 2.2 mmol) from step 3 below in place of 1-{4-[3-Cyclopentyl-4-(2,2-dimethyl-6-oxo-6H-[1,3]dioxin-4-yl)-3-hydroxy-butyl]-2-fluoro-phenyl}-cyclopropanecarbonitrile. Yield: 0.477 g, 57%.

$^1$H NMR (CDCl$_3$) δ: 1.79–2.05 (br, 8H), 2.14–2.19 (m, 2H), 2.21–2.29 (m, 1H), 2.49 (p, J=9.35 Hz, 1H), 2.65–2.76 (m, 1H), 2.83–2.95 (m, 4H), 3.00 (d, J=5.05 Hz, 2H), 3.02–3.10 (m, 2H), 3.66 (d, J=3.28 Hz, 2H), 7.12 (dd, J1=11.24 Hz, J2=1.64 Hz, 1H), 7.17 (dd, J1=7.96 Hz, J2=1.64 Hz, 1H), 7.38 (t, J=7.96 Hz, 1H).

Step 1

1-(4-Bromo-2-fluoro-phenyl)-cyclobutanecarbonitrile

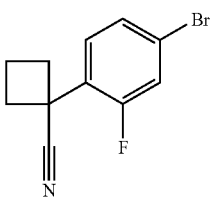

To a slurry of NaH (1.64 g, 60% suspension in mineral oil, 41.1 mmol) in DMSO (19 mL) stirred at room temperature, was added a solution of 1,3-dibromopropane (2.1 mL, 20.6 mmol) and (4-Bromo-2-fluoro-phenyl)-acetonitrile (4.0 g, 18.7 mmol) in diethyl ether (10 mL) slowly keeping the temprature of the reaction between 25 degrees Celsius and 35 degrees Celsius. Stir for two hours after the addition is complete, and pour into saturated ammonium chloride (150 mL). Add 100 ml of CH$_2$Cl$_2$ and separate the layers. Extract the aqueous phase with 2×50 mL CH$_2$Cl$_2$ and combine the organics. After drying the organic liquid over MgSO$_4$, the solids were removed by filtration, and the liquid was concentrated to an oil. The oil was purified by flash chromatography to yield the desired product. Yield: 1.43 g, 30%.

MS (APCI) 254 (M+H), 256 (M+2+H).

Step 2

1-{4-[3-Cyclopentyl-4-(2,2-dimethyl-6-oxo-6H-[1,3]dioxin-4-yl)-3-hydroxy-but-1-ynyl]-2-fluoro-phenyl}-cyclobutanecarbonitrile

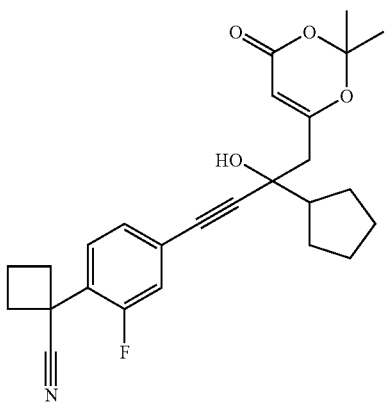

The desired product was prepared analogously to Example A(86) step 5, substituting 1-(4-Bromo-2-fluoro-phenyl)-cyclobutanecarbonitrile (1.06 g, 4.0 mmol) from step 1 above in place of 1-(4-bromo-2-fluoro-phenyl)-cyclopropanecarbonitrile. Yield: 1.226 g, 70%.

MS (ESI): 436 (M–H).

Step 3

1-{4-[3-Cyclopentyl-4-(2,2-dimethyl-6-oxo-6H-[1,3]dioxin-4-yl)-3-hydroxy-butyl]-2-fluoro-phenyl}-cyclobutanecarbonitrile

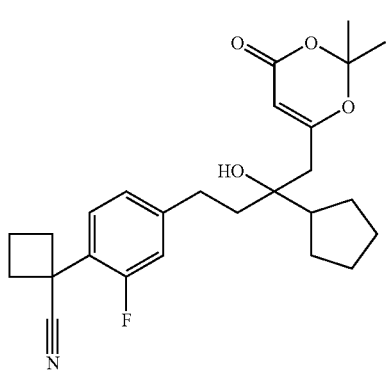

The desired product was prepared analogously to Example A(86) step 6, substituting 1-{4-[3-Cyclopentyl-4-(2,2-dimethyl-6-oxo-6H-[1,3]dioxin-4-yl)-3-hydroxy-but-1-ynyl]-2-fluoro-phenyl}-cyclobutanecarbonitrile (1.200 g, 2.7 mmol) from step 2 above in place of 1-{4-[3-Cyclopentyl-4-(2,2-dimethyl-6-oxo-6H-[1,3]dioxin-4-yl)-3-hydroxy-but-1-ynyl]-2-fluoro-phenyl}-cyclopropanecarbonitrile. Yield: 1.00 g, 84%.

MS (ESI): 440 (M−H).

Example A(93)

6-Cyclopentyl-6-[2-(4-hydroxy-3-isopropyl-phenyl)-ethyl]-dihydro-pyran-2,4-dione

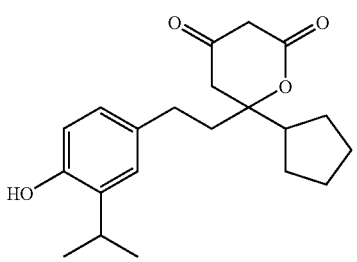

The title compound was prepared analogously to Example A(22) where Acetic acid 4-[2-(2-cyclopentyl-4,6-dioxo-tetrahydro-pyran-2-yl)-ethyl]-2-isopropyl-phenyl ester (Example A(94)) was substituted in place of acetic acid 4-[2-(2-cyclopentyl-4,6-dioxo-tetrahydro-pyran-2-yl)-ethyl]-2-ethyl-phenyl ester.

$^1$H NMR (CDCl$_3$): δ 1.24 (d, 6H, J=6.8 Hz), 1.47–1.81 (br m, 8H), 1.87–2.01 (m, 2H), 2.27 (m, 1H), 2.60 (m, 2H), 2.77 (s, 3H), 3.18 (m, 1H), 3.42 (s, 1H), 4.80 (s, 1H), 6.67 (d, 1H, J=8.1 Hz), 6.83 (dd, 1H, J=8.1, 2.3 Hz), 6.94 (d, 1H, J=2.3 Hz). Anal. Calcd. For C$_{21}$H$_{28}$O$_4$·0.3H$_2$O: C, 72.09; H, 8.24. Found: C, 72.12; H, 8.23.

Example A(94)

Acetic acid 4-[2-(2-cyclopentyl-4,6-dioxo-tetrahydro-pyran-2-yl)-ethyl]-2-isopropyl-phenyl ester

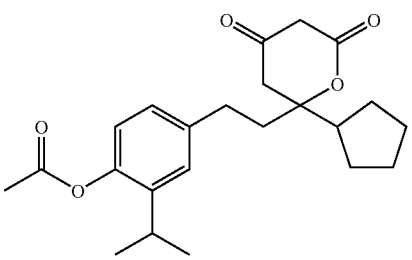

The title compound was prepared analogously to Example A(64) where Acetic acid 4-bromo-2-isopropyl-phenyl ester (from step 2) was substituted in place of 4-bromo-2-fluoro-1-isopropylbenzene.

Step 1

4-Bromo-2-isopropyl-phenol

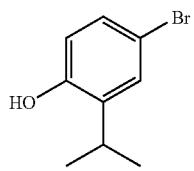

The title compound was prepared as described in Step 1 of Example A(2) where 2-isopropyl-phenol was substituted in place of 2-ethyl-phenol.

$^1$H NMR (CDCl$_3$): δ 1.23 (d, 6H, J=7.1 Hz), 3.17 (m, 1H), 4.87 (br s, 1H), 6.63 (d, 1H, J=8.5 Hz), 7.16 (dd, 1H, J=8.5, 2.3 Hz), 7.28 (d, 1H, J=2.5 Hz).

Step 2

Acetic acid 4-bromo-2-isopropyl-phenyl ester

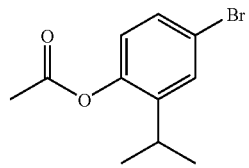

The title compound was prepared as described in Step 2 of Example A(22) where 4-Bromo-2-isopropyl-phenol from step 1, was substituted in place of 4-Bromo-2-ethyl-phenol.

$^1$H NMR (CDCl$_3$): δ 1.20 (d, 6H, J=7.1 Hz), 2.32 (s, 3H), 2.98 (m, 1H), 6.88 (d, 1H, J=8.6 Hz), 7.31 (dd, 1H, J=8.6, 2.3 Hz), 7.41 (d, 1H, J=2.5 Hz).

Example A(95)

6-[2-(3-Chloro-4-hydroxy-phenyl)-ethyl]-6-cyclopentyl-dihydro-pyran-2,4-dione

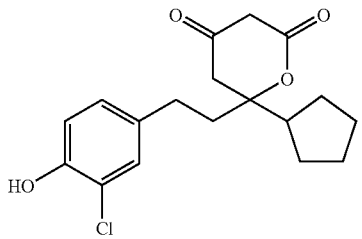

The title compound was prepared analogously to Example A(13) where 3-(3-Chloro-4-hydroxy-phenyl)-1-cyclopentyl-propan-1-one was substituted in place of 3-Cyclohex-1-enyl-1-cyclopentyl-propan-1-one.

$^1$H NMR (CDCl$_3$): δ 1.44–1.80 (br m, 8H), 1.93 (m, 2H), 2.26 (m, 1H), 2.60 (m, 2H), 2.73 (d, 1H, J=15.9 Hz), 2.78 (d, 1H, J=15.9 Hz), 3.43 (s, 2H), 5.44 (s, 1H), 6.94 (m, 2H), 7.10 (s, 1H). Anal. Calcd. For C$_{18}$H$_{21}$O$_4$Cl: C, 64.19; H, 6.28. Found: C, 64.33; H, 6.39.

Example A(96)

6-Cyclopentyl-6-[2-(3-ethyl-4-methoxy-phenyl)-ethyl]-dihydro-pyran-2,4-dione

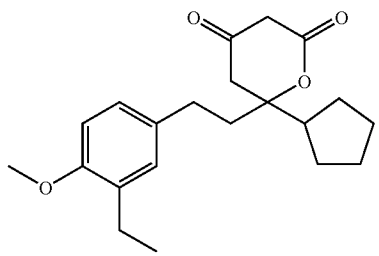

The title compound was prepared analogously to Example A(13) where 1-Cyclopentyl-3-(3-ethyl-4-methoxy-phenyl)-propan-1-one (from step 2) was substituted in place of 3-Cyclohex-1-enyl-1-cyclopentyl-propan-1-one.

$^1$H NMR (CDCl$_3$): δ 1.17 (t, 3H, J=7.3 Hz), 1.44–1.80 (brm, 8H), 1.95 (m, 2H), 2.28 (m, 1H), 2.57–2.63 (m, 4H), 2.77 (s, 2H), 3.42 (s, 2H), 3.80 (s, 3H), 6.75 (d, 1H, J=8.1 Hz), 6.91–6.94 (m, 2H). Anal. Calcd. For C$_{21}$H$_{28}$O$_4$.0.2H$_2$O: C, 72.47; H, 8.23. Found: C, 72.52; H, 8.25.

Step 1

4-Bromo-2-ethyl-1-methoxy-benzene

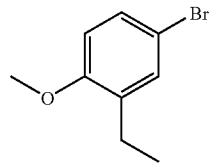

$^1$H NMR (CDCl$_3$): δ 1.17 (t, 3H, J=7.4 Hz), 2.59 (q, 2H, J=7.4 Hz), 3.80 (s, 3H), 6.70 (d, 1H, J=8.8 Hz), 7.26 (m, 2H).

Potassium carbonate (3.9 g, 28.3 mmol) and methyl iodide (0.59 mL, 9.43 mmol) were added to a solution of 4-Bromo-2-ethyl-phenol (1.9 g, 9.43 mmol, from step 1 of Example A(22)) dissolved in DMF (10 mL). The mixture was stirred for 16 h under N$_2$ and then partitioned between 1 N HCl and EtOAc. The organic layer was washed with saturated NaHCO$_3$, brine, dried over Na$_2$SO$_4$ and concentrated to a yellow oil. The oil was purifed by silica gel chromatography to give the title compound as a clear oil (1.37 g, 68%).

Step 2

1-Cyclopentyl-3-(3-ethyl-4-methoxy-phenyl)-propan-1-one

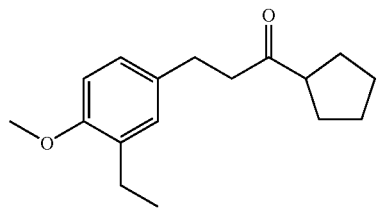

A mixture of bromide (1.3 g, 6.02 mmol, from step 1), 1-Cyclopentyl-2-propen-1-ol (1.14 g, 9.07 mmol), dichlorobis (triphenylphosphine) palladium (II) (85 mg, 0.12 mmol), sodium bicarbonate (0.61 g, 7.25 mmol) in N-methylpyrrolidinone (12 mL) was heated to 140° C. under N$_2$ for 5 h. The reaction mixture was partitioned between 1N HCl and EtOAc. The organic layer was washed with saturated NaHCO$_3$, brine, dried over Na$_2$SO$_4$ and concentrated to a brown oil. The oil was purifed by silica gel chromatography to give the title compound as a yellow oil (0.74 g, 47%).

$^1$H NMR (CDCl$_3$): δ ?1.17 (t, 3H, J=7.6 Hz), 1.54–1.80 (m, 9H), 1.17 (q, 2H, J=7.6 Hz), 2.73 (m, 2H), 2.84 (m, 2H), 3.80 (s, 3H), 6.75 (d, 1H, J=8.0 Hz), 6.97 (m, 2H).

Example A(97)

2-[4-(2-{2-cyclopentyl-5-[(2-ethyl-4-methyl-1H-imidazol-5-yl)methyl]-4-hydroxy-6-oxo-3,6-dihydro-2H-pyran-2-yl}ethyl)-2-fluorophenyl]-2-methyl-propanenitrile

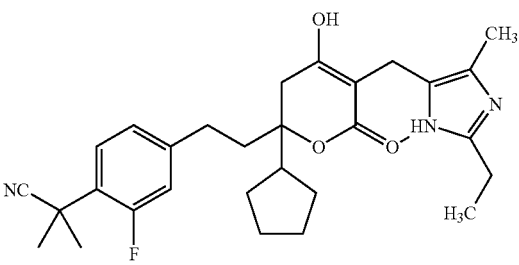

A solution of 2-{4-[2-(2-cyclopentyl-4-hydroxy-6-oxo-3, 6-dihydro-2H-pyran-2-yl)ethyl]-2-fluorophenyl}-2-methyl-propanenitrile (300 mg, 0.81 mmol) in anhydrous MeOH (8.0 mL) was treated with 2-ethyl-4-methyl-1H-imidazole-5-carbaldehyde (167 mg, 1.21 mmol), followed by borane-dimethylamine complex (62 mg, 1.05 mmol) at room temperature. The reaction was stirred for 12 hours before it was quenched by the addition of 1 N HCl. The mixture was extracted with 10% MeOH in CH$_2$Cl$_2$ (3×10 mL) and the combined organic layers were washed with brine, dried over Na$_2$SO$_4$. The solvent was removed and the residue was purified by HPLC to give product as a white powder (150 mg, 38% yield). $^1$H NMR (300 MHz, DMSO-d$_6$) δ: 1.15–1.20 (m, 3H), 1.30–1.65 (m, 8 H), 1.71 (s, 6 H), 1.85–1.93 (m, 2 H), 2.10 (s, 3 H), 2.25–2.40 (m, 2 H), 2.56–2.68 (m, 4 H), 3.32–3.44 (m, 2 H), 7.02–7.13 (m, 2 H), 7.35 (t, J=8.38 Hz, 1 H). Anal. Calcd. For $C_{29}H_{36}FN_3O_3 \cdot 0.1H_2O$: C, 70.30; H, 7.37; N, 8.48. Found: C, 70.09; H, 7.37; N, 8.47.

Step 4

Preparation of Compound 2-{4-[2-(2-cyclopentyl-4,6-dioxotetrahydro-2H-pyran-2-yl)ethyl]-2-fluorophenyl)-2-methylpropanenitrile

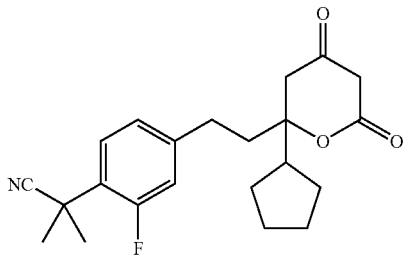

To a solution of 2-{4-[3-cyclopentyl-4-(2,2-dimethyl-4-oxo-4H-1,3-dioxin-6-yl)-3-hydroxybut-1-ynyl]-2-fluorophenyl}-2-methylpropanenitrile (4.25 g, 10.0 mmol) in MeOH (100 mL) was added Pd(OH)$_2$ (1.0 g, 20 wt %). The mixture was stirred under H$_2$ for 12 hours before it was filtered through a pad of celite. The solvent was removed and the residue was taken directly into next step without further purification.

The crude mixture was dissolved in anhydrous MeOH (100 mL) and treated with K$_2$CO$_3$ (2.8 g, 10 mmol). The reaction was heated at 45° C. for 40 min before it was cooled down to room temperature. The crude mixture was diluted with aqueous NH$_4$Cl and extracted with EtOAc (3×100 mL). The combined organic layers were washed with brine, dried over Na$_2$SO$_4$. The solvent was removed and the mixture was purified by flash column chromatography (EtOAc in hexanes, 10–40% gradient) to give the desired product (1.4 g, 35% for two steps). $^1$H NMR (CDCl$_3$) δ: 1.60–1.73(m, 6 H), 1.92–1.98 (m, 2 H), 2.22–2.30 (m, 1 H), 2.65–2.71 (m, 2 H), 2.75–2.80 (m, 2H), 6.88–6.96 (m, 2H), 7.37–7.43 (m, 1H).

Step 3

Preparation of Compound 2-{4-[3-cyclopentyl-4-(2,2-dimethyl-4-oxo-4H-1,3-dioxin-6-yl)-3-hydroxybut-1-ynyl]-2-fluorophenyl}-2-methylpropanenitrile

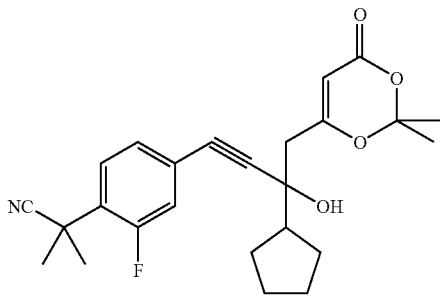

To a solution of 2-(4-bromo-2-fluorophenyl)-2-methylpropanenitrile (3.0 g, 12.4 mmol) in diisopropylamine (32 mL) and DMF (16 mL) was added 6-(2-cyclopentyl-2-hydroxybut-3-ynyl)-2,2-dimethyl-4H-1,3-dioxin-4-one (3.2 g, 12.4 mmol), PdCl$_2$(PPh$_3$)$_2$ (350 mg, 4 mol %), CuI (71 mg, 3 mol %). The mixture was heated to 90° C. for 30 min before it was cooled down to room temperature. The reaction was diluted with aqueous NH$_4$Cl, extracted with EtOAc (3×50 mL). The combined organic extracts were washed with brine, dried with Na$_2$SO$_4$ and evaporated to dryness. The mixture was purified by flash column chromatography (10–50% EtOAc in hexanes) to give the product (4.2 g, 79% yield). $^1$H NMR (300 MHz, CDCl$_3$) δ: 1.65–1.76 (m, 14 H), 1.79 (s, 6 H), 1.82–1.85 (m, 1 H), 2.24 (s, 1 H), 2.59 (s, 1 H), 2.67 (m, 2 H), 5.46 (m, 1 H), 7.11 (dd, J=12.15, 1.60 Hz, 1 H), 7.18 (dd, J=8.10, 1.70 Hz, 1 H), 7.45 (t, J=8.10 Hz, 1 H).

Step 2

Preparation of Compound 2-(4-bromo-2-fluorophenyl)-2-methylpropanenitrile

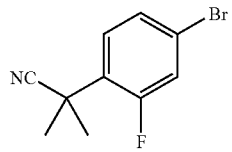

To a solution of MeI (3.2 mL, 49.3 mmol) in anhydrous DMF (82 mL) at 0° C. was added NaH (60%, 2.0 g), followed by (4-bromo-2-fluorophenyl)acetonitrile (3.5 g, 16.4 mmol). The mixture was slowly warmed up to room temperature and stirred for 3 hours. The reaction was quenched by the addition of saturated NH$_4$Cl and extracted with EtOAc (3×150 mL). The combined organic extracts were washed with brine, dried with Na$_2$SO$_4$ and evaporated to dryness. The mixture was purified by flash column chromatography (0–20% EtOAc in hexanes) to give the product (3.0 g, 77% yield). $^1$H NMR (300 MHz, CDCl$_3$) δ: 1.78 (s, 6 H), 7.26–7.42 (m, 3 H).

Step 1

Preparation of Compound (4-bromo-2-fluorophenyl)acetonitrile

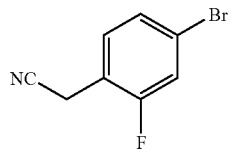

To a solution of 4-bromo-1-(bromomethyl)-2-fluorobenzene (5.0 g, 18.7 mmol) in DMF (80 mL) and H$_2$O (8 mL) was added KCN (1.21 g, 18.7 mmol). The mixture was heated to 40° C. for 3 hours before it was cooled down to room temperature. The reaction was diluted with H$_2$O (40 mL) and extracted with Et$_2$O (3×100 mL). The combined organic layers were washed with brine and dried over Na$_2$SO$_4$. The solvent was removed and the residue was purified by flash column chromatography (0–15% EtOAc in hexanes) to give the product (3.5 g, 87% yield). $^1$H NMR (300 MHz, CDCl$_3$) δ: 3.72 (s, 2 H), 7.26–7.35 (m, 3 H).

Example A(98)

2-[4-(2-{5-[(5-chloro-1-methyl-1H-benzimidazol-2-yl)methyl]-2-cyclopentyl-4-hydroxy-6-oxo-3,6-dihydro-2H-pyran-2-yl}ethyl)-2-fluorophenyl]-2-methylpropanenitrile

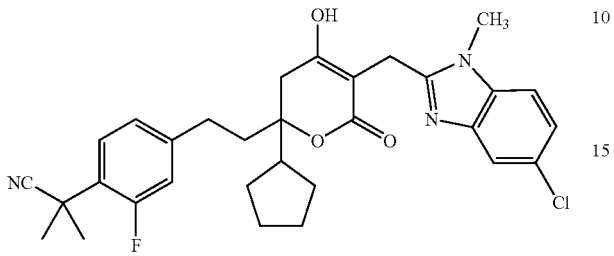

The title compound was prepared analogously to Example A(97), where 5-chloro-1-methyl-1H-benzimidazole-2-carbaldehyde was substituted in place of 2-ethyl-4-methyl-1H-imidazole-5-carbaldehyde. $^1$H NMR (300 MHz, DMSO-d$_6$) δ: 1.14–1.49 (m, 8 H), 1.52 (s, 6 H), 1.87–2.07 (m, 2 H), 2.15–2.25 (m, 2 H), 2.38–2.46 (m, 2 H), 2.56–2.62 (m, 1 H), 3.49–3.65 (m, 2 H), 3.58 (s, 3H), 6.86 (dd, J=8.01, 1.22 Hz, 1 H), 6.98 (m, 2 H), 7.14 (m, 2 H), 7.30 (d, J=8.67 Hz, 1 H). HRMS: calcd for C$_{31}$H$_{34}$ClFN$_3$O$_3$ (M+H$^+$) 550.2267. found 550.2273.

Step 3

5-chloro-1-methyl-1H-benzimidazole-2-carbaldehyde

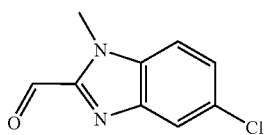

A solution of (5-chloro-1-methyl-1H-benzimidazol-2-yl)methanol (1.5 g, 7.7 mmol) dissolved in CH$_2$Cl$_2$ at room temperature was treated with Dess-Martin periodinane (4.9 g, 11.5 mmol). The reaction was stirred for 15 hours before the solvent was removed. The residue was purified by flash column chromatography (0–3% MeOH in CH$_2$Cl$_2$) to give the product (1.0 g, 66% yield). $^1$H NMR (300 MHz, CDCl$_3$) δ: 4.16 (s, 3 H), 7.40–7.47 (m, 2 H), 7.90–7.93 (m, 1 H), 10.11 (s, 1 H).

Step 2

(5-chloro-1-methyl-1H-benzimidazol-2-yl)methanol

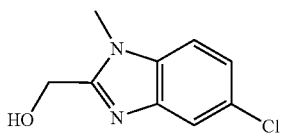

4-chloro-N$^1$-methylbenzene-1,2-diamine (15.0 g, 96 mmol) and glycolic acid (8.1 g, 106 mmol) were mixed together in a sealed tube. The mixture was heated at 150° C. for 5 hours before it was cooled down to room temperature. The residue was purified by flash column chromatography (0–5% MeOH in CH$_2$Cl$_2$) to give the product (8.5 g, 45% yield). $^1$H NMR (300 MHz, CDCl$_3$) δ: 3.80 (s, 3 H), 4.86 (s, 2 H), 7.13–7.22 (m, 2 H), 7.62–7.64 (m, 1 H).

Step 1

4-chloro-N'-methylbenzene-1,2-diamine

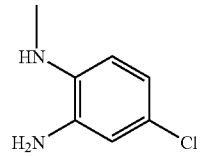

A solution of 1,4-dichloro-2-nitrobenzene (5 g, 26 mmol) dissolved in 33% MeNH$_2$ in EtOH (20 mL) was heated to 80° C. for 15 hours. The reaction was cooled to room temperature and the solvent was removed. The crude product was taken directly into next step without further purification.

The mixture dissolved in EtOH (250 mL) was treated with Zn dust (15 g), followed by dropwise addition of aqueous HCl (6 N, 40 mL). The reaction was stirred at room temperature for 3 hours. The solution was made basic by slow addition of saturated NaOH. The aqueous was extracted with CH$_2$Cl$_2$ (3×100 mL). The combined organic layers were washed with brine and dried over Na$_2$SO$_4$. The solvent was removed to afford product (1.7 g, 42% yield for two steps).

$^1$H NMR (300 MHz, CDCl$_3$) δ: 2.84 (s, 3 H), 6.54 (d, J=6.0 Hz, 1 H), 6.70 (d, J=3.0 Hz, 1 H), 6.79 (dd, J=3.0, 6.0 Hz, 1 H).

Example A(99)

2-[4-(2-{2-cyclopentyl-4-hydroxy-6-oxo-5-[(2-oxo-1,2-dihydropyridin-4-yl)methyl]-3,6-dihydro-2H-pyran-2-yl}ethyl)-2-fluorophenyl]-2-methylpropanenitrile

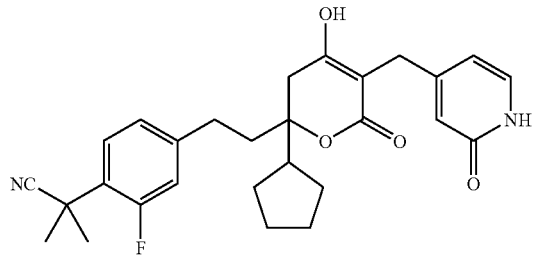

The title compound was prepared analogously to Example A(97), where 2-oxo-1,2-dihydropyridine-4-carbaldehyde was substituted in place of 2-ethyl-4-methyl-1H-imidazole-5-carbaldehyde. $^1$H NMR (300 MHz, DMSO-d$_6$): 1.25–1.78 (m, 8 H), 1.71 (s, 6 H), 1.87–1.93 (m, 2 H), 2.56–2.64 (m, 2 H), 2.71–2.76 (m, 1 H), 3.25–2.26 (m, 4 H), 7.00–7.03 (m, 1 H), 7.09–7.20 (m, 3 H), 7.23–7.28 (m, 1 H), 7.32–7.38 (m, 1 H). HRMS: calcd for C$_{28}$H$_{32}$FN$_2$O$_4$ (M+H$^+$) 479.2341. found 479.2331.

Step 1

2-oxo-1,2-dihydropyridine-4-carbaldehyde

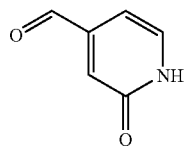

The title compound was prepared as described in the following reference: *J. Am. Chem. Soc.*, 1997, 3619–3620.

Example A(100)

2-(4-{2-[2-cyclopentyl-4-hydroxy-5-(3-methoxybenzyl)-6-oxo-3,6-dihydro-2H-pyran-2-yl]ethyl}-2-fluorophenyl)-2-methylpropanenitrile

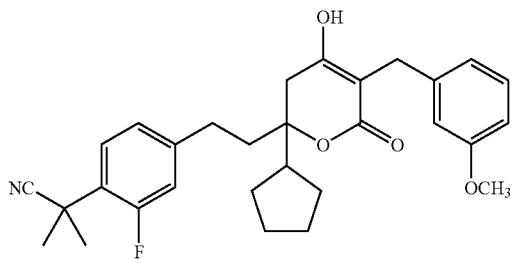

The title compound was prepared analogously to Example A(97), where 3-methoxybenzaldehyde was substituted in place of 2-ethyl-4-methyl-1H-imidazole-5-carbaldehyde.

$^1$H NMR (300 MHz, DMSO-d$_6$) δ: 1.24–1.66 (m, 8 H), 1.71 (s, 6 H), 1.83–1.93 (m, 2 H), 2.27–2.36 (m, 2 H), 2.54–2.59 (m, 2 H), 2.73–2.79 (m, 1 H), 3.42–3.56 (m, 2 H), 3.65 (s, 3 H), 6.69–6.77 (m, 3 H), 6.93–7.19 (m, 3 H), 7.30–7.36 (m, 1 H). Anal. Calcd. For C$_{30}$H$_{34}$FNO$_4$.0.3H$_2$O: C, 72.50; H, 7.02; N, 2.82. Found: C, 72.13; H, 6.97; N, 2.88.

Step 1

3-methoxybenzaldehyde

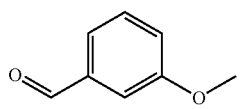

A solution of 3-hydroxybenzaldehyde (1.22 g, 10 mmol) in anhydrous acetone (50 mL) was treated with K$_2$CO$_3$ (2.76 g, 20 mmol) and MeI (0.9 mL, 15 mmol) at room temperature for 12 hours. The mixture was poured into water and extracted with EtOAc (3×30 mL). The combined organic layers were washed with brine and dried over Na$_2$SO$_4$. The solvent was removed and the product was purified by flash column chromatography (0–15% EtOAc in hexanes, 1.2 g, 88% yield). $^1$H NMR (300 MHz, CDCl$_3$) δ: 3.88 (s, 3 H), 7.17–7.21 (m, 1 H), 7.38–7.42 (m, 1 H), 7.45–7.47 (m, 2 H), 9.99 (s, 1 H).

Example A(101)

2-[4-(2-{2-cyclopentyl-4-hydroxy-5-[3-(methylsulfonyl)benzyl]-6-oxo-3,6-dihydro-2H-pyran-2-yl}ethyl)-2-fluorophenyl]-2-methylpropanenitrile

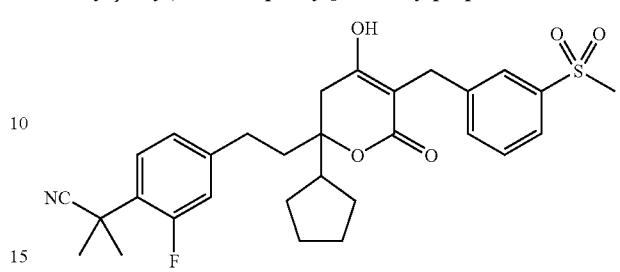

The title compound was prepared analogously to Example A(97), where 3-(methylsulfonyl)benzaldehyde was substituted in place of 2-ethyl-4-methyl-1H-imidazole-5-carbaldehyde. $^1$H NMR (300 MHz, DMSO-d$_6$) δ: 1.23–1.64 (m, 8 H), 1.70 (s, 6 H), 1.84–1.91 (m, 2 H), 2.26–2.34 (m, 1 H), 2.54–2.59 (m, 2 H), 2.68–2.74 (m, 1 H), 3.10 (s, 3 H), 3.17 (s, 1 H), 3.55–3.66 (m, 2 H), 6.92–6.95 (m, 1 H), 7.04–7.09 (m, 1 H), 7.30–7.35 (m, 1 H), 7.46–7.54 (m, 2 H), 7.69–7.74 (m, 2H). HRMS: calcd for C$_{30}$H$_{35}$FSNO$_5$ (M+H$^+$) 540.2215. found 540.2228.

Step 2

3-(methylsulfonyl)benzaldehyde

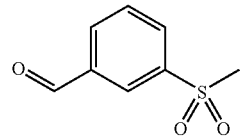

A solution of [3-(methylsulfonyl)phenyl]methanol (680 mg, 3.66 mmol) in anhydrous CH$_2$Cl$_2$ (20 mL) was treated with PCC (1.03 g, 4.75 mmol) at room temperature for 2 hours. The solvent was removed and the residue was purified by flash column chromatography (20–60% EtOAc in hexanes) to give the product (500 mg, 74% yield). $^1$H NMR (300 MHz, CDCl$_3$) δ: 3.13 (s, 3 H), 7.77–7.82 (m, 1 H), 8.18–8.24 (m, 2 H), 8.46–8.48 (m, 1 H), 10.12 (s, 1 H).

Step 1

[3-(methylsulfonyl)phenyl]methanol

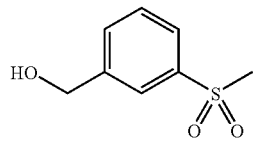

A solution of 3-(methylsulfonyl)benzoic acid (1.0 g, 5.0 mmol) in anhydrous THF (25 mL) was treated with BH$_3$.THF (1 M solution, 7.5 mL) at room temperature. The reaction was stirred for 12 hours before it was quenched by slow addition of MeOH. The solvent was removed and the residue was purified by flash column chromatography (0–5% MeOH in CH$_2$Cl$_2$) to give the product (0.84 g, 90% yield). $^1$H NMR (300 MHz, CDCl$_3$) δ: 3.06 (s, 3 H), 4.81 (d, J=6.0 Hz, 2 H), 7.54–7.59 (m, 1 H), 7.65–7.68 (m, 1 H), 7.85–7.88 (m, 1 H), 7.96 (s, 1 H).

Example A(102)

2-[4-(2-{5-[(4-chloro-1-methyl-1H-pyrazol-3-yl)methyl]-2-cyclopentyl-4-hydroxy-6-oxo-3,6-dihydro-2H-pyran-2-yl}ethyl)-2-fluorophenyl]-2-methylpropanenitrile

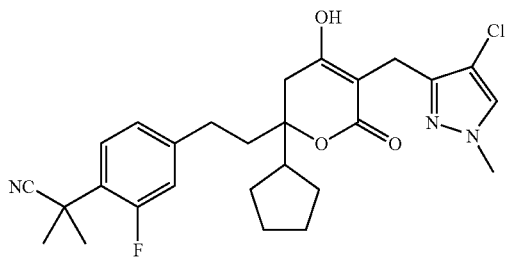

The title compound was prepared analogously to Example A(97), where 4-chloro-1-methyl-1H-pyrazole-3-carbaldehyde was substituted in place of 2-ethyl-4-methyl-1H-imidazole-5-carbaldehyde. $^1$H NMR (300 MHz, DMSO-$d_6$) δ: 1.46–1.78 (m, 8 H), 1.88 (s, 6 H), 2.21–2.26 (m, 2 H), 2.52–2.60 (m, 1 H), 2.78–2.94 (m, 4 H), 3.57–3.60 (m, 2 H), 3.72 (s, 3 H), 7.24–7.31 (m, 2 H), 7.51–7.56 (m, 1 H), 7.92 (s, 1 H). Anal. Calcd. For $C_{27}H_{31}FClN_3O_3 \cdot 1.0H_2O$: C, 62.60; H, 6.42; N, 8.11. Found: C, 62.36; H, 6.44; N, 8.47.

Example A(103)

2-(4-{2-[2-cyclopentyl-4-hydroxy-5-(imidazo[-1,2-a]pyridin-2-ylmethyl)-6-oxo-3,6-dihydro-2H-pyran-2-yl]ethyl}-2-fluorophenyl)-2-methylpropanenitrile

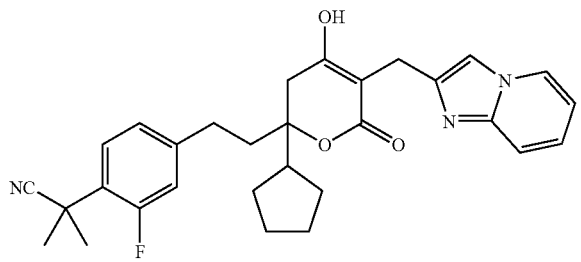

The title compound was prepared analogously to Example A(97), where imidazo[1,2-a]pyridine-2-carbaldehyde was substituted in place of 2-ethyl-4-methyl-1H-imidazole-5-carbaldehyde. $^1$H NMR (300 MHz, DMSO-$d_6$) δ: 1.23–1.58 (m, 8 H), 1.60 (s, 6 H), 1.82–1.90 (m, 2 H), 2.19–2.29 (m, 2 H) 2.46–2.66 (m, 3 H), 3.50–3.63 (m, 2 H), 6.76 (t, J=6.31 Hz, 1 H), 6.87 (d, J=8.29 Hz, 1 H), 7.12 (m, 3 H), 7.32 (d, J=9.04 Hz, 1 H), 7.51 (s, 1 H), 8.34 (d, J=6.22 Hz, 1 H). Anal. Calcd. For $C_{30}H_{32}FN_3O_3 \cdot 0.5H_2O$: C, 70.57; H, 6.51; N, 8.23. Found: C, 70.73; H, 6.55; N, 7.85.

Step 1

Imidazo[1,2-a]pyridine-2-carbaldehyde

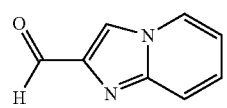

The title compound was prepared as described in the following reference: J. Heterocycl. Chem.; 1992; 691–697.

Example A(104)

2-{4-[2-(2-Cyclopentyl-4,6-dioxo-5-[1,2,4]triazolo[1,5-a]pyrimidin-2-ylmethyl-tetrahydro-pyran-2-yl)-ethyl]-2-fluoro-phenyl}-2-methyl-propionitrile

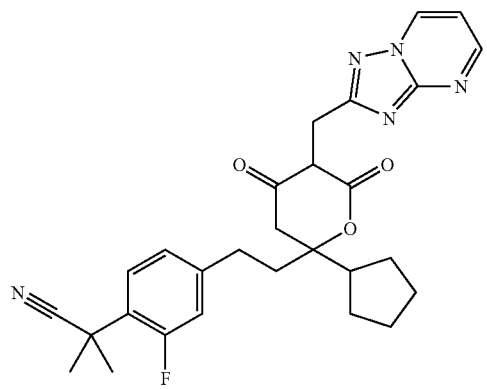

The title compound was prepared analogously to Example A(97), where [1,2,4]triazolo[1,5-a]pyrimidine-2-carbaldehyde was substituted in place of 2-ethyl-4-methyl-1H-imidazole-5-carbaldehyde in final step of that example. $^1$H NMR (400 MHz, CDCl$_3$) δ: 1.47–1.71 (m, 8H), 1.75 (s, 6H), 2.00 (m, 2H), 2.39 (m, 1H), 2.66 (dd, J=103, 18 Hz, 2H), 2.69 (m, 2H), 4.12 (s, 2H), 6.88 (d, J=12.9 Hz, 1H), 6.93 (d, J=8.1 Hz, 1H), 7.20 (m, 1H), 7.84 (t, J=8.1 Hz, 1H), 8.85 (m, 2H). MS (ESI): 504.1(M+H$^+$).

Example A(105)

(+)-2-{4-[2-(2-Cyclopentyl-4,6-dioxo-5-[1,2,4]triazolo[1,5-a]pyrimidin-2-ylmethyl-tetrahydro-pyran-2-yl)-ethyl]-2-fluoro-phenyl}-2-methyl-propionitrile

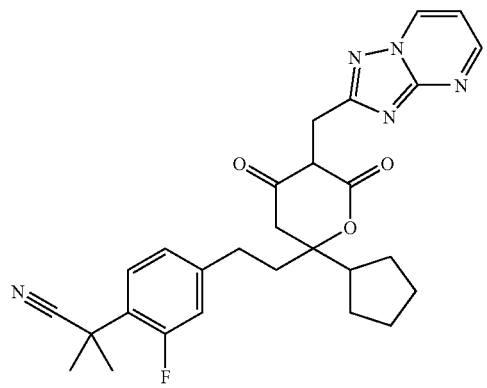

(+) isomer

The title compound was isolated by chiral chromatography of racemic material described in Example A(104). Conditions: Chiralpak OJ-RH, 150×4.6 mm, 0.6 mL/min, 30° C.; 35% acetonitrile, 65% water, 0.1% formic acid; retention time 17.6 min.

Example A(106)

(−)-2-{4-[2-(2-Cyclopentyl-4,6-dioxo-5-[1,2,4]triazolo[1,5-a]pyrimidin-2-ylmethyl-tetrahydro-pyran-2-yl)-ethyl]-2-fluoro-phenyl}-2-methyl-propionitrile

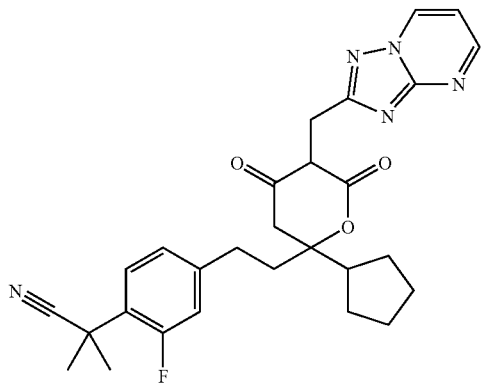

(−) isomer

The title compound was isolated by chiral chromatography of racemic material described in Example A(104). Conditions: Chiralpak OJ-RH, 150×4.6 mm, 0.6 mL/min, 30° C.; 35% acetonitrile, 65% water, 0.1% formic acid; retention time 21.7 min.

Example A(107)

2-(4-{2-[2-Cyclopentyl-5-(5-methyl-3H-imidazol-4-ylmethyl)-4,6-dioxo-tetrahydro-pyran-2-yl]-ethyl}-2-fluoro-phenyl)-2-methyl-propionitrile

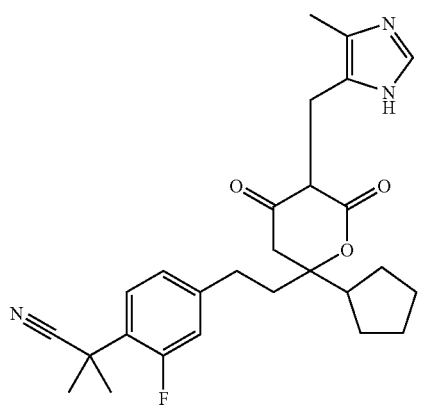

The title compound was prepared analogously to Example A(97), where 5-Methyl-3H-imidazole-4-carbaldehyde was substituted in place of 2-ethyl-4-methyl-1H-imidazole-5-carbaldehyde in the final step of that example. $^1$H NMR (400 MHz, CDCl$_3$) δ: 1.47–1.71 (m, 8H), 1.70 (s, 6H), 1.88 (m, 2H), 2.12 (s, 3H), 2.28 (m, 1H), 2.43 (d, J=103, 17.4 Hz, 1H), 2.50 (m, 2H), 2.58 (m, 3H), 7.02 (d, J=6.57 Hz, 1H), 7.11 (d, J=13.1 Hz, 1H), 7.34 (t, J=8.6 Hz, 1H), 7.78 (s, 1H). MS (ESI): 467.1 (M+H$^+$).

Example A(108)

2-(4-{2-[2-Cyclopentyl-5-(6-methyl-[1,2,4]triazolo[1,5-a]pyrimidin-2-ylmethyl)-4,6-dioxo-tetrahydro-pyran-2-yl]-ethyl}-2-fluoro-phenyl)-2-methyl-propionitrile

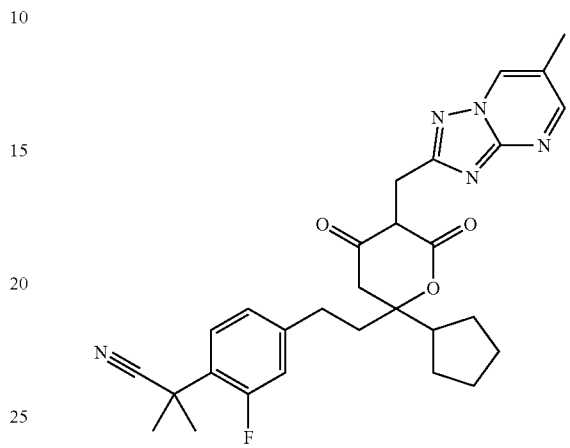

The title compound was prepared analogously to Example A(97), where 6-Methyl-[1,2,4]triazolo[1,5-a]pyrimidine-2-carbaldehyde was substituted in place of 2-ethyl-4-methyl-1H-imidazole-5-carbaldehyde in the final step of that example. $^1$H NMR (400 MHz, CDCl$_3$) δ: 1.48–1.71 (m, 8H), 1.76 (s, 6H), 2.00 (m, 2H), 2.06 (s, 1H), 2.10 (s, 1H), 2.38 (m, 1H), 2.39 (s, 3H), 2.68 (m, 2H), 2.81(m, 1H), 4.09 (s, 2H), 6.86 (d, J=12.9 Hz, 1H), 6.92 (d, J=8.1 Hz, 1H), 7.84 (t, J=8.1 Hz, 1H), 8.63 (s, 1H), 8.70 (s, 1H). MS (ESI): 518.6(M+H$^+$).

Step 2

Preparation of 6-methyl[1,2,4]triazolo[1,5-a]pyrimidine-2-carbaldehyde

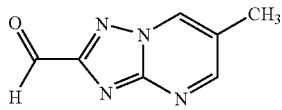

A mixture of (6-methyl[1,2,4]triazolo[1,5-a]pyrimidin-2-yl)methanol(15.7 g, 95.6 mmol), TEMPO (1.12 mg, 7.2 mmol), iodobenzene diacetate (33.9 g, 105.2 mmol) in CH$_2$Cl$_2$ (100 mL) was stirred at room temperature for 2 hours. Once the reaction was deemed complete, methyl-tert-butyl ether (50 mL) was added slowly to precipitate the product. The concentrated mother liquor was introduced into a silica gel column and eluted with 2% MeOH/CH$_2$Cl$_2$ to give additional amount of the aldehyde product as a while solid (12 g, 80%). $^1$H NMR (300 MHz, CDCl$_3$) δ: 2.54 (m, 3 H), 8.73 (m, 1 H), 8.85 (m, 1 H), 10.23 (m, 1 H). MS (APCI, M+H$^+$): 163.1.

Step 1

Preparation of (6-methyl[1,2,4]triazolo[1,5-a]pyrimidin-2-yl)methanol

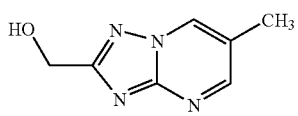

To a solution of (3-amino-1H-1,2,4-triazol-5-yl)methanol (16.6 g, 87.6 mmol) in acetic cid was added 3-ethoxymethacrolein (10.0 g, 87.6 mmol), and the mixture was heated to 80° C. for 4 hours. Upon cooling of the reaction, the product crystallized out of solution. The collected product was a white solid (14.0 g, 92%). $^1$H NMR (300 MHz, DMSO-D6) δ: 2.38 (m, 3 H) 4.63 (m, 2 H) 5.52 (m, 1 H) 8.75 (m, 1 H) 9.21 (m, 1 H). MS (APCI, M+H$^+$): 163.1, 165.1.

Example A(109)

(+)-2-(4-{2-[2-Cyclopentyl-5-(6-methyl-[1,2,4]triazolo[1,5-a]pyrimidin-2-ylmethyl)-4,6-dioxo-tetrahydro-pyran-2-yl]-ethyl}-2-fluoro-phenyl)-2-methyl-propionitrile

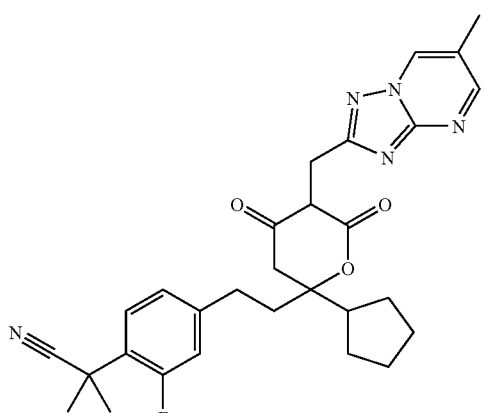

(+) isomer

The title compound was isolated by chiral chromatography of racemic material described in Example A(108). Conditions: Chiralpak AS-RH, 150×4.6 mm, 0.6 mL/min, 30° C.; 40% acetonitrile, 60% water, 0.1% formic acid; retention time 24.5 min.

Example A(110)

(−)-2-(4-{2-[2-Cyclopentyl-5-(6-methyl-[1,2,4]triazolo[1,5-a]pyrimidin-2-ylmethyl)-4,6-dioxo-tetrahydro-pyran-2-yl]-ethyl}-2-fluoro-phenyl)-2-methyl-propionitrile

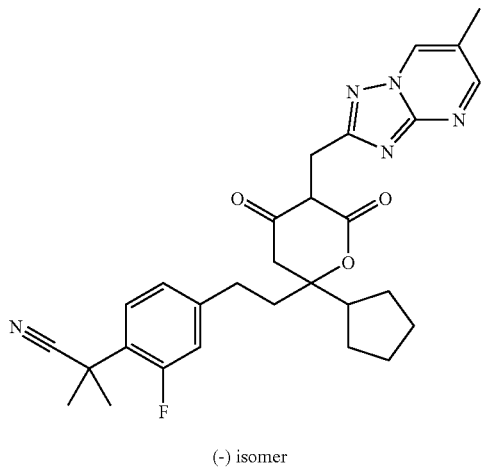

(−) isomer

The title compound was isolated by chiral chromatography of racemic material described in Example A(108). Conditions: Chiralpak AS-RH, 150×4.6 mm, 0.6 mL/min, 30° C.; 40% acetonitrile, 60% water, 0.1% formic acid; retention time 17.99 min.

Example A(111): 2-(4-{2-[5-(6-Chloro-[1,2,4]triazolo[1,5-a]pyrimidin-2-ylmethyl)-2-cyclopentyl-4,6-dioxo-tetrahydro-pyran-2-yl]-ethyl}-2-fluoro-phenyl)-2-methyl-propionitrile

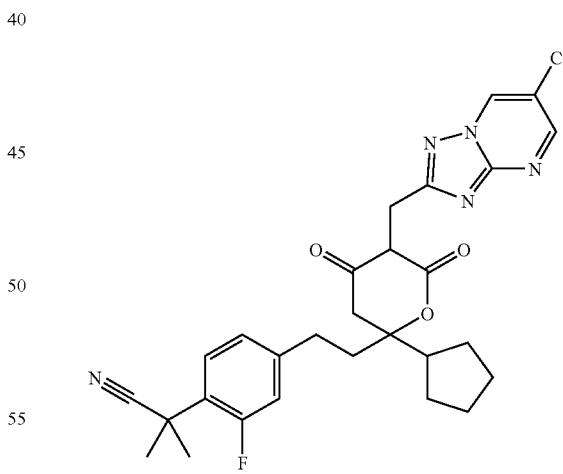

The title compound was prepared analogously to Example A(97), where 6-Chloro-[1,2,4]triazolo[1,5-a]pyrimidine-2-carbaldehyde was substituted in place of 2-ethyl-4-methyl-1H-imidazole-5-carbaldehyde in the final step of that example. $^1$H NMR (400 MHz, CDCl$_3$) δ: 1.47–1.71 (m, 8H), 1.75 (s, 6H), 2.00 (m, 2H), 2.39 (m, 1H), 2.65 (dd, J=101, 17.9 Hz, 2H), 2.68 (m, 2H), 4.11 (m, 2H), 6.87 (d, J=11.6 Hz, 1H), 6.93 (d, J=6.6 Hz, 1H), 7.35 (t, J=8.3 Hz, 1H), 8.79 (s, 1H), 8.88 (s, 1H). MS (ESI): 539.1 (M+H$^+$).

Step 2

Preparation of Compound 6-chloro[1,2,4]triazolo[1,5-a]pyrimidine-2-carbaldehyde

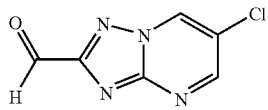

A mixture of (6-chloro[1,2,4]triazolo[1,5-a]pyrimidin-2-yl)methanol (9.86 g, 53.4 mmol), TEMPO (626 mg, 4.01 mmol), iodobenzene diacetate (18.9 g, 58.76 mmol) in CH$_2$Cl$_2$ (75 mL) was stirred at room temperature for 2 hours. Once the reaction was deemed complete, methyl-tert-butyl ether (50 mL) was added slowly to precipitate the product. as a while solid (8.72 g, 90%). $^1$H NMR (300 MHz, CDCl$_3$) δ: 8.93 (d, J=2.45 Hz, 1 H), 8.99 (d, J=2.64 Hz, 1 H), 10.25 (s, 1 H). MS (APCI): 183.0, 185.0 (M+H$^+$).

Step 1

Preparation of Compound (6-chloro[1,2,4]triazolo[1,5-a]pyrimidin-2-yl)methanol

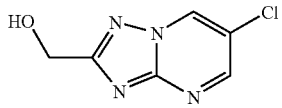

To a slurry of (3-amino-1H-1,2,4-triazol-5-yl)methanol (28.5 g, 150 mmol) in acetic acid was added chloromalonaldehyde (16 g, 150 mmol). The mixture was heated to 80° C. for 4 hours. Upon cooling of the reaction to room temperature, the product crystallized out as a white solid (25.5 g, 92%). $^1$H NMR (300 MHz, DMSO-D6) δ: 4.67 (s, 2 H), 5.62 (s, 1 H), 8.94 (d, J=2.45 Hz, 1 H), 9.81 (d, J=2.45 Hz, 1 H). MS (APCI): 185.0 (M+H$^+$).

Example A(112)

2-(4-{2-[2-Cyclopentyl-5-(5,7-dimethyl-[1,2,4]triazolo[1,5-a]pyrimidin-2-ylmethyl)-4,6-dioxo-tetrahydro-pyran-2-yl]-ethyl}-2-fluoro-phenyl)-2-ethyl-butyronitrile

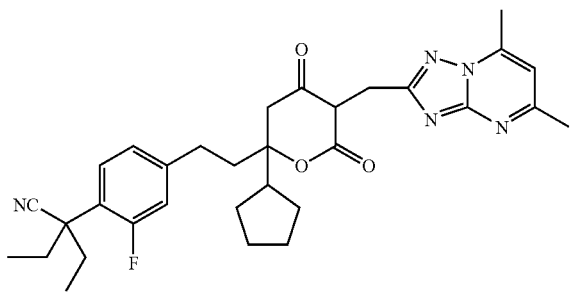

A solution of 2-{4-[2-(2-cyclopentyl-4,6-dioxo-tetrahydro-pyran-2-yl)-ethyl]-2-fluoro-phenyl}-2-ethyl-butyronitrile (300 mg, 0.75 mmol) in anhydrous MeOH (3.0 mL) was treated with 5,7-dimethyl-[1,2,4]triazolo[1,5-a]pyrimidine-2-carbaldehyde (198 mg, 1.1 mmol), followed by borane-dimethylamine complex (62 mg, 1.05 mmol) at room temperature. The reaction was stirred for 12 hours before it was quenched by the addition of CH$_2$Cl$_2$ (30 mL) and Amberlite IR 120(plus) (3 g). The reaction was stirred for 30 minutes, and then filtered. The filtrate was concentrated to an oil, dissolved in CH$_2$Cl$_2$ (25 mL, and then washed with 10 mL 1 N HCl. The aqueous layer was extracted with 2×25 mL CH$_2$Cl$_2$. The organic layers were combined and dried over Na$_2$SO$_4$. After removing the solids by filtration, the liquid was concentrated to an oil. The desired product was isolated by preparatory HPLC (76 mg, 18%). $^1$H NMR (400 MHz, CDCl$_3$) δ: 0.74 (t, J=7.45 Hz, 6 H), 1.37–1.59 (m, 8 H), 1.79–1.88 (m, 4 H), 1.94–2.03 (m, 2 H), 2.21 (t, J=8.84 Hz, 3 H), 2.36 (d, J=17.94 Hz, 1 H), 2.47–2.55 (m, 5 H), 2.59–2.63 (m, 4 H), 3.95 (d, J=3.54 Hz, 2 H), 6.66 (dd, J1=13.26 Hz, J2=1.64 Hz, 1 H), 6.72–6.75 (m, 2 H), 7.23 (t, J=8.21 Hz, 1 H).

Step 2

Preparation of Compound 2-{4-[2-(2-Cyclopentyl-4,6-dioxo-tetrahydro-pyran-2-yl)-ethyl]-2-fluoro-phenyl}-2-ethyl-butyronitrile

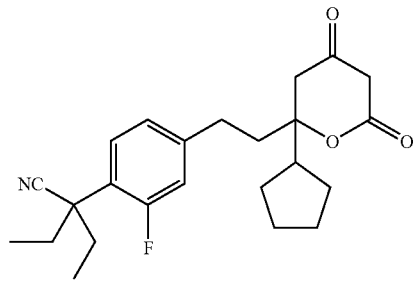

The desired product was prepared analogously to step 4 of Example A(97), substituting 2-{4-[3-cyclopentyl-4-(2,2-dimethyl-6-oxo-6H-[1,3]dioxin-4-yl)-3-hydroxy-butyl]-2-fluoro-phenyl}-2-ethyl-butyronitrile from step 1 below in place of 1-{4-[3-Cyclopentyl-4-(2,2-dimethyl-6-oxo-6H-[1,3]dioxin-4-yl)-3-hydroxy-butyl]-2-fluoro-phenyl}-cyclopropanecarbonitrile. $^1$H NMR (CDCl$_3$) δ: 1.01 (t, J=7.45 Hz, 6H), 1.62–1.90 (br, 8H), 2.03–2.17 (br, 4H), 2.20–2.29 (br, 2H), 2.37 (p, J=9.35 Hz, 1H), 2.75–2.82 (m, 2H), 2.86 (d, J=7.58 Hz, 2H), 3.53 (d, J=2.02 Hz, 2H), 6.94 (dd, J=13.01, 1.64 Hz, 1H), 7.04 (dd, J=7.83, 1.77 Hz, 1H), 7.57 (t, J=8.21 Hz, 1H).

Step 1

Preparation of Compound 2-(4-bromo-2-fluoro-phenyl)-2-ethyl-butryonitrile

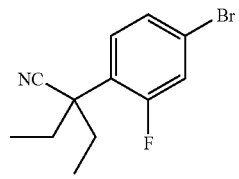

The desired product was prepared analogously to step 2 of Example A(97), substituting bromoethane in place of MeI. MS (APCI): 270 (M+H$^+$).

Example A(113)

1-(4-{2-[2-Cyclopentyl-5-(6-methyl-[1,2,4]triazolo[1,5-a]pyrimidin-2-ylmethyl)-4,6-dioxo-tetrahydro-pyran-2-yl]-ethyl}-2-fluoro-phenyl)-cyclopropanecarbonitrile

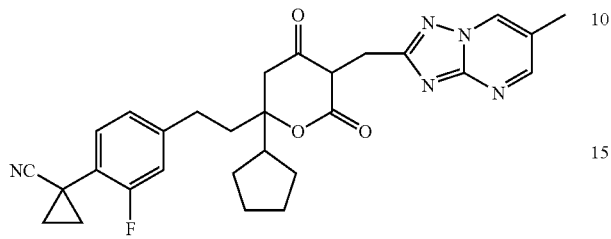

A solution of 1-{4-[2-(2-cyclopentyl-4,6-dioxo-tetrahydro-pyran-2-yl)-ethyl]-2-fluoro-phenyl}-cyclopropanecarbonitrile (568 mg, 1.54 mmol) in anhydrous MeOH (6.0 mL) was treated with 6-methyl-[1,2,4]triazolo[1,5-a]pyrimidine-2-carbaldehyde (324 mg, 2.0 mmol), followed by borane-dimethylamine complex (118 mg, 2.0 mmol) at room temperature. The reaction was stirred for 1 hour before it was cooled to −10° C. for 2 hours. The precipitate was removed by filtration, and the filtrate was concentrated to an oil. The oil was purified by flash chromatography (50 g SiO$_2$, 1:3->1:0 (93.5% ethyl acetate, 6% methanol, 0.5% acetic acid): (81.5% hexanes, 12% ethyl acetate, 6% methanol, 0.5% acetic acid)) to give the desired product as an oil. It was further purified by crystallization from ethyl acetate/hexanes to give a white powder (146 mg, 18%). $^1$H NMR (400 MHz, CDCl$_3$) δ: 1.41–1.64 (m, 8 H), 1.84–1.88 (m, 2 H), 2.22–2.28 (m, 2 H), 2.42 (s, 3 H), 2.49–2.59 (m, 4 H), 2.65–2.74 (m, 3 H), 3.97–4.05 (m, 2 H), 6.72–6.82 (m, 2 H), 7.05–7.10 (m, 1 H), 8.55 (s, 1 H), 8.67 (s, 1 H).

Step 2

Preparation of Compound 1–4-[2-(2-Cyclopentyl-4,6-dioxo-tetrahydro-pyran-2-yl)-ethyl]-2-fluoro-phenyl}-cyclopropanecarbonitrile

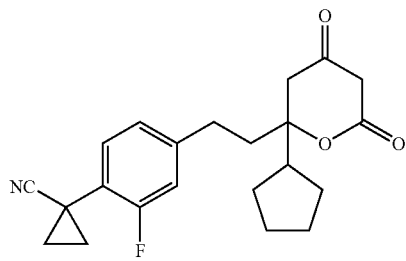

The desired product was prepared analogously to step 4 of Example A(97), substituting 1-{4-[3-Cyclopentyl-4-(2,2-dimethyl-6-oxo-6H-[1,3]dioxin-4-yl)-3-hydroxy-but-1-ynyl]-2-fluoro-phenyl}-cyclopropanecarbonitrile [prepared analogously to step 3 of Example A(97) substituting 1-(4-bromo-2-fluoro-phenyl)-cyclopropanecarbonitrile in place of 2-(4-bromo-2-fluorophenyl)-2-methylpropanenitrile)] in place of 2-{4-[2-(2-cyclopentyl-4,6-dioxotetrahydro-2H-pyran-2-yl)ethyl]-2-fluorophenyl}-2-methylpropanenitrile.
$^1$H NMR (CDCl$_3$) δ: 1.27–1.30 (m, 2H), 1.51–1.73 (m, 10H), 1.84–1.89 (m, 2H), 2.19 (p, J=8.08 Hz, 1H), 2.58–2.71 (m, 4H), 3.36 (d, J=4.04 Hz, 2H), 6.81–6.86 (m, 2H), 7.16–7.18 (m, 1H). MS (ESI): 368 (M–H).

Step 1

Preparation of Compound 1-(4-Bromo-2-fluoro-phenyl)-cyclopropanecarbonitrile

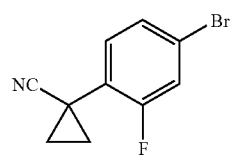

The desired product was prepared analogously to step 2 of Example A(97), substituting 1,2-bromoethane in place of MeI. $^1$H NMR (400 MHz, CDCl$_3$): 1.15 (dd, J=5.31, 2.27 Hz, 2H), 1.48 (dd, J=5.05, 2.53 Hz, 2H), 6.97–7.12 (m, 3H).

Example A(114)

1 {4-[2-(2-Cyclopentyl-4,6-dioxo-5-[1,2,4]triazolo[1,5-a]pyrimidin-2-ylmethyl-tetrahydro-pyran-2-yl)-ethyl]-2-fluoro-phenyl}-cyclopropanecarbonitrile

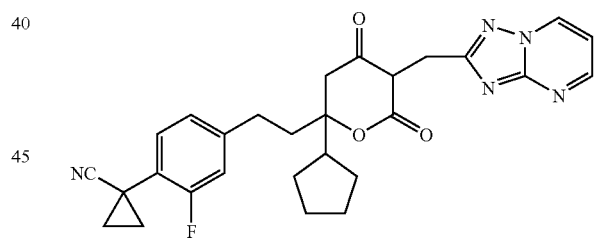

A solution of 1-{4-[2-(2-cyclopentyl-4,6-dioxo-tetrahydro-pyran-2-yl)-ethyl]-2-fluoro-phenyl}-cyclopropanecarbonitrile (568 mg, 1.54 mmol) in anhydrous MeOH (6.0 mL) was treated with [1,2,4]triazolo[1,5-a]pyrimidine-2-carbaldehyde (296 mg, 2.0 mmol), followed by borane-dimethylamine complex (118 mg, 2.0 mmol) at room temperature. The reaction was stirred for 1 hour and then was concentrated to an oil. The oil was purified by flash chromatography (50 g SiO$_2$, 70% ethyl acetate, 6% methanol, 0.5% acetic acid, 23.5% hexanes) to give the desired product as an oil. It was further purified by crystallization from ethyl acetate/hexanes to give a white powder (142 mg, 18%). $^1$H NMR (400 MHz, CDCl$_3$) δ: 1.11–1.18 (m, 2 H), 1.31–1.52 (m, 10 H), 1.75–1.80 (m, 2 H), 2.16 (t, J=8.84 Hz, 2 H), 2.34 (d, J=17.68 Hz, 1 H), 2.46 (t, J=7.83 Hz, 2 H), 2.59 (d, J=17.94 Hz, 1 H), 3.94 (d, J=3.79 Hz, 2 H), 6.62–6.70 (m, 2 H), 6.97 (t, J=7.83 Hz, 1 H), 7.02–7.04 (m, 1 H), 6.82–6.85 (m, 2 H).

Example A(115)

1-(4-{2-[5-(6-Chloro-[1,2,4]triazolo[1,5-a]pyrimidin-2-ylmethyl)-2-cyclopentyl-4,6-dioxo-tetrahydropyran-2-yl]-ethyl}-2-fluoro-phenyl)-cyclopropanecarbonitrile

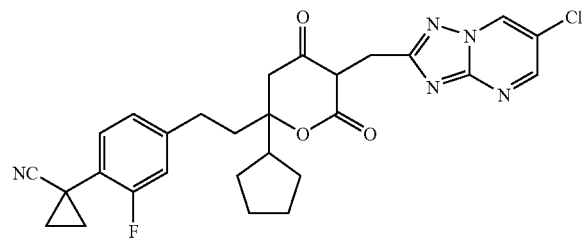

A solution of 1-{4-[2-(2-cyclopentyl-4,6-dioxo-tetrahydro-pyran-2-yl)-ethyl]-2-fluoro-phenyl}-cyclopropanecarbonitrile (568 mg, 1.54 mmol) in anhydrous MeOH (6.0 mL) was treated with 6-chloro-[1,2,4]triazolo[1,5-a]pyrimidine-2-carbaldehyde (365 mg, 2.0 mmol), followed by borane-dimethylamine complex (118 mg, 2.0 mmol) at room temperature. The reaction was stirred for 1 hour and then was concentrated to an oil. The oil was purified by flash chromatography (50 g SiO$_2$, 70% ethyl acetate, 6% methanol, 0.5% acetic acid, 23.5% hexanes). The resultant oil was further purified by flash 509 SiO$_2$, 1:3->1:0 (93.5% ethyl acetate, 6% methanol, 0.5% acetic acid): (81.5% hexanes, 12% ethyl acetate, 6% methanol, 0.5% acetic acid) to give the desired product as an oil. It was further purified by crystallization from ethyl acetate/hexanes to give a white powder (48.6 mg, 6%). $^1$H NMR (400 MHz, CDCl$_3$) δ: 1.19–1.24 (m, 2 H), 1.39–1.61 (m, 10 H), 1.83–1.87 (m, 2 H), 2.25 (t, J=8.59 Hz, 1 H), 2.38 (d, J=17.94 Hz, 1 H), 2.54 (t, J=7.71 Hz, 2 H), 2.64 (d, J=17.94 Hz, 1 H), 3.98 (d, J=5.56 Hz, 2 H), 6.71–6.77 (m, 2 H), 7.06 (t, J=7.83 Hz, 1 H), 8.66 (s, 1 H), 8.73 (s, 1 H).

Example A(116)

(+)-2-(4-{2-[2-Cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-2-fluoro-phenyl)-2-methyl-propionitrile

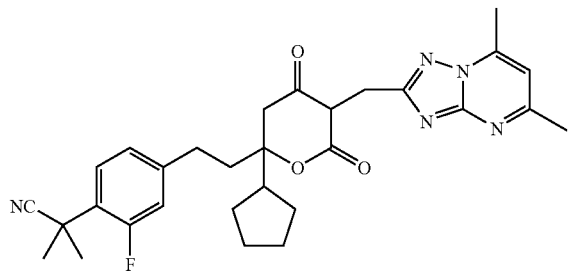

(+) enantiomer

The desired compound was separated from racemic 2-(4-{2-[2-Cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-2-fluoro-phenyl)-2-methyl-propionitrile (100 mg) using chiral HPLC (Chiralpak AS-RH, 150×4.6 mm, 0.6 mL/min, 50% CAN, 50% H$_2$O, 30° C.). (40 mg, 80% recovery, 14.743 min retention time).

Step 1

Preparation of (+/−) 2-(4-{2-[2-Cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-2-fluoro-phenyl)-2-methyl-propionitrile

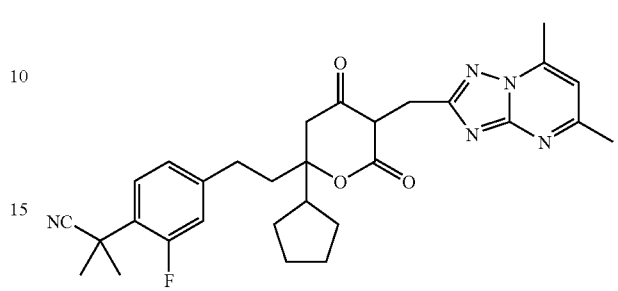

To a solution of 2-{4-[2-(2-cyclopentyl-4,6-dioxo-tetrahydro-pyran-2-yl)-ethyl]-2-fluoro-phenyl}-2-methyl-propionitrile (0.40 g, 1.1 mmol) in MeOH (7 mL) was added 5,7-dimethyl-[1,2,4]triazolo[1,5-a]pyrimidine-2-carbaldehyde (0.19 g, 1.08 mmol) and borane-dimethylamine complex (76 mg, 1.3 mmol) and stirred at room temperature for 3 hours. The reaction was quenched with 10 mL saturated NH$_4$Cl and 5 mL water. To this was added 20 mL CH$_2$Cl$_2$ and the pH of the aqueous phase was adjusted to 3. The layers were separated, and the aqueous layer was extracted with 3×30 mL 10% MeOH in CH$_2$Cl$_2$. The organic layers were combined, and dried over Na$_2$SO$_4$. After filtering off the solids, the liquid was concentrated by rotary evaporation to an oil. The oil was flash chromatographed, and the resulting product was further purified by preparatory HPLC. Yield: 28 mg, 5%. MS (ESI): 530 (M−H).

Example A(117)

(−)-2-(4-{2-[2-Cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-2-fluoro-phenyl)-2-methyl-propionitrile

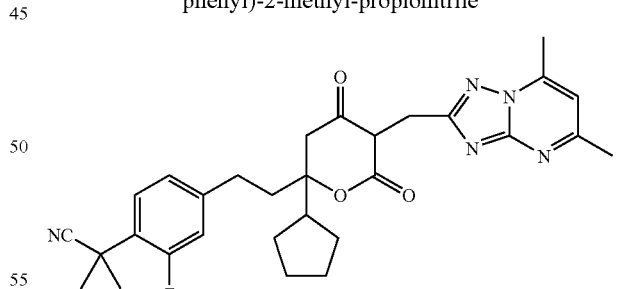

(-) enantiomer

The desired compound was separated from racemic 2-(4-{2-[2-Cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-2-fluoro-phenyl)-2-methyl-propionitrile (100 mg) using chiral HPLC (Chiralpak AS-RH, 150×4.6 mm, 0.6 mL/min, 50% CAN, 50% H$_2$O, 30° C.). (38 mg, 76% recovery, 7.536 min retention time).

Example A(118)

2-{4-[2-(2-cyclopentyl-4,6-dioxotetrahydro-2H-pyran-2-yl)ethyl]-2-fluorophenyl}-2-methylpropanenitrile

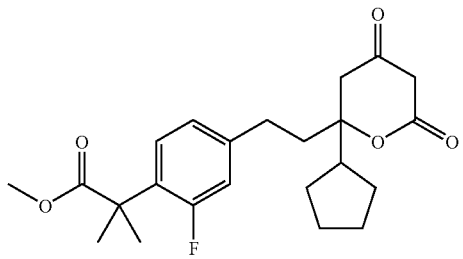

The desired product was prepared analogously to step 4 of Example A(97), substituting 2-{4-[3-Cyclopentyl-4-(2,2-dimethyl-6-oxo-6H-[1,3]dioxin-4-yl)-3-hydroxy-but-1-ynyl]-2-fluoro-phenyl}-2-methyl-propionic acid methyl ester in place of 2-{4-[3-cyclopentyl-4-(2,2-dimethyl-4-oxo-4H-1,3-dioxin-6-yl)-3-hydroxybut-1-ynyl]-2-fluorophenyl}-2-methylpropanenitrile. $^1$H NMR (300 MHz, CDCl$_3$) δ: 1.30–1.74 (m, 16H), 1.82–1.84 (m, 1H), 2.50–2.65 (m, 4H), 3.31 (s, 2H), 3.56 (s, 3H), 6.71 (t, J=10.0 Hz, 1H), 7.08–7.21 (m, 2H). MS(ESI): 403(M–H).

Step 3

2-{4-[3-cyclopentyl-4-(2,2-dimethyl-6-oxo-4H-1,3-dioxin-4-yl)-3-hydroxybut-1-2-fluoro-phenyl]-2-methyl-propionic acid methyl ester

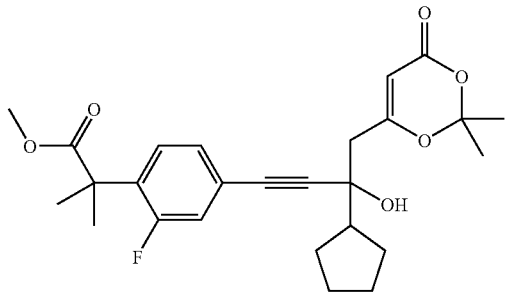

The desired product was prepared analogously to step 3 of Example A(97), substituting 2-(4-Bromo-2-fluoro-phenyl)-2-methyl-propionic acid methyl ester in place of 2-(4-bromo-2-fluorophenyl)-2-methylpropanenitrile. $^1$H NMR (CDCl$_3$) δ: 1.48 (s, 6H), 1.48–1.76 (m, 14H), 2.16–2.18 (m, 1H), 2.54 (s, 1H), 2.58 (d, J=2.8 Hz, 2H), 3.60 (s, 3H), 5.39 (s, 1H), 6.97–7.21 (m, 3H). MS(ESI): 457 (M–H).

Step 2

2-(4-Bromo-2-fluoro-phenyl)-2-methyl-propionic acid methyl ester

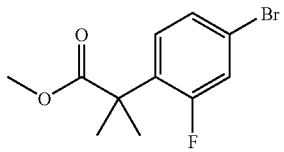

The desired product was prepared analogously to step 2 of Example A(97). $^1$H NMR (300 MHz, CDCl$_3$) δ: 1.47 (s, 6 H), 3.65 (s, 3H), 7.11–7.23 (m, 3H).

Step 1

Preparation of compound (4-Bromo-2-fluoro-phenyl)-acetic acid methyl ester

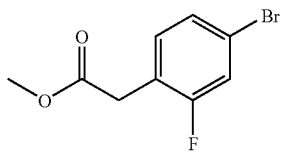

MeOH (16 mmol, 0.81 ml), TMSCl (20 mmol, 2.13 g) and (4-bromo-2-fluorophenyl) acetonitrile (10 mmol, 2.13 g) were sequentially added to a dry flask under a nitrogen atmosphere at room temperature. The reaction mixture was heated at 50° C. for 4 hours. After being cooled to room temperature, water (20 mmol, 0.36 ml) was added to the mixture, followed by the addition of Na$_2$CO$_3$ (10 mmol, 1.06 g) and CH$_2$Cl$_2$ (10 ml). Drying over MgSO$_4$ and concentrating at low pressure afforded product (0.85 g, 35% yield). $^1$H NMR (300 MHz, CDCl$_3$) δ: 3.57 (s, 2 H), 3.65 (s, 3H), 7.08 (t, J=8.3 Hz, 1H), 7.16–7.21 (m, 2H).

Example A(119)

6-Cyclopentyl-3-(5,7-dimethyl-[1,2,4]triazolo[1,5-a]pyrimidin-2-ylmethyl)-6-{2-[3-fluoro-4-(2-hydroxyethyl)-phenyl]-ethyl}-4-hydroxy-5,6-dihydro-pyran-2-one

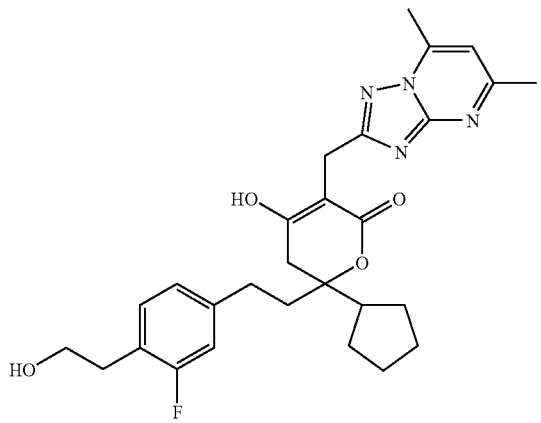

A solution of 6-Cyclopentyl-6-{2-[3-fluoro-4-(2-hydroxy-ethyl)-phenyl]-ethyl}-dihydro-pyran-2,4-dione (270 mg, 0.73 mmol) in anhydrous MeOH (7.0 mL) was treated with 1H-pyrazole-4-carbaldehyde (122 mg, 1.46 mmol), followed by addition of borane-dimethylamine complex (62 mg, 1.05 mmol) at room temperature. The reaction was stirred for 12 hours before it was quenched by the addition of 1 N HCl. The mixture was extracted with 10% MeOH in CH$_2$Cl$_2$ (3×10 mL), and the combined organic layers were washed with brine, then dried over MgSO$_4$. The solvent was removed, and the residue was purified by chromatography (80:14:6:0.5 of EtOAc:Hexane:MeOH:Acetic acid) to give the product (23 mg, 6.5% yield). $^1$H NMR (CDCl$_3$) δ: 1.19–1.69 (m, 10 H), 2.61 (s, 3H), 2.79 (s, 3H), 3.40–3.43 (m, 1H), 3.6–3.64 (m, 2H), 3.80–3.84 (m, 2H), 4.19–4.24 (m, 2H), 5.03 (m, 2H), 6.88 (s, 1H), 7.15–7.18 (m, 1H), 7.50–7.55 (m, 1H), 7.70–7.73 (m, 1H). MS(ESI): 507 (M–H).

Example A(120)

6-Cyclopentyl-6-2-[3-fluoro-4-(2-hydroxy-ethyl)-phenyl]-ethyl}-dihydro-pyran-2,4-dione

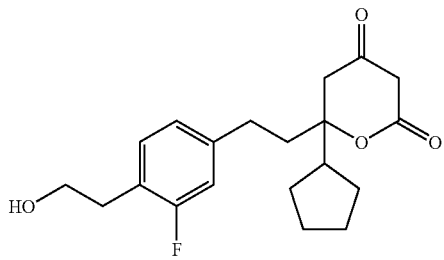

The desired product was prepared analogously to step 4 of Example A(97), substituting 6-{2-Cyclopentyl-4-[3-fluoro-4-(2-hydroxy-ethyl)-phenyl]-2-hydroxy-butyl}-2,2-dimethyl-[1,3]dioxin-4-one in place of 2-{4-[3-cyclopentyl-4-(2,2-dimethyl-4-oxo-4H-1,3-dioxin-6-yl)-3-hydroxybut-1-ynyl]-2-fluorophenyl}-2-methylpropanenitrile. $^1$H NMR (CDCl$_3$) δ: 1.20 (t, J=6.95 Hz, 1 H), 1.41–1.79 (m, 7 H), 1.87–2.00 (m, 2 H), 2.26 (m, 1 H), 2.65 (t, J=8.34 Hz, 2 H), 2.75 (d, J=2.53 Hz, 2 H), 2.87 (t, J=6.44 Hz, 2 H), 3.41 (d, J=2.27 Hz, 2 H), 3.47 (q, J=7.07 Hz, 1 H), 3.84 (t, J=6.57 Hz, 1 H), 6.82 (d, J=10.86 Hz, 1 H), 6.86 (d, J=7.58 Hz, 1 H), 7.15 (t, J=7.71 Hz, 1 H). MS (ESI): 347 (M–H).

Step 3

6-{2-Cyclopentyl-4-[3-fluoro-4-(2-hydroxy-ethyl)-phenyl]-2-hydroxy-but-3-ynyl}-2,2 dimethyl-[1,3]dioxin-4-one

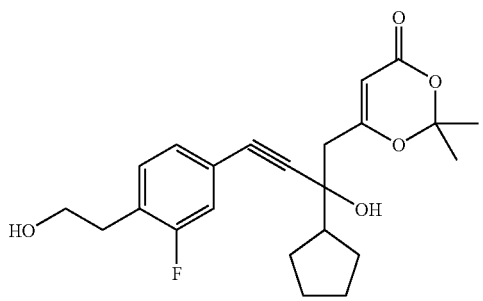

The desired product was prepared analogously to step 3 of Example A(97), substituting 2-(4-Bromo-2–2-fluoro-phenyl)-ethanol in place of 2-(4-bromo-2-fluorophenyl)-2-methylpropanenitrile. $^1$H NMR (CDCl$_3$) δ: 1.25 (t, J=7.20 Hz, 1 H), 1.36–1.41 (m, 2 H), 1.55–1.60 (m, 3 H), 1.65–1.70 (m, 3 H), 1.71 (s, 3 H), 1.72 (s, 3 H), 1.78–1.83 (m, 2 H), 2.90 (t, J=6.44 Hz, 2 H), 3.47 (q, J=6.99 Hz, 1 H), 3.85 (t, J=6.57 Hz, 2 H), 5.45 (s, 1 H), 7.04 (d, J=10.11 Hz, 1 H), 7.09 (d, J=7.83 Hz, 1 H), 7.19 (t, J=7.58 Hz, 1 H). MS (ESI): 401 (M–H).

Step 2

2-(4-Bromo-2–2-fluoro-phenyl)-ethanol

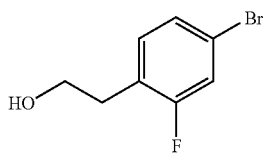

In a dried flask equipped with a reflux condenser and an argon line, 2-(4-Bromo-2-fluoro-phenyl)-acetic acid (1.35 g, 5.78 mmol) was dissolved in THF. To this solution, a solution of 1MBH$_3$.THF (11.57 ml, 11.57 mmol) was added at 0° C. for 4 hours. The reaction mixture was diluted with cold water (15 ml), washed with a saturated solution of NaHCO$_3$ (15 ml), and extracted with ether (3×20 ml). The combined organic layers were washed with brine and dried over MgSO$_4$. The solvent was removed, and the residue was purified by flash column chromatography (1–50% EtOAc in Hexane) to give the product (0.52 g, 41.0% yield). $^1$H NMR (CDCl$_3$) δ: 2.80(t, J=6.0 Hz, 2H), 3.78 (t, J=6.5 Hz, 2H), 7.06 (t, J=8.4 Hz, 1H), 7.14–7.18 (m, 2H).

Step 1

2-(4-Bromo-2–2-fluoro-phenyl)-acetic acid

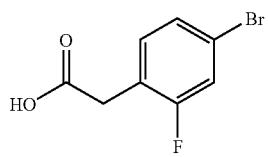

A mixture of (4-bromo-2-fluorophenyl)acetonitrile (8.55 g, 40 mmol) from step 1 in Example A (97); Potassium hydroxide (11.52 g, 320 mmol); Ethanol (80 ml) and water (16 ml) was heated at 70° C. for 24 hours. The mixture was then diluted with water (50 ml), and subsequently extracted with ether (3×75 ml). The pH of the aqueous layer was adjusted to approximately 3 with dropwise addition of 1N H$_2$SO$_4$. After the aqueous layer was extracted with ether (3×125 ml), the combined organic layers were washed with brine and dried over MgSO$_4$. The solvent was removed to give product (4.50 g, 48% yield). $^1$H NMR (CDCl$_3$) δ: 3.60 (s, 2H), 7.07–7.22 (m, 3H).

Example A(121)

6-Cyclopentyl-6-{2-[3-fluoro-4-(2-hydroxy-1,1-dimethyl-ethyl)-phenyl]-ethyl}-dihydro-pyran-2,4-dione

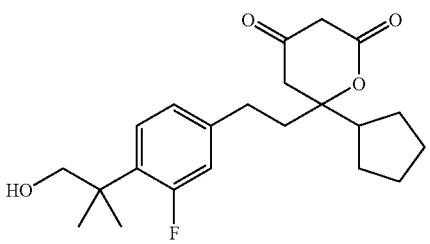

The desired product was prepared analogously to step 4 of Example A(97), substituting 6-{2-Cyclopentyl-4-[3-fluoro-4-(2-hydroxy-1,1-dimethyl-ethyl)-phenyl]-2-hydroxy-butyl}-2,2-dimethyl-[1,3]dioxin-4-one (1.70 g, 3.91 mmol) in place of 2-{4-[3-cyclopentyl-4-(2,2-dimethyl-4-oxo-4H-1,3-dioxin-6-yl)-3-hydroxybut-1-ynyl]-2-fluorophenyl}-2-methylpropanenitrile. $^1$H NMR (CDCl$_3$) δ: 1.35 (s, 6 H), 1.52–1.78 (m, 8 H), 1.90–1.99 (m, 2 H), 2.27 (m, 1 H), 2.65 (t, J=8.34 Hz, 2 H), 2.74 (d, J=2.27 Hz, 2 H), 3.40 (d, J=1.77 Hz, 2 H), 3.75 (s, 2 H), 6.80 (dd, J=13.64, 1.77 Hz, 1 H), 6.88 (dd, J=8.08, 1.77 Hz, 1 H), 7.22 (d, J=8.59 Hz, 1 H). MS (ESI): 375 (M–H).

Step 3

6-{2-Cyclopentyl-4-[3-fluoro-4-(2-hydroxy-1,1-dimethyl-ethyl)-phenyl]-2-hydroxy-but-3-ynyl}-2,2-dimethyl-[1,3]dioxin-4-one)

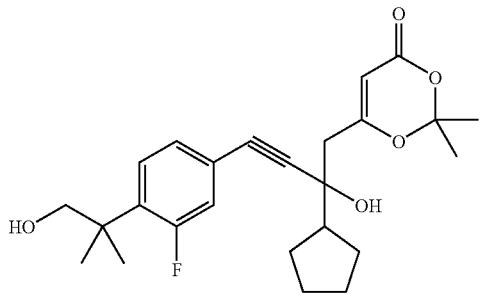

The desired product was prepared analogously to step 3 of Example A(97), substituting 2-(4-Bromo-2-fluoro-phenyl)-2-methyl-propan-1-ol in place of 2-(4-bromo-2-fluorophenyl)-2-methylpropanenitrile. $^1$H NMR (CDCl$_3$) δ: 1.35 (s, 6 H), 1.48–1.62 (m, 5 H), 1.71 (s, 3 H), 1.72 (s, 3 H), 1.77–1.87 (m, 2 H), 2.20 (m, 1 H), 2.61 (s, 1 H), 2.64 (d, J=3.03 Hz, 2 H), 3.76 (d, J=5.56 Hz, 2 H), 5.44 (s, 1 H), 7.01 (d, J=12.88 Hz, 1 H), 7.10 (d, J=8.08 Hz, 1 H), 7.26 (m, 1 H). MS (ESI): 429(M−H).

Step 2

2-(4-Bromo-2-fluoro-phenyl)-2-methyl-propan-1-ol

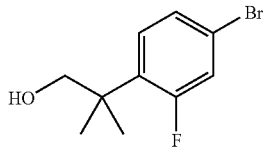

To a solution of 2-(4-Bromo-2-fluoro-phenyl)-2-methyl-propionaldehyde (1.37 g, 5.58 mmol) in MeOH (18 ml) at 0° C. was added NaBH$_4$ (0.21 g, 5.58 mmol). After being stirred for 2 hours at 0° C., the mixture was allowed to warm to room temperature. The reaction mixture was diluted with water (20 ml) and extracted with ether (3×75 ml). The combined organic layers were dried over MgSO$_4$. The solvent was removed, and the residue was purified by flash column chromatography (15–35% EtOAc in Hexane) to give the product (1.10 g, 80.0% yield). $^1$H NMR (CDCl$_3$) δ: 1.23 (s, 1 H) 1.35 (s, 3 H) 1.35 (s, 3 H) 3.75 (d, J=1.26 Hz, 2 H) 7.17 (d, J=2.27 Hz, 1 H) 7.20 (d, J=3.03 Hz, 1 H) 7.22 (m, 1 H).

Step 1

2-(4-Bromo-2-fluoro-phenyl)-2-methyl-propionaldehyde

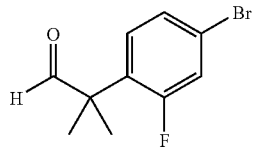

DIBAL-H (14 ml, 14.0 mmol) was added slowly to a solution of 2-(4-Bromo-2-fluoro-phenyl)-2-methyl-propionitrile (2.42 g, 10 mmol) in CH$_2$Cl$_2$ (10 ml) at 0° C., and the reaction mixture was stirred for 4 hours. To the reaction was added 10 ml of 1N HCl (10 ml). The layers were separated, and the aqueous layer was extracted with 3×50 ml ether. The combined organics were washed with 10 ml H$_2$O, and then dried over MgSO$_4$. After filtering off the solids, the mother liquor was concentrated to the desired product by rotary evaporation (1.56 g, 64% yield). $^1$H NMR (CDCl$_3$) δ: 1.29 (s, 6H), 7.05–7.26 (m, 3H), 9.53 (s, 1H).

Example A(122)

6-Cyclopentyl-6-[2-(3,5-difluoro-phenyl)-ethyl]-dihydro-pyran-2,4-dione

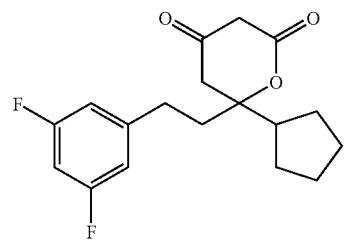

The desired product was prepared analogously to Example A(97), substituting 1-Bromo-3,5-difluoro-benzene in place of 2-(4-bromo-2-fluorophenyl)-2-methylpropanenitrile in step 2 of that example. $^1$H NMR (CDCl$_3$, 300 MHz) δ: 1.40–1.75 (m, 8 H), 1.82–2.12 (m, 2H), 2.25–2.74 (m, 1H), 2.67–2.81 (m, 4H), 3.45–3.59 (m, 2H), 6.82–6.94 (m, 1H), 6.95–7.06 (m, 1H), 7.25 (dd, J=8.40, 1.70 Hz).

Example A(123)

6-Cyclopentyl-3-(5,7-dimethyl-[1,2,4]triazolo[1,5-a]pyrimidin-2-ylmethyl)-6-[2-(3-ethyl-5-fluoro-4-hydroxy-phenyl)-ethyl]-4-hydroxy-5,6-dihydro-pyran-2-one

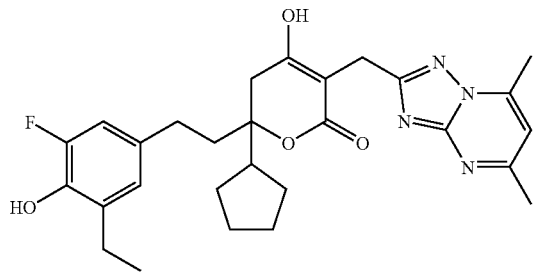

5,7-Dimethyl-[1,2,4]triazolo[1,5-a]pyrimidine-2-carbaldehyde (0.2 g, 0.57 mmol) was added to a solution of 6-Cyclopentyl-6-[2-(3-ethyl-5-fluoro-4-hydroxy-phenyl)-ethyl]-dihydro-pyran-2,4-dione (0.2 g, 0.53 mmol) in MeOH (6 mL). The reaction mixture was stirred for 15 mins and then treated with borane-dimethylamine complex (50 mg, 0.86 mmoL). After 15 hours the reaction mixture was quenched with 1N HCl and extracted with 10% MeOH in CH$_2$Cl$_2$. The combined organic layers were concentrated and recrystallized from EtOAc to give the product as a white soild (0.15 g, 52%). $^1$H NMR (400 MHz, DMSO-d$_6$): δ 1.09 (t, J=7.3 Hz, 3 H), 1.43–1.72 (br m, 8 H), 2.05–2.17 (m, 2 H), 2.43 (m, 1 H), 2.48–2.58 (m, 10 H), 2.66 (d, J=17.4 Hz, 1 H), 2.81 (d, J=17.4 Hz, 1 H), 3.74 (d, J=16.2 Hz, 1 H), 3.85 (d, J=16.2 Hz, 1 H), 6.76 (s, 1 H), 6.84 (d, J=11.6 Hz, 1 H) 7.07 (s, 1 H), 9.08 (s, 1 H), 11.01 (s, 1 H). MS: C$_{28}$H$_{32}$N$_4$O$_4$F (M+H$^+$) 509.10.

Example A(124)

6-Cyclopentyl-6-[2-(3-ethyl-5-fluoro-4-hydroxy-phenyl)-ethyl]-dihydro-pyran-2,4-dione

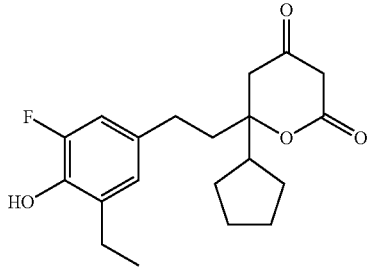

The title compound was prepared analogously to Example A(97) where acetic acid 4-bromo-2-ethyl-6-fluoro-phenyl ester (from step 4 below) was substituted in place of 2-(4-bromo-2-fluorophenyl)-2-methylpropanenitrile in that example. $^1$H NMR (400 MHz, CDCl$_3$) δ: 1.21 (t, J=7.6 Hz, 3 H), 1.44–1.75 (m, 8 H), 1.92 (m, 2 H), 2.27 (m, 1 H), 2.58 (m, 2 H), 2.64 (q, J=7.6 Hz, 2 H), 2.76 (m, 2 H), 3.43 (s, 2 H), 5.04 (s, 1 H), 6.68 (s, 1 H), 6.71 (d, J=10.6 Hz, 1 H). Anal. Calcd. For C$_{20}$H$_{25}$O$_4$F: C, 68.95; H, 7.23. Found: C, 68.71; H, 7.28.

Step 4

Preparation of Compound Acetic Acid 4-bromo-2-ethyl-6-fluoro-phenyl ester

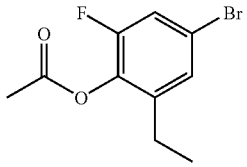

Acetyl chloride (0.39 mL, 5.5 mmol) followed by triethylamine (0.76 mL, 5.5 mmol) were added to a cooled 0° C. solution of 2-ethyl-6-fluoro-phenol (1 g, 4.5 mmol, from step 3) dissolved in CH$_2$Cl$_2$ (10 mL). The reaction was stirred for 2 hrs and then partitioned between 1N HCl and EtOAc. The organic layer was washed with saturated NaHCO$_3$, brine, dried over Na$_2$SO$_4$ and concentrated to a yellow oil. The oil was purified by silica gel chromatography (0% to 5% EtOAc in hexanes) to give the title compound as a clear oil (1 g, 84%). $^1$H NMR (400 MHz, CDCl$_3$): δ 1.18 (t, J=7.6 Hz, 3 H), 2.35 (s, 3 H), 2.54 (q, J=7.6 Hz, 2 H), 7.18 (m, 2 H).

Step 3

Preparation of Compound 4-Bromo-2-ethyl-6-fluoro-phenol

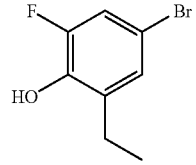

A solution of tetrabutyl ammonium tribromide (4.2 g, 8.6 mmol) in CHCl$_3$ (25 mL) was added to a stirred solution of 2-ethyl-6-fluoro-phenol (1.1 g, 7.9 mmol) dissolved in CHCl$_3$ (25 mL). The reaction mixture was stirred for 24 hrs and then quenched with 5% solution of sodium thiosulfate (30 mL). The biphasic mixture was stirred for 30 mins and then the layers were separated. The organic layer was washed with 1N HCl, saturated NaHCO$_3$, brine, dried over Na$_2$SO$_4$ and concentrated. The crude residue was purified by flash column chromatography (0–10% EtOAc in hexanes) to give the desired product (1 g, 60%). $^1$H NMR (400 MHz, CDCl$_3$): δ 1.21 (t, J=7.6 Hz, 3 H), 2.65 (q, J=7.6 Hz, 2 H), 5.09 (d, J=4.8 Hz, 1 H), 7.06 (s, 1 H), 7.09 (d, J=11.9 Hz, 1 H).

Step 2

Preparation of compound 2-Ethyl-6-fluoro-phenol

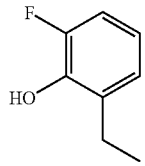

A mixture of 2-fluoro-6-(1-hydroxy-ethyl)-phenol (1.7 g, 10.9 mmol) and 10 wt % Pd/C (0.85 g, Degussa type) in MeOH (30 mL) was stirred under a balloon of H$_2$ for 6 hours. The reaction mixture was filtered through a pad of celite washing with EtOAc. The filtrate was concentrated to a yellow oil (1.35 g, 87%). $^1$H NMR (400 MHz, CDCl$_3$): δ 1.22 (t, J=7.6 Hz, 3 H), 2.68 (q, J=7.3 Hz, 2 H), 5.12 (s, 1 H), 6.76 (m, 1 H), 6.92 (m, 2 H).

Step 1

Preparation of compound 2-Fluoro-6-(1-hydroxy-ethyl)-phenol

Methyl lithium (25.5 mL, 35.7 mmol, 1.4M in ether) was added to a cooled −78° C. solution of 3-fluorosalicylaldehyde (2 g, 14.3 mmol) dissolved in THF (50 mL). The reaction mixture was stirred for 3 hours and then warmed up to room temperature. After 3 hours the reaction was quenched with saturated NH$_4$Cl and extracted with EtOAc. The organic extracts were washed with 1N HCl, brine, dried over Na$_2$SO$_4$ and concentrated to an oil. The oil was purified by flash column chromatography (0% to 20% EtOAc in hexanes) to give the title compound as a clear oil (2.2 g, 99%). $^1$H NMR (400 MHz, CDCl$_3$): δ 1.58 (d, J=6.6 Hz, 3 H), 2.68 (s, 1 H), 5.13 (m, 1 H), 6.78 (td, J=7.8, 4.8 Hz, 1 H), 6.87 (d, J=7.6, 1 H), 6.99 (m, 1 H), 7.33 (s, 1 H).

Example A(125)

6-Cyclopentyl-6-[2-(3-ethyl-5-fluoro-4-hydroxy-phenyl)-ethyl]-4-hydroxy-3-(6-methyl-[1,2,4]triazolo[1,5-a]pyrimidin-2-ylmethyl)-5,6-dihydro-pyran-2-one

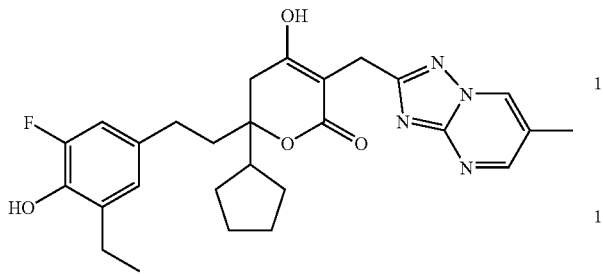

The title compound was prepared analogously to Example A(123), where 6-Methyl-[1,2,4]triazolo[1,5-a]pyrimidine-2-carbaldehyde was substituted in place of 5,7-Dimethyl-[1,2,4]triazolo[1,5-a]pyrimidine-2-carbaldehyde. $^1$H NMR (400 MHz, DMSO-$d_6$) δ: 1.14 (t, J=7.6 Hz, 3 H), 1.41–1.75 (m, 8 H), 2.13 (m, 2H), 2.41 (s, 3 H), 2.44 (m, 1 H), 2.47–2.62 (m, 4 H), 2.72 (d, J=17.7 Hz, 1 H), 2.82 (d, J=17.7 Hz, 1 H), 3.78 (d, J=16.2 Hz, 1 H), 3.86 (d, J=16.2 Hz, 1 H), 6.80 (s, 1 H), 6.86 (d, J=11.6 Hz, 1 H), 8.74 (s, 1 H), 8.90 (s, 1 H), 9.13 (s, 1 H), 10.93 (s, 1 H). MS: $C_{27}H_{31}N_4O_4F$ (M–H) 493.20.

Example A(126)

6-Cyclopentyl-6-[2-(3-ethyl-4-hydroxy-phenyl)-ethyl]-4-hydroxy-3-(6-methyl-[1,2,4]triazolo[1,5-a]pyrimidin-2-ylmethyl)-5,6-dihydro-pyran-2-one

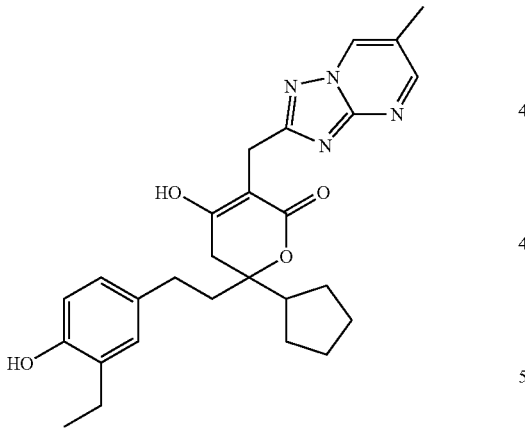

A solution of 6-Cyclopentyl-6-[2-(3-ethyl-4-hydroxy-phenyl)-ethyl]-dihydro-pyran-2,4-dione (150 mg, 0.45 mmol) in anhydrous MeOH (3.0 mL) was treated with 6-Methyl-[1,2,4]triazolo[1,5-a]pyrimidine-2-carbaldehyde (120 mg, 0.73 mmol), followed by borane-dimethylamine complex (40 mg, 0.68 mmol) at room temperature. The reaction was stirred for 5 hours before it was quenched by the addition of 0.5N HCl (25 mL). The mixture was extracted with 10% MeOH in $CH_2Cl_2$ (3×10 mL) and the combined organic layers were washed with brine, dried over $Na_2SO_4$, filtered and concentrated. The residue was purified by crystallization from EtOAc/Hexanes to give the product as a white solid (75 mg, 35% yield). $^1$H NMR (300 MHz, DMSO-$d_6$) δ: 1.08 (t, J=7.3 Hz, 3 H), 1.67 (m, 8 H), 2.07 (m, 2 H), 2.36 (s, 3 H), 2.47 (m, 7 H), 2.76 (m, 1H), 3.81 (q, J=7.3 Hz, 2 H), 6.70 (m, 3 H), 8.66 (s, 1 H), 8.94 (s, 1 H), 10.78 (s, 1 H).

Step 1

Preparation of compound 6-Cyclopentyl-6-[2-(3-ethyl-4-hydroxy-phenyl)-ethyl]-dihydro-pyran-2,4-dione

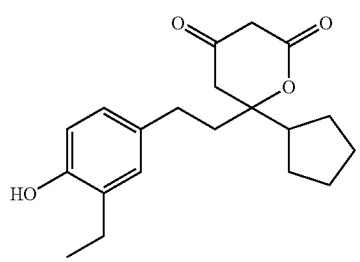

This compound was prepared analogously to example A(124), using 2-ethylphenol in place of 2-Ethyl-5-fluorophenol. The result was an off white solid. $^1$H NMR (300 MHz, CDCl$_3$): δ 1.22 (t, 3H, J=7.6 Hz), 1.43–1.78 (m, 8H), 1.8–2.01 (m, 2H), 2.28 (m, 1H), 2.57–2.63 (m, 4H), 2.76 (s, 2H), 3.42 (s, 2H), 4.63 (s, 1H), 6.68 (d, 1H, J=8.1 Hz), 6.84 (d, 1H, J=8.1 Hz), 6.90 (s, 1H). Anal. Calcd. For $C_{20}H_{26}O_4 \cdot 0.25H_2O$: C, 71.72; H, 7.98. Found: C, 71.10; H, 7.99.

Example A(127)

3-(6-Chloro-[1,2,4]triazolo[1,5-a]pyrimidin-2-ylmethyl)-6-cyclopentyl-6-[2-(3-ethyl-4-hydroxy-phenyl)-ethyl]-4-hydroxy-5,6-dihydro-pyran-2-one

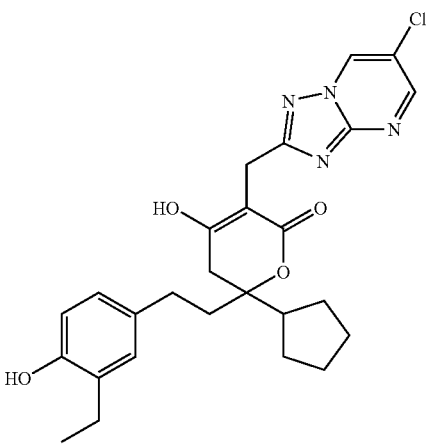

This compound was prepared analogously to example A(126), except that 6-Chloro-[1,2,4]triazolo[1,5-a]pyrimidine-2-carbaldehyde was used in place of 6-Methyl-[1,2,4]triazolo[1,5-a]pyrimidine-2-carbaldehyde. The result was a white solid. $^1$H NMR (300 MHz, DMSO-$d_6$) δ: 1.10 t, J=7.3 Hz, 3 H), 1.65 (m, 8 H), 2.04 (m, 2 H), 2.47 (m, 7 H), 2.75 (m, 1 H), 3.81 (q, J=7.3 Hz, 2 H), 6.68 (m, 3 H), 8.82 (s, 1 H), 9.43 (s 1 H), 10.83 (brs, 1 H).

Example A(128)

6-Cyclopentyl-6-{2-[3-ethyl-4-(2-hydroxy-ethoxy)-phenyl]-ethyl}-dihydro-pyran-2,4-dione

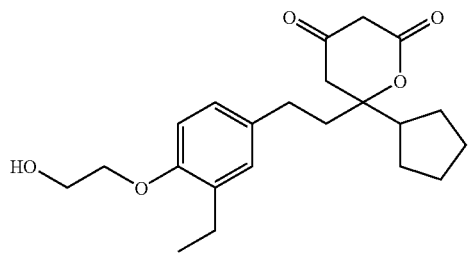

This compound was prepared analogously to example A(124), using 2-(4-Bromo-2-ethyl-phenoxy)-ethanol in place of 2-Ethyl-4-bromo-6-fluorophenol. The result was an off white solid.
$^1$H NMR (300 MHz, CDCl$_3$): δ 1.19 (t, 3H, J=7.6 Hz), 1.43–1.98 (m, 11H), 2.28 (m, 1H), 2.63 (m, 4H), 2.77 (s, 2H), 3.42 (s, 2H), 4.05 (m, 4H), 6.77 (d, J=9.1 Hz, 1 H), 6.93 (m, 2 H).

Step 1

Preparation of compound 2-(4-Bromo-2-ethyl-phenoxy)-ethanol

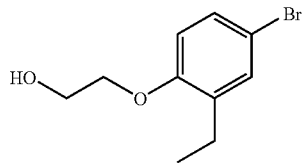

To a solution of 2-ethyl-4-bromophenol (3.5 g, 17.4 mmol) and ethylene carbonate (3.22 g, 37 mmol) in NMP (60 mL) was added potassium carbonate (5.17 g, 37.4 mmol). The resulting mixture was heated to 125° C. and maintained for 3 h. The reaction was cooled and poured into water (250 mL) and extracted with EtOAc (2×100 mL). The combined organics were washed with brine, dried over Na$_2$SO$_4$, filtered and concentrated. The residue was purified by flash column chromatography (10–20% EtOAc in hexanes) to give the product (3.5 g, 82% yield) as a clear oil. $^1$H NMR (300 MHz, CDCl$_3$) δ: 1.19 (t, J=7.6 Hz, 3 H), 1.89 (brs, 1 H), 2.61 (q, J=7.6 Hz, 2 H), 4.05 (m, 4 H), 6.70 (d, J=8.7 Hz, 1 H), 7.24 (m, 2 H).

Example A(129)

6-Cyclopentyl-6-[2-(3-fluoro-4-hydroxy-phenyl)-ethyl]-dihydro-pyran-2,4-dione

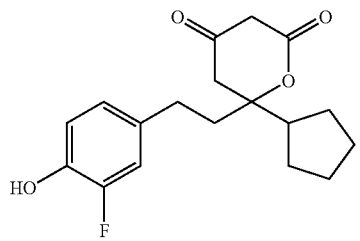

This compound was prepared analogously to example A(124), using 4-Bromo-2-fluoro-phenol in place of 2-Ethyl-4-bromo-6-fluorophenol. The result was an off white solid.
$^1$H NMR (300 MHz, CDCl$_3$): δ: 1.42–1.78 (m, 8 H), 2.01 (m, 2 H), 2.28 (m, 1 H), 2.63 (m, 2 H), 2.76 (s, 2 H), 3.42 (s, 2 H), 4.63 (s, 1 H), 6.74 (d, J=8.1 Hz, 1 H), 6.86 (d, J=8.1 Hz, 1 H), 7.13 (s, 1H).

Example A(130)

6-Cyclopentyl-6-[2-(3-cyclopropyl-4-methoxy-phenyl)-ethyl]-dihydro-pyran-2,4-dione

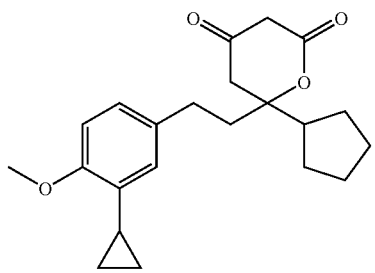

This compound was prepared analogously to example A(124), using 4-Bromo-2-cyclopropyl-1-methoxy-benzene in place of 2-Ethyl-4-bromo-6-fluorophenol. The result was an off white solid. $^1$H NMR (300 MHz, CDCl$_3$): δ: 0.64 (m, 2 H), 0.91 (m, 2 H), 1.69 (m, 10 H), 2.13 (m, 1 H), 2.26 (m, 1 H), 2.57 (t, J=8.5 Hz, 2 H), 2.76 (s, 2 H), 3.41 (s, 2 H), 3.84 (s, 3 H), 6.60 (s, 1 H), 6.77 (d, J=8.1 Hz, 1 H), 6.89 (d, J=8.1 Hz, 1 H).

Example A(131)

6-cyclopentyl-3-[(5,7-dimethyl[1,2,4]triazolo[1,5-a]pyrimidin-2-yl)methyl]-6-[2-(3-fluoro-4-{methyl[methyl(dimethylene)-I$^6$-sulfanyl]amino}phenyl)ethyl]-4-hydroxy-5,6-dihydro-2H-pyran-2-one

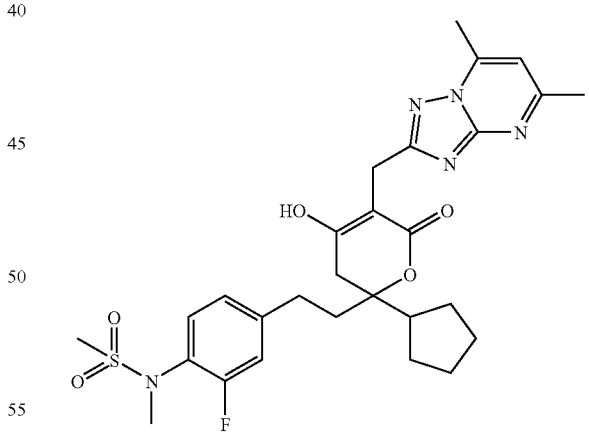

5,7-Dimethyl-[1,2,4]triazolo[1,5-a]pyrimidine-2-carbaldehyde (0.072 g, 0.41 mmol) was added to a solution of 6-cyclopentyl-6-[2-(3-fluoro-4-{methyl[methyl(dimethylene)-6-sulfanyl]amino}phenyl)ethyl]dihydro-2H-pyran-2,4(3H)-dione (0.14 g, 0.34 mmol) in MeOH (10 mL). The reaction mixture was stirred for 15 mins and then treated with borane-dimethylamine complex (30 mg, 0.51 mmoL). After 15 hours the reaction mixture was quenched with concentrated HCl, and concentrated to a residual oil. Purification by flash column chromatography (EtOAc then 0%–5% MeOH in CH$_2$Cl$_2$) gave the product as a white solid (100 mg, 51%). $^1$H NMR (CDCl$_3$): δ 1.40–2.24 (brm, 11H), 2.60 (s, 3H), 2.73 (m, 5H); 2.94 (s, 3H), 3.10 (m, 5H), 3.50(m, 2H), 3.74 (m, 1H), 6.77 (t, J=15.07 Hz, 1H), 6.95 (m, 2H), 7.05 (m, 1H). Anal. Calcd. For C$_{28}$H$_{34}$O$_5$N$_5$SF: C, 58.83; H, 5.99, N, 12.25. Found: C, 58.94; H, 6.07; N, 12.13.

Example A(132)

6-cyclopentyl-6-[2-(3-fluoro-4-{methyl[methyl(dimethylene)-6-sulfanyl]amino}phenyl)ethyl]dihydro-2H-pyran-2,4(3H)-dione

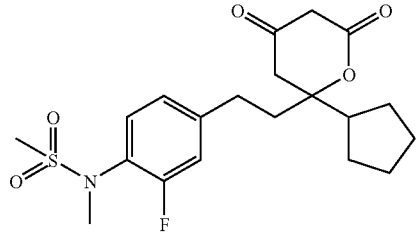

The title compound was prepared analogously to Example A(97), where N-(4-bromophenyl)-N-methylmethanesulfonamide (from step 1 below) was substituted in place of 2-(4-bromo-2-fluorophenyl)-2-methylpropanenitrile in step 3 of that example. $^1$H NMR (CDCl$_3$): δ 1.40–1.80 (brm, 8H), 2.01–2.69 (m, 3H), 2.78–2.83 (m, 3H), 2.94 (m, 4H), 3.10 (m, 5H), 6.77 (t, J=12.07 Hz, 1H), 6.95 (d, J=2.09 Hz, 1H), 7.05 (m, 1H). Anal. Calcd. For C$_{20}$H$_{26}$O$_5$NSF: C, 58.38; H, 6.37; N, 3.40. Found: C, 58.64; H, 6.46; N, 3.13.

Step 1

Preparation of Compound N-(4-bromo-2-fluorophenyl)-N-methylmethanesulfonamide

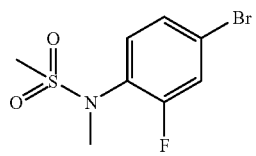

Methane sulfonyl chloride (2.03 ml, 26 mmol) was added to a solution of 4-bromo-2-fluoroaniline (5.0 g, 26 mmol) and pyridine (2.12 ml, 26 mmol) in dichloromethane (100 ml) at 0° C. The reaction mixture was stirred for 1 hr, after which time it was partitioned between dichloromethane (100 ml) and 1N hydrochloric acid (100 ml). The organics were separated and dried over magnesium sulfate, filtered and concentrated in vacuo to afford a yellow oil.

The crude oil was dissolved in dimethylformamide (50 mL) and treated with potassium carbonate (5.1 g, 37.5 mmol) followed by methyl iodide (2.33 ml, 37.4 mmol). The reaction mixture was stirred for 24 hrs after which time it was partitioned between diethylether (100 ml) and water (100 ml). The aqueous was extracted further with diethyl ether (2×100 ml). The combined organics were dried over magnesium sulfate, filtered and the solvent concentrated in vacuuo to afford the title compound as a brown oil (6.9 g).

$^1$H NMR (CDCl$_3$): δ 2.94 (s, 3H), 3.10 (s, 3H), 6.77 (t, J=4.96 Hz, 1H), 6.95 (d, J=4.96 Hz, 1H), 7.05 (m, 1H).

Example A(133)

6-cyclopentyl-3-[(5,7-dimethyl[1,2,4]triazolo[1,5-a]pyrimidin-2-yl)methyl]-4-hydroxy-6-[2-(4-{methyl[methyl(dimethylene)-I$^6$-sulfanyl]amino}phenyl)ethyl]-5,6-dihydro-2H-pyran-2-one

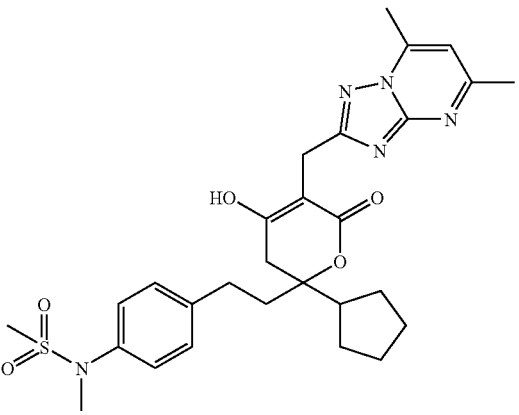

The title compound was prepared analogously to Example A(131), where N-{4-[2-(2-cyclopentyl-4,6-dioxotetrahydro-2H-pyran-2-yl)ethyl]phenyl}-N-methylmethanesulfonamide (from step 1 below) was substituted in place of 6-cyclopentyl-6-[2-(3-fluoro-4-{methyl[methyl(dimethylene)-6-sulfanyl]amino}phenyl)ethyl]dihydro-2H-pyran-2,4(3H)-dione. $^1$H NMR (CDCl$_3$): δ 1.40–1.80 (brm, 8H), 2.05–2.20 (m, 4H), 2.62 (s, 3H), 2.67 (m, 5H), 2.94 (s, 3H), 3.04 (m, 5H), 4.02 (s, 2H), 6.95 (m, 3H), 7.24 (s, 2H). Anal. Calcd. For C$_{28}$H$_{35}$O$_5$N$_5$S: C, 60.74; H, 6.37; N, 12.65. Found: C, 61.04; H, 6.46; N, 12.33.

Step 1

Preparation of compound N-{4-[2-(2-cyclopentyl-4,6-dioxotetrahydro-2H-pyran-2-yl)ethyl]phenyl}-N-methylmethanesulfonamide

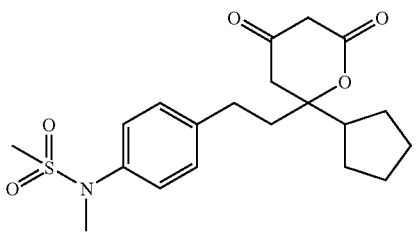

The title compound was prepared analogously to Example A(132), (where 4-bromo-aniline was used in place of 4-bromo-2-fluoroaniline in that example. $^1$H NMR (CDCl$_3$): δ 1.4–2.24 (brm, 11H), 2.60–2.89 (brm, 4H), 3.04 (m, 5H), 6.96 (dd, J=4.96 Hz, 2H), 7.23 (dd, J=4.96 Hz, 2H). Anal. Calcd. For C$_{20}$H$_{27}$NO$_5$S: C, 61.04; H, 6.91; N, 3.56. Found: C, 61.35; H, 6.94; N, 3.20.

Example A(134)

Preparation of compound 6-cyclopentyl-6-{2-[4-(1,1-dioxidoisothiazolidin-2-yl)-3-fluorophenyl]ethyl}dihydro-2H-pyran-2,4(3H)-dione

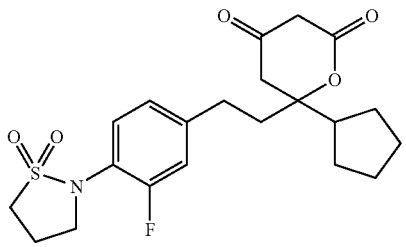

The title compound was prepared analogously to Example A(97), where 2-(4-bromo-2-fluorophenyl)isothiazolidine 1,1-dioxide (from step 2 below) was substituted in place of 2-(4-bromo-2-fluorophenyl)-2-methylpropanenitrile of that example. $^1$H NMR (CDCl$_3$): δ1.4–2.54 (brm, 12H), 2.80–2.99 (brm, 3H), 3.06 (m, 3H), 3.50 (m, 2H), 4.00 (m, 2H), 6.86 (m, 2H), 7.03 (d, J=2.96 Hz, 1H). Anal. Calcd. For C$_{21}$H$_{26}$NO$_5$SF: C, 59.56; H, 6.19; N, 3.31. Found: C, 59.57; H, 6.24; N, 3.20.

Step 2

Preparation of compound 2-(4-bromo-2-fluorophenyl)isothiazolidine 1,1-dioxide

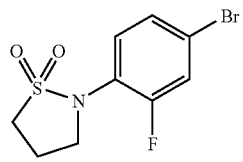

N-(4-bromo-2-fluorophenyl)-3-chloropropane-1-sulfonamide (8.27 g, 0.025M) and potassium carbonate (5.10 g, 0.0375M) was dissolved in dimethylformamide (50 ml) at room temperature under an atmosphere of nitrogen. The reaction mixture was stirred for a further 24 hrs after which time it was partitioned between diethylether (500 ml) and water (500 ml). The organics were washed with 1N HCl (300 ml) and then water (100 ml) The organics were then dried over magnesium sulfate, filtered and the solvent concentrated in vacuuo to afford the title compound as a brown oil (9.0 g). $^1$H NMR (CDCl$_3$): δ 2.40–2.50 (m, 2H), 3.25–3.40 (m, 2H), 4.00 (m, 2H); 6.78 (m, 2H), 7.10 (d, J=2.56 Hz, 1H),).

Step 1

Preparation of compound N-(4-bromo-2-fluorophenyl)-3-chloropropane-1-sulfonamide

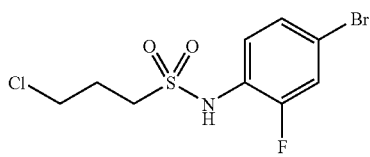

3-chloropropane-1-sulfonyl chloride (3.16 ml, 0.026M) was added to a solution of 4-bromo-2-fluoroaniline (5.00 g, 0.026M) and pyridine (2.12 ml, 0.026M) in dichloromethane (100 ml) at 0° C. The reaction mixture was stirred for 1 hr, after which time it was partitioned between dichloromethane (100 ml) and 1N hydrochloric acid (100 ml). The organics were separated and dried over magnesium sulfate, filtered and concentrated in vacuuo to afford the title compound as a yellow oil (8.3 g). $^1$H NMR (CDCl$_3$): δ2.54 (m, 2H), 2.90 (m, 2H), 3.64 (d, J=2.56 Hz, 2H), 6.91 (d, J=3.56 Hz, 1H), 7.07 (m, 2H).

Example A(135)

6-cyclopentyl-6-[2-(3-cyclopentyl-4-hydroxyphenyl)ethyl]-3-[(5,7-dimethyl[1,2,4]triazolo[1,5-a]pyrimidin-2-yl)methyl]-4-hydroxy-5,6-dihydro-2H-pyran-2-on

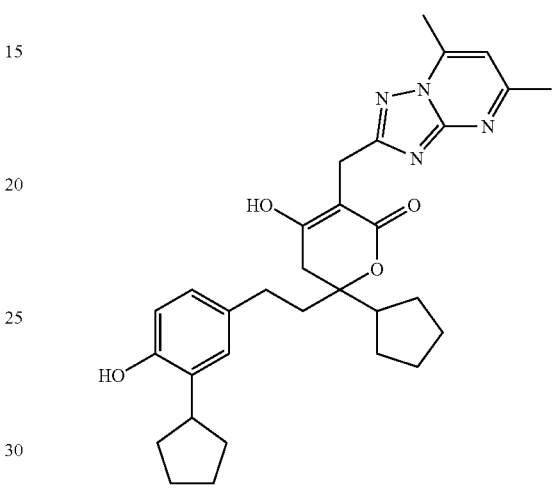

The title compound was prepared analogously to Example A(131) where 6-cyclopentyl-6-[2-(3-cyclopentyl-4-hydroxyphenyl)ethyl]dihydro-2H-pyran-2,4(3H)-dione (from step 1 below) was substituted in place of 6-cyclopentyl-6-[2-(3-fluoro-4-{methyl[methyl(dimethylene)-6-sulfanyl]amino}phenyl)ethyl]dihydro-2H-pyran-2,4(3H)-dione $^1$H NMR (CDCl$_3$): δ 1.40–1.80 (brm, 16H), 2.20 (m, 3H), 2.58 (s, 3H), 2.73 (m, 5H), 3.00 (m, 3H), 4.00 (s, 2H), 6.60 (d, J=2.07 Hz, 1H), 6.85 (d, J=2.07 Hz, 1H), 6.99 (s, 1H), 7.13 (s, 1H). Anal. Calcd. For C$_{31}$H$_{38}$O$_4$N$_4$: C, 70.16; H, 7.22; N, 10.56. Found: C, 70.54; H, 7.46; N, 10.13.

Step 1

Preparation of compound 6-cyclopentyl-6-[2-(3-cyclopentyl-4-hydroxyphenyl) ethyl]dihydro-2H-pyran-2,4(3H)-dione

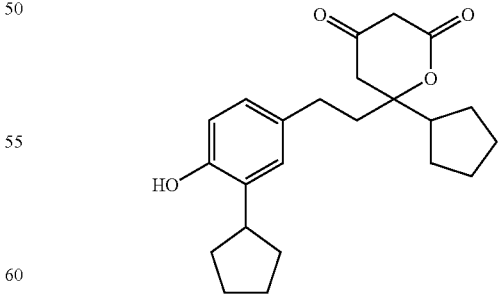

The title compound was prepared analogously to Example A(124) where 2-cyclopentyl phenol was used in place of 2-ethyl-5-fluorophenol in that example. $^1$H NMR (CDCl$_3$): δ 1.43–1.85 (br m, 16H), 1.87–2.21, (m, 3H), 2.70–3.18 (brm, 7H), 4.95 (s, 1H), 6.60 (d, J=8.1 Hz 1H), 6.84 (d, J=8.1 Hz, 1H), 7.12 (s, 1H). MS(APCI): 369 (M–H).

Example A(136)

6-cyclopentyl-3-[(5,7-dimethyl[1,2,4]triazolo[1,5-a]pyrimidin-2-yl)methyl]-4-hydroxy-6-[2-(4-hydroxy-3-propylphenyl)ethyl]-5,6-dihydro-2H-pyran-2-one

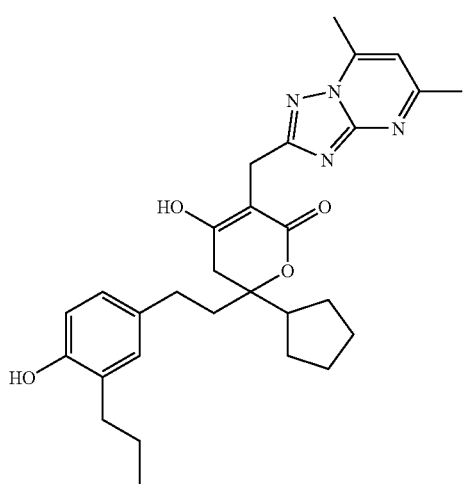

The title compound was prepared analogously to Example A(131), where 6-cyclopentyl-6-[2-(4-hydroxy-3-propylphenyl)ethyl]dihydro-2H-pyran-2,4(3H)-dione (from step 1 below) was substituted in place of 6-cyclopentyl-6-[2-(3-fluoro-4-{methyl[methyl(dimethylene)-6-sulfanyl]amino}phenyl)ethyl]dihydro-2H-pyran-2,4(3H)-dione. $^1$H NMR (CDCl$_3$): δ 1.00 (t, J=7.54 Hz, 3H), 1.40–1.80 (brm, 10H), 2.00–2.18(m, 5H), 2.59 (s, 3H), 2.73 (m, 5H), 2.95 (m, 2H), 4.00 (s, 2H), 6.67 (d, J=5.78 Hz, 1H), 6.95 (m, 2H), 7.21 (s, 1H). Anal. Calcd. For C$_{29}$H$_{36}$O$_4$N$_4$: C, 69.02; H, 7.19; N, 11.10. Found: C, 69.23; H, 7.43; N, 11.31.

Step 1

6-cyclopentyl-6-[2-(4-hydroxy-3-propylphenyl)ethyl]dihydro-2H-pyran-2,4 (3H)-dione

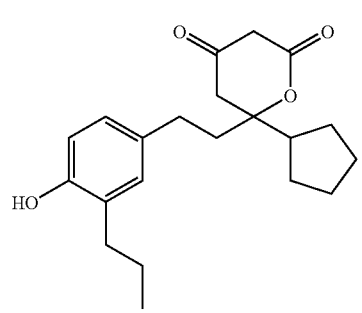

The title compound was prepared analogously to Example A(124), where 2-propylphenol was used in place of 2-ethyl-5-fluorophenol in that example. $^1$H NMR (CDCl$_3$): δ 1.00 (t, J=8.1 Hz 3H,), 1.33–1.85 (br m, 8H), 1.87–2.01 (m, 2H), 2.22 (m, 3H), 2.30 (m, 2H), 2.60–3.10 (brm, 6H), 5.78 (s, 1H), 6.70 (d, J=2.07 Hz 1H), 6.80 (s, 1H), 6.85 (d, J=2.07 Hz, 1H). MS (APCI): 343 (M−H).

Example A(137)

6-cyclopentyl-3-[(5,7-diethyl[1,2,4]triazolo[1,5-a]pyrimidin-2-yl)methyl]-4-hydroxy-6-[2-(4-hydroxy-3-propylphenyl)ethyl]-5,6-dihydro-2H-pyran-2-one

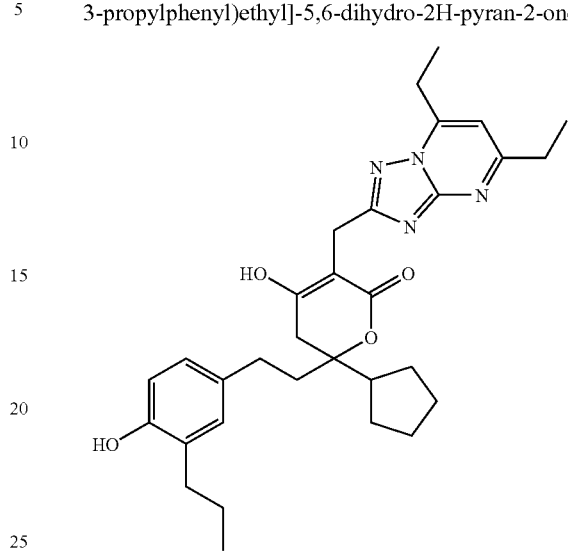

The title compound was prepared analogously to Example A(131), where 6-cyclopentyl-6-[2-(4-hydroxy-3-propylphenyl)ethyl]dihydro-2H-pyran-2,4(3H)-dione was substituted in place of 6-cyclopentyl-6-[2-(3-fluoro-4-{methyl[methyl(dimethylene)-sulfanyl]amino}phenyl)ethyl]dihydro-2H-pyran-2,4(3H)-dione and 5,7-diethyl[1,2,4]triazolo[1,5-a]pyrimidine-2-carbaldehyde was substituted in place of 5,7-Dimethyl-[1,2,4]triazolo[1,5-a]pyrimidine-2-carbaldehyde. $^1$H NMR (CDCl$_3$): δ 1.00 (t, J=7.54 Hz, 3H), 1.40–1.80 (brm, 16H), 2.00–2.18(m, 5H), 2.59 (m, 2H), 2.73 (m, 4H), 2.95 (m, 2H), 4.00 (s, 2H), 6.67 (d, J=5.78 Hz, 1H), 6.95 (m, 2H), 7.21 (s, 1H). Anal. Calcd. For C$_{32}$H$_{40}$O$_4$N$_4$: C, 70.56; H, 7.40; N, 10.29. Found: C, 70.23; H, 7.69; N, 10.31.

Example A(138)

6-cyclopentyl-3-[(5,7-diethyl[1,2,4]triazolo[1,5-a]pyrimidin-2-yl)methyl]-6-[2-(3-ethyl-4-hydroxyphenyl)ethyl]-4-hydroxy-5,6-dihydro-2H-pyran-2-one

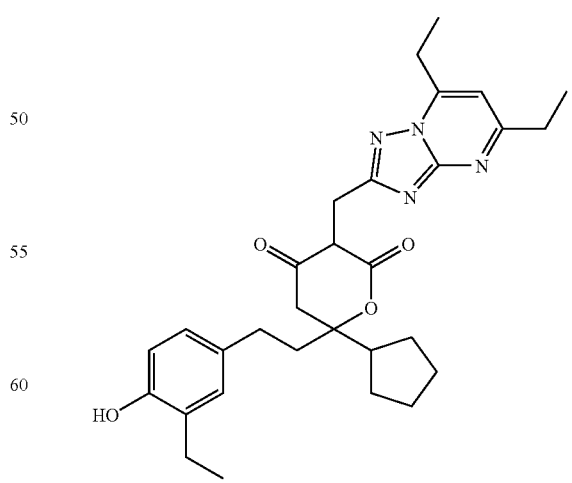

The title compound was prepared analogously to Example A(126), where 5,7-diethyl[1,2,4]triazolo[1,5-a]pyrimidine-2-carbaldehyde was substituted in place of 6-methyl-[1,2,4]

triazolo[1,5-a]pyrimidine-2-carbaldehyde. ¹H NMR (CDCl₃): δ 1.40–1.90 (brm, 17H), 2.09–2.40 (m, 5H), 2.60–2.80 (m, 6H), 3.00 (m, 2H), 3.25 (m, 2H), 3.95 (m, 1H), 6.64 (d, J=5.21 Hz, 1H), 6.78 (d, J=5.21 Hz, 1H), 7.00 (s, 1H), 7.22 (s, 1H). Anal. Calcd. For C₃₀H₃₈O₄N₄: C, 69.47; H, 7.38; N, 10.80. Found: C, 69.54; H, 7.40; N, 10.89.

Example A(139)

N-{2-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylphenoxy]ethyl}acetamide

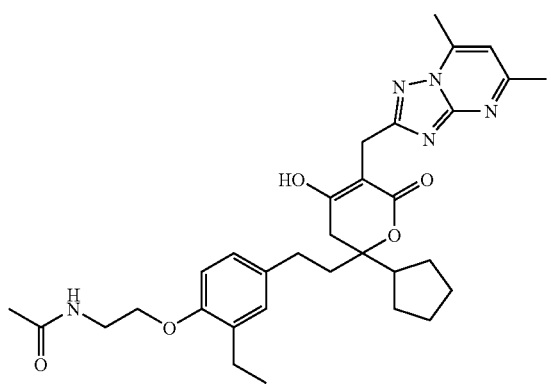

The title compound was prepared analogously to Example A(131), where N-(2-{4-[2-(2-cyclopentyl-4,6-dioxotetrahydro-2H-pyran-2-yl)ethyl]-2-ethyl phenoxy}ethyl)acetamide (from step 3 below) was substituted in place of 6-cyclopentyl-6-[2-(3-fluoro-4-{methyl[methyl(dimethylene)-6-sulfanyl]amino}phenyl)ethyl]dihydro-2H-pyran-2,4(3H)-dione. ¹H NMR (CDCl₃): δ 1.20 (t, J=9.54 Hz, 3H), 1.40–1.80 (brm, 10H), 2.00–2.40 (m, 3H), 2.60 (m, 5H), 2.87 (m, 5H), 2.99 (m, 2H), 3.35 (t, J=6.24 Hz, 2H), 3.80 (t, J=6.24 Hz, 2H), 4.02 (s, 2H), 6.65 (m, 2H), 6.95 (s, 1H), 6.99 (s, 1H).

Step 3

Preparation of compound N-(2-{4-[2-(2-cyclopentyl-4,6-dioxotetrahydro-2H-pyran-2-yl)ethyl]-2-ethylphenoxy}ethyl)acetamide

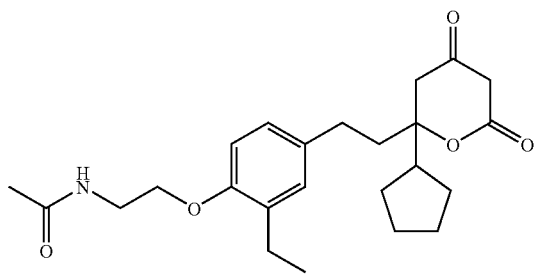

To a solution of {4-[3-cyclopentyl-4-(2,2-dimethyl-4-oxo-4H-1,3-dioxin-6-yl)but-1-ynyl]-2-ethylphenoxy}acetonitrile (1.90 g, 4.4 mmol) in EtOH (100 mL) was added Pd(OH)₂ (500 mg, 20 wt %). The mixture was stirred under H₂ for 3 hours before it was filtered through a pad of celite. The solvent was removed and the residue was taken directly into next step without further purification.

The crude mixture was dissolved in dichloromethane (10 ml) and acetyl chloride (0.041 ml, 0.579 mmol) followed by pyridine (0.046 ml, 0.579 mmol) were added. The reaction mixture was stirred at room temperature for 12 hours, after which time the mixture was partitioned between dichloromethane (100 ml) and 1N HCl (100 ml). The organics were separated, dried over sodium sulfate, filtered and concentrated in vacuuo. The crude mixture was taken on directly to the next step without further purification.

The crude mixture was dissolved in anhydrous MeOH (20 mL) and treated with K₂CO₃ (500 mg). The reaction was heated at 45° C. for 40 min before it was cooled down to room temperature. The crude mixture was diluted with aqueous NH₄Cl and extracted with EtOAc (3×100 mL). The combined organic layers were washed with brine, dried over Na₂SO₄. The solvent was removed and the mixture was purified by flash column chromatography (EtOAc in hexanes, 10–40% gradient) to give the desired product (200 mg). ¹H NMR (CDCl₃) δ: 1.23 (t, J=12.07 Hz, 3H) 1.60–1.83(m, 11 H), 2.00–2.38 (m, 3 H), 2.60 (m, 2 H), 2.82–3.20 (m, 6 H), 3.35 (m, 2 H), 3.90 (m, 2 H), 6.66(m, 2 H), 6.99 (s, 1 H).

Step 2

Preparation of compound {4-[3-cyclopentyl-4-(2,2-dimethyl-4-oxo-4H-1,3-dioxin-6-yl)but-1-ynyl]-2-ethylphenoxy}acetonitrile

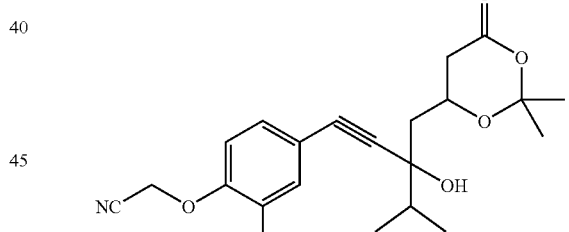

To a solution (4-bromo-2-ethylphenoxy)acetonitrile (1.99 g, 8.33 mmol) in diisopropylamine (9 mL) and DMF (3 mL) was added 6-(2-cyclopentyl-2-hydroxybut-3-ynyl)-2,2-dimethyl-4H-1,3-dioxin-4-one (2.00 g, 7.57 mmol), PdCl₂(PPh₃)₂ (211 mg, 4 mol %), CuI (115 mg, 8 mol %). The mixture was heated to 90° C. for 30 min before it was cooled down to room temperature. The reaction was diluted with aqueous NH₄Cl, extracted with EtOAc (3×50 mL). The combined organic extracts were washed with brine, dried with Na₂SO₄ and evaporated to dryness. The mixture was purified by flash column chromatography (10–50% EtOAc in hexanes) to give the product (1.9 g). ¹H NMR (300 MHz, CDCl₃) δ: 1.23 (t, J=12.07 Hz, 3H) 1.35–1.80 (m, 14H), 2.30 (m, 1H), 3.50 (m, 5 H), 4.62 (s, 2 H), 4.87 (s, 1 H), 6.90 (d, J=2.54 Hz, 1 H), 7.14 (m, 1 H), 7.38 (m, 1 H).

Step 1

Preparation of compound (4-bromo-2-ethylphenoxy)acetonitrile

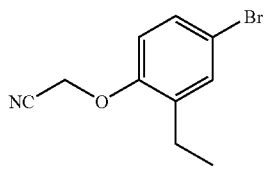

Bromoacetonitrile (1.19 ml, 9.94 mmol) was added to a solution of 4-bromo-2-ethylphenol (2.0 g, 9.94 mmol) and potassium carbonate (1.35 g, 9.94 mmol) in DMF (50 ml). The reaction was stirred for 12 hours and then partitioned between diethyl ether (200 ml) and water (200 ml). The organics were separated, dried over magnesium sulfate, filtered and concentrated in vacuuo to afford the title compound as a yellow oil (2.0 g). $^1$H NMR (CDCl$_3$): δ 1.13 (t, J=12.07 Hz, 3 H), 2.45 (m, 2H), 4.84 (s, 2H), 7.03–7.10 (m, 2H), 7.21 (m, 1H).

Example A(140)

2-(4-{2-[2-Cyclopentyl-5-(5,7-dimethyl-1,2,4)triazolo[1,5-a]pyrimidin-2-ylmethyl]-4-hydroxy-6-oxo-3,6-dihydro-2H-pyran-2-yl]-ethyl]-2,6-difluoro-phenyl]-2-methyl-propionitrile

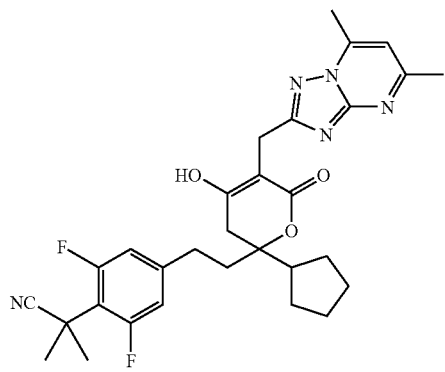

A solution of 2-{4-[2-(2-Cyclopentyl-4,6-dioxo-tetrahydro-pyran-2-yl)-ethyl]-2,6-difluoro-phenyl}-2-methyl-propionitrile (389 mg, 1.0 mmol) in anhydrous MeOH (4.0 mL) was treated with 5,7-dimethyl[1,2,4]triazolo[1,5-a]pyrimidine-2-carbaldehyde (76.6 mg, 1.30 mmol), followed by borane-dimethylamine complex at room temperature. The reaction was stirred for 12 hours before it was quenched by the addition of 1 N HCl. The mixture was extracted with 10% MeOH in CH$_2$Cl$_2$ (3×10 mL) and the combined organic layers were washed with brine, dried over MgSO$_4$. The solvent was removed and the residue was purified by flash column chromatography (80% EtOAc, 14% Hexane, 6% MeOH and 0.5% Acitic acid) to give the product (192 mg, 35% yield). $^1$H NMR (CDCl$_3$) δ: 1.52–1.75 (m, 6 H), 1.83 (s, 3 H), 1.93–1.99 (m, 3 H), 2.09 (s, 3 H), 2.36 (m, 1 H), 2.45 (d, J=17.94 Hz, 2 H), 2.60–2.64 (m, 2 H), 2.66 (s, 3 H), 2.72 (d, J=6.06 Hz, 1 H), 2.78 (d, J=7.33 Hz, 1 H), 2.79 (s, 3 H), 4.08 (s, 2 H), 6.68 (d, J=10.86 Hz, 2 H), 6.85 (s, 1 H). MS (ESI): 548 (M–H).

Example A(141)

2-{4-[2-(2-Cyclopentyl-4,6-dioxo-tetrahydro-pyran-2-yl)-ethyl]-2,6-difluoro-phenyl}-2-methyl-propionitrile

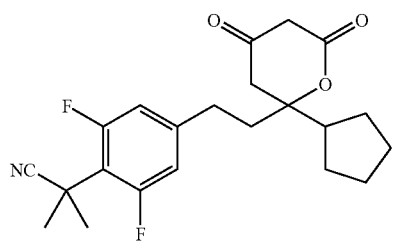

The desired product was prepared analogously to step 4 in Example A(97), substituting 2-{4-[3-Cyclopentyl-4-(2,2-dimethyl-6-oxo-6H-[1,3]dioxin-4-yl)-3-hydroxy-but-1-ynyl]-2,6-difluoro-phenyl}-2-methyl-propionitrile in place of 2-{4-[3-cyclopentyl-4-(2,2-dimethyl-4-oxo-4H-1,3-dioxin-6-yl)-3-hydroxybut-1-ynyl]-2-fluorophenyl}-2-methylpropanenitrile. $^1$H NMR (CDCl$_3$) δ: 1.38–1.48 (m, 4 H), 1.57–1.77 (m, 5 H), 1.85 (s, 6 H), 1.92 (t, J=8.59 Hz, 2 H), 2.25 (m, 1 H), 2.65 (dd, J=15.92, 7.58 Hz, 2 H), 2.75 (dd, J=28.80, 15.66 Hz, 2 H), 3.43 (d, J=4.55 Hz, 2 H), 6.71 (d, J=10.86 Hz, 1 H). MS (ESI): 388 (M–H).

Step 4

Preparation of compound 2-{4-[3-Cyclopentyl-4-(2,2-dimethyl-6-oxo-6H-[1,3]dioxin-4-yl)-3-hydroxy-but-1-ynyl]-2,6-difluoro-phenyl}-2-methyl-propionitrile

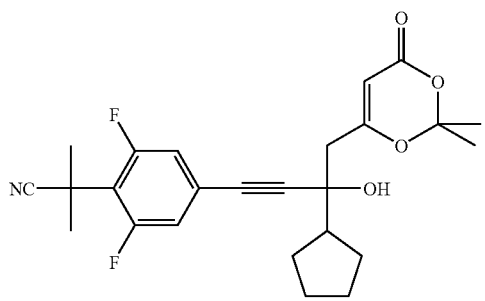

The desired product was prepared analogously to step 3 in Example A(97), substituting 2-(4-Bromo-2,6-difluoro-phenyl)-2-methyl-propionitrile in place of 2-(4-Bromo-2-fluoro-phenyl)-2-methyl-propionitrile. $^1$H NMR (CDCl$_3$) δ: 1.38–1.48 (m, 4 H), 1.57–1.77 (m, 5 H), 1.85 (s, 6 H), 1.92 (t, J=8.6 Hz, 2 H), 2.25 (m, 1 H), 2.65 (dd, J=15.9, 7.6 Hz, 2 H), 2.75 (dd, J=28.8, 15.7 Hz, 2 H), 3.43 (d, J=4.6 Hz, 2 H), 6.71 (d, J=10.9 Hz, 1 H). MS (ESI): 442 (M–H).

Step 3

Preparation of compound 2-(4-Bromo-2,6-difluoro-phenyl)-2-methyl-propionitrile

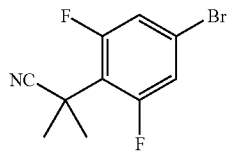

The desired product was prepared analogously to step 2 in Example A(97), substituting (4-Bromo-2,6-difluoro-phenyl)-acetonitrile in place of 1-(4-bromo-2-fluoro-phenyl)-acetonitrile. $^1$H NMR (CDCl$_3$) δ: 1.87 (s, 6H), 7.13 (d, J=9.3 Hz, 2 H).

Step 2

Preparation of compound (4-Bromo-2,6-difluoro-phenyl)-acetonitrile

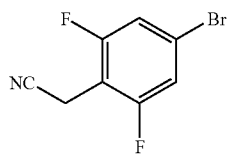

The desired product was prepared analogously to step 1 in Example A(97), substituting (4-Bromo-2,6-difluoro-phenyl)-acetonitrile from step 1 below in place of 1-(4-bromo-2-fluoro-phenyl)-c acetonitrile. $^1$H NMR (CDCl$_3$) δ: 3.59 (s, 2H), 7.18 (d, J=6.6 Hz, 2 H).

Step 1

Preparation of compound 5-Bromo-2-bromomethyl-1,3-difluoro-benzene

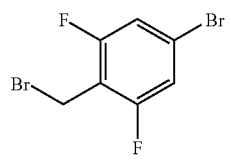

A solution of 5-Bromo-2-hydroxymethyl-1,3-difluoro-benzene (0.89 g, 4.0 mmol) and 30 wt % of hydrogen bromide in acetic acid was stirred at room temperature for 90 minutes before it was poured into 80 ml of water. The mixture was extracted with pentane (3×50 ml) and the combined organic layers were washed with water (3×20 ml), dried over MgSO$_4$ and concentrated at low pressure to afford the desired product (10.0 g, 98% yield). $^1$H NMR (CDCl$_3$) δ: 4.47 (s, 2H), 7.09–7.10 (m, 1H), 7.12–7.13 (m, 1H).

Example A (142)

2-(4-{2-[2-Cyclopentyl-5–5,7-dimethyl-[1,2,4]triazolo[1,5-a]pyrimidin-2-ylmethyl]-4-hydroxy-6-oxo-3,6-dihydro-2H-pyran-2-yl}-ethyl)-2,6-difluoro-phenyl)-2-methyl-propionitrile

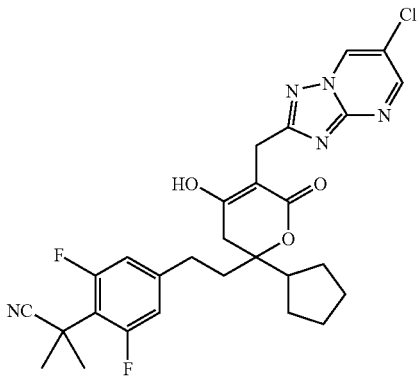

The desired product was prepared analogously to Example A (140), substituting 6-Chloro-[1,2,4]triazolo[1,5-a]pyrimidine-2-carbaldehyde in place of 5,7-Dimethyl-[1,2,4]triazolo[1,5-a]pyrimidine-2-carbaldehyde. $^1$H NMR (CDCl$_3$) δ: 1.57–1.71 (m, 4 H), 1.83 (s, 6 H), 1.94–2.00 (m, 3 H), 2.33–2.40 (m, 2 H), 2.46 (d, J=17.68 Hz, 1 H), 2.65 (t, J=9.09 Hz, 2 H), 2.75 (d, J=18.19 Hz, 2 H), 3.42 (d, J=2.02 Hz, 1 H), 3.75 (t, J=9.35 Hz, 1 H), 4.11 (s, 2 H), 6.68 (d, J=10.86 Hz, 2 H), 8.78 (d, J=2.53 Hz, 1 H), 8.87 (d, J=2.53 Hz, 1 H). MS (ESI): 555 (M–H).

Example A (143)

2-(4-{2-[2-Cyclopentyl-4-hydroxy-5-(6-methyl-[1,2,4]triazolo[1,5-a]pyrimidin-2-ylmethyl)-6-oxo-3,6-dihydro-2H-pyran-2-yl]-ethyl}-2,6-difluoro-phenyl)-2-methyl-propionitrile

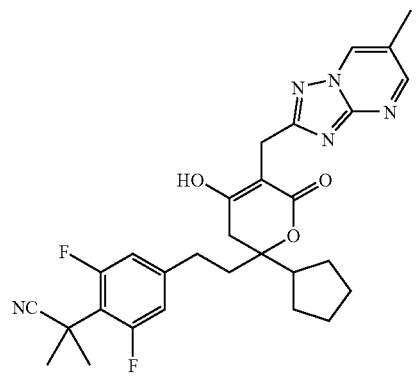

The desired product was prepared analogously to Example A (140), substituting 6-Methyl-[1,2,4]triazolo[1,5-a]pyrimidine-2-carbaldehyde in place of 5,7-Dimethyl-[1,2,4]triazolo[1,5-a]pyrimidine-2-carbaldehyde. $^1$H NMR (CDCl$_3$) δ: 1.34–1.40 (m, 2 H), 1.60–1.73 (m, 4 H), 1.83 (s, 6 H), 1.83–1.86 (m, 3 H), 1.93–1.99 (m, 2 H), 2.37 (m, 1 H), 2.42 (d, J=5.56 Hz, 1 H), 2.48 (s, 3 H), 2.64 (t, J=8.34 Hz, 2 H), 2.75 (d, J=17.94 Hz, 1 H), 4.09 (s, 2 H), 6.67 (d, J=11.12 Hz, 2 H), 8.61 (d, J=1.26 Hz, 1 H), 8.69 (d, J=2.27 Hz, 1 H). MS (ESI): 534 (M–H).

Example A (144)

2-{4-[2-(2-Cyclopentyl-4-hydroxy-6-oxo-5-[1,2,4]triazolo[1,5-a]pyrimidin-2-ylmethyl-3,6-dihydro-2H-pyran-2-yl)-ethyl]-2,6-difluoro-phenyl}-2-methyl-propionitrile

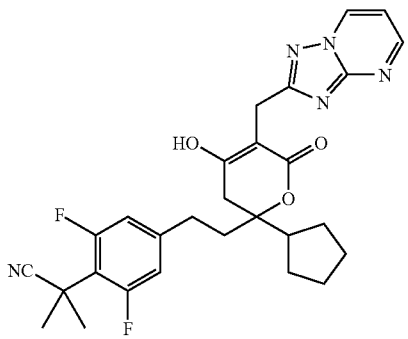

The desired product was prepared analogously to Example A (140), substituting [1,2,4]Triazolo[1,5-a]pyrimidine-2-carbaldehyde in place of 5,7-Dimethyl-[1,2,4]triazolo[1,5-a]pyrimidine-2-carbaldehyde. $^1$H NMR (CDCl$_3$) δ: 1.11 (t, J=7.1 Hz, 2H), 1.49–1.61 (m, 6H), 1.84 (s, 6H), 1.86–1.88 (m, 1H), 1.95–1.99 (m, 1H), 2.40–2.26 (m, 1H), 2.49 (d, J=17.94 Hz, 1H), 2.66 (t, J=8.85 Hz, 2H), 2.77 (d, J=17.69 Hz, 1H), 4.13 (s, 2H), 6.89 (d, J=10.87 Hz, 2H), 7.20 (t, J=6.06 Hz, 1 H), 8.85–8.87 (m, 2H). MS (ESI): 520 (M–H).

Example A(145)

2-{4-[2-(2-Cyclopentyl-4-methoxy-6-oxo-3,6-dihydro-2H-pyran-2-yl)-ethyl]-2-fluoro-phenyl}-2-methyl-propionitrile

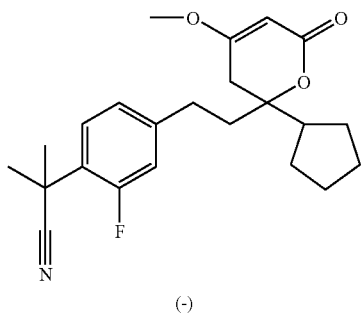

(−)

A magnetically stirring solution of 2-{4-[2-(2-cyclopentyl-4,6-dioxotetrahydro-2H-pyran-2-yl)ethyl]-2-fluorophenyl}-2-methylpropanenitrile (− rotation, 0.15 g, 0.40 mmol) was cooled to 0° C. DBU (0.18 mL, 1.21 mmol) was added followed by MeI (0.076 mL, 1.21 mmol) and reaction was stirred at 0° C. for 1 hour. The reaction mixture was partitioned between 1N HCl and EtOAc. The layers of the resulting reaction mixture were separated and the organic layer was washed with brine (1×10 mL), then dried over Na$_2$SO$_4$, filtered and concentrated in vacuo. The crude residue was purified by flash column chromatography (20% EtOAc in Hexanes) to give the desired product as a yellow oil (0.062 g, 41%). $^1$H NMR (400 MHz, CDCl$_3$): δ 1.18 (d, J=6.5 Hz, 3H), 1.40 (d, J=6.5 Hz, 3H), 1.50–1.78 (m, 8 H), 1.94–2.05 (m, 2 H), 2.18 (s, 3H), 2.64–2.73 (m, 3 H), 3.75 (s, 2 H), 5.17 (s, 1 H), 6.89–6.97 (m, 2 H), 7.35–7.40 (m, 1 H). MS (ESI): 386 (M+H).

Example A(146)

2-(2-Chloro-4-{2-[2-cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-phenyl)-2-methyl-propionitrile

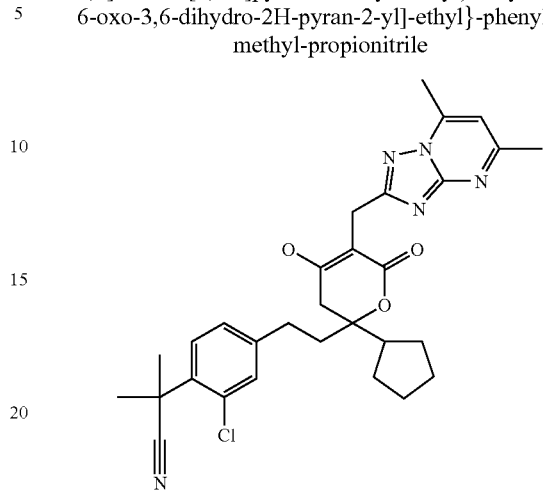

The title compound was prepared analogously to Example B(97), where 2-{2-Chloro-4-[2-(2-cyclopentyl-4,6-dioxotetrahydro-pyran-2-yl)-ethyl]-phenyl}-2-methyl-propionitrile was substituted in place of 6-[2-(3-Chloro-5-ethyl-4-methoxy-phenyl)-ethyl]-6-cyclopentyl-dihydro-pyran-2,4-dione in that example. $^1$H NMR (400 MHz, DMSO-d$_6$): δ 1.39–1.64 (m, 8H), 1.67 (s, 6H), 2.01–2.05 (m, 2H), 2.36–2.46 (m, 7H), 2.51–2.57 (m, 2H), 2.69 (d, J=17 Hz, 2H), 3.61 (d, J=16 Hz, 1H), 3.72 (d, J=16 Hz, 1H), 6.94 (s, 1H), 7.25 (s, 1H), 7.28 (s, 1H), 7.35 (d, J=8 Hz, 1H), 10.75 (s, 1H). IR (neat): 2243, 2355 (CN), 1666, 1625, 1543, 1390. Anal. Calcd. For C$_{30}$H$_{34}$ClN$_5$O$_3$·1.0H$_2$O: C, 63.65; H, 6.41; N, 12.37. Found: C, 63.60; H, 6.30; N, 12.21. MS(ESI): 549 (M+H)$^+$.

Example A(147)

2-{2-Chloro-4-[2-(2-cyclopentyl-4,6-dioxo-tetrahydro-pyran-2-yl)-ethyl]-phenyl}-2-methyl-propionitrile

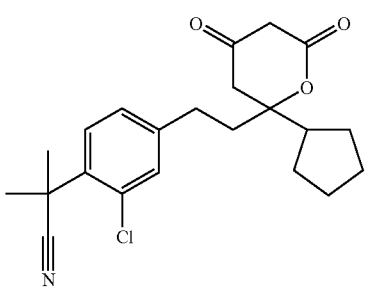

The title compound was prepared analogously to step 4 from Example A(97), where 2-(4-Bromo-2-chloro-phenyl)-2-methyl-propionitrile (described in step 4 below) was substituted in place of 2-(4-Bromo-2-fluoro-phenyl)-2-methyl-propionitrile in step 3 of that example. $^1$H NMR (400 MHz, CDCl$_3$): δ 1.39–1.71 (m, 8H), 1.81–1.87 (m, 8H), 2.10–2.15 (m, 1H), 2.59–2.68 (m, 2H), 3.51 (s, 2H), 3.75 (s, 2H), 7.11 (dd, J=8.1 Hz, 1.8), 7.27 (d, J=1.8 Hz, 1H), 7.37 (d, J=8.1 Hz, 1H). MS (ESI): 388 (M+H)$^+$.

Step 4

2-(4-Bromo-2-chloro-phenyl)-2-methyl-propionitrile

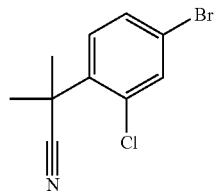

NaH (95%, 1.18 g, 49.35 mmol) was suspended in DMF (25 mL) and cooled to 0° C. 4-Bromo-2-chloro-phenyl)-acetonitrile (2.27 g, 9.87 mmol) from step 3 below, was dissolved in THF (10 mL) and slowly added via cannula and the reaction mixture stirred 20 min. MeI (6.10 mL, 98 mmol) was added and the resulting mixture was stirred overnight at room temperature. Reaction was quenched with H$_2$O (50 mL). Solvents were removed in vacuo and residue partitioned between EtOAc and 1N HCl (50 mL). The organic phase was dried over Na$_2$SO$_4$ and evaporated. The crude organic product was purified by flash column chromatography (5% EtOAc in hexanes) to give the product (2.23 g, 87%) as a clear oil. $^1$H NMR (400 MHz, CDCl$_3$): δ 7.34 (d, J=8.4 Hz, 1H), 7.43 (dd, J=8.4, 2.0 Hz, 1H), 7.61 (d, J=1.8 Hz, 1H).

Step 3

(4-Bromo-2-chloro-phenyl)-acetonitrile

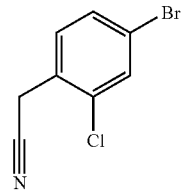

To a magnetically stirring solution of 4-Bromo-1-bromomethyl-2-chloro-benzene (3.59 g, 12.67 mmol) from step 2 below and tetrabutylammonium bromide (0.41 g, 1.27 mmol) in CH$_2$Cl$_2$/H$_2$O 1:1 (60.0 mL), was added a solution of KCN (2.48 g, 38.01 mmol) in H$_2$O (30 mL). The resulting orange mixture was stirred at room temperature for 3 hours. The layers of the resulting reaction mixture were separated and the organic layer was washed with NaHCO$_3$ sat solution (3×50 mL), then dried over Na$_2$SO$_4$, filtered and concentrated in vacuo. The crude residue was purified by flash chromatography (30% EtOAc in Hexanes) to yield the intermediate as a clear oil (3.59 g, 100%). $^1$H NMR (400 MHz, CDCl$_3$): δ 3.79 (s, 2H), 7.37–7.60 (m, 3H).

Step 2

4-Bromo-1-bromomethyl-2-chloro-benzene

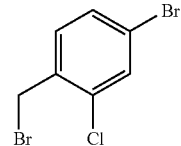

To a magnetically stirring solution of 4-Bromo-2-chloro-phenyl)-methanol (2.80 g, 12.67 mmol) from step 1 below in CH$_2$Cl$_2$ (60.0 mL) under argon at 0° C., was added carbon tetrabromide (4.41 g, 13.30 mmol) followed by triphenylphosphine (3.48 g, 13.30 mmol). The resulting mixture was stirred for 4 hours at room temperature. The resulting reaction mixture was concentrated in vacuo and the crude residue was purified by flash column chromatography (10% EtOAc in Hexanes) to yield the intermediate bromide as a clear oil (3.59 g, 100%). $^1$H NMR (400 MHz, CDCl$_3$): δ 4.53 (s, 2H), 7.29 (d, J=8.2 Hz, 1H), 7.39 (dd, J=8.2, 1.9 Hz, 1 H), 7.56 (d, J=1.9 Hz, 1H).

Step 1

(4-Bromo-2-chloro-phenyl)-methanol

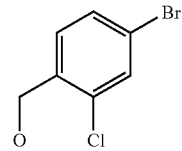

4-Bromo-2-chlorobenzoic acid (5 g, 21.23 mmol) was dissolved in dry THF (100 mL) and cooled to 0° C. A 1M solution of BH$_3$.THF in THF (31.85 mL, 31.85 mmol) was slowly added. The reaction was stirred overnight, allowing it to gradually reach room temperature. K$_2$CO$_3$ solid (1 g) and H$_2$O (100 mL) were added and the reaction was stirred for 30 minutes. THF was evaporated and residue extracted with EtOAc (30 mL). The organic phase was washed with 1N HCl (3×50 mL), brine (3×50 mL), dried over Na$_2$SO$_4$ and evaporated. The residue was purified by flash column chromatography (30% EtOAc in hexanes) to give the product (2.80 g, 50%) as a color less oil. $^1$H NMR (400 MHz, CDCl$_3$): δ 4.73 (d, J=5.8 Hz, 2H), 7.37 (d, J=8.1 Hz, 1H), 7.42 (dd, J=8.1 Hz, 1.7), 7.52 (d, J=1.7 Hz, 1H).

Example A(148)

1-(2-Chloro-{42-[2-cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-phenyl)-cyclopropanecarbonitrile

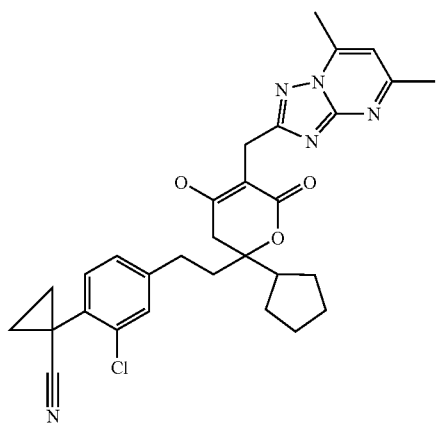

The title compound was prepared analogously to Example B(97), where 1-{2-Chloro-4-[2-(2-cyclopentyl-4,6-dioxo-tetrahydro-pyran-2-yl)-ethyl]-phenyl}-cyclopropanecarbonitrile (from step 2 below) was substituted in place of 6-[2-(3-Chloro-5-ethyl-4-methoxy-phenyl)-ethyl]-6-cyclopentyl-dihydro-pyran-2,4-dione in that example. $^1$H NMR (400 MHz, DMSO-d$_6$): δ 1.50–1.53 (m, 4H), 1.65–1.75 (m, 8H), 1.87–1.99 (m, 2H), 2.26–2.29 (m, 1H), 2.62 (s, 3H), 2.72 (s, 3H), 2.62–2.78 (m, 3H), 2.95 (d, J=17 Hz, 1H), 3.87(d, J=16 Hz, 1H), 3.98 (d, J=16 Hz, 1H), 7.20(s, 1H), 7.45 (dd, J=7.8, 1.3 Hz, 1H), 7.55–7.59 (m, 2H), 11 (brs, 1H). Anal. Calcd. For C$_{30}$H$_{32}$ClN$_5$O$_3$.0.4H$_2$O: C, 65.13; H, 5.98; N, 12.66. Found: C, 65.52; H, 6.02; N, 12.29. MS(ESI): 547(M+H)$^+$.

Example A(149)

1-{2-Chloro-4-[2-(2-cyclopentyl-4,6-dioxo-tetrahydro-pyran-2-yl)-ethyl]phenyl}-cyclopropanecarbonitrile

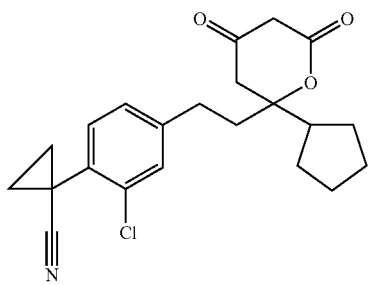

The title compound was prepared analogously to step 4 from Example A(97), where 1-(4-Bromo-2-chloro-phenyl)-cyclopropanecarbonitrile (from step 1 below) was substituted in place of 2-(4-Bromo-2-fluoro-phenyl)-2-methyl-propionitrile in step 3 of that example. $^1$H NMR (400 MHz, CDCl$_3$): δ 1.26–1.33 (m, 4H), 1.53–1.75 (m, 8H), 1.90–1.95 (m, 2H), 2.24–2.29 (m, 1H), 2.64–2.69 (m, 2H), 2.77 (d, J=6.5 Hz, 2H), 3.43 (d, J=3.5 Hz, 2H), 7.03 (dd, J=7.8, 1.7 Hz, 1H), 7.23 (d, J=1.7 Hz, 1H), 7.26 (d, J=7.8 Hz, 1H). IR (neat): 3084, 2931 (CN), 1584, 1561, 1466. Anal. Calcd. For C$_{22}$H$_{24}$ClNO$_3$.0.25H$_2$O: C, 67.69; H, 6.33; N, 3.59. Found: C, 67.55; H, 6.34; N, 3.58. MS(ESI): 384(M+H)$^+$.

Step 1

2-(4-Bromo-2-chloro-phenyl)-2-methyl-propionitrile

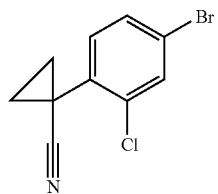

The title compound was prepared analogously to step 4 from Example A(147), where 1-Bromo-2-chloroethane was substituted in place of methyl iodide of that example. $^1$H NMR (400 MHz, CDCl$_3$): δ 7.22 (d, J=8.2 Hz, 1H), 7.39 (dd, J=8.2 Hz, 1.9, 1H), 7.61 (d, J=1.9 Hz, 1H).

Example A(150)

6-Cyclopentyl-3-(5,7-dimethyl-[1,2,4]triazolo[1,5-a]pyrimidin-2-ylmethyl)-6-[2-(5-ethyl-4-hydroxy-2-methoxy-phenyl)-ethyl]-4-hydroxy-5,6-dihydro-pyran-2-one

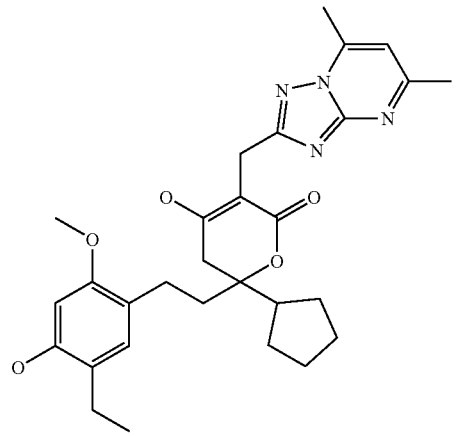

The title compound was prepared analogously to Example B(97), where 6-Cyclopentyl-6-[2-(5-ethyl-4-hydroxy-2-methoxy-phenyl)-ethyl]-dihydro-pyran-2,4-dione (from step 2 below) was substituted in place of 6-[2-(3-Chloro-5-ethyl-4-methoxy-phenyl)-ethyl]-6-cyclopentyl-dihydro-pyran-2,4-dione in that example. $^1$H NMR (400 MHz, DMSO-d$_6$): δ 1.01 (t, J=7.4 Hz, 3H), 1.41–1.76 (m, 8H), 1.87–2.12 (m, 2H), 2.37–2.53 (m, 11H), 2.58 (d, J=17 Hz, 1H), 2.73 (d, J=17 Hz, 1H), 3.59 (s, 3H), 3.70 (d, J=17 Hz, 1H), 3.80 (d, J=17 Hz, 1H), 6.34 (s, 1H), 6.73 (s, 1H), 7.0 (s, 1H), 9.0 (s, 1H), 10.62 (s, 1H). Anal. Calcd. For C$_{29}$H$_{36}$N$_4$O$_5$.0.5CH$_2$Cl$_2$0.5H$_2$O: C, 61.93; H, 6.69; N, 9.79. Found: C, 62.02; H, 7.08; N, 9.48. MS(ESI): 521 (M+H)$^+$.

Example A(151)

6-Cyclopentyl-6-[2-(5-ethyl-4-hydroxy-2-methoxy-phenyl)-ethyl]-dihydro-pyran-2,4-dione

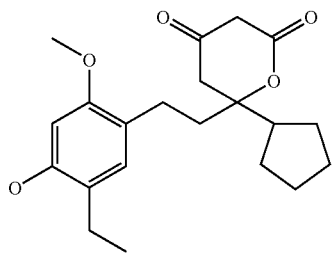

The title compound was prepared analogously to step 4 from Example A(97), where 4-bromo-2-ethyl-5-methoxyphenyl acetate (described in step 1 below) was substituted in place of 2-(4-Bromo-2-fluoro-phenyl)-2-methyl-propionitrile in step 3 of that example. $^1$H NMR (400 MHz, CDCl$_3$): δ 1.19 (t, J=7.4 Hz, 3H) 1.53–1.54 (m, 8H), 1.81–1.95 (m, 2H), 2.31–2.36 (m, 1H), 2.52 (q, J=7.4 Hz, 2H), 2.59–2.65 (m, 2H), 2.75 (d, J=7.3 Hz, 2H), 3.41 (s, 2H), 3.74 (s, 3H), 4.71 (s, 1H), 6.35 (s, 1H), 6.80 (s, 1H). Anal.

Calcd. For $C_{21}H_{28}O_5 \cdot 0.25H_2O$: C, 69.11; H, 7.87. Found: C, 69.13; H, 8.00. MS(ESI): 359 (M+H)$^+$.

Step 1

Preparation of compound
4-bromo-2-ethyl-5-methoxyphenyl acetate

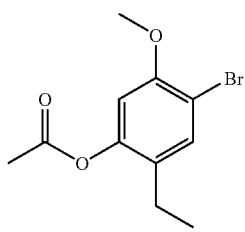

The title compound was prepared analogously to step 4 from Example A(124), where 2'-hydroxy-4'-methoxy acetophenone was substituted in place of 2-fluoro-6-(1-hydroxy-ethyl)-phenol in step 2 of that example. $^1$H NMR (400 MHz, CDCl$_3$): δ 1.16 (t, J=7.4 Hz, 3H), 2.32 (s, 3H), 2.45 (q, J=7.4 Hz, 2H), 3.85 (s, 3H), 6.59 (s, 1H), 7.42 (s, 1H).

Example A(152)

(+)-2-(2-Chloro-4-{2-[2-cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-phenyl)-2-methyl-propionitrile

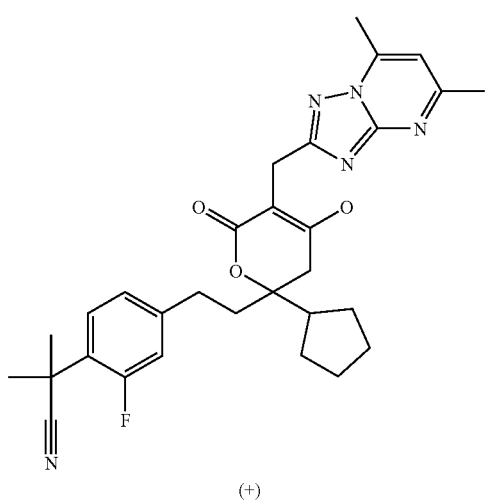

The title compound was prepared analogously to Example B(97), where (+)-2-{4-[2-(2-cyclopentyl-4,6-dioxotetrahydro-2H-pyran-2yl)ethyl]2-fluorophenyl}-2-methylpropanenitrile was substituted in place of 6-[2-(3-Chloro-5-ethyl-4-methoxy-phenyl)-ethyl]-6-cyclopentyl-dihydro-pyran-2,4-dione in that example. $^1$H NMR (400 MHz, DMSO-d$_6$): δ 1.25–1.57 (m, 8H), 1.72 (s, 6H), 2.11–2.17 (m, 2H), 2.50–2.56 (m, 8H), 2.63–2.65 (m, 2H), 2.78(d, J=16 Hz, 1H), 3.71(d, J=16 Hz, 1H), 3.84 (d, J=16 Hz, 1H), 7.06 (s, 1H), 7.17–7.23 (m, 2H), 7.36–7.42 (m, 1H), 10.88 (s, 1H). Anal. Calcd. For $C_{30}H_{36}FN_5O_3 \cdot 1.0H_2O$: C, 65.56; H, 6.60; N, 12.74. Found: C, 65.50; H, 6.41; N, 12.61. MS(ESI): 532 (M+H)$^+$.

Step 4

(+)-2-{4-[2-(2-cyclopentyl-4,6-dioxotetrahydro-2H-pyran-2-yl)ethyl]-2-fluorophenyl}-2-methylpropanenitrile

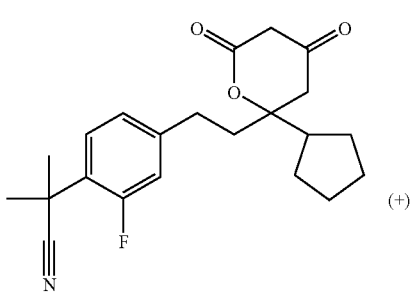

The title compound was prepared analogously to from Example A(97), where (+)-6-(2-cyclopentyl-2-hydroxybut-3-ynyl)-2,2-dimethyl-4H-1,3-dioxin-4-one was substituted in place of the racemic material. $^1$H NMR (CDCl$_3$) δ: 1.60–1.73(m, 6 H), 1.92–1.98 (m, 2 H), 2.22–2.30 (m, 1 H), 2.65–2.71 (m, 2 H), 2.75–2.80 (m, 2 H), 6.88–6.96 (m, 2 H), 7.37–7.43 (m, 1 H). MS(ESI): 372 (M+H)$^+$.

Step 3

Preparation of compound (+)-6-(2-cyclopentyl-2-hydroxybut-3-ynyl)-2,2-dimethyl-4H-1,3-dioxin-4-one

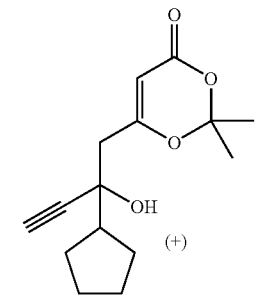

To the optically pure (+)-1-cyclopentyl-1-[(2,2-dimethyl-4-oxo-4H-1,3-dioxin-6-yl)methyl]prop-2-ynyl ethyl oxalate (2.5 g, 15.1 mmol) in 50 ml of MeOH was added K$_2$CO$_3$ (2.0 g). The mixture was stirred at 23° C. for 8 h. After complete conversion, the mixture was neutralized with 1N HCl at cold temperature. The aqueous solution was extracted with MTBE (×3) and the organic layer was washed with brine and dry over MgSO$_4$. After removal of MTBE, 1.75 g of the desired product (+ enantiomer) was produced with 95.5% ee and 96% yield.

Step 2

Preparation of compound (−)-6-(2-cyclopentyl-2-hydroxybut-3-ynyl)-2,2-dimethyl-4H-1,3-dioxin-4-one

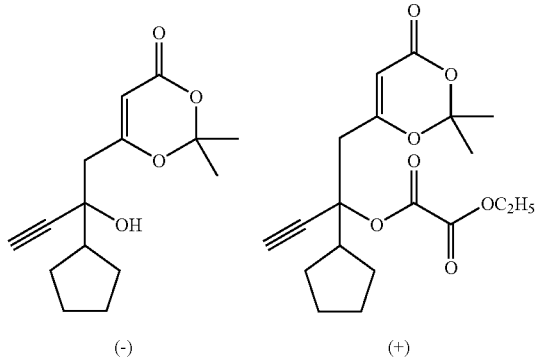

To a 250 ml three-necked flask equipped with a pH electrode was added 72 ml of phosphate buffer (pH 4.0, 0.5M) and *Candida rugosa* lipase (5 g, Amano AY). The mixture was stirred vigorously and then the racemic oxalate (from step 1 below, 6 g) in 18 ml of acetonitrile was added. The reaction mixture was allowed to stir at 23° C. and the pH was kept at 4.0 using a pH titrator. The reaction was monitored with HPLC and stopped after 50% conversion (<20 hrs). The mixture was extracted by MTBE (×3) and the combined organic layer was dried over $MgSO_4$. After removal of the solvent, the crude product was separated carefully by silica-gel chromatography, using heptane/EtOAC, which afforded 2.6 g of the oxalate (+enantiomer, 43% yield, 96% ee) and 2.0 g of product (− enantiomer, 46% yield, 92% ee). $^1$H NMR (300 MHz, $CDCl_3$): δ 1.45–1.80 (m, 8 H), 1.72 (s, 3 H), 1.74 (s, 3 H), 2.13–2.18 (m, 1 H), 2.49 (s, 1 H), 2.56 (s, 1H), 2.58 (s, 2 H), 5.43 (s, 1 H).

Step 1

Preparation of compound 1-cyclopentyl-1-[(2,2-dimethyl-4-oxo-4H-1,3-dioxin-6-yl)methyl]prop-2-ynyl ethyl oxalate

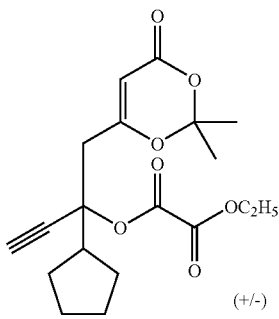

To a solution of racemic 6-(2-cyclopentyl-2-hydroxybut-3-ynyl)-2,2-dimethyl-4H-1,3-dioxin-4-one (10 g, 37.9 mmol) in $CH_2Cl_2$ (200 ml) was added triethylamine (3.0 eq, 113.7 mmol) at 0° C. Then ethyl chlorooxoacetate (3.0 eq, 113.7 mmol) in $CH_2Cl_2$ (10 ml) was added dropwise over a 30-minute period under argon. The solution was allowed to stir overnight at room temperature. After removal of solvent, the crude product was purified using a flash column (heptane: EtOAc, 3:1) to afford the desired oxalate (13.5 g, >95%). API-MS: $[M+Na^+]$: 387;

Example A(153)

Preparation of compound (−)-2-(4-{2-[2-Cyclopentyl-5-(5,7-dimethyl-[1,2,4]triazololo [1,5-a]pyrimidin-2-ylmethyl)-4-hydroxy-6-oxo-3,6-dihydro-2H-pyran-2-yl]-ethyl}-2-fluorophenyl)-2-methylpropionitrile

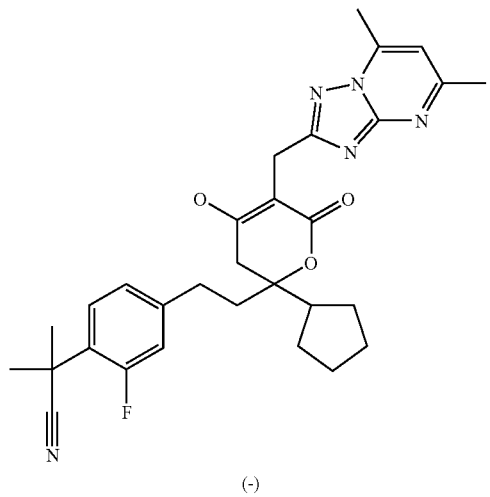

The title compound was prepared analogously to Example B(97), where (−)-2-{4-[2-(2-cyclopentyl-4,6-dioxotetrahydro-2H-pyran-2yl)ethyl]2-fluorophenyl}-2-methylpropanenitrile (from step 1 below) was substituted in place of 6-[2-(3-Chloro-5-ethyl-4-methoxy-phenyl)-ethyl]-6-cyclopentyl-dihydro-pyran-2,4-dione in that example. $^1$H NMR (400 MHz, DMSO-$d_6$): δ 1.25–1.57 (m, 8H), 1.72 (s, 6H), 2.11–2.17 (m, 2H), 2.50–2.56 (m, 8H), 2.63–2.65 (m, 2H), 2.78(d, J=16 Hz 1H), 3.71(d, J=16 Hz, 1H), 3.84 (d, J=16 Hz, 1H), 7.06 (s, 1H), 7.17–7.23 (m, 2H), 7.36–7.42 (m, 1H), 10.88 (s, 1H). Anal. Calcd. For $C_{30}H_{34}FN_5O_3$.0.3 EtOAc: C, 65.15; H, 6.57; N, 12.55. Found: C, 66.86; H, 6.59; N, 12.21. MS(ESI): 532 $(M+H)^+$.

Step 1

Preparation of compound (−)-2-{4-[2-(2-cyclopentyl-4,6-dioxotetrahydro-2H-pyran-2-yl)ethyl]-2-fluorophenyl}-2-methylpropanenitrile

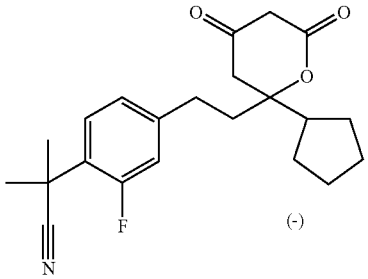

The title compound was prepared analogously to from Example A(97), where (−)-6-(2-cyclopentyl-2-hydroxybut-3-ynyl)-2,2-dimethyl-4H-1,3-dioxin-4-one was substituted in place of the racemic material. $^1$H NMR (400 MHz, $CDCl_3$): δ 1.60–1.73(m, 6 H), 1.92–1.98 (m, 2 H), 2.22–2.30 (m, 1 H), 2.65–2.71 (m, 2 H), 2.75–2.80 (m, 2 H), 6.88–6.96 (m, 2 H), 7.37–43 (m, 1 H).

Example A(154)

6-Cyclopentyl-3-(5,7-dimethyl-[1,2,4]triazolo[1,5-a]pyrimidin-2-ylmethyl)-6-[2-(5-ethyl-4-hydroxy-2-methoxy-phenyl)-ethyl]-4-hydroxy-5,6-dihydro-pyran-2-one

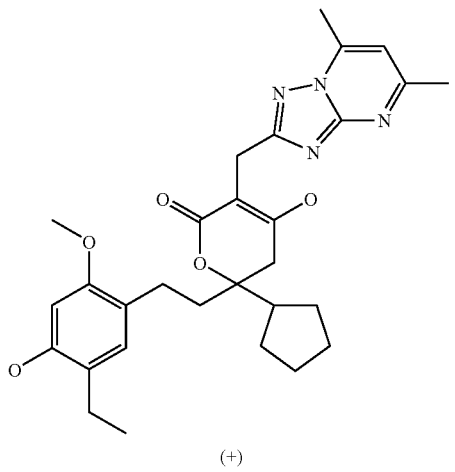

(+)

The title compound was prepared via chiral separation of Example A(150), 6-Cyclopentyl-3-(5,7-dimethyl-[1,2,4]triazolo[1,5-a]pyrimidin-2-ylmethyl)-6-[2-(5-ethyl-4-hydroxy-2-methoxy-phenyl)-ethyl]-4-hydroxy-5,6-dihydro-pyran-2-one. The method used involved a Chiralpak AS-RH, 150×4.6 mm column, 0.6 mL/min, 50% CAN; 50% $H_2O$, 30 min. $^1$H NMR (400 MHz, DMSO-$d_6$): δ 1.01 (t, J=7.4 Hz, 3H), 1.41–1.76 (m, 8H), 1.87–2.12 (m, 2H), 2.37–2.53 (m, 11H), 2.58 (d, J=17 Hz, 1H), 2.73 (d, J=17 Hz, 1H), 3.59 (s, 3H), 3.70 (d, J=17 Hz, 1H), 3.80 (d, J=17 Hz, 1H), 6.34 (s, 1H), 6.73 (s, 1H), 7.0 (s, 1H), 9.0 (s, 1H), 10.62 (s, 1H). MS(ESI): 521 (M+H)$^+$. Retention time using the conditions above was 8.64 min. 100% ee, (+) rotation.

Example A(155)

Preparation of compound (−)-6-Cyclopentyl-3-(5,7-dimethyl-[1,2,4]triazolo[1,5-a]pyrimidin-2-ylmethyl)-6-[2-(5-ethyl-4-hydroxy-2-methoxy-phenyl)-ethyl]-4-hydroxy-5,6-dihydro-pyran-2-one

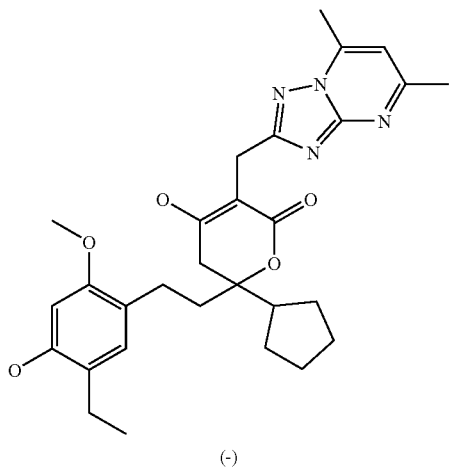

(−)

The title compound was prepared via chiral separation of Example A(150), 6-Cyclopentyl-3-(5,7-dimethyl-[1,2,4]triazolo[1,5-a]pyrimidin-2-ylmethyl)-6-[2-(5-ethyl-4-hydroxy-2-methoxy-phenyl)-ethyl]-4-hydroxy-5,6-dihydro-pyran-2-one. The method used involved a Chiralpak AS-RH, 150×4.6 mm column, 0.6 mL/min, 50% CAN; 50% $H_2O$, 30 min. $^1$H NMR (400 MHz, DMSO-$d_6$): δ 1.01 (t, J=7.4 Hz, 3H), 1.41–1.76 (m, 8H), 1.87–2.12 (m, 2H), 2.37–2.53 (m, 11H), 2.58 (d, J=17 Hz, 1H), 2.73 (d, J=17 Hz, 1H), 3.59 (s, 3H), 3.70 (d, J=17 Hz, 1H), 3.80 (d, J=17 Hz, 1H), 6.34 (s, 1H), 6.73 (s, 1H), 7.0 (s, 1H), 9.0 (s, 1H), 10.62 (s, 1H). MS(ESI): 521 (M+H)$^+$. Retention time using the conditions above was 6.13 min. 100% ee, (−) rotation.

Example A(156)

6-Cyclopentyl-6-[2-(5-ethyl-4-hydroxy-2-methoxy-phenyl)-ethyl]-4-hydroxy-3-(5-methyl-1H-imidazol-4-ylmethyl)-5,6-dihydro-pyran-2-one

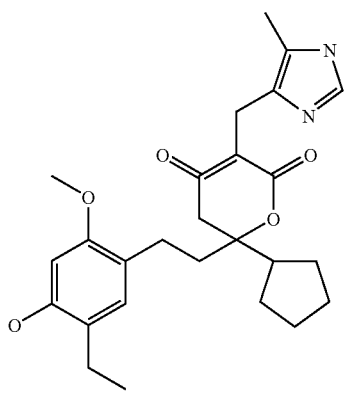

The title compound was prepared analogously to Example A(126), where 6-Cyclopentyl-6-[2-(5-ethyl-4-hydroxy-2-methoxy-phenyl)-ethyl]-dihydro-pyran-2,4-dione was substituted in place of 6-Cyclopentyl-6-[2-(3-ethyl-4-hydroxy-phenyl)-ethyl-dihydro-pyran-2,4-dione and 4-methyl-5-imidazol carboxaldehyde was substituted in place of 6-Methyl-[1,2,4]triazolo[1,5-a]pyrimidine-2-carbaldehyde of that example. $^1$H NMR (400 MHz, DMSO-$d_6$): δ 0.86 (t, J=7.5 Hz, 3H), 1.10–1.56 (m, 10H), 1.73–1.68 (m, 1H), 1.92 (s, 3H), 2.21–2.5 (m, 6H), 3.20–3.22 (m, 2H), 3.44 (s, 3H), 6.17 (s, 1H), 6.50 (s, 1H), 7.53 (s, 1H). Anal. Calcd. For $C_{26}H_{34}N_2O_5 \cdot 1H_2O$: C, 66.08; H, 7.68; N, 5.93. Found: C, 65.93; H, 7.66; N, 5.89. MS(ESI): 455.2 (M+H)$^+$.

Example A(157)

6-Cyclopentyl-6-[2-(5-ethyl-4-hydroxy-2-methoxy-phenyl)-ethyl]-3-(2-ethyl 5-methyl-1H-imidazol-4-ylmethyl)-4-hydroxy-5,6-dihydro-pyran-2-one

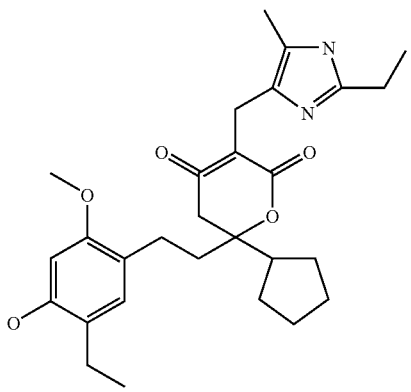

The title compound was prepared analogously to Example A(126), where 6-Cyclopentyl-6-[2-(5-ethyl-4-hydroxy-2-methoxy-phenyl)-ethyl]-dihydro-pyran-2,4-dione was substituted in place of 6-Cyclopentyl-6-[2-(3-ethyl-4-hydroxyphenyl)-ethyl-dihydro-pyran-2,4-dione and 2-ethyl-5-formyl-4-methylimidazole was substituted in place of 6-Methyl-[1,2,4]triazolo[1,5-a]pyrimidine-2-carbaldehyde of that example. ¹H NMR (400 MHz, DMSO-d₆): δ 1.07–1.34 (m, 6H), 1.49–1.81 (m, 10H), 2.13 (s, 3H), 2.28–2.35 (m, 1H), 2.39–2.68 (m, 8H), 3.40 (d, J=6.9 Hz, 2H), 3.68 (s, 3H), 6.41 (s, 1H), 6.74 (s, 1H). Anal. Calcd. For C₂₈H₃₈N₂O₅.1H₂O: C, 67.18; H, 8.05; N, 5.60. Found: C, 67.50; H, 8.09; N, 5.60. MS(ESI): 483.2 (M+H)⁺.

Example A(158)

3-[(6-chloro[1,2,4]triazolo[1,5-a]pyrimidin-2-yl)methyl]-6-cyclopentyl-6-[2-(5-ethyl-4-hydroxy-2-methoxyphenyl)ethyl]-4-hydroxy-5,6-dihydro-2H-pyran-2-one

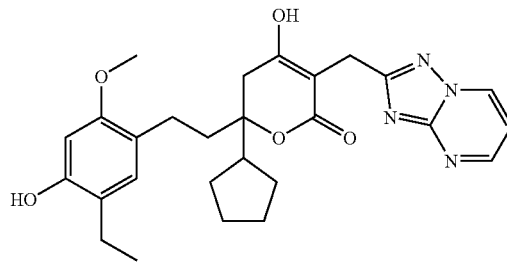

The title compound was prepared analogously to Example A(150), where 6-chloro[1,2,4]triazolo[1,5-a]pyrimidine-2-carbaldehyde was substituted in place of 5,7-dimethyl[1,2,4]triazolo[1,5-a]pyrimidine-2-carbaldehyde. ¹H NMR (300 MHz, DMSO-d₆) δ: 1.02 (t, J=7.44 Hz, 3 H), 1.30–1.69 (m, 8 H), 1.85–1.92 (m, 2 H), 2.25–2.44 (m, 7 H), 3.62 (s, 3 H), 3.71 (s, 2 H), 6.36 (s, 1 H), 6.72 (s, 1 H), 8.81 (d, J=2.64 Hz, 1 H), 9.47 (d, J=2.45 Hz, 1 H). Anal. Calcd. For C27H31ClN4O5.0.5H2O: C, 60.50; H, 6.02; N, 10.45. Found: C, 60.43; H, 6.22; N, 10.20.

Example A(159)

6-cyclopentyl-6-[2-(5-ethyl-4-hydroxy-2-methoxyphenyl)ethyl]-4-hydroxy-3-[(6-methyl[1,2,4]triazolo[1,5-a]pyrimidin-2-yl)methyl]-5,6-dihydro-2H-pyran-2-one

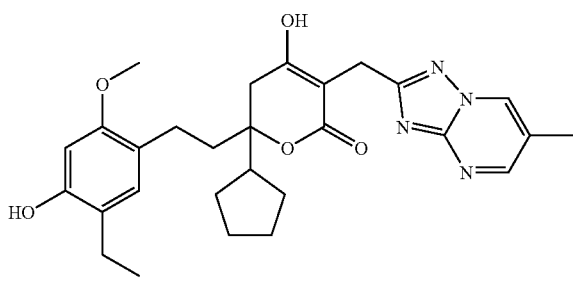

The title compound was prepared analogously to Example A(150), where 6-methyl[1,2,4]triazolo[1,5-a]pyrimidine-2-carbaldehyde was substituted in place of 5,7-dimethyl[1,2,4]triazolo[1,5-a]pyrimidine-2-carbaldehyde. ¹H NMR (300 MHz, DMSO-d₆) δ: 0.95 (t, J=7.44 Hz, 3 H), 1.30–1.64 (m, 8 H), 1.84–1.92 (m, 2 H), 2.27–2.38 (m, 7 H), 3.55 (s, 3 H), 3.68–3.70 (m, 2 H), 6.30 (s, 1 H), 6.68 (s, 1 H), 8.61 (d, J=3.0 Hz, 1 H), 8.74 (s, 1H), 8.95 (s, 1 H). HRMS calcd for C₂₈H₃₅N₄O₅ (M+H)⁺: 507.2602. found 507.2616.

Example A(160)

3-(6-Chloro-[1,2,4]triazolo[1,5-a]pyrimidin-2-ylmethyl)-6-cyclopentyl-6-[2-(5-ethyl-4-hydroxy-2-methyl-phenyl)-ethyl]-4-hydroxy-5,6-dihydro-pyran-2-one

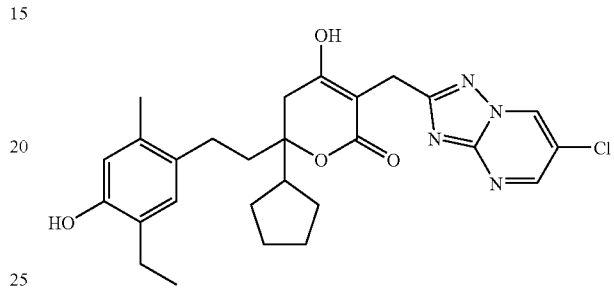

6-Chloro-[1,2,4]triazolo[1,5-a]pyrimidine-2-carbaldehyde (0.16 g, 0.85 mmol) was added to a solution of 6-cyclopentyl-6-[2-(5-ethyl-4-hydroxy-2-methyl-phenyl)-ethyl]-dihydro-pyran-2,4-dione (0.2 g, 0.53 mmol, from step 1 below) in MeOH (7 mL). The reaction mixture was stirred for 20 mins and then treated with borane-dimethylamine complex (63 mg, 1.1 mmoL). After 15 hours the reaction mixture was quenched with conc HCl and concentrated to a brown oil. Purification by flash silica gel chromatography (50% EtOAc in hexanes then 0% to 5% MeOH in CH₂Cl₂) gave the product as a white solid (50 mg, 14%). ¹H NMR (400 MHz, DMSO-d₆) δ: 1.06 (t, J=7.6 Hz, 3 H), 1.36–1.68 (br m, 8 H), 1.88 (m, 2 H), 2.04 (m, 3 H), 2.43–2.56 (m, 4 H), 2.75 (d, J=16.9 Hz, 1 H), 3.29–3.44 (m, 2H), 4.64 (s, 2 H), 6.51 (s, 1 H), 6.72 (m, 2 H), 8.84 (s, 1 H), 9.59 (d, J=4.0 Hz, 1 H), 10.77 (s, 1 H). MS (ESI): 513.30 (M+H⁺).

Step 1

6-Cyclopentyl-6-[2-(5-ethyl-4-hydroxy-2-methyl-phenyl)-ethyl]-dihydro-pyran-2,4-dione

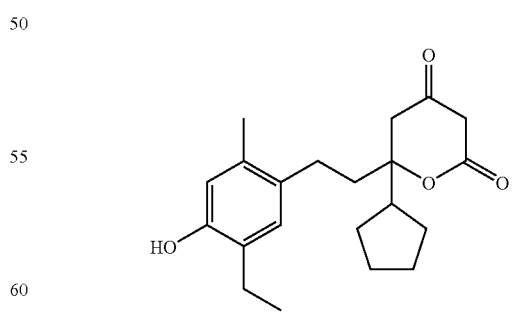

The title compound was prepared analogously to Example A(124) where 1-(2-hydroxy-4-methyl-phenyl)-ethanone was substituted in place of 2-fluoro-6-(1-hydroxy-ethyl)-phenol in step 2 of that example. ¹H NMR (400 MHz, CDCl₃): δ 1.20 (t, J=7.6 Hz, 3 H), 1.55–1.94 (br m, 10 H), 2.19 (s, 3 H), 2.32 (m, 1 H), 2.58 (m, 4 H), 2.79 (s, 2 H), 3.42 (s, 2 H), 4.53 (s, 1 H), 6.56 (s, 1 H), 6.81 (s, 1 H).

Example A(161)

3-(6-Chloro-[1,2,4]triazolo[1,5-a]pyrimidin-2-ylmethyl)-6-cyclopentyl-6-[2-(5-ethyl-2-fluoro-4-hydroxy-phenyl)-ethyl]-4-hydroxy-5,6-dihydro-pyran-2-one

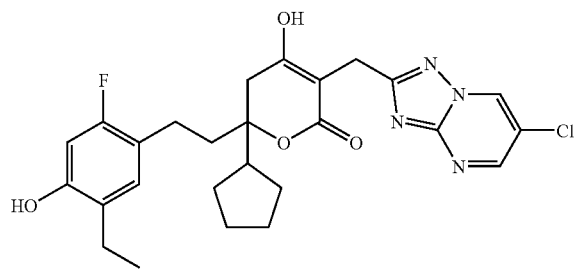

The title compound was prepared analogously to Example A(160) where 1-(4-fluoro-2-hydroxy-phenyl)-ethanone was substituted in place of 1-(2-hydroxy-4-methyl-phenyl)-ethanone in step 1 of that example. $^1$H NMR (400 MHz, DMSO-$d_6$) δ: 1.00 (t, J=7.6 Hz, 3 H), 1.24–1.58 (br m, 8 H), 1.90 (m, 2 H), 2.29–2.49 (m, 4 H), 2.64 (d, J=17.2 Hz, 1 H), 3.32–3.37 (m, 2H), 4.58 (s, 2 H), 6.43 (d, J=11.7 Hz, 1 H), 6.61 (d, J=5.1 Hz, 1 H), 6.80 (d, J=9.4 Hz, 1 H), 9.43 (s, 1 H), 9.53 (d, J=5.1 Hz, 1 H), 10.7 (s, 1 H).

Example A(162)

6-Cyclopentyl-3-(5,7-dimethyl-[1,2,4]triazolo[1,5-a]pyrimidin-2-ylmethyl)-6-[2-(2-ethyl-pyridin-4-yl)-ethyl]-4-hydroxy-5,6-dihydro-pyran-2-one

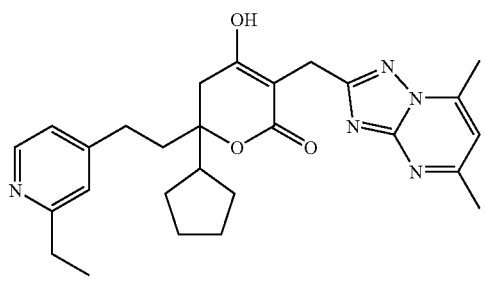

The title compound was prepared analogously to Example A(123) where 6-cyclopentyl-6-[2-(2-ethyl-pyridin-4-yl)-ethyl]-dihydro-pyran-2,4-dione (Example A(163) was substituted in place of 6-cyclopentyl-6-[2-(3-ethyl-5-fluoro-4-hydroxy-phenyl)-ethyl]-dihydro-pyran-2,4-dione. $^1$H NMR (400 MHz, DMSO-$d_6$) δ: 1.24 (t, J=7.6 Hz, 3 H), 1.44–1.75 (br m, 8 H), 2.2 (m, 2 H), 2.50–2.86 (m, 13 H), 3.76 (d, J=16.0 Hz, 1 H), 3.89 (d, J=16.0 Hz, 1 H), 7.11 (s, 1 H), 7.18 (s, 2 H), 8.39 (s, 1 H), 11.12 (s, 1 H). MS (ESI): 476.25 (M+H$^+$).

Example A(163)

6-Cyclopentyl-6-[2-(2-ethyl-pyridin-4-yl)-ethyl]-dihydro-pyran-2,4-dione

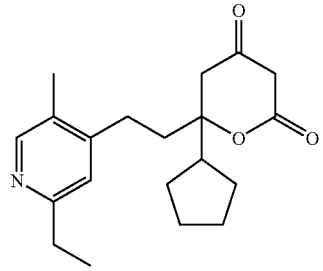

The title compound was prepared analogously to Example A(97) where 4-bromo-2-ethyl-pyridine (from step 3 below) was substituted in place of 2-(4-bromo-2-fluorophenyl)-2-methylpropanenitrile in step 3 of that example. $^1$H NMR (400 MHz, CDCl$_3$): δ 1.30 (t, J=7.6 Hz, 3 H), 1.37–1.76 (br m, 8 H), 1.96 (m, 2 H), 2.28 (s, 1 H), 2.68 (m, 2 H), 2.79 (m, 4 H), 3.44 (s, 2 H), 6.91 (s, 1 H), 6.95 (s, 1 H), 8.42 (s, 1 H). Anal. Calcd. For C$_{19}$H$_{25}$NO$_3$.0.5H$_2$O:C, 70.34; H, 8.08; N, 4.32. Found: C, 70.37; H, 7.96; N, 4.34.

Step 3

4-Bromo-2-ethyl-pyridine

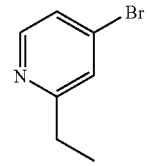

A mixture of 2-ethyl-4-nitro-pyridine (2.3 g, 15.1 mmol) and acetyl bromide (9 mL) were heated together at 75° C. for 16 hours. More acetyl bromide (10 mL) was added and the reaction was heated to 100° C. for 5 hrs. The reaction mixture was poured into ice, made basic with 20% NaOH and extracted with EtOAc. The organic extracts were washed with brine, dried over Na$_2$SO$_4$ and concentrated to a black oil. Purification by flash silica gel chromatography (0% to 25% EtOAc) gave the product as an oil (1.72 g, 62%). $^1$H NMR (400 MHz, CDCl$_3$): δ 1.30 (t, J=7.6 Hz, 3 H), 2.81 (d, J=7.6 Hz, 2 H), 7.28 (dd, J=5.3, 1.8 Hz, 1 H), 7.35 (d, J=1.8 Hz, 1 H), 8.34 (d, J=5.3 Hz, 1 H).

Step 2

2-Ethyl-4-nitro-pyridine

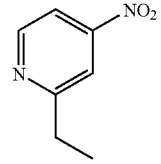

A solution of phosphorous trichloride (7.2 mL, 82 mmol) in CH$_2$Cl$_2$ was added to a cooled 0° C. solution of 2-ethyl-4-nitro-pyridine 1-oxide (3 g, 17.8 mmol) in CH$_2$Cl$_2$. The reaction was stirred for 2 hours and then warmed up to rt. After 3 hours the mixture was poured into ice, made basic with 15% NaOH and extracted with EtOAc. The organic extracts were dried over Na$_2$SO$_4$ and concentrated to a yellow oil that solidified on standing (2.56 g, 95%). $^1$H NMR (400 MHz, CDCl$_3$): δ 1.40 (t, J=7.6 Hz, 3 H), 3.14 (d, J=7.6 Hz, 2 H), 8.04 (d, J=5.6 Hz, 1 H), 8.06 (s, 1 H), 8.92 (d, J=5.6 Hz, 1 H).

Step 1

2-Ethyl-4-nitro-pyridine 1-oxide

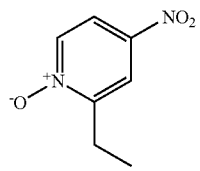

Hydrogen peroxide (4.8 mL, 47 mmol, 30% wt in H$_2$O) was added to a solution of 2-ethylpyridine (5 g, 47 mmol) in AcOH (30 mL). The reaction was refluxed for 24 hours and then concentrated to a dark oil.

The oil was dissolved in H$_2$SO$_4$ (11.4 mL) and cooled to 0° C. HNO$_3$ (9.2 mL) was added slowly and after the addition was complete the reaction mixture was heated to 100° C. for 16 hours. The mixture was poured into ice, made basic with 15% NaOH and extracted with CH$_2$Cl$_2$. The organic layers were washed with brine, dried over Na$_2$SO$_4$ and concentrated. Purification by by flash column chromatography (40% to 60% EtOAc in hexanes) gave the title compound as a yellow solid (3.13 g, 53%). $^1$H NMR (400 MHz, CDCl$_3$): δ 1.37 (t, J=7.3 Hz, 3 H), 2.96 (d, J=7.3 Hz, 2 H), 7.99 (dd, J=7.1, 3.1 Hz, 1 H), 8.10 (d, J=3.1 Hz, 1 H), 8.31 (d, J=7.1 Hz, 1 H).

Example A(164)

3-(6-Chloro-[1,2,4]triazolo[1,5-a]pyrimidin-2-ylmethyl)-6-cyclopentyl-6-[2-(2-ethyl-pyridin-4-yl)-ethyl]-4-hydroxy-5,6-dihydro-pyran-2-one

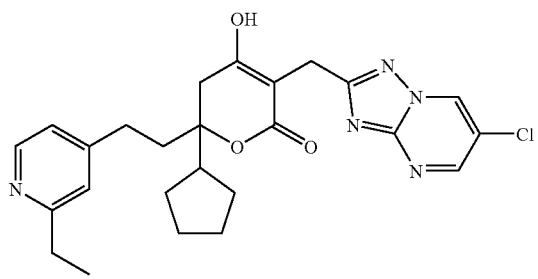

The title compound was prepared analogously to Example A(160) where 6-cyclopentyl-6-[2-(2-ethyl-pyridin-4-yl)-ethyl]-dihydro-pyran-2,4-dione (Example A(163)) was substituted in place of 6-cyclopentyl-6-[2-(5-ethyl-4-hydroxy-2-methyl-phenyl)-ethyl]-dihydro-pyran-2,4-dione. $^1$H NMR (400 MHz, DMSO-d$_6$) δ: 1.18 (t, J=6.1 Hz, 3 H), 1.34–1.66 (br m, 8 H), 1.99 (m, 1 H), 2.12 (m, 1 H), 2.33 (m, 2 H), 2.50–2.62 (m, 3 H), 2.70 (d, J=6.1 Hz, 2 H), 3.69 (d, J=16.0 Hz, 1 H), 3.80 (d, J=16.0 Hz, 1 H), 5.77 (s, 1 H), 7.10 (m, 2 H), 8.33 (d, J=4.8, 1 H), 8.86 (d, J=2.5, 1 H), 9.53 (d, J=6.1 Hz, 1 H).

Example A(165)

3-(6-Chloro-[1,2,4]triazolo[1,5-a]pyrimidin-2-ylmethyl)-6-cyclopentyl-6-[2-(2-ethyl-pyridin-4-yl)-ethyl]-4-hydroxy-5,6-dihydro-pyran-2-one

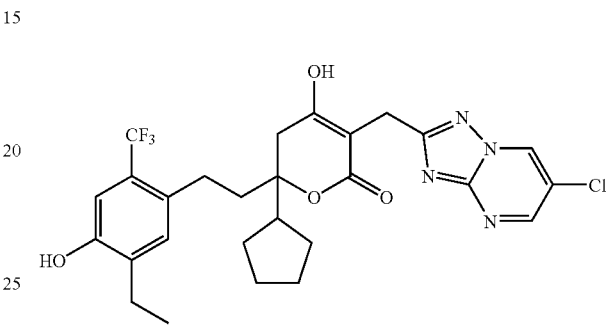

The title compound was prepared analogously to Example A(160) where 1-(2-hydroxy-4-trifluoromethyl-phenyl)-ethanone (from step 1 below) was substituted in place of 1-(2-hydroxy-4-methyl-phenyl)-ethanone in step 1 of that example. $^1$H NMR (400 MHz, DMSO-d$_6$) δ: 1.07 (t, J=7.3 Hz, 3 H), 1.34–1.66 (br m, 8 H), 1.91–2.11 (m, 2 H), 2.37–2.70 (m, 7 H), 3.75 (s, 2 H), 5.77 (s, 1 H), 7.00 (s, 1 H), 7.07 (s, 1 H), 8.84 (s, 1 H), 9.52 (s, 1 H), 9.75 (s, 1 H).

Step 1

1-(2-Hydroxy-4-trifluoromethyl-phenyl)-ethanone

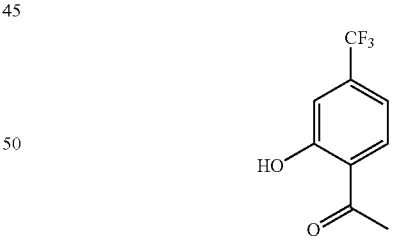

4-Ethoxy-1,1,1-trifluoro-3-buten-2-one (5 g, 29.7 mmol) followed by 2,4-pentadione (3.05 ml, 29.7 mmol) were added to a cooled 0° C. suspension of NaH (2.38 g, 59.4 mmol) in THF (120 mL). The reaction mixture was refluxed for 4 hrs and then partitioned between 1N HCl and EtOAc. The organic layers were washed with brine, dried over Na$_2$SO$_4$ and concentrated to a red oil. Purification by flash column chromatography (0% to 10% EtOAc in hexanes) gave the title compound as a yellow oil (1.73 g, 29%). $^1$H NMR (400 MHz, CDCl$_3$): δ 2.69 (s, 3H), 7.15 (d, J=9.9 Hz, 1 H), 7.25 (s, 1 H), 7.86 (d, J=8.3 Hz, 1 H), 12.29 (s, 1 H).

Example A(166)

6-Cyclopentyl-3-(5,7-dimethyl-[1,2,4]triazolo[1,5-a]pyrimidin-2-ylmethyl)-6-[2-(5-ethyl-2-hydroxy-phenyl)-ethyl]-4-hydroxy-5,6-dihydro-pyran-2-one

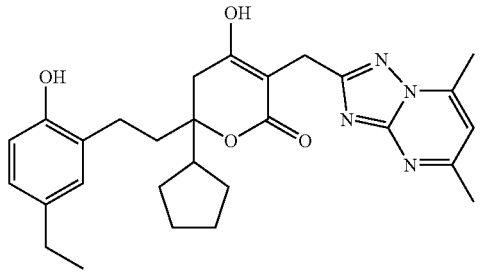

5,7-Dimethyl-[1,2,4]triazolo[1,5-a]pyrimidine-2-carbaldehyde (0.19 g, 1.1 mmol) was added to a solution of 6-cyclopentyl-6-[2-(5-ethyl-2-hydroxy-phenyl)-ethyl]-dihydro-pyran-2,4-dione (0.3 g, 0.91 mmol Example A(169)) in MeOH (8 mL). The reaction mixture was stirred for 15 mins and then treated with borane-dimethylamine complex (47 mg, 0.80 mmoL). After 24 hours the reaction mixture was filtered through a glass frit to remove a fine white ppt. The filtrate was concentrated and purified by prep HPLC to give the product (175 mg, 40%). $^1$H NMR (400 MHz, DMSO-$d_6$) δ: 1.07 (t, J=7.6 Hz, 3 H), 1.41–1.72 (br m, 8 H), 1.97 (m, 1 H), 2.10 (m, 1 H), 2.41–2.73 (m, 13 H), 3.70 (d, J=16.2 Hz, 1 H), 3.79 (d, J=16.2 Hz, 1 H), 6.66 (d, J=8.1 Hz, 1 H), 6.81 (d, J=8.1 Hz, 1 H), 6.84 (s, 1 H), 7.02 (s, 1 H), 9.02 (s, 1 H), 10.88 (s, 1 H). MS (ESI): 491.20 (M+H$^+$).

Example A(167)

Enantiomer 1 of 6-Cyclopentyl-3-(5,7-dimethyl-[1,2,4]triazolo[1,5-a]pyrimidin-2-ylmethyl)-6-[2-(5-ethyl-2-hydroxy-phenyl)-ethyl]-4-hydroxy-5,6-dihydro-pyran-2-one

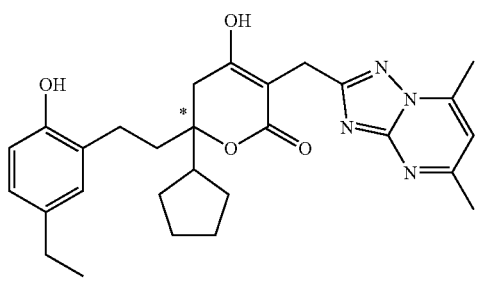

Enantiomer 1

The title compound was separated from racemic 6-cyclopentyl-3-(5,7-dimethyl-[1,2,4]triazolo[1,5-a]pyrimidin-2-ylmethyl)-6-[2-(5-ethyl-2-hydroxy-phenyl)-ethyl]-4-hydroxy-5,6-dihydro-pyran-2-one (118 mg, Example A(166)) using chiral HPLC (Chiralpak AS-H, 120 bar, 2.5 mL/min, 30% MeOH). (42.4 mg, 4.695 min retention time).

Example A(168)

Enantiomer 2 of 6-Cyclopentyl-3-(5,7-dimethyl-[1,2,4]triazolo[1,5-a]pyrimidin-2-ylmethyl)-6-2-(5-ethyl-2-hydroxy-phenyl)-ethyl]-4-hydroxy-5,6-dihydro-pyran-2-one

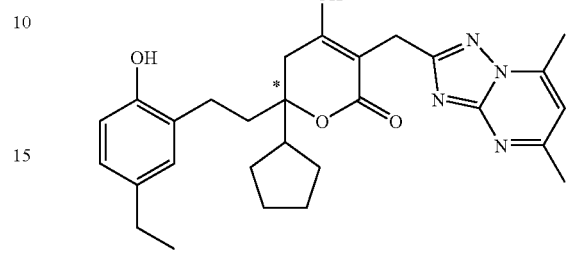

Enantiomer 2

The title compound was separated from racemic 6-Cyclopentyl-3-(5,7-dimethyl-[1,2,4]triazolo[1,5-a]pyrimidin-2-ylmethyl)-6-[2-(5-ethyl-2-hydroxy-phenyl)-ethyl]-4-hydroxy-5,6-dihydro-pyran-2-one (118 mg, Example A(166)) using chiral HPLC (Chiralpak AS-H, 120 bar, 2.5 mL/min, 30% MeOH). (41.3 mg, 7.341 min retention time).

Example A(169)

6-Cyclopentyl-6-[2-(5-ethyl-2-hydroxy-phenyl)-ethyl]-dihydro-pyran-2,4-dione

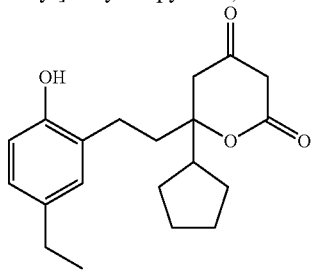

The title compound was prepared analogously to Example A(124) where 1-benzyloxy-2-bromo-4-ethyl-benzene (from step 1 of Example D(8) was substituted in place of acetic acid 4-bromo-2-ethyl-6-fluoro-phenyl ester. $^1$H NMR (400 MHz, CDCl$_3$): δ 1.19 (t, J=7.6 Hz, 3 H), 1.41–2.07 (br m, 10 H), 2.35 (m, 1 H), 2.54 (q, J=7.6 Hz, 2 H), 2.57–2.82 (br m, 4 H), 3.45 (d, J=21.2 Hz, 1 H), 3.47 (d, J=21.2 Hz, 1 H), 4.84 (s, 1 H), 6.64 (d, J=7.8 Hz, 1 H), 6.91 (m, 2 H).). Anal. Calcd. For C$_{20}$H$_{26}$O$_4$.0.2H$_2$O: C, 71.91; H, 7.97. Found: C, 71.96; H, 7.96.

Example A(170)

3-(6-Chloro-[1,2,4]triazolo[1,5-a]pyrimidin-2-ylmethyl)-6-cyclopentyl-6-[2-(5-ethyl-2-hydroxy-phenyl)-ethyl]-4-hydroxy-5,6-dihydro-pyran-2-one

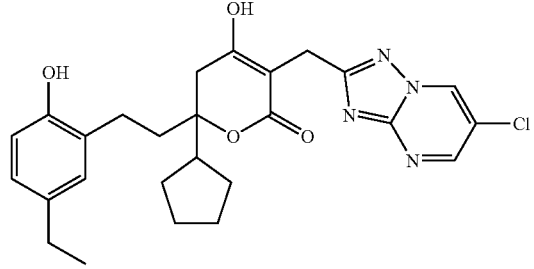

The title compound was prepared analogously to Example A(166) where 6-chloro-[1,2,4]triazolo[1,5-a]pyrimidine-2- carbaldehyde was substituted in place of 5,7-dimethyl-[1,2,4]triazolo[1,5-a]pyrimidine-2-carbaldehyde. $^1$H NMR (400 MHz, DMSO-d$_6$) δ: 1.09 (t, J=7.6 Hz, 3 H), 1.37–1.71 (br m, 8 H), 2.01 (m, 2 H), 2.39–2.54 (m, 5 H), 2.61 (d, J=17.7 Hz, 1H), 2.77 (d, J=17.7 Hz, 1 H), 3.80 (s, 2 H), 6.67 (d, J=8.1 Hz, 1 H), 6.82 (d, J=8.1 Hz, 1 H), 6.86 (s, 1 H), 8.86 (s, 1 H), 9.05 (s, 1 H), 9.45 (s, 1 H), 10.9 (s, 1 H). Anal. Calcd. For $C_{26}H_{29}N_4O_4Cl_{0.5}H_2O$: C, 61.71; H, 5.98; N, 11.07. Found: C, 61.73; H, 5.98; N, 10.99.

Example A(171)

Enantiomer 1 of 3-(6-Chloro-[1,2,4]triazolo[1,5-a]pyrimidin-2-ylmethyl)-6-cyclopentyl-6-[2-(5-ethyl-2-hydroxy-phenyl)-ethyl]-4-hydroxy-5,6-dihydro-pyran-2-one

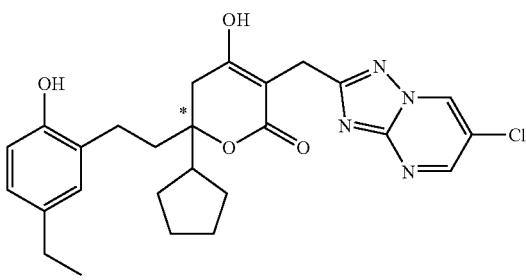

Enantiomer 1

The title compound was separated from racemic 3-(6-chloro-[1,2,4]triazolo[1,5-a]pyrimidin-2-ylmethyl)-6-cyclopentyl-6-[2-(5-ethyl-2-hydroxy-phenyl)-ethyl]-4-hydroxy-5,6-dihydro-pyran-2-one (98 mg, Example A(170)) using chiral HPLC (Chiralpak AS-H, 140 bar, 2.5 mL/min, 20% MeOH). (26 mg, 12.409 min retention time).

Example A(172)

Enantiomer 2 of 3-(6-Chloro-[1,2,4]triazolo[1,5-a]pyrimidin-2-ylmethyl)-6-cyclopentyl-6-[2-(5-ethyl-2-hydroxy-phenyl)-ethyl]-4-hydroxy-5,6-dihydro-pyran-2-one

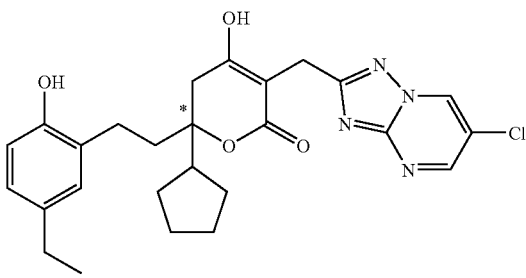

Enantiomer 2

The title compound was separated from racemic 3-(6-chloro-[1,2,4]triazolo[1,5-a]pyrimidin-2-ylmethyl)-6-cyclopentyl-6-[2-(5-ethyl-2-hydroxy-phenyl)-ethyl]-4-hydroxy-5,6-dihydro-pyran-2-one (98 mg, Example A(170)) using chiral HPLC (Chiralpak AS-H, 140 bar, 2.5 mL/min, 20% MeOH). (26 mg, 16.775 min retention time).

Example A(173)

6-Cyclopentyl-6-[2-(5-ethyl-2-hydroxy-phenyl)-ethyl]-4-hydroxy-3-(6-methyl-[1,2,4]triazolo[1,5-a]pyrimidin-2-ylmethyl)-5,6-dihydro-pyran-2-one

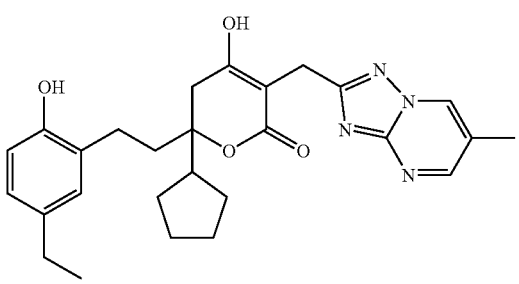

The title compound was prepared analogously to Example A(166) where 6-methyl-[1,2,4]triazolo[1,5-a]pyrimidine-2-carbaldehyde was substituted in place of 5,7-dimethyl-[1,2,4]triazolo[1,5-a]pyrimidine-2-carbaldehyde. $^1$H NMR (400 MHz, DMSO-d$_6$) δ: 0.99 (t, J=7.6 Hz, 3 H), 1.29–1.62 (br m, 8 H), 1.92 (m, 2 H), 2.24 (s, 3 H), 2.32–2.50 (m, 6 H), 2.63 (d, J=11.6 Hz, 1 H), 3.66 (s, 2 H), 6.58 (d, J=8.1 Hz, 1 H), 6.74 (m, 2 H), 8.57 (s, 1 H), 8.74 (s, 1 H), 8.95 (s, 1 H), 10.85 (s, 1 H). MS (ESI): 477.10 (M+H$^+$).

Example A(174)

Enantiomer 1 of 6-Cyclopentyl-6-[2-(5-ethyl-2-hydroxy-phenyl)-ethyl]-4-hydroxy-3-(6-methyl-[1,2,4]triazolo[1,5-a]pyrimidin-2-ylmethyl)-5,6-dihydro-pyran-2-one

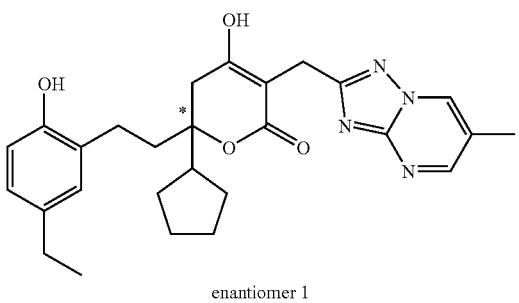

enantiomer 1

The title compound was separated from racemic 6-cyclopentyl-6-[2-(5-ethyl-2-hydroxy-phenyl)-ethyl]4-hydroxy-3-(6-methyl-[1,2,4]triazolo[1,5-a]pyrimidin-2-ylmethyl)-5,6-dihydro-pyran-2-one (97 mg, Example A(173)) using chiral HPLC (Chiralpak AS-H, 120 bar, 2.5 mL/min, 25% MeOH). (42 mg, 7.534 min retention time).

Example A(175)

Enantiomer 2 of 6-Cyclopentyl-6-[2-(5-ethyl-2-hydroxy-phenyl)-ethyl]-4-hydroxy-3-(6-methyl-[1,2,4]triazolo[1,5-a]pyrimidin-2-ylmethyl)-5,6-dihydro-pyran-2-one

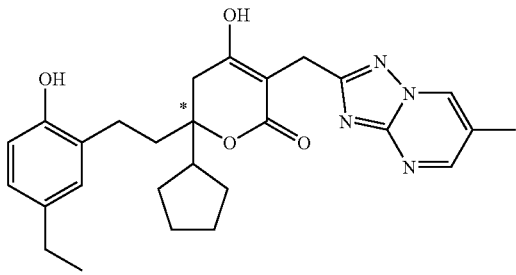

enantiomer 2

The title compound was separated from racemic 6-cyclopentyl-6-[2-(5-ethyl-2-hydroxy-phenyl)-ethyl]4-hydroxy-3-(6-methyl-[1,2,4]triazolo[1,5-a]pyrimidin-2-ylmethyl)-5,6-dihydro-pyran-2-one (97 mg, Example A(173)) using chiral HPLC (Chiralpak AS-H, 120 bar, 2.5 mL/min, 25% MeOH). (37 mg, 10.983 min retention time).

Example A(176)

6-Cyclopentyl-6-[2-(5-ethyl-2-hydroxy-phenyl)-ethyl]-4-hydroxy-3-[1,2,4]triazolo[1,5-a]pyrimidin-2-ylmethyl-5,6-dihydro-pyran-2-one

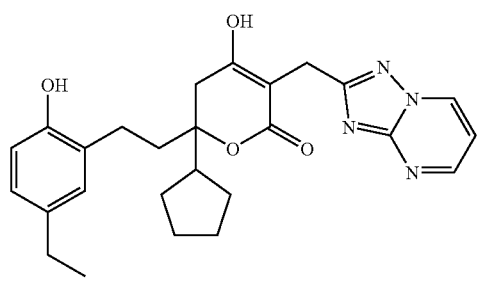

The title compound was prepared analogously to Example A(166) where [1,2,4]triazolo[1,5-a]pyrimidine-2-carbaldehyde was substituted in place of 5,7-dimethyl-[1,2,4]triazolo[1,5-a]pyrimidine-2-carbaldehyde. $^1$H NMR (400 MHz, DMSO-$d_6$) δ: 1.21 (t, J=7.6 Hz, 3 H), 1.50–1.82 (br m, 8 H), 2.12 (m, 2 H), 2.54–2.67 (m, 5 H), 2.71 (d, J=17.7 Hz, 1H), 2.87 (d, J=17.7 Hz, 1 H), 3.90 (s, 2 H), 6.79 (d, J=8.1 Hz, 1 H), 6.94 (dd, J=8.1, 2.0 Hz, 1 H), 6.98 (s, 1 H), 7.37 (dd, J=6.8, 4.3 Hz, 1 H), 8.90 (dd, J=4.3, 2.0 Hz, 1 H), 9.17 (s, 1 H), 9.22 (dd, J=6.6, 1.8 Hz, 1 H), 11.06 (s, 1 H). Anal. Calcd. For $C_{26}H_{30}N_4O_4 \cdot 0.6H_2O$: C, 65.97; H, 6.64; N, 11.84. Found: C, 66.02; H, 6.53; N, 11.71.

Example A(177)

6-Cyclopentyl-3-(5,7-dimethyl-[1,2,4]triazolo[1,5-a]pyrimidin-2-ylmethyl)-6-{2-[5-ethyl-2-(2-methoxy-ethoxy)-phenyl]-ethyl}-4-hydroxy-5,6-dihydro-pyran-2-one

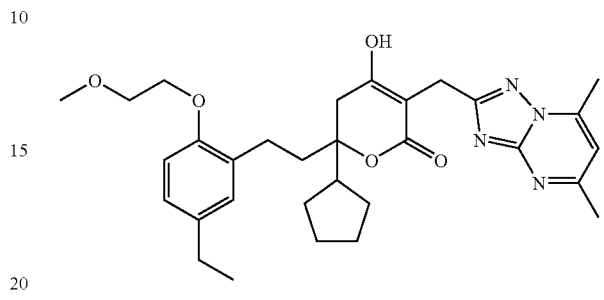

The title compound was prepared analogously to Example A(123) where 6-cyclopentyl-6-{2-[5-ethyl-2-(2-methoxy-ethoxy)-phenyl]-ethyl}-dihydro-pyran-2,4-dione (Example A(178)) was substituted in place of 6-cyclopentyl-6-[2-(3-ethyl-5-fluoro-4-hydroxy-phenyl)-ethyl]-dihydro-pyran-2,4-dione. $^1$H NMR (400 MHz, DMSO-$d_6$) δ: 1.07 (t, J=7.6 Hz, 3 H), 1.39–1.73 (br m, 8 H), 2.05 (m, 1 H), 2.40–2.61 (m, 13 H), 2.77 (d, J=17.4 Hz, 1 H), 3.27 (s, 3 H), 3.58 (m, 2 H), 3.71 (d, J=16.2 Hz, 1 H), 3.80 (d, J=16.2 Hz, 1 H), 3.99 (m, 2 H), 6.82 (d, J=8.3 Hz, 1 H), 6.91 (dd, J=2.0 Hz, 1 H), 6.96 (dd, J=8.3, 2.0 Hz, 1 H), 7.02 (s, 1 H), 10.8 (s, 1 H). Anal. Calcd. For $C_{31}H_{40}N_4O_5 \cdot 0.3H_2O$: C, 67.20; H, 7.39; N, 10.11. Found: C, 67.21; H, 7.35; N, 10.11.

Example A(178)

6-Cyclopentyl-6-{2-[5-ethyl-2-(2-methoxy-ethoxy)-phenyl]-ethyl}-dihydro-pyran-2,4-dione

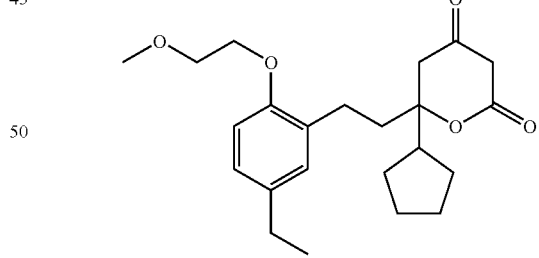

The title compound was prepared analogously to Example A(124) where 2-bromo-4-ethyl-1-(2-methoxy-ethoxy)-benzene (from step 1 below) was substituted in place of acetic acid 4-bromo-2-ethyl-6-fluoro-phenyl ester. $^1$H NMR (400 MHz, CDCl$_3$): δ 1.19 (t, J=7.6 Hz, 3 H), 1.39–2.06 (br m, 10 H), 2.35 (m, 1 H), 2.59–2.64 (m, 3 H), 2.69–2.81 (m, 3 H), 3.38 (d, J=21.2 Hz, 1 H), 3.41 (s, 3 H), 3.58 (d, J=21.2 Hz, 1 H), 3.71 (m, 2 H), 4.08 (m, 2 H), 6.74 (d, J=8.3 Hz, 1 H), 6.91 (s, 1 H), 6.99 (d, J=8.3 Hz, 1 H). MS (ESI): 387.10 (M−H+).

Step 1

2-Bromo-4-ethyl-1-(2-methoxyethoxy)-benzene

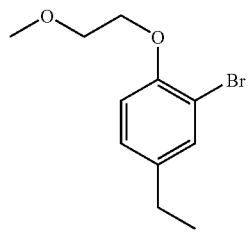

Potassium carbonate (8.25 g, 60 mol) followed by 2-bromoethyl methyl ether (1.87 mL, 20 mmol) were added to a solution of 2-bromo-4-ethyl-phenol (4 g, 20 mmol, from step 1 of Example B(98)) in DMF (25 mL). The mixture was stirred for 20 hours and then partitioned between 1N HCl and EtOAc. The organic layers were washed with brine, dried over $Na_2SO_4$ and concentrated. The crude yellow oil was purified by flash column chromatography (0% to 10% EtOAc in hexanes) to give the desired product (4.63 g, 90%). $^1$H NMR (400 MHz, $CDCl_3$): δ 1.20 (t, J=7.6 Hz, 3 H), 2.57 (q, J=7.6 Hz, 2 H), 3.48 (s, 3 H), 3.79 (t, J=5.1 Hz, 2 H), 4.15 (t, J=4.8 Hz, 2 H), 6.85 (d, J=8.3 Hz, 1 H), 7.06 (dd, J=8.3, 2.3 Hz, 1 H), 7.37 (d, J=2.3 Hz, 1 H).

Example A(179)

6-Cyclopentyl-6-{2-[5-ethyl-2-(2-methoxy-ethoxy)-phenyl]-ethyl}-4-hydroxy-3-(6-methyl-[1,2,4]triazolo[1,5-a]pyrimidin-2-ylmethyl)-5,6-dihydro-pyran-2-one

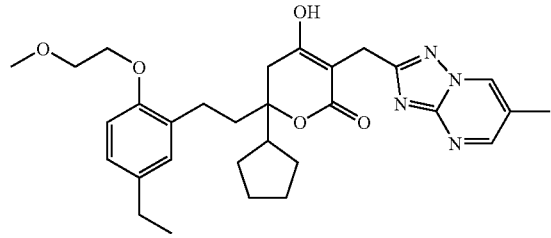

The title compound was prepared analogously to Example A(126) where 6-cyclopentyl-6-{2-[5-ethyl-2-(2-methoxy-ethoxy)-phenyl]-ethyl}-dihydro-pyran-2,4-dione (Example A(178)) was substituted in place of 6-Cyclopentyl-6-[2-(3-ethyl-4-hydroxy-phenyl)-ethyl]-dihydro-pyran-2,4-dione. $^1$H NMR (400 MHz, DMSO-$d_6$) δ: 1.24 (t, J=7.6 Hz, 3 H), 1.51–1.87 (br m, 8 H), 2.24 (m, 2 H), 2.48 (s, 3 H), 2.55 (m, 1 H), 2.60–2.73 (m, 5 H), 2.90 (d, J=18.0 Hz, 1 H), 3.43 (s, 3 H), 3.75 (t, J=6.1 Hz, 2 H), 3.88 (d, J=17.7 Hz, 1 H), 3.93 (d, J=17.7 Hz, 1 H), 4.16 (d, J=5.1 Hz, 2 H), 6.98 (d, J=8.3 Hz, 1 H), 7.08 (s, 1 H), 7.12 (d, J=8.3 Hz, 1 H), 8.81 (s, 1 H), 9.0 (s, 1 H), 11.03 (s, 1 H). MS (ESI): 535.15 (M+H$^+$).

Example A(180)

6-Cyclopentyl-3-(5,7-dimethyl-[1,2,4]triazolo[1,5-a]pyrimidin-2-ylmethyl)-6-[2-(5-ethyl-4-hydroxy-2,3-dihydro-benzofuran-7-yl)-ethyl]-4-hydroxy-5,6-dihydro-pyran-2-one

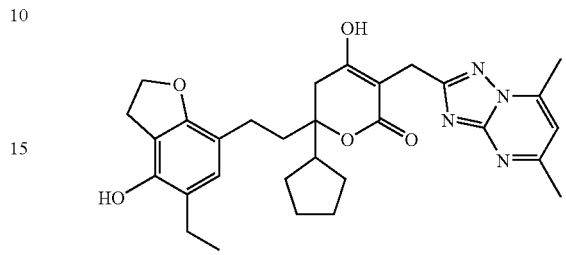

The title compound was prepared analogously to Example A(123) where 6-Cyclopentyl-6-[2-(5-ethyl-4-hydroxy-2,3-dihydro-benzofuran-7-yl)-ethyl]-dihydro-pyran-2,4-dione (Example A(181)) was substituted in place of 6-cyclopentyl-6-[2-(3-ethyl-5-fluoro-4-hydroxy-phenyl)-ethyl]-dihydro-pyran-2,4-dione. $^1$H NMR (400 MHz, DMSO-$d_6$) δ: 1.08 (t, J=7.3 Hz, 3 H), 1.45–1.75 (br m, 8 H), 2.01 (m, 1 H), 2.15 (m, 1 H), 2.39–2.65 (m, 12 H), 2.80 (d, J=17.4 Hz, 1 H), 3.09 (t, J=8.8 Hz, 2 H), 3.77 (d, J=15.9 Hz, 1 H), 3.85 (d, J=15.9 Hz, 1 H), 4.47 (t, J=11.4 Hz, 2 H), 6.64 (s, 1 H), 7.09 (s, 1 H), 8.58 (s, 1 H), 10.89 (s, 1 H). Anal. Calcd. For $C_{30}H_{36}N_4O_5 \cdot 0.4H_2O$: C, 66.74; H, 6.87; N, 10.38. Found: C, 66.71; H, 6.65; N, 10.21.

Example A(181)

6-Cyclopentyl-6-[2-(5-ethyl-4-hydroxy-2,3-dihydro-benzofuran-7-yl)-ethyl]-dihydro-pyran-2,4-dione

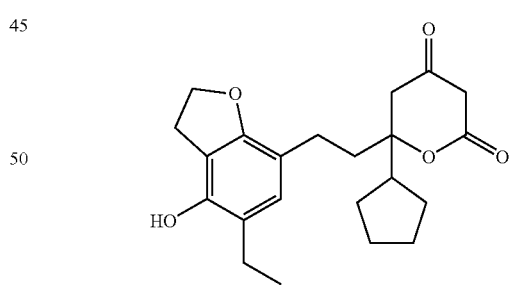

The title compound was prepared analogously to Example A(124) where 5-ethyl-2,3-dihydro-benzofuran-4-ol (from step 2 below) was substituted in place of 2-ethyl-6-fluoro-phenol in step 3 of that example. $^1$H NMR (400 MHz, $CDCl_3$): δ 1.19 (t, J=7.6 Hz, 3H), 1.42–2.05 (br m, 10 H), 2.30 (m, 1 H), 2.47–2.60 (m, 4 H), 2.72 (d, J=16.2 Hz, 1 H), 2.76 (d, J=16.2 Hz, 1 H), 3.12 (t, J=8.6 Hz, 2 H), 3.43 (m, 2 H), 4.56 (t, J=8.6 Hz, 2 H), 6.64 (s, 1 H). MS (ESI): 373.10 (M−H+).

Step 2

5-Ethyl-2,3-dihydro-benzofuran-4-ol

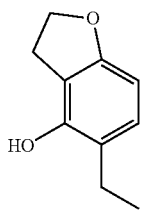

A mixture of 1-(4-Hydroxy-benzofuran-5-yl)-ethanone (1.37 g, 7.8 mmol) and 10 wt % Pd/C (0.7 g, Degussa type) in MeOH (20 mL) was stirred under a balloon of H$_2$ for 24 hours. The reaction mixture was filtered through a pad of celite washing with EtOAc. The filtrate was concentrated to an oil (0.9 g, 70%). $^1$H NMR (400 MHz, CDCl$_3$): δ 1.21 (t, J=7.6 Hz, 3 H), 2.56 (q, J=7.6 Hz, 2 H), 3.14 (t, J=8.6 Hz, 2 H), 4.59 (t, J=8.6 Hz, 2 H), 4.68 (s, 1H), 6.37 (d, J=8.1 Hz, 1 H), 6.37 (d, J=8.1 Hz, 1 H).

Step 1

1-(4-Hydroxy-benzofuran-5-yl)-ethanone

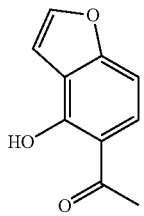

The title compound was prepared as described in the following reference: *Tetrahedron* 1995, 51, 4909–4922. $^1$H NMR (400 MHz, CDCl$_3$): δ 1.58 (s, 3 H), 7.00 (dd, J=2.0, 1.0 Hz, 1 H), 7.05 (dd, J=8.8, 1.0 Hz, 1 H), 7.57 (d, J=2.0 Hz, 1 H), 7.66 (d, J=8.8 Hz, 1 H), 13.3 (s, 1 H).

Example A(182)

6-Cyclopentyl-6-[2-(5-ethyl-4-hydroxy-2,3-dihydro-benzofuran-7-yl)-ethyl]-4-hydroxy-3-(6-methyl-[1,2,4]triazolo[1,5-a]pyrimidin-2-ylmethyl)-5,6-dihydro-pyran-2-one

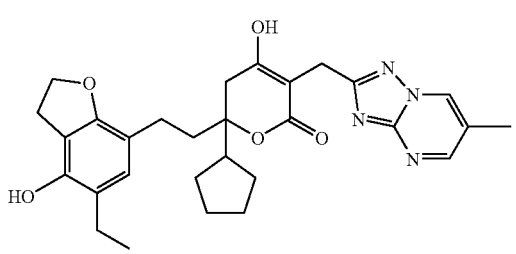

The title compound was prepared analogously to Example A(126) where 6-cyclopentyl-6-[2-(5-ethyl-4-hydroxy-2,3-dihydro-benzofuran-7-yl)-ethyl]-dihydro-pyran-2,4-dione (Example A(181)) was substituted in place of 6-cyclopentyl-6-[2-(3-ethyl-4-hydroxy-phenyl)-ethyl]-dihydro-pyran-2,4-dione. $^1$H NMR (400 MHz, DMSO-d$_6$) δ: 1.09 (t, J=7.3 Hz, 3H), 1.39–1.75 (br m, 8 H), 2.06 (m, 2 H), 2.40–2.62 (m, 9 H), 2.80 (d, J=17.7 Hz, 1 H), 3.11 (t, J=8.3 Hz, 2 H), 3.78 (d, J=15.9 Hz, 1 H), 3.84 (d, J=15.9 Hz, 1H), 4.48 (t, J=8.6 Hz, 2 H), 6.66 (s, 1 H), 8.61 (s, 1 H), 8.73 (s, 1 H), 8.87 (s, 1 H), 10.97 (s, 1 H). MS (ESI): 519.10 (M+H$^+$).

Example A(183)

6-Cyclopentyl-3-(5,7-dimethyl-[1,2,4]triazolo[1,5-a]pyrimidin-2-ylmethyl)-6-{2-[3-ethyl-4-(2-methoxy-ethoxy)-phenyl]-ethyl}-4-hydroxy-5,6-dihydro-pyran-2-one

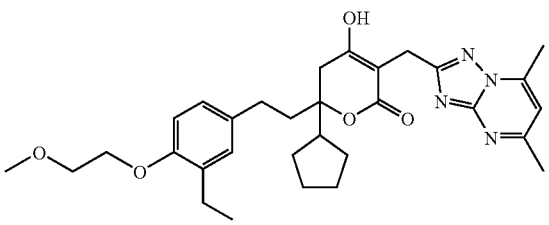

The title compound was prepared analogously to Example A(123) where 6-cyclopentyl-6-{2-[3-ethyl-4-(2-methoxy-ethoxy)-phenyl]-ethyl}-dihydro-pyran-2,4-dione (Example A(184)) was substituted in place of 6-cyclopentyl-6-[2-(3-ethyl-5-fluoro-4-hydroxy-phenyl)-ethyl]-dihydro-pyran-2,4-dione. $^1$H NMR (400 MHz, DMSO-d$_6$) δ: 1.13 (t, J=7.6 Hz, 3H), 1.46–1.76 (br m, 8 H), 2.15 (m, 2H), 2.45–2.64 (m, 12H), 2.85 (d, J=17.4 Hz, 1H), 3.40 (s, 3H), 3.71 (t, J=4.6 Hz, 2H), 3.79 (d, J=16.2 Hz, 1H), 3.89 (d, J=16.2 Hz, 1H), 4.12 (d, J=4.8 Hz, 2H), 6.89 (d, J=8.3 Hz, 1H), 7.01 (s, 1H), 7.06 (dd, J=8.3, 2.3 Hz, 1H), 7.10 (s, 1H), 10.95 (s, 1H). Anal. Calcd. For C$_{31}$H$_{40}$N$_4$O$_5$·0.75H$_2$O: C, 66.23; H, 7.44; N, 9.97. Found: C, 66.23; H, 7.36; N, 9.81.

Example A(184)

6-Cyclopentyl-6-{2-[3-ethyl-4-(2-methoxy-ethoxy)-phenyl]-ethyl}-dihydro-pyran-2,4-dione

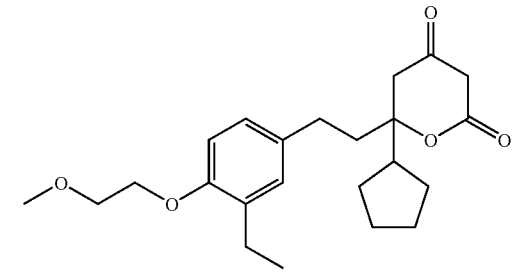

The title compound was prepared analogously to Example A(178) where 4-bromo-2-ethyl-phenol (from step 1) was substituted in place of 2-bromo-4-ethyl-phenol in step 1 of that example. $^1$H NMR (400 MHz, CDCl$_3$): δ 1.18 (t, J=7.3 Hz, 3H), 1.46–1.78 (br m, 8H), 1.89–2.02 (m, 2H), 2.27 (s, 1H), 2.62 (m, 4H), 2.76 (s, 2H), 3.42 (s, 2H), 3.45 (s, 3H), 3.76 (t, J=4.8 Hz, 2H), 4.09 (t, J=5.0 Hz, 2H), 6.75 (d, J=9.1 Hz, 1H), 6.91 (m, 2H). Anal. Calcd. For $C_{23}H_{32}O_5$: C, 71.11; H, 8.31. Found: C, 71.07; H, 8.27.

Step 1

4-Bromo-2-ethyl-phenol

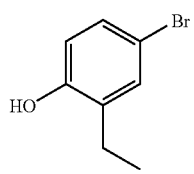

A solution of tetrabutyl ammonium tribromide (41.4 g, 86 mmol) in $CHCl_3$ (100 mL) was added to a stirred solution of 2-ethyl phenol (10 g, 81.8 mmol) dissolved in $CHCl_3$ (100 mL). The reaction mixture was stirred for 1 hr and then quenched with 5% solution of sodium thiosulfate (100 mL). The biphasic mixture was stirred for 30 mins and then the layers were separated. The organic layer was washed with 1N HCl, saturated $NaHCO_3$, brine, dried over $Na_2SO_4$ and concentrated. The crude residue was purified by flash column chromatography (0–10% EtOAc in hexanes) to give the desired product (14.3 g, 87%). $^1$H NMR (400 MHz, $CDCl_3$): δ 1.22 (t, J=7.5 Hz, 3 H), 2.60 (q, J=7.5 Hz, 2H), 6.64 (d, J=8.5 Hz, 1 H), 7.17 (dd, J=8.5, 2.5 Hz, 1 H), 7.24 (d, J=2.5 Hz, 1 H).

Example A(185)

6-Cyclopentyl-6-{2-[3-ethyl-4-(2-meth xy-ethoxy)-phenyl]-ethyl}-4-hydroxy-3-(6-methyl-[1,2,4]triazolo[1,5-a]pyrimidin-2-ylmethyl)-5,6-dihydro-pyran-2-one

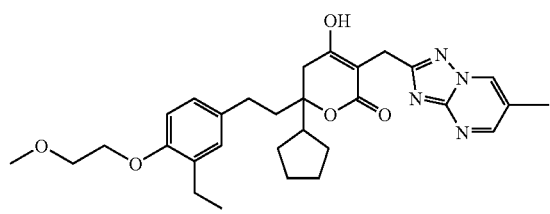

The title compound was prepared analogously to Example A(126) where 6-cyclopentyl-6-{2-[3-ethyl-4-(2-methoxyethoxy)-phenyl]-ethyl}-dihydro-pyran-2,4-dione (Example A(184)) was substituted in place of 6-Cyclopentyl-6-[2-(3-ethyl-4-hydroxy-phenyl)-ethyl]-dihydro-pyran-2,4-dione. $^1$H NMR (400 MHz, DMSO-$d_6$) δ: 1.09 (t, J=7.6 Hz, 3 H), 1.40–1.76 (br m, 8H), 2.08 (m, 2H), 2.35 (s, 3H), 2.40 (m, 1 H), 2.52 (m, 5H), 2.79 (d, J=14.9 Hz, 1H), 3.33 (s, 3H), 3.67 (t, J=3.0 Hz, 2 H), 3.74 (d, J=15.9 Hz, 1H), 3.82 (d, J=15.9 Hz, 1 H), 4.06 (d, J=3.0 Hz, 2 H), 6.83 (d, J=8.1 Hz, 1 H), 6.97 (s, 1 H), 6.98 (d, J=8.1 Hz, 1 H), 8.70 (s, 1 H), 8.85 (s, 1 H), 10.85 (s, 1 H). MS (ESI): 535.20 (M+H$^+$).

Example A(186)

6-Cyclopentyl-3-(5,7-dimethyl-[1,2,4]triazolo[1,5-a]pyrimidin-2-ylmethyl)-6-[2-(3-ethyl-5-hydroxy-phenyl)-ethyl]-4-hydroxy-5,6-dihydro-pyran-2-one

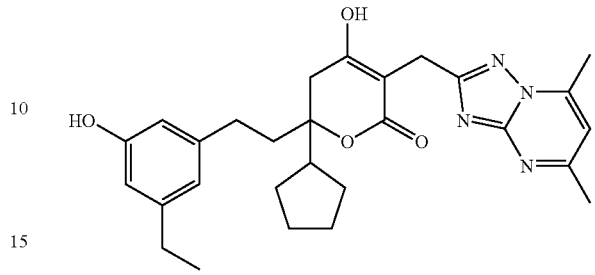

The title compound was prepared analogously to Example A(123) where 6-cyclopentyl-6-[2-(3-ethyl-5-hydroxy-phenyl)-ethyl]-dihydro-pyran-2,4-dione (from step 2 below) was substituted in place of 6-cyclopentyl-6-[2-(3-ethyl-5-fluoro-4-hydroxy-phenyl)-ethyl]-dihydro-pyran-2,4-dione. $^1$H NMR (400 MHz, DMSO-$d_6$) δ: 1.29 (t, J=7.6 Hz, 3H), 1.59–1.87 (br m, 8H), 2.28 (m, 2H), 2.60–2.73 (m, 12H), 2.96 (d, J=17.9 Hz, 1H), 3.90 (d, J=16.4 Hz, 1H), 4.01 (d, J=16.2 Hz, 1H), 6.60 (s, 1H), 6.65 (s, 1H), 6.66 (s, 1H), 7.24 (s, 1H), 9.34 (s, 1H), 11.10 (s, 1H). Anal. Calcd. For $C_{28}H_{34}N_4O_4 \cdot 0.4 AcOH$: C, 67.21; H, 6.97; N, 10.89. Found: C, 67.48; H, 7.05; N, 10.53.

Step 2

6-Cyclopentyl-6-[2-(3-ethyl-5-hydroxy-phenyl)-ethyl]-dihydro-pyran-2,4-dione

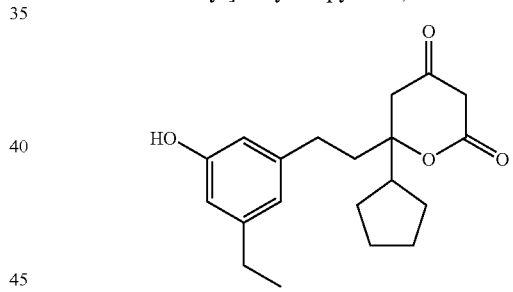

The title compound was prepared analogously to Example A(124) where 3-bromo-5-ethyl-phenol was substituted in place of 4-bromo-2-ethyl-6-fluoro-phenol in step 4 of that example. $^1$H NMR (400 MHz, $CDCl_3$): δ 1.20 (t, J=7.6 Hz, 3 H), 1.45–1.76 (br m, 8 H), 1.96 (m, 2 H), 2.27 (m, 1 H), 2.58 (m, 4 H), 2.76 (s, 2 H), 3.42 (s, 2 H), 4.75 (s, 1 H), 6.44 (s, 1 H), 6.53 (s, 1 H), 6.55 (s, 1 H). MS (ESI): 329.00 (M–H$^+$).

Step 2

3-Bromo-5-ethyl-phenol

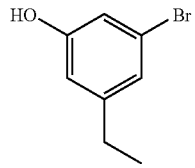

Example A(187)

6-Cyclopentyl-3-(5,7-dimethyl-[1,2,4]triazolo[1,5-a]pyrimidin-2-ylmethyl)-6-[2-(5-ethyl-2-hydroxy-4-methoxy-phenyl)-ethyl]-4-hydroxy-5,6-dihydro-pyran-2-one

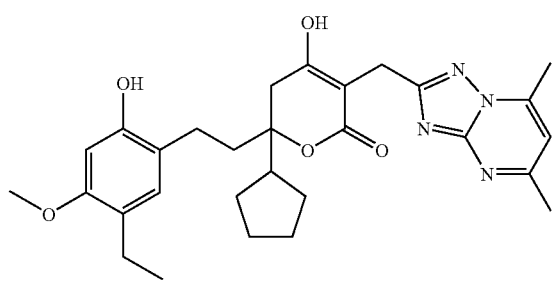

The title compound was prepared analogously to Example A(124) where 6-cyclopentyl-6-[2-(5-ethyl-2-hydroxy-4-methoxy-phenyl)-ethyl]-dihydro-pyran-2,4-dione was substituted in place of 6-cyclopentyl-6-[2-(3-ethyl-5-fluoro-4-hydroxy-phenyl)-ethyl]-dihydro-pyran-2,4-dione. $^1$H NMR (400 MHz, DMSO-$d_6$) δ: 1.06 (t, J=7.3 Hz, 3 H), 1.47–1.78 (br m, 8 H), 1.97 (m, 1 H), 2.15 (m, 2H), 2.42–2.69 (m, 11 H), 2.80 (d, J=17.6 Hz, 1 H), 3.74 (s, 3 H), 3.78 (d, J=16.4 Hz, 1 H), 3.85 (d, J=16.4 Hz, 1 H), 6.44 (s, 1 H), 6.79 (s, 1 H), 7.10 (s, 1 H), 9.13 (s, 1 H), 10.90 (s, 1 H). MS (ESI): 521.20 (M+H$^+$).

Step 4

6-Cyclopentyl-6-[2-(5-ethyl-2-hydroxy-4-methoxy-phenyl)-ethyl]-dihydro-pyran-2,4-dione

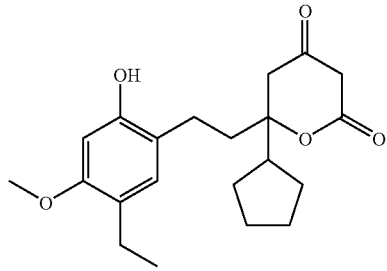

The title compound was prepared analogously to Example A(124) where 1-benzyloxy-2-bromo-4-ethyl-5-methoxy-benzene (from step 3 below) was substituted in place of acetic acid 4-bromo-2-ethyl-6-fluoro-phenyl ester. MS (ESI): 361.10 (M+H$^+$).

Step 3

1-Benzyloxy-2-bromo-4-ethyl-5-methoxy-benzene

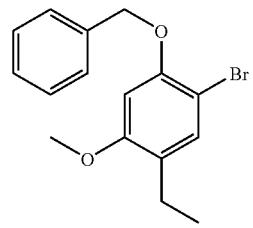

Sodium hydroxide (0.39 g, 9.7 mmol) and hydrazine monohydrate (0.57 mL, 11.7 mmol) were added to a solution of 1-(4-benzyloxy-5-bromo-2-methoxy-phenyl)-ethanone (1.3 g, 3.9 mmol) dissolved in triethylene glycol (5 mL). The reaction mixture was heated to 170° C. for 24 hours and then partitioned between 1N HCl and EtOAc. The organic layer was washed with brine, dried over Na$_2$SO$_4$ and concentrated. The residue was purified by flash silica gel chromatography (0% to 5% EtOAc in hexanes) to give the title compound (0.52 g, 40%). $^1$H NMR (400 MHz, CDCl$_3$): δ 1.14 (t, J=7.3 Hz, 3 H), 2.53 (q, J=7.3 Hz, 2 H), 3.75 (s, 3 H), 5.14 (s, 2 H), 6.48 (s, 1 H), 7.26 (s, 1 H), 7.32 (m, 1 H), 7.39 (m, 2 H), 7.49 (d, J=8.3 Hz, 2 H).

Step 2

1-(4-Benzyloxy-5-bromo-2-methoxy-phenyl)-ethanone

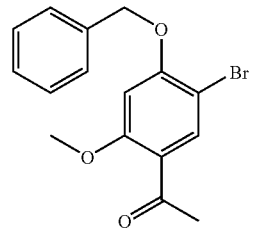

A solution of tetrabutyl ammonium tribromide (12.1 g, 25 mmol) in CHCl$_3$ (75 mL) was added to a stirred solution of 1-(4-benzyloxy-2-hydroxy-phenyl)-ethanone (6.07 g, 25.1 mmol) dissolved in CHCl$_3$ (75 mL). The reaction mixture was stirred for 18 hrs and then quenched with 5% solution of sodium thiosulfate (100 mL). The biphasic mixture was stirred for 30 mins and then the layers were separated. The organic layer was washed with 1N HCl, saturated NaHCO$_3$, brine, dried over Na$_2$SO$_4$ and concentrated to a brown oil.

The oil was dissolved in DMF (30 mL) and treated with potassium carbonate (10.4 g, 75.3 mmol) followed by methyl iodide (1.9 mL, 30 mmol). The mixture was stirred for 20 hours and then partitioned between 1N HCl and EtOAc. The organic layers were washed with brine, dried over Na$_2$SO$_4$ and concentrated. The oil was purified by flash column chromatography (0% to 15% EtOAc in hexanes) to give the desired product (2.39 g, 28%). $^1$H NMR (400 MHz, CDCl$_3$): δ 2.55 (s, 3 H), 3.85 (s, 3 H), 5.23 (s, 2 H), 6.48 (s, 1 H), 7.32–7.43 (m, 3 H), 7.47 (d, J=8.3 Hz, 2 H), 8.06 (s, 1 H).

Step 1

1-(4-Benzyloxy-2-hydroxy-phenyl)-ethanone

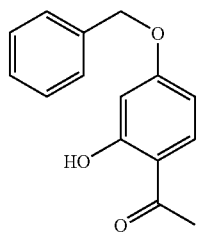

Potassium carbonate (27.2 g, 0.2 mol) followed by benzyl bromide (7.04 mL, 59.2 mmol) were added to a solution of 1-(2,4-dihydroxy-phenyl)-ethanone (10 g, 66 mmol) in DMF (90 mL): The mixture was stirred for 2 hours and then partitioned between 1N HCl and EtOAc. The organic layers were washed with brine, dried over $Na_2SO_4$ and concentrated. Purification by flash column chromatography (0% to 20% EtOAc in hexanes) followed by recrystallization gave the title compound as a white solid (8.7 g, 55%). $^1$H NMR (400 MHz, $CDCl_3$): δ 2.55 (s, 3 H), 5.09 (s, 2 H), 6.50 (s, 1 H), 6.51 (dd, J=9.1, 3.9 Hz, 1 H), 7.34–7.43 (m, 5 H), 7.64 (d, J=9.1 Hz, 1 H), 12.73 (s, 1 H).

Example A(188)

1-(4-{2-[2-Cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-2-fluoro-phenyl)-cyclopentanecarbonitrile

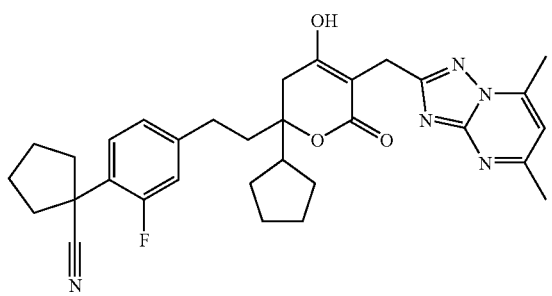

The title compound was prepared analogously to Example A(97) 2-[4-(2-{2-cyclopentyl-5-[(2-ethyl-4-methyl-1H-imidazol-5-yl)methyl]-4-hydroxy-6-oxo-3,6-dihydro-2H-pyran-2-yl}ethyl)-2-fluorophenyl]-2-methylpropanenitrile where 1-{4-[2-(2-Cyclopentyl-4,6-dioxo-tetrahydro-pyran-2-yl)-ethyl]-2-fluoro-phenyl}-cyclopentanecarbonitrile Example A(189) was substituted in place of 2-{4-[2-(2-cyclopentyl-4-hydroxy-6-oxo-3,6-dihydro-2H-pyran-2-yl)ethyl]-2-fluorophenyl}-2-methylpropanenitrile and 5,7-Dimethyl-[1,2,4]triazolo[1,5-a]pyrimidine-2-carbaldehyde was substituted in place of 2-ethyl-4-methyl-1H-imidazole-5-carbaldehyde. $^1$H NMR (400 MHz, $CDCl_3$) δ: 1.44–1.96 (m, 17 H), 2.14–2.22 (m, 2H), 2.56–2.62 (m, 8 H), 2.70–2.74 (m, 2 H), 3.79 (d, J=16 Hz, 1 H), 3.92 (d, J=16 Hz, 1 H), 7.12 (s, 1 H), 7.24 (s, 1 H), 7.26 (d, J=5 Hz, 1 H), 7.42–7.47 (m, 1 H), 10.9 (s, 1 H). Anal. Calcd. For $C_{32}H_{36}FN_5O_3$: C, 68.92; H, 6.51; N, 12.56. Found: C, 68.74; H, 6.60; N, 12.47. MS (ESI): 558 (M+H)$^+$.

Example A(189)

1-{4-[2-(2-Cyclopentyl-4,6-dioxo-tetrahydro-pyran-2-yl)-ethyl]-2-fluoro-phenyl}-cyclopentanecarbonitrile(

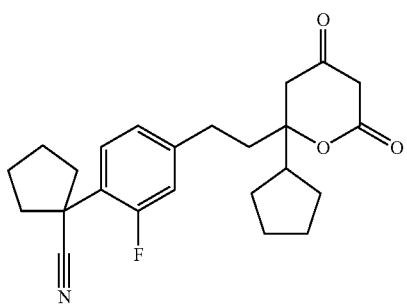

The title compound was prepared analogously to step 4 from Example A(97) where 1-{4-[3-Cyclopentyl-4-(2,2-dimethyl-6-oxo-6H-[1,3]dioxin-4-yl)-3-hydroxy-but-1-ynyl]-2-fluoro-phenyl}-cyclopentanecarbonitrile (from step 2 below) was substituted in place of 2-{4-[3-cyclopentyl-4-(2,2-dimethyl-4-oxo-4H-1,3-dioxin-6-yl)-3-hydroxybut-1-ynyl]-2-fluorophenyl}-2-methylpropanenitrile. $^1$H NMR ($CDCl_3$) δ: 1.18–1.74 (m, 16 H), 1.92–2.17 (m, 2 H), 2.5–2.52 (m, 1 H), 2.66–2.68 (m, 2 H), 2.77 (s, 2 H), 3.43 (s, 2 H), 6.89–6.94 (m, 2 H), 7.33–7.37 (m, 1 H). MS (ESI): 398 (M+H)$^+$.

Step 2

1-{4-[3-Cyclopentyl-4-(2,2-dimethyl-6-oxo-6H-[1,3] dioxin-4-yl)-3-hydroxy-but-1-ynyl]-2-fluoro-phenyl}-cyclopentanecarbonitrile

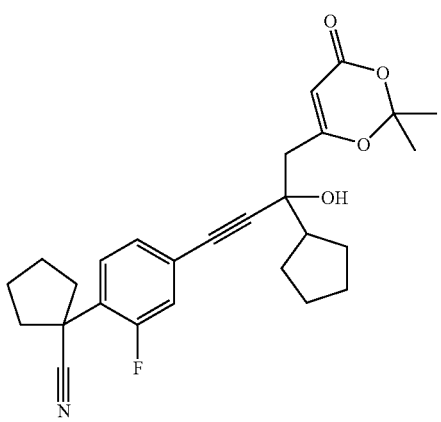

The title compound was prepared analogously to step 3 from Example A(97) where 1-(4-Bromo-2-fluoro-phenyl)-cyclopentanecarbonitrile (described in step 1 below) was substituted in place of 2-(4-Bromo-2-fluoro-phenyl)-2-methyl-propionitrile in step 3 of that example. MS (ESI): 452 (M+H)$^+$.

183

Step 1

2-(4-Bromo-2-chloro-phenyl)-2-methyl-propionitrile

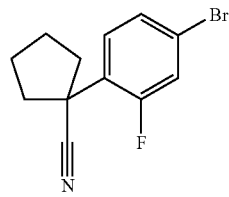

(4-bromo-2-fluorophenyl)acetonitrile (1 g, 4.67 mmol) described in step 1 from Example A(97), benzyltriethylammonium chloride (0.02 g, 0.09 mmol) and 1,4-Dibromobutane (1.43 g, 0.79 mmol) were dissolved 50% aqueous NaOH (3 mL) and the resulting mixture was stirred for 3 hours at 50° C. Reaction was quenched with 4N HCl (50 mL extracted with EtOAc. The organic phase was dried over $Na_2SO_4$ and evaporated. The crude organic product was purified by flash column chromatography (5% EtOAc in hexanes) to give the product (1.25 g, 100%) as a clear oil). $^1$H NMR (CDCl$_3$) δ: 1.93–2.17 (m, 4H), 2.50–2.55 (m, 2 H), 3.42–3.46 (m, 2 H), 7.26–7.34 (m, 3 H).

Example A(190)

1-(4-{2-[2-Cyclopentyl-4-hydroxy-5-(6-methyl-[1,2,4]triazolo[1,5-a]pyrimidin-2-ylmethyl)-6-oxo-3,6-dihydro-2H-pyran-2-yl]-ethyl}-2-fluoro-phenyl)-cyclopentanecarbonitrile

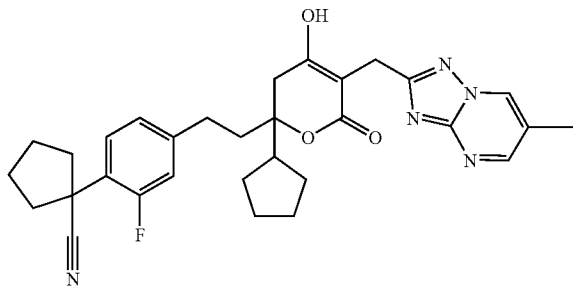

The title compound was prepared analogously to Example A(97) where 6-Methyl-[1,2,4]triazolo[1,5-a]pyrimidine-2-carbaldehyde was substituted in place of 2-ethyl-4-methyl-1H-imidazole-5-carbaldehyde and 1-{4-[2-(2-Cyclopentyl-4,6-dioxo-tetrahydro-pyran-2-yl)-ethyl]-2-fluoro-phenyl}-cyclopentanecarbonitrile (Example A(189) (was substituted in place of 2-{4-[2-(2-cyclopentyl-4-hydroxy-6-oxo-3,6-dihydro-2H-pyran-2-yl)ethyl]-2-fluorophenyl}-2-methylpropanenitrile. $^1$H NMR (400 MHz, CDCl$_3$) δ: 1.35–2.16 (m, 16 H), 2.42–2.82 (m, 7 H), 3.33 (s, 3 H), 3.74 (d, J=16 Hz, 1 H), 3.84 (d, J=16 Hz, 1 H), 7.14–7.19 (m, 2 H), 7.36–7.41 (m, 1 H), 8.71 (s, 1 H), 9 (s, 1 H), 10.9 (s, 1 H). Anal. Calcd. For $C_{31}H_{34}FN_5O_{3.0.75}H_2O$: C, 66.83; H, 6.42; N, 12.57. Found: C, 66.93; H, 6.18; N, 12.45. MS (ESI): 544 (M+H)$^+$.

184

Example A(191)

1-(4-{2-[5-(6-Chloro-[1,2,4]triazolo[1,5-a]pyrimidin-2-ylmethyl)-2-cyclopentyl-4-hydroxy-6-oxo-3,6-dihydro-2H-pyran-2-yl]-ethyl}-2-fluoro-phenyl)-cyclopentanecarbonitrile

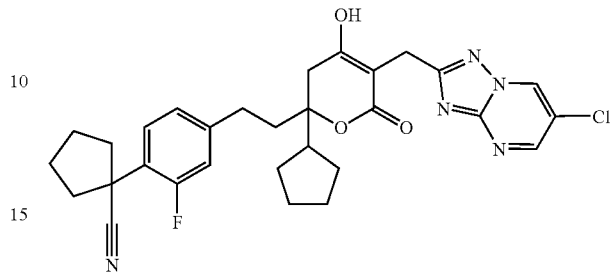

The title compound was prepared analogously to Example A(97) where 6-Chloro-[1,2,4]triazolo[1,5-a]pyrimidine-2-carbaldehyde was substituted in place of 2-ethyl-4-methyl-1H-imidazole-5-carbaldehyde and 1-{4-[2-(2-Cyclopentyl-4,6-dioxo-tetrahydro-pyran-2-yl)-ethyl]-2-fluoro-phenyl}-cyclopentanecarbonitrile (Example A(189) (was substituted in place of 2-{4-[2-(2-cyclopentyl-4-hydroxy-6-oxo-3,6-dihydro-2H-pyran-2-yl)ethyl]-2-fluorophenyl}-2-methylpropanenitrile. $^1$H NMR (400 MHz, CDCl$_3$) δ: 1.41–1.98 (m, 17 H), 2.30–2.68 (m, 6 H), 3.62 (d, J=16 Hz, 1 H), 3.71 (d, J=16 Hz, 1 H), 6.99–7.03 (m, 2 H), 7.21–7.25 (m, 1 H), 8.74 (s, 1 H), 9.45 (s, 1 H), 10.8 (s, 1 H). Anal. Calcd. For $C_{30}H_{31}ClFN_5O_3$: C, 63.88; H, 5.54; N, 12.42. Found: C, 63.73; H, 5.71; N, 12.17. MS (ESI): 564 (M+H)$^+$.

Example A(192)

6-Cyclopentyl-3-(5,7-dimethyl-[1,2,4]triazolo[1,5-a]pyrimidin-2-ylmethyl)-4-hydroxy-6-[2-(4-hydroxy-3-methoxymethyl-phenyl)-ethyl]-5,6-dihydro-pyran-2-one

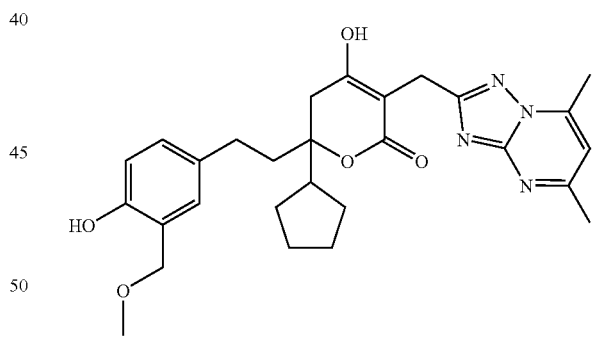

The title compound was prepared analogously to Example A(97) where 6-Cyclopentyl-6-[2-(4-hydroxy-3-methoxymethyl-phenyl)-ethyl]-dihydro-pyran-2,4-dione (Example A(194)) was substituted in place of 2-{4-[2-(2-cyclopentyl-4-hydroxy-6-oxo-3,6-dihydro-2H-pyran-2-yl)ethyl]-2-fluorophenyl}-2-methylpropanenitrile and 5,7-Dimethyl-[1,2,4]triazolo[1,5-a]pyrimidine-2-carbaldehyde was substituted in place of 2-ethyl-4-methyl-1H-imidazole-5-carbaldehyde in that example. $^1$H NMR (400 MHz, DMSO-d$_6$): δ 1.5–2.0 (m, 11H) 2.46–2.75 (m, 11H), 3.25 (s, 3H), 3.73 (d, J=16 Hz, 1H), 3.80 (d, J=16 Hz, 1H), 4.32 (s, 2H), 6.70 (d, J=8 Hz, 1H), 6.94–7.04 (m, 3H), 9.20 (s, 1H). Anal. Calcd. For $C_{28}H_{34}N_4O_5 \cdot 1.5H_2O$: C, 63.02; H, 6.99; N, 10.50. Found: C, 63.92; H, 6.74; N, 10.42. MS (ESI): 507.2 (M+H)$^+$.

Example A(193)

6-Cyclopentyl-3-(5,7-dimethyl-[1,2,4]triazolo[1,5-a]pyrimidin-2-ylmethyl)-4-hydroxy-6-[2-(4-hydroxy-3-hydroxymethyl-phenyl)-ethyl]-5,6-dihydro-pyran-2-one

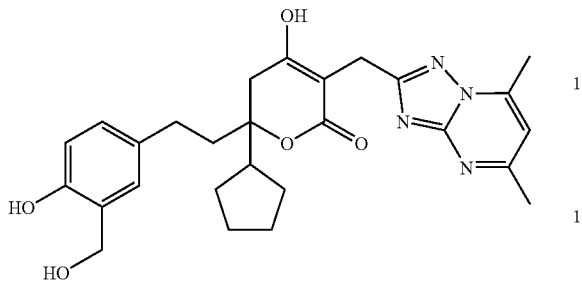

The title compound was prepared analogously to Example A(97) where 6-Cyclopentyl-6-[2-(4-hydroxy-3-hydroxymethyl-phenyl)-ethyl]-dihydro-pyran-2,4-dione (Example A(195)) was substituted in place of 2-{4-[2-(2-cyclopentyl-4-hydroxy-6-oxo-3,6-dihydro-2H-pyran-2-yl)ethyl]-2-fluorophenyl}-2-methylpropanenitrile and 5,7-Dimethyl-[1,2,4]triazolo[1,5-a]pyrimidine-2-carbaldehyde was substituted in place of 2-ethyl-4-methyl-1H-imidazole-5-carbaldehyde from that example. $^1$H NMR (400 MHz, DMSO-d$_6$): δ 1.34–2.09 (m, 11H) 2.0–2.21 (m, 2H), 2.47–2.74 (m, 10H), 3.74 (d, J=16 Hz, 1H), 3.80 (d, J=16 Hz, 1H), 4.44 (s, 2H), 6.65 (d, J=8 Hz, 1H), 6.88 (d, J=8 Hz, 1H), 7.04 (s, 1H), 7.09 (s, 1H), 9.06 (s, 1H). Anal. Calcd. For $C_{27}H_{32}N_4O_5 \cdot H_2O$: C, 62.96; H, 6.75; N, 10.88. Found: C, 62.97; H, 6.57; N, 10.83. MS (ESI): 493.2 (M+H)$^+$.

Example A(194)

6-Cyclopentyl-6-[2-(4-hydroxy-3-methoxymethyl-phenyl)-ethyl]-dihydro-pyran-2,4-dione

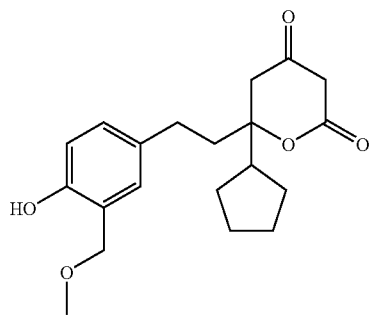

The title compound was prepared analogously to step 4 from Example A(97) where Acetic acid 2-acetoxy-5-[3-cyclopentyl-4-(2,2-dimethyl-6-oxo-6H-[1,3]dioxin-4-yl)-3-hydroxy-but-1-ynyl]-benzyl ester (from step 2 below) was substituted in place of 2-{4-[3-cyclopentyl-4-(2,2-dimethyl-4-oxo-4H-1,3-dioxin-6-yl)-3-hydroxybut-1-ynyl]-2-fluorophenyl}-2-methylpropanenitrile. The product was obtained together with Example A(195) 6-Cyclopentyl-6-[2-(4-hydroxy-3-hydroxymethyl-phenyl)-ethyl]-dihydro-pyran-2,4-dione below. $^1$H NMR (400 MHz, CDCl$_3$): δ 1.48–1.82 (m, 8H), 1.87–2.09 (m, 3H), 2.22–2.28 (m, 1H), 2.55–2.61 (m, 2H), 2.76 (s, 2H), 3.41 (s, 2H), 3.45 (2, 3H), 4.62 (2, 2H), 6.78–6.82 (m, 1H), 6.96–6.99 (m, 1H), 7.38 (s, 1H). ESIMS (MH–): 345.

Example A(195)

6-Cyclopentyl-6-[2-(4-hydroxy-3-hydroxymethyl-phenyl)-ethyl]-dihydro-pyran-2,4-dione

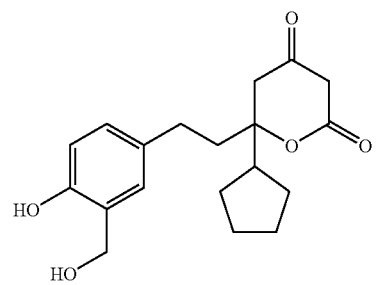

The title compound was prepared analogously to step 4 from Example A(97) where Acetic acid 2-acetoxy-5-[3-cyclopentyl-4-(2,2-dimethyl-6-oxo-6H-[1,3]dioxin-4-yl)-3-hydroxy-but-1-ynyl]-benzyl ester (from step 2 below) was substituted in place of 2-{4-[3-cyclopentyl-4-(2,2-dimethyl-4-oxo-4H-1,3-dioxin-6-yl)-3-hydroxybut-1-ynyl]-2-fluorophenyl}-2-methylpropanenitrile. The product was obtained together with compound from Example A(194). 6-Cyclopentyl-6-[2-(4-hydroxy-3-methoxymethyl-phenyl)-ethyl]-dihydro-pyran-2,4-dione above $^1$H NMR (400 MHz, CDCl$_3$): δ 1.30–1.80 (m, 9H), 1.83–1.86 (m, 2H), 2.15–2.18 (m, 1H), 2.49–2.54 (m, 2H), 2.67 (s, 2H), 3.33 (s, 2H), 4.76 (s, 2H), 6.71–6.91 (m, 3H). ESIMS (MH–): 331.

Step 2

Acetic Acid 2-acetoxy-5-[3-cyclopentyl-4-(2,2-dimethyl-6-oxo-6H-[1,3]dioxin-4-yl)-3-hydroxy-but-1-ynyl]-benzyl ester

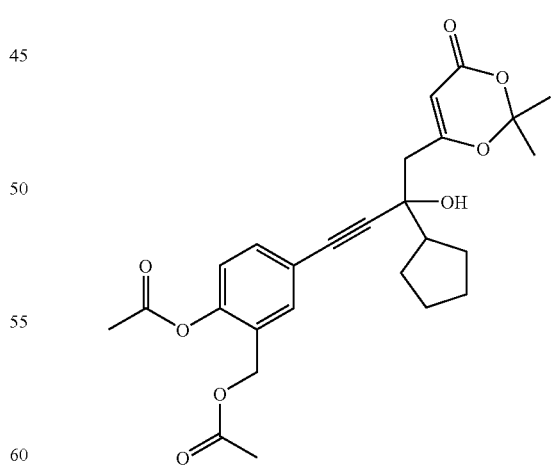

The title compound was prepared analogously to step 3 from Example A(97) where Acetic acid 2-acetoxy-5-bromo-benzyl ester (described in step 1 below) was substituted in place of 2-(4-Bromo-2-fluoro-phenyl)-2-methyl-propionitrile in step 3 of that example. MS (ESI): 471 (M+H)$^+$.

Step 1

2-(4-Bromo-2-chloro-phenyl)-2-methyl-[1,3]dioxolane

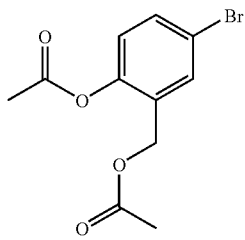

Acetyl chloride (4.38 mL g, 61.56 mmol followed by TEA (8.58 mL, 61.56 mmol were added to a solution of 5-bromo-2-hydroxyphenol (5 g, 24.63 mmol in $CH_2CL_2$ (120 mL). The resulting mixture was stirred overnight at room temperature. The $CH_2Cl_2$ was then evaporated and residue was partitioned between EtOAc and 1N HCl. The organic phase was dried over $Na_2SO_4$ and evaporated. The crude organic product was purified by flash column chromatography (30% EtOAc in hexanes) to give the product (7.07 g, 100%) as a pale yellow oil). $^1H$ NMR ($CDCl_3$) δ 2.09 (s, 3H), 2.32 (s, 3H), 5.03 (s, 2H), 6.99 (d, J=8.6 Hz, 1H), 7.47 (dd, J=8, 2.3 Hz, 1H), 7.58 (d, J=2.3 Hz, 1H). ESIMS (MH+): 286.2.

Example A(196)

6-Cyclopentyl-3-(5,7-dimethyl-[1,2,4]triazolo[1,5-a]pyrimidin-2-ylmethyl)-6-{2-[3-fluoro-4-(1-hydroxy-ethyl)-phenyl]-ethyl}-4-hydroxy-5,6-dihydro-pyran-2-one

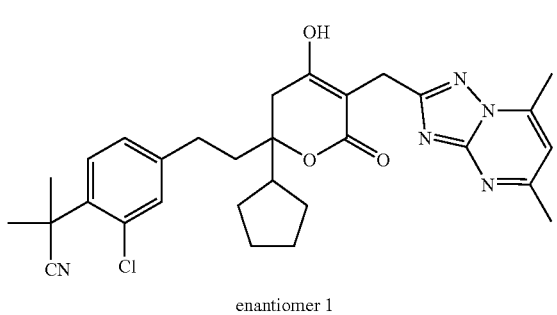

enantiomer 1

The title compound was separated from racemic Example A(146) (2-(2-Chloro-4-{2-[2-cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-phenyl)-2-methyl-propionitrile. using chiral HPLC: Chiralpak AS-H, 140 Bar, 2.5 mL/min, 35% MeOH. 70% recovery. (3.61 min retention time).

Example A(197)

6-Cyclopentyl-3-(5,7-dimethyl-[1,2,4]triazolo[1,5-a]pyrimidin-2-ylmethyl)-6-{2-[3-fluoro-4-(1-hydroxy-ethyl)-phenyl]-ethyl}-4-hydroxy-5,6-dihydro-pyran-2-one

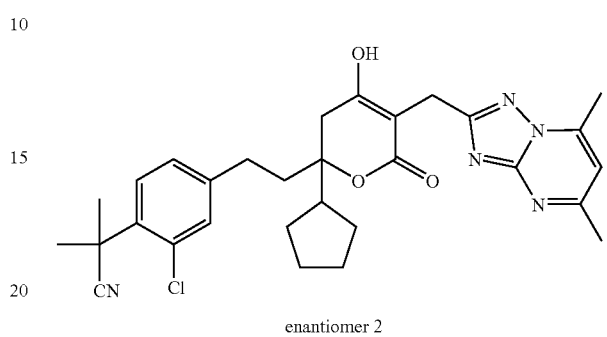

enantiomer 2

The title compound was separated from racemic Example A(146) (2-(2-Chloro-4-{2-[2-cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-phenyl)-2-methyl-propionitrile. using chiral HPL (Chiralpak AS-H, 140 Bar, 2.5 mL/min, 35% MeOH. 70% recovery. (12 min retention time).

Example A(198)

2-(2-Chloro-4-{2-[5-(6-chloro-[1,2,4]triazolo[1,5-a]pyrimidin-2-ylmethyl)-2-cyclopentyl-4-hydroxy-6-oxo-3,6-dihydro-2H-pyran-2-yl]-ethyl}-phenyl)-2-methyl-propionitrile

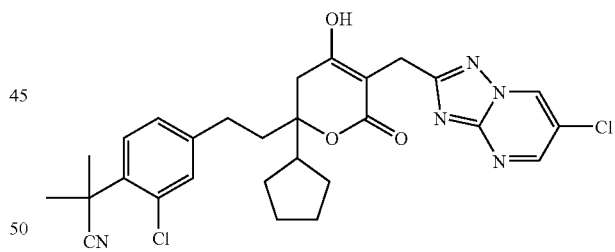

The title compound was prepared analogously to Example A(97) where 6-Chloro-[1,2,4]triazolo[1,5-a]pyrimidine-2-carbaldehyde was substituted in place of 2-ethyl-4-methyl-1H-imidazole-5-carbaldehyde and 2-{2-Chloro-4-[2-(2-cyclopentyl-4,6-dioxo-tetrahydro-pyran-2-yl)-ethyl]-phenyl}-2-methyl-propionitrile from Example A(147) (was substituted in place of 2-{4-[2-(2-cyclopentyl-4-hydroxy-6-oxo-3,6-dihydro-2H-pyran-2-yl)ethyl]-2-fluorophenyl}-2-methylpropanenitrile. $^1H$ NMR (400 MHz, $CDCl_3$) δ: 1.17–1.59 (m, 8H), 1.56–1.6 (m, 2H)), 1.82 (s, 6H), 1.88–2.01 (m, 2H), 2.31–2.79 (m, 3H), 3.79 (d, J=16 Hz, 1H), 3.89 (d, J=16 Hz, 1H), 7.34–7.52 (m, 3H), 8.91 (d, J=2.5 Hz, 1H), 9.63 (d, J=2.5 Hz, 1H), 10.9 (s, 1H). $C_{28}H_{29}Cl_2N_5O_3$: C, 60.65; H, 5.27; N, 12.63. Found: C, 60.45; H, 5.19; N, 12.40. MS (ESI): 555.2(M+H+).

Example A(199)

2-(2-Chloro-4-{2-[2-cyclopentyl-4-hydroxy-5-(6-methyl-[1,2,4]triazolo[1,5-a]pyrimidin-2-ylmethyl)-6-oxo-3,6-dihydro-2H-pyran-2-yl]-ethyl}-phenyl)-2-methyl-propionitrile

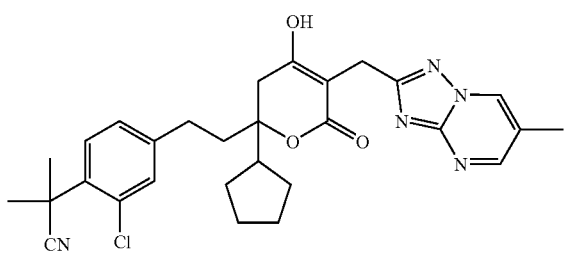

The title compound was prepared analogously to Example A(97) where 6-Methyl-[1,2,4]triazolo[1,5-a]pyrimidine-2-carbaldehyde was substituted in place of 2-ethyl-4-methyl-1H-imidazole-5-carbaldehyde and 2-{2-Chloro-4-[2-(2-cyclopentyl-4,6-dioxo-tetrahydro-pyran-2-yl)-ethyl]-phenyl}-2-methyl-propionitril from Example A(147) (was substituted in place of 2-{4-[2-(2-cyclopentyl-4-hydroxy-6-oxo-3,6-dihydro-2H-pyran-2-yl)ethyl]-2-fluorophenyl}-2-methylpropanenitrile. $^1$H NMR (400 MHz, CDCl$_3$) δ: 1.17–1.59 (m, 8H), 1.59–1.62 (m, 2H)), 1.62 (s, 6H), 1.82–2.01 (m, 2H), 2.19 (s, 3H), 2.38–2.65 (m, 3H), 3.55 (d, J=16 Hz, 1H), 3.65 (d, J=16 Hz, 1H), 7.15–7.32 (m. 3H), 8.53 (d, J=2.3 Hz, 1H), 8.82 (s, 1H), 10.7 (s, 1H). C$_{29}$H$_{32}$ClN$_5$O$_3$: C, 65.22; H, 6.04; N, 13.11. Found: C, 65.15; H, 5.99; N, 13.10. MS (ESI): 535.2(M+H$^+$).

Example A(200)

1-(2-Chloro-4-{2-[2-cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-phenyl)-cyclopropanecarbonitrile

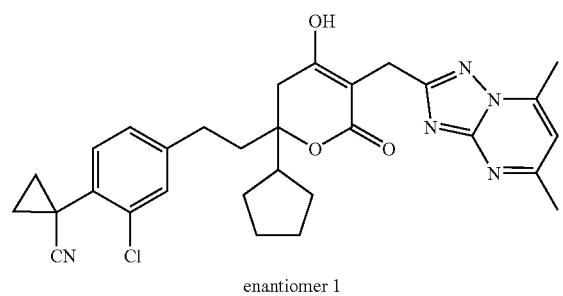

enantiomer 1

The title compound was separated from racemic Example A(148) (1-(2-Chloro-4-{2-[2-cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-phenyl)-cyclopropanecarbonitrile. using chiral HPLC (Chiralpak AS-H, 120 Bar, 2.5 mL/min, 35% MeOH). 70% recovery. (2.31 min retention time).

Example A(201)

1-(2-Chloro-4-{2-[2-cyclopentyl-5-(5,7-dimethyl-[1,2,4]triazolo[1,5a]pyrimidin 2-ylmethyl)-4-hydroxy-6-oxo-3,6-dihydro-2H-pyran-2-yl]-ethyl}-phenyl)-cyclopropanecarbonitrile

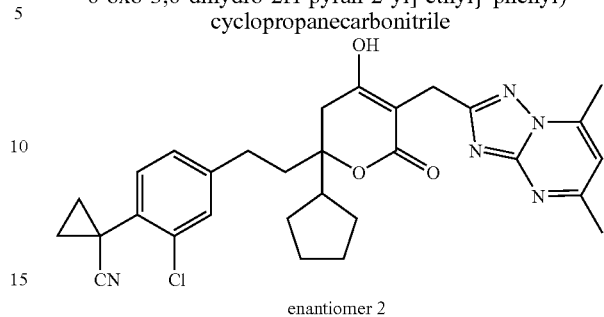

enantiomer 2

The title compound was separated from racemic Example A(148) (1-(2-Chloro-4-{2-[2-cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-phenyl)-cyclopropanecarbonitrile. using chiral HPLC (Chiralpak AS-H, 120 Bar, 2.5 mL/min, 50% MeOH). 70% recovery. (10.26 min retention time).

Example A(202)

2-(2-Chloro-4-{2-[2-cyclopentyl-4-hydroxy-5-(6-methyl-[1,2,4]triazolo[1,5-a]pyrimidin-2-ylmethyl)-6-oxo-3,6-dihydro-2H-pyran-2-yl]-ethyl}-phenyl)-2-methyl-propionitrile

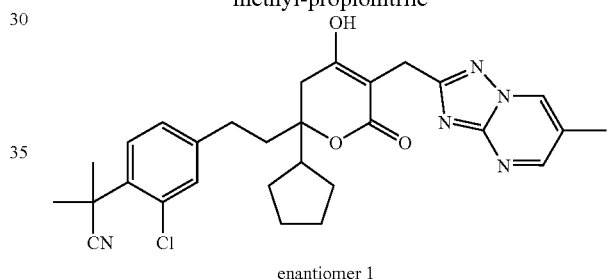

enantiomer 1

The title compound was separated from racemic Example A(199) (using chiral HPLC (Chiralpak AS-H, 130 Bar, 2.5 mL/min, 25% MeOH. 70% recovery. (7.16 min retention time).

Example A(203)

2-(2-Chloro-4-{2-[2-cyclopentyl-4-hydroxy-5-(6-methyl-[1,2,4]triazolo[1,5-a]pyrimidin-2-ylmethyl)-6-oxo-3,6-dihydro-2H-pyran-2-yl]-ethyl}-phenyl)-2-methyl-propionitrile

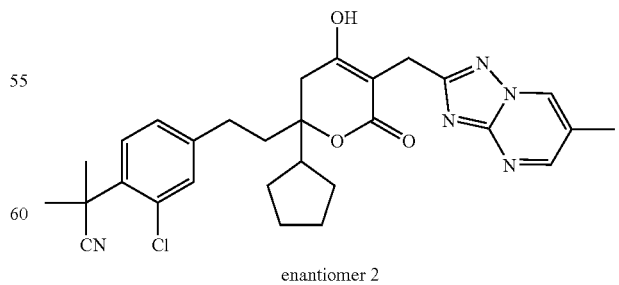

enantiomer 2

The title compound was separated from racemic Example A(199) using chiral HPL (Chiralpak AS-H, 130 Bar, 2.5 mL/min, 25% MeOH. 70% recovery. (14.71 min retention time).

Example A(204)

2-(2-Chloro-4-{2-[5-(6-chloro-[1,2,4]triazolo[1,5-a]pyrimidin-2-ylmethyl)-2-cyclopentyl-4-hydroxy-6-oxo-3,6-dihydro-2H-pyran-2-yl]-ethyl}-phenyl)-2-methyl-propionitrile

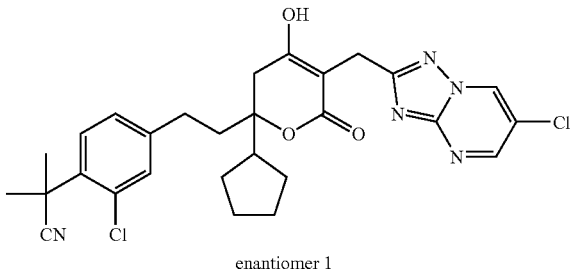

enantiomer 1

The title compound was separated from racemic Example A(198) using chiral HPLC (Chiralpak AS-H, 140 Bar, 2.5 mL/min, 20% MeOH. 70% recovery. (17.33 min retention time).

Example A(205)

2-(2-Chloro-4-{2-[5-(6-chloro-[1,2,4]triazolo[1,5-a]pyrimidin-2-ylmethyl)-2-cyclopentyl-4-hydroxy-6-oxo-3,6-dihydro-2H-pyran-2-yl]-ethyl}-phenyl)-2-methyl-propionitrile

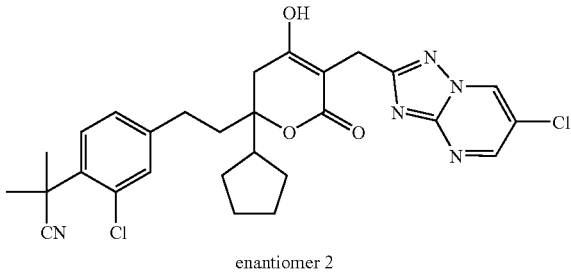

enantiomer 2

The title compound was separated from racemic Example A(198) using chiral HPLC (Chiralpak AS-H column, 140 Bar, 2.5 mL/min, 20% MeOH. 70% recovery. (28.93 min retention time).

Example A(206)

3-[(6-ethyl[1,2,4]triazolo[1,5-a]pyrimidin-2-yl)methyl]-6-cyclopentyl-6-[2-(5-ethyl-4-hydroxy-2-methoxyphenyl)ethyl]-4-hydroxy-5,6-dihydro-2H-pyran-2-one

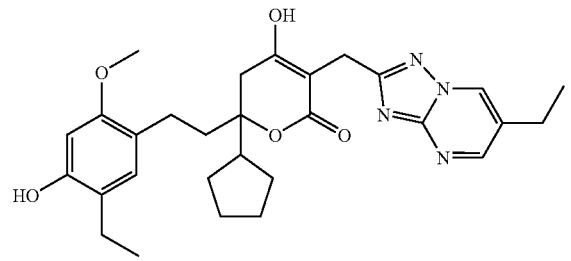

The title compound was prepared analogously to Example A (150), where 6-ethyl[1,2,4]triazolo[1,5-a]pyrimidine-2-carbaldehyde was substituted in place of 5,7-dimethyl[1,2,4]triazolo[1,5-a]pyrimidine-2-carbaldehyde. $^1$H NMR (300 MHz, DMSO-$d_6$) δ: 1.03 (t, J=7.44 Hz, 3 H), 1.23 (t, J=7.44 Hz, 3 H), 1.36–1.74 (m, 8 H), 1.89–2.01 (m, 2 H), 2.33–2.45 (m, 4 H), 2.55–2.60 (m, 1 H), 2.64–2.79 (m, 4 H), 3.62 (s, 3 H), 3.72–3.78 (m, 2 H), 6.37 (s, 1 H), 6.75 (s, 1 H), 8.73 (d, J=1.88 Hz, 1 H), 8.86 (s, 1 H), 9.02 (s, 1 H). Anal. calcd for $C_{29}H_{36}N_4O_5$ 0.8$H_2O$: C, 65.10; H, 7.08; N, 10.47. Found C, 65.03; H, 6.77; N, 10.34.

Example A(207)

6-cyclopentyl-6-[2-(5-ethyl-4-hydroxy-2-methoxyphenyl)ethyl]-4-hydroxy-3-([1,2,4]triazolo[1,5-a]pyrimidin-2-ylmethyl)-5,6-dihydro-2H-pyran-2-one

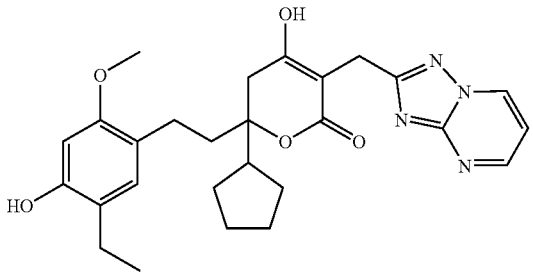

The title compound was prepared analogously to Example A(150), where [1,2,4]triazolo[1,5-a]pyrimidine-2-carbaldehyde was substituted in place of 5,7-dimethyl[1,2,4]triazolo[1,5-a]pyrimidine-2-carbaldehyde. $^1$H NMR (300 MHz, DMSO-$d_6$) δ: 0.96 (t, J=7.44 Hz, 3 H), 1.30–1.69 (m, 8 H), 1.81–1.90 (m, 2 H), 2.28–2.38 (m, 4 H), 2.49–2.52 (m, 1 H), 2.65–2.70 (m, 1 H), 3.55 (s, 3 H), 3.70 (s, 2 H), 6.29 (s, 1 H), 6.68 (s, 1 H), 8.70–8.73 (m, 1 H), 8.94 (s, 1 H), 9.03–9.06 (m, 1 H). Anal. Calcd for $C_{27}H_{32}N_4O_5$.0.3$H_2O$: C, 65.12; H, 6.60; N, 11.25. Found: C, 65.33; H, 6.32; N, 10.93.

Example A(208)

6-cyclopentyl-6-[2-(5-ethyl-4-hydroxy-2-methoxyphenyl)ethyl]-4-hydroxy-3-([1,2,4]triazolo[1,5-a]pyrimidin-2-ylmethyl)-5,6-dihydro-2H-pyran-2-one

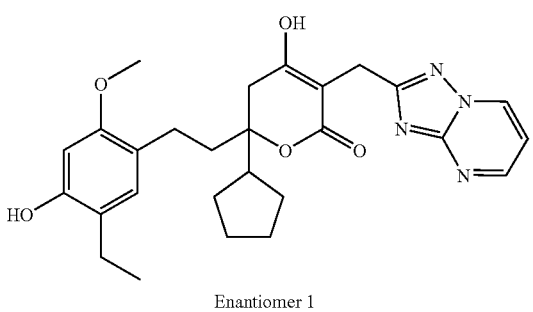

Enantiomer 1

The title compound was isolated by chiral SFC of racemic material described in example A(207) Condition: ChiralPac AD-H column, 140 bar, 25% MeOH, 2.5 mL/min, retention time 13.20 min.

Example A(209)

6-cyclopentyl-6-[2-(5-ethyl-4-hydroxy-2-methoxyphenyl)ethyl]-4-hydroxy-3-([1,2,4]triazolo[1,5-a]pyrimidin-2-ylmethyl)-5,6-dihydro-2H-pyran-2-one

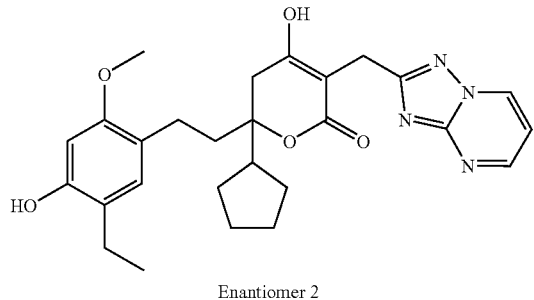

Enantiomer 2

The title compound was isolated by chiral SFC of racemic material described in example A(207) Condition: ChiralPac AD-H column, 140 bar, 25% MeOH, 2.5 mL/min, retention time 20.11 min.

Example A(210)

3-[(6-chloro[1,2,4]triazolo[1,5-a]pyrimidin-2-yl)methyl]-6-cyclopentyl-6-[2-(5-ethyl-4-hydroxy-2-methoxyphenyl)ethyl]-4-hydroxy-5,6-dihydro-2H-pyran-2-one

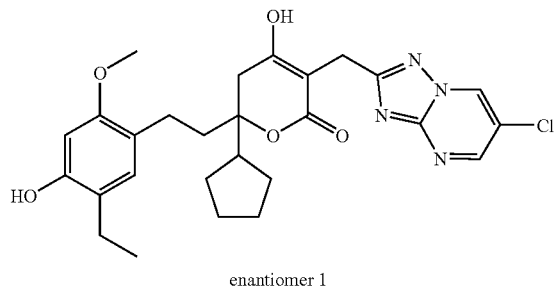

enantiomer 1

The title compound was isolated by chiral SFC of racemic material described in example A(158). Condition: ChiralPac AS-H column, 140 bar, 40% MeOH, 2.5 mL/min, retention time 7.77 min.

Example A(211)

(−)-3-[(6-chloro[1,2,4]triazolo[1,5-a]pyrimidin-2-yl)methyl]-6-cyclopentyl-6-[2-(5-ethyl-4-hydroxy-2-methoxyphenyl)ethyl]-4-hydroxy-5,6-dihydro-2H-pyran-2-one

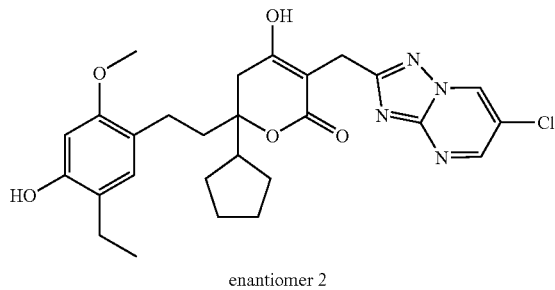

enantiomer 2

The title compound was isolated by chiral SFC of racemic material described in example A(158). Condition: ChiralPac AS-H column, 140 bar, 40% MeOH, 2.5 mL/min, retention time 15.0 min.

Example A(212)

3-[(6-methyl[1,2,4]triazolo[1,5-a]pyrimidin-2-yl)methyl]-6-cyclopentyl-6-[2-(5-ethyl-4-hydroxy-2-methoxyphenyl)ethyl]-4-hydroxy-5,6-dihydro-2H-pyran-2-one

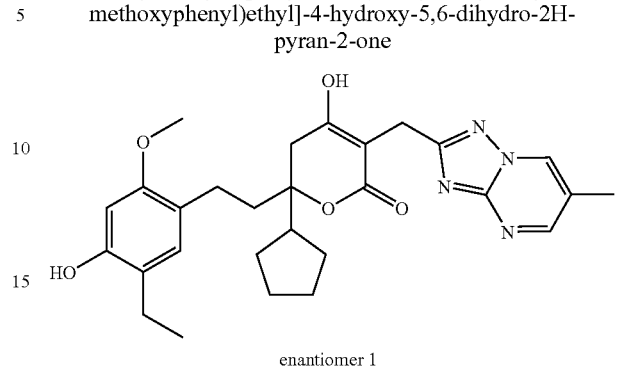

enantiomer 1

The title compound was isolated by chiral SFC of racemic material described in example A(159). Condition: ChiralPac AS-H column, 140 bar, 40% MeOH, 2.5 mL/min, retention time 5.65 min.

Example A(213)

3-[(6-methyl[1,2,4]triazolo[1,5-a]pyrimidin-2-yl)methyl]-6-cyclopentyl-6-[2-(5-ethyl-4-hydroxy-2-methoxyphenyl)ethyl]-4-hydroxy-5,6-dihydro-2H-pyran-2-one

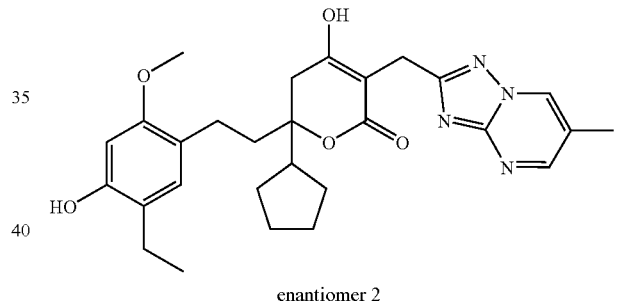

enantiomer 2

The title compound was isolated by chiral SFC of racemic material described in example A(159). Condition: ChiralPac AS-H column, 140 bar, 40% MeOH, 2.5 mL/min, retention time 8.77 min.

Example A(214)

3-[(6-chloro[1,2,4]triazolo[1,5-a]pyrimidin-2-yl)methyl]-6-cyclopentyl-6-{2-[3-fluoro-4-(1-hydroxy-1-methylethyl)phenyl]ethyl}-4-hydroxy-5,6-dihydro-2H-pyran-2-one

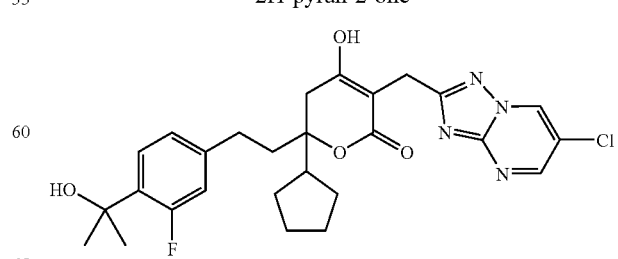

The title compound was prepared analogously to Example A(97), where 6-chloro[1,2,4]triazolo[1,5-a]pyrimidine-2- carbaldehyde was substituted in place of 2-ethyl-4-methyl-1H-imidazole-5-carbaldehyde. ¹H NMR (300 MHz, DMSO-d₆) δ: 1.44 (s, 6 H), 1.52–1.70 (m, 8 H), 1.96–2.10 (m, 2 H), 2.37–2.42 (m, 1 H), 2.55–2.64 (m, 3 H), 2.74–2.80 (m, 1 H), 3.73–3.86 (m, 2 H), 5.17 (s, 1 H), 6.88–6.93 (m, 1 H), 6.99–7.02 (m, 1 H), 7.47–7.52 (m, 1 H), 8.86 (d, J=3.0 Hz, 1 H), 9.58 (d, J=3.0 Hz, 1 H). Anal: calcd for $C_{27}H_{30}ClFN_4O_4 \cdot 0.9H_2O$: C, 59.48; H, 5.88; N, 10.28. Found: C, 59.52; H, 5.86; N, 9.90.

Example A(215)

6-cyclopentyl-6-{2-[3-fluoro-4-(1-hydroxy-1-methylethyl)phenyl]ethyl}dihydro-2H-pyran-2,4(3H)-dione

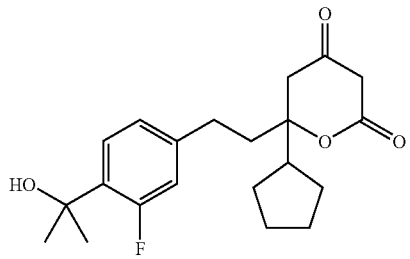

To a solution of methyl acetoacetate (3.9 mL, 36.0 mmol) in anhydrous THF (90 mL) at 0° C. was added NaH (60%, 1.44 g, 36.0 mmol) portionwise. After 10 min, the solution was cooled further to −40° C. n-BuL(1.6 M, 22.5 mL) was added dropwise and the resulting solution was stirred at that temperature for 30 min. A solution of 1-cyclopentyl-3-[3-fluoro-4-(1-hydroxy-1-methylethyl)phenyl]propan-1-one (2.5 g, 9.0 mmol) in THF (4 mL) was added and the mixture was slowly warmed up to 25° C. and stirred for 4 hours. The reaction was quenched by the addition of NH₄Cl and the mixture was extracted with EtOAc (3×50 mL). The combined organic layers were washed with brine, dried over Na₂SO₄. The solvent was removed and the crude product was taken directly into next step without futher purification.

The crude product from previous step was dissolved in THF (40 mL) and the solution was treated with 2.0 N NaOH (18 mL). The resulting mixture was stirred at 25° C. for 4 hours before it was quenched by the addition of 1 N HCl. The mixture was extracted with EtOAc (3×30 mL) and the combined organic layers were washed with brine, dried over Na₂SO₄. The solvent was removed and the crude product was purified by column chromatography to give the desired product in 58% yield (two steps). ¹H NMR (CDCl₃) δ: 1.43–1.77 (m, 8 H), 1.62 (s, 6 H), 1.92–1.99 (m, 2 H), 2.23–2.32 (m, 1 H), 2.64–2.71 (m, 2 H), 2.75–2.78 (m, 2H), 3.41–3.45 (m, 2 H), 6.81–6.84 (m, 1 H), 6.90–6.92 (m, 1 H), 7.44–7.48 (m, 1 H).

Step 2

Preparation of Compound 1-cyclopentyl-3-[3-fluoro-4-(1-hydroxy-1-methylethyl) phenyl]propan-1-one

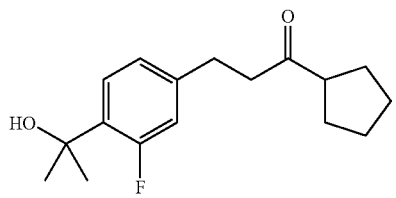

To a solution of 2-(4-bromo-2-fluorophenyl)propan-2-ol (5.8 g, 25.0 mmol) in anhydrous NMP (63 mL) was added 1-Cyclopentyl-2-propen-1-ol (3.15 g, 25.0 mmol), NaHCO₃ (4.2 g, 50 mmol) and PdCl₂(PPh₃)₂ (350 mg, 2 mol %). The mixture was heated to 140° C. for 4 hours before it was cooled down to room temperature. The reaction was diluted with aqueous NH₄Cl, extracted with EtOAc (3×50 mL). The combined organic extracts were washed with brine, dried with Na₂SO₄ and evaporated to dryness. The mixture was purified by flash column chromatography (10–50% EtOAc in hexanes) to give the product (2.5 g, 36% yield). ¹H NMR (300 MHz, CDCl₃) δ: 1.56–1.82 (m, 8 H), 1.62 (s, 6 H), 2.74–2.78 (m, 2 H), 2.82–2.89 (m, 2 H), 6.84–6.88 (m, 1 H), 6.93–6.95 (m, 1 H), 7.40–7.44 (m, 1 H).

Step 1

Preparation of Compound 2-(4-bromo-2-fluorophenyl)propan-2-ol

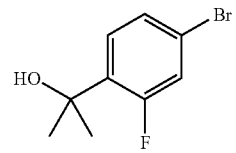

A solution of 4-bromo-2-fluorobenzoic acid (10 g) in anhydrous MeOH (200 mL) was added conc. sulfuric acid (0.5 mL). The mixture was heated to reflux for 15 hours before it was cooled down to room temperature. The solvent was removed and the residue was taken up in EtOAc (100 mL) and washed with sat. NaHCO₃, brine and dried over Na₂SO₄. The crude product was taken into next step without further purification.

To a solution of methyl 4-bromo-2-fluorobenzoate (12 g, 51.5 mmol) in anhydrous ether (140 mL) at 0° C. was added MeMgBr (3.0 M, 70 g) dropwise. The mixture was slowly warmed up to room temperature and stirred for 3 hours. The reaction was quenched by the addition of saturated NH₄Cl and extracted with EtOAc (3×150 mL). The combined organic extracts were washed with brine, dried with Na₂SO₄ and evaporated to dryness. The mixture was purified by flash column chromatography (0–20% EtOAc in hexanes) to give the product (12 g, 95% yield). ¹H NMR (300 MHz, CDCl₃) δ: 1.62 (s, 6 H), 7.18–7.23 (m, 1 H), 7.25–7.28 (m, 1 H), 7.44–7.49 (m, 1 H).

Example A(216)

3-[(6-chloro[1,2,4]triazolo[1,5-a]pyrimidin-2-yl)methyl]-6-cyclopentyl-6-{2-[3-fluoro-4-(1-hydroxy-1-methylethyl)phenyl]ethyl}-4-hydroxy-5,6-dihydro-2H-pyran-2-one

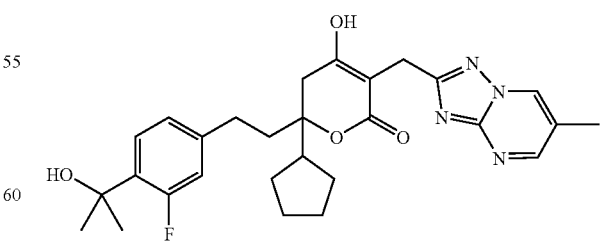

The title compound was prepared analogously to Example A(214), where 6-methyl[1,2,4]triazolo[1,5-a]pyrimidine-2-carbaldehyde was substituted in place of 6-chloro[1,2,4]triazolo[1,5-a]pyrimidine-2-carbaldehyde. ¹H NMR (400

MHz, DMSO-$d_6$) δ: 1.25–1.32 (m, 1 H), 1.39 (s, 6 H), 1.43–1.64 (m, 7 H), 1.90–2.07 (m, 2 H), 2.29 (s, 3 H), 2.32–2.36 (m, 2 H), 2.46–2.54 (m, 2 H), 2.67–2.71 (m, 1 H), 3.64–3.76 (m, 2 H), 6.85 (dd, J=13.14, 1.52 Hz, 1 H), 6.92 (dd, J=8.08, 1.52 Hz, 1 H), 7.43 (m, 1 H), 8.62 (d, J=2.27 Hz, 1 H), 8.88 (dd, J=2.27, 1.01 Hz, 1 H). Anal. calcd for $C_{28}H_{33}FN_4O_4 \cdot 1.2H_2O$: C, 63.43; H, 6.73; N, 10.57. Found: C, 63.19; H, 6.51; N, 10.41.

Example A(217)

6-cyclopentyl-3-[(5,7-dimethyl[1,2,4]triazolo[1,5-a]pyrimidin-2-yl)methyl]-6-{2-[3-fluoro-4-(1-hydroxy-1-methylethyl)phenyl]ethyl}-4-hydroxy-5,6-dihydro-2H-pyran-2-one

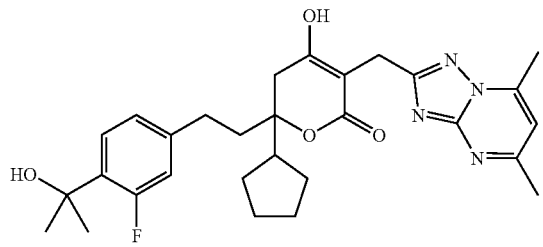

The title compound was prepared analogously to Example A(214), where 5,7-dimethyl[1,2,4]triazolo[1,5-a]pyrimidine-2-carbaldehyde was substituted in place of 6-chloro[1,2,4]triazolo[1,5-a]pyrimidine-2-carbaldehyde. $^1$H NMR (400 MHz, DMSO-$d_6$) δ: 1.29–1.34 (m, 1 H), 1.39 (s, 6 H), 1.44–1.64 (m, 7 H), 2.02–2.07 (m, 2 H), 2.31–2.37 (m, 1 H), 2.40 (s, 3 H), 2.48 (s, 3 H), 2.50–2.55 (m, 3 H), 2.70–2.74 (m, 1 H), 3.63–3.78 (m, 2 H), 6.84–6.87 (m, 1 H), 6.96–6.98 (m, 2 H), 7.43–7.47 (m, 1 H). Anal. calcd for $C_{29}H_{35}FN_4O_4 \cdot 0.8H_2O$: C, 64.86; H, 6.87. Found: C, 64.96; H, 6.61.

Example A(218)

6-cyclopentyl-3-[(5,7-dimethyl[1,2,4]triazolo[1,5-a]pyrimidin-2-yl)methyl]-6-{2-[3-fluoro-4-(1-hydroxy-1-methylethyl)phenyl]ethyl}-4-hydroxy-5,6-dihydro-2H-pyran-2-one (enantiomer A)

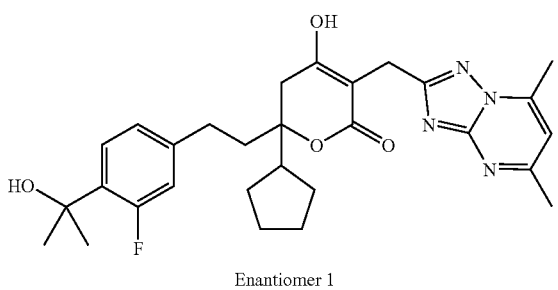

Enantiomer 1

The title compound was isolated by chiral SFC of racemic material described in example A(217). Condition: ChiralPac AD-H column, 140 bar, 40% MeOH, 2.5 mL/min, retention time 6.16 min.

Example A(219)

6-cyclopentyl-3-[(5,7-dimethyl[1,2,4]triazolo[1,5-a]pyrimidin-2-yl)methyl]-6-{2-[3-fluoro-4-(1-hydroxy-1-methylethyl)phenyl]ethyl}-4-hydroxy-5,6-dihydro-2H-pyran-2-one (enantiomer B)

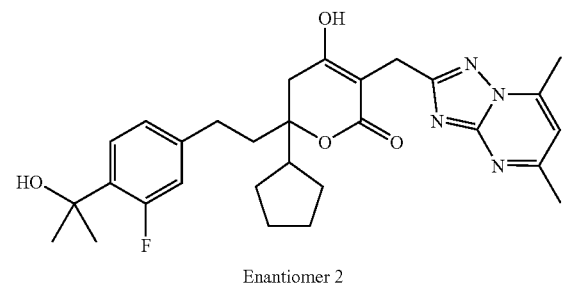

Enantiomer 2

The title compound was isolated by chiral SFC of racemic material described in example A(120). Condition: ChiralPac AD-H column, 140 bar, 40% MeOH, 2.5 mL/min, retention time 9.13 min.

Example A(220)

6-cyclopentyl-6-{2-[3-fluoro-4-(1-hydroxy-1-methylethyl)phenyl]ethyl}-4-hydroxy-3-([1,2,4]triazolo[1,5-a]pyrimidin-2-ylmethyl)-5,6-dihydro-2H-pyran-2-one

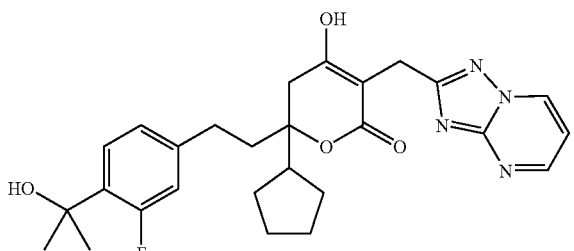

The title compound was prepared analogously to Example A(214), where I[1,2,4]triazolo[1,5-a]pyrimidine-2-carbaldehyde was substituted in place of 6-chloro[1,2,4]triazolo[1,5-a]pyrimidine-2-carbaldehyde. $^1$H NMR (400 MHz, DMSO-$d_6$) δ: 1.25–1.32 (m, 1 H), 1.39 (s, 6 H), 1.43–1.64 (m, 7 H), 1.91–2.08 (m, 2 H), 2.30–2.36 (m, 1 H), 2.46–2.55 (m, 3H), 2.68–2.73 (m, 1 H), 3.67–3.79 (m, 2 H), 6.86 (dd, J=13.01, 1.39 Hz, 1 H), 6.94 (dd, J=8.08, 1.52 Hz, 1 H), 7.19 (dd, J=6.82, 4.29 Hz, 1 H), 7.44 (m, 1 H), 8.73 (dd, J=4.29, 1.77 Hz, 1 H), 9.03 (dd, J=6.82, 2.02 Hz, 1 H). Anal. calcd for $C_{27}H_{31}FN_4O_4 \cdot 0.4H_2O$: C, 64.63; H, 6.39; N, 11.17. Found: C, 64.63; H, 6.15; N, 10.71.

Example A(221)

2-(4-{2-[2-cyclopentyl-4-hydroxy-5-(imidazo[1,2-a]pyrimidin-2-ylmethyl)-6-oxo-3,6-dihydro-2H-pyran-2-yl]ethyl}-2-fluorophenyl)-2-methylpropanenitrile

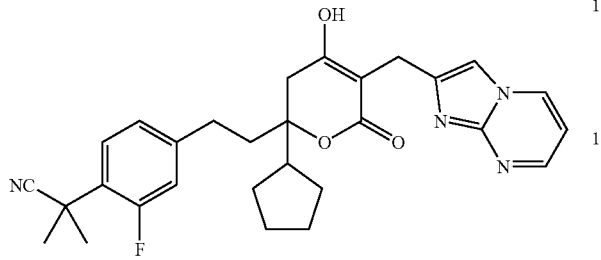

The title compound was prepared analogously to Example A(97), where imidazo[1,2-a]pyrimidine-2-carbaldehyde was substituted in place of 2-ethyl-4-methyl-1H-imidazole-5-carbaldehyde. $^1$H NMR (400 MHz, DMSO-$d_6$) δ: 1.16–1.45 (m, 8 H), 1.56 (s, 6 H), 1.78–1.85 (m, 2H), 1.93–1.96 (m, 2 H), 2.19–2.27 (m, 1 H), 2.46–2.51 (m, 3 H), 2.62–2.67 (m, 1 H), 6.92 (d, J=9.60 Hz, 1 H), 7.00 (d, J=11.62 Hz, 1 H), 7.19 (t, J=8.46 Hz, 1 H), 7.29 (s, 1 H), 7.69 (s, 1 H), 8.66 (s, 1H), 8.94 (d, J=5.81 Hz, 1 H). HRMS calcd for $C_{29}H_{32}FN_4O_3(M+H)^+$. 503.2453. Found: 503.2455.

Example A(222)

2-(4-{2-[2-cyclopentyl-4-hydroxy-5-(imidazo[1,2-a]pyrimidin-3-ylmethyl)-6-oxo-3,6-dihydro-2H-pyran-2-yl]ethyl}-2-fluorophenyl)-2-methylpropanenitrile

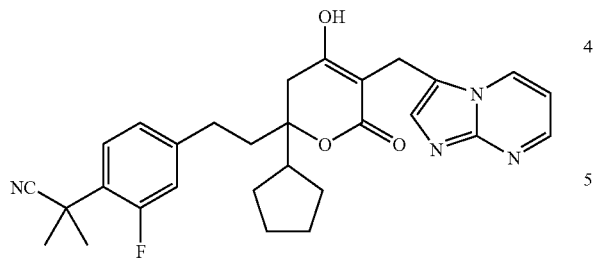

The title compound was prepared analogously to Example A(97), where imidazo[1,2-a]pyrimidine-3-carbaldehyde was substituted in place of 2-ethyl-4-methyl-1H-imidazole-5-carbaldehyde. $^1$H NMR (400 MHz, DMSO-$d_6$) δ: 1.24–1.58 (m, 8 H), 1.64 (s, 6 H), 1.79–1.85 (m, 2H), 2.21–2.31 (m, 1 H), 2.47–2.60 (m, 3 H), 2.71–2.75 (m, 1 H), 3.10 (s, 2 H), 6.91 (dd, J=8.08, 1.52 Hz, 1 H), 7.02 (dd, J=13.01, 1.39 Hz, 1 H), 7.26 (t, J=8.46 Hz, 1 H), 7.55 (dd, J=6.95, 4.42 Hz, 1 H), 7.87 (s, 1 H), 8.87 (dd, J=4.17, 1.39 Hz, 1 H), 9.15 (dd, J=6.95, 1.64 Hz, 1 H). HRMS calcd for $C_{29}H_{32}FN_4O_3(M+H)^+$. 503.2453. Found: 503.2458.

Example A(223)

3-[(6-chloro[1,2,4]triazolo[1,5-a]pyrimidin-2-yl)methyl]-6-cyclopentyl-4-hydroxy-6-{2-[4-hydroxy-3-(2,2,2-trifluoroethyl)phenyl]ethyl}-5,6-dihydro-2H-pyran-2-one

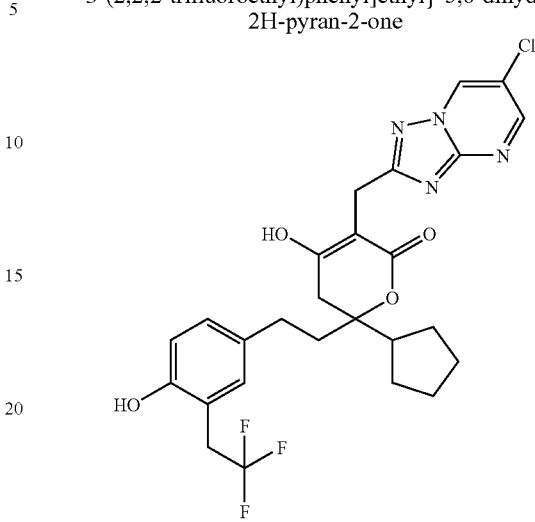

6-chloro-[1,2,4]triazolo[1,5-a]pyrimidine-2-carbaldehyde (0.131 g, 0.72 mmol) was added to a solution of example A(228) 6-cyclopentyl-6-{2-[4-hydroxy-3-(2,2,2-trifluoroethyl)phenyl]ethyl}dihydro-2H-pyran-2,4(3H)-dione (0.230 g, 0.60 mmol) in MeOH (10 mL). The reaction mixture was stirred for 15 mins and then treated with borane-dimethylamine complex (53 mg, 0.9 mmoL). After 15 hours the reaction mixture was quenched with concentrated HCl, and concentrated to a residual oil. Purification by flash column chromatography (EtOAc then 0%–5% MeOH in $CH_2Cl_2$) gave the product as a white solid (17 mg). $^1$H NMR (DMSO): δ 1.30–1.80 (brm, 8H), 2.08–2.18 (brm, 3H), 2.74 (s, 2H), 2.99(m, 2H); 3.15 (m, 2H), 3.47 (m, 3 H), 6.81 (m, 2H), 7.00(s, 1H), 8.76 (s, 1H), 8.82 (s, 1H). Anal. Calcd. For $C_{26}H_{26}O_4N_4ClF_3$: C, 56.68; H, 4.75; N, 10.17. Found: C, 56.50; H, 4.69; N, 10.20.

Example A(224)

6-cyclopentyl-4-hydroxy-6-{2-[4-hydroxy-3-(2,2,2-trifluoroethyl)phenyl]ethyl}-3-[(6-methyl[1,2,4]triazolo[1,5-a]pyrimidin-2-yl)methyl]-5,6-dihydro-2H-pyran-2-one

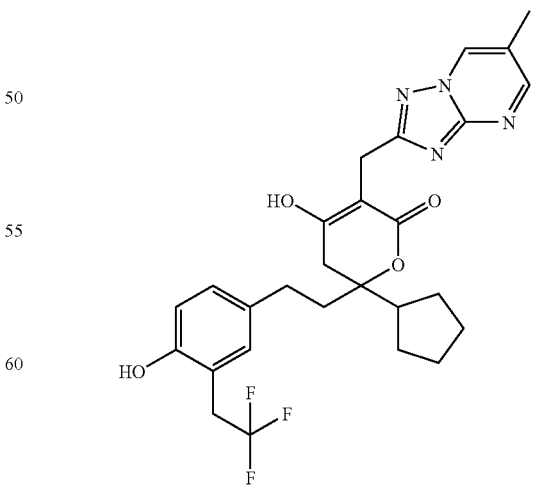

6-methyl-[1,2,4]triazolo[1,5-a]pyrimidine-2-carbaldehyde (0.88 g, 0.546 mmol) was added to a solution of example A(228) 6-cyclopentyl-6-{2-[4-hydroxy-3-(2,2,2-trifluoroethyl)phenyl]ethyl}dihydro-2H-pyran-2,4(3H)-dione (0.175 g, 0.455 mmol) and borane-dimethylamine complex (53 mg, 0.9 mmoL) in MeOH (10 mL). The reaction was stirred at room temperature for 15 hours, after which time the mixture was concentrated to a residual oil, and purified by preparatory HPLC to afford the title compound as a white solid (50 mg). $^1$H NMR (DMSO): δ 1.35–1.85 (brm, 8H), 2.00–2.20 (brm, 3H), 2.50 (s, 3H), 2.74 (s, 2H), 2.99(m, 2H); 3.04 (m, 2H), 3.54 (m, 3H), 6.81 (m, 2H), 7.00(s, 1H), 8.55 (s, 1H), 8.72 (s, 1H). Anal. Calcd. For $C_{27}H_{29}O_4N_4F_3$: C, 61.14; H, 5.51; N, 9.06. Found: C, 61.21; H, 5.60; N, 9.14.

Example A(225)

6-cyclopentyl-3-[(5,7-dimethyl[1,2,4]triazolo[1,5-a]pyrimidin-2-yl)methyl]-4-hydroxy-6-{2-[4-hydroxy-3-(2,2,2-trifluoroethyl)phenyl]ethyl}-5,6-dihydro-2H-pyran-2-one

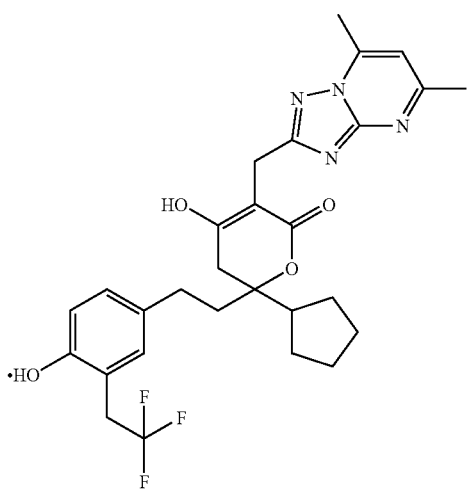

The title compound was prepared analogously to Example A(224) where 5,7-dimethyl-[1,2,4]triazolo[1,5-a]pyrimidine-2-carbaldehyde was used in place of 6-methyl-[1,2,4]triazolo[1,5-a]pyrimidine-2-carbaldehyde in that example. $^1$H NMR (DMSO): δ 1.40–1.90 (brm, 8H), 1.99–2.28 (brm, 3H), 2.58 (s, 3H), 2.73 (m, 5H), 3.00(m, 2H); 3.10 (m, 2H), 3.47 (m, 3H), 6.79 (m, 2H), 7.05(m, 2H), 8.83 (bs, 1H), 10.0 (bs, 1H). Anal. Calcd. For $C_{28}H_{31}O_4N_4F_3$: C, 61.76; H, 5.74; N, 10.29. Found: C, 61.50; H, 5.50; N, 10.14.

Example A(226)

3-[(6-chloro[1,2,4]triazolo[1,5-a]pyrimidin-2-yl)methyl]-6-cyclopentyl-4-hydroxy-6-{2-[4-hydroxy-3-(2,2,2-trifluoroethyl)phenyl]ethyl}-5,6-dihydro-2H-pyran-2-one

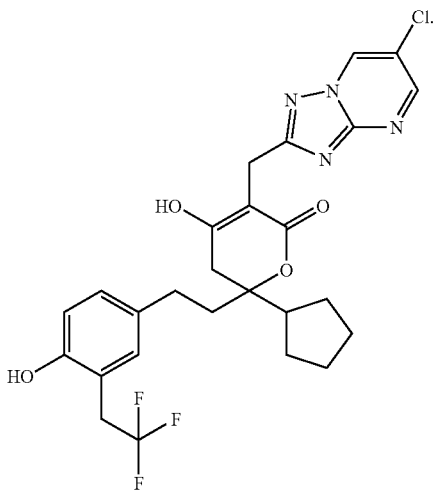

enantiomer 1

The title compound was separated from racemic Example A(223), 3-[(6-chloro[1,2,4]triazolo[1,5-a]pyrimidin-2-yl)methyl]-6-cyclopentyl-4-hydroxy-6-{2-[4-hydroxy-3-(2,2,2-trifluoroethyl)phenyl]ethyl}-5,6-dihydro-2H-pyran-2-one using chiral HPLC (AS-H, 120 Bar, 2.5 mL/min, 30% MeOH). (4.76 min retention time).

Example A(227)

3-[(6-chloro[1,2,4]triazolo[1,5-a]pyrimidin-2-yl)methyl]-6-cyclopentyl-4-hydroxy-6-{2-[4-hydroxy-3-(2,2,2-trifluoroethyl)phenyl]ethyl}-5,6-dihydro-2H-pyran-2-one

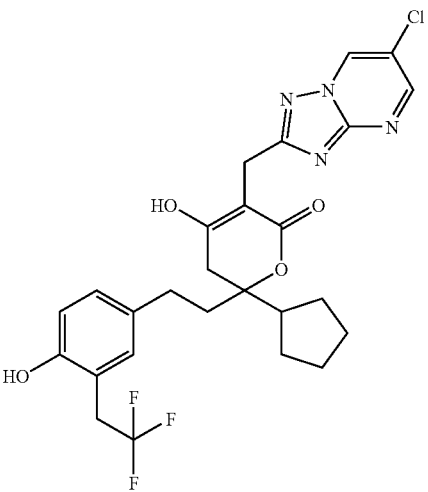

enantiomer 2

The title compound was separated from racemic Example A(223), 3-[(6-chloro[1,2,4]triazolo[1,5-a]pyrimidin-2-yl)methyl]-6-cyclopentyl-4-hydroxy-6-{2-[4-hydroxy-3-(2,2,2-trifluoroethyl)phenyl]ethyl}-5,6-dihydro-2H-pyran-2-one using chiral HPLC (AS-H, 120 Bar, 2.5 mL/min, 30% MeOH). (9.617 min retention time).

Example A(228)

6-cyclopentyl-6-{2-[4-hydroxy-3-(2,2,2-trifluoroethyl)phenyl]ethyl}dihydro-2H-pyran-2,4(3H)-dione

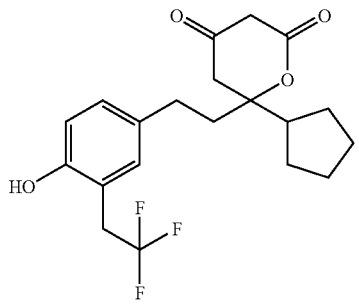

The title compound was prepared analogously to Example A(124) where 4-bromo-2-(2,2,2-trifluoroethyl)phenol from step 6 below was used in place of 2-ethyl-5-fluorophenol in that example. $^1$H NMR (CDCl$_3$): δ 1.35–1.70 (brm, 6H), 1.93, (brm, 2H), 2.04–2.21 (brm, 3H), 2.83–3.12 (brm, 8H), 6.78 (dd, J=2.81 Hz 2H), 6.99 (s, 1H). MS(APCI): 385 (M–H).

Step 6

Preparation of Compound
4-bromo-2-(2,2,2-trifluoroethyl)phenol

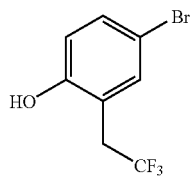

Tetrabutylammonium tribromide (6.56 g) was dissolved in chloroform (50 ml) and added dropwise to a solution of 2-(2,2,2-trifluoroethyl)phenol (2.4 g) in chloroform (50 ml). The reaction mixture was stirred at room temperature for 2 hrs, after which time 5% sodium thiosulfate solution (100 ml) was added and the resultant stirred for 30 mins. The mixture was then partitioned between dichloromethane (100 ml) and 1N HCl (200 ml). The organics were separated and dried over magnesium sulfate. The solvent was then removed in vacuo, the crude residue was then purified by column chromatography on silica gel eluting with 90:10 hexanes:ethl acetate to afford the title compound as a yellow oil (3.24 g). $^1$H NMR (CDCl$_3$): δ 3.50 (q, J=21.48 Hz 2H), 6.70 (d, J=2.54 Hz, 1H), 7.32 (d, J=2.54 Hz, 1H), 7.45 (s, 1H).

Step 5

Preparation of Compound
2-(2,2,2-trifluoroethyl)phenol

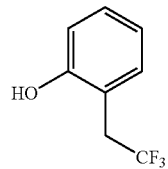

Sodium Borohydride (0.930 g) was added to a solution of 2-(1-chloro-2,2,2-trifluoroethyl)phenol (2.6 g) in THF (30 ml). The reaction mixture was then stirred for 14 hrs at room temperature under an atmosphere of nitrogen, after which time the reaction was quenched with 1N HCl (50 ml) and partitioned between 1NHCl (100) and ethyl acetate (200 ml), the organics were separated and dried over magnesium sulfate, filtered and solvent evaporated in vacuuo to afford title compound as a semi solid (2.4 g). $^1$H NMR (CDCl$_3$): δ 3.50 (q, J=21.06 Hz 2H), 6.80 (m, 1H), 7.00 (m, 1H), 7.25 (m, 2H).

Step 4

Preparation of Compound
2-(1-chloro-2,2,2-trifluoroethyl)phenol

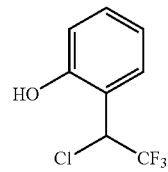

Thionyl chloride (2.28 ml) was added to a solution of 2-(2,2,2-trifluoro-1-hydroxyethyl)phenol (3.0 g) and pyridine (1.23 ml) in toluene (50 ml). The reaction was stirred at room temperature for 1 hr, after which time the toluene was removed in vacuuo and the residue partitioned between ethyl acetate (100 ml) and 1 HCl (100 ml). The organics were separated and dried over magnesium sulfate, filtered and solvent removed in vacuuo to afford the title compound as a clear oil (3.0 g). $^1$H NMR (CDCl$_3$): δ 5.93 (m, 1H), 6.90 (d, J=4.52 Hz, 1H), 7.10 (m, 1H), 7.35 (m, 1H), 7.69 (m, 1H).

Step 3

Preparation of Compound
2-(2,2,2-trifluoro-1-hydroxyethyl)phenol

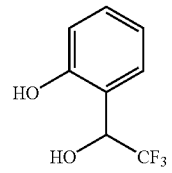

Boron Tribromide (10 ml) (1M soln in DCM) was added to a solution of 2,2,2-trifluoro-1-(2-methoxyphenyl)ethanol (1.5 g) in dichloromethane (20 ml). The reaction mixture was stirres at room temperature under a atmosphere of nitrogen for 56 hrs. The mixture was then partitioned between DCM (100 ml) and 1N HCl (100 ml), organics washed with water (100 ml), dried over magnesium sulfate, filtered and solvent removed in vacuuo to afford the title compound as a clear yellow oil (1.5 g). $^1$H NMR (CDCl$_3$): δ 3.50 (bs, 1H), 5.25 (m, 1H), 6.73 (bs, 1H), 7.00 (m, 2H), 7.32 (d, J=2.56 Hz, 1H), 7.45 (m, 1H).

Step 2

Preparation of Compound 2,2,2-trifluoro-1-(2-methoxyphenyl)ethanol

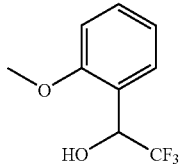

10% palladium on carbon (1.5 g) was added to a solution of 2,2,2-trifluoro-1-(2-methoxyphenyl)ethanone (3.0 g) in methanol (50 ml). The resultant was hydrogenated at room temperature for 12 hrs. After which time the catalyst was filtered off through a plug of celite and the solvent concentrated in vacuuo. The crude was purified by column chromatography on silica gel eluting with 100% hexanes the 80:20 hexanes:ethylacetate to afford the title compound as a yellow oil (3.0 g). $^1$H NMR (CDCl$_3$): δ 3.75 (d, J=2.56 Hz, 1H), 3.96 (s, 3H), 5.35 (m, 1H), 7.05 (m, 2H), 7.50 (m, 2H).

Step 1

Preparation of Compound 2,2,2-trifluoro-1-(2-methoxyphenyl)ethanone

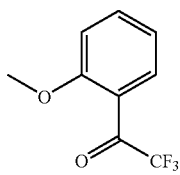

2 Methoxy Phenyl magnesium bromide (35 ml) was added slowly to a solution of methyl trifluoroacetate (5.0 g) in diethyl ether (100 ml) @ −78° C. The reaction mixture was warmed to room temperature over 12 hrs and the quenched with saturated ammonium chloride solution (100 ml). The mixture was then partitioned between ethyl acetate (500 ml) and water (250 ml) The organics were separated and dried over magnesium sulfate filtered and concentrated in vacuuo. The crude residue was purified by column chromatography on silica gel eluting with 100% hexanes, 90:10 and 80:20, hexanes:ethyl acetate, to afford title compound as a yellow oil. (4.0 g). $^1$H NMR (CDCl$_3$): δ 3.57 (s, 3H), 7.00 (m, 2H), 7.35 (m, 1H), 7.63, (d, J=2.54 Hz 2H).

Example A(229)

6-cyclopentyl-6-[2-(3-ethyl-4-hydroxyphenyl)ethyl]-4-hydroxy-3-[(5-methyl[1,2,4]triazolo[1,5-a]pyrimidin-2-yl)methyl]-5,6-dihydro-2H-pyran-2-one

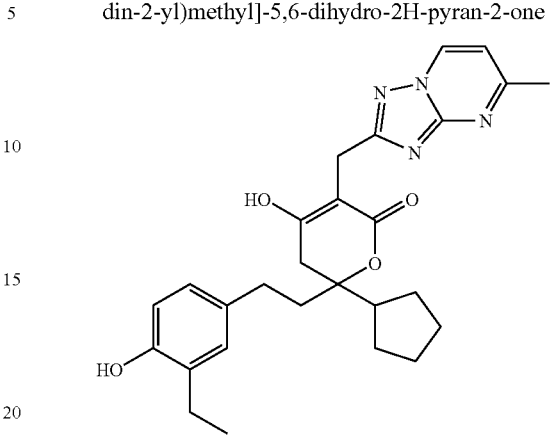

The title compound was prepared analogously to Example A(224) where 5-methyl-[1,2,4]triazolo[1,5-a]pyrimidine-2-carbaldehyde was used in place of 6-methyl-[1,2,4]triazolo[1,5-a]pyrimidine-2-carbaldehyde and 6-cyclopentyl-6-[2-(3-ethyl-4-hydroxyphenyl)ethyl]dihydro-2H-pyran-2,4(3H)-dione was used in place of 6-cyclopentyl-6-{2-[4-hydroxy-3-(2,2,2-trifluoroethyl)phenyl]ethyl}dihydro-2H-pyran-2,4(3H)-dione in that example. $^1$H NMR (DMSO): δ 1.15 (t, J=7.54 Hz, 3H), 1.30–1.80 (brm, 8H), 2.00–2.40 (brm, 3H), 2.50 (q, J=10.74 Hz 2H), 2.68 (s, 1H), 2.70(s, 2H); 2.92 (m, 2H), 3.69 (m, 3H), 6.64 (d, J=3.56 Hz, 1H), 6.66 (d, J=3.56 Hz, 1H), 7.00 (m, 2H), 8.55 (d, J=6.97 Hz, 1H). Anal. Calcd. For C$_{27}$H$_{32}$O$_4$N$_4$: C, 68.05; H, 6.77; N, 11.76. Found: C, 68.24; H, 6.80; N, 11.77.

Example A(230)

3-[(6-bromo [1,2,4]triazolo[1,5-a]pyrimidin-2-yl)methyl]-6-cyclopentyl-6-[2-(3-ethyl-4-hydroxyphenyl)ethyl]-4-hydroxy-5,6-dihydro-2H-pyran-2-one

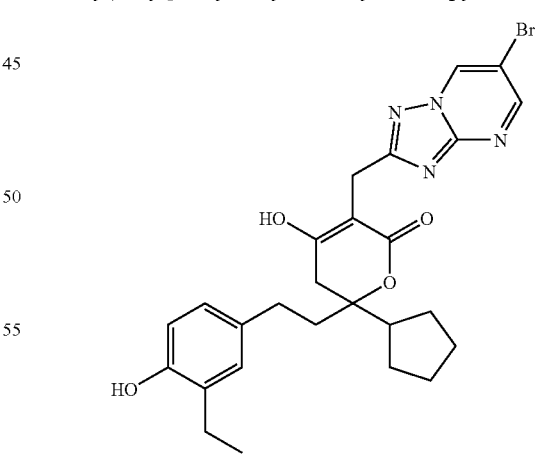

The title compound was prepared analogously to Example A(224) where 6-bromo-[1,2,4]triazolo[1,5-a]pyrimidine-2-carbaldehyde was used in place of 6-methyl-[1,2,4]triazolo[1,5-a]pyrimidine-2-carbaldehyde and 6-cyclopentyl-6-[2-(3-ethyl-4-hydroxyphenyl)ethyl]dihydro-2H-pyran-2,4(3H)-dione was used in place of 6-cyclopentyl-6-{2-[4- hydroxy-3-(2,2,2-trifluoroethyl)phenyl]ethyl}dihydro-2H-pyran-2,4(3H)-dione in that example. ¹H NMR (DMSO): δ 1.15 (t, J=7.54 Hz, 3H), 1.30–1.90 (brm, 8H), 2.00–2.40 (brm, 3H), 2.50 (q, J=10.74 Hz 2H), 2.75 (m, 2H); 2.90 (m, 2H), 3.50 (m, 3H), 6.64 (d, J=5.26 Hz, 1H), 6.70 (d, J=5.26 Hz, 1H), 7.00 (s, 1H), 8.75 (s, 1H), 9.19 (s, 1H). Anal. Calcd. For $C_{26}H_{29}O_4N_4Br$ C, 57.68; H, 5.40; N, 10.35. Found: C, 57.50; H, 5.50; N, 10.30.

Step 2

6-bromo-[1,2,4]triazolo[1,5-a]pyrimidine-2-carbaldehyde

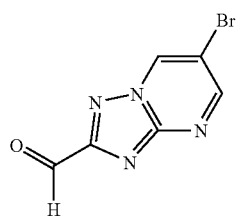

A slurry of (6-bromo-[1,2,4]triazolo[1,5-a]pyrimidin-2-yl)-methanol (6.5 g, 28.51 mmol) from step 1 above in dichloromethane (60 mL) was added PhI(OAc)2 (10.1 mg, 31.4 mmol) and with catalytic TEMPO (334 mg, 2.14 mmol). After reaction at room temperature for 3 hours, the reaction is complete. MTBE is added slowly (50 mL) to crystallize the product, filtration followed by drying the product by vacuum oven overnight. The filtrate was concentrated and purified by flash chromatography (2% MeOH in $CH_2Cl_2$) to give the desired product as light white solid (combine total 4.8 g, 75% yield). ¹H NMR (300 MHz, CDCl3) □ ppm 8.96 (d, J=2.45 Hz, 1H) 9.09 (d, J=2.45 Hz, 1H) 10.22 (s, 1H). MS: (APCI) 228 (M+H).

Step 1

(6-Bromo-[1,2,4]triazolo[1,5-a]pyrimidin-2-yl)-methanol

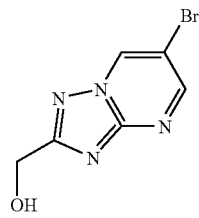

To a slurry of (5-amino-1H-[1,2,4]triazol-3-yl)-methanol (6.29 g, 33.12 mmol) in acetic acid (25 ml) was added bromomalonaldehyde (5 g, 33.12 mmol). The mixture was heated at 60° C. for hours, and then cooled to room temperature. The light yellow solid was formed. After the solid were removed by filtration followed by drying in vacuum oven provides the light yellow solid as desired product, the filtrate was concentrate by rotary evaporation to give yellow oil. The crude oil was purified by flash chromatography (2% MeOH in CH2Cl2) to give the desired product as light yellow solid (combine total 6.5 g, 86% yield). ¹H NMR (300 MHz, DMSO-D6) δ ppm 4.65 (d, J=5.46 Hz, 2 H) 5.50–5.67 (m, 1 H) 8.94 (d, J=2.45 Hz, 1 H) 9.83 (d, J=2.26 Hz, 1 H). MS: (APCI) 230 (M+H)

Example A(231)

3-[(6-chloro[1,2,4]triazolo[1,5-a]pyrimidin-2-yl)methyl]-6-cyclopentyl-6-[2-(3,5-diethyl-4-hydroxyphenyl)ethyl]-4-hydroxy-5,6-dihydro-2H-pyran-2-one

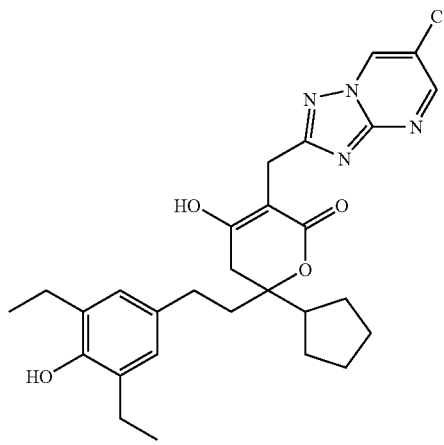

The title compound was prepared analogously to Example A(224) where 6-chloro-[1,2,4]triazolo[1,5-a]pyrimidine-2-carbaldehyde was used in place of 6-methyl-[1,2,4]triazolo[1,5-a]pyrimidine-2-carbaldehyde and 6-cyclopentyl-6-[2-(3,5-diethyl-4-hydroxyphenyl)ethyl]dihydro-2H-pyran-2,4(3H)-dione (Example A(235)) was used in place of 6-cyclopentyl-6-{2-[4-hydroxy-3-(2,2,2-trifluoroethyl)phenyl]ethyl}dihydro-2H-pyran-2,4(3H)-dione in that example. ¹H NMR (DMSO): δ 1.15 (t, J=3.89 Hz, 6H), 1.30–1.80 (brm, 8H), 2.00–2.20 (brm, 5H), 2.43 (q, J=20.06 Hz 4H), 2.85 (m, 4H), 3.55 (m, 3H), 6.70 (s, 2H), 8.76 (s, 1H), 8.82 (s, 1H). Anal. Calcd. For $C_{28}H_{33}O_4N_4Cl$, C, 64.05; H, 6.34; N, 10.67. Found: C, 64.35; H, 6.50; N, 10.75.

Example A(232)

6-cyclopentyl-6-[2-(3,5-diethyl-4-hydroxyphenyl)ethyl]-3-[(5,7-dimethyl[1,2,4]triazolo[1,5-a]pyrimidin-2-yl)methyl]-4-hydroxy-5,6-dihydro-2H-pyran-2-one

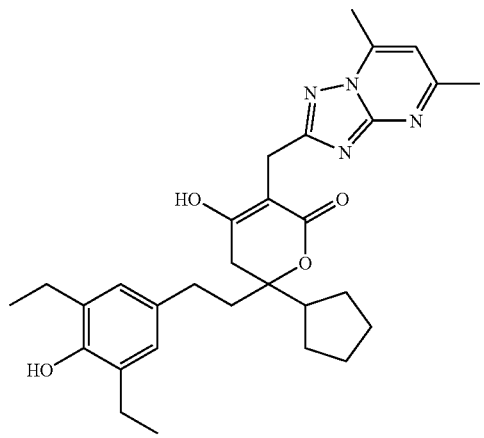

The title compound was prepared analogously to Example A(224) where 5,7-dimethyl[1,2,4]triazolo[1,5-a]pyrimidine-2-carbaldehyde was used in place of 6-methyl-[1,2,4]triazolo[1,5-a]pyrimidine-2-carbaldehyde and 6-cyclopentyl-6-[2-(3,5-diethyl-4-hydroxyphenyl)ethyl]dihydro-2H-pyran-2,4(3H)-dione (Example A(235)) was used in place of 6-cyclopentyl-6-{2-[4-hydroxy-3-(2,2,2-trifluoroethyl)phenyl]ethyl}dihydro-2H-pyran-2,4(3H)-dione in that example. ¹H NMR (DMSO): δ 1.15 (t, J=7.54 Hz, 6H), 1.30–1.80 (brm, 8H), 2.00–2.20 (brm, 5H), 2.43 (q, J=19.06 Hz 4H), 2.60 (s, 3H), 2.80 (brm, 7H), 3.34 (m, 3H), 6.70 (s, 2H), 6.99 (s, 1H). Anal. Calcd. For $C_{30}H_{38}O_4N_4$, C, 69.47; H, 7.38; N, 10.80. Found: C, 69.45; H, 7.35; N, 10.75.

Example A(233)

6-cyclopentyl-6-[2-(3,5-diethyl-4-hydroxyphenyl) ethyl]-4-hydroxy-3-[(6-methyl[1,2,4]triazolo [1,5-a] pyrimidin-2-yl)methyl]-5,6-dihydro-2H-pyran-2-one

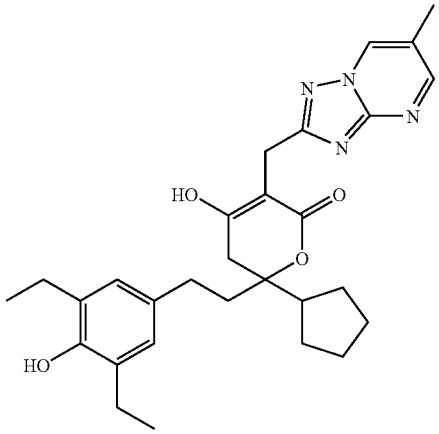

The title compound was prepared analogously to Example A(224) where 6-cyclopentyl-6-[2-(3,5-diethyl-4-hydroxyphenyl)ethyl]dihydro-2H-pyran-2,4(3H)-dione (Example A(235)) was used in place of 6-cyclopentyl-6-{2-[4-hydroxy-3-(2,2,2-trifluoroethyl)phenyl]ethyl}dihydro-2H-pyran-2,4(3H)-dione in that example. ¹H NMR (DMSO): δ 1.17 (t, J=2.56 Hz, 6H), 1.30–1.80 (brm, 6H), 1.99–2.21 (brm, 5H), 2.45 (q, J=19.06 Hz 4H), 2.50 (s, 3H), 2.80 (m, 4H), 3.34 (m, 3H), 6.70 (s, 2H), 8.55 (s, 1H), 8.72 (s, 1H), 9.30 (s, 1H). Anal. Calcd. For $C_{29}H_{36}O_4N_4$; C, 69.03; H, 7.19; N, 11.10. Found: C, 69.00; H, 7.05; N, 11.20.

Example A(234)

6-cyclopentyl-6-[2-(3,5-diethyl-4-hydroxyphenyl) ethyl]-4-hydroxy-3-([1,2,4]triazolo[1,5-a]pyrimidin-2-ylmethyl)-5,6-dihydro-2H-pyran-2-one

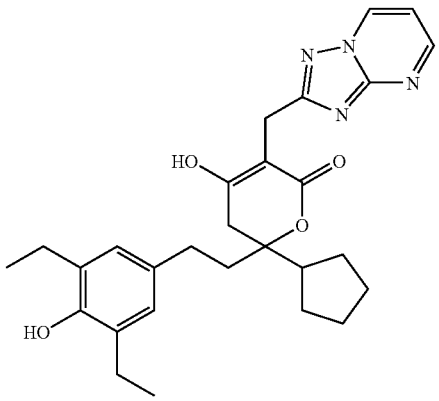

The title compound was prepared analogously to Example A(224) where [1,2,4]triazolo[1,5-a]pyrimidine-2-carbaldehyde was used in place of 6-methyl[1,2,4]triazolo[1,5-a]pyrimidine-2-carbaldehyde and 6-cyclopentyl-6-[2-(3,5-diethyl-4-hydroxyphenyl)ethyl]dihydro-2H-pyran-2,4(3H)-dione (Example A(235)) was used in place of 6-cyclopentyl-6-{2-[4-hydroxy-3-(2,2,2-trifluoroethyl)phenyl]ethyl}dihydro-2H-pyran-2,4(3H)-dione in that example. ¹H NMR (DMSO): δ 1.20 (t, J=2.56 Hz, 6H), 1.30–1.80 (brm, 6H), 2.00–2.18 (brm, 5H), 2.40 (q, J=20.06 Hz 4H), 2.80 (m, 4H), 3.45 (m, 3H), 6.70 (s, 2H), 7.17 (d, J=2.54 Hz, 1H), 8.80 (m, 2H), 9.29 (s, 1H). Anal. Calcd. For $C_{28}H_{34}O_4N_4$, C, 68.55; H, 6.99, N, 11.42. Found: C, 68.80; H, 7.31; N, 11.45.

Example A(235)

6-cyclopentyl-6-[2-(3,5-diethyl-4-hydroxyphenyl) ethyl]dihydro-2H-pyran-2,4(3H)-dione

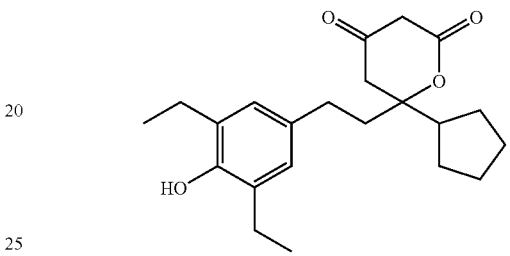

The title compound was prepared analogously to Example A(124) where 2,6-diethylphenol (Selassie, Cynthia et al. J. Chem. Soc, Perkin Trans 2. EN; 2002; 1112–1117) was used in place of 2-ethyl-5-fluorophenol in that example. ¹H NMR (CDCl₃): δ 1.17 (t, J=9.57 Hz, 6H) 1.30–2.21 (br m, 11H), 2.45, (m, 4H), 2.70–3.10 (brm, 6H), 6.69 (s, 2H). MS(APCI): 357 (M–H).

Example A(236)

1-(4-{2-[2-Cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-2-fluoro-phenyl)-cyclobutanecarbonitrile

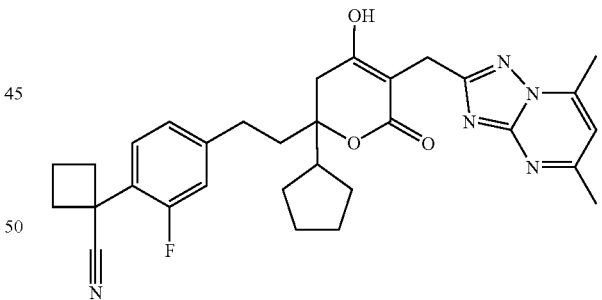

A solution of example A(237) in anhydrous MeOH (6 mL) was treated with 5,7-dimethyl-[1,2,4]triazolo[1,5-a]pyrimidine-2-carbaldehyde (0.352 g, 2.0 mmol), followed by borane-dimethylamine complex (118 mg, 2.0 mmol) at room temperature. The reaction was stirred for 2 hours, and the solids were filtered away. The organic liquid was concentrated to a thick oil, and then purified by flash chromatography (50 g SiO₂, 3:10->3:5 (93.5% ethyl acetate, 6% methanol, 0.5% acetic acid): (81.5% hexanes, 12% ethyl acetate, 6% methanol, 0.5% acetic acid)) to give the desired product as an oil. It was further purified by crystallization from ethyl acetate/hexanes to give a white powder (89 mg, 11%). ¹H NMR (400 MHz, CDCl₃) δ: 1.31–1.65 (m, 8H), 1.89–2.00 (m, 4H), 2.28–2.34 (m, 1H), 2.36–2.44 (m, 1H), 2.50 (d, J=3.54 Hz, 1H), 2.54–2.65 (m, 6H), 2.67–2.78 (m, 7H), 4.08 (d, J=4.80 Hz, 2H), 6.79 (dd, J=11.49 Hz, H), 6.84–6.81 (m, 2H), 7.04 (t, J=7.96 Hz, H).

Example A(237)

1-{4-[2-(2-Cyclopentyl-4,6-dioxo-tetrahydro-pyran-2-yl)-ethyl]-2-fluoro-phenyl}-cyclobutanecarbonitrile

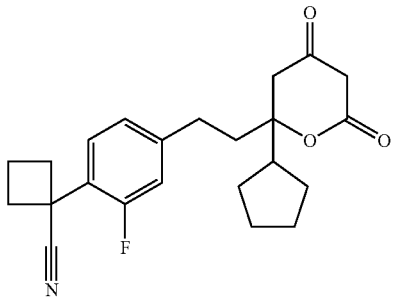

To a solution of 1-{4-[3-cyclopentyl-4-(2,2-dimethyl-6-oxo-6H-[1,3]dioxin-4-yl)-3-hydroxy-but-1-ynyl]-2-fluoro-phenyl}-cyclobutanecarbonitrile (6.0 g, 13.7 mmol) from step 3 below was added Pd(OH)$_2$/C (2.0 g) and ethanol (100 mL). The reaction was placed under a nitrogen atmosphere using a balloon filled with hydrogen. The slurry was stirred vigorously for 18 hours. The reaction was filtered to remove all of the solids, and the liquid was concentrated to an oil. The oil was dissolved in methanol (100 mL), and solution of NaOH (1.64 g, 41 mmol) dissolved in water (30 mL). The reaction was stirred for 18 hours, and then acetic acid (1 mL) was added. The liquid was concentrated to an oil, then redissolved in CH$_2$Cl$_2$, and washed with 1 N HCl. The organic layer was dried over MgSO$_4$, filtered, and then concentrated to give the desired product (4.338 g, 83%). MS (ESI): 382 (M–H$^+$).

Step 3

1-{4-[3-Cyclopentyl-4-(2,2-dimethyl-6-oxo-6H-[1,3]dioxin-4-yl)-3-hydroxy-but-1-ynyl]-2-fluoro-phenyl}-cyclobutanecarbonitrile

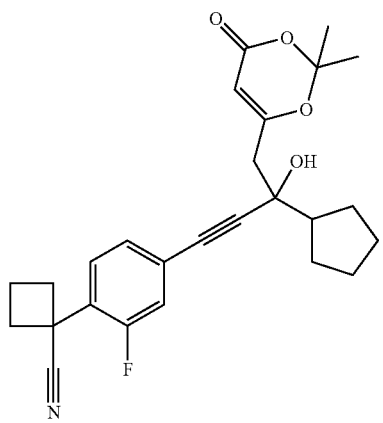

The title compound was prepared analogously to step 3 from Example A(97) where 1-(4-bromo-2-fluoro-phenyl)-cyclobutanecarbonitrile from step 2 below, was substituted in place of 2-(4-Bromo-2-fluoro-phenyl)-2-methyl-propionitrile in step 3 of that example. MS (ESI): 438.0 (M+H$^+$).

Step 2

1-(4-Bromo-2-fluoro-phenyl)-cyclobutanecarbonitrile

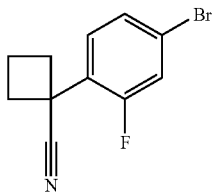

A solution of (4-bromo-2-fluoro-phenyl)-acetonitrile (4.0 g, 18.7 mmol) from step 1 and 1,3-dibromopropane (2.1 mL, 20.6 mmol) in Et$_2$O (5 mL) was slowly added to a slurry of NaH (1.64 g, 41.1 mmol, 60% in mineral oil) in DMSO (19 mL) at room temperature, being careful to keep the temperature below 35 degrees Celsius. The reaction was stirred for 2.5 hours, and then poured into 150 mL of saturated ammonium chloride. To this mixture was added CH$2_2$Cl$_2$, and the layers were separated. The aqueous layer was extracted with 2×50 mL of CH$_2$Cl$_2$, and the organic layers were combined. After drying the liquid over MgSO$_4$, the solids were filtered away, and the organic was concentrated to an oil. It was further purified by flash chromatography (90 g SiO$_2$, 1:99->1:20 (EtOAc/Hexanes) to give the desired product (2.81 g, 59%). $^1$H NMR (400 MHz, CDCl$_3$) δ: 2.06–2.16 (m, H), 2.51–2.63 (m, H), 2.66–2.76 (qd, J=9347 Hz, 2H), 2.86–2.94 (m, 2H), 7.16–7.22 (t, J=8.21 Hz, H), 7.30–7.41 (m, 2H).

Step 1

(4-Bromo-2-fluoro-phenyl)-acetonitrile

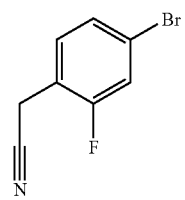

To a solution of 4-bromo-1-bromomethyl-2-fluoro-benzene (100 g, 373 mmol) in DMF (190 mL) and water (10 mL) was added sodium cyanide (22 g, 448 mmol). The reaction was heated to 70 degrees Celsius for 3 hours, concentrated to a volume of 100 mL, and then the solution was diluted with 100 mL of ethyl acetate. After the solids were removed by filtration, water (250 mL) was added and the layers were separated. The organic layer was further washed with 3×100 mL of water. The organic layer was dried over MgSO$_4$, filtered to remove solids, and then concentrated. Purification by distillation gave the desired product (37.124 g, 46%). B.P.=72–75 degrees Celsius.

Example A(238)

1-[4-[2-(2-Cyclopentyl-4-hydroxy-6-oxo-5-[1,2,4]triazolo[1,5-a]pyrimidin-2-ylmethyl-3,6-dihydro-2H-pyran-2-yl)-ethyl]-2-fluoro-phenyl}-cyclobutanecarbonitrile

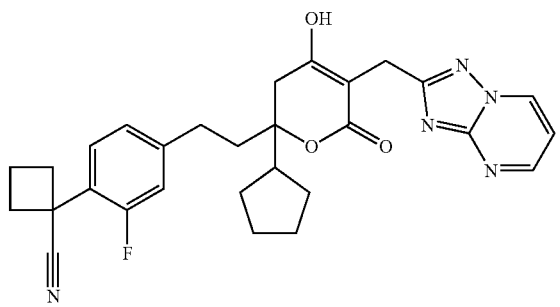

The title compound was prepared analogously to example A(236) substituting [1,2,4]triazolo[1,5-a]pyrimidine-2-carbaldehyde in place of 5,7-dimethyl-[1,2,4]triazolo[1,5-a]pyrimidine-2-carbaldehyde. $^1$H NMR (400 MHz, CDCl$_3$) δ: 1.35–1.56 (m, 8H), 1.79–1.89 (m, 3H), 2.19–2.25 (m, 1H), 2.27–2.33 (m, 1H), 2.43–2.54 (m, 5H), 2.59–2.69 (m, 4H), 3.98–4.06 (m, 2H), 6.69 (dd, J1=1.52 Hz, J2=11.62 Hz, 1H), 6.76 (dd, J1=7.83 Hz, J2=1.52 Hz, 1H), 6.94 (t, J=7.96 Hz, 1H), 7.11 (dd, J1=6.82 Hz, J2=4.29 Hz, 1H), 8.66 (dd, J1=6.69 Hz, J2=1.89 Hz, 1H), 8.71 (dd, J1=4.42 Hz, J2=1.89 Hz, 1H).

Example A(239)

1-(4-{2-[2-Cyclopentyl-4-hydroxy-5-(6-methyl-[1,2,4]triazolo[1,5-a]pyrimidin-2-ylmethyl)-6-oxo-3,6-dihydro-2H-pyran-2-yl]-ethyl}-2-fluoro-phenyl)-cyclobutanecarbonitrile

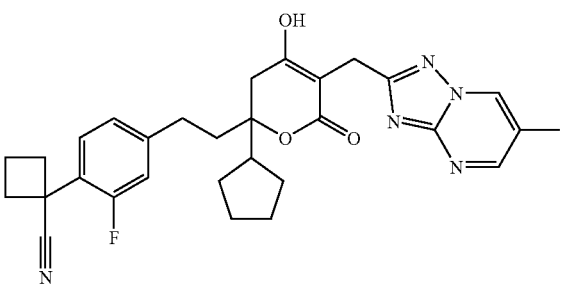

The title compound was prepared analogously to example A(236) substituting 6-methyl-[1,2,4]triazolo[1,5-a]pyrimidine-2-carbaldehyde in place of 5,7-dimethyl-[1,2,4]triazolo[1,5-a]pyrimidine-2-carbaldehyde. $^1$H NMR (400 MHz, CDCl$_3$) δ: 1.54–1.82 (m, 8H), 2.01–2.13 (m, 3H), 2.38–2.48 (m, 2H), 2.48–2.57 (m, 4H), 2.67–2.77 (m, 4H), 2.82–2.85 (m, 1H), 2.88 (d, J=6.06 Hz, 2H), 4.19 (s, 2H), 6.92 (dd, J1=11.62 Hz, J2=1.26 Hz, 1H), 6.99 (d, J=8.08 Hz, 1H), 7.17 (t, J=7.96 Hz, 1H), 8.69 (s, 1H), 8.78 (d, J=1.52 Hz, 1H).

Example A(240)

2-(4-{2-[2-Cyclopentyl-4-hydroxy-5-(6-methyl-[1,2,4]triazolo[1,5-a]pyrimidin-2-ylmethyl)-6-oxo-3,6-dihydro-2H-pyran-2-yl]-ethyl}-2-fluoro-phenyl)-propionitrile

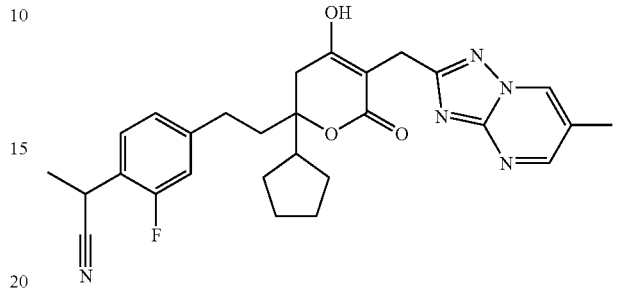

The title compound was prepared analogously to example A(236) substituting 2-{4-[2-(2-cyclopentyl-4,6-dioxo-tetrahydro-pyran-2-yl)-ethyl]-2-fluoro-phenyl}-propionitrile from example A(241) in place of 1-(4-{2-[2-cyclopentyl-5-(5,7-dimethyl-[1,2,4]triazolo[1,5 -a]pyrimidin-2-ylmethyl)-4-hydroxy-6-oxo-3,6-dihydro-2H-pyran-2-yl]-ethyl}-2-fluoro-phenyl)-cyclobutanecarbonitrile and 6-methyl-[1,2,4]triazolo[1,5-a]pyrimidine-2-carbaldehyde in place of 5,7-dimethyl-[1,2,4]triazolo[1,5-a]pyrimidine-2-carbaldehyde. $^1$H NMR (400 MHz, CDCl$_3$) δ: 1.66–2.00 (m, 8H), 2.30 (s, 2H), 2.36 (s, 2H), 2.49–2.62 (m, 4H), 2.69–2.85 (m, 3H), 3.49–3.59 (m, 1H), 3.89–3.94 (m, 1H), 4.01–4.08 (m, 2H), 4.18 (s, 1H).

Example A(241)

2-{4-[2-(2-Cyclopentyl-4,6-dioxo-tetrahydro-pyran-2-yl)-ethyl]-2-fluoro-phenyl}-propionitrile

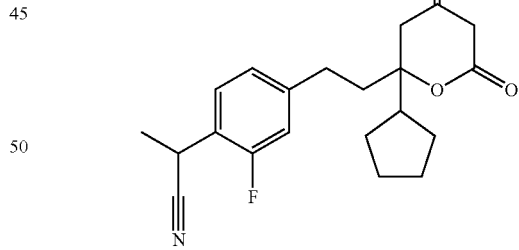

The title compound was prepared analogously to example A(237) substituting 2{4-[3-cyclopentyl-4-(2,2-dimethyl-6-oxo-6H-[1,3]dioxin-4-yl)-3-hydroxy-but-1-ynyl]-2-fluoro-phenyl}-propionitrile from step 2 below in place of 1-{4-[3-cyclopentyl-4-(2,2-dimethyl-6-oxo-6H-[1,3]dioxin-4-yl)-3-hydroxy-but-1-ynyl]-2-fluoro-phenyl}-cyclobutanecarbonitrile. $^1$H NMR (400 MHz, CDCl$_3$) δ: 1.33–1.50 (m, 3H), 1.56 (d, J=7.33 Hz, 3H), 1.62–1.75 (m, 5H), 1.85–1.93 (m, 2H), 2.15–2.26 (m, 1H), 2.58–2.68 (m, 3H), 2.72 (d, J=6.57 Hz, 2H), 3.38 (d, J=3.54 Hz, 2H), 4.09 (q, J=7.33 Hz, 1H), 6.84 (d, J=11.12 Hz, 1H), 6.93 (d, J=7.83 Hz, 1H), 7.34 (t, J=7.83 Hz, 1H).

Step 2

2-{4-[3-Cyclopentyl-4-(2,2-dimethyl-6-oxo-6H-[1,3]dioxin-4-yl)-3-hydroxy-but-1-ynyl]-2-fluoro-phenyl}-propionitrile

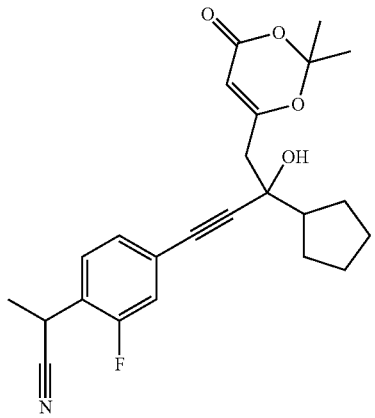

The title compound was prepared analogously to 1-{4-[3-Cyclopentyl-4-(2,2-dimethyl-6-oxo-6H-[1,3]dioxin-4-yl)-3-hydroxy-but-1-ynyl]-2-fluoro-phenyl}-cyclobutanecarbonitrile in step 3 of example A(236) substituting 2-(4-bromo-2-fluoro-phenyl)-propionitrile from step 1 below in place of 1-(4-bromo-2-fluoro-phenyl)-cyclobutanecarbonitrile. MS (ESI): 437.0 (M+H$^+$).

Step 1

2-(4-Bromo-2-fluoro-phenyl)-propionitrile

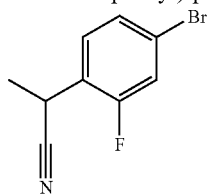

The title compound was prepared analogously to 1-(4-Bromo-2-fluoro-phenyl)-cyclobutanecarbonitrile in step 2 of example A(236) substituting iodomethane in place of 1,3-dibromopropane. MS (APCI): 253 (M+H$^+$), 255 (M+2+H$^+$).

Example A(242)

(+)-1-(4-{2-[2-Cyclopentyl-5-(6-methyl-[1,2,4]triazolo[1,5-a]pyrimidin-2-ylmethyl)-4,6-dioxo-tetrahydro-pyran-2-yl]-ethyl}-2-fluoro-phenyl)-cyclopropanecarbonitrile

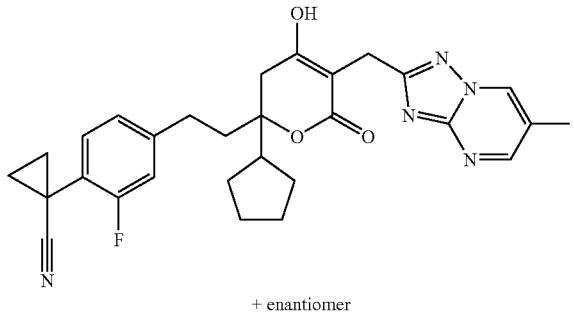

+ enantiomer

The title compound was prepared by using chiral SFC to separate the racemic example A(113). Optical rotation determined to be (+).

Example A(243)

(−)-1-(4-{2-[2-Cyclopentyl-5-(6-methyl-[1,2,4]triazolo[1,5-a]pyrimidin-2-ylmethyl)-4,6-dioxo-tetrahydro-pyran-2-yl]-ethyl}-2-fluoro-phenyl)-cyclopropanecarbonitrile

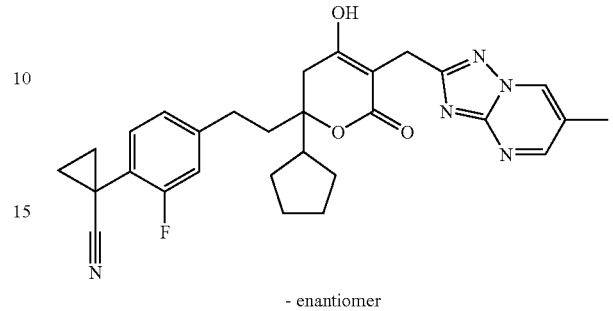

- enantiomer

The title compound was prepared by using chiral SFC to separate the racemic example A(113). Optical rotation determined to be (−).

Example A(244)

(+)-1-{4-[2-(2-Cyclopentyl-4,6-dioxo-5-[1,2,4]triazolo[1,5-a]pyrimidin-2-ylmethyl-tetrahydro-pyran-2-yl)-ethyl]-2-fluoro-phenyl}-cyclopropanecarbonitrile

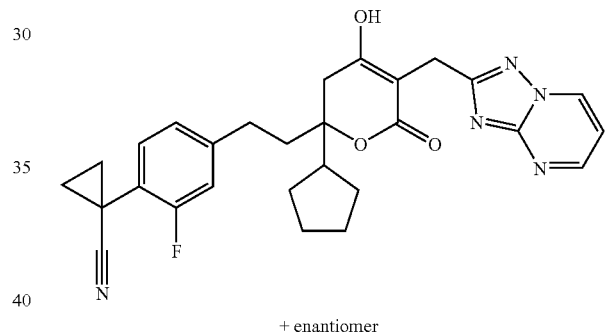

+ enantiomer

The title compound was prepared by using chiral SFC to separate the racemic example A(114). Optical rotation determined to be (+).

Example A(245)

(−)-1-{4-[2-(2-Cyclopentyl-4,6-dioxo-5-[1,2,4]triazolo[1,5-a]pyrimidin-2-ylmethyl-tetrahydro-pyran-2-yl)-ethyl]-2-fluoro-phenyl}-cyclopropanecarbonitrile

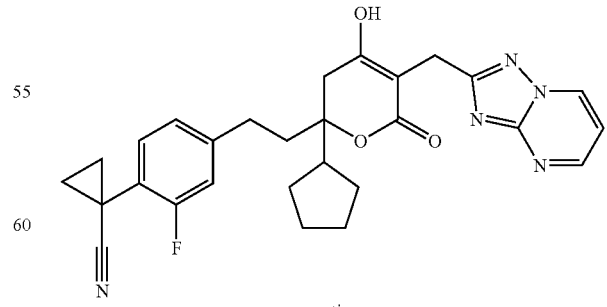

- enantiomer

The title compound was prepared by using chiral SFC to separate the racemic example A(114). Optical rotation determined to be (−).

Example A(246)

(+)-1-(4-{2-[5-(6-Chloro-[1,2,4]triazolo[1,5-a]pyrimidin-2-ylmethyl)-2-cyclopentyl-4,6-dioxo-tetrahydro-pyran-2-yl]-ethyl}-2-fluoro-phenyl)-cyclopropanecarbonitrile

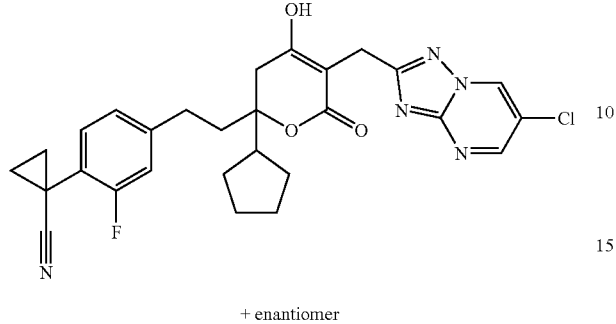

+ enantiomer

The title compound was prepared by using chiral SFC to separate the racemic example A(115). Optical rotation determined to be (+).

Example A(247)

(−)-1-(4-{2-[5-(6-Chloro-[1,2,4]triazolo[1,5-a]pyrimidin-2-ylmethyl)-2-cyclopentyl-4,6-dioxo-tetrahydro-pyran-2-yl]-ethyl}-2-fluoro-phenyl)-cyclopropanecarbonitrile

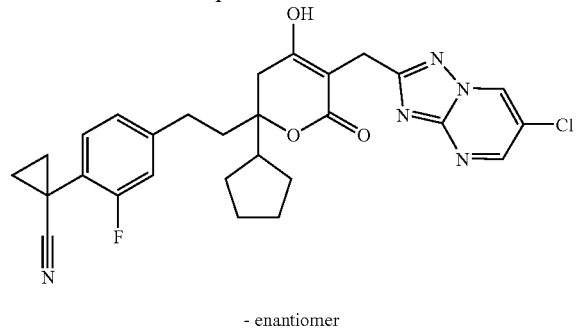

− enantiomer

The title compound was prepared by using chiral SFC to separate the racemic example A(115). Optical rotation determined to be (−).

Example A(248)

(+)-2-(4-{2-[5-(6-Chloro-[1,2,4]triazolo[1,5-a]pyrimidin-2-ylmethyl)-2-cyclopentyl-4,6-dioxo-tetrahydro-pyran-2-yl]-ethyl}-2-fluoro-phenyl)-2-methyl-propionitrile

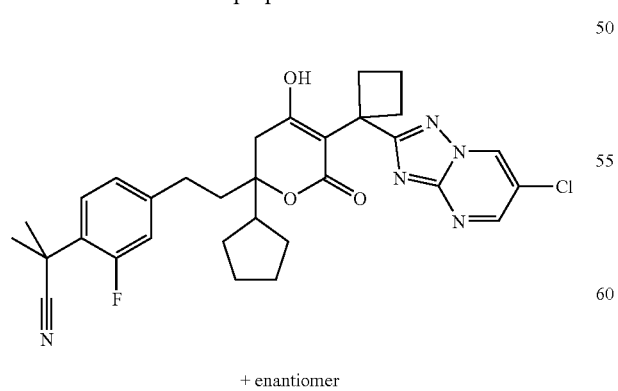

+ enantiomer

The title compound was prepared by using chiral SFC to separate the racemic example A(111) Optical rotation determined to be (+).

Example A(249)

(−)-2-(4-{2-[5-(6-Chloro-[1,2,4]triazolo[1,5-a]pyrimidin-2-ylmethyl)-2-cyclopentyl-4,6-dioxo-tetrahydro-pyran-2-yl]-ethyl}-2-fluoro-phenyl)-2-methyl-propionitrile

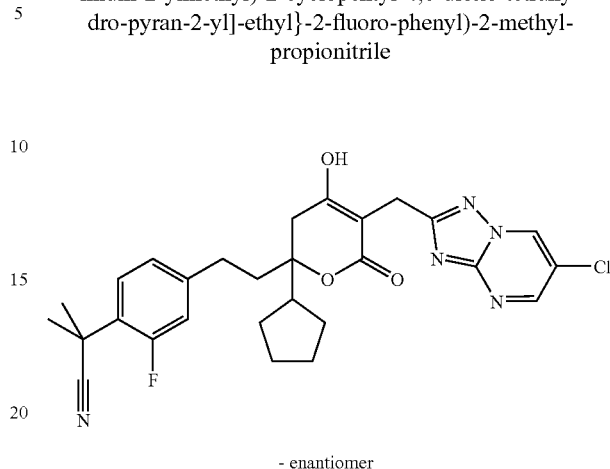

− enantiomer

The title compound was prepared by using chiral SFC to separate the racemic A(15). Optical rotation determined to be (−).

Step 2

Preparation of Compound 6-chloro[1,2,4]triazolo[1,5-a]pyrimidine-2-carbaldehyde

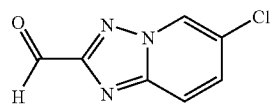

A mixture of (6-chloro[1,2,4]triazolo[1,5-a]pyrimidin-2-yl)methanol (9.86 g, 53.4 mmol), TEMPO (626 mg, 4.01 mmol), iodobenzene diacetate (18.9 g, 58.76 mmol) in $CH_2Cl_2$ (75 mL) was stirred at room temperature for 2 hours. Once the reaction was deemed complete, methyl-tert-butyl ether (50 mL) was added slowly to precipitate the product. as a while solid (8.72 g, 90%). $^1$H NMR (300 MHz, CDCl$_3$) δ: 8.93 (d, J=2.45 Hz, 1 H), 8.99 (d, J=2.64 Hz, 1 H), 10.25 (s, 1H). MS (APCI): 183.0, 185.0 (M+H$^+$).

Step 1

Preparation of Compound (6-chloro[1,2,4]triazolo[1,5-a]pyrimidin-2-yl)methanol

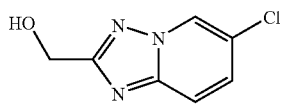

To a slurry of (3-amino-1H-1,2,4-triazol-5-yl)methanol (28.5 g, 150 mmol) in acetic acid was added chloromalonal dehyde (16 g, 150 mmol). The mixture was heated to 80° C. for 4 hours. Upon cooling of the reaction to room temperature, the product crystallized out as a white solid (25.5 g, 92%). ¹H NMR (300 MHz, DMSO-D6) δ: 4.67 (s, 2 H), 5.62 (s, 1 H), 8.94 (d, J=2.45 Hz, 1 H), 9.81 (d, J=2.45 Hz, 1 H). MS (APCI): 185.0 (M+H⁺).

Example A(250)

(−)-1-(4-{2-[2-Cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-2-fluoro-phenyl)-cyclopropanecarbonitrile

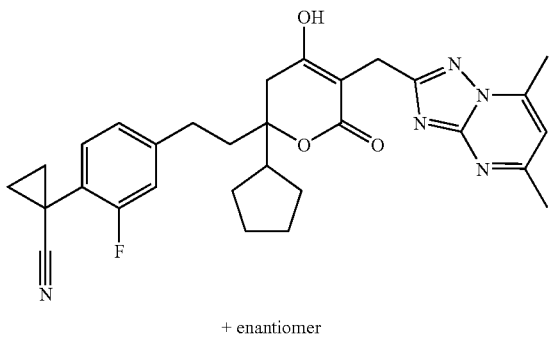

+ enantiomer

The title compound was prepared by using chiral SFC to separate the racemic 1-(4-{2-[5-(6-Chloro-[1,2,4]triazolo[1,5-a]pyrimidin-2-ylmethyl)-2-cyclopentyl-4,6-dioxo-tetrahydro-pyran-2-yl]-ethyl}-2-fluoro-phenyl)-cyclopropanecarbonitrile. Optical rotation determined to be (−).

Example A(251)

(+)-1-(4-{2-[2-Cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-2-fluoro-phenyl)-cyclopropanecarbonitrile

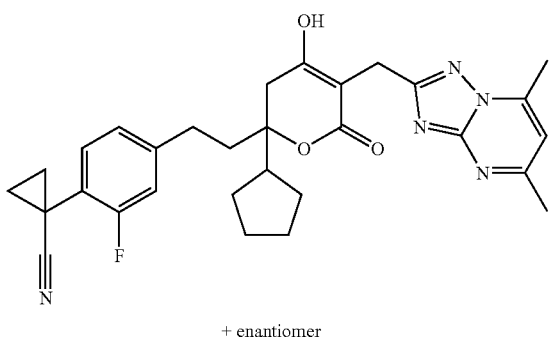

+ enantiomer

The title compound was prepared by using chiral SFC to separate the racemic 1-(4-{2-[5-(6-Chloro-[1,2,4]triazolo[1,5-a]pyrimidin-2-ylmethyl)-2-cyclopentyl-4,6-dioxo-tetrahydro-pyran-2-yl]-ethyl}-2-fluoro-phenyl)-cyclopropanecarbonitrile. Optical rotation determined to be (+).

Example A(252)

2-(4-{2-[2-Cyclopentyl-5-(6-ethyl-[1,2,4]triazolo[1,5-a]pyrimidin-2-ylmethyl)-4-hydroxy-6-oxo-3,6-dihydro-2H-pyran-2-yl]-ethyl}-2,6-difluoro-phenyl)-2-methyl-propionitrile (3428-187 PF-00389530)

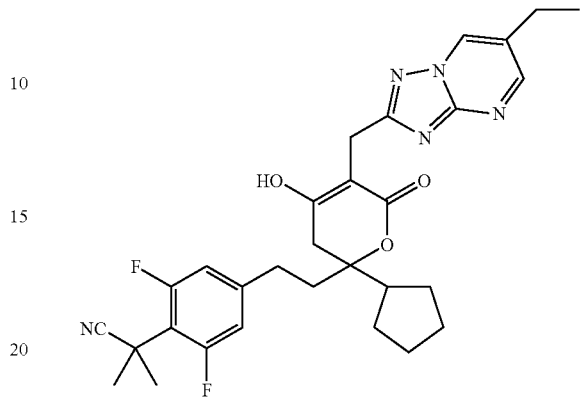

A solution of 2-{4-[2-(2-Cyclopentyl-4-hydroxy-6-oxo-3,6-dihydro-2H-pyran-2-yl)-ethyl]-2,6-difluoro-phenyl}-2-methyl-propionitrile (272 mg, 0.7 mmol) in anhydrous MeOH (1.5 mL) was treated with 6-ethyl-[1,2,4]triazolo[1,5-a]pyrimidine-2-carbaldehyde (324 mg, 2.0 mmol), followed by borane-dimethylamine complex (191.7 mg, 1.05 mmol) at room temperature. The reaction was stirred for 12 hours. The precipitate was removed by filtration, and the filtrate was concentrated to a crude oil. The crude oil was purified by flash chromatography (25 g SiO₂, 1:3:1:0 (93.5% ethyl acetate, 6% methanol, 0.5% acetic acid): (81.5% hexanes, 12% ethyl acetate, 6% methanol, 0.5% acetic acid)) to give product as an oil. It was further purified by preparatory HPLC. Yield: 19.0 mg, 8.0%. ¹H NMR (CDCl₃) δ: 1.37 (t, J=3.75 Hz, 3H)), 1.48–1.75 (m, 8H), 1.84 (s, 6H), 1.91–2.02 (m, 2H), 2.32–2.49 (m, 3H), 2.61–2.70 (m, 2H), 2.79–2.86 (m, 2H), 4.10 (s, 2H), 6.69 (d, J=10.86 Hz, 2H), 8.62 (s, 1H), 8.73 (s, 1H). MS (ESI): 548 (M−H).

Example A(253)

2-(4-{2-[2-Cyclopentyl-4-hydroxy-5-(5-methyl-[1,2,4]triazolo[1,5-a]pyrimidin-2-ylmethyl)-6-oxo-3,6-dihydro-2H-pyran-2-yl]-ethyl}-2,6-difluoro-phenyl)-2-methyl-propionitrile (3428-020 PF-00460708)

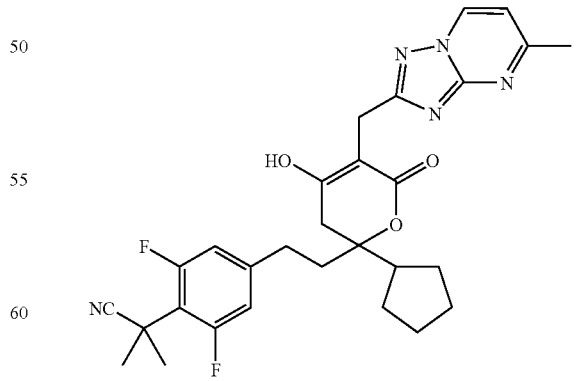

The desired product was prepared analogously to Example A (112), substituting 5-Methyl-[1,2,4]triazolo[1,5-a]pyrimidine-2-carbaldehyde (86.0 mg, 0.53 mmol) in place of 5,7-dimethyl[1,2,4]triazolo[1,5-a]pyrimidine-2-carbalde-

Example A(254)

2-(4-{2-[2-Cyclopentyl-5-(5,7-dimethyl-1,2,4]triazolo[1,5-a]pyrimidin-2-ylmethyl)-4-hydroxy-6-oxo-3,6-dihydro-2H-pyran-2-yl]-ethyl}-2,6-difluoro-phenyl)-2-methyl-propionitrile (3428-192 PF-00398981)

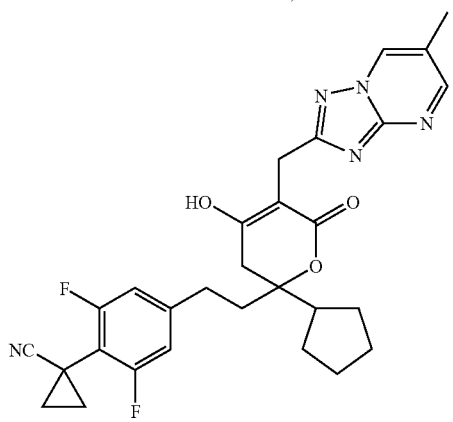

The desired product was prepared analogously to Example A (112), substituting 1{4-[2-(2-Cyclopentyl-4,6-dioxo-tetrahydro-pyran-2-yl)-ethyl]-2,6-difluoro-phenyl}cyclopropanecarbonitrile in place of 2-{4-[2-(2-Cyclopentyl-4,6-dioxo-tetrahydro-pyran-2-yl)-ethyl]-2-fluoro-phenyl}-2-ethyl-butyronitrile. Yield: 18.0 mg, 5.0%. $^1$H NMR (CDCl$_3$) δ: 1.34 (t, J=2.50 Hz, 2H), 1.63–1.74 (m, 9H), 1.81–1.91 (m, 2H), 2.36–2.44 (m, 4H), 2.49 (s, 3H), 2.64–2.74 (m, 4H), 4.10 (s, 2H), 6.70 (d, J=7.4 Hz, 2H), 8.62 (d, J=2.3 Hz, 1H), 8.70 (d, J=2.2 Hz, 1H). MS (ESI): 532 (M−1).

Example A(255)

1-{4-[2-(2-Cyclopentyl-4,6-dioxo-tetrahydro-pyran-2-yl)-ethyl]-2,6-difluoro-phenyl}-cyclopropanecarbonitrile

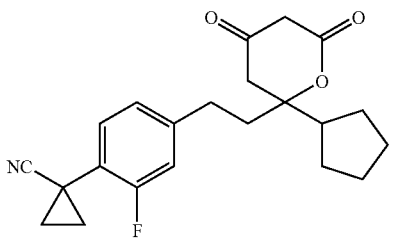

The desired product was prepared analogously to step of example A (97), substituting 1-{4-[3-Cyclopentyl-4-(2,2-dimethyl-6-oxo-6H-[1,3]dioxin-4-yl)-3-hydroxy-but-1-ynyl]-2,6-difluorophenyl}-cyclopropanecarbonitrile (1.0 g, 2.66 mmol) from Step 2 below in place of 2{4-[3-cyclopentyl-4-(2,2-dimethyl-4-oxo-4H-1,3-dioxin-6-yl)-3-hydroxy-but-1-ynyl]-2-fluorophenyl}-2-methylpropanenitrile. Yield: 0.43 g, 42%. δ: $^1$H NMR (CDCl$_3$) δ: 1.35 (t, J=2.8 Hz, 2H), 1.56–1.73 (m, 10H), 1.92 (t, J=4.45 Hz, 2H), 2.21–2.30 (m, 1H), 2.65–2.79 (m, 4H), 3.44 (d, J=5.6 Hz, 2H), 6.71(d, J=8.6 Hz, 2H). MS (ESI): 386 (M−1).

Step 2

1-{4-[3-Cyclopentyl-4-(2,2-dimethyl-6-oxo-6H-[1,3]dioxin-4-yl)-3-hydroxy-but-1-ynyl]-2,6-difluorophenyl}-cyclopropanecarbonitrile

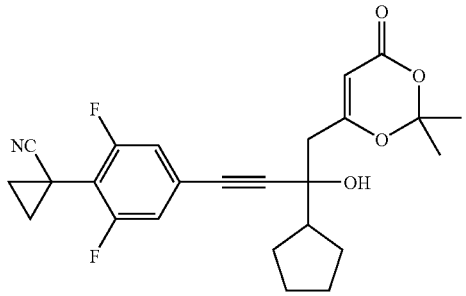

The desired product was prepared analogously to Example A (97) step 3, substituting 1-(4-Bromo-2,6-difluoro-phenyl)-cyclopropanecarbonitrile (1.07 g, 4.16 mmol) from step 1 below in place of 1-(4-bromo-2-fluoro-phenyl)-cyclopropanecarbonitrile. Yield: 1.20 g, 80.0%. $^1$H NMR (CDCl$_3$) δ: 1.37 (t, J=2.8 Hz, 2H), 1.62–1.70 (m, 6H), 1.72 (s, 3H), 1.73 (s, 3H), 1.74–1.83 (m, 4H), 2.22–2.27 (m, 1H), 2.66 (s, 2H), 5.44 (s, 1H), 6.92 (d, J=8.0 Hz, 2H). MS (ESI): 440 (M−1).

Step 1

1-(4-Bromo-2,6-difluoro-phenyl)-cyclopropanecarbonitrile

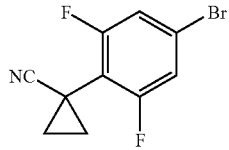

The desired product was prepared analogously to Example A (141) step 3, substituting 1,2-bromoethane in place of MeI. Yield: 1.07 g, 74.4%. $^1$H NMR (CDCl$_3$) δ: 1.36 (t, 2.8 Hz, 2H), 1.77 (t, J=2.7 Hz, 2H), 7.13 (d, J=6.8 Hz, 2H).

Example A(256)

1-(4-{2-[5-(6-Chloro-[1,2,4]triazolo[1,5-a]pyrimidin-2-ylmethyl)-2-cyclopentyl-4-hydroxy-6-oxo-3,6-dihydro-2H-pyran-2-yl]-ethyl}-2,6-difluoro-phenyl)-cyclopropanecarbonitrile

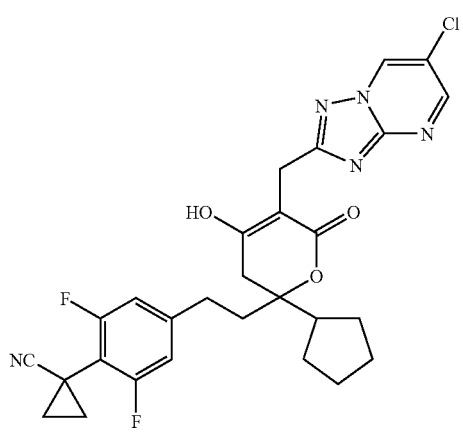

The desired product was prepared analogously to Example A (112), substituting 6-Chloro-[1,2,4]triazolo[1,5- a]pyrimidine-2-carbaldehyde (180.9 mg, 1.0 mmol) in place of 5,7-Dimethyl-[1,2,4]triazolo[1,5-a]pyrimidine-2-carbaldehyde. Yield: 85.0 mg, 23%. $^1$H NMR (CDCl$_3$) δ: 1.34 (t, J=2.70 Hz, 2H), 1.69–1.71 (m, 4H), 1.94–1.99 (m, 3H), 2.35–2.49 (m, 4H), 2.65–2.78 (m, 4H), 3.42 (d, J=3.8 Hz, 2H), 4.11 (d, J=4.0 Hz, 2H), 6.70 (d, J=4.6 Hz), 8.80 (s, 1H), 8.87 (s, 1H). MS (ESI): 552 (M−1).

Example A(257)

(+)-2-(4-{2-[2-Cyclopentyl-4-hydroxy-5-(6-methyl-[1,2,4]triazolo[1,5a]pyrimidin-2-ylmethyl)-6-oxo-3,6-dihydro-2H-pyran-2-yl]ethyl}-2,6-difluoro-phenyl)-2-methyl-propionitrile

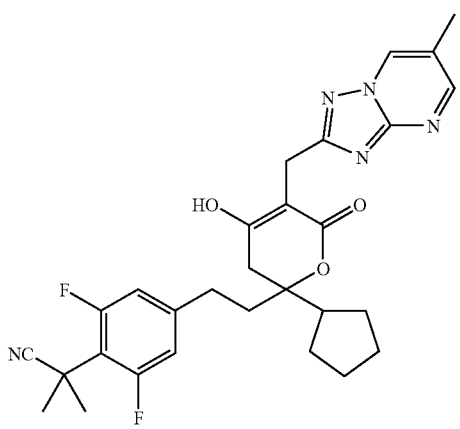

(+) enantiomer

The title compound was isolated by chiral SFC of racemic material described in example A (143) Condition: ChiralPac AS-H column, 250×4.6 mm, 120 bar, 30% MeOH, 50 mL/min, retention time 4.84 min.

Example A(258)

(−)-2-(4-{2-[2-Cyclopentyl-4-hydroxy-5-(6-methyl-[1,2,4]triazolo[1,5-a]pyrimidin-2-ylmethyl)-6-oxo-3,6-dihydro-2H-pyran-2-yl]-ethyl}-2,6-difluoro-phenyl)-2-methyl-propionitrile (3428-175 PF-00419774)

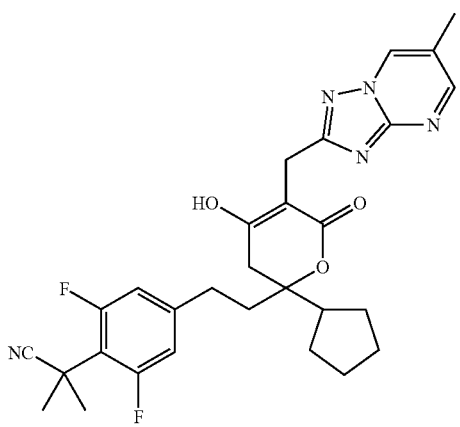

(−) enantiomer

The title compound was isolated by chiral SFC of racemic material described in example A (143) Condition: ChiralPac AS-H column, 250×4.6 mm, 120 bar, 30% MeOH, 50 mL/min, retention time 2.85 min.

Example A(259)

(+)-2-(4-{2-[5-(6-Chloro-[1,2,4]triazolo[1,5-a]pyrimidin-2-ylmethyl)-2-cyclopentyl-4-hydroxy-6-oxo-3,6-dihydro-2H-pyran-2-yl]-ethyl}-2,6-difluoro-phenyl)-2-methyl-propionitrile

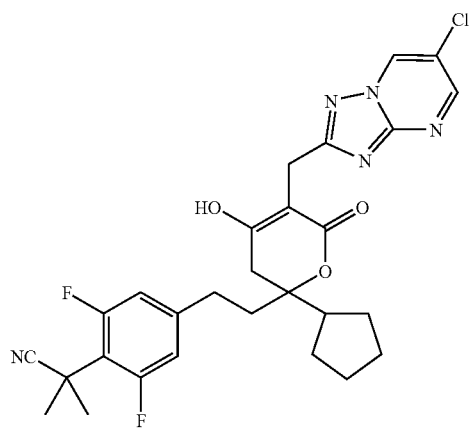

(+) enantiomer

The title compound was isolated by chiral SFC of racemic material described in example A (142) Condition: ChiralPac AS-H column, 250×20 mm, 110 bar, 30% MeOH, 2.5 mL/min, retention time 4.86 min.

Example A(260)

(−)-2-(4-{2-[5-(6-Chloro-[1,2,4]triazolo[1,5-a]pyrimidin-2-ylmethyl)-2-cyclopentyl-4-hydroxy-6-oxo-3,6-dihydro-2H-pyran-2-yl]-ethyl}-2,6-difluoro-phenyl)-2-methyl-propionitrile

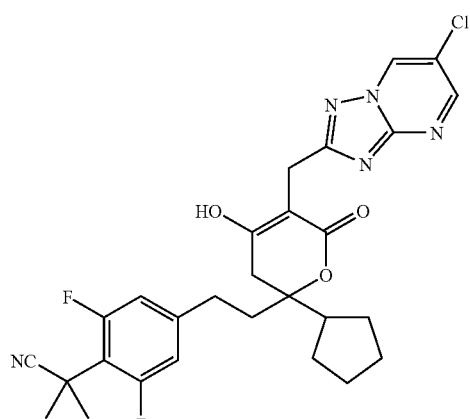

(−) enantiomer

The title compound was isolated by chiral SFC of racemic material described in example A (142) Condition: ChiralPac AS-H column, 250×20 mm, 110 bar, 30% MeOH, 2.5 mL/min, retention time 3.31 min.

Example A(261)

2-(4-{2-[2-Cyclopentyl-4-hydroxy-5-(6-methyl-[1,2,4]triazolo[1,5-a]pyrimidin-2-ylmethyl)-6-oxo-3,6-dihydro-2H-pyran-2-yl]-ethyl}-2-fluoro-5-methoxy-phenyl)-2-methyl-propionitrile

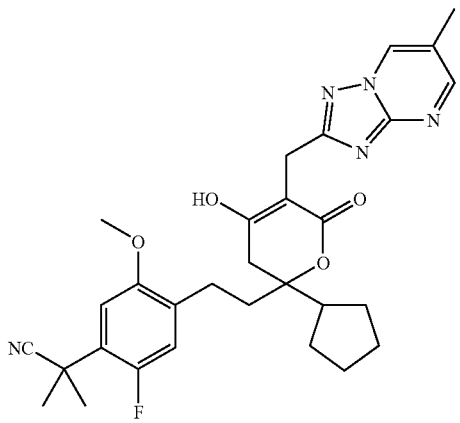

The desired product was prepared analogously to Example A (112), substituting 2-{4-[2-(2-Cyclopentyl-4-hydroxy-6-oxo-3,-dihydro-2H-pyran-2-yl)-ethyl]-2-fluoro-5-methoxy-phenyl}-2-methyl-propionitrile from Step 4 below in place of 2-{4-[2-(2-Cyclopentyl-4,6-dioxo-tetrahydro-pyran-2-yl)-ethyl]-2-fluoro-phenyl}-2-ethyl-butyronitrile. Yield: 0.071 g, 16%. $^1$H NMR (CDCl$_3$) δ: 1.54–1.63 (m, 4H), 1.77 (s, 6H), 1.91–1.97 (s, 4H), 2.37–2.45 (m, 1H), 2.48 (s, 3H), 2.57–2.80 (m, 4H), 3.75–3.85 (m, 5H), 4.10 (d, J=5.5 HZ, 2H), 6.84 (d, J=2.1 Hz, 1H), 6.89 (d, 6.6 Hz, 1H), 8.62 (d, J=2.3 Hz, 1H), 8.69 (d, J=2.2 Hz, 1H). MS (ESI): 546 (M−1).

Step 4

2-{4-[2-(2-Cyclopentyl-4-hydroxy-6-oxo-3,6-dihydro-2H-pyran-2-yl)-ethyl]-2-fluoro-5-methoxy-phenyl}-2-methyl-propionitrile

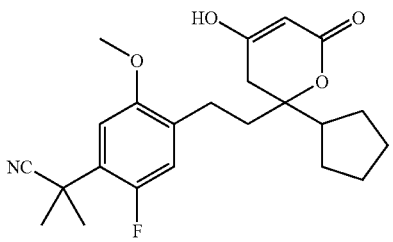

The desired product was prepared analogously to Example A (97), step 4, substituting 2-{4-[3-Cyclopentyl-4-(2,2-dimethyl-6-oxo-6H-[1,3]dioxin-4-yl)-3-hydroxy-but-1-ynyl]-2-fluoro-5-methoxy-phenyl}-2-methyl-propionitrile (2.0 g, 4.39 mmol) from Step 6 below in place of 2-{4-[3-cyclopentyl-4-(2,2-dimethyl-4-oxo-4H-1,3-dioxin-6-yl)-3-hydroxybut-1-ynyl]-2-fluorophenyl}-2-methylpropanenitrile. Yield: 0.87 g, 49%. $^1$H NMR (CDCl$_3$) δ: 1.39–1.48 (m, 2H), 1.59–1.68 (m, 5H), 1.79 (s, 6H), 1.83–1.95 (m, 3H), 2.30–2.37 (m, 1H), 2.54–2.69 (m, 4H), 3.83 (s, 3H), 5.30 (s, 1H), 6.86 (d, J=11.9 Hz, 1H), 6.95 (d, J=6.6 Hz, 1H). MS (ESI): 400 (M−1).

Step 6

2-{4-[3-Cyclopentyl-4-(2,2-dimethyl-6-oxo-6H-[1,3]dioxin-4-yl)-3-hydroxy-but-1-ynyl]-2-fluoro-5-methoxy-phenyl}-2-methyl-propionitrile

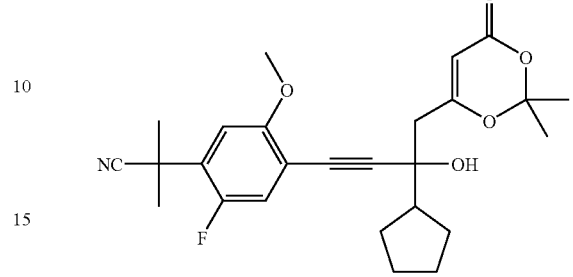

The desired product was prepared analogously to Example A (97) step 3, substituting 2-(4-Bromo-2,6-difluoro-phenyl)-2-methyl-propionitrile (5.2 g, 20.32 mmol) from step 5 below in place of 1-(4-bromo-2-fluoro-phenyl)-cyclopropanecarbonitrile. Yield: 8.72 g, 96.0%. $^1$H NMR (CDCl$_3$) δ: 1.50–1.61 (m, 8H), 1.72 (s, 3H), 1.75 (s, 3H), 1.80 (s, 6H), 2.20–2.29 (m, 1H), 2.61 (s, 1H), 2.65 (d, J=9.1 Hz, 2H), 3.87 (s, 3H), 5.53 (s, 1H), 7.00 (d, J=6.5 Hz, 1H), 7.03 (d, J=11.6 Hz, 1H). MS (ESI): 454 (M−1).

Step 5

2-(4-Bromo-2-fluoro-5-methoxy-phenyl)-2-methyl-propionitrile

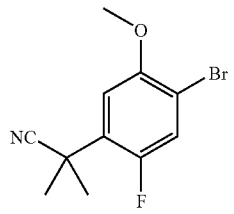

The desired product was prepared analogously to Example A (97) step 2, substituting (4-Bromo-2-fluoro-5-methoxy-phenyl)-acetonitrile (1.95 g, 8.0 mmol) from step 4 below in place of 1-(4-bromo-2-fluoro-phenyl)-cyclopropanecarbonitrile. Yield: 8.72 g, 96.0%. $^1$H NMR (CDCl$_3$) δ: 1.34 (s, 6H), 3.92 (s, 3H), 7.06 (d, J=6.8 Hz, 1H), 7.33 (d, J=10.6 Hz, 1H).

Step 4

(4-Bromo-2-fluoro-5-methoxy-phenyl)-acetonitrile

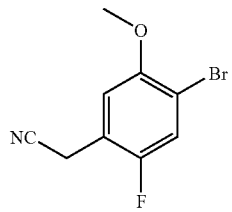

The desired product was prepared analogously to Example A (97) step 1, substituting (4-Bromo-2-fluoro-5-methoxy-phenyl)-acetonitrile (1.95 g, 8.0 mmol) from step 3 below in place of 1-(4-bromo-2-fluoro-phenyl)-cyclopropanecarbonitrile. Yield: 2.26 g, 99.9%. $^1$H NMR (CDCl$_3$) δ: 3.74 (s, 2H), 3.91 (s, 3H), 6.95 (d, J=6.4 Hz, 1H), 7.35 (d, J=4.6 Hz, 1H).

Step 3

1-Bromo-4-bromomethyl-5-fluoro-2-methoxy-benzene

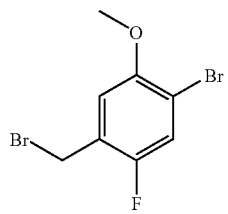

The desired product was prepared analogously to Example A (141) step 1, substituting (4-Bromo-2-fluoro-5-methoxy-phenyl)-acetonitrile (1.95 g, 8.0 mmol) from step 3 below in place of 1-(4-bromo-2-fluoro-phenyl)-cyclopropanecarbonitrile. Yield: 2.45 g, 82.2%. $^1$H NMR (CDCl$_3$) δ: 3.82 (s, 3H), 4.40 (s, 2H), 6.82 (d, J=5.8 Hz, 1H), 7.24 (d, J=10.58 Hz, 1H).

Step 2

(4-Bromo-2-fluoro-5-methoxy-phenyl)-methanol

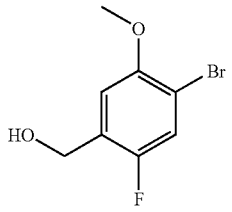

To a solution of 4-Bromo-2-fluoro-5-methoxy-benzaldehyde (4.03 g, 17.33 mmol) from step (1) below in Methanol at 0° C. was added NaBH$_4$ (0.65 g, 17.33 mmol). After the reaction mixture was stirred at 0° C. for 2 hours, it was allowed to warm to room temperature. The organic layer was taken up in ethyl ether, washed with water and dried over MgSO$_4$, filtered and concentrated. The residue was purified by flash chromatography (25–45% EtOAc in hexanes) to give the product. Yield: 3.90 g, 99.0%. $^1$H NMR (CDCl$_3$) δ: 3.90 (s, 3H), 4.74 (d, J=6.02 Hz, 2H), 6.82 (d, J=6.1 Hz, 1H), 7.29 (d, J=10.58 Hz, 1H).

Step 1

4-Bromo-2-fluoro-5-methoxy-benzaldehyde

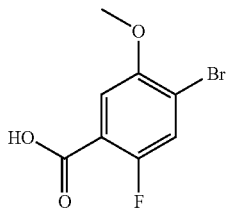

Bromine (15 ml, 300 mmol) was added slowly to a solution of 2-Fluoro-5-methoxy-benzaldehyde (23.12 g, 150 mmol) in chloroform (500 ml), and the mixture was stirred at room temperature for 5 days. The mixture was poured into water (200 ml) and extracted with chloroform (2×200 mL). The organics were washed with water (200 mL) and brine (200 mL), dried over MgSO$_4$, filtered and concentrated. The residue was purified by flash column chromatography (2–16% EtOAc in hexanes) to give the product. Yield: 20.7 g, 60%. $^1$H NMR (CDCl$_3$) δ: 3.93 (s, 3H), 7.08–7.13 (m, 1H), 7.29 (d, J=12.4 Hz, 1H).

Example A(262)

2-(4-{2-[2-Cyclopentyl-4-hydroxy-5-(6-methyl-[1,2,4]triazolo[1,5-a]pyrimidin-2-ylmethyl)-6-oxo-3,6-dihydro-2H-pyran-2-yl]-ethyl}-2,6-difluoro-phenyl)-2-ethyl-butyronitrile

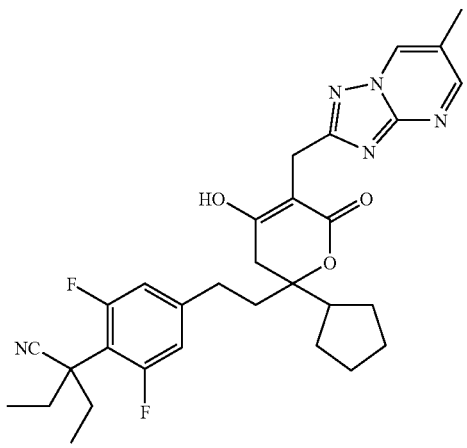

The desired product was prepared analogously to Example A (112), substituting 6-Methyl-[1,2,4]triazolo [1,5-a]pyrimidine-2-carbaldehyde (243.2 mg, 1.5 mmol) in place of 5,7-Dimethyl-[1,2,4]triazolo[1,5-a]pyrimidine-2-carbaldehyde. Yield: 178.0 mg, 32%. $^1$H NMR (CDCl$_3$) δ: 1.01 (tt, J=3.75, 3.70 Hz, 6H), 1.32–1.58 (m, 6H), 1.99–2.09 (m, 5H), 2.19–2.43 (m, 4H), 2.49 (s, 3H), 2.63–2.79 (m, 4H), 4.10 (s, 2H), 6.68 (d, J=11.1 Hz, 2H), 8.63 (s, 1H), 8.70 (s, 1H). MS (ESI): 562 (M−1).

Step 3

2-{4-[2-(2-Cyclopentyl-4,6-dioxo-tetrahydro-pyran-2-yl)-ethyl]-2,6-difluoro-phenyl}-2-ethyl-butyronitrile

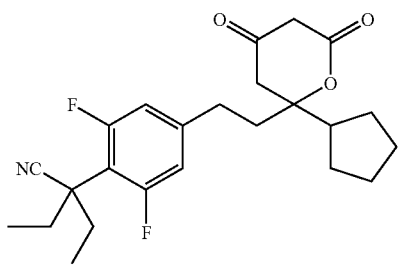

The desired product was prepared analogously to Example A (97), step 4, substituting 2-{4-[3-Cyclopentyl-4-(2,2-dimethyl-6-oxo-6H-[1,3]dioxin-4-yl)-3-hydroxybut-1-ynyl]-2,6-difluorophenyl}-2-ethyl-butyronitrile (3.11 g, 6.55 mmol) from Step 2 below in place of 2-{4-[3-cyclopentyl-4-(2,2-dimethyl-4-oxo-4H-1,3-dioxin-6-yl)-3-hydroxybut-1-ynyl]-2-fluorophenyl}-2-methylpropanenitrile. Yield: 1.52 g, 56%. $^1$H NMR (CDCl$_3$) δ: 1.03 (t, J=3.65 Hz, 6H), 1.18–1.29 (m, 2H), 1.38–1 42 (m, 1H), 1.60–1.82 (m, 4H), 1.92–2.09 (m, 5H), 2.23–2.29 (m, 3H), 2.63–2.80 (m, 4H), 3.45 (d, J=3.6 Hz, 2H) 6.73 (d, J=10.8 Hz, 2H). MS (ESI): 416 (M−1).

Step 2

2-{4-[3-Cyclopentyl-4-(2,2-dimethyl-6-oxo-6H-[1,3]dioxin-4-yl)-3-hydroxy-but-1-ynyl]-2,6-difluoro-phenyl}-2-ethyl-butyronitrile

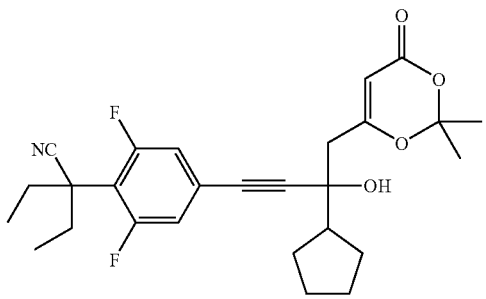

The desired product was prepared analogously to Example A (97) step 3, substituting 2-(4-Bromo-2,6-difluoro-phenyl)-2-methyl-propionitrile (5.28 g, 20.32 mmol) from step 1 below in place of 1-(4-bromo-2-fluoro-phenyl)-cyclopropanecarbonitrile. Yield: 3.0 g, 58.0%. $^1$H NMR (CDCl$_3$) δ: 1.04 (t, J=3.65 Hz, 6H), 1.17–1.39 (m, 3H), 1.57–1.67 (m, 1H), 1.73 (s, 3H), 1.74 (s, 3H), 1.82–1.87 (m, 1H), 2.02–2.07 (m, 4H), 2.22–2.29 (m, 4H), 2.57 (s, 1H), 2.66 (s, 2H), 5.45 (s, 1H), 6.93 (d, J=10.3 Hz, 2H). MS (ESI): 470 (M−1).

Step 1

2-(4-Bromo-2,6-difluoro-phenyl)-2-ethyl-butyronitrile

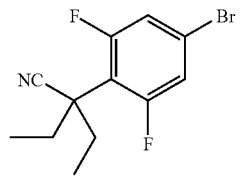

The desired product was prepared analogously to Example A (141) step 3, substituting bromoethane in place of MeI. Yield: 3.16 g, 91.4%. $^1$H NMR (CDCl$_3$) δ: 1.04 (t, J=3.65 Hz, 6H), 2.01–2.07 (m, 2H), 2.20–2.27 (m, 2H), 7.13 (d, J=9.3 Hz, 2H).

Example A(263)

(+)-2-(4-{2-[2-Cyclopentyl-4-hydroxy-5-(6-methyl-[1,2,4]triazolo[1,5-a]pyrimidin-2-ylmethyl)-6-oxo-3,6-dihydro-2H-pyran-2-yl]-ethyl}-2,6-difluoro-phenyl)-2-ethyl-butyronitrile

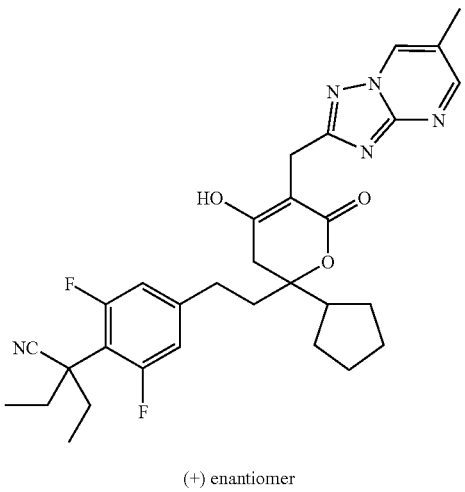

(+) enantiomer

The title compound was isolated by chiral SFC of racemic material described in example A (262) (4649-011 PF-00433966) Condition: ChiralPac AS-H column, 250×4.6 mm, 120 bar, 30% MeOH, 2.5 mL/min, retention time 4.62 min.

Example A(254)

(−)-2-(4-{2-[2-Cyclopentyl-4-hydroxy-5-(6-methyl-[1,2,4]triazolo[1,5-a]pyrimidin-2-ylmethyl)-6-oxo-3,6-dihydro-2H-pyran-2-yl]-ethyl}-2,6-difluoro-phenyl)-2-ethyl-butyronitrile

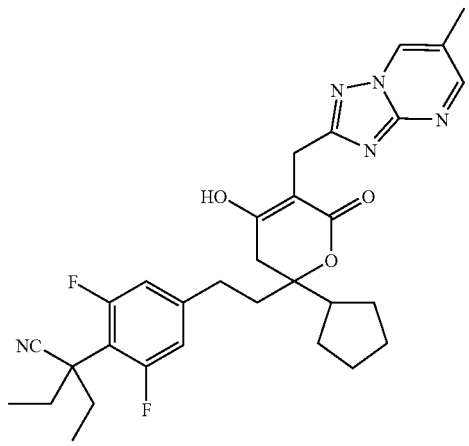

(-) enantiomer

The title compound was isolated by chiral SFC of racemic material described in example A (262) Condition: ChiralPac AS-H column, 250×4.6 mm, 120 bar, 30% MeOH, 2.5 mL/min, retention time 2.54 min.

Example A(265)

2-(4-{2-[5-(6-Chloro-[1,2,4]triazolo[1,5-a]pyrimidin-2-ylmethyl)-2-cyclopentyl-4-hydroxy-6-oxo-3,6-dihydro-2H-pyran-2-yl]-ethyl}-2-fluoro-phenyl)-2-ethyl-butyronitrile

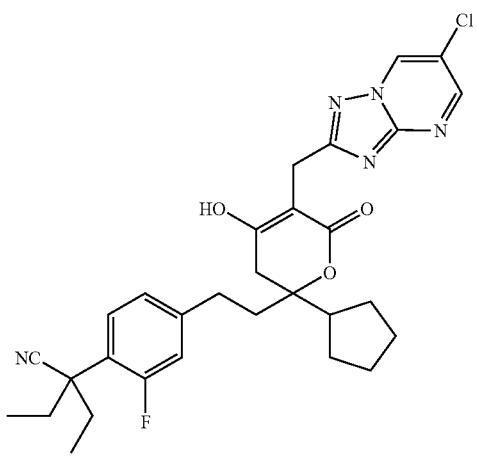

The desired product was prepared analogously to Example A (112), substituting 6-Chloro-[1,2,4]triazolo[1,5-a]pyrimidine-2-carbaldehyde (273.9 mg, 1.5 mmol) in place of 5,7-Dimethyl-[1,2,4]triazolo[1,5-a]pyrimidine-2-carbaldehyde. Yield: 70.0 mg, 12%. $^1$H NMR (CDCl$_3$) δ: 1.01 (tt, J=3.7, 3.7 Hz, 6H), 1.49–1.72 (m, 8H), 1.97–2.06 (m, 4H), 2.21–2.27 (m, 2H), 2.20–2.34 (m, 1H), 2.49 (d, J=14.71 Hz, 1H), 2.66 (t, J=4.15 Hz, 2H), 2.84 (d, J=17.1 Hz, 1H), 4.10 (s, 2H), 6.70 (d, J=11.1 Hz, 2H), 8.80 (s (1H), 8.90 (s, 1H). MS (ESI): 583 (M−1).

Example A(266)

(+)-2-(4-{2-[5-(6-Chloro-[1,2,4]triazolo[1,5-a]pyrimidin-2-ylmethyl)-2-cyclopentyl-4-hydroxy-6-oxo-3,6-dihydro-2H-pyran-2-yl]-ethyl}-2-fluoro-phenyl)-2-ethyl-butyronitrile

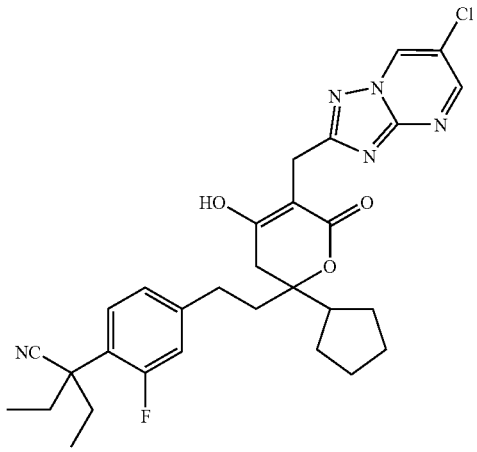

(+) enantiomer

The title compound was isolated by chiral SFC of racemic material described in example A (265) Condition: ChiralPac AS-H column, 250×4.6 mm, 120 bar, 30% MeOH, 2.5 mL/min, retention time 4.69 min.

Example A(267)

(−)-2-(4-{2-[5-(6-Chloro-[1,2,4]triazolo[1,5-a]pyrimidin-2-ylmethyl)-2-cyclopentyl-4-hydroxy-6-oxo-3,6-dihydro-2H-pyran-2-yl]-ethyl}-2-fluoro-phenyl)-2-ethyl-butyronitrile)

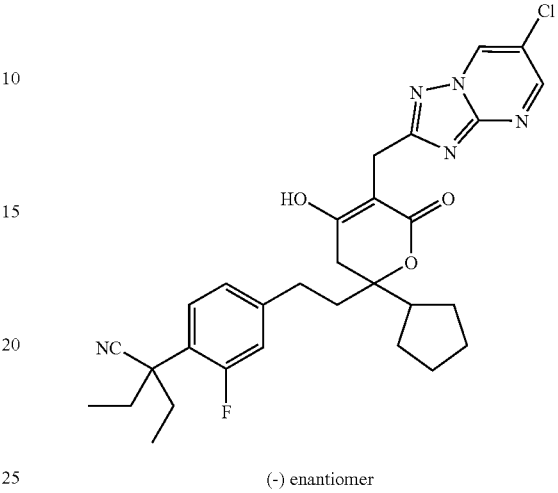

(−) enantiomer

The title compound was isolated by chiral SFC of racemic material described in example A (265) Condition: ChiralPac AS-H column, 250×4.6 mm, 120 bar, 30% MeOH, 2.5 mL/min, retention time 2.90 min.

Example A(268)

2-(4-{2-[2-Cyclopentyl-4-hydroxy-5-(6-methyl-[1,2,4]triazolo[1,5-a]pyrimidin-2-ylmethyl)-6-oxo-3,6-dihydro-2H-pyran-2-yl]-ethyl}-2-fluoro-phenyl)-N-ethyl-isobutyramide

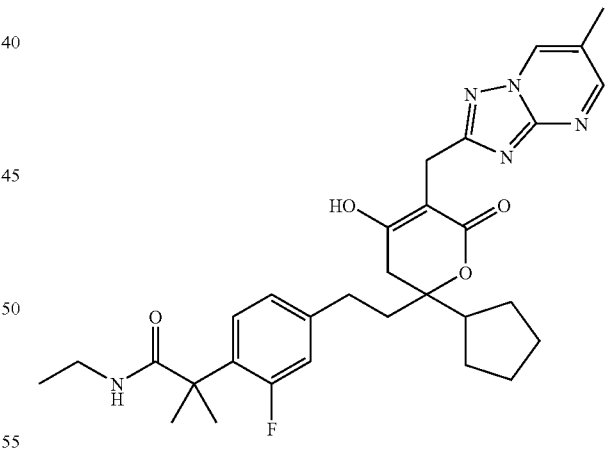

The desired product was prepared analogously to Example A (112), substituting 6-Methyl-[1,2,4]triazolo[1,5-a]pyrimidine-2-carbaldehyde (243.2 mg, 1.5 mmol) in place of 5,7-Dimethyl-[1,2,4]triazolo[1,5-a]pyrimidine-2-carbaldehyde. Yield: 66.0 mg, 14.0%. $^1$H NMR (CDCl$_3$) δ: 1.05 (t, J=3.7 Hz, 2H), 1.52 (s, 6H), 1.60–1.76 (m, 2H), 2.02–2.09 (m, 4H), 2.36–2.44 (m, 2H), 2.48 (s, 3H), 2.62–2.79 (m, 4H), 3.15–3.27 (m, 3H), 4.05 (S, 2H), 6.81 (d, J=11.4 Hz, 1H), 6.94 (d, J=6.8 Hz, 1H), 7.20–7.22 (m, 1H), 8.61 (d, J=2.1 Hz, 1H), 8.69 (d, J=2.3 Hz, 1H). MS (ESI): 562 (M−1).

Example A(269)

6-Cyclopentyl-6-{2-[3-fluoro-4-(2-hydroxy-1,1-dimethyl-ethyl)-phenyl]-ethyl}-4-hydroxy-3-(6-methyl-[1,2,4]triazolo[1,5-a]pyrimidin-2-ylmethyl)-5,6-dihydro-pyran-2-one

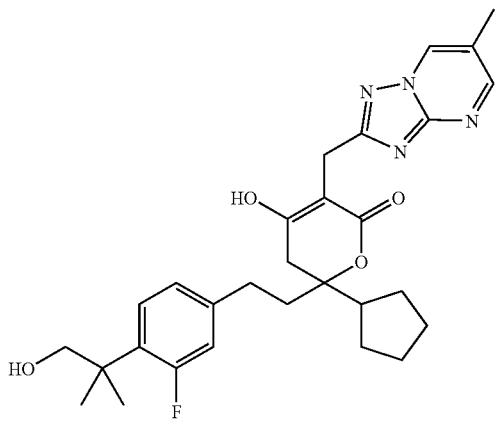

The desired product was prepared analogously to Example A (112), substituting 6-Methyl-[1,2,4]triazolo[1,5-a]pyrimidine-2-carbaldehyde (243.2 mg, 1.5 mmol) in place of 5,7-Dimethyl-[1,2,4]triazolo[1,5-a]pyrimidine-2-carbaldehyde. Yield: 35.0 mg, 10.0%. $^1$H NMR (CDCl$_3$) δ: 1.35 (s, 6H), 1.53–1.77 (m, 6H), 1.99–2.05 (m, 4H), 2.32–2.44 (m, 2H), 2.48 (s, 3H), 3.75 (s, 2H), 4.08 (s, 2H), 6.80 (dd, J=13.19, 1.6 Hz, 1H), 7.00 (dd, J=10.5, 1.8 Hz, 1H), 7.20–7.24 (m, 1H), 8.62 (d, J=2.5 Hz, 1H), 8.69 (d, J=2.3 Hz, 1H). MS (ESI): 521 (M−1).

Example A(271)

2-(4-{2-[2-Cyclopentyl-4-hydroxy-5-(6-methyl-[1,2,4]triazolo[1,5-a]pyrimidin-2-ylmethyl)-6-oxo-3,6-dihydro-2H-pyran-2-yl]-ethyl}-2-fluoro-phenyl)-2-methyl-propionic acid methyl ester

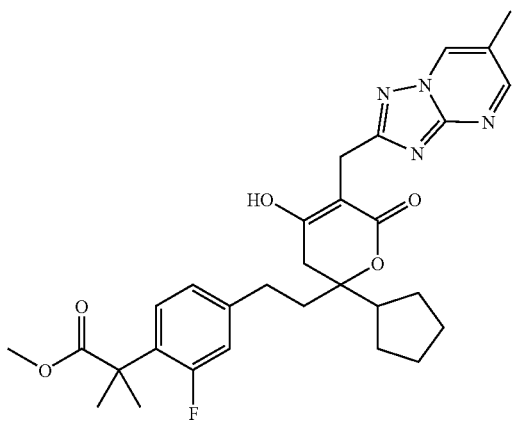

The desired product was prepared analogously to Example A (112), substituting 6-Methyl-[1,2,4]triazolo[1,5-a]pyrimidine-2-carbaldehyde (176.0 mg, 0.967 mmol) in place of 5,7-Dimethyl-[1,2,4]triazolo[1,5-a]pyrimidine-2-carbaldehyde. Yield: 29.0 mg, 4.0%. $^1$H NMR (CDCl$_3$) δ: 1.35–1.44 (m, 2H), 1.53 (s, 6H), 1.55–1.74 (m, 8H), 2.41–2.46 (m, 2H), 2.49 (s, 3H), 2.63–2.79 (m, 3H), 3.66 (s, 3H), 4.10 (s, 2H), 6.80 (dd, J=10.4, 1.8 Hz, 1H), 6.93 (dd, J=9.6, 1.5 Hz, 1H), 7.19–7.24 (m, 1H), 8.62 (d, J=1.3 Hz, 1H), 8.70 (d, J=2.3 Hz, 1H). MS (ESI): 549 (M−1).

Example A(271)

3-(6-Chloro-[1,2,4]triazolo[1,5-a]pyrimidin-2-ylmethyl)-6-cyclopentyl-6-[2-(3-ethyl-4-hydroxy-phenyl)-ethyl]-4-hydroxy-5,6-dihydro-pyran-2-one

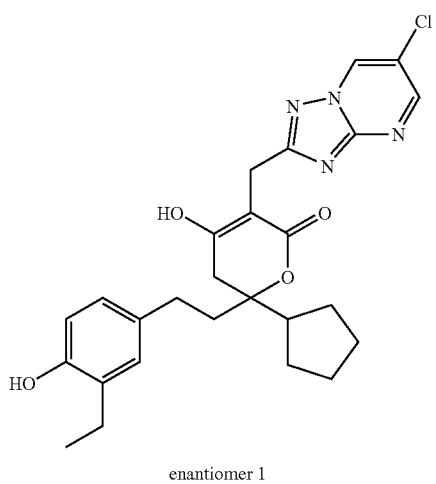

enantiomer 1

The title compound was isolated by chiral SFC of racemic material described in example A(127) Condition: ChiralPac AD-H column, 140 bar, 25% MeOH, 2.5 mL/min.

Example A(272)

3-(6-Chloro-[1,2,4]triazolo[1,5-a]pyrimidin-2-ylmethyl)-6-cyclopentyl-6-[2-(3-ethyl-4-hydroxy-phenyl)-ethyl]-4-hydroxy-5,6-dihydro-pyran-2-one

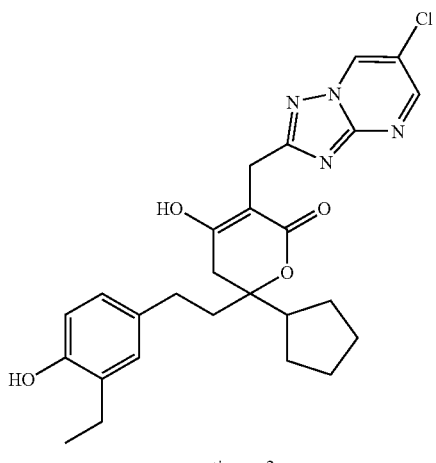

enantiomer 2

Example A(273)

Enantiomer 1 of 6-Cyclopentyl-3-(5,7-dimethyl-[1,2,4]triazolo[1,5-a]pyrimidin-2-ylmethyl)-6-[2-(5-ethyl-4-hydroxy-2,3-dihydro-benzofuran-7-yl)-ethyl]-4-hydroxy-5,6-dihydro-pyran-2-one

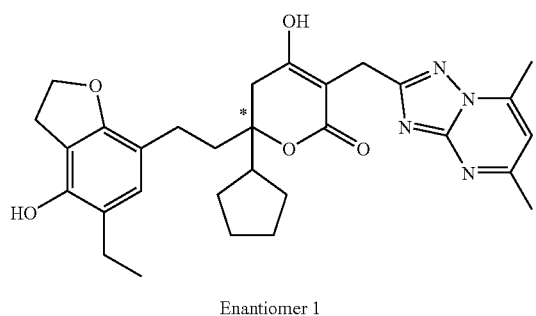

Enantiomer 1

The title compound was separated from racemic 6-cyclopentyl-3-(5,7-dimethyl-[1,2,4]triazolo[1,5-a]pyrimidin-2-ylmethyl)-6-[2-(5-ethyl-4-hydroxy-2,3-dihydro-benzofuran-7-yl)-ethyl]-4-hydroxy-5,6-dihydro-pyran-2-one, (280 mg) using chiral HPLC (Chiralpak AS-H, 140 bar, 2.5 mL/min, 40% MeOH) (113 mg, 5.140 min retention time).

Example A(274)

Enantiomer 2 of 6-Cyclopentyl-3-(5,7-dimethyl-[1,2,4]triazolo[1,5-a]pyrimidin-2-ylmethyl)-6-[2-(5-ethyl-4-hydroxy-2,3-dihydro-benzofuran-7-yl)-ethyl]-4-hydroxy-5,6-dihydro-pyran-2-one

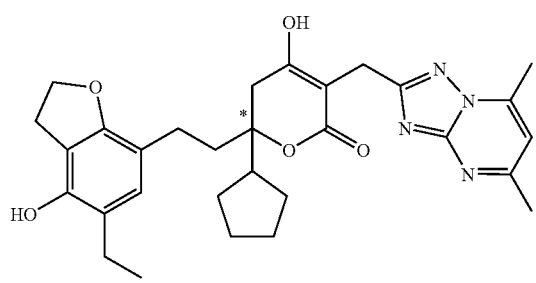

Enantiomer 2

The title compound was separated from racemic 6-cyclopentyl-3-(5,7-dimethyl-[1,2,4]triazolo[1,5-a]pyrimidin-2-ylmethyl)-6-[2-(5-ethyl-4-hydroxy-2,3-dihydro-benzofuran-7-yl)-ethyl]-4-hydroxy-5,6-dihydro-pyran-2-one (280 mg) using chiral HPLC (Chiralpak AS-H, 140 bar, 2.5 mL/min, 40% MeOH) (106 mg, 8.992 min retention time).

The title compound was isolated by chiral SFC of racemic material described in example A(127) Condition: ChiralPac AD-H column, 140 bar, 25% MeOH, 2.5 mL/min.

Example A(275)

6-Cyclopentyl-3-(5,7-dimethyl-[1,2,4]triazolo[1,5-a]pyrimidin-2-ylmethyl)-6-[2-(5-ethyl-pyridin-3-yl)-ethyl]-4-hydroxy-5,6-dihydro-pyran-2-one

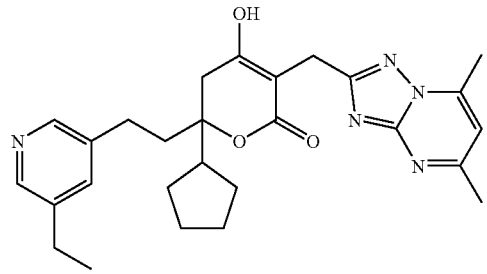

The title compound was prepared analogously to Example A(27) where 6-Cyclopentyl-6-[2-(5-ethyl-pyridin-3-yl)-ethyl]-dihydro-pyran-2,4-dione from step 2 below was substituted in place of 6-cyclopentyl-6-[2-(3-ethyl-5-fluoro-4-hydroxy-phenyl)-ethyl]-dihydro-pyran-2,4-dione. $^1$H NMR (400 MHz, DMSO-d$_6$) δ: 1.14 (t, J=7.6 Hz, 3 H), 1.40–1.73 (br m, 8 H), 2.14 (m, 2H), 2.44–2.67 (m, 12 H), 2.78 (d, J=17.7 Hz, 1 H), 3.72 (d, J=16.4 Hz, 1 H), 3.83 (d, J=16.2 Hz, 1 H), 7.04 (s, 1 H), 7.50 (s, 1 H), 8.25 (s, 2 H), 10.90 (s, 1 H).

Step 2

6-Cyclopentyl-6-[2-(5-ethyl-pyridin-3-yl)-ethyl]-dihydro-pyran-2,4-dione

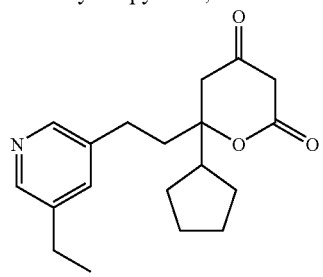

The title compound was prepared analogously to Example A(1) where 3-bromo-5-ethyl-pyridine (from step 1 below) was substituted in place of 2-(4-bromo-2-fluorophenyl)-2-methylpropanenitrile in step 3 of that example. MS (ESI): 316.10 (M+H)$^+$.

Step 1

3-Bromo-5-ethyl-pyridine

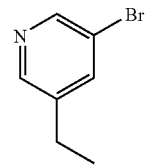

Sodium hydroxide (10 g, 0.25 mol) and hydrazine monohydrate (10 mL) were added to a solution of 3-acetyl-5-bromopyridine (5 g, 25 mmol) dissolved in diethylene glycol (18 mL). The reaction mixture was heated to 140° C. for 6 hours and then partitioned between H$_2$O and Ether. The organic layers were washed with brine, dried over MgSO$_4$ and concentrated. The residue was purified by flash silica gel chromatography (0% to 40% EtOAc in hexanes) to give the title compound (3 g, 65%). $^1$H NMR (400 MHz, CDCl$_3$): δ 1.26 (t, J=7.6 Hz, 3 H), 2.65 (q, J=7.6 Hz, 2 H), 7.67 (s, 1 H), 8.37 (s, 1 H), 8.51 (s, 1 H).

Section B: Pyrone Prepared by Heck Route

Scheme 2

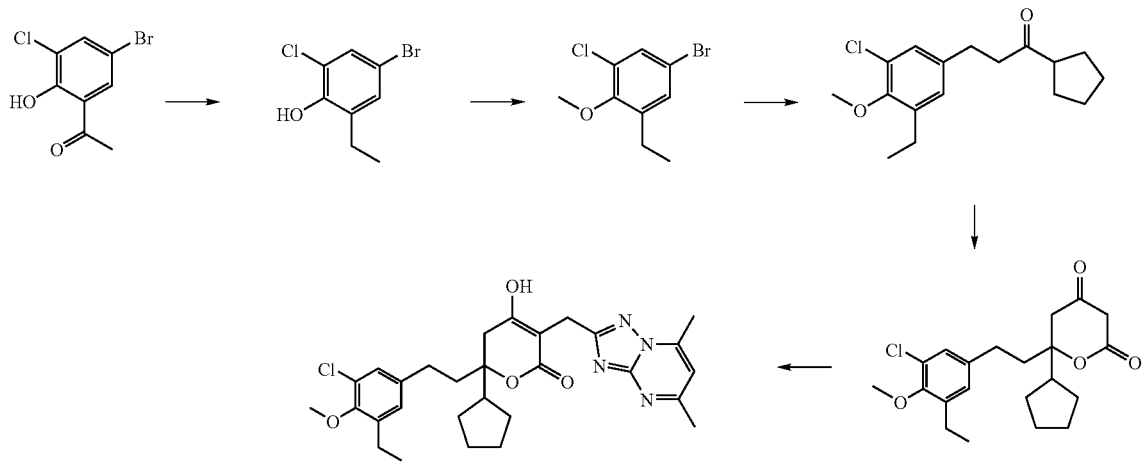

Example B(1)

6-Cyclopentyl-3-(5,7-dimethyl-[1,2,4]triazolo[1,5-a-pyrimidin-2-ylmethyl)-6-[2-(3-fluoro-4-methoxy-phenyl)-ethyl]-4-hydroxy-5,6-dihydro-pyran-2-one

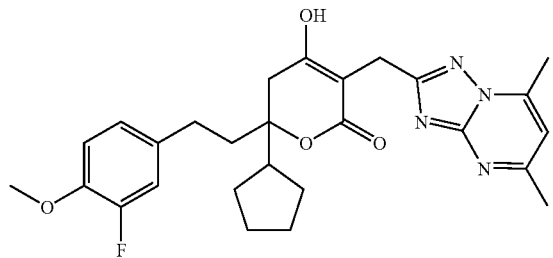

The title compound was prepared by coupling the 6-Cyclopentyl-6-[2-(3-fluoro-4-methoxy-phenyl)-ethyl]-dihydro-pyran-2,4-dione from Step 1 below, to 5,7-Dimethyl-[1,2,4]triazolo[1,5-□]pyrimidine-2-carbaldehyde using the Me$_2$NHBH$_3$ method described in the synthesis of Example B(31).

$^1$H NMR (DMSO-d$_6$): δ 1.39–1.71 (br m, 8H), 2.11 (m, 2H), 2.40 (m, 10H), 2.76 (d, 1H, J=17.5 Hz), 3.71 (d, 1H, J=16.2 Hz), 3.80 (s, 3H), 3.85 (d, 1H, J=16.2 Hz), 7.05 (m, 4H), 10.83 (s, 1H). Anal. Calcd. For C$_{27}$H$_{31}$N$_4$O$_4$F.0.5H$_2$O: C, 64.40; H, 6.41; N, 11.13. Found: C, 64.33; H, 6.34; N, 11.12.

Step 1

6-Cyclopentyl-6-[2-(3-fluoro-4-methoxy-phenyl)-ethyl]-dihydro-pyran-2,4-dione

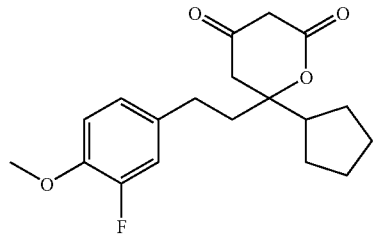

The title compound was prepared analogously to Example A(64), where 4-Bromo-2-fluoroanisole was substituted in place of 4-bromo-2-fluoro-1-isopropylbenzene of that example. $^1$H NMR (CDCl$_3$): δ 1.43–1.82 (brm, 8H), 1.92 (m, 2H), 2.27 (m, 1H), 2.62 (t, J=8.5 Hz, 2H), 2.76 (s, 2H), 3.43 (s, 2H), 3.86 (s, 3H), 6.85 (m, 3H). Anal. Calcd. For C$_{19}$H$_{23}$FO$_4$: C, 68.24; H, 6.93. Found: C, 68.46; H, 6.84.

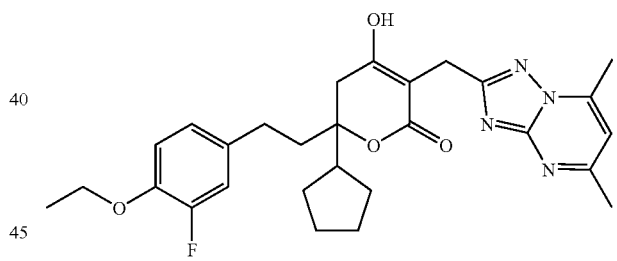

Example B(2)

6-Cyclopentyl-3-(5,7-dimethyl-[1,2,4]triazolo[1,5-a]pyrimidin-2-ylmethyl)-6-[2-(4-ethoxy-3-fluoro-phenyl)-ethyl]-4-hydroxy-5,6-dihydro-pyran-2-one The title compound was prepared by coupling 6-Cyclopentyl-6-[2-(4-ethoxy-3-fluoro-phenyl)-ethyl]-dihydro-pyran-2,4-dione from Step 1 to 5,7-Dimethyl-[1,2,4]triazolo[1,5-α]pyrimidine-2-carbaldehyde using the Me$_2$NHBH$_3$ method described in the synthesis of Example B(31).

$^1$H NMR (DMSO-d$_6$): d 1.33 (t, 3H, J=7.0 Hz), 1.39–1.71 (br m, 8H), 2.11 (m, 2H), 2.40–2.58 (m, 10H), 2.78 (d, 1H, J=17.5 Hz), 3.72 (d, 1H, J=16.1 Hz), 3.84 (d, 1H, J=16.1 Hz), 4.06 (q, 2H, J=7.0 Hz), 7.05 (m, 4H), 10.90 (s, 1H). Anal. Calcd. For C$_{28}$H$_{33}$N$_4$O$_4$F.0.4 AcOH: C, 64.94; H, 6.55; N, 10.52. Found: C, 65.05; H, 6.53; N, 10.55.

Step 1

6-Cyclopentyl-6-[2-(4-ethoxy-3-fluoro-phenyl)-ethyl]-dihydro-pyran-2,4-dione

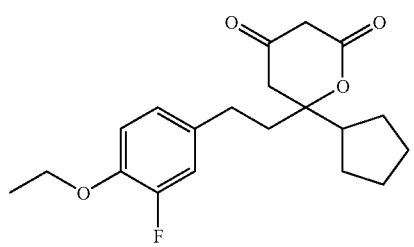

The title compound was prepared analogously to Example A(64), where 4-Bromo-1-ethoxy-2-fluoro-benzene was substituted in place of 4-bromo-2-fluoro-1-isopropylbenzene of that example.

Example B(3)

6-[2-(3-tert-Butyl-phenyl)-ethyl]-6-cyclopentyl-3-(5,7-dimethyl-[1,2,4]triazolo[1,5-a]pyrimidin-2-ylmethyl)-4-hydroxy-5,6-dihydro-pyran-2-one

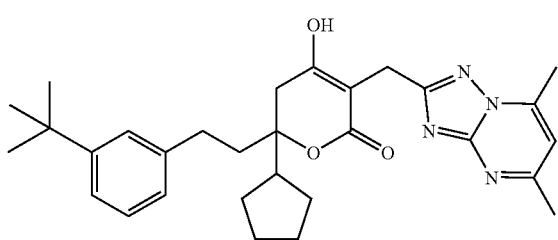

The title compound was prepared by coupling the 6-[2-(3-tert-Butyl-phenyl)-ethyl]-6-cyclopentyl-dihydro-pyran-2,4-dione from Step 1 to 5,7-Dimethyl-[1,2,4]triazolo[1,5-α]pyrimidine-2-carbaldehyde using the Me$_2$NHBH$_3$ method described in the synthesis of Example B(31). $^1$H NMR (DMSO-d$_6$): d 1.29 (s, 9H), 1.46–1.76 (br m, 8H), 2.19 (m, 2H), 2.47 (s, 3 Hz), 2.56–2.70 (m, 7H), 2.87 (d, 1H, J=17.5 Hz), 3.80 (d, 1H, J=16.2 Hz), 3.90 (d, 1H, J=16.2 Hz), 7.12 (m, 2H), 7.28 (m, 3H), 10.92 (s, 1H). Anal. Calcd. For C$_{30}$H$_{38}$N$_4$O$_3$.0.4 AcOH: C, 70.24; H, 7.58; N, 10.64. Found: C, 70.27; H, 7.42; N, 10.59.

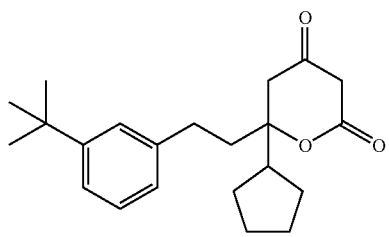

Step 1

6-[2-(3-tert-Butyl-phenyl)-ethyl]-6-cyclopentyl-dihydro-pyran-2,4-dione

The title compound was prepared analogously to Example A(64), where trifluoro-methanesulfonic acid 3-tert-butyl-phenyl ester was substituted in place of 4-bromo-2-fluoro-1-isopropylbenzene of that example.

$^1$H NMR (CDCl$_3$): δ 1.31 (s, 9H), 1.35–1.81 (m, 4H), 1.97 (m, 2H), 2.29 (m, 1H), 2.68 (t, 2H, J=8.7 Hz), 2.78 (s, 2H), 2.86 (s, 2H), 3.42 (s, 2H), 4.08 (s, 2H), 6.96 (m, 1H), 7.15 (s, 1H), 7.23 (m, 2H). Anal. Calcd. For C$_{22}$H$_{30}$O$_3$.0.10H$_2$O: C, 76.75; H, 8.84. Found: C, 76.89; H, 9.03. ESIMS (M–H$^-$): 341.2.

Example B(4)

6-Cyclopentyl-6-{2-[4-(3,5-dimethyl-isoxazol-4-yl)-phenyl]-ethyl}-3-(5,7-dimethyl-[1,2,4]triazolo[1,5-a]pyrimidin-2-ylmethyl)-4-hydroxy-5,6-dihydro-pyran-2-one

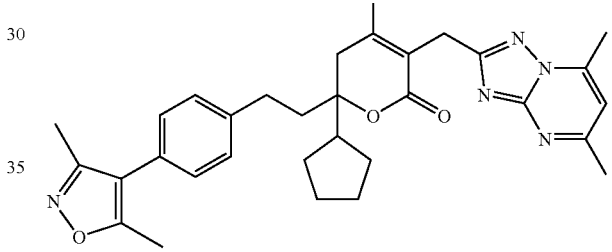

The title compound was prepared by coupling 6-Cyclopentyl-6-{2-[4-(3,5-dimethyl-isoxazol-4-yl)-phenyl]-ethyl}-dihydro-pyran-2,4-dione (Example A(18)) to 5,7-Dimethyl-[1,2,4]triazolo[1,5-α]pyrimidine-2-carbaldehyde using the Me$_2$NHBH$_3$ method described in the synthesis of Example B(31).

$^1$H NMR (DMSO-d$_6$): d 1.39–1.72 (br m, 8H), 2.19 (m, 2H), 2.21 (s, 3H), 2.39 (s, 3 Hz), 2.47–2.70 (m, 10H), 2.81 (d, 1H, J=17.5 Hz), 3.71 (d, 1H, J=16.1 Hz), 3.85 (d, 1H, J=16.2 Hz), 7.04 (s, 1H), 7.27 (d, 2H, J=8.1 Hz), 7.36 (d, 2H, J=8.1 Hz), 10.98 (s, 1H). Anal. Calcd. For C$_{31}$H$_{35}$N$_5$O$_4$.0.6H$_2$O: C, 67.39; H, 6.61; N, 12.68. Found: C, 67.39; H, 6.52; N, 12.45.

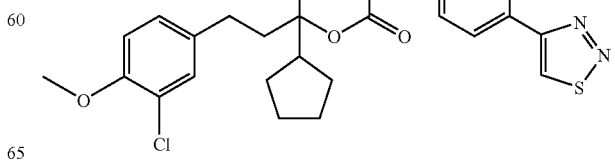

Example B(5)

6-[2-(3-Chloro-4-methoxy-phenyl)-ethyl]-6-cyclopentyl-4-hydroxy-3-(4-[1,2,3]thiadiazol-4-yl-benzyl)-5,6-dihydro-pyran-2-one The title compound was prepared by coupling the 6-[2-(3-Chloro-4-methoxy-phenyl)-ethyl]-6-cyclopentyl-dihydro-pyran-2,4-dione to 4-[1,2,3]thiadiazol-4-yl-benzaldehyde using the Me$_2$NHBH$_3$ method described in the synthesis of Example B(31).

$^1$H NMR (DMSO-d$_6$): d 1.36–1.71 (br m, 8H), 1.92 (m, 2H), 2.37 (m, 1H), 2.56 (m, 3H), 2.84 (d, 1H, J=17.5 Hz), 3.60 (d, 1H, J=14.3 Hz), 3.71 (d, 1H, J=14.3 Hz), 3.79 (s, 3H), 6.96 (s, 2H), 7.19 (s, 1H), 7.41 (d, 2H, J=8.1 Hz), 8.08 (d, 2H, J=8.3 Hz), 9.59 (s, 1H), 11.01 (s, 1H) Anal. Calcd. For C$_{28}$H$_{29}$N$_2$O$_4$ClS.0.75H$_2$O: C, 62.44; H, 5.71; N, 5.20. Found: C, 62.43; H, 5.58; N, 5.30.

Example B(6)

6-[2-(3-Chloro-4-methoxy-phenyl)-ethyl]-6-cyclopentyl-3-[4-(2,5-dimethyl-pyrrol-1-yl)-benzyl]-4-hydroxy-5,6-dihydro-pyran-2-one

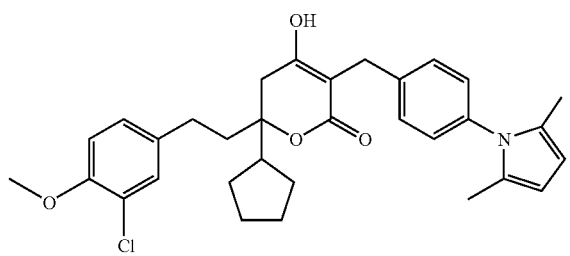

The title compound was prepared by coupling 6-[2-(3-Chloro-4-methoxy-phenyl)-ethyl]-6-cyclopentyl-dihydro-pyran-2,4-dione to 4-(2,5-Dimethyl-pyrrol-1-yl)-benzaldehyde using the Me$_2$NHBH$_3$ method described in the synthesis of Example B(31).

$^1$H NMR (DMSO-d$_6$): δ 1.32–1.66 (br m, 8H), 1.89 (m, 2H), 1.90 (s, 6H), 2.30 (m, 1H), 2.52 (m, 2H), 2.61 (d, 1H, J=17.7 Hz), 2.79 (d, 1H, J=17.7 Hz), 3.57 (d, 1H, J=14.4 Hz), 3.65 (d, 1H, J=14.4 Hz), 3.80 (s, 3H), 5.77 (s, 2H), 7.01 (t, 1H, J=8.6 Hz), 7.10 (t, 1H, J=8.4 Hz), 7.10 (d, 2H, J=8.3 Hz), 7.21 (s, 1H), 7.31 (d, 2H, J=8.1 Hz), 10.91 (s, 1H) Anal. Calcd. For C$_{32}$H$_{36}$N$_1$O$_4$C0.05 H$_2$O: C, 70.77; H, 6.887; N, 2.58. Found: C, 70.92; H, 6.79; N, 2.54.

Example B(7)

6-Cyclopentyl-3-(5,7-dimethyl-[1,2,4]triazolo[1,5-a]pyrimidin-2-ylmethyl)-6-[2-(3-ethyl-4-hydroxy-phenyl)-ethyl]-4-hydroxy-5,6-dihydro-pyran-2-one

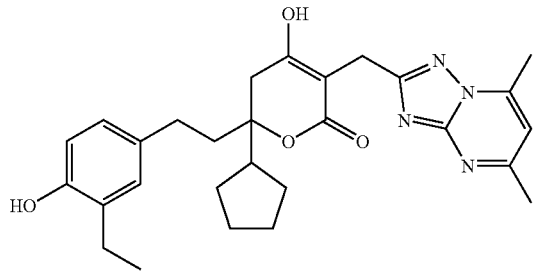

The title compound was prepared by coupling 6-Cyclopentyl-6-[2-(3-ethyl-4-hydroxy-phenyl)-ethyl]-dihydro-pyran-2,4-dione (from Example A(22)) to 5,7-Dimethyl-[1,2,4]triazolo[1,5-α]pyrimidine-2-carbaldehyde using the Me$_2$NHBH$_3$ method described in the synthesis of Example B(31).

$^1$H NMR (DMSO-d$_6$): d 0.96 (t, 3H, J=7.4 Hz), 1.30–1.58 (br m, 8H), 1.95 (m, 2H), 2.41 (m, 12H), 2.63 (d, 1H, J=17.5 Hz), 3.61 (d, 1H, J=15.8 Hz), 3.72 (d, 1H, J=15.8 Hz), 6.52 (d, 1H, J=8.1 Hz), 6.74 (m, 2H), 6.93 (s, 1H), 8.84 (s, 1H). Anal. Calcd. For C$_{28}$H$_{34}$N$_4$O$_4$.0.5 AcOH: C, 66.90; H, 6.97; N, 10.76. Found: C, 66.89; H, 6.97; N, 10.83.

Example B(8)

6-[2-(3-tert-Butyl-4-hydroxy-phenyl)-ethyl]-6-cyclopentyl-3-(5,7-dimethyl-[1,2,4]triazolo[1,5-a]pyrimidin-2-ylmethyl)-4-hydroxy-5,6-dihydro-pyran-2-one

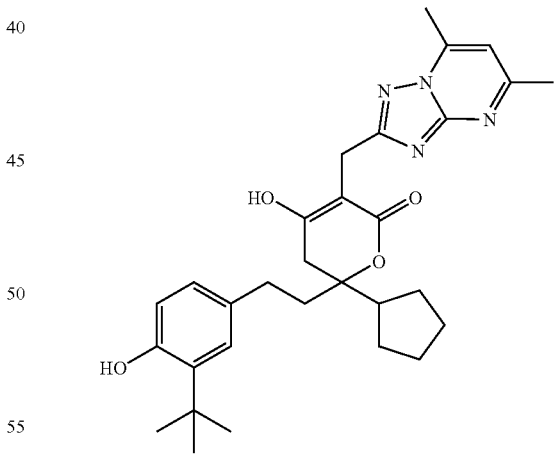

The title compound was prepared by coupling 6-[2-(3-tert-Butyl-4-hydroxy-phenyl)-ethyl]-6-cyclopentyl-dihydro-pyran-2,4-dione from Example A(2), to 5,7-Dimethyl-[1,2,4]triazolo[1,5-α]pyrimidine-2-carbaldehyde (described in Step 3 of example B(75)) using the Me$_2$NHBH$_3$ method described in the synthesis of Example B(31) $^1$H NMR (CDCl$_3$): δ 1.37 (s, 9H), 1.43–1.86 (br m, 8H), 1.93–2.05 (m, 2H), 2.37 (m, 1H), 2.53–2.79 (m, 10), 3.49 (s, 2H), 4.06 (d, J=15.4 Hz, 1H), 4.11 (d, J=15.4 Hz, 1H), 6.58 (d, J=8.1 Hz 1H)), 6.81–6.84 (m, 2H), 7.00 (s, 1H).

Example B(9)

6-Cyclopentyl-3-(5,7-dimethyl-[1,2,4]triazolo[1,5]pyrimidin-2-ylmethyl)-4-hydroxy-6-[2-(4-methoxy-3-methyl-phenyl)-ethyl]-5,6-dihydro-pyran-2-one

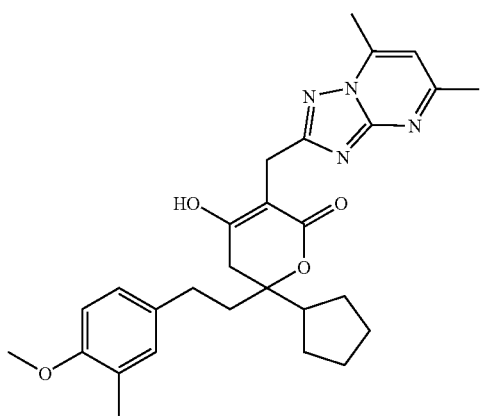

The title compound was prepared by coupling 6-Cyclopentyl-6-[2-(4-methoxy-3-methyl-phenyl)-ethyl]-dihydro-pyran-2,4-dione from Step 1 below to 5,7-Dimethyl-[1,2,4]triazolo[1,5-α]pyrimidine-2-carbaldehyde (described in Step 3 of example B(75)) using the Me$_2$NHBH$_3$ method described in Example B(31). $^1$H NMR (CDCl$_3$): δ 1.52–1.92 (brm, 8H), 2.05 (m, 2H), 2.16 (s, 3H), 2.35 (m, 1H), 2.51–2.71 (m, 8H), 2.79 (s, 3H), 3.78 (s, 3H), 4.05 (d, J=15.6 Hz, 1H), 4.12 (d, J=15.6 Hz, 1H), 6.71 (d, J=8.5 Hz, 1H), 6.84 (s, 1H), 6.94 (m, 2H). Anal. Calcd. For C$_{28}$H$_{34}$N$_4$O$_4$: C, 68.55; H, 6.99; N, 11.43. Found: C, 68.42; H, 6.76; N, 11.57.

Step 1

6-Cyclopentyl-6-[2-(4-methoxy-3-methyl-phenyl)-ethyl]-dihydro-pyran-2,4-dione

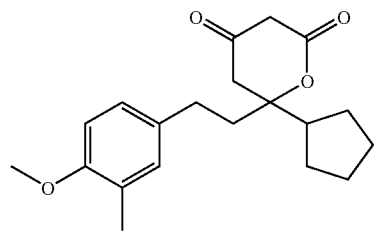

6-Cyclopentyl-6-[2-(4-methoxy-3-methyl-phenyl)-ethyl]-dihydro-pyran-2,4-dione was prepared analogously to Example A(82), where 4-Bromo-1-methoxy-2-methyl-benzene was substituted in place of 2-Bromopyridine in Step 1 of that example.

Example B(10)

6-Cyclopentyl-3-(5,7-dimethyl-[1,2,4]triazolo[1,5]pyrimidin-2-ylmethyl)-6-[2-(4-ethoxy-3-methyl-phenyl)-ethyl]-4-hydroxy-5,6-dihydro-pyran-2-one

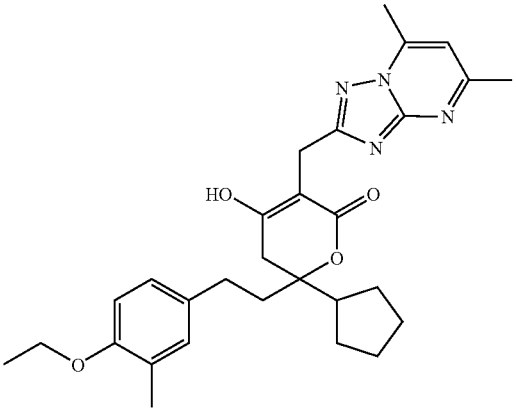

The title compound was prepared by coupling 6-Cyclopentyl-6-[2-(4-ethoxy-3-methyl-phenyl)-ethyl]-dihydro-pyran-2,4-dione from Example A(3), to 5,7-Dimethyl-[1,2,4]triazolo[1,5-α]pyrimidine-2-carbaldehyde (described in Step 3 of example B(75)) using the Me$_2$NHBH$_3$ method described in the synthesis of Example B(31).
$^1$H NMR (CDCl$_3$): δ 1.39 (t, J=7 Hz, 3H), 1.52–1.81 (brm, 8H), 2.05 (m, 2H), 2.16 (s, 3H), 2.35 (m, 1H), 2.50–2.71 (m, 8H), 2.79 (s, 3H), 3.98 (q, J=7 Hz, 2H), 4.05 (d, J=15.5 Hz, 1H), 4.12 (d, J=15.5 Hz, 1H), 6.69 (d, J=8.8 Hz, 1H), 6.84 (s, 1H), 6.91 (m, 2H). Anal. Calcd. For C$_{29}$H$_{36}$N$_4$O$_4$: C, 69.02; H, 7.19; N, 11.10. Found: C, 69.42; H, 7.34; N, 11.22.

Example B(11)

6-Cyclopentyl-3-(5,7-dimethyl-[1,2,4]triazolo[1,5]pyrimidin-2-ylmethyl)-4-hydroxy-6-[2-(4-isopropoxy-3-methyl-phenyl)-ethyl]-5,6-dihydro-pyran-2-one

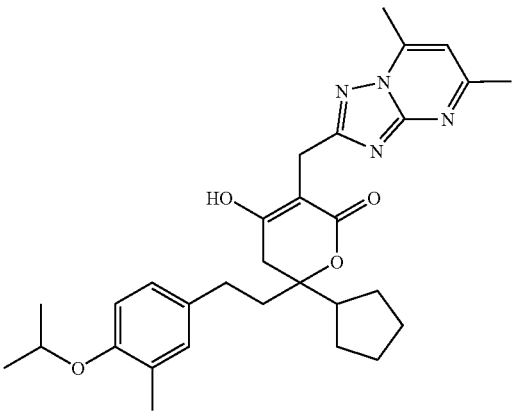

The title compound was prepared by coupling 6-Cyclopentyl-6-[2-(4-isopropoxy-3-methyl-phenyl)-ethyl]-dihydro-pyran-2,4-dione from Example A(4), to 5,7-Dimethyl-[1,2,4]triazolo[1,5-α]pyrimidine-2-carbaldehyde (described in Step 3 of example B(75)) using the Me$_2$NHBH$_3$ method described in the synthesis of Example B(31).

¹H NMR (CDCl₃): δ 1.30 (d, J=6.2 Hz, 6H), 1.52–1.81 (brm, 8H), 1.99 (m, 2H), 2.15 (s, 3H), 2.38 (m, 1H), 2.50–2.71 (m, 8H), 2.79 (s, 3H), 4.05 (d, J=15.5 Hz, 1H), 4.12 (d, J=15.5 Hz, 1H), 4.43 (m, 1H), 6.71 (d, J=8.1 Hz, 1H), 6.84 (s, 1H), 6.88 (m, 2H). Anal. Calcd. For $C_{30}H_{38}N_4O_4$: C, 69.47; H, 7.38; N, 10.80. Found: C, 69.18; H, 7.54; N, 10.66.

Example B(12)

6-Cyclopentyl-3-(5,7-dimethyl-[1,2,4]triazolo[1,5] pyrimidin-2-ylmethyl)-6-[2-(3-ethyl-phenyl)-ethyl]-4-hydroxy-5,6-dihydro-pyran-2-one

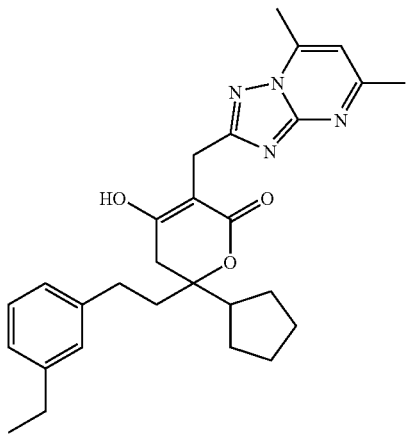

The title compound was prepared by coupling 6-Cyclopentyl-6-[2-(3-ethyl-phenyl)-ethyl]-dihydro-pyran-2,4-dione from Step 1 below to 5,7-Dimethyl-[1,2,4]triazolo[1,5-α]pyrimidine-2-carbaldehyde (described in Step 3 of example B(75)) using the Me₂NHBH₃ method described in the synthesis of Example B(31).

¹H NMR (CDCl₃): δ 1.20 (t, J=7.5 Hz, 3H), 1.52–1.81 (brm, 8H), 2.04 (m, 2H), 2.39 (m, 1H), 2.50–2.73 (m, 10H), 2.79 (s, 3H), 4.05 (d, J=15.5 Hz, 1H), 4.12 (d, J=15.5 Hz, 1H), 6.84 (s, 1H), 6.98 (m, 3H), 7.17 (t, J=7.6 Hz, 1H). Anal. Calcd. For $C_{28}H_{34}N_4O_3$: C, 70.86; H, 7.22; N, 11.81. Found: C, 70.68; H, 7.06; N, 11.64.

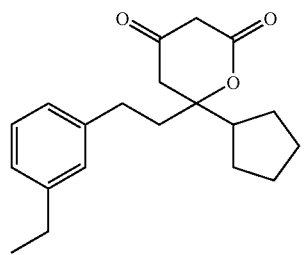

Step 1

6-Cyclopentyl-6-[2-(3-ethyl-phenyl)-ethyl]-dihydro-pyran-2,4-dione

6-Cyclopentyl-6-[2-(3-ethyl-phenyl)-ethyl]-dihydro-pyran-2,4-dione was prepared analogously to Example A(82), where 3-ethyl-bromobenzene was substituted in place of 2-Bromopyridine in Step 1 of that example.

Example B(13)

6-[2-(3-Chloro-4-methoxy-phenyl)-ethyl]-6-cyclopentyl-3-(5,7-dimethyl-[1,2,4]triazolo[1,5-a]pyrimidin-2-ylmethyl)-dihydro-pyran-2,4-dione

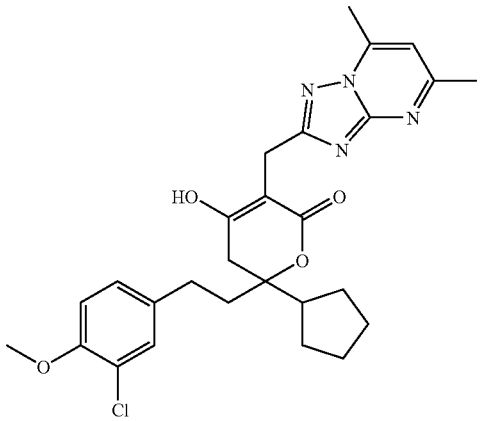

6-[2-(3-Chloro-4-methoxy-phenyl)-ethyl]-6-cyclopentyl-dihydro-pyran-2,4-dione from Step 1 below (1 g, 2.90 mmol) was combined with 5,7-Dimethyl-[1,2,4]triazolo[1,5-α]pyrimidine-2-carbaldehyde (0.5 g, 2.90 mmol) (described in Step 3 of example B(75)) in dry THF (15 mL) with magnetic stirring. To this solution was added AlCl₃ (0.76 g, 5.81 mmol) as a soln in THF (6 mL) dropwise over 1 min. The resulting yellow solution was stirred at room temperature for 3 hours. The reaction was quenched with solid Na₂CO₃·10H₂O (1.63 g, 5.81 mmol) and stirred at room temperature for 10 min. Next, the mixture was treated with MgSO₄ (2.5 g) and the slurry allowed to stand for 1.5 hours. The yellow mixture was filtered through celite and the filtrate was concentrated. The crude residue was dissolved in EtOAc (50 mL) and treated with PtO₂ and stirred with H₂ (one balloon pressure). This was maintained for 1 hour then filtered through celite. The filtrate was concentrated and the residue chromatographed on silica gel eluting with CH₂Cl₂ through 0.75% MeOH in CH₂Cl₂ to yield the title compound as a white solid.

¹H NMR (CDCl₃): δ 1.37–1.85 (brm, 8H), 1.98 (m, 2H), 2.37 (m, 1H), 2.49–2.80 (m, 11H), 3.86 (s, 3H), 4.05 (d, J=15.6 Hz, 1H), 4.12 (d, J=15.6 Hz, 1H), 6.81 (d, J=8.6 Hz, 1H), 6.85 (s, 1H), 7.00 (d, J=8.6 Hz, 1H), 7.12 (s, 1H). Anal. Calcd. For $C_{27}H_{31}ClN_4O_4$: C, 63.46; H, 6.11; N, 10.96. Found: C, 63.23; H, 6.27; N, 10.74.

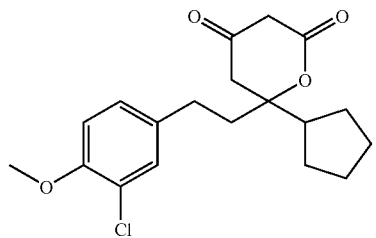

Step 1

6-[2-(3-Chloro-4-methoxy-phenyl)-ethyl]-6-cyclopentyl-dihydro-pyran-2,4-dione

6-[2-(3-Chloro-4-methoxy-phenyl)-ethyl]-6-cyclopentyl-dihydro-pyran-2,4-dione was prepared analogously to Example A(82), where 4-Bromo-2-chloro-1-methoxy-benzene was substituted in place of 2-Bromopyridine in Step 1 of that example.

Example B(14)

3-(5-Chloro-1-isopropyl-1H-benzoimidazol-2-ylmethyl)-6-cyclopentyl-6-[2-(3-fluoro-4-isopropoxy-phenyl)-ethyl]-4-hydroxy-5,6-dihydro-pyran-2-one

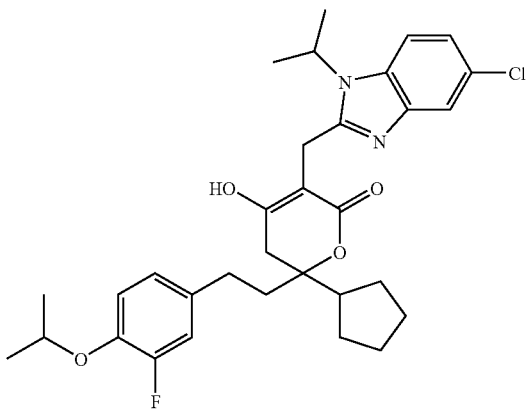

The title compound was prepared by coupling 6-Cyclopentyl-6-[2-(3-fluoro-4-isopropoxy-phenyl)-ethyl]-dihydro-pyran-2,4-dione from Step 1 below to 5-Chloro-1-isopropyl-1H-benzoimidazole-2-carbaldehyde using the AlCl$_3$/reduction procedure described in Example B(13). ESIMS (MH+): 570.3

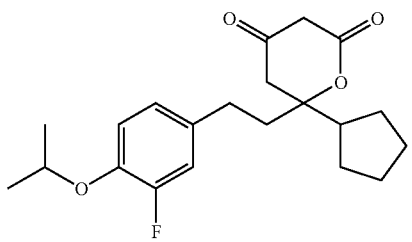

Step 1

6-Cyclopentyl-6-[2-(3-fluoro-4-isopropoxy-phenyl)-ethyl]-dihydro-pyran-2,4-dione 6-Cyclopentyl-6-[2-(3-fluoro-4-isopropoxy-phenyl)-ethyl]-dihydro-pyran-2,4-dione was prepared analogously to Example A(82), where 4-Bromo-2-fluoro-1-isopropoxy-benzene was substituted in place of 2-Bromopyridine in Step 1 of that example.

Example B(15)

6-Cyclopentyl-6-[2-(3-fluoro 4-isopropoxy-phenyl)-ethyl]-4-hydroxy-3-(5-methyl-isoxazol-3-ylmethyl)-5,6-dihydro-pyran-2-one

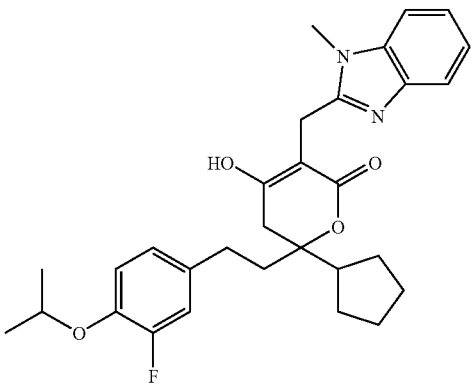

The title compound was prepared by coupling 6-Cyclopentyl-6-[2-(3-fluoro-4-isopropoxy-phenyl)-ethyl]-dihydro-pyran-2,4-dione from Step 1 of Example B(14), to 5-Methyl-isoxazole-3-carbaldehyde using the AlCl$_3$/reduction procedure described for Example B(13).

$^1$H NMR (CDCl$_3$): δ 1.32 (d, J=6 Hz, 6H), 1.44–1.92 (brm, 8H), 2.05 (m, 2H), 2.44–2.88 (m, 8H), 2.95 (s, 3H), 4.47 (m, 1H), 6.72–6.92 (m, 2H), 7.66 (m, 2H). ESIMS (MH+): 458.3.

Example B(16)

6-Cyclopentyl-6-[2-(3-fluoro-4-isopropoxy-phenyl)-ethyl]-4-hydroxy-3-(1-methyl-1H-benzoimidazol-2-ylmethyl)-5,6-dihydro-pyran-2-one The title compound was prepared by coupling 6-Cyclopentyl-6-[2-(3-fluoro-4-isopropoxy-phenyl)-ethyl]-dihydro-pyran-2,4-dione from Step 1 of Example B(14), to 1-Methyl-1H-benzoimidazole-2-carbaldehyde using the AlCl$_3$/reduction procedure described for Example B(13).

$^1$H NMR (CDCl$_3$): δ 1.32 (d, J=6 Hz, 6H), 1.45–1.91 (brm, 8H), 2.05 (m, 2H), 2.44–2.88 (m, 8H), 2.91 (s, 3H), 4.48 (m, 1H), 6.75–6.92 (m, 3H) 7.22–7.45 (m, 3H) 7.66 (s, 1H). ESIMS (MH+): 507.2.

Example B(17)

6-[2-(3-Chloro-4-methoxy-phenyl)-ethyl]-6-cyclopentyl-4-hydroxy-3-(4-methoxy-benzyl)-5,6-dihydro-pyran-2-one

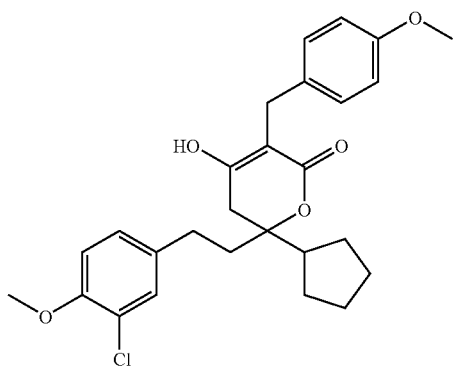

The title compound was prepared by coupling 6-[2-(3-Chloro-4-methoxy-phenyl)-ethyl]-6-cyclopentyl-dihydro-pyran-2,4-dione from Step 1 of Example B(13), to 4-Methoxy-benzaldehyde using the AlCl$_3$/reduction procedure described for Example B(13). $^1$H NMR (CDCl$_3$): δ 1.45–1.85 (brm, 8H), 1.98 (m, 2H), 2.29 (t, J=7.6 Hz, 1H) 2.44–3.02 (m, 7H), 3.88 (s, 3H), 3.94 (s, 3H), 6.73–7.85 (m, 7H). ESIMS (MH+): 471.7.

Example B(18)

6-Cyclopentyl-3-(5,7-dimethyl-[1,2,4]triazolo[1,5-pyrimidin-2-ylmethyl)-6-[2-(3-fluoro-4-isopropoxy-phenyl)-ethyl]-4-hydroxy-5,6-dihydro-pyran-2-one

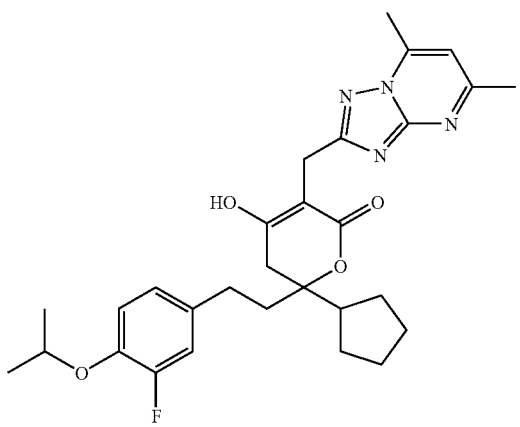

The title compound was prepared by coupling 6-Cyclopentyl-6-[2-(3-fluoro-4-isopropoxy-phenyl)-ethyl]-dihydro-pyran-2,4-dione from Step 1 of Example B(14), to 5,7-Dimethyl-[1,2,4]triazolo[1,5-☐]pyrimidine-2-carbaldehyde (described in Step 3 of example B(75)) using the Me$_2$NHBH$_3$ method described in the synthesis of Example B(31). $^1$H NMR (CDCl$_3$): δ 1.30 (d, J=6.2 Hz, 6H), 1.52–1.81 (brm, 8H), 1.99 (m, 2H), 2.38 (m, 1H), 2.50–2.72 (m, 8H), 2.78 (s, 3H), 4.05 (d, J=15.5 Hz, 1H), 4.12 (d, J=15.5 Hz, 1H), 4.45 (m, 1H), 6.84 (s, 1H), 6.86–6.93 (m, 3H). Anal. Calcd. For C$_{29}$H$_{35}$FN$_4$O$_4$: C, 66.65; H, 6.75; N, 10.72. Found: C, 66.28; H, 6.87; N, 10.52.

Example B(19)

6-[2-(3-Chloro-4-fluoro-phenyl)-ethyl]-6-cyclopentyl-3-(5,7-dimethyl-[1,2,4]triazolo[1,5]pyrimidin-2-ylmethyl)-4-hydroxy-5,6-dihydro-pyran-2-one

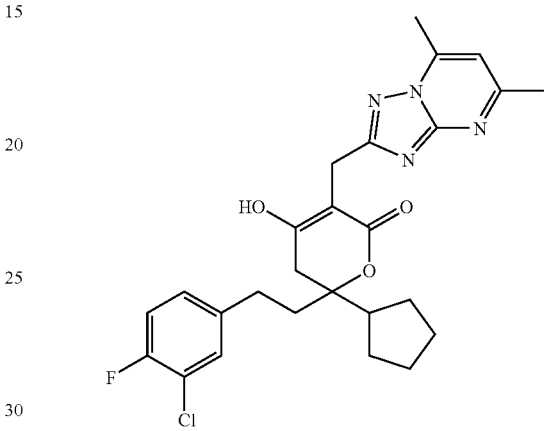

The title compound was prepared by coupling 6-[2-(3-Chloro-4-fluoro-phenyl)-ethyl]-6-cyclopentyl-dihydro-pyran-2,4-dione from Step 1 below to 5,7-Dimethyl-[1,2,4]triazolo[1,5-α]pyrimidine-2-carbaldehyde (described in Step 3 of example B(75)), using the Me$_2$NHBH$_3$ method described in the synthesis of Example B(31). $^1$H NMR (CDCl$_3$): δ 1.44–1.92 (brm, 8H), 2.05 (m, 2H), 2.35 (m, 1H) 2.44–2.88 (m, 11H), 4.05 (s, 2H), 6.85 (s, 1H), 6.99 (m, 2H) 7.15 (d, J=7.5 Hz, 1H). Anal. Calcd. For C$_{26}$H$_{28}$ClFN$_4$O$_3$: C, 62.58; H, 5.66; N, 11.23. Found: C, 62.42; H, 5.46; N, 11.55.

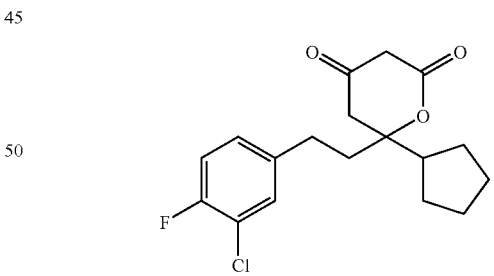

Step 1

6-[2-(3-Chloro-4-fluoro-phenyl)-ethyl]-6-cyclopentyl-dihydro-pyran-2,4-dione

6-[2-(3-Chloro-4-fluoro-phenyl)-ethyl]-6-cyclopentyl-dihydro-pyran-2,4-dione was prepared analogously to Example A(82), where 4-Bromo-2-chloro-1-fluoro-benzene was substituted in place of 2-Bromopyridine in Step 1 of that example.

Example B(20)

6-[2-(3-Chloro-4-ethoxy-phenyl)-ethyl]-6-cyclopentyl-3-(5,7-dimethyl-[1,2,4]triazolo[1,5]pyrimidin-2-ylmethyl)-4-hydroxy-5,6-dihydro-pyran-2-one

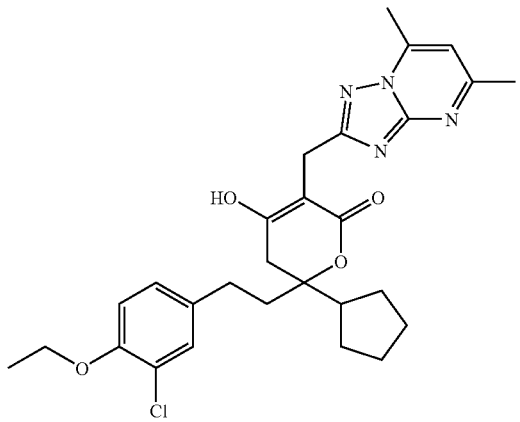

The title compound was prepared by coupling 6-[2-(3-Chloro-4-ethoxy-phenyl)-ethyl]-6-cyclopentyl-dihydro-pyran-2,4-dione from Step 1 below to 5,7-Dimethyl-[1,2,4]triazolo[1,5-α]pyrimidine-2-carbaldehyde (described in Step 3 of example B(75), using the Me$_2$NHBH$_3$ method described in the synthesis of Example B(31). $^1$H NMR (CDCl$_3$): δ 1.39 (t, J=7.2 Hz, 3H), 1.52–1.82 (brm, 8H), 2.05 (m, 2H), 2.35 (m, 1H), 2.50–2.71 (m, 8H), 2.79 (s, 3H), 3.96 (q, J=7.2 Hz, 2H), 4.05 (d, J=15.5 Hz, 1H), 4.12 (d, J=15.5 Hz, 1H), 6.67 (d, J=8.4 Hz, 1H), 6.84 (s, 1H), 6.91 (m, 2H). Anal. Calcd. For C$_{28}$H$_{33}$ClN$_4$O$_4$: C, 64.05; H, 6.34; N, 10.67. Found: C, 64.40; H, 6.26; N, 10.88.

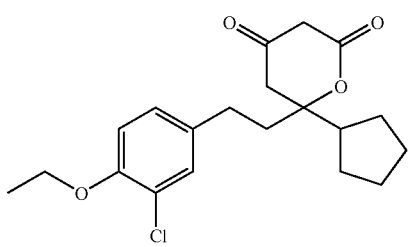

Step 1

6-[2-(3-Chloro-4-ethoxy-phenyl)-ethyl]-6-cyclopentyl-dihydro-pyran-2,4-dione

6-[2-(3-Chloro-4-ethoxy-phenyl)-ethyl]-6-cyclopentyl-dihydro-pyran-2,4-dione was prepared analogously to Example A(82), where 4-Bromo-2-chloro-1-ethoxy-benzene was substituted in place of 2-Bromopyridine in Step 1 of that example.

Example B(21)

6-[2-(3-Chloro-4-methoxy-phenyl)-ethyl]-6-cyclopentyl-4-hydroxy-3-(4-methanesulfonyl-benzyl)-5,6-dihydro-pyran-2-one

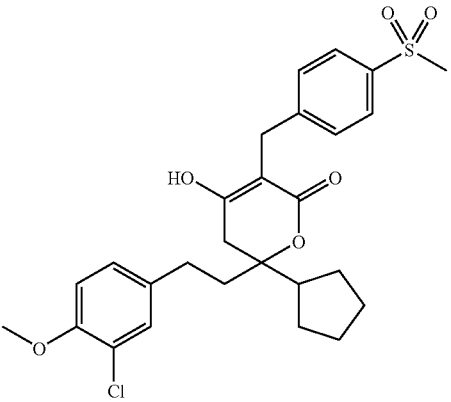

The title compound was prepared by coupling 6-[2-(3-Chloro-4-methoxy-phenyl)-ethyl]-6-cyclopentyl-dihydro-pyran-2,4-dione from Step 1 of Example B(13), to 4-Methanesulfonyl-benzaldehyde using the Me$_2$NHBH$_3$ method described in the synthesis of Example B(31). $^1$H NMR (CDCl$_3$): δ 1.45–1.86 (brm, 8H), 1.96 (m, 2H), 2.29 (t, J=7.6 Hz, 1H) 2.44–3.02 (m, 7H), 3.91 (s, 3H), 3.94 (s, 3H), 6.88–7.85 (m, 7H).

Example B(22)

4-{6-[2-(3-Chloro-4-methoxy-phenyl)-ethyl]-6-cyclopentyl-4-hydroxy-2-oxo-5,6-dihydro-2-pyran-3-ylmethyl}-benzonitrile

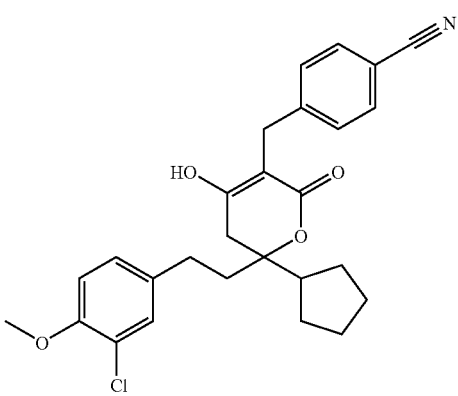

The title compound was prepared by coupling 6-[2-(3-Chloro-4-methoxy-phenyl)-ethyl]-6-cyclopentyl-dihydro-pyran-2,4-dione from Step 1 of Example B(13), to 4-Formyl-benzonitrile using the Me$_2$NHBH$_3$ method described in the synthesis of Example B(31). $^1$H NMR (CDCl$_3$): δ 1.45–1.86 (brm, 8H), 2.02 (m, 2H), 2.29 (m, 1H) 2.44–3.02 (m, 7H), 3.94 (s, 3H), 6.88–7.85 (m, 7H). Anal. Calcd. For C$_{27}$H$_{28}$ClNO$_4$: C, 69.59; H, 6.06; N, 3.01. Found: C, 69.40; H, 6.22; N, 3.07.

Example B(23)

3-{6-[2-(3-Chloro-4-methoxy-phenyl)-ethyl]-6-cyclopentyl-4-hydroxy-2-oxo-5,6-dihydro-2-pyran-3-ylmethyl}-benzonitrile

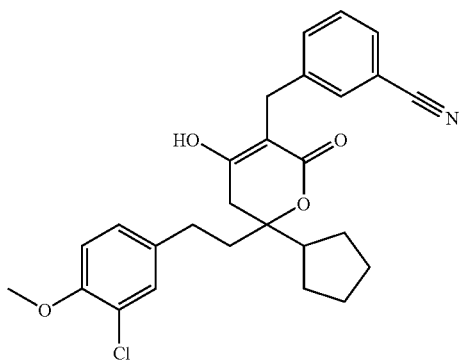

The title compound was prepared by coupling 6-[2-(3-Chloro-4-methoxy-phenyl)-ethyl]-6-cyclopentyl-dihydro-pyran-2,4-dione from Step 1 of Example B(13), to 3-Formyl-benzonitrile using the Me$_2$NHBH$_3$ method described in the synthesis of Example B(31). $^1$H NMR (CDCl$_3$): δ 1.43–1.86 (brm, 8H), 2.02 (m, 2H), 2.29 (m, 1H) 2.44–3.02 (m, 7H), 3.95 (s, 3H), 6.88–7.91 (m, 7H). Anal. Calcd. For C$_{27}$H$_{28}$ClNO$_4$: C, 69.59; H, 6.06; N, 3.01. Found: C, 69.67; H, 6.14; N, 3.13.

Example B(24)

6-[2-(3-Chloro-4-methoxy-phenyl)-ethyl]-6-cyclopentyl-4-hydroxy-3-(4-pyrazol-1-yl-benzyl)-5,6-dihydro-pyran-2-one

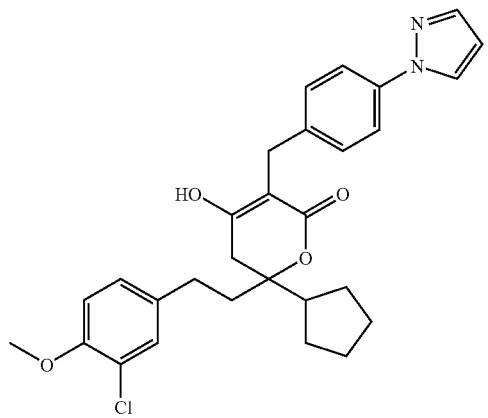

The title compound was prepared by coupling 6-[2-(3-Chloro-4-methoxy-phenyl)-ethyl]-6-cyclopentyl-dihydro-pyran-2,4-dione from Step 1 of Example B(13), to 4-Pyrazol-1-yl-benzaldehyde using the Me$_2$NHBH$_3$ method described in the synthesis of Example B(31).ESIMS (MH+): 508.1.

Example B(25)

6-[2-(3-Chloro-4-methoxy-phenyl)-ethyl]-6-cyclopentyl-4-hydroxy-3-(4-[1,2,4]triazol-1-yl-benzyl)-5,6-dihydro-pyran-2-one

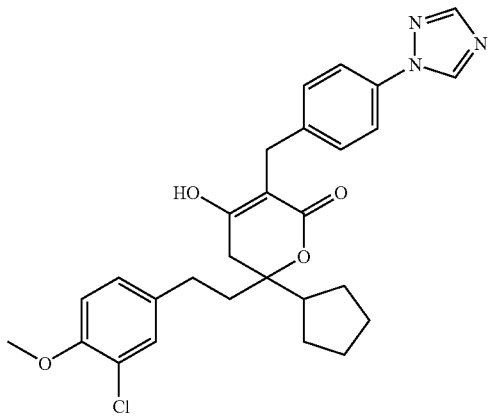

The title compound was prepared by coupling 6-[2-(3-Chloro-4-methoxy-phenyl)-ethyl]-6-cyclopentyl-dihydro-pyran-2,4-dione from Step 1 of Example B(13), to 4-[1,2,4]Triazol-1-yl-benzaldehyde using the Me$_2$NHBH$_3$ method described in the synthesis of Example B(31).ESIMS (MH+): 509.1.

Example B(26)

6-[2-(3-Chloro-4-cyclopropylmethoxy-phenyl)-ethyl]-6-cyclopentyl-4-hydroxy-3-(1-methyl-1H-benzoimidazol-2-ylmethyl)-5,6-dihydro-pyran-2-one

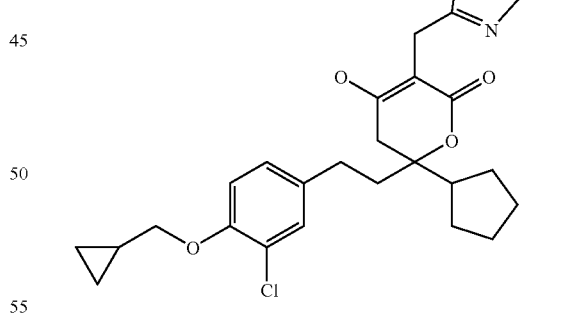

The title compound was prepared analogously to Example B(31), carbaldehyde where 6-[2-(3-Chloro-4-cyclopropyl-methoxy-phenyl)-ethyl]-6-cyclopentyl-dihydro-pyran-2,4-dione was substituted in place of 6-[2-(3-Chloro-4-isopropoxy-phenyl)-ethyl]-6-cyclopentyl-dihydro-pyran-2,4-dione and 1-methyl-2-formylbenzimidazole was substituted in place of 5,7-Dimethyl-[1,2,4]triazolo[1,5-a]pyrimidine-2-carbaldehyde of that example.

$^1$H NMR (DMSO-d$_6$): δ 0.10 (d, J=4.7, 2H), 0.33–0.36 (m, 2H), 0.98–2.04 (m, 14H), 2.17–2.26 (m, 2H), 2.29 (d, J=17, 1H), 2.54 (d, J=17 Hz, 1H), 3.56 (s, 3H), 3.60–3.65

(m, 2H), 3.85 (brs, 1H), 6.71–7.26 (m, 7H). Anal. Calcd. For C$_{31}$H$_{35}$ClN$_2$O$_4$.0.5H$_2$O: C, 68.43; H, 6.67; N, 5.15. Found: C, 68.36; H, 6.58; N, 4.81. ESIMS (MH+): 536.

Example B(27)

6-[2-(3-Chloro-4-isopropoxy-phenyl)-ethyl]-6-cyclopentyl-4-hydroxy-3-(1-methyl-1H-benzoimidazol-2-ylmethyl)-5,6-dihydro-pyran-2-one

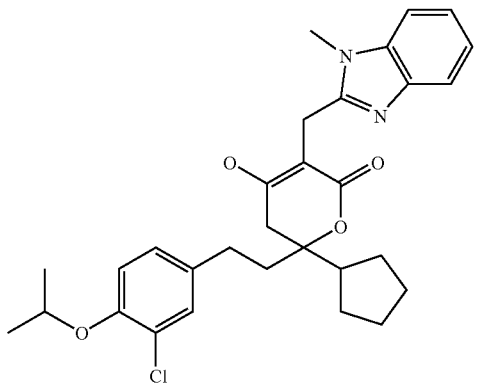

The title compound was prepared analogously to Example B(31), where 1-methyl-2-formylbenzimidazole was substituted in place of 5,7-Dimethyl-[1,2,4]triazolo[1,5-a]pyrimidine-2-carbaldehyde of that example.

$^1$H NMR (DMSO-d$_6$):δ 0.90–1.36 (m, 14H), 1.54–1.61 (m, 2H), 2.20–2.39 (m, 3H), 2.57–2.73 (m, 4H), 4.10 (s, 3H), 4.44–4.49 (m, 1H), 6.49–6.48 (m, 7H), 13.5 (brs, 1H); Anal. Calcd. For C$_{30}$H$_{35}$ClN$_4$O$_4$: C, 68.89; H, 6.74; N, 5.36. Found: C, 69.11; H, 6.73; N, 5.36. ESIMS (MH+): 524.

Example B(28)

6-[2-(3-Chloro-4-cyclopropylmethoxy-phenyl)-ethyl]-6-cyclopentyl-3-(5,7-dimethyl-[1,2,4]triazolo[1,5-a]pyrimidin-2-ylmethyl)-4-hydroxy-5,6-dihydro-pyran-2-one

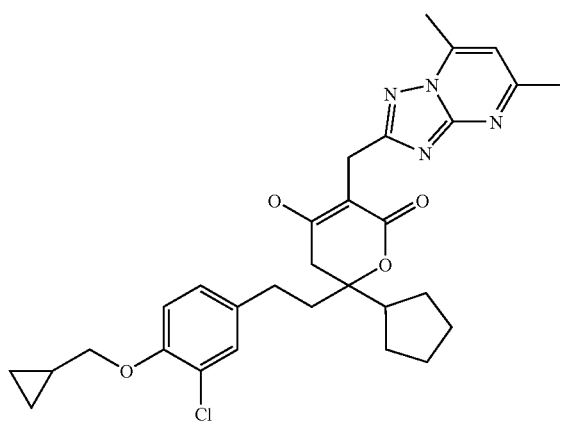

The title compound was prepared analogously to Example B(31), where 6-[2-(3-Chloro-4-cyclopropylmethoxy-phenyl)-ethyl]-6-cyclopentyl-dihydro-pyran-2,4-dione was substituted in place of 6-[2-(3-Chloro-4-isopropoxy-phenyl)-ethyl]-6-cyclopentyl-dihydro-pyran-2,4-dione of that example.

$^1$H NMR (DMSO-d$_6$): δ 0.35–0.38 (m, 2H), 0.61–0.64 (m, 2H), 1.26–1.85 (m, 8H), 1.94–2.05 (m, 1H), 2.18 (s, 2H), 2.37–2.79 (m, 12H), 3.83 (d, J=6.8 Hz, 2H), 4.09 (s, 1H), 6.79 (d, J=8.1 Hz, 1H), 6.95 (dd, J=8.1, 2.2 Hz, 1H), 7.11 (d, J=2.2 Hz, 1H), 7.26 (s, 1H), 14.1 (brs, 1H). Anal. Calcd. For C$_{30}$H$_{35}$ClN$_4$O$_4$.0.2 AcOH: C, 64.84; H, 6.41; N, 9.95. Found: C, 64.82; H, 6.42; N, 9.69. ESIMS (MH+): 552.

Example B(29)

6-[2-(3-Chloro-4-methoxy-phenyl)-ethyl]-3-(4-chloro-1-methyl-1H-pyrazol-3-ylmethyl)-6-cyclopentyl-4-hydroxy-5,6-dihydro-pyran-2-one

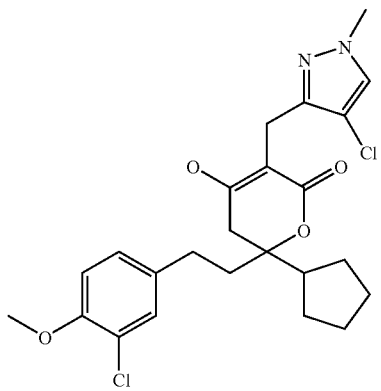

The title compound was prepared analogously to Example B(31), where 6-[2-(3-Chloro-4-methoxy-phenyl)-ethyl]-6-cyclopentyl-dihydro-pyran-2,4-dione was substituted in place of 6-[2-(3-Chloro-4-isopropoxy-phenyl)-ethyl]-6-cyclopentyl-dihydro-pyran-2,4-dione and 4-chloro-1-methyl-1H-pyrazole-3-carbalehyde was substituted in place of 5,7-Dimethyl-[1,2,4]triazolo[1,5-a]pyrimidine-2-carbaldehyde of that example.

$^1$H NMR (DMSO-d$_6$): δ 1.50–1.71 (m, 8H), 2.01–2.05 (m, 2H), 2.39–2.41 (m, 1H), 2.49–2.57 (m, 2H), 2.74 (d, J=16 Hz, 1H), 3.18 (d, J=5.3 Hz, 1H), 3.39 (d, J=16.0 Hz, 1H), 3.47 (d, J=16 Hz, 1H), 3.60 (s, 3H), 3.83 (s, 3H), 7.05 (d, J=8.3 Hz, 1H), 7.11 (dd, J=8.3. 2.0 Hz, 1H), 7.23 (d, J=2.0 Hz, 1H), 7.76 (s, 1H), 10.64 (s, 1H). Anal. Calcd. For C$_{24}$H$_{28}$Cl$_2$N$_2$O$_4$: C, 60.13; H, 5.89; N, 5.84. Found: C, 59.94; H, 5.95; N, 5.69. ESIMS (MH+): 480.

Example B(30)

6-[2-(3-Chloro-4-methoxy-phenyl)-ethyl]-6-cyclopentyl-4-hydroxy-3-(1H-imidazol-2-ylmethyl)-5,6-dihydro-pyran-2-one

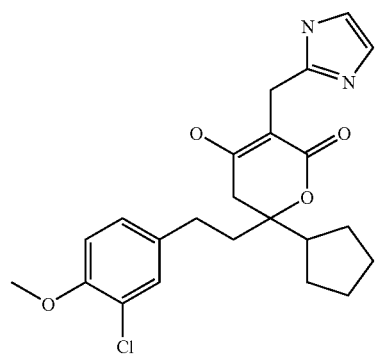

The title compound was prepared analogously to Example B(31), where 6-[2-(3-Chloro-4-methoxy-phenyl)-ethyl]-6- cyclopentyl-dihydro-pyran-2,4-dione was substituted in place of 6-[2-(3-Chloro-4-isopropoxy-phenyl)-ethyl]-6-cyclopentyl-dihydro-pyran-2,4-dione and imidazole-2-carboxaldehyde was substituted in place of 5,7-Dimethyl-[1,2,4]triazolo[1,5-a]pyrimidine-2-carbaldehyde of that example.

¹H NMR (DMSO-d₆): δ 1.05–1.55 (m, 8H), 1.79–1.83 (m, 2H), 2.21–2.29 (m, 2H), 2.42–2.45 (m, 2H), 2.62–2.76 (m, 3H), 3.70 (s, 3H), 4.64 (s, 1H), 6.93 (d, J=8.3 Hz, 1H), 6.99–7.02 (m, 1H), 7.15 (d, J=2.0 Hz, 1H), 7.39 (s, H), 7.48 (s, 1H), 11.76 (brs, 1H). ESIMS (MH+): 431.

Example B(31)

6-[2-(3-Chloro-4-isopropoxy-phenyl)-ethyl]-6-cyclopentyl-3-(5,7-dimethyl-[1,2,4]triazolo[1,5-a]pyrimidin-2-ylmethyl)-4-hydroxy-5,6-dihydro-pyran-2-one

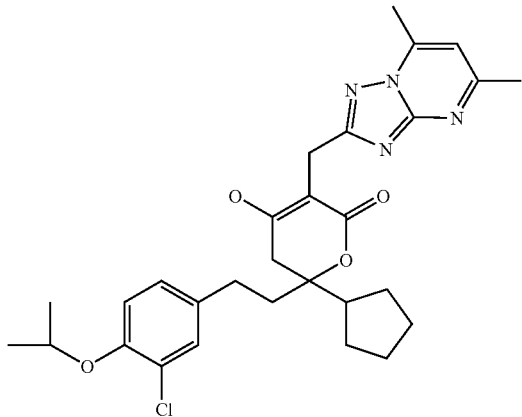

6-[2-(3-Chloro-4-isopropoxy-phenyl)-ethyl]-6-cyclopentyl-dihydro-pyran-2,4-dione (0.3 g, 0.79 mmol) and 5,7-Dimethyl-[1,2,4]triazolo[1,5-a]pyrimidine-2-carbaldehyde (0.17 g, 0.95 mmol, described in Step 3 of example B(75)) were dissolved in 3:1 MeOH/CH₂Cl₂ (4 mL). To this suspension, Me₂NH.BH₃ (0.07 g, 1.19 mmol) was added as a solid from top. After stirring 1 h at room temperature, the reaction mixture became clear and it was stirred for an additional 5 hours. After this time, 1 M HCl (1 mL) was added and the reaction stirred for 30 minutes at room temperature, the solvent was the evaporated to half the volumen and extracted 3 times with 10% MeOH/CH₂Cl₂ (10 mL). The organic phase was dried over MgSO₄ and evaporated. The residue purified by flash column chromatography (80% EtOAc in hexanes) to eliminate unreacted pyrone and reduced 5,7-Dimethyl-[1,2,4]triazolo[1,5-a]pyrimidine-2-carbaldehyde, then 3% MeOH/CH₂Cl₂ to give the product (0.1 g, 24%) as a white solid.

¹H NMR (DMSO-d₆): δ 1.14 (d, J=6.3, 6H), 1.4–1.53 (m, 8H), 1.7–1.75 (m, 2H), 1.95–1.98 (m, 1H), 2.35–2.44 (m, 8H), 3.19 (s, 2H), 3.57 (d, J=16 Hz, 1H), 3.69 (d, J=16 Hz, 1H), 4.41–4.47 (m, 1H), 6.91–6.93 (s, 1H), 7–7.07 (m, 2H), 7.10 (d, J=2.0, 1H), 10.7 (brs, 1H). Anal. Calcd. For C₂₉H₃₅N₄O₄: C, 64.61; H, 6.54; N, 10.39. Found: C, 64.30; H, 6.81; N, 10.35. ESIMS (MH+): 540.

Example B(32)

6-[2-(5-Chloro-2,4-dimethoxy-phenyl)-ethyl]-3-(4-chloro-1-methyl-1H-pyrazol-3-ylmethyl)-6-cyclopentyl-4-hydroxy-5,6-dihydro-pyran-2-one

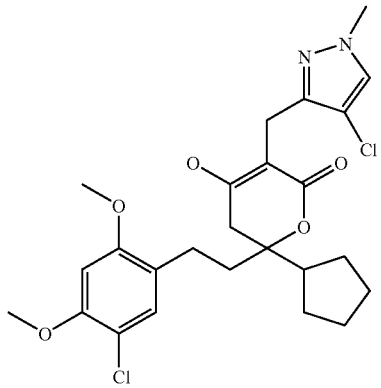

The title compound was prepared analogously to Example B(31), where 6-[2-(5-Chloro-2,4-dimethoxy-phenyl)-ethyl]-6-cyclopentyl-dihydro-pyran-2,4-dione (described in Step 1 of example B(35)) was substituted in place of 6-[2-(3-Chloro-4-isopropoxy-phenyl)-ethyl]-6-cyclopentyl-dihydro-pyran-2,4-dione and 4-chloro-1-methyl-1H-pyrazole-3-carbalehyde was substituted in place of 5,7-Dimethyl-[1,2,4]triazolo[1,5-a]pyrimidine-2-carbaldehyde of that example.

¹H NMR (DMSO-d₆): δ 1.35–1.70 (m, 8H), 1.90–1.99 (m, 2H), 2.33–2.38 (m, 1H), 2.39–2.53 (m, 3H), 2.72 (d, J=17 Hz, 1H), 3.34–3.47 (m, 2H), 3.57 (s, 3H), 3.78 (s, 3H), 3.85 (s, 3H), 6.73 (s, 1H), 7.07 (s, 1H), 7.73 (s, 1H), 10.61 (s, 1H). Anal. Calcd. For C₂₅H₃₀Cl₂N₂O₅: C, 58.94; H, 5.94; N, 5.50. Found: C, 58.78; H, 6.02; N, 5.39. ESIMS (MH+): 510.

Example B(33)

6-Cyclopentyl-6-[2-(4-cyclopropylmethoxy-3-fluoro-phenyl)-ethyl]-3-(5,7-dimethyl-[1,2,4]triazolo[1,5-a]pyrimidin-2-ylmethyl)-4-hydroxy-5,6-dihydro-pyran-2-one

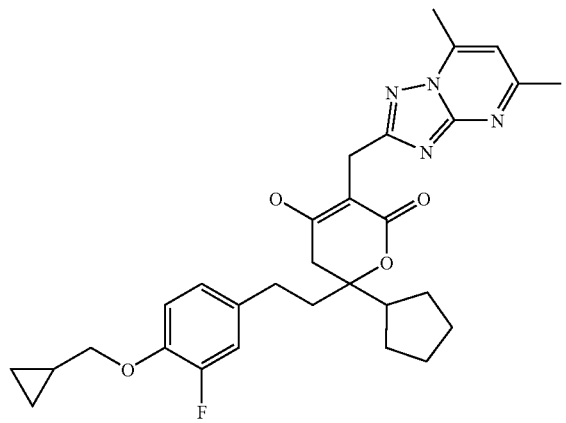

The title compound was prepared analogously to Example B(31), where 6-Cyclopentyl-6-[2-(4-cyclopropylmethoxy-3-fluoro-phenyl)-ethyl]-dihydro-pyran-2,4-dione (prepared in Step 2 below) was substituted in place of 6-[2-(3-Chloro-4-isopropoxy-phenyl)-ethyl]-6-cyclopentyl-dihydro-pyran-2,4-dione of that example.

¹H NMR (DMSO-d₆): δ 0.09–0.11 (m, 2H), 0.32–0.39 (m, 2H), 0.98–1.48 (m, 8H), 1.84–1.90 (m, 2H), 2.16–2.22 (m, 1H), 2.28–2.33 (m, 10H), 2.56 (d, J=16 Hz, 1H), 3.47–3.63 (m, 4H), 6.76–6.86 (m, 4H), 10.65 (brs, 1H). Anal. Calcd. For $C_{30}H_{35}FN_4O_4 \cdot 0.25H_2O$: C, 66.84; H, 6.64; N, 10.39. Found: C, 67.07; H, 6.74; N, 10.05. ESIMS (MH+): 535.

Step 1

4-Bromo-1-cyclopropylmethoxy-2-fluoro-benzene

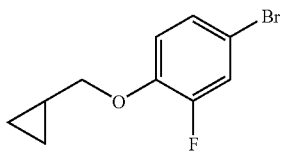

The title compound was prepared analogously to Step 1 in Example A(52), where (bromomethyl)-cyclopropane was substituted instead of methyl α-bromobutyrate of that example. ¹H NMR (CDCl₃) δ 0.32–0.42 (m, 2H), 0.62–0.68 (m, 2H), 1.23–1.33 (m, 1H), 3.85 (d, J=6.9 Hz, 2H), 6.82 (t, J=8.8 Hz, 1H), 7.14–7.18 (m, 1H), 7.23 (dd, J=10.5, 2.3 Hz, 1H). ESIMS (MH+): 246.1.

Step 2

6-Cyclopentyl-6-[2-(4-cyclopropylmethoxy-3-fluoro-phenyl)-ethyl]-dihydro-pyran-2,4-dione

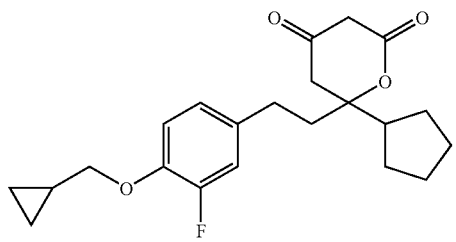

The title compound was prepared analogously to Example A(27), where 4-Bromo-1-cyclopropylmethoxy-2-fluoro-benzene from Step 1 below was substituted in place of 1-(4-Bromo-2-chloro-phenyl)-ethanone in Step 3 of that example ¹H NMR (CDCl₃-d₆): δ 0.32–0.37 (m, 2H), 0.61–0.67 (m, 2H), 1.26–1.30 (m, 1H), 1.57–1.84 (m, 8H), 1.89–1.96 (m, 2H), 2.26 (t, J=8.4 Hz, 1H), 2.61 (t, J=8.4 Hz, 2H), 2.75 (s, 2H), 3.42 (s, 2H), 3.84 (d, J=6.9 Hz, 2H), 6.78–6.89 (m, 3H). Anal. Calcd. For $C_{22}H_{27}FO_4$: C, 70.57; H, 7.27. Found: C, 70.63; H, 7.40. ESIMS (MNa+): 397.1.

Example B(34)

6-Cyclopentyl-3-(5,7-dimethyl-[1,2,4]triazolo[1,5-a]pyrimidin-2-ylmethyl)-4-hydroxy-6-[2-(4-isopropoxy-phenyl)-ethyl]-5,6-dihydro-pyran-2-one The title compound was prepared analogously to Example B(31), where 6-Cyclopentyl-6-[2-(4-isopropoxy-phenyl)-ethyl]-dihydro-pyran-2,4-dione was substituted in place of 6-[2-(3-Chloro-4-isopropoxy-phenyl)-ethyl]-6-cyclopentyl-dihydro-pyran-2,4-dione of that example.

¹H NMR (DMSO-d₆): δ 1.39 (d, J=6.1, 6H), 1.43–1.86 (m, 8H), 2.22–2.28 (m, 2H), 2.54–2.57 (m, 1H), 2.57–2.70 (m, 9H), 2.94 (d, J=17 Hz, 1H), 3.86 (d, J=16 Hz, 1H), 3.97 (d, J=16 Hz, 1H), 4.65–4.71 (m, 1H), 6.93 (d, J=8.6 Hz, 2H), 7.20 (s, 1H), 7.27 (d, J=8.6 Hz, 2H), 10.99 (s, 1H). Anal. Calcd. For $C_{29}H_{36}N_4O_4 \cdot 0.25H_2O$: C, 68.41; H, 7.23; N, 11.00. Found: C, 68.40; H, 7.23; N, 10.99. ESIMS (MH+): 505.

Step 1

6-Cyclopentyl-6-[2-(4-isopropoxy-phenyl)-ethyl]-dihydro-pyran-2,4-dione

The title compound was prepared analogously to Example A(27), where 1-Bromo-4-isopropoxy-benzene was substituted in place of 1-(4-Bromo-2-chloro-phenyl)-ethanone in Step 3 of that example.

¹H NMR (CDCl₃-d₆): δ 1.32 (d, J=6.2 Hz, 6H), 1.58–1.7 (m, 8H), 1.89–1.99 (m, 1H), 2.2–2.31 (m, 2H), 2.61 (t, J=8.6 Hz, 2H), 2.77 (s, 2H), 3.43 (s, 2H), 4.52 (septet, J=12, 6 Hz, 1H), 6.82 (d, J=8.5 Hz, 2H), 7.03 (d, J=8.5 Hz, 2H). Anal. Calcd. For $C_{21}H_{28}O_4$: C, 73.23; H, 8.19. Found: C, 73.43; H, 8.44. ESIMS (MH+): 345.2.

Example B(35)

6-[2-(5-Chloro-2,4-dimethoxy-phenyl)-ethyl]-6-cyclopentyl-4-hydroxy-3-(2-methyl-1H-imidazol-4-ylmethyl)-5,6-dihydro-pyran-2-one

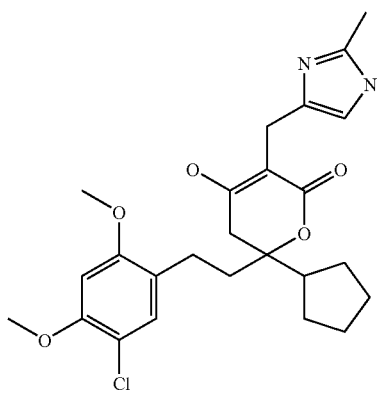

The title compound was prepared analogously to Example B(31), where 6-[2-(5-Chloro-2,4-dimethoxy-phenyl)-ethyl]-6-cyclopentyl-dihydro-pyran-2,4-dione (described below), as substituted in place of 6-[2-(3-Chloro-4-isopropoxy-phenyl)-ethyl]-6-cyclopentyl-dihydro-pyran-2,4-dione and 2-methyl-1H-imidazole-4-carbaldehyde was substituted in place of 5,7-Dimethyl-[1,2,4]triazolo[1,5-a]pyrimidine-2-carbaldehyde of that example.

$^1$H NMR (DMSO-d$_6$): δ 1.08–1.58 (m, 10H), 2.02–2.42 (m, 9H), 3.20–3.22 (m, 2H), 3.53 (s, 3H), 3.61 (s, 3H), 6.47 (s, 1H), 6.53 (s, 1H), 6.86 (s, 1H), 10.9 (s, 1H). Anal. Calcd. For C$_{25}$H$_{31}$ClN$_2$O$_5$.1.5H$_2$O: C, 59.82; H, 6.83; N, 5.58. Found: C, 59.87; H, 6.58; N, 5.46. ESIMS (MH+): 475.

Step 1

6-[2-(5-chloro-2,4-dimethoxyphenyl)ethyl]-6-cyclopentyldihydro-2H-pyran-2,4(3H)-dione

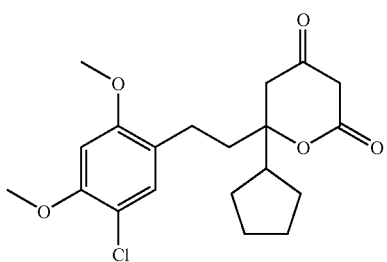

A solution of 6-[2-(2,4-dimethoxyphenyl)ethyl]-6-cyclopentyldihydro-2H-pyran-2,4(3H)-dione (from example A(39); 4.50 g, 13 mmol) in CH$_2$Cl$_2$ (20 mL) was cooled to −5° C. and treated with a solution of SO$_2$Cl$_2$ (1.94 g, 14.3 mmol) in CH$_2$Cl$_2$ (10 mL) dropwise under nitrogen. The reaction mixture was stirred for an additional 15 minutes at −5° C., then allowed to warm gradually to room temperature. After a total reaction time of 2 h, an aqueous solution of NaHCO$_3$ (5 wt %) was added to achieve a pH of 8 in the aqueous phase. The volatiles were removed in vacuo. The residue was treated with water and extracted with ethyl acetate (3×25 mL). The combined ethyl acetate extract was acidified to a pH 2 using 2 N HCl, then washed with water. The organic phase was dried over Na$_2$SO$_4$, filtered, and concentrated to a yellowish solid. Recrystallization from ether afforded the title product as a white solid (2.18 g, 44%).

$^1$H NMR (CDCl$_3$) δ 1.74 (m, 8H), 2.32 (m, 1H), 2.58 (m, 2H), 2.78 (s, 2H), 3.43 (s, 2H), 3.82 (s, 3H), 3.92 (s, 3H), 6.44 (s, 1H), 7.07 (s, 1H). HRMS calcd for C$_{20}$H$_{25}$O$_5$Cl (M+H$^+$): 381.1469. found 381.1475.

Example B(36)

6-Cyclopentyl-6-[2-(2,3-dihydro-benzo[1,4]dioxin-6-yl)-ethyl]-3-(5,7-dimethyl-[1,2,4]triazolo[1,5-a]pyrimidin-2-ylmethyl)-4-hydroxy-5,6-dihydro-pyran-2-one

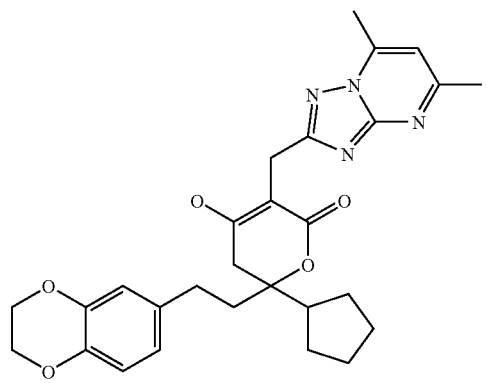

The title compound was prepared analogously to Example B(31), where 6-Cyclopentyl-6-[2-(2,3-dihydro-benzo[1,4]dioxin-6-yl)-ethyl]-dihydro-pyran-2,4-dione (from Step 1 below) was substituted in place of 6-[2-(3-Chloro-4-isopropoxy-phenyl)-ethyl]-6-cyclopentyl-dihydro-pyran-2,4-dione of that example.

$^1$H NMR (DMSO-d$_6$): δ 1.31–1.55 (m, 8H), 1.82–1.91 (m, 2H), 2.20–2.22 (m, 1H), 2.33–2.63 (m, 10H), 3.54 (d, J=16 Hz, 1H), 3.65 (d, J=16 Hz, 1H), 4.01 (s, 4H), 6.47–6.57 (m, 3H), 6.88 (s, 1H), 10.65 (s, 1H). Anal. Calcd. For C$_{28}$H$_{32}$N$_4$O$_5$: C, 66.65; H, 6.39; N, 11.10. Found: C, 66.80; H, 6.75; N, 11.38. ESIMS (MH+): 505.

Step 1

6-Cyclopentyl-6-[2-(2,3-dihydro-benzo[1,4]dioxin-6-yl)-ethyl]-dihydro-pyran-2,4-dione

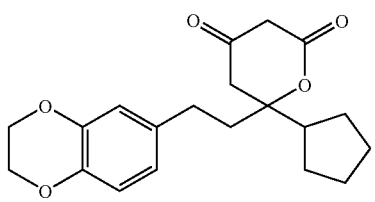

The title compound was prepared analogously to Example A(27), where 1-Bromo-1,2-(ethylene-dioxy)benzene was substituted in place of 1-(4-Bromo-2-chloro-phenyl)-ethanone in Step 3 of that example.

¹H NMR (CDCl₃-d₆): δ 1.5–1.6 (m, 8H), 1.71–1.97 (m, 2H), 2.2–2.3 (m, 1H), 2.57 (t, J=8.5 Hz, 2H), 2.76 (s, 2H), 3.42 (s, 2H), 4.24 (s, 4H), 6.59–6.85 (m, 2H), 6.78 (d, J=8.3 Hz, 1H). Anal. Calcd. For $C_{20}H_{24}O_5$: C, 69.75; H, 7.02. Found: C, 69.83; H, 7.31. ESIMS (MH+): 345.2.

Example B(37)

6-Cyclopentyl-6-[2-(3,5-dichloro-4-ethoxy-phenyl)-ethyl]-3-(5,7-dimethyl-[1,2,4]triazolo[1,5-a]pyrimidin-2-ylmethyl)-4-hydroxy-5,6-dihydro-pyran-2-one

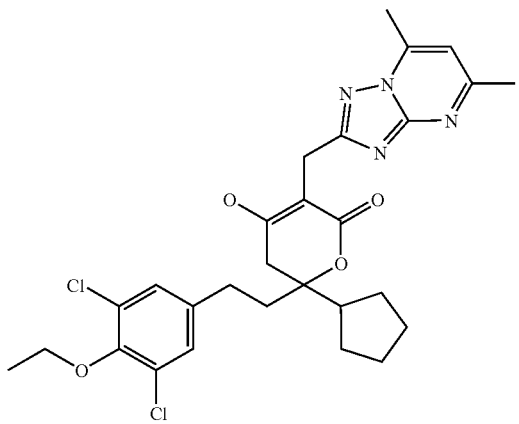

The title compound was prepared analogously to Example B(31), where 6-Cyclopentyl-6-[2-(3,5-dichloro-4-ethoxy-phenyl)-ethyl]-dihydro-pyran-2,4-dione (from Step 2 below) was substituted in place of 6-[2-(3-Chloro-4-isopropoxy-phenyl)-ethyl]-6-cyclopentyl-dihydro-pyran-2,4-dione of that example.

¹H NMR (DMSO-d₆): δ 1.53 (t, J=6.9, 3H), 1.59–1.9 (m, 8H), 2.26–2.32 (m, 2H), 2.67–2.98 (m, 11H), 3.89 (d, J=16 Hz, 1H), 4.0 (d, J=16 Hz, 1H), 4.17 (q, J=6.9 Hz, 2H), 7.23 (s, 1H), 7.51 (s, 2H), 11.01 (s, 1H). Anal. Calcd. For $C_{28}H_{32}Cl_2N_4O_4 \cdot 0.75H_2O$: C, 58.60; H, 5.64; N, 9.59. Found: C, 58.60; H, 5.64; N, 9.59. ESIMS (MH+): 560.

Step 1

4-Bromo-1-cyclopropylmethoxy-2-fluoro-benzene

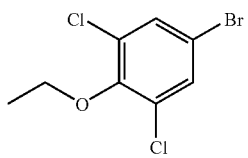

The title compound was prepared analogously to Step 1 in Example A(52), where iodoethane was substituted instead of methyl α-bromobutyrate and 4-Bromo-2,6-dichloro-phenol was substituted instead of 4-Bromo-2-fluorophenol of that example.

¹H NMR (CDCl₃) δ 0.32–0.42 (m, 2H), 0.62–0.68 (m, 2H), 1.23–1.33 (m, 1H), 3.85 (d, J=6.9 Hz, 2H), 6.82 (t, J=8.8 Hz, 1H), 7.14–7.18 (m, 1H), 7.23 (dd, J=10.5, 2.3 Hz, 1H). ESIMS (MH+): 246.1.

Step 2

6-Cyclopentyl-6-[2-(3,5-dichloro-4-ethoxy-phenyl)-ethyl]-dihydro-pyran-2,4-dione

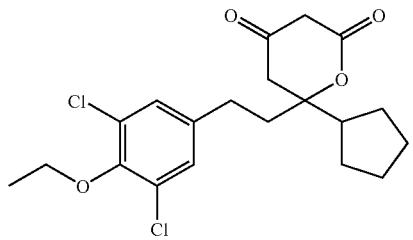

The title compound was prepared analogously to Example A(27), where 5-Bromo-1,3-dichloro-2-ethoxy-benzene (from Step 1 above) was substituted in place of 1-(4-Bromo-2-chloro-phenyl)-ethanone in Step 3 of that example.

Example B(38)

6-Cyclopentyl-6-[2-(3,4-dichloro-phenyl)-ethyl]-3-(5,7-dimethyl-[1,2,4]triazolo[1,5-a]pyrimidin-2-ylmethyl)-4-hydroxy-5,6-dihydro-pyran-2-one

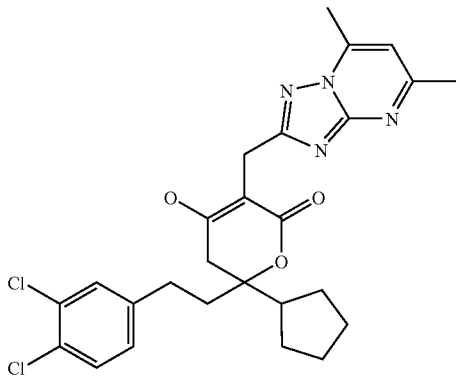

The title compound was prepared analogously to Example B(31), where 6-Cyclopentyl-6-[2-(3,4-dichloro-phenyl)-ethyl]-dihydro-pyran-2,4-dione was substituted in place of 6-[2-(3-Chloro-4-isopropoxy-phenyl)-ethyl]-6-cyclopentyl-dihydro-pyran-2,4-dione of that example.

¹H NMR (DMSO-d₆): δ 1.5–2.0 (m, 8H), 2.18–2.24 (m, 2H), 2.45–2.54 (m, 1H), 2.60–2.93 (m, 10H), 3.81 (d, J=16 Hz, 1H), 3.93 (d, J=16 Hz, 1H), 7.15 (s, 1H), 7.42 (dd, J=8.2, 2.0 Hz, 1H), 7.58 (d, J=2.0 Hz, 1H), 7.62 (d, J=8.2 Hz, 1H), 10.94 (s, 1H). Anal. Calcd. For $C_{26}H_{28}Cl_2N_4O_3$: C, 60.59; H, 5.48; N, 10.87; Found: C, 60.71; H, 5.79; N, 10.98. ESIMS (MH+): 516.

Step 1

6-Cyclopentyl-6-[2-(3,4-dichloro-phenyl)-ethyl]-dihydro-pyran-2,4-dione

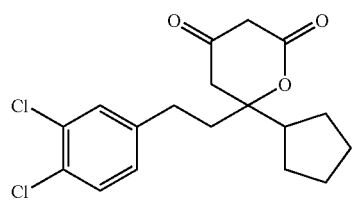

The title compound was prepared analogously to Example A(27), where 4-Bromo-1,2-dichloro-benzene was substituted in place of 1-(4-Bromo-2-chloro-phenyl)-ethanone in Step 3 of that example.

Example B(39)

6-(4-Cyclohexyl-butyl)-6-cyclopentyl-3-(5,7-dimethyl-[1,2,4]triazolo[1,5-α]pyrimidin-2-ylmethyl)-4-hydroxy-5,6-dihydro-pyran-2-one

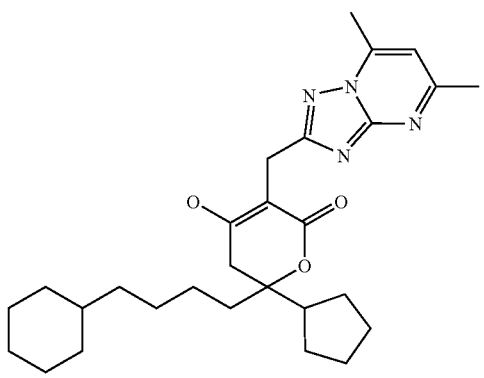

The title compound was prepared analogously to Example B(31), where 6-(4-Cyclohexyl-butyl)-6-cyclopentyl-dihydro-pyran-2,4-dione was substituted in place of 6-[2-(3-Chloro-4-isopropoxy-phenyl)-ethyl]-6-cyclopentyl-dihydro-pyran-2,4-dione of that example.

$^1$H NMR (DMSO-d$_6$): δ 0.76–1.93 (m, 25H), 2.27–2.32 (m, 1H), 2.50–2.75 (m, 10H), 3.69 (d, J=16 Hz, 1H), 3.80 (d, J=16 Hz, 1H), 7.08 (s, 1H), 10.77 (s, 1H). Anal. Calcd. For C$_{28}$H$_{40}$N$_4$O$_3$.0.5 CH$_3$OH: C, 68.92; H, 8.39; N, 11.28; Found: C, 69.24; H, 8.34; N, 11.00. ESIMS (MH+): 481.

Example B(40)

6-Cyclopentyl-3-(5,7-dimethyl-[1,2,4]triazolo[1,5-a]pyrimidin-2-ylmethyl)-4-hydroxy-6-[2-(2,2,3,3-tetrafluoro-2,3-dihydro-benzo[1,4]dioxin-6-yl)-ethyl]-5,6-dihydro-pyran-2-one

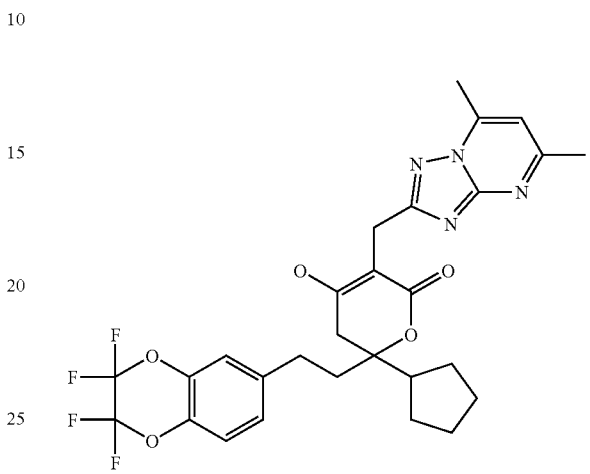

The title compound was prepared analogously to Example B(31), where 6-Cyclopentyl-6-[2-(2,2,3,3-tetrafluoro-2,3-dihydro-benzo[1,4]dioxin-6-yl)-ethyl]-dihydro-pyran-2,4-dione (prepared in Step 1 below) was substituted in place of 6-[2-(3-Chloro-4-isopropoxy-phenyl)-ethyl]-6-cyclopentyl-dihydro-pyran-2,4-dione of that example.

$^1$H NMR (DMSO-d$_6$): δ 0.98–1.68 (m, 8H), 1.93–2.02 (m, 2H), 2.27–2.68 (m, 11H), 3.56 (d, J=16 Hz, 1H), 3.68 (d, J=16 Hz, 1H), 6.90 (s, 1H), 7.12 (dd, J=8.5, 1.8 Hz, 1H), 7.19 (s, 1H), 7.22 (d, J=1.8 Hz, 1H), 10.69 (s, 1H). Anal. Calcd. For C$_{28}$H$_{28}$F$_4$N$_4$O$_5$.0.5H$_2$O: C, 57.43; H, 4.99; N, 9.57. Found: C, 57.42; H, 4.89; N, 9.65. ESIMS (MH+): 577.

Step 1

6-Cyclopentyl-6-[2-(2,2,3,3-tetrafluoro-2,3-dihydro-benzo[1,4]dioxin-6-yl)-ethyl]-dihydro-pyran-2,4-dione

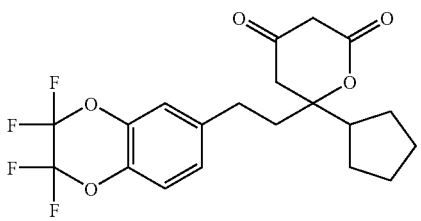

The title compound was prepared analogously to Example A(27), where 6-Bromo-2,2,3,3-tetrafluoro-2,3-dihydro-benzo[1,4]dioxine was substituted in place of 1-(4-Bromo-2-chloro-phenyl)-ethanone in Step 3 of that example

Example B(41)

6-Cyclopentyl-3-(5,7-dimethyl-[1,2,4]triazolo[1,5-a]pyrimidin-2-ylmethyl)-4-hydroxy-6-[2-(4-propoxyphenyl)-ethyl]-5,6-dihydro-pyran-2-one

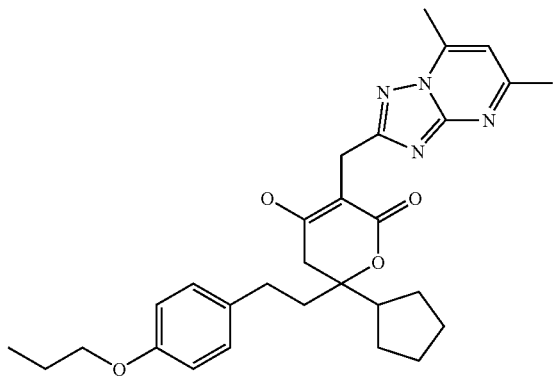

The title compound was prepared analogously to Example B(31), where 6-Cyclopentyl-6-[2-(4-propoxy-phenyl)-ethyl]-dihydro-pyran-2,4-dione was substituted in place of 6-[2-(3-Chloro-4-isopropoxy-phenyl)-ethyl]-6-cyclopentyl-dihydro-pyran-2,4-dione of that example $^1$H NMR (DMSO-d$_6$): δ 0.79 (t, J=7.4, 3H), 1.20–1.57 (m, 10H), 1.85–1.96 (m, 2H), 2.20–2.44 (m, 10H), 2.61 (d, J=16 Hz, 1H), 3.53 (d, J=16 Hz, 1H), 3.63–3.72 (m, 3H), 6.62 (d, J=8.4 Hz, 2H), 6.87 (s, 1H), 6.95 (d, J=8.4 Hz, 2H), 10.65 (s, 1H). Anal. Calcd. For C$_{29}$H$_{36}$N$_4$O$_4$: C, 69.02; H, 7.19; N, 11.10. Found: C, 69.25; H, 7.40; N, 10.92. ESIMS (MH+): 505.

Example B(42)

6-Cyclopentyl-6-{2-[4-(3,5-dimethyl-isoxazol-4-ylmethoxy)-phenyl]-ethyl}-3-(5,7-dimethyl-[1,2,4]triazolo[1,5-a]pyrimidin-2-ylmethyl)-4-hydroxy-5,6-dihydro-pyran-2-one

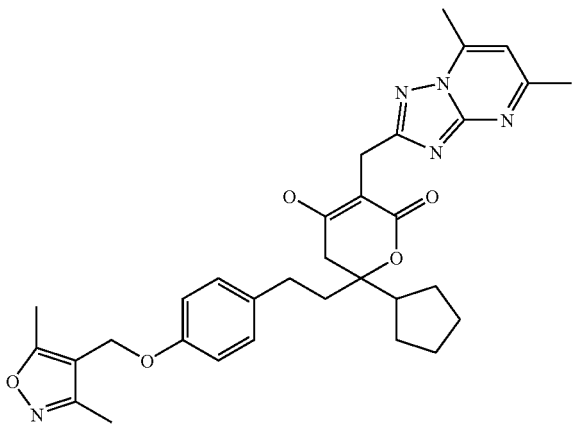

The title compound was prepared analogously to Example B(31), where 6-Cyclopentyl-6-{2-[4-(3,5-dimethyl-isoxazol-4-ylmethoxy)-phenyl]-ethyl}-dihydro-pyran-2,4-dione 6-Cyclopentyl-6-(2-{4-[(3,5-dimethylisoxazol-4-yl)methoxy]phenyl}ethyl)-4-hydroxy-5,6-dihydro-2H-pyran-2-one was substituted in place of 6-[2-(3-Chloro-4-isopropoxy-phenyl)-ethyl]-6-cyclopentyl-dihydro-pyran-2,4-dione of that example $^1$H NMR (DMSO-d$_6$): 1.36–1.71 (m, 8H), 2.08–2.09 (m, 2H), 2.22 (s, 3H), 2.40 (s, 3H), 2.48–2.56 (m, 10H), 2.77 (d, J=16 Hz, 1H), 3.70 (d, J=16 Hz, 1H), 3.82 (d, J=16 Hz, 1H), 4.88 (s, 2H), 6.90 (d, J=8.2 Hz, 2H), 7.04 (s, 1H), 7.17 (d, J=8.2, 2H), 10.69 (s, 1H). Anal. Calcd. For C$_{32}$H$_{37}$N$_5$O$_5$: C, 67.23; H, 6.52; N, 12.25. Found: C, 67.36; H, 6.80; N, 12.45. ESIMS (MH+): 572.

Example B(43)

6-[2-(3-chloro-4-methoxyphenyl)ethyl]-3-[(5-chloro-1-methyl-1H-benzimidazol-2-yl)methyl]-6-cyclopentyl-4-hydroxy-5,6-dihydro-2H-pyran-2-one

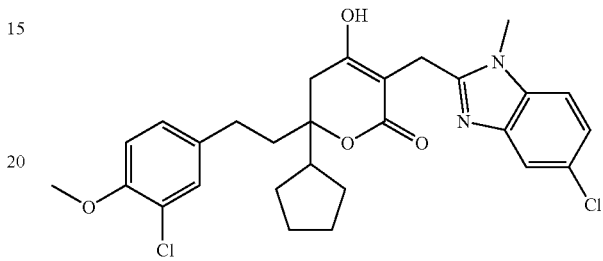

The title compound was prepared analogously to Example B(31), where 6-cyclopentyl-6-[2-(3-fluoro-4-methoxyphenyl)ethyl]dihydro-2H-pyran-2,4(3H)-dione was substituted in place of 6-[2-(3-chloro-4-isopropoxyphenyl)ethyl]-6-cyclopentydihydro-2H-pyran-2,4(3H)-dione and 5-chloro-1-methyl-1H-benzimidazole-2-carbaldehyde was substituted in place of 5,7-Dimethyl-[1,2,4]triazolo[1,5-α]pyrimidine-2-carbaldehyde.

$^1$H NMR (300 MHz, CDCl$_3$) δ: 1.51–1.75 (m, 8H), 1.96–2.02 (m, 2H), 2.51–2.58 (m, 2H), 2.70–2.82 (m, 3H), 3.86 (s, 3H), 3.87 (s, 2H), 3.89 (s, 3H), 6.82 (t, J=8.01 Hz, 1H), 6.96–7.05 (m, 1H), 7.14–7.19 (m, 1H), 7.25–7.28 (m, 2H), 7.64 (s, 1H). HRMS calcd for C$_{28}$H$_{31}$Cl$_2$N$_2$O$_4$ (M+H$^+$): 529.1656. Found: 529.1637.

Example B(44)

6-[2-(3-chloro-4-isopropylphenyl)ethyl]-6-cyclopentyl-3-[(5,7-dimethyl[1,2,4]triazolo[1,5-a]pyrimidin-2-yl)methyl]-4-hydroxy-5,6-dihydro-2H-pyran-2-one

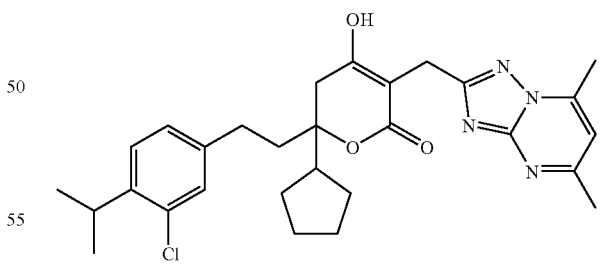

The title compound was prepared analogously to Example B(31), where 6-cyclopentyl-6-[2-(3-chloro-4-isopropylphenyl)ethyl]dihydro-2H-pyran-2,4(3H)-dione was substituted in place of 6-[2-(3-chloro-4-isopropoxyphenyl)ethyl]-6-cyclopentyldihydro-2H-pyran-2,4(3H)-dione.

$^1$H NMR (300 MHz, CDCl$_3$) δ: 1.20 (d, J=6.78 Hz, 6H), 1.47–1.74 (m, 8H), 1.96–2.02 (m, 2H), 2.32–2.40 (m, 1H), 2.50–2.61 (m, 3H), 2.66 (s, 3H), 2.71–2.73 (m, 1H), 2.79 (s, 3H), 3.29–3.38 (m, 1H), 4.09 (s, 2H), 6.84 (s, 1H), 7.00 (dd,

J=7.91, 1.51 Hz, 1H), 7.10 (s, 1H), 7.16 (d, J=7.91 Hz, 1H). HRMS calcd for C$_{29}$H$_{36}$ClN$_4$O$_3$ (M+H$^+$): 523.2471. Found: 523.2465.

Example B(45)

6-cyclopentyl-3-[(5,7-dimethyl[1,2,4]triazolo[1,5-a]pyrimidin-2-yl)methyl]-6-[2-(3-fluoro-4-isopropylphenyl)ethyl]-4-hydroxy-5,6-dihydro-2H-pyran-2-one

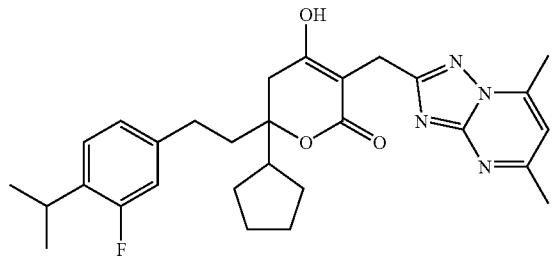

The title compound was prepared analogously to Example B(31), where 6-cyclopentyl-6-[2-(3-fluoro-4-isopropylphenyl)ethyl]dihydro-2H-pyran-2,4(3H)-dione was substituted in place of 6-[2-(3-chloro-4-isopropoxyphenyl)ethyl]-6-cyclopentyldihydro-2H-pyran-2,4(3H)-dione.

$^1$H NMR (CDCl$_3$, 300 MHz) δ: 1.21 (d, J=6.97 Hz, 6H), 1.24–1.26 (m, 2H), 1.46–1.76 (m, 6H), 1.97–2.03 (m, 2H), 2.35–2.41 (m, 1H), 2.48–2.54 (m, 1H), 2.61–2.65 (m, 2H), 2.67 (s, 3H), 2.70–2.73 (m, 1H), 2.79 (s, 3H), 3.12–3.20 (m, 1H), 4.03–4.15 (m, 2H), 6.76 (dd, J=11.49, 1.51 Hz, 1H), 6.85 (s, 1H), 6.88 (d, J=1.51 Hz, 1H), 7.11 (t, J=7.91 Hz, 1H). HRMS calcd for C$_{29}$H$_{36}$FN$_4$O$_3$ (M+H$^+$): 507.2766. Found: 507.2751.

Example B(46)

6-cyclopentyl-3-[(5,7-dimethyl[1,2,4]triazolo[1,5-a]pyrimidin-2-yl)methyl]-6-[2-(3-ethyl-4-fluorophenyl)ethyl]dihydro-2H-pyran-2,4(3H)-dione

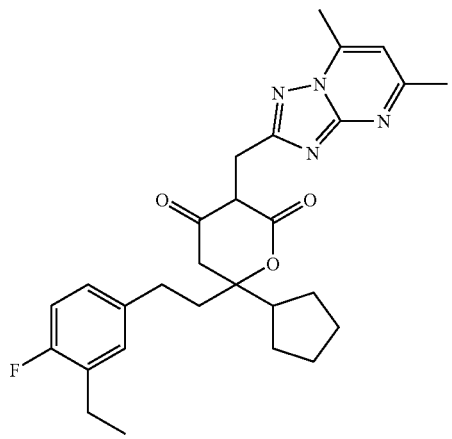

The title compound was prepared analogously to Example B(31), where 6-cyclopentyl-6-[2-(3-ethyl-4-fluorophenyl)ethyl]dihydro-2H-pyran-2,4(3H)-dione was substituted in place of 6-[2-(3-chloro-4-isopropoxyphenyl)ethyl]-6-cyclopentyldihydro-2H-pyran-2,4(3H)-dione in the final Step of that example.

$^1$H NMR (CDCl$_3$): δ 0.80 (m, 2H), 1.06 (m, 2H), 1.19 (t, J=7.63 Hz, 3H), 1.45–1.80 (brm, 8H), 2.06 (m, 2H), 2.45 (m, 2H), 2.65 (m, 2H), 2.70 (s, 3H), 2.80 (s, 3H), 4.13 (d, J=5.09 Hz, 2H), 6.74 (m, 1H), 6.80 (m, 2H), 7.15 (m, 1H). Anal. Calcd. For C$_{28}$H$_{33}$O$_3$N$_4$F: C, 68.27; H, 6.75; N, 11.37. Found: C, 68.14; H, 6.46; N, 11.53.

Example B(47)

6-[2-(3-chloro-4-methoxyphenyl)ethyl]-6-cyclopentyl-3-(1,3-thiazol-2-ylmethyl)dihydro-2H-pyran-2,4(3H)-dione

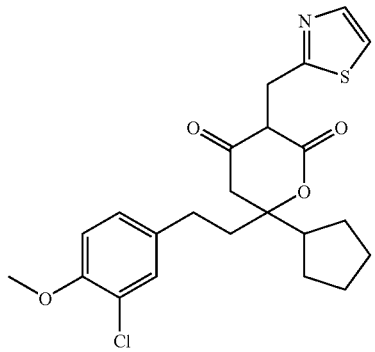

The title compound was prepared analogously to Example B(31), where 1,3-thiazole-2-carbaldehyde was substituted in place of 5,7-dimethyl[1,2,4]triazolo[1,5-a]pyrimidine-2-carbaldehyde and 6-[2-(3-chloro-4-methoxyphenyl)ethyl]-6-cyclopentyldihydro-2H-pyran-2,4(3H)-dione was substituted in place of 6-[2-(3-chloro-4-isopropoxyphenyl)ethyl]-6-cyclopentyldihydro-2H-pyran-2,4(3H)-dione in final Step of that example.

$^1$H NMR (CDCl$_3$): δ 1.44–1.70 (bm, 8H), 2.0 (m, 2H), 2.40 (m, 1H), 2.60 (m, 3H), 2.76 (d, J=17.90 Hz, 1H), 3.88 (s. 3H), 4.56 (d, J=15.07 Hz, 1H), 4.76 (d, J=15.07 Hz, 1H), 6.70 (d, J=2.07 Hz, 1H), 6.98, (d, J=2.07 Hz, 1H), 7.11 (s, 1H), 7.63, (d, J=3.96 Hz, 1H), 7.87 (d, J=3.96 Hz, 1H). Anal. Calcd. For C$_{24}$H$_{28}$O$_3$SNCl: C, 64.63; H, 6.33; N, 3.14. Found: C, 64.55; H, 6.64; N, 3.10.

Example B(48)

6-[2-(3-chloro-4-methoxyphenyl)ethyl]-6-cyclopentyl-3-[(1-methyl-1H-imidazol-2-yl)methyl]dihydro-2H-pyran-2,4(3H)-dione

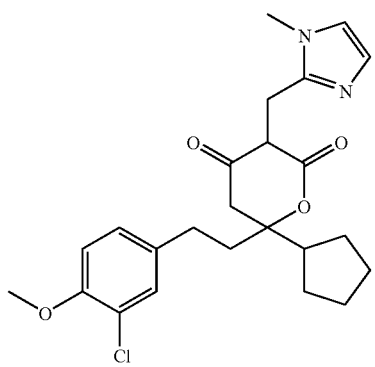

The title compound was prepared analogously to Example B(31), where 1-methyl-1H-imidazole-2-carbaldehyde was substituted in place of 5,7-dimethyl[1,2,4]triazolo[1,5-a]pyrimidine-2-carbaldehyde and 6-[2-(3-chloro-4-methoxyphenyl)ethyl]-6-cyclopentyldihydro-2H-pyran-2,4(3H)-dione was substituted in place of 6-[2-(3-chloro-4-isopropoxyphenyl)ethyl]-6-cyclopentyldihydro-2H-pyran-2,4(3H)-dione in that example.

$^1$H NMR (CDCl$_3$): δ 1.44–1.70 (bm, 8H), 2.0 (m, 2H), 2.20 (m, 3H), 2.30 (m, 2H), 2.99 (m, 2H), 3.01 (M. 2H), 3.46 (s, 3H) 3.78 (m, 1H), 3.89 (s, 3H), 6.72 (d, J=2.15 Hz, 1H), 6.83, (d, J=2.15 Hz, 1H), 6.90 (s, 1H), 7.14, (d, J=3.07 Hz, 1H), 7.24 (d, J=3.06 Hz, 1H). Anal. Calcd. For C$_{25}$H$_{31}$O$_3$N$_2$Cl: C, 67.78; H, 7.05; N, 6.32. Found: C, 67.48; H, 7.25; N, 6.37.

Example B(49)

6-cyclopentyl-3-[(5,7-dimethyl [1,2,4]triazolo[1,5-a]pyrimidin-2-yl)methyl]-6-[2-(3-isopropylphenyl)ethyl]dihydro-2H-pyran-2,4(3H)-dione

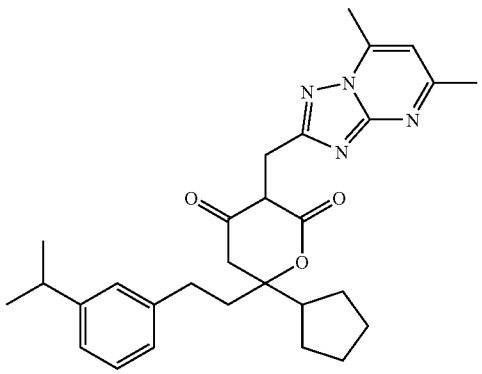

The title compound was prepared analogously to Example B(31), where 6-cyclopentyl-6-[2-(3-isopropylphenyl)ethyl]dihydro-2H-pyran-2,4(3H)-dione (described below) was substituted in place of 6-[2-(3-chloro-4-isopropoxyphenyl)ethyl]-6-cyclopentyldihydro-2H-pyran-2,4(3H)-dione in that example.

$^1$H NMR (CDCl$_3$): δ 0.88 (m, 1H), 1.21 (d, J=6.78 Hz, 6H), 1.26 (s, 2H), 1.48–1.77 (brm, 8H), 2.04 (m, 2H), 2.41 (m, 1H), 2.52–2.58 (m, 2H), 2.67 (s, 3H), 2.79 (s, 3H), 2.87 (m, 2H) 4.09 (s, 2H), 6.84 (s, 1H), 6.98 (d, J=7.54 Hz, 1H), 7.00 (m, 2H), 7.18 (t, J=7.54 Hz 1H). Anal. Calcd. For C$_{29}$H$_{36}$O$_3$N$_4$: C, 71.28; H, 7.43; N, 11.47. Found: C, 71.51; H, 7.25; N, 11.37.

Step 1

6-Cyclopentyl-6-[2-(3-isopropyl-phenyl)-ethyl]-dihydro-pyran-2,4-dione

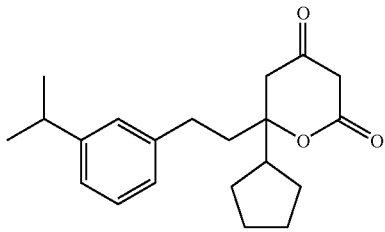

The title compound was prepared analogously to Example A(64), where 3-bromo-isopropyl-benzene was substituted in place of 4-Bromo-2-fluoro-1-isopropyl benzene in Step 3 of that example.

$^1$H NMR (CDCl$_3$): ? 1.24 (d, 6H, J=8.5 Hz)1.40–1.75 (m, 4H), 1.99 (m, 2H), 2.29 (pentet, 1H, J=8.1 Hz), 2.66 (t, 2H, J=8.5 Hz), 2.78 (s, 2H), 2.87 (m, 1H), 3.42 (s, 3H), 6.97 (m, 2H), 7.10 (m, 1H), 7.22 (m, 1H). Anal. Calcd. For C$_{21}$H$_{28}$O$_3$.0.25H$_2$O: C, 75.75; H, 8.63. Found: C, 75.68; H, 8.48. ESIMS (M−H$^{-1}$): 327.2.

Example B(50)

6-cyclopentyl-3-[(5,7-dimethyl[1,2,4]triazolo [1,5-a]pyrimidin-2-yl)methyl]-6-[2-(4-isopropylphenyl)ethyl]dihydro-2H-pyran-2,4(3H)-dione

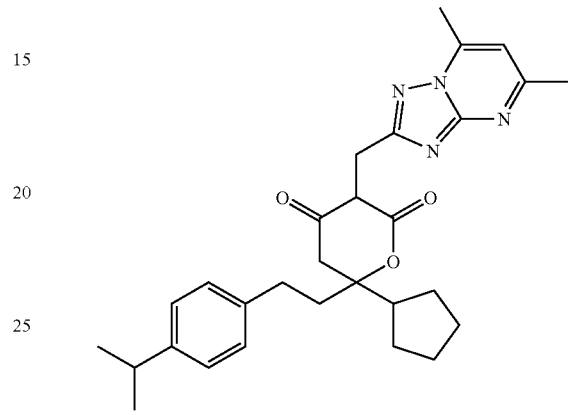

The title compound was prepared analogously to Example B(31), where 6-cyclopentyl-6-[2-(4-isopropylphenyl)ethyl]dihydro-2H-pyran-2,4(3H)-dione was substituted in place of 6-[2-(3-chloro-4-isopropoxyphenyl)ethyl]-6-cyclopentyldihydro-2H-pyran-2,4(3H)-dione in that example.

$^1$H NMR (CDCl$_3$): δ 0.98 (m, 1H), 1.24 (d, J=6.78 Hz, 6H), 1.31 (s, 2H), 1.40–1.77 (brm, 8H), 2.06 (m, 2H), 2.41 (m, 1H), 2.50–2.59 (m, 2H), 2.68 (s, 3H), 2.79 (s, 3H), 2.95 (m, 2H) 4.25 (s, 2H), 6.90 (s, 1H), 7.15 (d, J=8.10 Hz, 1H), 7.30 (d, J=8.10 Hz 1H), Anal. Calcd. For C$_{29}$H$_{36}$O$_3$N$_4$: C, 71.28; H, 7.43; N, 11.47. Found: C, 71.35; H, 7.55; N, 11.47.

Example B(51)

6-[2-(3-chlorophenyl)ethyl]-6-cyclopentyl-3-[(5,7-dimethyl[1,2,4]triazolo[1,5-a]pyrimidin-2-yl)methyl]dihydro-2H-pyran-2,4(3H)-dione

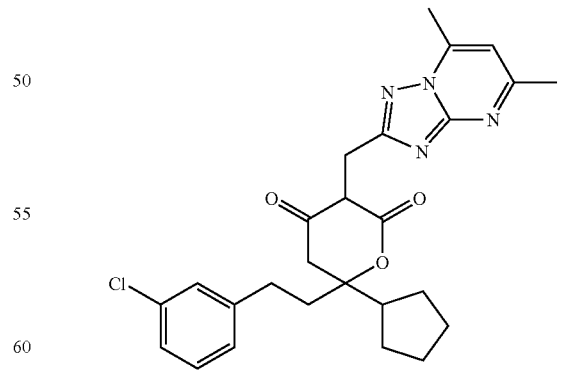

The title compound was prepared analogously to Example B(31), where 6-[2-(3-chlorophenyl)ethyl]-6-cyclopentyldihydro-2H-pyran-2,4(3H)-dione was substituted in place of 6-[2-(3-chloro-4-isopropoxyphenyl)ethyl]-6-cyclopentyldihydro-2H-pyran-2,4(3H)-dione in that example.

¹H NMR (CDCl₃): δ 1.30 (m, 1H), 1.40–1.80 (brm, 8H), 2.10 (m, 2H), 2.41 (m, 1H), 2.52–2.58 (m, 2H), 2.67 (s, 3H), 2.80 (s, 3H), 2.87 (m, 2H) 4.09 (s, 2H), 6.84 (s, 1H), 6.98 (d, J=6.25 Hz, 1H), 7.20 (t, J=8.35 Hz 2H), 7.30 (m, 1H) Anal. Calcd. For C₂₆H₂₉O₃N₄Cl: C, 64.92; H, 6.08; N, 11.65. Found: C, 65.14; H, 6.25; N, 11.73.

Example B(52)

6-[2-(5-chloro-2,4-dimethoxyphenyl)ethyl]-6-cyclopentyl-3-[(5,7-dimethyl[1,2,4]triazolo[1,5-a]pyrimidin-2-yl)methyl]dihydro-2H-pyran-2,4(3H)-dione

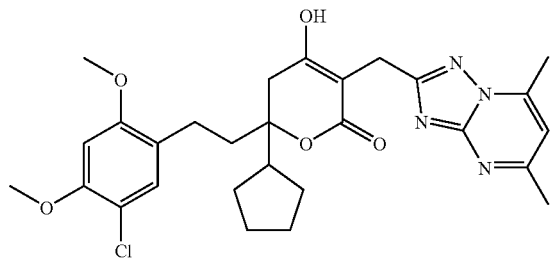

The title compound was prepared by treating a suspension of 6-[2-(5-chloro-2,4-dimethoxyphenyl)ethyl]-6-cyclopentyldihydro-2H-pyran-2,4(3H)-dione (350 mg, 0.917 mmol) and 5,7-dimethyl[1,2,4]triazolo[1,5-a]pyrimidine-2-carboxaldehyde (described in Step 3 of example B(75))(242 mg, 1.375 mmol, 1.5 equiv, from Step 3 of Example B(75)) in MeOH (10 mL) with dimethylamine borane (65 mg, 1.1 mmol, 1.2 equiv). The resulting mixture was stirred at room temperature for 18 h. A 1 M solution of HCl (3 mL) was added to the reaction mixture to acidify to a pH of 3. The mixture diluted with water and extracted with dichloromethane containing 10% methanol (3×10 mL). The organic layers were combined, dried over Na₂SO₄, filtered and concentrated to a white amorphous foam. The foam was chromatographed on silica gel, eluting with 2% methanol in dichloromethane affording a white solid. This solid was recrystallized from ethyl acetate/hexanes to give 100 mg (19%) of the product as a fine white powder. Isolated as a monohydrate.

¹H NMR d (300 MHz, CDCl₃) 1.58–1.76 (m, 8H), 1.94–1.99 (m, 2H), 2.38–2.43 (m, 1H), 2.57–2.77 (m, 2H), 2.69 (s, 3H), 2.81 (s, 3H), 3.82, (s, 3H), 3.85–3.92 (m, 2H), 3.80 (s, 3H), 4.08 (ABQ pattern, 2H, J=15 Hz), 6.45 (s, 1H), 6.89 (s, 1H), 7.04 (s, 1H). MS calcd for C₂₈H₃₃ClN₄O₅: 540.05. found (M+H⁺): 541.04. Anal. Calcd for C₂₈H₃₃ClN₄O₅ H₂O: C, 60.19; H, 6.32; N, 10.03. Found C, 60.76; H, 5.98; N, 9.54.

Step 1

(5-Amino-1H-1,2,4-triazol-3-yl)methanol glycolate

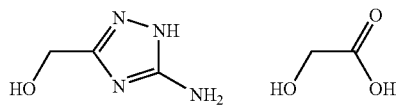

The title compound was prepared by a slight modification of a reported procedure (Allen, C. F. H. *J. Org. Chem*, 1959, 24, 793): A 5-L 3-necked flask was charged with aminoguanidine bicarbonate (275.6 g, 2.025 mol) and octyl alcohol (5.5 mL, to control foaming). To the mixture was added 70% aqueous glycolic acid (440 g, 4.05 mol, 2 equiv) gradually, during which time evolution of CO₂ was observed. When foaming and gas evolution had ceased, concentrated nitric acid (2.2 mL) was added so that it wet the sides of the flask above the liquid. The reaction mixture was refluxed for 40 h, then cooled to 5° C. and maintained at this temperature for 40 min. The resulting slurry was filtered, and the solid washed with EtOH and dried in vacuo at 30° C. to give the crude product as a white solid (313 g). The mother liquor was stirred at 0° C. (ice bath) for 1 h and filtered, affording a second batch of material (51 g). These two batches were combined and recrystallized from hot EtOH, affording 271.5 g, (70.5%).

¹H NMR (300 MHz, DMSO-d₆) δ 3.89 (2H), 4.24 (2H), 5.58 (2H). LC-MS (APCI) calcd for C₃H₆N₄O: 114.05. found (M+H⁺): 115.1 m/z.

Step 2

(5,7-Dimethyl[1,2,4]triazolo[1,5-a]pyrimidin-2-yl)methanol

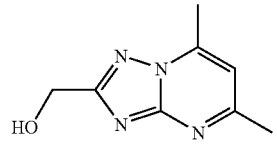

The title compound was prepared by a slight modification of a reported procedure (Lippman, E.; Becker, V., Z. *Chem.*, 1974, 14, 405): A solution of (5-amino-1H-1,2,4-triazol-3-yl)methanol glycolate (30.7 g, 0.161 mol, from Step 1, above) and 2,4-pentadione (32.3 g, 0.323 mol, 2 equiv) in a mixture of EtOH (750 mL) and AcOH (250 mL) was refluxed 20 h. At the beginning the reaction mixture was clear solution, then gradually turned yellow towards the end of the heating period. The solvent was removed under reduced pressure, and the resulting yellow paste triturated with EtOH (100 mL) and stirred for 15 min. The slurry was chilled to 5° C. (ice bath) with stirring for 30 min, filtered, and washed with cold (0–5° C.) EtOH. The product was dried in vacuo at 25–30° C. to give 24 g (83.7%).

¹H NMR (300 MHz, DMSO-d₆) δ 2.57 (3H), 2.71 (3H), 4.63 (2H), 5.5 (1H, OH), 7.13 (1H). LC-MS (APCI) calcd for C₈H₁₀N₄O: 178.19. found (M+H⁺): 179.1 m/z.

Example B(53)

6-[2-(Chloro-4-methoxyphenyl)ethyl]-6-cyclopentyl-3-[(1,3-dimethyl-1H-1,2,4-triazol-5-yl)methyl]-4-hydroxy-5,6-dihydro-2H-pyran-2-one

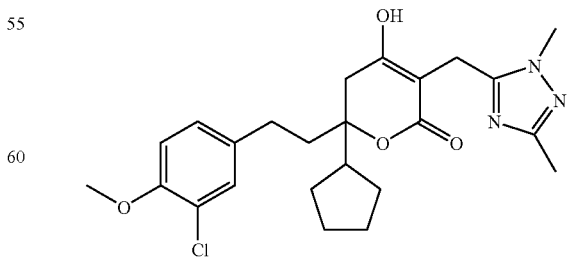

A suspension of 6-[2-(3-chloro-4-methoxyphenyl)ethyl]-6-cyclopentyldihydro-2H-pyran-2,4(3H)-dione (140 mg, 0.4 mmol) in 1:1H₂O/DME (4 mL) was treated sequentially with a 0.5 M aqueous solution of Na₂CO₃ (0.88 mL, 1.1 equiv), a 0.5 M aqueous solution of NaI (0.88 mL, 1.1 equiv), and a 0.1 M solution of 5-(chloromethyl)-1,3-dimethyl-1H-1,2,4-triazole in 1:1H₂O/DME (4.4 mL, 1.1 equiv, from Step 1, below). The reaction mixture was stirred and heated at 80° C. for 18 h. The mixture was then cooled and treated with 0.4 mL (1 equiv) each of a 1 M HCl solution and a 1 M acetic acid solution in water. The volatiles were removed in vacuo, and the residue was dissolved in DMSO to a concentration of 0.01 M. The product was purified by HPLC in multiple injections using a Pecke Hi-Q 5 μm, 20×100 mm column with a 5–90% CH₃CN/0.05% TFA gradient. A run time of 8.1 min, a flow rate of 30.0 mL/min, and a monitoring wavelength of 260 nm were used. The product-containing fractions were combined and lyophilized, affording the product as a powder. Yield: 11%.

¹H NMR (300 MHz, DMSO-d₆) δ 1.2–1.68 (m, 8H), 2.13 (s, 3H), 2.29 (m, 1H), 2.4–2.53 (m, 5H, overlap with DMSO-d₅), 2.70 (d, J=18 Hz, 1H), 3.62 (m, 2H, overlap with H₂O), 3.72 (s, 3H), 3.74 (s, 3H), 6.96 (d, J=8.4 Hz, 1H), 7.04 (dd, J=8.4, 1.8 Hz, 1H), 7.18 (d, J=1.8 Hz, 1H). LC-MS calcd for $C_{24}H_{30}ClN_3O_4$: 459.19. found (M+H⁺): 460.1 m/z.

Step 1

5-(Chloromethyl)-1,3-dimethyl-1H-1,2,4-triazole

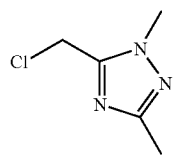

The title compound was prepared by a modification of a reported method (Kuebel, B. DE 3118258, Dec. 2, 1982): A 2 L-round bottomed flask equipped with a magnetic stirrer was charged with acetamidine hydrochloride (94.5 g, 1.0 mol) and methanol (500 mL). Methylhydrazine (50.0 g, 1.1 mol) was added slowly via a dropping funnel over 30 min at room temperature under nitrogen blanket. After 2 d, the solvent was removed in vacuo, and the resulting residue triturated with ethyl acetate, filtered, and washed with ethyl acetate (3×400 mL). After drying the residue in a vacuum oven at 50° C., the crude intermediate amidrazone, N'-methylethanehydrazonamide hydrochloride (109.8 g) was used directly in the next step. This intermediate (109.8 g) was suspended in dichloromethane (400 mL), cooled to 0–5° C., and treated slowly with triethylamine (100.2 g) at this temperature. Chloroacetyl chloride (103.7 g, 1.02 mol) was added slowly over 30 min at 0–5° C. via a dropping funnel. The reaction mixture was allowed to warm to room temperature and stirred for 18 h under nitrogen blanket. The solvent was then removed under reduced pressure, affording a residue (432.6 g) containing the N-chloroacetyl amidrazone intermediate. Polyphosphoric acid, PPA (400 g) was added to this material in a 2 L-3 necked flask, which was equipped with an overhead stirrer, a water condenser and a thermometer. The reaction mixture was stirred and heated at 120–130° C. for 4 h. Upon cooling to 80° C., water (400 mL) was added slowly and stirring continued for an additional 2 h. Aqueous NaOH (100 g/150 mL) was used to adjust the pH from 3 to 9. The organic material was extracted with chloroform (4×1 L), and the resulting solution treated with activated charcoal, dried with Na₂SO₄, filtered, and evaporated carefully. The dark oily residue thus obtained was extracted with a mixture of ether (700 mL) and pentane (300 mL) to separate the product from insoluble impurities. The yellow supernatant was decanted and the solvent removed carefully in vacuo (30° C. and ~10 Torr), affording 60.0 g (46% overall) of the title product as an oil (95% pure by NMR).

¹H NMR (300 MHz, CDCl₃) δ 2.35 (s, 3H, C—CH₃), 3.87 (s, 3H, N—CH₃), and 4.62 (s, 2H, CH₂). ¹³C NMR (300 MHz, CDCl₃) δ 14.05 (C—CH₃), 34.37 (CH₂), 35.81 (N—CH₃), 151.20 (q-C) and 60.22 (q-C). An NOE between CH₂ and the N—CH₃ was observed, consistent with the reported regioisomer. LC-MS (APCI) calcd for $C_5H_8ClN_3$: 145.04. found (M+H⁺) 146.1 m/z (with chorine isotope pattern).

Example B(54)

2-({6-[-(3-chloro-4-methoxyphenyl)ethyl]-6-cyclopentyl-4-hydroxy-2-oxo-5,6-dihydro-2H-pyran-3-yl}methyl)-6-methylpyrimidin-4(3H)-one

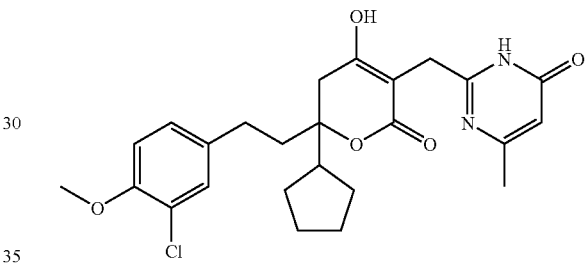

The title compound was prepared as described in Example B(53) employing 2-(chloromethyl)-6-methylpyrimidin-4(3H)-one in place of 5-(chloromethyl)-1,3-dimethyl-1H-1,2,4-triazole. Yield: 26%.

¹H NMR (300 MHz, DMSO-d₆) δ 1.25–1.65 (m, 8H), 1.88 (s, 3H), 1.9–2.1 (m, 2H), 2.35 (m, 1H), 2.4–2.54 (m, 3H, overlap with DMSO-d₅), 2.66 (d, J=18 Hz, 1H), 3.45 (ABQ, J=15 Hz, 2H), 3.74 (s, 3H), 5.98 (s, 1H), 6.96 (d, J=8 Hz, 1H), 7.04 (d, J=8, Hz, 1H), 7.17 (S, 1H). LC-MS calcd for $C_{25}H_{29}ClN_2O_5$: 472.18. found (M+H⁺): 473.1 m/z.

Step 1

2-(Chloromethyl)-6-methylpyrimidin-4(3H)-one

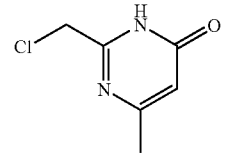

Prepared according to a reported procedure: Okabe, T.; Hirano, M.; Mukai, K. U.S. Pat. No. 4,326,058 (Apr. 20, 1982). Yield: 12%.

¹H NMR (300 MHz, DMSO-d₆) δ 2.18 (s, 3H), 4.42 (s, 2H), 6.16 (s, 1H), 12.61 (br s, 1H). LC-MS (APCI) calcd for $C_6H_7ClN_2O$: 158.02. found (M+H⁺): 159.0 m/z.

Example B(55)

2-({6-[2-(3-Chloro-4-methoxyphenyl)ethyl]-6-cyclopentyl-4-hydroxy-2-oxo-5,6-dihydro-2H-pyran-3-yl}methyl)quinazolin-4(3H)-one

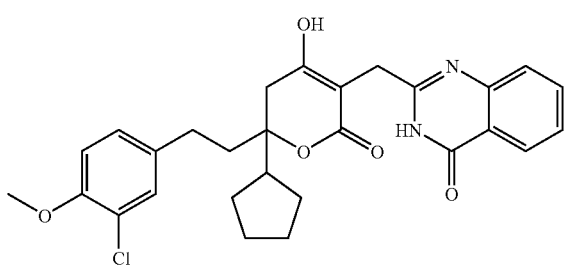

The title compound was prepared as described in Example B(53), employing 2-(bromomethyl)quinazolin-4(3H)-one in place of 5-(chloromethyl)-1,3-dimethyl-1H-1,2,4-triazole. Yield: 16%.

$^1$H NMR (300 MHz, DMSO-$d_6$) δ 1.25–1.70 (m, 8H), 2.20–2.25 (m, 2H), 2.35 (m, 1H), 2.45–2.60 (m, 3H, overlap with DMSO-$d_5$), 2.73 (d, J=18 Hz, 1H), 3.52 (m, 2H, overlap with H$_2$O peak), 3.76 (s, 3H), 6.92 (d, J=8 Hz, 1H), 6.96 (d, J=8 Hz, 1H), 7.06 (d, J=8 Hz, 1H), 7.21 (s, 1H), 7.36 (t, J=8 Hz, 1 H), 7.50 (t, J=8 Hz, 1H), 7.97 (d, J=8 Hz, 1H). LC-MS calcd for $C_{28}H_{29}ClN_2O_5$: 508.18. found (M+H$^+$): 509.1 m/z.

Step 1

2-(Bromomethyl)quinazolin-4(3H)-one

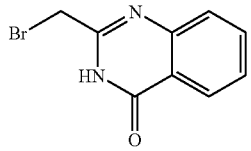

The title compound was made by a slight modification of a reported procedure (Bergman, J.; Brynolf, A. *Tetrahedron* 1990, 46, 1295). A 3-necked 500-mL round bottomed flask was charged with 2-(methyl)quinazolin-4(3H)-one (50.09 g, 0.303 mol), 200 mL of dry DMF, and N-bromosuccinimide (54.53 g, 0.303 mol, 1 equiv). The reaction mixture was warmed to 40° C. and maintained at this temperature for 2 h. The mixture was cooled to room temperature and allowed to stand for 4 d. The resulting tan slurry was filtered, and the filter cake washed with ether (3×50 mL), and dried in vacuo. The crude solid was suspended in mixture of 95% ethanol (600 mL) and water (6 mL) and the mixture heated to boiling. The hot slurry was cooled to room temperature, chilled in an ice bath, and filtered. The cake was washed with chilled 95% ethanol (50 mL), followed by ether (2×50 mL), then dried in vacuo, affording 52.90 g of material containing 11% starting material. This was recrystallized from hot (95° C.) DMF (750 mL). Upon cooling to room temperature, the slurry was filtered, and the cake washed with DMF (80 mL), and methanol (3×50 mL), then dried in vacuo at 50° C., affording 39.40 g (54%). The product was found to be 98% pure by both HPLC and $^1$H NMR.

$^1$H NMR (300 MHz, DMSO-$d_6$) δ 4.40 (s, 2H), 7.55 (t, J=8 Hz, 1H), 7.67 (d, J=8 Hz, 1H), 7.84 (t, J=8 Hz, 1H), 8.12 (d, J=8 Hz, 1H), 12.57 (br s, 1H). LC-MS (APCI) calcd for $C_9H_7BrN_2O$: 238.0. found (M+H$^+$) 239.1, 241.1 (1:1) m/z.

Example B(56)

2-([6-[2-(3-Chloro-4-methoxyphenyl)ethyl]-6-cyclopentyl-4-hydroxy-2-oxo-5,6-dihydro-2H-pyran-3-yl)methyl)thieno[3,2-d]pyrimidin-4(3H)-one

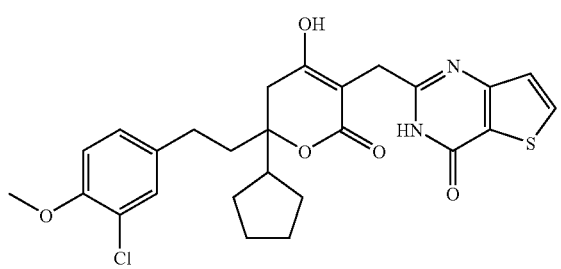

The title compound was prepared as described in Example B(53), using 2-(chloromethyl)thieno[3,2-d]-pyrimidine-4(3H)-one (Step 1) in place of 5-(chloromethyl)-1,3-dimethyl-1H-1,2,4-triazole. Yield: 22%.

$^1$H NMR (300 MHz, DMSO-$d_6$) δ 1.5–1.7 (m, 8H), 1.90–2.18 (m, 2H), 2.35 (m, 1H), 2.52 (m, 3H,), 2.70 (d, J=18 Hz, 1H), 3.53 (ABQ, J=15 Hz, 2H), 3.72 (s, 3H, overlap with H$_2$O peak), 6.72 (d, J=5.1 Hz, 1H), 6.96 (d, J=8.6 Hz, 1H), 7.04 (dd, J=8.6, 2.1 Hz, 1H), 7.18 (d, J=2.1 Hz, 1H), 7.97 (t, J=5.1 Hz, 1 H). LC-MS (APCI) calcd for $C_{26}H_{27}ClN_2O_5S$: 514.13. found (M+H$^+$) 515.0 m/z.

Step 1

2-(Chloromethyl)thieno[3,2-d]-pyrimidine-4(3H)-one

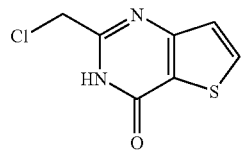

This compound was prepared by a modification of a method reported for related fused pyrimidine-4(3H)-ones: (1) Shishoo, C. J.; Devani, M. B.; Pathak, U.S.; Ananthan, S.; Bhadti, V. S.; Ullas, G. V.; Jain, K. S.; Rathod, I. S.; Talati, D. S.; Doshi, N. H. *J. Heterocyclic Chem.* 1984, 21, 375, and (2) Gerecke, M.; Kyburz, E.; Borer, R.; Gassner, W. *Heterocycles* 1994, 39, 693). An oven-dried 1-L round bottomed flask was charged with chloroacetonitrile (21.86 g, 0.29 mol, 1.3 equiv), methyl 3-aminothiophene-2-carboxylate (35 g, 0.223 mol), and 4 M HCl in 1,4-dioxane (350 mL). The reaction mixture was stirred at room temperature for 1 d. The mixture was evaporated to dryness. The residue was dissolved in water (600 mL) and treated with aqueous 10% sodium bicarbonate to a pH of 8. The resulting slurry was filtered, and the cake washed with water and dried, affording 38.2 g (85%) of the title product.

$^1$H NMR (DMSO-d$_6$) δ 4.58 (s, 2H), 7.42 (d, J=5.3 Hz, 1H), 8.22 (d, J=5.3 Hz, 1H), 12.84 (br s, 1H). LC-MS (APCI) calcd for C$_7$H$_5$ClN$_2$OS: 200.0. Found (M+H$^+$): 201.0 m/z.

Example B(57)

2-({6-[2-(3-chloro-4-methoxyphenyl)ethyl]-6-cyclopentyl-4-hydroxy-2-oxo-5,6-dihydro-2H-pyran-3-yl}methyl)-6,7-dimethoxyquinazolin-4(3H)-one

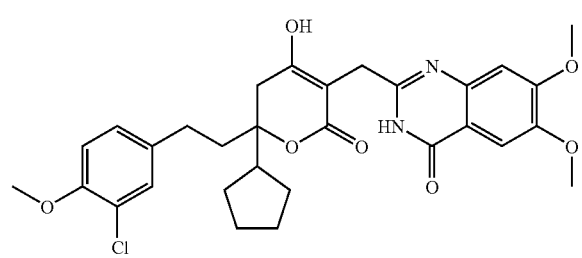

The title compound was prepared as described in Example B(53), using 2-(chloromethyl)-6,7-dimethoxyquinazolin-4(3H)-one (Step 1) in place of 5-(chloromethyl)-1,3-dimethyl-1H-1,2,4-triazole. Yield: 18%.

$^1$H NMR (300 MHz, DMSO-d$_6$) δ 1.55–1.67 (m, 8H), 1.85–2.1 (m, 2H), 2.36 (m, 1H), 2.5–2.6 (m, 3H), 2.71 (d, J=18 Hz, 1H), 3.59 (s, m overlap, 5H), 3.73 (s, 3H, overlap with H$_2$O peak), 3.79 (s, 3H, overlap with H$_2$O peak), 6.64 (s, 1H), 6.90 (d, J=8.7 Hz, 1H), 7.03 (dd, J=8.7, 1.6 Hz, 1H), 7.20 (d, J=1.6 Hz, 1H), 7.34 (s, 1 H). LC-MS (APCI) calcd for C$_{30}$H$_{33}$ClN$_2$O$_7$: 568.20. found (M+H$^+$) 569.1 m/z.

Step 1

2-(Chloromethyl)-6,7-dimethoxyquinazolin-4(3H)-one

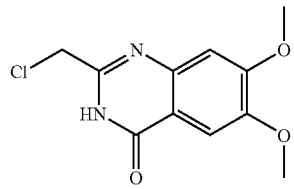

The title compound was prepared as described in Step 1 of Example B(56), except using methyl 2-amino-4,5-dimethoxy benzoate in place of methyl 3-aminothiophene-2-carboxylate. The crude product (20 g) obtained from 22.8 g (0.108 mol) of 2-amino-4,5-dimethoxy benzoate was recrystallized from a hot (70° C.) mixture of ethyl acetate (600 mL) and methanol (200 mL), to give 13.3 g (50%) of the title product.

$^1$H NMR (DMSO-d$_6$) δ 3.87 (s, 3H), 3.90 (s, 3H), 4.52 (s, 2H), 7.15 (s, 1H), 7.43 (s, 1H), 12.4 (v br s, 1H). LC-MS (APCI, Neg) calcd for C$_{11}$H$_{11}$ClN$_2$O$_3$: 254.05. found (M−H$^+$) 253.0 m/z.

Example B(58)

7-[(6-{2-[3-Chloro-4-(cyclopropylmethoxy)phenyl]ethyl}-6-cyclopentyl-4-hydroxy-2-oxo-5,6-dihydro-2H-pyran-3-yl)methyl]-3-methyl-5H-[1,3]thiazolo[3,2-a]pyrimidin-5-one

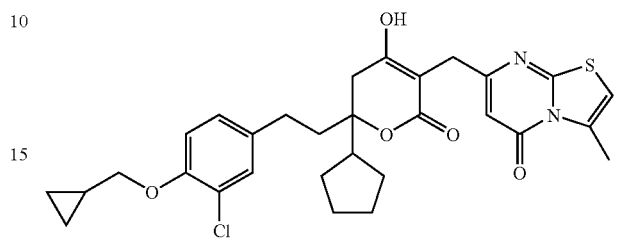

The title compound was prepared as described in Example B(53), using 7-(chloromethyl)-3-methyl-5H-(1,3]thiazolo [3,2-a]pyrimidin-5-one (prepared according to a reported procedure: Doria, G.; Passarotti, C.; Sala, R.; Magrini, R.; Sberze, P.; Tibolla, M.; Cesarani, R.; Arcari, G.; Castello, R.; Toti, D. Farmaco Ed. Sci. 1985, 40, 885) in place of 5-(chloromethyl)-1,3-dimethyl-1H-1,2,4-triazole, and using 6-{-[3-chloro-4-(cyclopropylmethoxy)phenyl]ethyl}-6-cyclopentyldihydro-2H-pyran-2,4(3H)-dione (from Step 4, below) in place of 6-[2-(3-chloro-4-methoxyphenyl)ethyl]-6-cyclopentyldihydro-2H-pyran-2,4(3H)-dione. Yield: 1%.

$^1$H NMR (300 MHz, DMSO-d$_6$) ☐ 0.31 (m, 2H), 0.56 (m, 2H), 1.22 (m, 1H), 1.23–1.65 (m, 8H), 1.92 (m, 2H), 2.33 (m, 1H), 2.48–2.75 (s, m, 7H, overlap with DMSO-d$_5$), 3.45 (m, 2H, overlap with H$_2$O peak), 3.84 (d, J=7.8 Hz, 2H), 4.87 (s, 2H), 5.20 (s, 1H), 6.16 (s, 1H), 6.93 (d, J=9 Hz, 1H), 7.01 (dd, J=9, 1.5 Hz, 1H), 7.18 (d, J=1.5 Hz, 1H). LC-MS (APCI) calcd for C$_{30}$H$_{33}$ClN$_2$O$_5$S: 568.18. found (M+H$^+$) 569.0 m/z.

Step 1

3-[4-(Benzyloxy)-3-chlorophenyl]-1-cyclopentylpropan-1-one

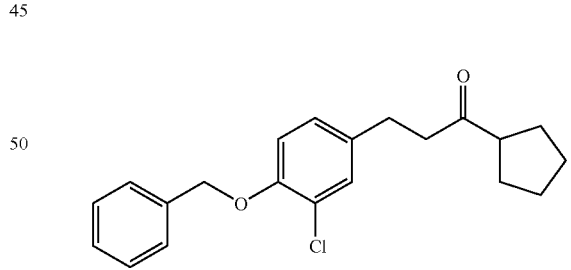

A solution of 3-[4-(benzyloxy)-3-chlorophenyl]propanoic acid (80 g, 0.28 mol, obtained as described: Kuchar, M.; Brunova, B.; Rejholec, V.; Roubal, Z.; Nemecek, O. Collect. Czech. Chem. Commun 1981, 46, 1173) in DCE (500 mL) was treated with oxalyl chloride (26.5 mL, 0.30 mol, 1.05 equiv). After stirring for 2 min, DMF (0.2 mL) was added, and stirring continued for an additional 3 h. The volatiles were removed in vacuo, affording a quantitative yield of the acid chloride, a green oil, which was used directly in the next step. The crude acid chloride thus obtained was dissolved in CH$_2$Cl$_2$ (1 L), and added dropwise via an addition funnel to 2-mercaptopyridine (30.5 g, 0.28 mol, 1 equiv) in CH$_2$Cl$_2$ (3 L). The reaction mixture was stirred for an additional 3 h at 23° C. The mixture was treated with 1.0 N NaOH (320 mL), and extracted with ethyl acetate (3×200 mL). The combined extracts were washed with aqueous NaHCO$_3$ and brine, dried over MgSO$_4$, filtered, and evaporated. The resulting crude S-pyridin-2-yl 3-[4-(benzyloxy)-3-chlorophenyl]propanethioate, an amber oil, was used directly in the next step. This thioester intermediate was dissolved in THF (450 mL), the solution chilled in a dry ice bath to −70° C., and treated dropwise at this temperature with a 2M solution of cyclopentylmagnesium bromide in diethyl ether (145 mL, 0.28 mol, 1 equiv). When the addition was complete, a sample taken from the resulting peach-colored slurry was treated with 5% HCl, and subjected to TLC analysis on silica gel using 20% ethyl acetate in hexanes. A UV-active spot at Rf=0.5 stained orange with 2,4-DNP. The reaction mixture was warmed to room temperature, then treated with 5% aqueous HCl (350 mL) and diethyl ether (20 mL). The layers were separated and the organic phase washed with aqueous NaHCO$_3$ and brine, dried over MgSO$_4$, filtered, and evaporated, affording an amber oil (93 g). This was chromatographed on silica gel using 10% ethyl acetate in hexanes, affording 48 g (51% overall) of the cyclopentyl ketone as a pale yellow oil.

$^1$H NMR (DMSO-d$_6$) d 1.45–1.8 (m, 8H), 2.7–2.9 (m, 5H), 5.15 (s, 2H), 7.10 (s, 2H), 7.3–7.5 (m, 6H). LC-MS (neg) calcd for C$_{21}$H$_{23}$ClO$_2$, 342.14. found [M−1]: 341.1.

Step 2

3-(3-Chloro-4-hydroxyphenyl)-1-cyclopentylpropan-1-one

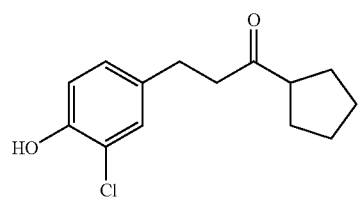

A mixture of 3-[4-(benzyloxy)-3-chlorophenyl]-1-cyclopentylpropan-1-one (48 g, 0.140 mole), from Step 1, and 10% palladium-on-carbon (11.52 g of 50 wt % wet, 0.005 mol, 3.5 mole %) in ethyl acetate (500 mL) was degassed and purged with hydrogen three times. The reaction was stirred with 1 atm H$_2$ for 4 h, resulting in complete conversion. The mixture was filtered through a fine fritted glass funnel and the filtrate concentrated in vacuo, affording a yellow oil which crystallized on cooling. This material was recrystallized from two parts of isopropyl ether, affording 22 g (62%) of the title product. mp 88–90° C.

$^1$H NMR (DMSO-d$_6$) δ 1.4–1.75 (m, 8H), 2.5–2.7 (m, 4H), 2.9 (m, 1H), 6.83 (d, J=8.3 Hz, 1H), 6.94 (dd, J=8.3, 1.9 Hz, 1H), 7.15 (d, J=1.9 Hz, 1H), 9.86 (br s, 1H). MS calcd for C$_{14}$H$_{17}$ClO$_2$, 252.09. found [M+1]: 253.10.

Step 3

3-[3-Chloro-4-(cyclopropylmethoxy)phenyl]-1-cyclopentylpropan-1-one

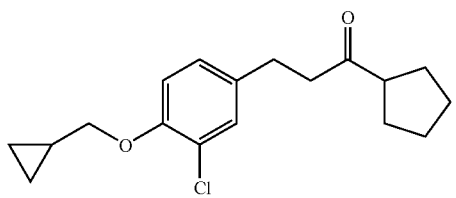

A solution of 3-(3-chloro-4-hydroxyphenyl)-1-cyclopentylpropan-1-one ((25 g, 0.099 mol, from Step 2) in 1:1 DMF/CH$_3$CN (200 mL) was treated with K$_2$CO$_3$ (15 g, 0.109 mol, 1.1 equiv), and the mixture stirred for 15 min. A solution of (bromomethyl)cyclopropane (17.4 g, 0.129 mol, 1.3 equiv) in DMF (50 mL) was added dropwise, and the reaction mixture heated to 100° C. for 1 h. The volatiles were removed in vacuo. The residue was dissolved in a minimal amount of ethyl acetate, and this solution washed with water, dried over Na$_2$SO$_4$, filtered, and evaporated. Chromatographic purification of the residue on silica gel using hexanes/ethyl acetate afforded 29.12 g (96%) of the title compound.

$^1$H NMR (CDCl$_3$) δ 0.32 (m, 2H), 0.58 (m, 2H), 1.23 (m, 1H), 1.64 (m, 8H), 2.70 (m, 5H), 3.8 (d, J=6 Hz, 2H), 6.78 (d, J=9 Hz, 1H), 6.93 (d, J=9 Hz, 1H), 7.13 (s, 1H). MS calcd for C$_{18}$H$_{23}$ClO$_2$, 306.83. found [M+1)]: 307.0.

Step 4

6-{-[3-Chloro-4-(cyclopropylmethoxy)phenyl]ethyl}-6-cyclopentyldihydro-2H-pyran-2,4(3H)-dione

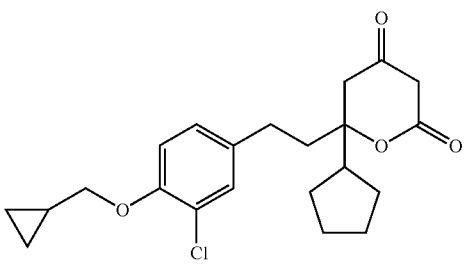

An oven-dried, 500-mL 3-necked round-bottomed flask, cooled under a blanket of N$_2$, was charged with NaH (1.48 g, 61.74 mmol) and 25 mL dry THF. The slurry was cooled to −40° C. in a dry ice/CH$_3$CN bath and treated slowly with a cold solution of methyl acetoacetate (6.83 g, 58.8 mmol) in THF (30 mL), delivered via syringe at such a rate that the internal temperature stays within a 5° C. interval. The mixture was stirred for 30 min, then cooled to −70° C. with a dry ice/acetone bath. The mixture was treated with n-BuLi (23.5 mL, 61.74 mmol) at −70° C., and stirred at this temperature for an additional 45 min. To the resulting solution of acetoacetate dianion was added a solution of 3-[3-chloro-4-(cyclopropylmethoxy)phenyl]-1-cyclopentylpropan-1-one (15.03 g, 49 mmol, from Step 3) in THF (50 mL) via an addition funnel, at such a rate that a reaction temperature of −70° C. is maintained. After stirring at this temperature for an additional 1 h, the reaction mixture was allowed to warm to room temperature over 3 h, then quenched with 4 M NH$_4$Cl (aq) (30.87 mL). After stirring at room temperature for 10 min, the mixture is concentrated in vacuo. To the oily residue was added water, then the mixture extracted with ethyl acetate (3×100 mL). The ethyl acetate solution was dried over Na$_2$SO$_4$, filtered, and concentrated to a viscous resin, which was chromatographed on silica gel with 5:1 hexanes/ethyl acetate, affording 14.82 g (71%) of the hydroxy ester intermediate. This intermediate was dissolved in THF (100 mL) added to 1 M NaOH (aq) (3 L), and the resulting mixture stirred at room temperature for 3 h. The mixture was acidified with 1 M aqueous HCl (1.5 L) to a pH 2. The product was extracted into dichloromethane (3×400 mL), and the extract dried over Na$_2$SO$_4$, filtered, and concentrated to a resin. The resin was chromatographed on silica gel using 3:1 hexanes/ethyl acetate, and the resulting foam crystallized from ethyl acetate/hexanes to obtain 4.45 g, (23% overall) of the product as an off-white solid.

$^1$H NMR (300 MHz, CDCl$_3$) d 0.38 (d, J=5 Hz, 2H), 0.65 (d, J=7.5 Hz, 2H), 1.32 (m, 1H), 1.40–1.85 (m, 8H), 1.95 (m, 2H), 2.27 (m, 1H), 2.61 (t, J=8.2 Hz, 2H), 2.77 (s, 2H), 3.43 (s, 2H), 3.86 (d, J=6.7 Hz, 2H), 6.84 (d, 1H, J=8.1 Hz, 1H), 6.96 (d, J=8.1 Hz, 1H), 7.16 (s, 1H). MS calcd for C$_{22}$H$_{27}$ClO$_4$: 390.90. MS. found, [M+1]: 391.

Example B(59)

7-({6-[2-(5-Chloro-2,4-dimethoxyphenyl)ethyl]-6-cyclopentyl-4-hydroxy-2-oxo-5,6-dihydro-2H-pyran-3-yl}methyl)-3-methyl-5H-[1,3]thiazolo[3,2-a]pyrimidin-5-one

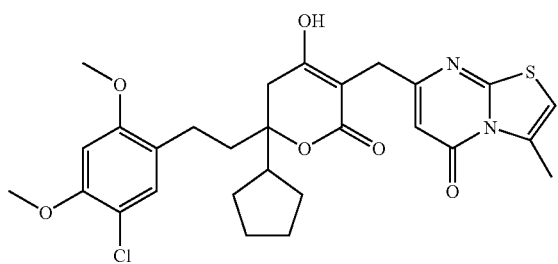

The title compound was prepared as described in Example B(53), using 7-(chloromethyl)-3-methyl-5H-[1,3]thiazolo[3,2-a]pyrimidin-5-one (prepared according to a reported procedure: Doria, G.; Passarotti, C.; Sala, R.; Magrini, R.; Sberze, P.; Tibolla, M.; Cesarani, R.; Arcari, G.; Castello, R.; Toti, D. Farmaco Ed. Sci. 1985, 40, 885) in place of 5-(chloromethyl)-1,3-dimethyl-1H-1,2,4-triazole, and using 6-[2-(5-chloro-2,4-dimethoxyphenyl)ethyl]-6-cyclopentyldihydro-2H-pyran-2,4(3H)-dione in place of 6-[2-(3-chloro-4-methoxyphenyl)ethyl]-6-cyclopentyldihydro-2H-pyran-2,4(3H)-dione. Yield: 18%.

$^1$H NMR (300 MHz, DMSO-d$_6$) δ 1.23–1.73 (m, 8H), 1.78–2.0 (m, 2H), 2.35 (m, 1H), 2.48–2.58 (m, 2H, overlap with DMSO-d$_5$), 2.64 (s, m, overlap, 4H), 2.78 (d, J=18 Hz, 1H), 3.44 (s, 3H), 3.78 (s, 3H, overlap with H$_2$O peak), 3.85 (s, 3H), 5.80 (s, 1H), 6.70 (s, 1H), 6.97 (s, 1H), 7.11 (s, 1H), 10.96 (br s, 1H). LC-MS (APCI) calcd for C$_{28}$H$_{31}$ClN$_2$O$_6$S: 558.16. found (M+H$^+$) 559.0 m/z.

Example B(60)

Methyl 5-({6-cyclopentyl-4-hydroxy-6-[2-(4-methoxyphenyl)ethyl]-2-oxo-5,6-dihydro-2H-pyran-3-yl)methyl)isoxazol-3-ylcarbamate

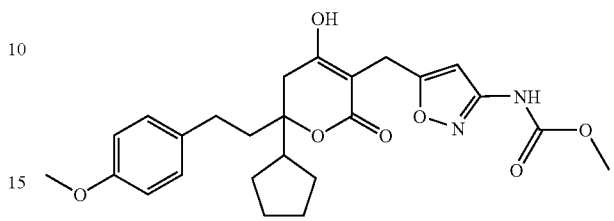

The title compound was prepared as described in Example B(53), using methyl 5-(bromomethyl)isoxazol-3-ylcarbamate (prepared as described: Sircar, J. C.; Capiris, T. U.S. Pat. No. 4,489,077, Dec. 18, 1984) in place of 5-(chloromethyl)-1,3-dimethyl-1H-1,2,4-triazole, and using 6-cyclopentyl-6-[2-(4-methoxyphenyl)ethyl]dihydro-2H-pyran-2,4(3H)-dione in place of 6-[2-(3-chloro-4-methoxyphenyl)ethyl]-6-cyclopentydihydro-2H-pyran-2,4(3H)-dione. Yield: 13%.

$^1$H NMR (300 MHz, DMSO-d$_6$) δ 1.15–1.65 (m, 8H), 1.80 (m, 2H), 2.25 (m, 1H), 2.39–2.51 (m, 3H, overlap with DMSO-d$_5$), 2.68 (d, J=17.4 Hz, 1H), 3.51 (s, 2H), 3.56 (s, 3H), 3.61 (s, 3H), 6.24 (s, 1H), 6.72 (d, J=8.4 Hz, 2H), 6.95 (d, J=8.4 Hz, 2H), 10.47 (s, 1H), 11.15 (br s, 1H). LC-MS (APCI) calcd for C$_{25}$H$_{30}$N$_2$O$_7$: 470.21. found (M+H$^+$) 471.1 m/z.

Example B(61)

7-({6-Cyclopentyl-4-hydroxy-6-[2-(4-methoxyphenyl)ethyl]-2-oxo-5,6-dihydro-2H-pyran-3-yl}methyl)-3-methyl-5H-[1,3]thiazolo[3,2-a]pyrimidin-5-one

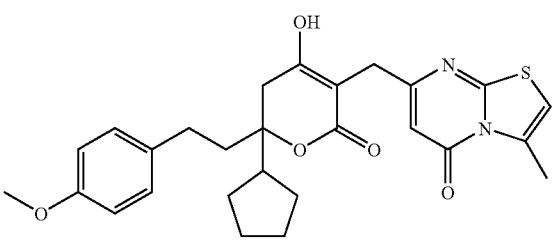

The title compound was prepared as described in Example B(53), using 7-(chloromethyl)-3-methyl-5H-[1,3]thiazolo[3,2-a]pyrimidin-5-one (prepared according to a reported procedure: Doria, G.; Passarotti, C.; Sala, R.; Magrini, R.; Sberze, P.; Tibolla, M.; Cesarani, R.; Arcari, G.; Castello, R.; Toti, D. Farmaco Ed. Sci. 1985, 40, 885) in place of 5-(chloromethyl)-1,3-dimethyl-1H-1,2,4-triazole, and using 6-cyclopentyl-6-[2-(4-methoxyphenyl)ethyl]dihydro-2H-pyran-2,4(3H)-dione in place of 6-[2-(3-chloro-4-methoxyphenyl)ethyl]-6-cyclopentyldihydro-2H-pyran-2,4(3H)-dione. Yield: 17%.

$^1$H NMR (300 MHz, DMSO-d$_6$) δ 1.2–1.65 (m, 8H), 1.87 (m, 2H), 2.31 (m, 1H), 2.48–2.53 (d, m, 3H, overlap with DMSO-d$_5$), 2.59 (s, 3H), 2.71 (d, J=17.1 Hz, 1H), 3.38

(ABQ pattern, J=15.8 Hz, 2H), 3.64 (s, 3H), 5.77 (s, 1H), 6.73 (d, J=8.7 Hz, 2H), 6.91 (s, 1H), 6.98 (d, J=8.7 Hz, 2H), 10.9 (br s, 1H). LC-MS (APCI) calcd for C$_{27}$H$_{30}$N$_2$O$_5$S: 494.19. found (M+H$^+$) 495.0 m/z.

Example B(62)

6-[2-(5-Chloro-2,4-dimethoxyphenyl)ethyl]-6-cyclopentyl-3-[(3-ethyl-1,2,4-oxadiazol-5-yl)methyl]-4-hydroxy-5,6-dihydro-2H-pyran-2-one

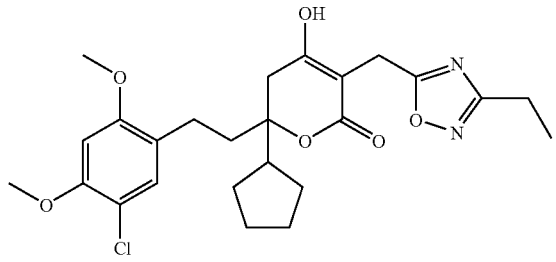

The title compound was prepared as described in Example B(53), using 5-(chloromethyl)-3-ethyl-1,2,4-oxadiazole (Step 1, below) in place of 5-(chloromethyl)-1,3-dimethyl-1H-1,2,4-triazole, and using 6-[2-(5-chloro-2,4-dimethoxyphenyl)ethyl]-6-cyclopentyldihydro-2H-pyran-2,4(3H)-dione in place of 6-[2-(3-chloro-4-methoxyphenyl)ethyl]-6-cyclopentyldihydro-2H-pyran-2,4(3H)-dione. Yield: 7%.

$^1$H NMR (300 MHz, DMSO-d$_6$) δ 1.10 (t, J=7.8 Hz, 3H), 1.25–1.73 (m, 8H), 1.89 (m, 2H), 2.33 (m, 1H), 2.43–2.53 (m, 2H, overlap with DMSO-d$_5$), 2.58 (q, m, overlap, 3H), 2.76 (d, J=18 Hz, 1H), 3.75 (ABQ pattern, J=16 Hz, 2H), 3.77 (s, 3H), 3.84 (s, 3H), 6.71 (s, 11), 7.10 (s, 1H), 11.31 (br s, 1H). LC-MS (APCI) calcd for C$_{25}$H$_{31}$ClN$_2$O$_6$: 490.19. found (M+H$^+$) 491.0 m/z.

Step 1

5-(Chloromethyl)-3-ethyl-1,2,4-oxadiazole

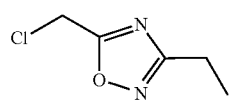

To crude N-hydroxypropanimidamide (80 g, 0.91 mol), obtained from propionitrile and hydroxylamine (Moloney, G. P.; Martin, G. R.; Mathews, N.; Maclennan, S.; Dodsworth, S.; Sang, P. Y.; Knight, C.; Maxwell, M.; Glen, R. C. *J. Chem. Soc Perkin I* 1999, 19, 2725), was added chloroacetyl chloride (411 g, 3.64 mol, 4 equiv). After the initial exothermic reaction subsided, the mixture was refluxed for 70 min. The reaction mixture was cooled to room temperature, and the excess chloroacetyl chloride evaporated. The residue was dissolved in ethyl acetate, diluted with hexanes, and filtered to remove dark solid impurities. The filtrate was evaporated, treated with ice-cold aqueous NaHCO$_3$, and extracted with ethyl acetate (2×150 mL). The extract was dried over Na$_2$SO$_4$, filtered, and the solvent evaporated, affording 76.25 g of an oil. This was subjected to fractional distillation, affording 16.5 g (14%) of the title product (bp 36° C./0.05 Torr; lit bp 88° C./35 Torr: Hagerty, J. D. U.S. Pat. No. 3,956,498, May 11, 1976).

$^1$H NMR (CDCl$_3$) d 1.31 (t, J=7 Hz, 3H), 2.75 (q, J=7 Hz, 2H), 4.64 (s, 2H). LC-MS (APCI) calcd for C$_5$H$_7$ClN$_2$O: 146.02. found (M+H$^+$): 147.0 m/z.

Example B(63)

2-({6-[2-(5-Chloro-2,4-dimethoxyphenyl)ethyl]-6-cyclopentyl-4-hydroxy-2-oxo-5,6-dihydro-2H-pyran-3-yl}methyl)-6,7-dimethoxyquinazolin-4(3H)-one

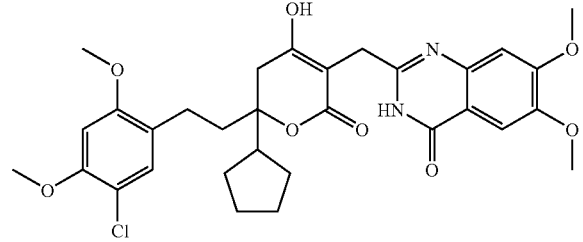

The title compound was prepared as described in Example B(53), using 2-(chloromethyl)-6,7-dimethoxyquinazolin-4(3H)-one (Example B(57), Step 1) in place of 5-(chloromethyl)-1,3-dimethyl-1H-1,2,4-triazole, and using 6-[2-(5-chloro-2,4-dimethoxyphenyl)ethyl]-6-cyclopentyldihydro-2H-pyran-2,4(3H)-dione in place of 6-[2-(3-chloro-4-methoxyphenyl)ethyl]-6-cyclopentyldihydro-2H-pyran-2,4 (3H)-dione. Yield: 20%.

$^1$H NMR (300 MHz, DMSO-d$_6$) δ 1.27–1.75 (m, 8H), 1.85 (m, 2H), 2.05 (m, 1H), 2.37 (m, 1H), 2.50 (m, 2H, overlap with DMSO-d$_5$), 2.53 (d, J=18 Hz, 1H), 2.69 (d, J=18 Hz, 1H), 3.59 (m, 2H, overlap with H$_2$O), 3.62 (s, 3H, overlap with H$_2$O), 3.67 (s, 3H, overlap with H$_2$O), 3.81 (s, 3H, overlap with H$_2$O), 3.84 (s, 3H, overlap with H$_2$O), 6.61 (s, 1H), 6.63 (s, 1H), 7.13 (s, 1H), 7.39 (s, 1H). LC-MS (APCI) calcd for C$_{31}$H$_{35}$ClN$_2$O$_8$: 598.21. found (M+H$^+$) 599.1 m/z.

Example B(64)

2-({6-[2-(5-Chloro-2,4-dimethoxyphenyl)ethyl]-6-cyclopentyl-4-hydroxy-2-oxo-5,6-dihydro-2H-pyran-3-yl}methyl)thieno[3,2-d]pyrimidin-4(3H)-one

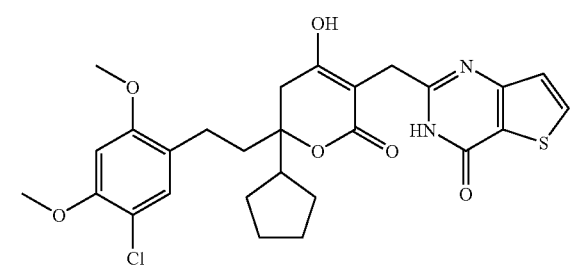

The title compound was prepared as described in Example B(53), using 2-(chloromethyl)thieno[3,2-d]-pyrimidine-4 (3H)-one (Example B(56), Step 1) in place of 5-(chloromethyl)-1,3-dimethyl-1H-1,2,4-triazole, and using 6-[2-(5-chloro-2,4-dimethoxyphenyl)ethyl]-6-cyclopentyldihydro- 2H-pyran-2,4(3H)-dione in place of 6-[2-(3-chloro-4-methoxyphenyl)ethyl]-6-cyclopentyldihydro-2H-pyran-2,4(3H)-dione. Yield: 20%.

$^1$H NMR (300 MHz, DMSO-$d_6$) δ 1.24–1.67 (m, 8H), 1.90 (m, 1H), 2.04 (m, 1H), 2.32 (m, 1H), 2.40–2.54 (m, 3H, overlap with DMSO-$d_5$), 2.71 (d, J=18 Hz, 1H), 3.52 (ABQ pattern, J=15 Hz, 2H, overlap with H$_2$O), 3.69 (s, 3H), 3.80 (s, 3H), 6.65 (s, 1H), 6.71 (d, J=5.4 Hz, 1H), 7.05 (s, 1H), 7.96 (d, J=5.4 Hz, 1H), 10.88 (br s, 1H), 12.26 (br s, 1H). LC-MS (APCI) calcd for $C_{27}H_{29}ClN_2O_6S$: 544.14. found (M+H$^+$) 544.9 m/z.

Example B(65)

2-({6-[2-(5-Chloro-2,4-dimethoxyphenyl)ethyl]-6-cyclopentyl-4-hydroxy-2-oxo-5,6-dihydro-2H-pyran-3-yl}methyl)quinazolin-4(3H)-one

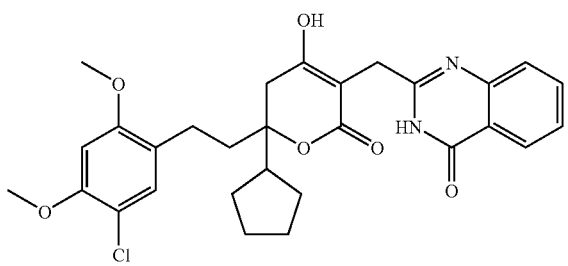

The title compound was prepared as described in Example B(53), using 2-(bromomethyl)-quinazolin-4(3H)-one (Example B(55), Step 1) in place of 5-(chloromethyl)-1,3-dimethyl-1H-1,2,4-triazole, and using 6-[2-(5-chloro-2,4-dimethoxyphenyl)ethyl]-6-cyclopentyldihydro-2H-pyran-2,4(3H)-dione in place of 6-[2-(3-chloro-4-methoxyphenyl)ethyl]-6-cyclopentyldihydro-2H-pyran-2,4(3H)-dione. Yield: 19%.

$^1$H NMR (300 MHz, DMSO-$d_6$) δ 1.33–1.74 (m, 8H), 1.99 (m, 1H), 2.23 (m, 1H), 2.37 (m, 1H), 2.45–2.53 (m, 2H, overlap with DMSO-$d_5$), 2.58 (d, J=17.5 Hz, 1H), 2.78 (d, J=17.5 Hz, 1H), 3.59 (ABQ pattern, J=16.6 Hz, 2H), 3.73 (s, 3H), 3.84 (s, 3H), 6.69 (s, 1H), 7.01 (d, J=8 Hz, 1H), 7.13 (s, 1H), 7.42 (t, J=8 Hz, 1H), 7.57 (t, J=8 Hz, 1H), 8.03 (d, J=8 Hz, 1H). LC-MS (APCI) calcd for $C_{29}H_{31}ClN_2O_6$: 538.19. found (M+H$^+$) 539.0 m/z.

Example B(66)

6-({6-Cyclopentyl-4-hydroxy-6-[2-(4-methoxyphenyl)ethyl]-2-oxo-5,6-dihydro-2H-pyran-3-yl}methyl)-2-pyridin-2-ylpyrimidin-4(3H)-one

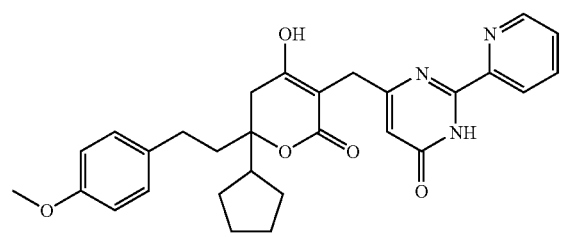

The title compound was prepared as described in Example B(53), using 6-(chloromethyl)-2-pyridin-2-ylpyrimidin-4(3H)-one in place of 5-(chloromethyl)-1,3-dimethyl-1H-1,2,4-triazole, and using 6-cyclopentyl-6-[2-(4-methoxyphenyl)ethyl]dihydro-2H-pyran-2,4(3H)-dione in place of 6-[2-(3-chloro-4-methoxyphenyl)ethyl]-6-cyclopentyldihydro-2H-pyran-2,4(3H)-dione. Yield: 11%.

$^1$H NMR (300 MHz, DMSO-$d_6$) δ 1.32–1.67 (m, 8H), 1.92 (m, 2H), 2.38 (m, 1H), 2.45–2.52 (m, 2H, overlap with DMSO-$d_5$), 2.60 (d, J=17.7 Hz, 1H), 2.80 (d, J=17.7 Hz, 1H), 3.52 (m, 2H, overlap with H$_2$O), 3.66 (s, 3H, overlap with H$_2$O), 6.07 (s, 3H), 6.68 (d, J=8.4 Hz, 2H), 6.95 (d, J=8.4 Hz, 2H), 7.60 (dd, J=7.5, 4.8 Hz, 1H), 7.93 (td, J=8 Hz, 1.5 Hz, 1H), 8.18 (d, J=8 Hz, 1H), 8.70 (d, J=4.8 Hz, 1H), 10.98 (br s, 1H). LC-MS (APCI) calcd for $C_{29}H_{31}N_3O_5$: 501.23. found (M+H$^+$) 502.1 m/z.

Example B(67)

6-[(6-{2-[4-(Benzyloxy)phenyl]ethyl}-6-cyclopentyl-4-hydroxy-2-oxo-5,6-dihydro-2H-pyran-3-yl)methyl]-2-cyclopropylpyrimidin-4(3H)-one

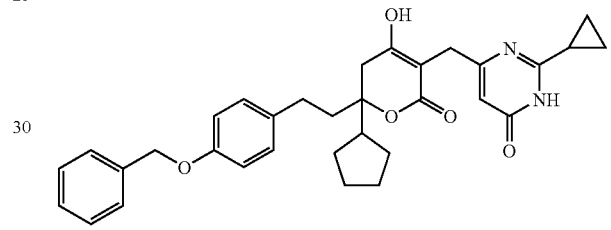

The title compound was prepared as described in Example B(53), using 6-(chloromethyl)-2-cyclopropylpyrimidin-4(3H)-one in place of 5-(chloromethyl)-1,3-dimethyl-1H-1,2,4-triazole, and using 6-{2-[4-(benzyloxy)phenyl]ethyl}-cyclopentyldihydro-2H-pyran-2,4-(3H)-dione (Step 6, below) in place of 6-[2-(3-chloro-4-methoxyphenyl)ethyl]-6-cyclopentyldihydro-2H-pyran-2,4(3H)-dione. Yield: 12%.

$^1$H NMR (300 MHz, DMSO-$d_6$) δ 0.91 (m, 4H), 1.15–1.65 (m, 8H), 1.82–1.92 (m, 3H), 2.34 (m, 1H), 2.38–2.58 (m, 3H, overlap with DMSO-$d_5$), 2.75 (d, J=18 Hz, 1H), 3.29 (ABQ pattern, J=16.7 Hz, 2H), 5.05 (s, 2H), 5.72 (s, 1H), 6.90 (d, J=8.4 Hz, 2H), 7.05 (d, J=8.4 Hz, 2H), 7.43–7.28 (m, 5H). LC-MS (APCI) calcd for $C_{33}H_{36}N_2O_5$: 540.26. found (M+H$^+$) 541.1 m/z.

Step 1

3-(4-Hydroxyphenyl)propionic acid methyl ester

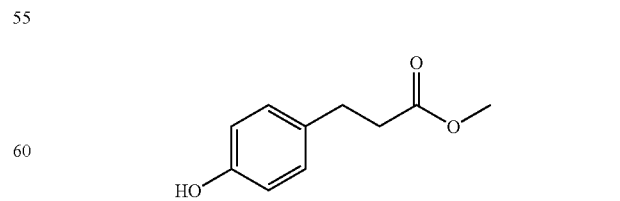

A solution of HCl in dioxane (4.0 M, 7.4 mL) was added to a solution of 4-hydroxyphenylpropionic acid (15.0 g, 90.3 mmol) in MeOH (500 mL). The reaction mixture was stirred overnight and then evaporated. The residue was evaporated from benzene (2×50 mL) to provide the product as an oil, which was used without further purification.

Step 2

3-(4-Benzyloxyphenyl)propionic acid methyl ester

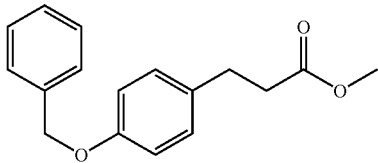

Benzyl bromide (12.9 mL, 108 mmol), K$_2$CO$_3$ (15.0 g, 109 mmol) and the 3-(4-hydroxyphenyl)propionic acid methyl ester from Step 1 above were combined in acetone (300 mL) and refluxed 40 h. The crude reaction mixture was filtered and the cake washed with acetone (2×100 mL). The filtrate was evaporated and the residue was triturated with MeOH (50 mL, 6 mL, 4 mL) to provide the product as a solid which was used without further purification.

Step 3

3-(4-Benzyloxyphenyl)propionic acid

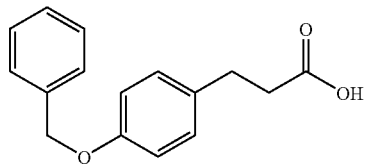

An aqueous solution of NaOH (1 M, 270 mL) was added to a mixture of the 3-(4-benzyloxyphenyl)propionic acid methyl ester from Step 2 above in MeOH (600 mL) and the reaction was stirred overnight. The crystalline ppt was collected by filtration, air dried and then partitioned between EtOAc/Et$_2$O/1 M HCl (500 mL, 250 mL, 150 mL). The organic phases were dried over MgSO$_4$ and evaporated to give the product as a white solid (16.2 g, 70%, 3 Steps).

$^1$H NMR (CDCl$_3$) δ 2.61–2.68 (m, 2H), 2.86–2.93 (m, 2H), 5.03 (s, 2H), 6.88–6.93 (m, 2H), 7.10–7.15 (m, 2H), 7.28–7.45 (m, 5H).

Step 4

3-(4-Benzyloxyphenyl)thiopropionic acid S-pyridin-2-yl ester

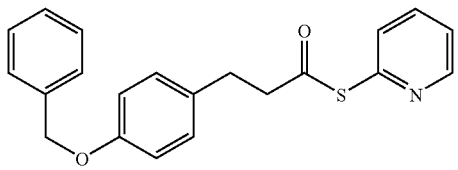

3-(4-Benzyloxyphenyl)propionic acid (5.40 g, 21.1 mmol) from Step 3 above, triphenylphosphine (7.18 g, 27.4 mmol) and 2,2'-dipyridyl disulfide (5.80 g, 26.3 mmol) were combined successively in CH$_2$Cl$_2$ (24 mL). The reaction mixture was stirred 1 h and then loaded directly onto a column for purification by flash chromatography (33% EtOAc in hexanes) to give a residue. This residue was washed with hexanes (20 mL) and the solid, partially crystalline material was collected by filtration and air dried to give the product (7.11 g, 97%).

$^1$H NMR(CDCl$_3$) δ 2.98 (s, 4H), 5.04 (s, 2H), 6.88–6.94 (m, 2H), 7.10–7.16 (m, 2H), 7.25–7.45 (m, 6H), 7.57–7.60 (m, 1H), 7.70–7.77 (m, 1H), 8.60–8.64 (m, 1H).

Step 5

3-(4-Benzyloxyphenyl)-1-cyclopentylpropan-1-one

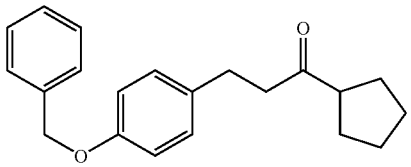

3-(4-Benzyloxyphenyl)thiopropionic acid S-pyridin-2-yl ester (3.00 g, 8.58 mmol) from Step 4 above was dissolved in dry THF (45 mL) and cooled to –78° C. A solution of cyclopentylmagnesium bromide in Et$_2$O (2.0 M, 4.51 mL, 9.02 mmol) was added dropwise along the sides of the reaction vessel. After stirring 35 min, the cooling bath was removed. The reaction mixture was quenched with saturated aq. NH$_4$Cl upon reaching ambient temperature and extracted with Et$_2$O (500 mL). The organic phase was washed with brine (50 mL), dried over MgSO$_4$ and evaporated. The residue was purified by flash column chromatography (10% EtOAc in hexanes) to give the product (2.22 g, 84%) as a white semi-crystalline material.

$^1$H NMR (CDCl$_3$) δ 1.48–1.83 (m, 8H), 2.69–2.77 (m, 2H), 2.79–2.88 (m, 3H), 5.03 (s, 2H), 6.86–6.92 (m, 2H), 7.07–7.12 (m, 2H), 7.28–7.45 (m, 5H).

Step 6

6-[2-(4-Benzyloxyphenyl)ethyl]-6-cyclopentyldihydropyran-2,4-dione

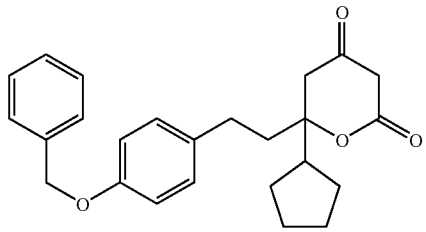

Methylacetoacetate (1.63 mL, 15.1 mmol) was dissolved in dry THF (42 mL) and cooled to 0° C. NaH (60% in mineral oil, 0.604 g, 15.1 mmol) were carefully added and the reaction mixture was stirred for 20 min. A solution of BuLi in hexanes (1.6 M, 9.44 mL, 15.1 mmol) was added dropwise and the resulting mixture was stirred an additional 20 min. A solution of 3-(4-benzyloxyphenyl)-1-cyclopentylpropan-1-one (2.33 g, 7.55 mmol) from Step 5 above in THF (37 mL) was added dropwise. After stirring 1 h, the reaction mixture was quenched with saturated aq NH$_4$Cl (100 mL) and extracted with Et$_2$O (600 mL). The organic phase was dried over MgSO$_4$ and evaporated. The residue was then stirred overnight in a mixture of 0.1 M NaOH (370 mL) and THF (37 mL). After the addition of an aq solution of 10% aq KHSO$_4$ (50 mL) the resulting mixture was stirred 30 min and then extracted with Et$_2$O (600 mL). The organic phase was washed with brine, dried over MgSO$_4$ and evaporated.

The residue was purified by flash column chromatography (50% EtOAc in hexanes) to give the product (1.54 g, 52%) as a white foam.

$^1$H NMR (CDCl$_3$) δ 1.39–2.04 (m, 10H), 2.21–2.33 (m, 1H), 2.56–2.67 (m, 2H), 2.76 (s, 2H), 3.41 (s, 2H), 5.03 (s, 2H), 6.87–6.93 (m, 2H), 7.02–7.08 (m, 2H), 7.28–7.44 (m, 5H).

Example B(68)

2-({6-[2-(5-Chloro-2,4-dimethoxyphenyl)ethyl]-6-cyclopentyl-4-hydroxy-2-oxo-5,6-dihydro-2H-pyran-3-yl}methyl)-6-methylpyrimidin-4(3H)-one

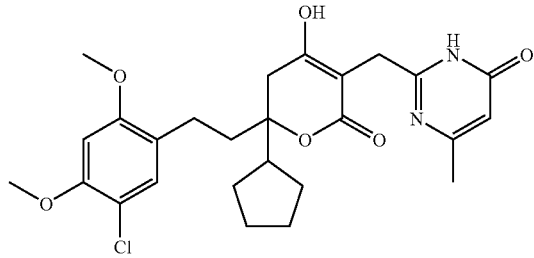

The title compound was prepared as described in Example B(53), using 2-(chloromethyl)-6-methylpyrimidin-4(3H)-one (Example B(54), Step 1) in place of 5-(chloromethyl)-1,3-dimethyl-1H-1,2,4-triazole, and using 6-[2-(5-chloro-2,4-dimethoxyphenyl)ethyl]-6-cyclopentyldihydro-2H-pyran-2,4(3H)-dione in place of 6-[2-(3-chloro-4-methoxyphenyl)ethyl]-6-cyclopentyldihydro-2H-pyran-2,4(3H)-dione. Yield: 19%.

$^1$H NMR (300 MHz, DMSO-d$_6$) δ 1.25–1.75 (m, 8H), 1.87 (s, m overlap, 4H), 2.05 (m, 1H), 2.36 (m, 1H), 2.43–2.50 (m, 2H, overlap with DMSO-d$_5$), 2.56 (d, J=17.5 Hz, 1H), 2.67 (d, J=17.5 Hz, 1H), 3.48 (m, 2H, overlap with H$_2$O), 3.77 (s, 3H), 3.84 (s, 3H), 5.98 (s, 1H), 6.71 (s, 1H), 7.09 (s, 1H). LC-MS (APCI) calcd for C$_{26}$H$_{31}$ClN$_2$O$_6$: 502.19. found (M+H$^+$) 503.0 m/z.

Example B(69)

6-Cyclopentyl-6-{2-[4-(difluoromethyl)-3-fluorophenyl]ethyl}-3-[(1,3-dimethyl-1H-1,2,4-triazol-5-yl)methyl]-4-hydroxy-5,6-dihydro-2H-pyran-2-one

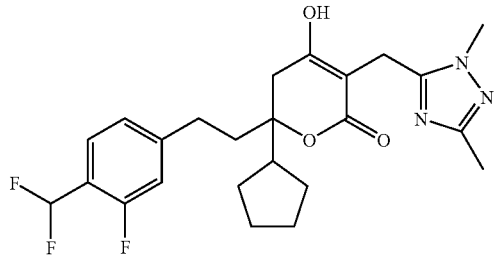

The title compound was prepared as described in Example B(53), using 6-cyclopentyl-6-{2-[4-(difluoromethyl)-3-fluorophenyl]ethyl}-dihydro-2H-pyran-2,4(3H)-dione (Step 3, below) in place of 6-[2-(3-chloro-4-methoxyphenyl)ethyl]-6-cyclopentyldihydro-2H-pyran-2,4(3H)-dione. Yield: 12%.

$^1$H NMR (300 MHz, DMSO-d$_6$) δ 1.18–1.68 (m, 8H), 2.04 (m, 2H), 2.13 (s, 3H), 2.34 (m, 1H), 2.40–2.63 (m, 3H, overlap with DMSO-d$_5$), 2.71 (d, J=17.4 Hz, 1H), 3.48 (m, 2H, overlap with H$_2$O), 3.76 (s, 3H), 7.15 (t, J=55 Hz, 1H), 7.18 (m, 2H), 7.52 (t, J=7.8 Hz, 1H). LC-MS (APCI) calcd for C$_{24}$H$_{28}$F$_3$N$_3$O$_3$: 463.21. found (M+H$^+$): 464.1 m/z.

Step 1

4-Bromo-1-(difluoromethyl)-2-fluorobenzene

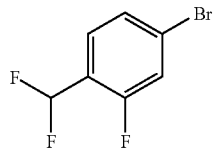

A solution of 2-fluoro-4-bromobenzaldehyde (50 g, 0.245 mol) in CH$_2$Cl$_2$ (500 mL) was treated with a solution of DAST (44 g, 0.271 mol, 1.1 equiv) in CH$_2$Cl$_2$ (200 mL) dropwise at such a rate that the internal temperature was maintained below 35° C. The reaction temperature was also controlled using an ice/water bath. Once the addition was completed, the reaction was stirred at room temperature for 14 h. The reaction mixture was poured over crushed ice and neutralized with NaHCO$_3$. The organic layer was separated, the aqueous layer extracted with CH$_2$Cl$_2$, and the combined extracts dried over Na$_2$SO$_4$ and concentrated. The residue was purified by fractional distillation to give 44 g (80%) of desired product (bp 43° C./1 Torr).

$^1$H NMR (DMSO-d$_6$) d 7.10 (t, 1H, J=54 Hz), 7.46 (m, 3H). MS(APCI) calcd for C$_7$H$_4$F$_3$Br, 225.06. found [M–19 (—F)]: 206 m/z.

Step 2

1-Cyclopentyl-3-[4-(difluoromethyl)-3-fluorophenyl]propan-1-one

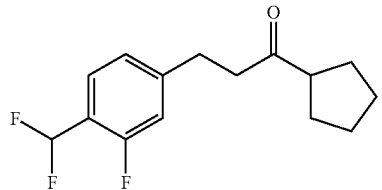

A mixture of 1-cyclopentyl-2-propen-1-ol (34 g, 0.266 mol), 2-fluoro-4-bromo-difluoromethyl benzene, (40 g, 0.177 mol, 1.5 equiv), and NaHCO$_3$ (17.8 g, 0.212 mol, 1.2 equiv) in anhydrous NMP (200 mL) was heated to 140° C. for 1 h, resulting in complete conversion by TLC. The reaction mixture was poured into water and extracted with CH$_2$Cl$_2$. The organic layer was separated, washed with brine and dried over anhydrous Na$_2$SO$_4$. After the removal of the solvent, the residue was purified by column chromatography using hexanes/ethyl acetate, and the product-containing fractions combined and concentrated. The residue was fractionally distilled through a Vigreux column to give 16 g (33%) of the desired product (bp 100° C./0.2 Torr).

$^1$H NMR (CDCl$_3$) d 1.57 (m, 8H), 2.81 (m, 4H), 3.09 (m, 1H), 6.86 (t, 1H, J=57 Hz), 6.95 (m, 2H), 7.51 (t, 1H, J=7.5 Hz). MS (APCI) calcd for C$_{16}$H$_{17}$F$_3$O, 270.29. found [M–19 (—F)]: 251.02 m/z.

Step 3

6-Cyclopentyl-6-{2-[4-(difluoromethyl)-3-fluorophenyl]ethyl}-dihydro-2H-pyran-2,4(3H)-dione

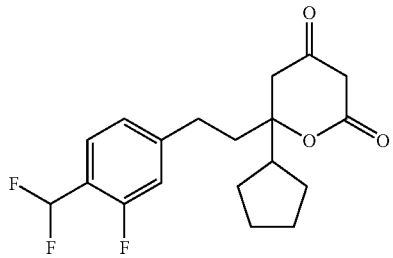

The title compound was prepared as described in Step 4 of Example B(58), using 1-cyclopentyl-3-[4-(difluoromethyl)-3-fluorophenyl]propan-1-one (Step 2, above) in place of 3-[3-chloro-4-(cyclopropylmethoxy)phenyl]-1-cyclopentylpropan-1-one, with the exception that the intermediate hydroxyester was not purified. The crude product, a viscous yellow oil, was dissolved in a minimal amount of ethyl ether, diluted with hexanes and cooled, affording 4 g (16%) of the product as a white solid.

$^1$H NMR (CDCl$_3$) d 1.66 (m, 8H), 1.94 (t, 2H), 2.26 (m, 1H), 2.75 (m, 4H), 3.42 (s, 2H), 6.67–7.04 (m, 3H,), 7.5 (t, 1H, J=7.5). MS calcd for C$_{19}$H$_{21}$F$_3$O$_3$: 354.363. found [M−19(—F)]: 335.2 m/z.

Example B(70)

6-{2-[3-Chloro-4-(cyclopropylmethoxy)phenyl]ethyl}-6-cyclopentyl-3-[(1,3-dimethyl-1H-1,2,4-triazol-5-yl)methyl]-4-hydroxy-5,6-dihydro-2H-pyran-2-one

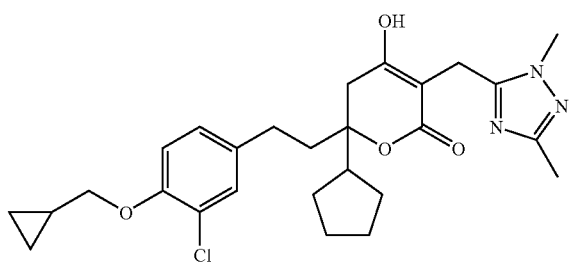

The title compound was prepared as described in Example B(53), using 6-{-[3-chloro-4-(cyclopropylmethoxy)phenyl]ethyl}-6-cyclopentyldihydro-2H-pyran-2,4(3H)-dione (Example B(58), Step 4) in place of 6-[2-(3-chloro-4-methoxyphenyl)ethyl]-6-cyclopentyldihydro-2H-pyran-2,4(3H)-dione. Yield: 9%.

$^1$H NMR (300 MHz, DMSO-d$_6$) δ 0.26 (m, 2H), 0.50 (m, 2H), 1.13–1.65 (m, 9H), 1.92 (m, 2H), 2.08 (s, 3H), 2.29 (m, 1H), 2.35–2.50 (m, 3H, overlap with DMSO-d$_5$), 2.69 (d, J=17.7 Hz, 1H), 3.57 (ABQ pattern, J=15.6 Hz, 2H, overlap with H$_2$O peak), 3.69 (s, 3H, overlap with H$_2$O peak), 3.80 (d, J=6.9 Hz, 2H), 6.93 (d, J=8.4 Hz, 1H), 7.00 (dd, J=8.4 Hz, 1.9 Hz, 1H), 7.16 (d, J=1.9 Hz, 1H). LC-MS (APCI) calcd for C$_{27}$H$_{34}$ClN$_3$O$_4$: 499.22. found (M+H$^+$): 500.1 m/z.

Example B(71)

6-[2-(5-Chloro-2,4-dimethoxyphenyl)ethyl]-6-cyclopentyl-3-[(1,3-dimethyl-1H-1,2,4-triazol-5-yl)methyl]-4-hydroxy-5,6-dihydro-2H-pyran-2-one

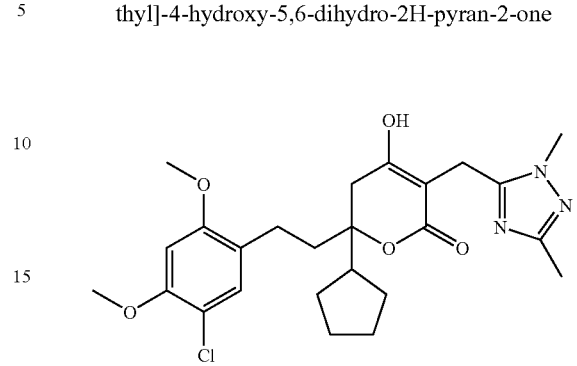

The title compound was prepared as described in Example B(53), using 6-[2-(5-chloro-2,4-dimethoxyphenyl)ethyl]-6-cyclopentyldihydro-2H-pyran-2,4(3H)-dione in place of 6-[2-(3-chloro-4-methoxyphenyl)ethyl]-6-cyclopentyldihydro-2H-pyran-2,4(3H)-dione. Yield: 14%.

$^1$H NMR (300 MHz, DMSO-d$_6$) δ 1.2–1.7 (m, 8H), 1.87 (m, 2H), 2.19 (s, 3H), 2.32 (m, 1H), 2.35–2.52 (m, 2H, overlap with DMSO-d$_5$), 2.56 (d, J=17.7 Hz, 1H), 2.76 (d, J=17.7 Hz, 1H), 3.68 (s, 2H), 3.78 (s, 6H), 3.85 (s, 3H), 6.71 (s, 1H), 7.11 (s, 1H). LC-MS (APCI) calcd for C$_{25}$H$_{32}$ClN$_3$O$_5$: 489.20. found (M+H$^+$): 490.1 m/z.

Example B(72)

Methyl 5-[(6-cyclopentyl-6-{2-[4-(difluoromethyl)-3-fluorophenyl]ethyl}-4-hydroxy-2-oxo-5,6-dihydro-2H-pyran-3-yl)methyl]isoxazol-3-ylcarbamate

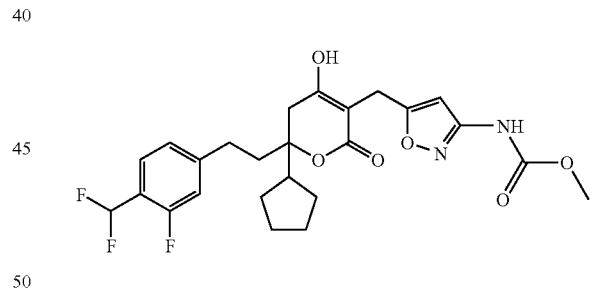

The title compound was prepared as described in Example B(53), using methyl 5-(bromomethyl)isoxazol-3-ylcarbamate (prepared as described: Sircar, J. C.; Capiris, T. U.S. Pat. No. 4,489,077, Dec. 18, 1984) in place of 5-(chloromethyl)-1,3-dimethyl-1H-1,2,4-triazole, and using 6-cyclopentyl-6-{2-[4-(difluoromethyl)-3-fluorophenyl]ethyl}-dihydro-2H-pyran-2,4(3H)-dione(Example B(69), Step 3) in place of 6-[2-(3-chloro-4-methoxyphenyl)ethyl]-6-cyclopentyldihydro-2H-pyran-2,4(3H)-dione. Yield: 6%.

$^1$H NMR (300 MHz, DMSO-d$_6$) δ 1.18–1.75 (m, 8H), 1.94 (m, 2H), 2.35 (m, 1H), 2.40–2.70 (m, 3H, overlap with DMSO-d$_5$), 2.76 (d, J=18.3 Hz, 1H), 3.59 (m, 2H, overlap with H$_2$O), 3.63 (s, 3H), 6.31 (s, 1H), 7.08 (t, J=55 Hz, overlap with m, combined: 3H), 7.50 (t, J=7.5 Hz, 1H), 10.55 (s, 1H), 11.26 (s, 1H). LC-MS (APCI) calcd for C$_{25}$H$_{27}$F$_3$N$_2$O$_6$: 508.18. found (M+H$^+$): 509.1 m/z.

Example B(73)

6-[2-(5-Chloro-2,4-dimethoxyphenyl)ethyl]-6-cyclopentyl-4-hydroxy-3-[(3-pyridin-2-yl-1,2,4-oxadiazol-5-yl)methyl]-5,6-dihydro-2H-pyran-2-one

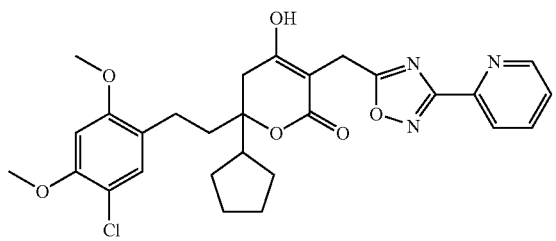

The title compound was prepared as described in Example B(53), using 2-[5-(chloromethyl)-1,2,4-oxadiazol-3-yl]pyridine (from Step 1, below) in place of 5-(chloromethyl)-1,3-dimethyl-1H-1,2,4-triazole, and using 6-[2-(5-chloro-2,4-dimethoxyphenyl)ethyl]-6-cyclopentyldihydro-2H-pyran-2,4(3H)-dione in place of 6-[2-(3-chloro-4-methoxyphenyl)ethyl]-cyclopentyldihydro-2H-pyran-2,4(3H)-dione. Yield: 9%.

$^1$H NMR (300 MHz, DMSO-$d_6$) δ 1.25–1.75 (m, 8H), 1.76–2.03 (m, 2H), 2.34 (m, 1H), 2.4–2.55 (m, 2H, overlap with DMSO-$d_5$), 2.62 (d, J=17.7 Hz, 1H), 2.81 (d, J=17.7 Hz, 1H), 3.74 (s, 3H, overlap with H$_2$O), 3.80 (s, 3H), 3.90 (ABQ pattern, J=16.8 Hz, 2H), 6.66 (s, 1H), 7.13 (s, 1H), 7.55 (m, 1H), 7.81 (m, 2H), 8.70 (d, J=4.8 Hz, 1H), 11.43 (br s, 1H). LC-MS (APCI) calcd for C$_{28}$H$_{30}$ClN$_3$O$_6$: 539.18. found (M+H$^+$): 540.1 m/z.

Step 1

2-[5-(Chloromethyl)-1,2,4-oxadiazol-3-yl]pyridine

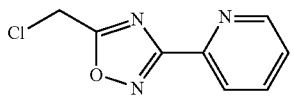

The title compound was prepared by a modification of a reported method: a) Mylari, B. L.; Beyer, T. A.; Scott, P. J.; Aldinger, C. E.; Dee, M. F.; Siegel, T. W.; Zembrowski, W. J. *J. Med. Chem.* 1992, 35, 457, and b) Palazzo, G.; Tavella, M.; Strani, G.; Silvestrini, B.; *J. Med. Pharm. Chem.* 1961, 4, 351. To a suspension of N'-hydroxypyridine-2-carboximidamide (25.0 g, 0.182 mol) in chloroform (350 mL) was added chloroacetyl chloride (20.5 g, 0.182 mol, 1 equiv) and triethylamine (20.23 g, 0.2 mol, 1.1 equiv). When most of the triethylamine had been added, the suspension turned to a clear light-yellow solution. The solution was allowed to stand at room temperature for 1 d. The mixture was extracted with water (3×75 mL), resulting in the precipitation of a crystalline solid. The resulting slurry was filtered, and filter cake triturated with ethanol, re-filtered, and dried, affording 29.62 g (73%) of the O-chloroacetyl amidoxime intermediate. This intermediate was refluxed in xylenes (300 mL) for 3 h, and the volatiles removed completely in vacuo, affording 25.55 g (72% overall) of the pure 1,2,4-oxadiazole. $^1$H NMR (DMSO-$d_6$) □ 5.20 (s, 2H), 7.62 (m, 1H), 8.06 (m, 2H), 8.76 (m, 1H). LC-MS (APCI) calcd for C$_8$H$_6$ClN$_3$O: 195.02. found (M+H$^+$): 196.0 m/z.

Example B(74)

6{2-[3-Chloro-4-(difluoromethoxy)phenyl]ethyl}-6-cyclopentyl-3-[(1,3-dimethyl-1H-1,2,4-triazol-5-yl)methyl]-4-hydroxy-5,6-dihydro-2H-pyran-2-one

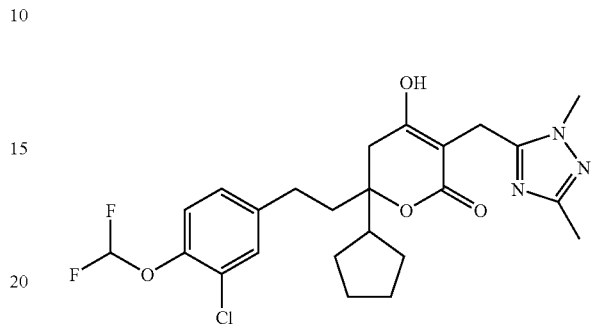

The title compound was prepared as described in Example B(53), using 6{2-[3-chloro-4-(difluoromethoxy)phenyl]ethyl}-6-cyclopentadihydro-2H-pyran-2,4(3H)-dione (from Step 2, below) in place of 6-[2-(3-chloro-4-methoxyphenyl)ethyl]-6-cyclopentyldihydro-2H-pyran-2,4(3H)-dione. Yield: 1%.

$^1$H NMR (300 MHz, DMSO-$d_6$) δ 1.22–1.75 (m, 8H), 2.03 (m, 2H), 2.11 (s, 3H), 2.35 (m, 1H), 2.45–2.60 (m, 3H, overlap with DMSO-$d_5$), 2.75 (d, J=18.3 Hz, 1H), 3.61 (m, 2H, overlap with H$_2$O), 3.74 (s, 3H), 7.24 (t, J=73 Hz, overlap with m, combined: 3H), 7.42 (m, 1H). LC-MS (APCI) calcd for C$_{24}$H$_{28}$ClF$_2$N$_3$O$_4$: 495.17. found (M+H$^+$): 496.1 m/z.

Step 1

3-[3-Chloro-4-(difluoromethoxy)phenyl]-1-cyclopentylpropan-1-one

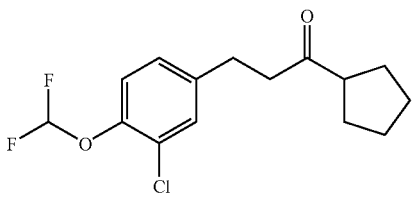

A mixture of 3-(3-chloro-4-hydroxyphenyl)-1-cyclopentylpropan-1-one (15 g, 59.35 mmol, Example B(58), Step 2)), methyl 2-chloro-2,2-difluoroacetate (17.15 g, 118.7 mmol, 2 equiv) and K$_2$CO$_3$ (12.4 g, 124.6 mmol, 2.1 equiv) in dry DMF (150 mL) was stirred at 75–80° C. for 2 h. The mixture was poured into water and extracted with ethyl acetate. The organic layer was washed with aqueous 1 M NaOH and brine. The organic phase was dried over Na$_2$SO$_4$, filtered, and concentrated in vacuo. The residue was subjected to fractional distillation affording 15.3 g (72%) of material that was about 80% pure by $^1$H NMR (bp 70° C./2 Torr).

$^1$H NMR (CDCl$_3$) δ 1.63 (m, 9H), 2.84 (m, 5H), 6.49 (t, 1H, J=72), 7.11 (m, 2H), 7.27 (s, 1H). MS calcd for C$_{15}$H$_{17}$F$_2$O$_2$Cl, 302.744. found [M−19(—F)]: 283.7 m/z.

Step 2

6-{2-[3-Chloro-4-(difluoromethoxy)phenyl]ethyl}-
6-cyclopentadihydro-2H-pyran-2,4(3H)-dione

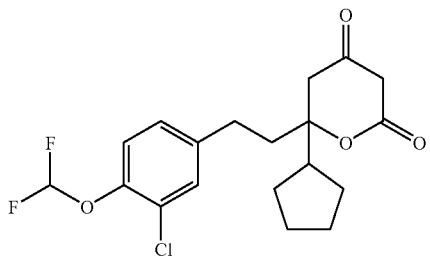

The title compound was prepared as described in Example B(58), Step 4, using 3-[3-Chloro-4-(difluoromethoxy)phenyl]-1-cyclopentylpropan-1-one in place of 3-[3-chloro-4-(cyclopropylmethoxy)phenyl]-1-cyclopentylpropan-1-one, with the exception that the intermediate hydroxy ester was not purified. The residue obtained from the cyclization Step was purified by reverse phase column chromatography ($C_{18}$ stationary phase using acetonitrile/water/methanol mixture in a polarity gradient). After concentration in vacuo, the residual oil was dissolved in a minimal amount of ethyl ether, and diluted with hexanes. Upon cooling, a white solid was obtained. Yield 891 mg (5% overall).

$^1$H NMR (CDCl$_3$) δ 1.62(m, 8H), 1.95 (m, 2H), 2.26 (m, 1H), 2.75 (m, 4H), 3.42 (s, 2H), 6.84 (m, 3H,), 7.5 (t, 1H, J=7.5). MS calcd for $C_{19}H_{21}ClF_2O_4$: 386.0. found (M−1): 385.0 m/z.

Example B(75)

2-(4-{2-[2-Cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-2-fluoro-phenyl)-2-methyl-propionitrile

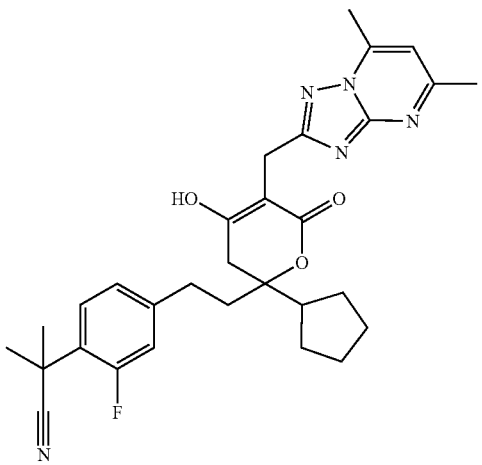

To a solution of 2-{4-[2-(2-cyclopentyl-4,6-dioxo-tetrahydro-pyran-2-yl)-ethyl]-2-fluoro-phenyl}-2-methyl-propionitrile (0.40 g, 1.1 mmol) from example A(81), in MeOH (7 mL) was added 5,7-dimethyl-[1,2,4]triazolo[1,5-a]pyrimidine-2-carbaldehyde (0.19 g, 1.08 mmol, described in Step 3 of example B(75)) from Step 3 below and borane-dimethylamine complex (76 mg, 1.3 mmol) and stirred at room temperature for 3 hours. The reaction was quenched with 10 mL saturated NH$_4$Cl and 5 mL water. To this was added 20 mL CH$_2$Cl$_2$ and the pH of the aqueous phase was adjusted to 3. The layers were separated, and the aqueous layer was extracted with 3×30 mL 10% MeOH in CH$_2$Cl$_2$. The organic layers were combined, and dried over Na$_2$SO$_4$. After filtering off the solids, the liquid was concentrated by rotary evaporation to an oil. The oil was flash chromatographed, and the resulting product was further purified by preparatory HPLC. Yield: 28 mg, 5%.

MS (ESI): 530 (M−H).

Step 1

(5-Amino-1H-[1,2,4]triazol-3-yl)-methanol

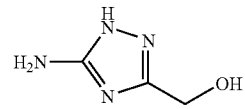

A solution of glycolic acid (70% in water, 70 mL, 805 mmol) was added to aminoguanidine bicarbonate (55.12 g, 405 mmol) carefully. After foaming subsided, concentrated nitric acid (0.5 mL) was added and the entire reaction was refluxed for 40 hours. The reaction was cooled to 5° C. for 30 minutes, and the solids were filtered. The solids were then triturated with EtOH for 1 hour. The product was then filtered and dried under nitrogen (40.36 g, 52% yield).

MS (ESI): 115 (M+H).

Step 2

(5,7-Dimethyl-[1,2,4]triazolo[1,5-a]pyrimidin-2-yl)-methanol

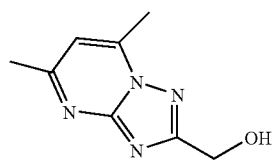

To a slurry of (5-amino-1H-[1,2,4]triazol-3-yl)-methanol (9.5 g, 50 mmol) from Step 1 above in acetic acid (200 mL) was added 2,4-pentanedione (5.13 mL, 50 mmol). The mixture was heated to reflux for 4 hours, and then cooled to room temperature. The product was isolated by removing the solvent by rotary evaporation (8.5 g, 95% yield).

MS (ESI): 179 (M+H).

Step 3

5,7-Dimethyl-[1,2,4]triazolo[1,5-a]pyrimidine-2-carbaldehyde

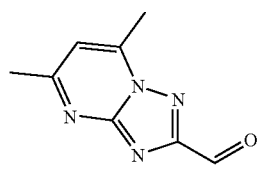

A slurry of 5,7-Dimethyl-[1,2,4]triazolo[1,5-a]pyrimidin-2-yl)-methanol (0.3 g, 1.7 mmol) from Step 2 above and IBX (1.4 g, 5.0 mmol) in 1,2-dichloroethane (22 mL) was stirred at 80° C. for 18 hours. The reaction was cooled to room temperature, and diluted with 100 mL CH$_2$Cl$_2$. After the solids were removed by filtration, the solvent was removed by rotary evaporation to give a yellow solid. The solid was purified by flash chromatography to give the desired product (229 mg, 77% yield).

$^1$H NMR (CDCl$_3$) δ: 2.72 (s, 3H), 2.86 (s, 3H), 6.96 (s, 1H), 10.24 (s, 1H).

Example B(76)

1-(4-{2-[2-Cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-2-fluoro-phenyl)-cyclopropanecarbonitrile

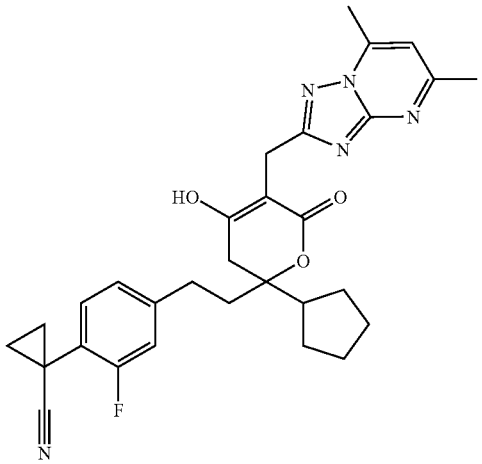

The desired product was prepared analogously to example B(75), substituting 1-{4-[2-(2-Cyclopentyl-4,6-dioxo-tetrahydro-pyran-2-yl)-ethyl]-2-fluoro-phenyl}-cyclopropanecarbonitrile (0.24 g, 0.65 mmol) from Example A(86), in place of 2-{4-[2-(2-cyclopentyl-4,6-dioxo-tetrahydro-pyran-2-yl)-ethyl]-2-fluoro-phenyl}-2-methyl-propionitrile. Yield: 64 mg, 19%.

$^1$H NMR (CDCl$_3$) δ: 1.25–1.30 (m, 2H), 1.42–1.68 (m, 10H), 1.88–1.93 (m, 2H), 2.30 (p, J=8.59 Hz, 1H), 2.44–2.73 (m, 10H), 4.05 (d, J=3.03 Hz, 2H), 6.76–6.84 (m, 3H), 7.09–7.22 (m, 1H).

Example B(77)

3-benzyl-6-cyclopentyl-6-[2-(4-methoxyphenyl) ethyl]dihydro-2H-pyran-2,4(3H)-dione

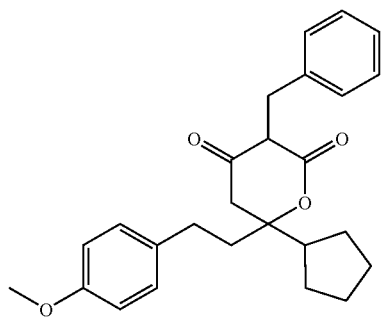

DBU (28.6 ul, 0.191 mmol) was added to a solution of 6-cyclopentyl-6-[2-(4-methoxyphenyl)ethyl]dihydro-2H-pyran-2,4(3H)-dione (55 mg, 0.174 mmol, described below) in benzene (1.9 ml), under an atmosphere of argon. Benzyl bromide (21 ul, 0.174 mmol) was then added. The reaction mixture was stirred at room temperature for 20 minutes, followed by the addition of 5 crystals of sodium iodide. The reaction mixture was stirred for a further 24 hrs, after which time the mixture was filtered through a plug of Celite. The filtrate was concentrated in vacuo and the residue purified by prep HPLC to afford the title compound as a white solid (9.0 mg).

$^1$H NMR (CDCl$_3$): δ 1.43–1.80 (bm, 8H), 2.20 (m, 2H), 2.24 (m, 1H), 2.72 (m, 2H), 3.06 (m, 3H), 3.30 (m, 1H), 3.76 (m, 4H), 6.72 (d, J=8.64 Hz, 2H), 6.78 (d, J=8.64 Hz, 2H), 6.94 (m, 3H), 7.23 (m, 2H). Exact Mass: Calcd, 406.51. Found, 406.21.

Step 1

6-cyclopentyl-6-[2-(4-methoxyphenyl)ethyl]dihydro-2H-pyran-2,4(3H)-dione

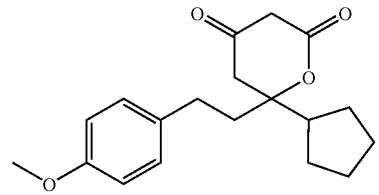

This compound was prepared analogously to Example A(82), where 4-Bromo-1-methoxy-benzene was substituted in place of 2-Bromopyridine in Step 1 of that example.

Example B(78)

3-benzyl-6-[2-(3-chloro-4-methoxyphenyl) ethyl]-6-cyclopentyldihydro-2H-pyran-2,4(3H)-dione

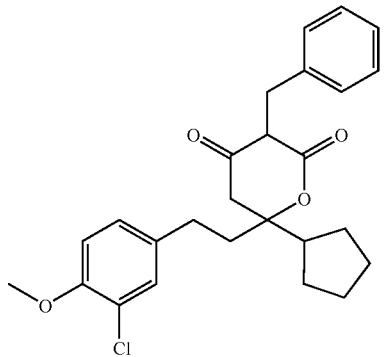

DBU (28.6 ul, 0.191 mmol) was added to a solution of 6-[2-(3-chloro-4-methoxyphenyl)ethyl]-6-cyclopentyldihydro-2H-pyran-2,4(3H)-dione (60.6 mg, 0.172 mmol) in benzene (2.0 ml), under an atmosphere of argon. Benzyl bromide (20.5 ul, 0.172 mmol) was then added. The reaction mixture was stirred at room temperature for 20 minutes, followed by the addition of 5 crystals of sodium iodide. The reaction mixture was stirred for a further 24 hrs, after which time the mixture was filtered through a plug of Celite. The filtrate was concentrated in vacuo and the residue purified by prep HPLC to afford the title compound as a white solid (11.1 mg).

$^1$H NMR (CDCl$_3$): δ 1.40–1.90 (bm, 8H), 2.21 (m, 3H), 2.74 (m, 2H), 3.01 (t, J=3.10 Hz, 1H), 3.10 (t, J=3.10 Hz, 1H), 3.72 (d, J=2.07 Hz, 1H), 3.89 (s, 3H), 6.91 (d, J=2.24 Hz, 1H), 7.17 (m, 3H), 7.30 (m, 4H). Exact Mass: Calcd, 440.96. Found, 440.18.

Step 1

{6-[2-(3-Chloro-4-methoxy-phenyl)-ethyl]-6-cyclopentyl-dihydro-pyran-2,4-dione

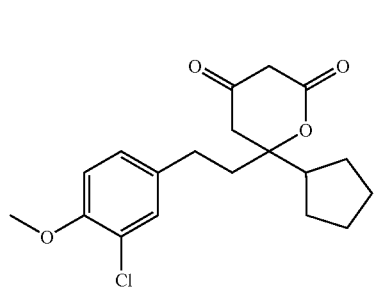

This compound was prepared analogously to Example A(82), where 4-Bromo-2-chloro-1-methoxy-benzene was substituted in place of 2-Bromopyridine in Step 1 of that example.

$^1$H NMR (CDCl$_3$): δ 1.41–1.86 (brm, 8H), 1.96 (m, 2H), 2.29 (t, J=7.6 Hz, 1H), 2.61 (t, J=8.6 Hz, 2H), 2.81 (s, 2H), 3.40 (s, 2H), 3.89, (s, 3H), 6.45 (d, J=8.5 Hz, 1H), 7.0 (d, J=8.5 Hz, 1H), 7.15 (brs, 1H). ESIMS (MH+): 351.8.

Example B(79)

3-allyl-6-[2-(3-chloro-4-methoxyphenyl)ethyl]-6-cyclopentyldihydro-2H-pyran-2,4(3H)-dione

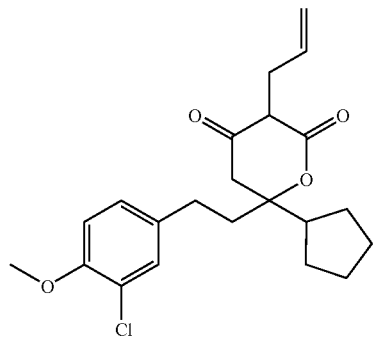

The title compound was prepared analogously to Example B(78), where allyl bromide was substituted in place of benzyl bromide in that example.

$^1$H NMR (CDCl$_3$): δ 1.44–1.95 (bm, 8H), 2.19 (m, 3H), 2.45 (m, 1H), 2.65 (m, 3H), 3.01 (t, J=3.10 Hz, 1H), 3.10 (t, J=2.56 Hz, 2H), 3.14 (m, 1H), 3.89 (s, 3H), 5.35 (m, 2H), 6.01 (m, 1H), 6.85 (d, J=1.92 Hz, 1H), 7.17 (m, 2H). Exact Mass: Calcd, 390.90. Found, 390.16.

Example B(80)

6-[2-(3-chloro-4-methoxyphenyl)ethyl]-6-cyclopentyl-3-(pyridin-3-ylmethyl)dihydro-2H-pyran-2,4(3H)-dione

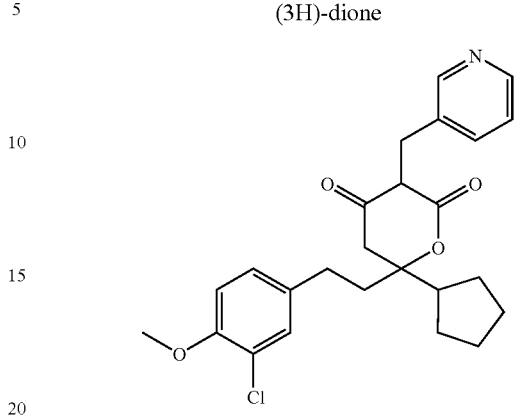

DBU (55 ul, 0.367 mmol) was added to a solution of 6-[2-(3-chloro-4-methoxyphenyl)ethyl]-6-cyclopentyldihydro-2H-pyran-2,4(3H)-dione (58.6 mg, 0.167 mmol) in benzene (16.0 ml) and acetonitrile (3 ml), under an atmosphere of argon. 3-(chloromethyl)pyridine hydrochloride (27.4 mg, 0.167 mmol) was then added. The reaction mixture was stirred at room temperature for 24 hrs, after which time the mixture was filtered through a plug of Celite. The filtrate was concentrated in vacuo and the residue purified by prep HPLC to afford the title compound as a white solid (8.60 mg).

$^1$H NMR (CDCl$_3$): δ 1.40–1.80 (bm, 8H), 1.90 (m, 2H), 2.30 (m, 1H), 2.51 (m, 3H), 2.74 (d, J=17.27 Hz, 1H), 3.74 (m, 3H), 3.85 (s, 3H), 6.73 (d, J=8.32 Hz, 1H), 6.89 (m, 1H), 7.02 (s, 1H), 7.30 (m, 1H), 7.92 (m, 1H), 8.26 (s, 1H), 8.55 (s, 1H).

Example B(81)

6-[2-(3-chloro-4-methoxyphenyl)ethyl]-6-cyclopentyl-3-(pyridin-2-ylmethyl)dihydro-2H-pyran-2,4(3H)-dione

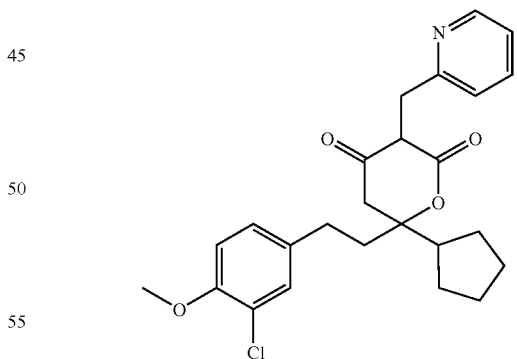

The title compound was prepared analogously to Example B(80) where 2-(chloromethyl)pyridine hydrochloride was substituted in place of 3-(chloromethyl)pyridine hydrochloride in that example.

$^1$H NMR (CDCl$_3$): δ 1.30–1.80 (bm, 8H), 1.97 (m, 3H), 2.37 (m, 2H), 2.57 (m, 3H), 2.69 (s, 1H), 2.75 (s, 1H), 3.87 (s, 3H), 6.83 (d, J=8.32 Hz, 1H), 6.97 (d, J=1.92 Hz, 1H), 7.12 (s, 1H), 7.26 (s, 1H), 7.43 (d, J=7.68 Hz, 1H), 7.74 (t, J=7.68 Hz, 1H), 8.40 (d, J=4.80 Hz, 1H). Exact Mass: Calcd, 441.95. Found, 441.17.

Example B(82)

6-[2-(3-chloro-4-methoxyphenyl)ethyl]-6-cyclopentyl-3-(pyridin-4-ylmethyl)dihydro-2H-pyran-2,4(3H)-dione

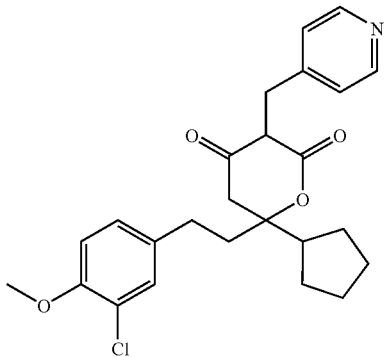

The title compound was prepared analogously to Example B(80) where 4-(chloromethyl)pyridine hydrochloride was substituted in place of 3-(chloromethyl)pyridine hydrochloride in that example.

$^1$H NMR (CDCl$_3$): δ 1.25–1.80 (bm, 8H), 1.97 (m, 3H), 2.33 (m, 2H), 2.52 (m, 3H), 2.77 (d, J=16.95 Hz, 1H), 3.74 (s, 1H), 3.83 (s, 3H), 6.80 (d, J=8.32 Hz, 1H), 6.93 (m, 1H), 7.06 (s, 1H), 7.39 (bs, 2H), 8.50 (bs, 2H).

Example B(83): 6-[2-(3-chloro-4-methoxyphenyl)ethyl]-6-cyclopentyl-3-(imidazo[1,2-a]pyrimidin-2-ylmethyl)dihydro-2H-pyran-2,4(3H)-dione

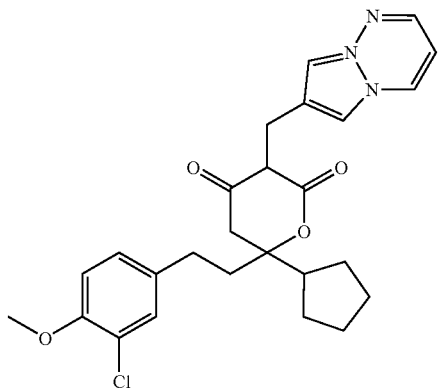

Potassium carbonate (35.4 mg, 0.256 mmol) was added to a solution of 6-[2-(3-chloro-4-methoxyphenyl)ethyl]-6-cyclopentyldihydro-2H-pyran-2,4(3H)-dione (30 mg, 0.085 mmol), 2-(chloromethyl)imidazo[1,2-a]pyrimidine (17.2 mg, 0.103 mmol) and sodium iodide (5 crystals) in acetone (40 ml). The reaction mixture was stirred at reflux for 24 hrs, after which time the mixture was acidified to pH=3 and the product was extracted with ethyl acetate (3×25 ml). The combined organics were washed with brine (30 ml), dried over anhydrous sodium sulfate and filtered. The filtrate was concentrated in vacuo and purified by prep HPLC to afford the title compound as a white solid (8.8 mg).

$^1$H NMR (CDCl$_3$): δ 1.40–1.88 (bm, 11H), 2.24 (m, 2H), 2.48–2.59 (bm, 3H), 3.79 (s, 3H), 4.03 (d, J=14.08 Hz, 1H), 4.18 (d, J=14.08 Hz, 1H), 6.94 (d, J=1.60 Hz, 2H), 7.03 (d, J=1.60 Hz, 2H), 8.08 (s, 1H), 8.82 (bs, 1H), 8.85 (bs, 1H). Exact Mass: Calcd, 481.97. Found, 481.18.

Example B(84)

6-[2-(3-chloro-4-methoxyphenyl)ethyl]-6-cyclopentyl-3-[(1-methyl-1H-benzimidazol-2-yl)methyl]dihydro-2H-pyran-2,4(3H)-dione

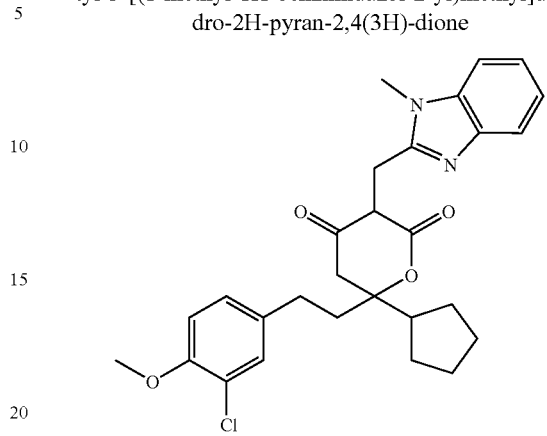

6-[2-(3-chloro-4-methoxyphenyl)ethyl]-6-cyclopentyldihydro-2H-pyran-2,4(3H)-dione (127 mg, 0.362 mmol) was dissolved in a mixture of dimethoxy ethylene glycol (1.8 ml) and water (1.8 ml). The solution was heated to 80° C. Sodium carbonate (42.2 mg, 0.398 mmol) was then added to the mixture followed by 2-(chloromethyl)-1-methyl-1H-benzimidazole (42.2 mg, 0.398 mmol). The reaction mixture was stirred at 80° C. for 5 hrs, after which time the mixture was acidified to pH 5 and the product was extracted with ethyl acetate (3×25 ml). The combined organics were washed with brine (30 ml), dried over anhydrous sodium sulfate and filtered. The filtrate was concentrated in vacuo and purified by prep HPLC to afford the title compound as a white solid (13.5 mg).

$^1$H NMR (CDCl$_3$): δ 1.30–1.80 (bm, 11H), 2.22 (m, 1H), 2.50 (t, J=8.29 Hz, 2H), 2.92 (d, J=8.10 Hz, 2H), 3.78 (s, 3H), 4.01 (s, 3H), 4.26 (d, J=7.35 Hz, 1H), 6.87 (d, J=2.26 Hz, 1H), 6.90 (s, 1H), 7.00 (d, J=2.07 Hz, 2H), 7.44 (m, 3H), 7.54 (m, 1H), 7.84 (m, 1H). Exact Mass: Calcd, 495.01. Found, 494.20.

Example B(85)

6-[2-(3-chloro-4-methoxyphenyl)ethyl]-6-cyclopentyl-3-(quinolin-2-ylmethyl)dihydro-2H-pyran-2,4(3H)-dione

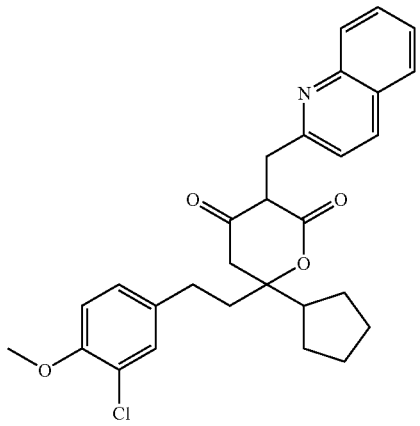

The title compound was prepared analogously to Example B(84), where 2-(chloromethyl)quinoline hydrochloride was substituted in place of 2-(chloromethyl)-1-methyl-1H-benzimidazole in that example.

¹H NMR (CDCl₃): δ 1.44–1.80 (bm, 8H), 2.20 (m, 3H), 2.72 (m, 2H), 3.01 (m, 2H), 3.21 (m, 1H), 3.40 (m, 1H), 3.72 (d, J=4.10 Hz, 1H), 3.89 (s, 3H), 6.91 (m, 1H), 7.17 (m, 2H), 7.36 (m, 3H), 7.82 (t, J=8.66 Hz, 2H), 8.09 (bs, 1H). Exact Mass: Calcd, 492.01. Found, 491.19.

Example B(86)

6-Cyclopentyl-6-[2-(2,4-dimethoxy-phenyl)-ethyl]-4-hydroxy-3-[2-(3-methyl-isoxazol-5-yl)-acetyl]-5,6-dihydro-pyran-2-one

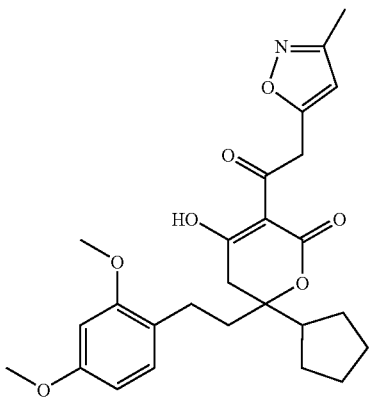

To a solution of 6-cyclopentyl-6-[2-(2,4-dimethoxy-phenyl)-ethyl]-dihydro-pyran-2,4-dione (52 mg, 0.15 mmol) from Step 2 below, triethylamine (0.075 mL, 0.68 mmol) and (3-Methyl-isoxazol-5-yl)-acetic acid (0.027 g, 0.196 mmol) in CH₂Cl₂ (1.5 mL) were added DMAP (1 mg), and EDC (37 mg, 0.196 mmol). The reaction was stirred at room temperature for 18 hours, and then diluted with CH₂Cl₂. The organic was washed with water, and the layers were separated. The organic layer was dried under vacuum, and then purified by preparatory HPLC to give the desired compound (26.2 mg, 37% yield).

¹H NMR (CDCl₃) δ: 1.47–1.75 (m, 8H), 1.85–1.91 (m, 2H), 2.21 (s, 3H), 2.26–2.32 (m, 1H), 2.48–2.53 (m, 2H), 2.71 (d, J=18.09 Hz, 1H), 2.86 (d, J=18.09 Hz, 1H), 3.69 (s, 3H), 3.71 (s, 3H), 4.40–4.57 (m, 2H), 6.00 (s, 1H), 6.31–6.36 (m, 2H), 6.91 (d, J=7.91 Hz, 1H).

Step 1

3-[2-(2,4-dimethoxyphenyl)ethyl]-1-cyclopentylpropan-1-one

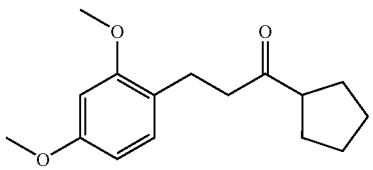

A solution of 2,4-dimethoxybenzaldehyde (10.27 g, 45 mmol) and methyl cyclopentyl ketone (6.06 g, 54 mmol) in anhydrous ethanol (81 mL) was treated with 5 M NaOH (aq) (18 mL, 90 mmol) and the mixture stirred at room temperature for 18 h. The volatiles were removed in vacuo. The residue was extracted with ether (100 mL) and the extract washed with water (3×60 mL), then with brine. The ethereal solution was dried over MgSO₄, filtered, and concentrated in vacuo, affording the intermediate chalcone in a crude yield of 14.63 g. The crude intermediate (14.52 g) was dissolved in 110 mL ethyl acetate, treated with platinum oxide (5 mole %) and stirred over 1 atm of H₂ at room temperature overnight. The Pt was filtered through a fine fritted funnel and the black residue washed with ethyl acetate. The filtrate was concentrated in vacuo to give a yellowish resin. The resin was chromatographed using silica gel and 6:1 hexanes/ethyl acetate, yielding 6.02 g (41%) of the ketone as a colorless oil.

¹H NMR (CDCl₃): δ 1.48–1.81 (m, 8H), 2.67 (m, 2H), 2.80 (m, 3H), 3.76 (s, 3H), 3.75 (s, 3H), 6.37 (dd, 1H, J=8.1, 2.1 Hz), 6.41 (d, 1H, J=2.1 Hz), 7.00 (d, 1H, J=8.1 Hz). MS(APCI) calcd for C₁₆H₂₂O₃: 262.2. found (M+H⁺): 263.1.

Step 2

6-[2-(2,4-dimethoxyphenyl)ethyl]-6-cyclopentyldihydro-2H-pyran-2,4(3H)-dione

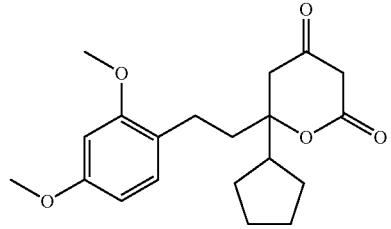

Methylacetoacetate (1.63 mL, 15.1 mmol) was dissolved in dry THF (42 mL) and cooled to 0° C. NaH (60% in mineral oil, 0.604 g, 15.1 mmol) were carefully added and the reaction mixture was stirred for 20 min. A solution of BuLi in hexanes (1.6 M, 9.44 mL, 15.1 mmol) was added dropwise and the resulting mixture was stirred an additional 20 min. A solution of 3-(2,4-dimethoxyphenyl)-1-cyclopentylpropan-1-one (2.33 g, 7.55 mmol) from Step 1 above in THF (37 mL) was added dropwise. After stirring 1 h, the reaction mixture was quenched with saturated aq NH₄Cl (100 mL) and extracted with Et₂O (600 mL). The organic phase was dried over MgSO₄ and evaporated. The residue was then stirred overnight in a mixture of 0.1 M NaOH (370 mL) and THF (37 mL). After the addition of an aq solution of 10% aq KHSO₄ (50 mL) the resulting mixture was stirred 30 min and then extracted with Et₂O (600 mL). The organic phase was washed with brine, dried over MgSO₄ and evaporated. The residue was purified by flash column chromatography (50% EtOAc in hexanes) to give the product (1.54 g, 52%) as a white foam.

¹H NMR (CDCl₃) δ 1.43 (m, 2H), 1.78 (m, 8H), 2.33 (m, 1H), 2.58 (m, 2H), 2.78 (s, 2H), 3.43 (s, 2H), 3.78 (s, 6H), 6.37 (s, 1H), 6.47 (s, 1H), 6.93 (d, 1H, J=7.93 Hz). MS (APCI) calcd for C₂₀H₂₆O₅: 346.2. found (M+1): 347.0.

Example B(87)

6-[2-(3-Chloro-4-methoxy-phenyl)-ethyl]-6-cyclopentyl-4-hydroxy-3-(2-pyridin-2-yl-acetyl)-5,6-dihydro-pyran-2-one

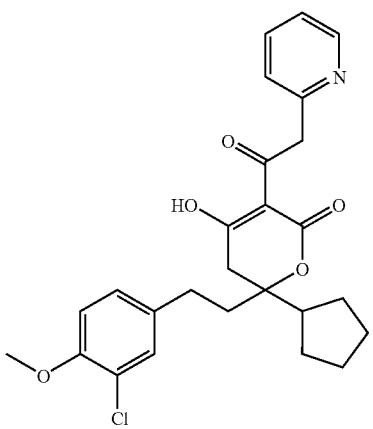

The target compound was synthesized analogously to Example B(86), substituting pyridin-2-yl-acetic acid (22 mg, 0.16 mmol) in place of (3-methyl-isoxazol-5-yl)-acetic acid and 6-[2-(3-Chloro-4-methoxy-phenyl)-ethyl]-6-cyclopentyl-dihydro-pyran-2,4-dione (63 mg, 0.123 mmol) from Step 2 below in place of 6-cyclopentyl-6-[2-(2,4-dimethoxyphenyl)-ethyl]-dihydro-pyran-2,4-dione. Yield=32 mg, 55% yield.

$^1$HNMR(CDCl$_3$)δ: 1.41–1.74 (m, 8H), 1.92–1.98 (m, 2H), 2.40 (p, J=8.00 Hz, 1H), 2.56–2.62 (m, 2H), 2.69 (d, J=17.27 Hz, 1H), 2.87 (d, J=17.27 Hz, 1H), 3.88 (s, 3H), 4.40 (s, 2H), 6.84 (d, J=8.32 Hz, 1H), 6.96 (d, J=8.32 Hz, 1H), 7.12 (s, 1H), 7.27 (s, 1H), 7.67 (d, J=6.72 Hz, 1H), 8.51 (d, J=4.80 Hz, 1H), 8.58 (s, 1H).

Step 1

3-(3-Chloro-4-methoxy-phenyl)-1-cyclopentyl-propan-1-one

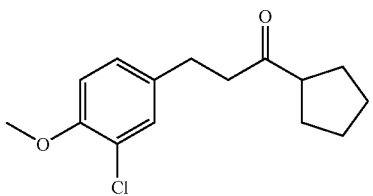

To a magnetically stirring solution of 4-bromo-2-chloroanisole (0.50 g, 2.61 mmol) and 1-Cyclopentyl-2-propen-1-ol (1.5 eq, 0.49 g, 3.88 mmol) in anhydrous N-methylpyrrolidinone (3.0 mL), under argon at room temperature, was added sodium bicarbonate (1.2 eq, 0.26 g, 3.10 mmol) followed by dichlorobis (triphenylphosphine) palladium (II) (0.02 eq, 36.7 mg, 0.05 mmol). The resulting mixture was heated to 140° C. in an oil bath and maintained for 4 hours. The resulting dark reaction mixture was cooled to room temperature and poured into water (50 mL) and extracted with EtOAc (2×25 mL). The organics were washed with water (50 mL) and brine (50 mL) then dried over Na$_2$SO$_4$, filtered and concentrated. The crude residue was purified by flash chromatography (1% through 10% EtOAc in Hexanes) to yield the intermediate ketone as a slightly yellow oil (0.49 g, 79%).

Step 2

6-[2-(3-Chloro-4-methoxy-phenyl)-ethyl]-6-cyclopentyl-dihydro-pyran-2,4-dione

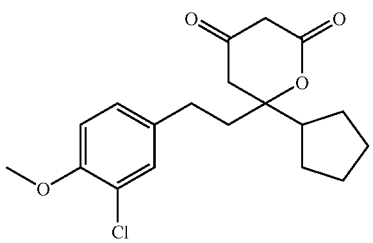

The title compound was prepared analogously to Example B(86), Step 2 substituting 3-(3-chloro-4-methoxy-phenyl)-1-cyclopentyl-propan-1-one from Step 1 above in place of 3-(2,4-dimethoxyphenyl)-1-cyclopentylpropan-1-one.

$^1$H NMR (CDCl$_3$): δ 1.41–1.86 (brm, 8H), 1.96 (m, 2H), 2.29 (t, J=7.6 Hz, 1H), 2.61 (t, J=8.6 Hz, 2H), 2.81 (s, 2H), 3.40 (s, 2H), 3.89, (s, 3H), 6.45 (d, J=8.5 Hz, 1H), 7.0 (d, J=8.5 Hz, 1H), 7.15 (brs, 1H). ESIMS (MH+): 351.8.

Example B(88)

3-Acetyl-6-[2-(3-chloro-4-methoxy-phenyl)-ethyl]-6-cyclopentyl-4-hydroxy-5,6-dihydro-pyran-2-one

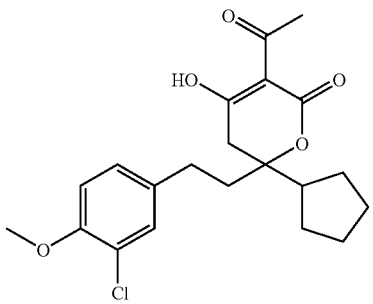

The target compound was synthesized analogously to Example B(87), substituting acetic acid (0.009 mL, 0.155 mmol) in place of pyridin-2-yl-acetic acid. Yield=18.4 mg, 38% yield, $^1$H NMR (CDCl$_3$) δ: 1.57–1.77 (m, 8H), 1.94–2.00 (m, 2H), 2.35 (p, J=8.64 Hz, 1H), 2.59–2.64 (m, 5H), 2.68–2.90 (m, 2H), 3.87 (s, 3H), 6.84 (d, J=8.32 Hz, 1H), 7.00 (d, J=8.64 Hz, 1H), 7.16 (s, 1H).

Example B(89)

7-[(6-Cyclopentyl-6-{2-[4-(difluoromethyl)-3-fluorophenyl]ethyl}-4-hydroxy-2-oxo-5,6-dihydro-2H-pyran-3-yl)methyl]-3-methyl-5H-[1,3]thiazolo[3,2-a]pyrimidin-5-one

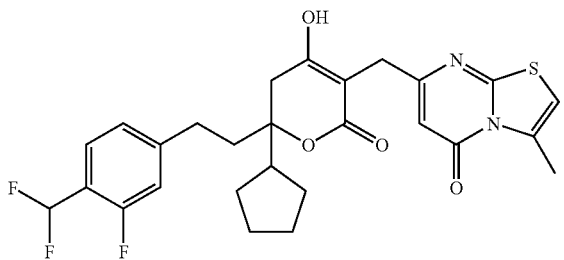

The title compound was prepared as described in Example B(54) where 6-Cyclopentyl-6-{2-[4-(difluoromethyl)-3-fluorophenyl]ethyl}-dihydro-2H-pyran-2,4(3H)-dione (described in Step 3 of Example B(69)) was used in place of 6-[2-(5-Chloro-2,4-dimethoxyphenyl)ethyl]-6-cyclopentyldihydro-2H-pyran-2,4(3H)-dione and 7-(Chloromethyl)-3-methyl-5H-[1,3]thiazolo[3,2-a]pyrimidin-5-one (prepared according to a reported procedure: Doria, G.; Passarotti, C.; Sala, R.; Magrini, R.; Sberze, P.; Tibolla, M.; Cesarani, R.; Arcari, G.; Castello, R.; Toti, D. *Farmaco Ed. Sci.* 1985, 40, 885) was used in place of 6-Hydroxy-8-mercaptopurine monohydrate.

$^1$H NMR (300 MHz, DMSO-D6) δ 1.55 (m, 8 H) 1.94 (m, 2 H) 2.33 (m, 1 H) 2.44 (d, J=1.7 Hz, 2 H) 2.58 (s, 3 H,) 2.58 (1 H buried under singlet) 2.71 (d, J=18.0 Hz, 1 H) 3.38 (dd, J=15.0, 6.0 Hz, 2 H) 5.77 (s, 1 H) 6.90 (m, 1 H) 7.10 (m, 3 H) 7.27 (s, 1 H) 7.44 (t, J=7.74 Hz, 1 H). MS (APCI) calcd for $C_{27}H_{27}F_3N_2O_4S$: 532.16. found (M+H$^+$) 533.0.

Example B(90)

6-[2-(5-chloro-2,4-dimethoxyphenyl)ethyl]-6-cyclopentyl-4-hydroxy-3-(imidazo[1,2-a]pyrimidin-2-ylmethyl)-5,6-dihydro-2H-pyran-2-one

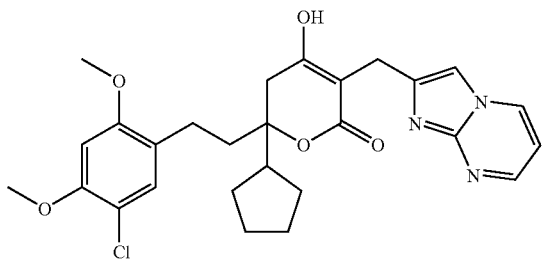

The title compound was prepared as described in Example B(54) where 2-(Chloromethyl)imidazo[1,2-a]pyrimidine (described below) was used in place of 6-Hydroxy-8-mercaptopurine monohydrate with the exception that it was purified on a Phenomenex Synergi 4u Hydro-RP 21.2 ID×150 mm column using a gradient of A: H2O/0.05% TFA, B: CAN/0.05% TFA. The gradient consisted of 5–40% of B for 6 minutes, then 40–70% of B for 9 minutes at a flow of 30 mL/min and collection of fractions using UV at 260 nm.

$^1$H NMR (300 MHz, DMSO-D$_6$) d 1.55 (m, 8 H) 1.79 (m, 2 H) 2.25 (m, 1 H) 2.43 (m, 2 H) 2.45 (1 H, overlapped with DMSO) 2.67 (d, J=17.56 Hz, 1 H) 3.60 (s, 2 H) 3.67 (s, 3 H) 3.77 (s, 3 H) 6.62 (s, 1 H) 6.93 (dd, J=6.80, 4.15 Hz, 1 H) 7.04 (s, 1 H) 7.44 (s, 1 H) 8.37 (dd, J=4.15, 1.89 Hz, 1 H) 8.77 (dd, J=6.80, 1.89 Hz, 1 H). MS (APCI) calcd for $C_{27}H_{30}ClN_3O_5$: 511.19. found (M+H$^+$) 512.0.

Step 1

2-(chloromethyl)imidazo[1,2-a]pyrimidine

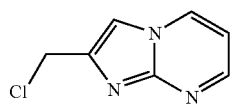

A solution of 2-Aminopyridine (19.02 g, 0.2 mol) in anhydrous DME (70 mL) was added to 1,3-dichloroacetone (25.39 g, 0.2 mol) to form a slurry in a 250-mL 3-necked round bottomed flask outfitted with a reflux condenser and a N$_2$ line. The mixture heated at 65° C. for 18 h, warmed to 80° C. for 3 h and allowed to cool back to room temperature over 2 h. The DME was removed in vacuo and H$_2$O was added to dissolve the resulting solid. Saturated NaHCO$_3$ was added to basify the solution to a pH to 8 and ethyl acetate was used to extract the product (3×300 mL). Both phases were stored in the freezer overnight. The organic phase was dried over Na$_2$SO$_4$, filtered and concentrated to give an orange solid. The aqueous layer was extracted again with ethyl acetate (2×200 mL), then CH$_2$Cl$_2$ (2×200 mL) and these organic layers were dried over Na$_2$SO$_4$, filtered and concentrated to an orange solid. The two solids were combined and dissolved in hot 5–10% MeOH in CH$_2$Cl$_2$, and allowed to cool. The resulting orange crystals were filtered and washed with cold CH$_2$Cl$_2$. A small amount of ether was added to the mother liquor and scratched and put in the freezer. The resulting solid was filtered cold and washed with cold ether. The two batches of solid were combined and dried in the vacuum oven to yield 4.93 g (14%) of the desired product.

$^1$H NMR (CDCl$_3$) d 4.78 (s, 2 H) 6.87 (dd, J=6.6 Hz, J=4.3 Hz, 1 H) 7.61 (s, 1 H) 8.45 (d, J=6.8 Hz 1 H) 8.53 (d, J=1.9 Hz, 1 H). MS (APCI) calcd for $C_7H_6ClN_3$: 167.60. found (M+H$^+$) 168.0.

Example B(91)

6 N-[4-(2-{2-cyclopentyl-5-[(5,7-dimethyl[1,2,4]triazolo[1,5-a]pyrimidin-2-yl)methyl]-4,6-dioxotetrahydro-2H-pyran-2-yl}ethyl)-2-ethylphenyl]-N-methylmethanesulfonamide

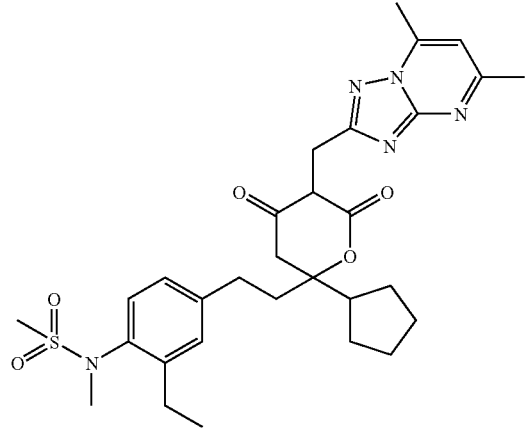

The title compound was prepared analogously to Example B(31), where {4-[2-(2-cyclopentyl-4,6-dioxotetrahydro-2H-pyran-2-yl)ethyl]-2-ethylphenyl}-N-methylmethanesulfonamide (described in Example A(87)) was substituted in place of 6-[2-(3-chloro-4-isopropoxyphenyl)ethyl]-6-cyclopentyldihydro-2H-pyran-2,4(3H)-dione in the final step of that example.

$^1$H NMR (CDCl$_3$): δ 1.20 (t, J=7.54 Hz, 3H), 1.40–1.80 (brm, 8H), 2.59 (m, 2H), 2.62 (m, 2H), 2.67 (m, 5H), 2.79 (m, 5H), 2.95 (m, 5H), 3.20 (m, 5H), 6.54 (d, J=2.07 Hz, 1H), 6.95 (s, 1H), 6.98 (d, J=2.07 Hz, 1H), 7.07 (m, 1H). Anal. Calcd. For $C_{30}H_{39}O_5N_5S$: C, 61.94; H, 6.75; N, 12.04. Found: C, 61.64; H, 6.46; N, 12.13.

Example B(92)

2-[4-(2-{2-cyclopentyl-4-hydroxy-5-[(1-methyl-1H-indol-5-yl)methyl]-6-oxo-3,6-dihydro-2H-pyran-2-yl}ethyl)-2-fluorophenyl]-2-methylpropanenitrile

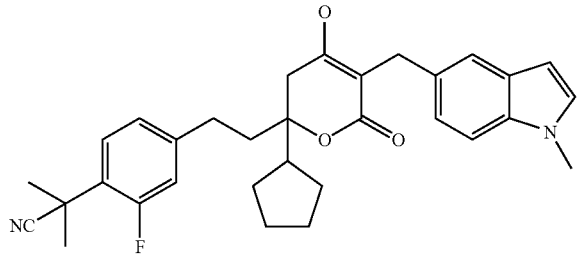

The title compound was prepared analogously to Example B(75), where 1-methyl-1H-indole-5-carbaldehyde was substituted in place of 5,7-Dimethyl-[1,2,4]triazolo[1,5-☐]pyrimidine-2-carbaldehyde in the final step of that example.

$^1$H NMR (DMSO-D$_6$, 300 MHz) δ (ppm): 1.20–1.60 (m, 8 H), 1.69 (s, 6 H), 1.80–1.89 (m, 2 H), 2.27–2.36 (m, 1 H), 2.45–2.55 (m, 1 H), 2.74–2.80 (m, 1 H), 3.32 (s, 2 H), 3.50–3.68 (m, 2 H), 3.73 (s, 3 H), 6.24 (d, J=3.01 Hz, 1 H), 6.78 (dd, J=8.10, 0.94 Hz, 1 H), 6.95–7.05 (m, 2 H), 7.16–7.26 (m, 3 H), 7.32 (s, 1 H). HRMS calcd for C$_{32}$H$_{36}$FN$_2$O$_3$ (M+H$^+$): 512.2705. Found: 512.2710.

Example B(93)

2-(4-{2-[2-cyclopentyl-4-hydroxy-6-oxo-5-(1H-pyrazol-4-ylmethyl)-3,6-dihydro-2H-pyran-2-yl]ethyl}-2-fluorophenyl)-2-methylpropanenitrile

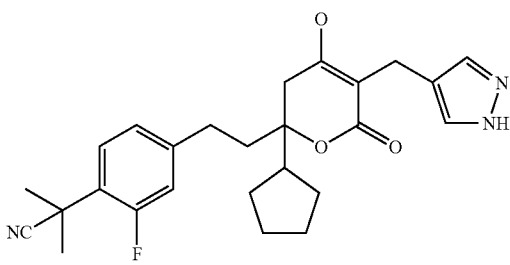

The title compound was prepared analogously to Example B(75), where 1H-pyrazole-4-carbaldehyde was substituted in place of 5,7-Dimethyl-[1,2,4]triazolo[1,5-☐]pyrimidine-2-carbaldehyde in the final step of that example.

$^1$H NMR (300 MHz, DMSO-D$_6$) δ (ppm) 1.25–1.65 (m, 8 H), 1.71 (s, 6 H), 1.85–1.91 (m, 2 H), 2.28–2.35 (m, 1 H), 2.54–2.60 (m, 3 H), 2.66–2.72 (m, 1 H), 3.29–3.34 (m, 2 H), 6.97 (d, J=8.10 Hz, 1 H), 7.08 (dd, J=13.19, 1.13 Hz, 1 H), 7.35 (m, 3 H). Anal. Calcd for C$_{26}$H$_{30}$N$_3$O$_3$F.0.5H$_2$O: C, 67.80; H, 6.79; N, 9.12. Found: C, 67.98; H, 6.63; N, 9.22.

Example B(94)

6-Cyclopentyl-3-(5,7-dimethyl-[1,2,4]triazolo[1,5-a]pyrimidin-2-ylmethyl)-4-hydroxy-6-[2-(4-hydroxy-3-isopropyl-phenyl)-ethyl]-5,6-dihydro-pyran-2-one

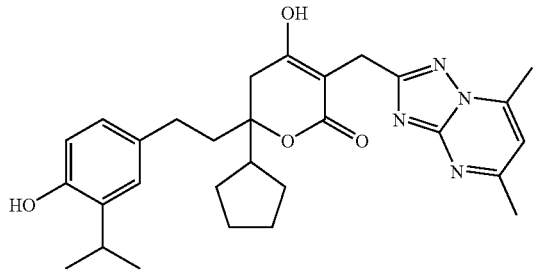

The title compound was prepared by coupling 6-Cyclopentyl-6-[2-(4-hydroxy-3-isopropyl-phenyl)-ethyl]-dihydro-pyran-2,4-dione (Example A(93): ) to 5,7-Dimethyl-[1,2,4]triazolo[1,5-☐]pyrimidine-2-carbaldehyde using the Me$_2$NHBH$_3$ method described in the synthesis of Example B(31).

$^1$H NMR (DMSO-d$_6$): d 1.23 (t, 6H, J=5.6 Hz), 1.45–1.87 (br m, 8H), 2.14 (m, 1H), 2.24 (m, 1H), 2.50–2.71 (m, 10H), 2.88 (d, 1H, J=17.0 Hz), 3.26 (m, 1H), 3.84 (d, 1H, J=16.0 Hz), 3.94 (d, 1H, J=16.0 Hz), 6.78 (d, 1H, J=8.1 Hz), 6.94 (d, 1H, J=8.1 Hz), 7.00 (s, 1H), 7.16 (s, 1H), 9.11 (s, 1H), 11.00 (br s, 1H). ESIMS: (M+H)$^+$505.25.

Example B(95)

6-[2-(3-Chloro-4-hydroxy-phenyl)-ethyl]-6-cyclopentyl-3-(5,7-dimethyl-[1,2,4]triazolo[1,5-a]pyrimidin-2-ylmethyl)-4-hydroxy-5,6-dihydro-pyran-2-one

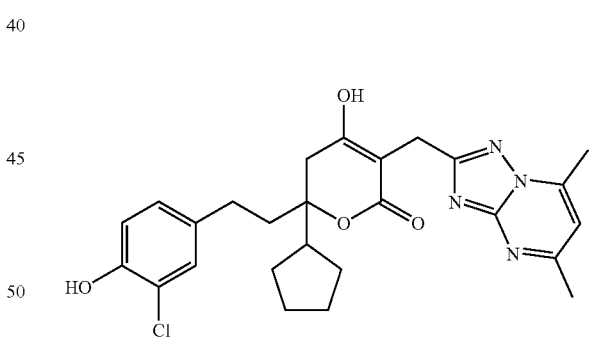

The title compound was prepared by coupling 6-[2-(3-Chloro-4-hydroxy-phenyl)-ethyl]-6-cyclopentyl-dihydropyran-2,4-dione (Example A(95))) to 5,7-Dimethyl-[1,2,4]triazolo[1,5-☐]pyrimidine-2-carbaldehyde using the Me$_2$NHBH$_3$ method described in the synthesis of Example B(31).

$^1$H NMR (DMSO-d$_6$): d 1.32–1.63 (br m, 8H), 2.02 (m, 2H), 2.34–2.50 (m, 10H), 2.72 (d, 1H, J=17.4 Hz), 3.65 (d, 1H, J=16.0 Hz), 3.76 (d, 1H, J=16.0 Hz), 6.81 (d, 1H, J=8.3 Hz), 6.96–6.99 (m, 2H), 7.07 (s, 1H), 9.82 (s, 1H), 10.85 (br s, 1H). Anal. Calcd. For C$_{26}$H$_{29}$N$_4$O$_4$Cl.0.2 H$_2$O: C, 62.38; H, 5.92; N, 11.19. Found: C, 62.35; H, 5.96; N, 10.98.

Example B(96)

6-Cyclopentyl-3-(5,7-dimethyl-[1,2,4]triazolo[1,5-a]pyrimidin-2-ylmethyl)-6-[2-(3-ethyl-4-methoxy-phenyl)-ethyl]-4-hydroxy-5,6-dihydro-pyran-2-one

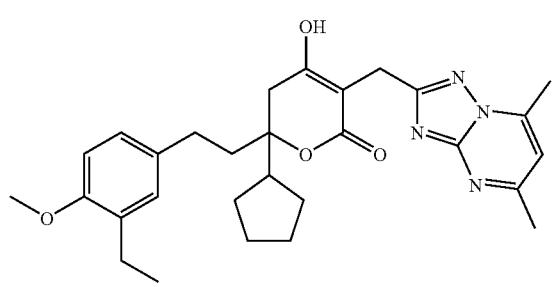

The title compound was prepared by coupling 6-Cyclopentyl-6-[2-(3-ethyl-4-methoxy-phenyl)-ethyl]-dihydro-pyran-2,4-dione (Example A(96)) to 5,7-Dimethyl-[1,2,4]triazolo[1,5-□]pyrimidine-2-carbaldehyde using the Me$_2$NHBH$_3$ method described in the synthesis of Example B(31).

$^1$H NMR (DMSO-d$_6$): d 1.06 (t, 3H, J=7.5 Hz), 1.40–1.70 (br m, 8H), 2.08 (m, 2H), 2.45–2.54 (m, 12H), 2.76 (d, 1H, J=17.0 Hz), 3.68–3.85 (m, 5H), 6.81 (d, 1H, J=8.3 Hz), 6.94 (s, 1H), 7.00–7.04 (m, 2H). ESIMS: (M+H)$^+$ 505.20.

Example B(97)

6-[2-(3-Chloro-5-ethyl-4-methoxy-phenyl)-ethyl]-6-cyclopentyl-3-(5,7-dimethyl-[1,2,4]triazolo[1,5-a]pyrimidin-2-ylmethyl)-4-hydroxy-5,6-dihydro-pyran-2-one

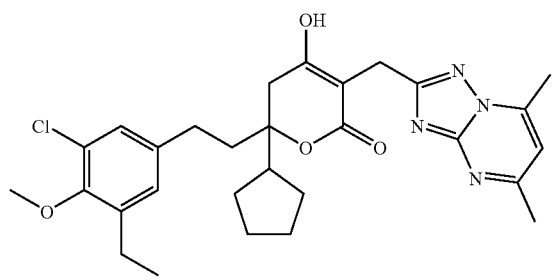

5,7-Dimethyl-[1,2,4]triazolo[1,5-a]pyrimidine-2-carbaldehyde (0.11 g, 0.63 mmol) was added to a solution of 6-[2-(3-Chloro-5-ethyl-4-methoxy-phenyl)-ethyl]-6-cyclopentyl-dihydro-pyran-2,4-dione (0.2 g, 0.53 mmol) in MeOH (5 mL). The reaction mixture was stirred for 15 mins and then treated with borane-dimethylamine complex (47 mg, 0.80 mmoL). After 15 hours the reaction mixture was quenched with 1N HCl and extracted with 10% MeOH in CH$_2$Cl$_2$. The combined organic layers were concentrated and purified by prep HPLC to give the product (50 mg, 17% yield). $^1$H NMR (400 MHz, DMSO-d$_6$): δ 0.98 (t, J=7.6 Hz, 3 H), 1.27–1.59 (br m, 8 H), 2.00 (m, 2 H), 2.33–2.49 (m, 12 H), 2.62 (d, J=17.0 Hz, 1 H), 3.59 (d, J=16.2 Hz, 1 H), 3.61 (s, 3 H), 3.69 (d, J=16.2 Hz, 1 H), 6.91 (s, 1 H), 6.92 (s, 1 H), 7.00 (s, 1 H). MS: C$_{29}$H$_{36}$N$_4$O$_4$Cl (M+H$^+$) 539.15.

Step 4

Preparation of Compound 6-[2-(3-Chloro-5-ethyl-4-methoxy-phenyl)-ethyl]-6-cyclopentyl-dihydro-pyran-2,4-dione

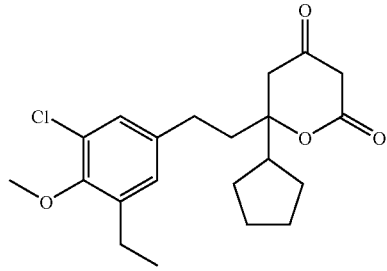

Methyl acetoacetate (1.11 mL, 10.2 mmol) was added to a cooled 0° C. suspension of NaH (0.4 g, 10.2 mmol, 60% dispersion in mineral oil) in THF (15 ml). After 30 min n-BuLi (4.08 mL, 10.2 mmol, 2.5M in hexanes) was added. The resulting dianion was stirred for an additional 30 min and then treated with a solution of 3-(3-Chloro-5-ethyl-4-methoxy-phenyl)-1-cyclopentyl-propan-1-one (1.0 g, 3.4 mmol) in THF (3 ml). After stirring for 4 h at 0° C., the reaction mixture was quenched with 1N HCl and extracted with EtOAc. The organic layers were washed with brine, dried over Na$_2$SO$_4$ and concentrated to a yellow oil that was used without further purification.

The oil was dissolved in methanol (10 mL), treated with potassium carbonate (1.4 g, 10.2 mmol), and refluxed under N$_2$ for 90 min. The reaction mixture was partitioned between 1N HCl and EtOAc. The organic layers were washed with brine, dried over Na$_2$SO$_4$ and concentrated to a yellow oil that was purified by silica gel chromatography (0% to 30% EtOAc in hexanes) to give the title compound as a gum (0.25 g, 20% yield). $^1$H NMR (400 MHz, CDCl$_3$) δ: 1.21 (t, J=7.6 Hz, 3 H) 1.42–1.78 (m, 8 H), 1.92 (m, 2 H), 2.27 (m, 1 H), 2.57–2.69 (m, 4 H), 2.76 (m, 2 H), 3.43 (s, 2 H), 3.81 (s, 3 H), 6.85 (s, 1 H), 6.99 (s, 1 H).

Step 3

Preparation of Compound 3-(3-Chloro-5-ethyl-4-methoxy-phenyl)-1-cyclopentyl-propan-1-one

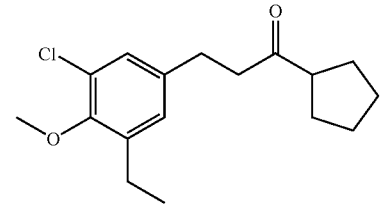

A mixture of 5-bromo-1-chloro-3-ethyl-2-methoxy-benzene (2 g, 8 mmol), 1-Cyclopentyl-2-propen-1-ol (1.3 g, 10.4 mmol), dichlorobis(triphenylphosphine) palladium (II) (110 mg, 0.16 mmol), and sodium bicarbonate (0.81 g, 9.6 mmol) in N-methylpyrrolidinone (15 mL) was heated to 140° C. under N$_2$ for 5 h. The reaction mixture was partitioned between 1N HCl and EtOAc. The organic layer was washed with saturated NaHCO$_3$, brine, dried over Na$_2$SO$_4$ and concentrated to black oil. The oil was purified by flash column chromatography (0% to 10% EtOAc in hexanes) to give the desired product (1.9 g, 82%). $^1$H NMR (400 MHz, CDCl$_3$): δ 1.20 (t, J=7.6 Hz, 3 H), 1.53–1.81 (m, 8 H), 2.65 (q, J=7.6 Hz, 2 H), 2.74 (m, 2 H), 2.79–2.87 (m, 3 H), 3.81 (s, 3 H), 6.90 (s, 1 H), 7.03 (m, 1 H).

Step 2

Preparation of Compound
5-Bromo-1-chloro-3-ethyl-2-methoxy-benzene

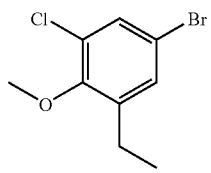

Potassium carbonate (3.9 g, 28 mmol) followed by methyl iodide (0.58 mL, 9.3 mmol) were added to a solution of 4-bromo-2-chloro-6-ethyl-phenol (2.2 g, 9.3 mmol) in DMF (10 mL). The mixture was stirred for 20 hours and then partitioned between 1N HCl and EtOAc. The organic layers were washed with saturated NaHCO$_3$, brine, dried over Na$_2$SO$_4$ and concentrated. The crude yellow oil was purified by flash column chromatography (0% to 3% EtOAc in hexanes) to give the desired product (21 g, 91%) $^1$H NMR (400 MHz, CDCl$_3$): δ 1.22 (t, J=7.6 Hz, 3 H), 2.66 (q, J=7.6 Hz, 2 H), 3.82 (s, 3 H), 7.22 (s, 1 H), 7.37 (s, 1 H).

Step 1

Preparation of Compound
4-Bromo-2-chloro-6-ethyl-phenol

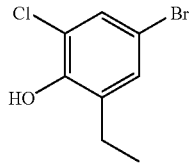

Sodium hydroxide (1.2 g, 30 mmol) and hydrazine monohydrate (1.75 mL, 36 mmol) were added to a solution of 5'-bromo-3'-chloro-2'-hydroxyacetophenone (3 g, 12 mmol) dissolved in triethylene glycol (15 mL). The reaction mixture was heated to 160° C. for 72 hours and then partitioned between 1N HCl and EtOAc. The organic layer was washed with saturated NaHCO$_3$, brine, dried over Na$_2$SO$_4$ and concentrated. The residue was purified by flash silica gel chromatography (0% to 10% EtOAc in hexanes) to give the title compound (2.34 g, 83%). $^1$H NMR (400 MHz, CDCl$_3$): δ 1.22 (t, J=7.6 Hz, 3 H), 2.65 (q, J=7.6 Hz, 2 H), 5.55 (s, 1 H), 7.17 (s, 1 H), 7.31 (s, 1 H).

Example B(98)

6-Cyclopentyl-3-(5,7-dimethyl-[1,2,4]triazolo[1,5-a]
pyrimidin-2-ylmethyl)-6-[2-(5-ethyl-2-methoxy-
phenyl)-ethyl]-4-hydroxy-5,6-dihydro-pyran-2-one

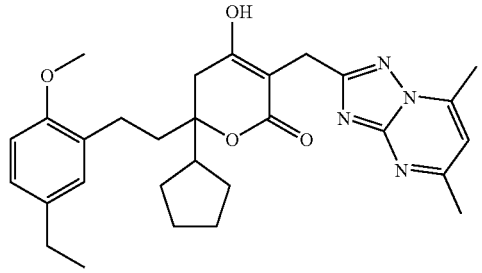

The title compound was prepared analogously to Example B(97), where 2-bromo-4-ethyl-phenol (from step 1 below) was substituted in place of 4-Bromo-2-chloro-6-ethyl-phenol in that example. $^1$H NMR (400 MHz, DMSO-d$_6$) δ: 1.16 (t, J=7.58 Hz, 3 H), 1.46–1.77(m, 8 H), 2.00 (m, 1H), 2.16 (m, 1 H), 2.45–2.63 (m, 12 H), 2.80 (d, J=17.2 Hz, 1 H), 3.71 (s, 3 H), 3.76 (d, J=16.2 Hz, 1 H), 3.86 (d, J=16.4 Hz, 1 H), 6.85 (d, J=8.3 Hz, 1 H), 6.99 (s, 1 H), 7.03 (d, J=8.3 Hz, 1 H), 7.08 (s, 1 H). MS: C$_{29}$H$_{37}$N$_4$O$_4$ (M+H$^+$) 505.25.

Step 1

Preparation of Compound 2-Bromo-4-ethyl-phenol

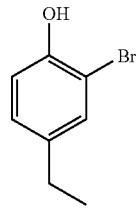

Bromine (11.6 mL, 0.23 mol) was added slowly to a cooled 0° C. of 4-ethylphenol (2 g, 0.21 mol) dissolved in CH$_2$Cl$_2$ (125 mL). After the addition was complete the reaction mixture was stirred for 5 mins and then quenched with 1N NaOH. The reaction mixture was diluted with H$_2$O and the layers separated. The organic layer was concentrated to an orange oil. Purification by flash column chromatography (0% to 5% EtOAc in hexanes) gave the title compound as a clear oil (4 g, 98%). $^1$H NMR (400 MHz, CDCl$_3$): δ 1.20 (t, J=7.6 Hz, 3 H), 2.58 (q, J=7.5 Hz, 2 H), 5.36 (s, 1 H), 6.93 (d, J=8.3 Hz, 1 H), 7.03 (d, J=8.3 Hz, 1 H), 7.28 (s, 1 H).

Example B(99)

6-Cyclopentyl-3-(5,7-dimethyl-[1,2,4]triazolo[1,5-a]
pyrimidin-2-ylmethyl)-6-[2-(4-ethoxy-3-ethyl-phe-
nyl)-ethyl]-4-hydroxy-5,6-dihydro-pyran-2-one

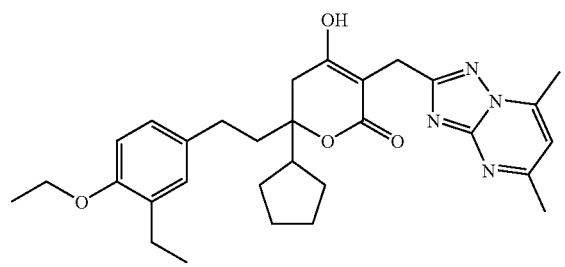

The title compound was prepared analogously to Example B(97), where 4-Bromo-1-ethoxy-2-ethyl-benzene (from step 2 below) was substituted in place of 5-Bromo-1-chloro-3-ethyl-2-methoxy-benzene in that example. $^1$H NMR (400 MHz, DMSO-d$_6$): δ 0.90 (t, J=7.3 Hz, 3 H), 1.16 (t, J=7.1 Hz, 3 H), 1.23–1.53 (br m, 8 H), 1.92 (m, 2 H), 2.22–2.42 (m, 12 H), 2.64 (d, J=17.4 Hz, 1 H), 3.56 (d, J=16.2 Hz, 1 H), 3.66 (d, J=16.2 Hz, 1 H), 3.82 (d, J=7.3 Hz, 2 H), 6.63 (d, J=8.3 Hz, 1 H), 6.77 (s, 1 H), 6.82 (d, J=8.3 Hz, 1 H), 6.88 (s, 1 H), 10.67 (s, 1H). Anal. Calcd. For C$_{30}$H$_{38}$N$_4$O$_4$: C, 68.63; H, 7.30; N, 10.67. Found: C, 68.73; H, 7.22; N, 10.60.

Step 2

Preparation of Compound
4-Bromo-1-ethoxy-2-ethyl-benzene

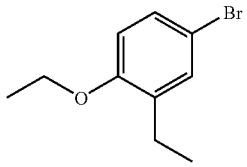

Potassium carbonate (3.3 g, 23.6 mmol) followed by iodoethane (0.63 mL, 7.9 mmol) were added to a solution of 4-bromo-2-ethyl-phenol (1.6 g, 7.9 mmol) in DMF (10 mL). The mixture was stirred for 20 hours and then partitioned between 1N HCl and EtOAc. The organic layers were washed with saturated NaHCO$_3$, brine, dried over Na$_2$SO$_4$ and concentrated. The crude yellow oil was purified by flash column chromatography (hexanes) to give the desired product (1.3 g, 72%).

$^1$H NMR (400 MHz, CDCl$_3$): δ 1.18 (t, J=7.3 Hz, 3 H), 1.41 (t, J=7.1 Hz, 3 H), 2.60 (q, J=7.6 Hz, 2 H), 3.99 (q, J=7.1 Hz, 2 H), 6.68 (d, J=8.1 Hz, 1 H), 7.24 (m, 2 H).

Step 1

Preparation of Compound 4-Bromo-2-ethyl-phenol

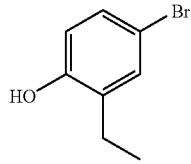

A solution of tetrabutyl ammonium tribromide (19.7 g, 41 mmol) in CHCl$_3$ (100 mL) was added to a stirred solution of 2-ethylphenol (5 g, 41 mmol) dissolved in CHCl$_3$ (150 mL). The reaction mixture was stirred for 2 hrs and then quenched with 5% solution of sodium thiosulfate (150 mL). The biphasic mixture was stirred for 30 mins and then the layers were separated. The organic layer was washed with 1N HCl, saturated NaHCO$_3$, brine, dried over Na$_2$SO$_4$ and concentrated. The crude residue was purified by flash column chromatography (0–10% EtOAc in hexanes) to give the desired product (8.1 g, 98%). $^1$H NMR (400 MHz, CDCl$_3$): δ 1.22 (t, J=7.5 Hz, 3H), 2.60 (q, J=7.5 Hz, 2 H), 6.64 (d, J=8.5 Hz, 1 H), 7.17 (dd, J=8.5, 2.5 Hz, 1 H), 7.24 (d, J=2.5 Hz, 1 H).

Example B(100)

6-[2-(3-Chloro-5-ethyl-4-hydroxy-phenyl)-ethyl]-6-cyclopentyl-3-(5,7-dimethyl-[1,2,4]triazolo[1,5-a]pyrimidin-2-ylmethyl)-4-hydroxy-5,6-dihydro-pyran-2-one

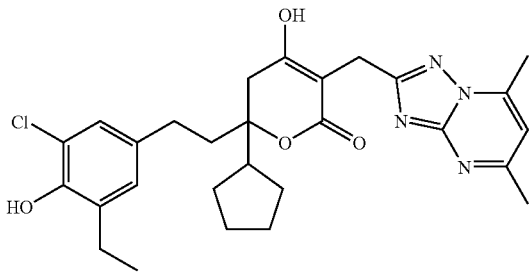

The title compound was prepared analogously to Example B(97), where 6-[2-(3-Chloro-5-ethyl-4-hydroxy-phenyl)-ethyl]-6-cyclopentyl-dihydro-pyran-2,4-dione (Example 8) was substituted in place of 6-[2-(3-Chloro-5-ethyl-4-methoxy-phenyl)-ethyl]-6-cyclopentyl-dihydro-pyran-2,4-dione.

$^1$H NMR (400 MHz, DMSO-d$_6$) δ: 1.12 (t, J=7.3 Hz, 3 H), 1.46–1.75(m, 8 H), 2.14 (m, 2 H), 2.44–2.64 (m, 12 H), 2.83 (d, J=17.4 Hz, 1 H), 3.78 (d, J=16.2 Hz, 1 H), 3.88 (d, J=16.2 Hz, 1 H), 6.94 (s, 1 H), 7.05 (s, 1 H), 7.10 (s, 1 H), 6.86 (s, 1 H), 10.90 (s, 1 H). Anal. Calcd. For C$_{28}$H$_{33}$N$_4$O$_4$Cl.H$_2$O: C, 61.93; H, 6.50; N, 10.32. Found: C, 62.02; H, 6.29; N, 10.13.

Example B(101)

6-[2-(3-Chloro-5-ethyl-4-hydroxy-phenyl)-ethyl]-6-cyclopentyl-dihydro-pyran-2,4-dione

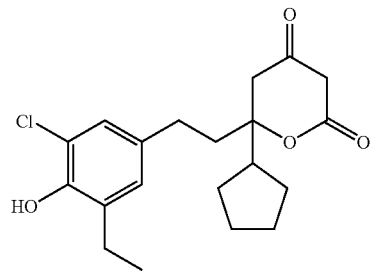

Trifluoroacetic acid (0.07 mL, 0.88 mmol) was added to a solution of 6-{2-[3-Chloro-5-ethyl-4-(2-methoxy-ethoxymethoxy)-phenyl]-ethyl}-6-cyclopentyl-dihydro-pyran-2,4-dione (0.2 g, 0.44 mmol) dissolved in CH$_2$Cl$_2$ (4 mL). The reaction mixture was stirred for 2 hours at room temperature and then partitioned between H$_2$O and EtOAc. The organic extracts were washed with brine, dried over Na$_2$SO$_4$ and concentrated to an oil. The oil was purified by flash column chromatography (0% to 30% EtOAc in hexanes) to give the title compound as a solid. (0.12 g, 75%). $^1$H NMR (400 MHz, CDCl$_3$): δ 1.21 (t, J=7.6 Hz, 3 H), 1.58–173 (br m, 8 H), 1.92 (m, 2 H), 2.26 (m, 1 H), 2.57 (m, 2 H), 2.65 (q, J=7.6 Hz, 2 H), 2.76 (s, 2 H), 3.43 (s, 2 H), 5.47 (s, 1 H), 6.81 (s, 1 H), 6.95 (s, 1 H). MS: C$_{20}$H$_{24}$O$_4$Cl (M−H) 363.10.

Step 2

Preparation of Compound 6-{2-[3-Chloro-5-ethyl-4-(2-methoxy-ethoxymethoxy)-phenyl]-ethyl}-6-cyclopentyl-dihydro-pyran-2,4-dione

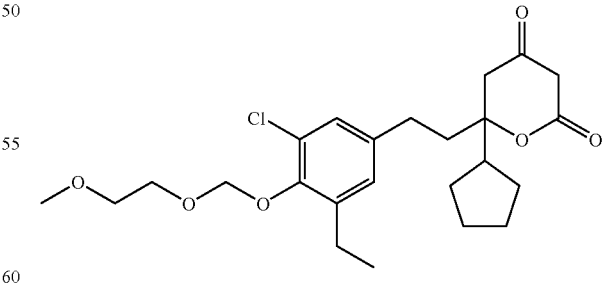

The title compound was prepared analogously to Example B(97) where 5-bromo-1-chloro-3-ethyl-2-(2-methoxy-ethoxymethoxy)-benzene (from step 1 below) was substituted in place of 5-bromo-1-chloro-3-ethyl-2-methoxy-benzene in that example. $^1$H NMR (400 MHz, CDCl$_3$): δ 1.21 (t, J=7.6 Hz, 3 H), 1.32–180 (br m, 8 H), 1.92 (m, 2 H), 2.26

(m, 1 H), 2.59 (m, 2 H), 2.69 (q, J=7.6 Hz, 2 H), 2.76 (s, 2 H), 3.40 (s, 3 H), 3.43 (s, 2 H), 3.61 (m, 2 H), 3.98 (m, 2 H), 5.14 (s, 2 H), 6.86 (s, 1 H), 7.00 (s, 1 H).

Step 1

Preparation of Compound 5-Bromo-1-chloro-3-ethyl-2-(2-methoxy-ethoxymethoxy)-benzene

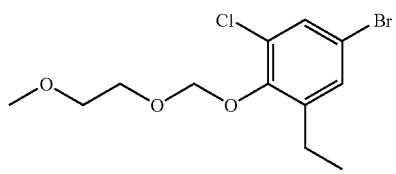

A solution of 4-Bromo-2-chloro-6-ethyl-phenol dissolved in THF (10 mL) was added to a cooled 0° C. suspension of NaH (0.43 g, 10.8 mmol, 60% dispersion in mineral oil) in THF (20 ml). After the addition was complete the reaction mixture was warmed up to room temperature and stirred for 30 mins. 2-Methoxyethoxymethyl chloride (1.34 mL, 11.7 mmol) was added and the reaction was stirred for 15 hours. The reaction mixture was quenched with 1N HCl and extracted with EtOAc. The organic layers were washed with brine, dried over $Na_2SO_4$ and concentrated to a yellow oil. Purification by flash column chromatography (0% to 10% EtOAc in hexanes) gave the title compound as a clear oil (2.4 g, 76%). $^1$H NMR (400 MHz, CDCl$_3$): δ 1.21 (t, J=7.3 Hz, 3 H), 2.70 (q, J=7.6 Hz, 2 H), 3.40 (s, 3 H), 3.61 (m, 2 H), 3.98 (m, 2 H), 5.15 (s, 2 H), 7.24 (s, 1 H), 7.37 (s, 1 H).

Example B(102)

6-Cyclopentyl-3-(5,7-dimethyl-[1,2,4]triazolo[1,5-a]pyrimidin-2-ylmethyl)-6-[2-(3-ethyl-4-isopropoxy-phenyl)-ethyl]-4-hydroxy-5,6-dihydro-pyran-2-one

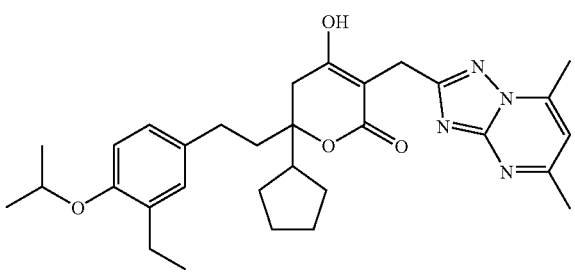

The title compound was prepared analogously to Example B(97) where 4-Bromo-2-ethyl-1-isopropoxy-benzene (from step 1 below) was substituted in place of 5-Bromo-1-chloro-3-ethyl-2-methoxy-benzene of that example. $^1$H NMR (400 MHz, DMSO-d$_6$) δ: 1.00 (t, J=7.6 Hz, 3 H), 1.20 (d, J=6.1 Hz, 6 H), 1.34–1.63(m, 8 H), 2.03 (m, 2 H), 2.40–2.51 (m, 12 H), 2.72 (d, J=17.7 Hz, 1 H), 3.66 (d, J=16.2 Hz, 1 H), 3.77 (d, J=16.2 Hz, 1 H), 4.46 (m, 1 H), 6.76 (d, J=8.3 Hz, 1 H) 6.88 (s, 1 H), 6.92 (d J=8.1 Hz, 1 H), 6.99 (s, 1 H), 10.81 (s, 1 H). MS: $C_{31}H_{40}N_4O_4$ (M+H$^+$) 533.30.

Step 1

Preparation of Compound 4-Bromo-2-ethyl-1-isopropoxy-benzene

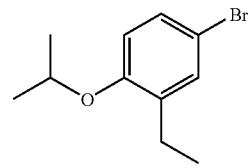

Potassium carbonate (3.1 g, 22.4 mmol) followed by 2-iodopropane (0.75 mL, 7.5 mmol) were added to a solution of 4-bromo-2-ethyl-phenol (1.5 g, 7.5 mmol) in DMF (10 mL). The mixture was heated at 60° C. for 20 hours and then partitioned between 1N HCl and EtOAc. The organic layers were washed with saturated NaHCO$_3$, brine, dried over Na$_2$SO$_4$ and concentrated. The crude yellow oil was purified by flash column chromatography (hexanes) to give the desired product (1.35 g, 75%). $^1$H NMR (400 MHz, CDCl$_3$): δ 1.16 (t, J=7.6 Hz, 3 H), 1.32 (d, J=6.1 Hz, 6 H), 2.58 (q, J=7.6 Hz, 2 H), 4.49 (m, 1 H), 6.70 (d, J=8.6 Hz, 1 H), 7.23 (m, 2 H).

Example B(103)

6-Cyclopentyl-3-(5,7-dimethyl-[1,2,4]triazolo[1,5-a]pyrimidin-2-ylmethyl)-6-[2-(2-fluoro-4-methoxy-phenyl)-ethyl]-4-hydroxy-5,6-dihydro-pyran-2-one

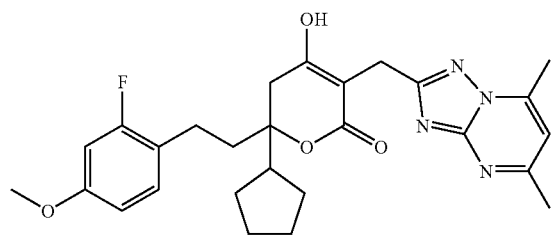

The title compound was prepared analogously to Example B(97) where 1-Cyclopentyl-3-(2-fluoro-4-methoxy-phenyl)-propan-1-one was substituted in place of 3-(3-chloro-5-ethyl-4-methoxy-phenyl)-1-cyclopentyl-propan-1-one in that example. $^1$H NMR (400 MHz, DMSO-d$_6$) δ: 1.16–1.54 (m, 8 H), 1.83 (m, 2 H), 2.20–2.35 (m, 10 H), 2.56 (d, J=17.4 Hz, 1 H), 3.49 (d, J=16.2 Hz, 1 H), 3.51 (s, 3 H), 3.59 (d, J=16.2 Hz, 1 H), 6.82 (m, 2 H), 6.82 (s, 1 H), 7.03 (t, J=8.6 Hz, 1 H), 10.81 (s, 1 H). Anal. Calcd. For $C_{27}H_{31}N_4O_4F$: C, 65.57; H, 6.32; N, 11.33. Found: C, 65.53; H, 6.34; N, 11.34.

Step 2

Preparation of Compound 1-Cyclopentyl-3-(2-fluoro-4-methoxy-phenyl)-propan-1-one

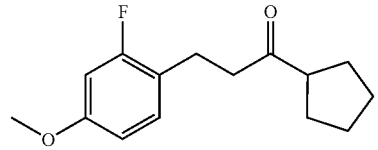

Ba(OH)$_2$ (0.2 g, 1.2 mmol) was added to a solution of 2-fluoro-4-methoxy benzaldehyde (0.91 g, 5.9 mmol) and 1-Cyclopentyl-ethanone (1 g, 8.9 mmol) dissolved in EtOH (10 mL). The reaction mixture was stirred together for 20 hours and then partitioned between 1N HCl and EtOAc. The organic layer was washed with saturated NaHCO₃, brine, dried over Na₂SO₄ and concentrated. Flash column chromatography (0% to 10% EtOAc in hexanes) gave 1-cyclopentyl-3-(2-fluoro-4-methoxy-phenyl)-propenone as a yellow oil contaminated with some unreacted aldehyde.

The crude oil was dissolved in EtOH and 10 wt % Pd/C (0.25 g, Degussa type) was added. The mixture was stirred under a balloon of H₂ for 30 mins and then filtered through a pad of celite washing with EtOAc. The filtrate was concentrated and purified by flash column chromatography (0% to 20% EtOAc in hexanes) to give the title compound as an oil (0.57 g, 39%). ¹H NMR (400 MHz, CDCl₃): δ 1.53–1.80 (m, 8 H), 2.73 (m, 2 H), 2.84 (m, 3 H), 3.77 (s, 3 H), 6.56–6.62 (m, 2 H), 7.08 (t, 1 H).

Step 1

Preparation of Compound 1-Cyclopentyl-ethanone

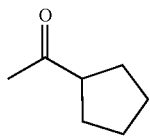

Cyclopentylmagnesium bromide (250 mL, 0.5 mol, 2M sol in THF) was added to a cooled −78° C. solution of acetic anhydride (39 mL, 0.42 mol) dissolved in THF (100 mL). The reaction mixture was stirred for 2 hours. The reaction was quenched with saturated NH₄Cl and extracted with ether. The organic layers were washed with brine, dried over Na₂SO₄ and concentrated to a black oil. Vacuum distillation gave the product as a yellow oil (16 g, 33% yield) ¹H NMR (CDCl₃): δ 1.55–1.84 (br m, 8H), 2.16 (s, 3H), 2.87 (m, 1H).

Example B(104)

6-Cyclopentyl-3-(5,7-dimethyl-[1,2,4]triazolo[1,5-a]pyrimidin-2-ylmethyl)-6-{2-[3-ethyl-4-(2-hydroxy-ethoxy)-phenyl]-ethyl}-4-hydroxy-5,6-dihydro-pyran-2-one

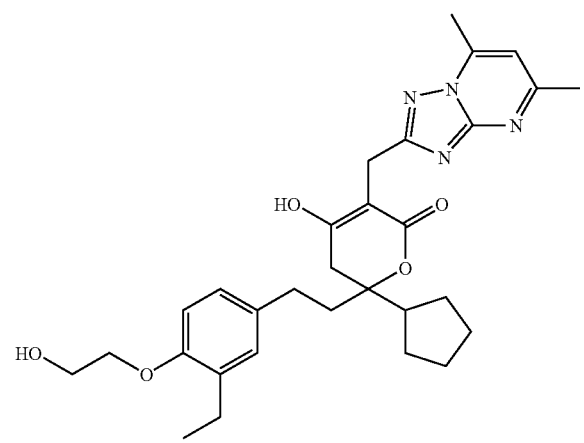

This compound was prepared analogously to example C(112), except that 6-Cyclopentyl-6-{2-[3-ethyl-4-(2-hydroxy-ethoxy)-phenyl]-ethyl}-dihydro-pyran-2,4-dione was used in place of 2-[4-(2-Cyclopentyl-4,6-dioxo-tetrahydro-pyran-2-ylmethoxy)-2-fluoro-phenyl]-2-methyl-propionitrile The result was a white solid. ¹H NMR (300 MHz, CDCl₃): δ: 1.20 (t, J=7.5 Hz, 3H), 1.52–1.81 (m, 9H), 2.04 (m, 2H), 2.39 (m, 1H), 2.62 (m, 10H), 2.79 (s, 3H), 4.05 (d, J=15.5 Hz, 1H), 4.25 (m, 4H), 4.12 (d, J=15.5 Hz, 1H), 6.84 (s, 1H), 6.98 (m, 3H).

Example B(105)

6-Cyclopentyl-3-(5,7-dimethyl-1,2,4]triazolo[1,5-a]pyrimidin-2-ylmethyl)-6-[2-(3-fluoro-4-hydroxy-phenyl)-ethyl]-4-hydroxy-5,6-dihydro-pyran-2-one

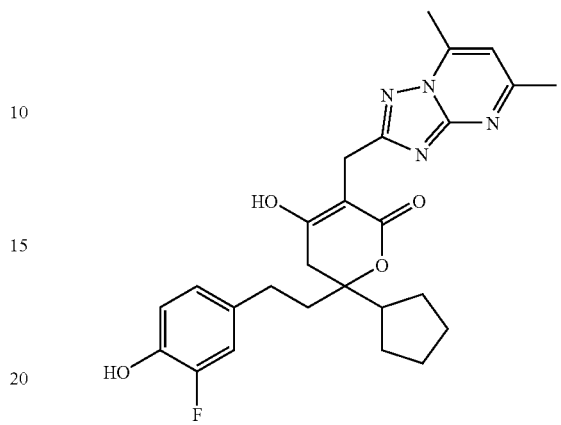

This compound was prepared analogously to example C(112), except that 6-Cyclopentyl-6-[2-(3-fluoro-4-hydroxy-phenyl)-ethyl]-dihydro-pyran-2,4-dione was used in place of 2-[4-(2-Cyclopentyl-4,6-dioxo-tetrahydro-pyran-2-ylmethoxy)-2-fluoro-phenyl]-2-methyl-propionitrile. The result was a white solid. ¹H NMR (CDCl₃): δ: 1.44–1.92 (brm, 8H), 2.05 (m, 2H), 2.35 (m, 1H) 2.44–2.88 (m, 11H), 4.05 (s, 2H), 6.85 (s, 1H), 6.99 (m, 2H), 7.15 (d, J=7.5 Hz, 1H).

Example B(106)

[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-fluorophenoxy]acetonitrile

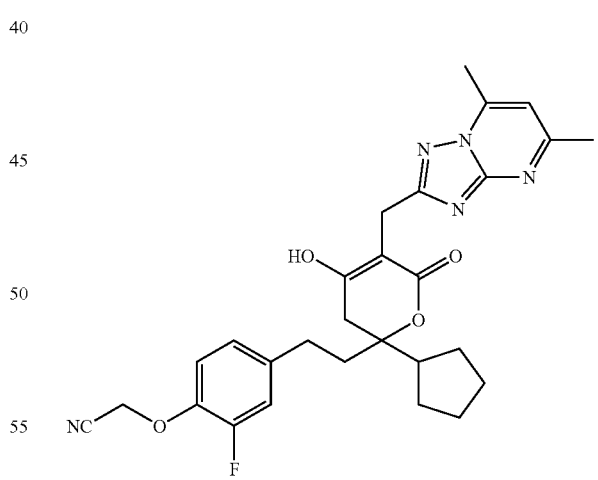

The title compound was prepared analogously to Example A(131), where {4-[2-(2-cyclopentyl-4,6-dioxotetrahydro-2H-pyran-2-yl)ethyl]-2-fluorophenoxy}acetonitrile (from step 3 below) was substituted in place of 6-cyclopentyl-6-[2-(3-fluoro-4-{methyl[methyl(dimethylene)-6-sulfanyl]amino}phenyl)ethyl]dihydro-2H-pyran-2,4(3H)-dione. ¹H NMR (CDCl₃): δ 1.40–2.24 (brm, 7H), 2.0–2.18 (m, 5H), 2.63 (s, 3H); 2.74 (m, 5H), 3.20 (m, 2H), 4.00(s, 2H); 4.74 (s, 2H); 6.77–7.10 (m, 4H).

Step 3

{4-[2-(2-cyclopentyl-4,6-dioxotetrahydro-2H-pyran-2-yl)ethyl]-2-fluorophenoxy}acetonitrile

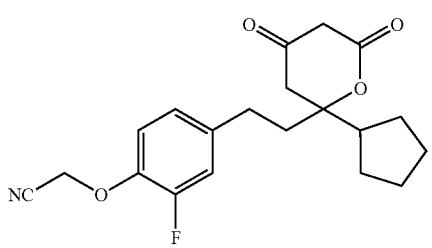

Methyl acetoacetate (3.2 mL, 29.4 mmol) was added to a cooled 0° C. suspension of NaH (1.17 g, 29.4 mmol, 60% dispersion in mineral oil) in THF (50 ml). After 30 min n-BuLi (11.7 mL, 29.4 mmol, 2.5M in hexanes) was added. The resulting dianion was stirred for an additional 30 min and then treated with a solution of [4-(3-Cyclopentyl-3-oxo-propyl)-2-fluoro-phenoxy]-acetonitrile (2.7 g, 9.8 mmol) in THF (30 ml). After stirring for 4 h at 0° C., the reaction mixture was quenched with 1N HCl and extracted with EtOAc. The organic layers were washed with brine, dried over Na$_2$SO$_4$ and concentrated to a yellow oil that was used without further purification.

The oil was dissolved in toluene (10 mL) and treated with Otera catalyst (100 mg). The reaction mixture was heated to 80° C. under N$_2$ for 30 min. The reaction mixture was concentrated and crystallized from CH$_2$Cl$_2$ to give the title compound (0.2 g, 24% yield). MS (APCI): 358 (M–H).

Step 2

[4-(3-Cyclopentyl-3-oxo-propyl)-2-fluoro-phenoxy]-acetonitrile

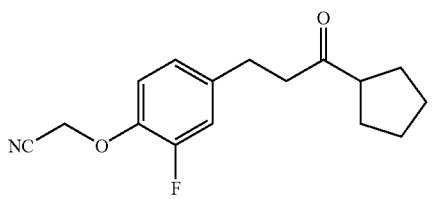

A mixture of (4-bromo-2-fluorophenoxy)acetonitrile (2.5 g, 10.8 mmol), 1-Cyclopentyl-2-propen-1-ol (2.0 g, 16.2 mmol), dichlorobis (triphenylphosphine) palladium (II) (151 mg, 0.22 mmol), and sodium bicarbonate (1.08 g, 12.9 mmol) in N-methylpyrrolidinone (20 mL) was heated to 140° C. under N$_2$ for 5 hours. The reaction mixture was partitioned between 1N HCl and EtOAc. The organic layer was washed with saturated NaHCO$_3$, brine, dried over Na$_2$SO$_4$ and concentrated to a black oil. The oil was purified by flash column chromatography (Hexanes to 10% EtOAc in hexanes) to give the desired product (2.7 g, 93%). $^1$H NMR (CDCl$_3$): δ 1.52–1.83 (m, 8H), 2.75 (m, 2H), 2.85 (m, 3H), 4.80 (s, 2H), 6.92–7.06 (m, 3H).

Step 1

Preparation of (4-bromo-2-fluorophenoxy)acetonitrile

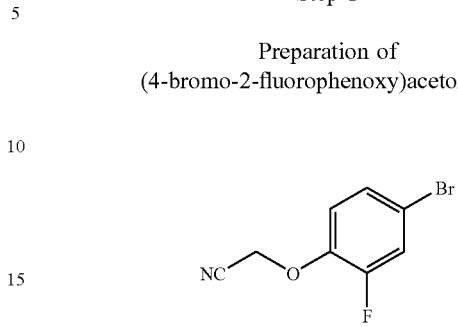

Bromoacetonitrile (1.81 ml, 0.026M) was added to a solution of 4-bromo-2-fluorophenol (5.0 g, 0.026M) and potassium carbonate (3.54 g, 0.026M) in DMF (50 ml). The reaction was stirred for 12 hours and then partitioned between diethyl ether (200 ml) and water (200 ml). The organics were separated, dried over magnesium sulfate, filtered and concentrated in vacuuo to afford the title compound as a yellow oil (6.0 g). $^1$H NMR (CDCl$_3$): δ 4.84 (s, 2H), 7.03–7.10 (m, 2H), 7.21 (m, 1H).

Example B(107)

6-Cyclopentyl-6-[2-(3-cyclopropyl-4-methoxy-phenyl)-ethyl]-3-(5,7-dimethyl-[1,2,4]triazolo[1,5-a]pyrimidin-2-ylmethyl)-4-hydroxy-5,6-dihydro-pyran-2-one

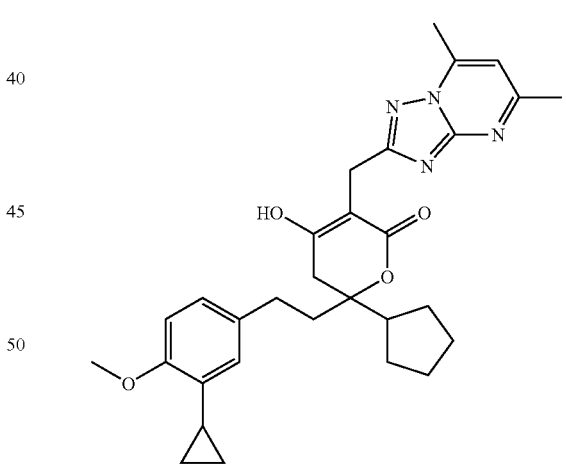

This compound was prepared analogously to example C (112), except that 6-Cyclopentyl-6-[2-(3-cyclopropyl-4-methoxy-phenyl)-ethyl]-dihydro-pyran-2,4-dione was used in place of 2-[4-(2-Cyclopentyl-4,6-dioxo-tetrahydro-pyran-2-ylmethoxy)-2-fluoro-phenyl]-2-methyl-propionitrile The result was a white solid. $^1$H NMR (300 MHz, CDCl$_3$): δ: 0.61 (m, 2 H), 0.88 (m, 2 H), 1.55 (m, 8 H), 1.97 (m, 2 H), 2.11 (m, 1 H), 2.36 (m, 1 H), 2.57 (m, 5 H), 2.67 (s, 3 H), 2.79 (s, 3 H), 3.82 (s, 3 H), 4.08(m, 2 H), 6.59 (s, 1 H), 6.73 (d, J=8.3 Hz, 1 H), 6.84 (s, 1 H), 6.89 (d, J=8.3 Hz, 1 H).

Example B(108)

6-Cyclopentyl-6-[2-(3,5-dichloro-4-ethoxy-phenyl)-ethyl]-dihydro-pyran-2,4-dione

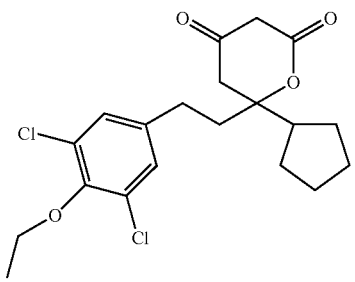

The title compound was prepared analogously to Example B(97), where 5-Bromo-1,3-dichloro-2-ethoxy-benzene was substituted in place of 5-Bromo-1-chloro-3-ethyl-2-methoxy-benzene. $^1$H NMR (400 MHz, CDCl$_3$): δ 1.45 (t, J=7.0 Hz, 3H), 1.49–1.76 (m, 8H), 1.87–1.98 (m, 2H), 2.22–2.31 (m, 1H), 2.57–2.64 (m, 2H), 2.75 (d, J=6 Hz, 2H), 3.44 (s, 2H), 4.07 (q, J=7 Hz, 2H), 7.07 (s, 2H). ESIMS (M+H)$^+$: 400.

Step 1

4-bromo-2,6-dichlorophenyl ethyl ether

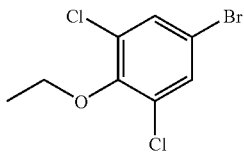

The title compound was prepared analogously to step 2 in Example A(125), where 5-Bromo-1,3-dichloro-phenol was substituted in place of 4-bromo-2-ethyl-phenol in that example.

$^1$H NMR (400 MHz, CDCl$_3$): δ 1.46 (t, J=7.0 Hz, 3H), 4.10 (q, J=7 Hz, 2H), 7.09 (s, 2H).

Example B(109)

4-{3-[2-Cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-propionylamino}-piperidine-1-carboxylic acid tert-butyl ester

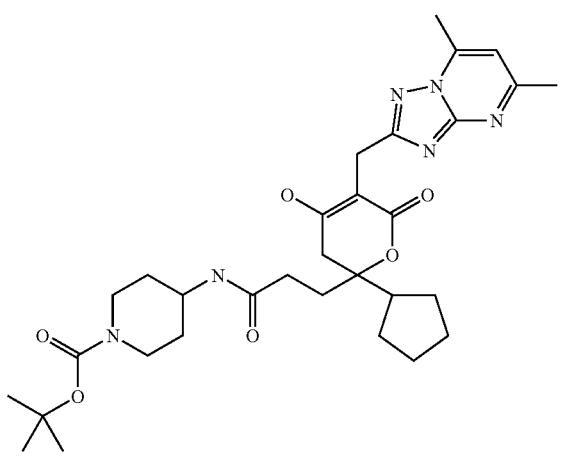

The title compound was prepared analogously to Example B(97), where 4-(4-Cyclopentyl-4-oxo-butyrylamino)-piperidine-1-carboxylic acid tert-butyl ester (from step 2 below) was substituted in place of 3-(3-chloro-5-ethyl-4-methoxy-phenyl)-1-cyclopentyl-propa-1-one in step 4 of that example. $^1$H NMR (400 MHz, DMSO-d$_6$): δ 1.34 (s, 9H), 1.35–1.61 (m, 18H), 1.97–2.15 (m, 4H), 2.49 (s, 3H), 2.59 (s, 3H), 3.64–3.76 (m, 5H), 7.03 (s, 1H), 7.79 (d, J=7.5, 1H). ESIMS (M+H)$^+$: 597.

Step 2

4-(4-Cyclopentyl-4-oxo-butyrylamino)-piperidine-1-carboxylic acid tert-butyl ester

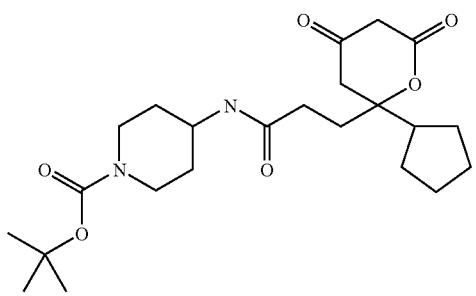

The title compound was prepared analogously to step 4 from Example B(97), where 4-(4-Cyclopentyl-4-oxo-butyrylamino)-piperidine-1-carboxylic acid tert-butyl ester (described in step 1 below) was substituted in place of 5-bromo-1-chloro-3-ethyl-2-methoxy-benzene in step 3 of that example. $^1$H NMR (400 MHz, DMSO-d$_6$): δ 1.24–1.42 (m, 8H), 1.45 (s, 9H), 1.59–2.32 (m, 4H), 2.62 (d, J=16 Hz, 1H), 2.71 (d, J=16 Hz, 1H), 2.80–2.84 (s, 9H), 3.39 (d, J=18 Hz, 1H), 3.56 (d, J=18 Hz, 1H), 3.86 (m, 2H). MS(ESI):435 (MH–).

Step 1

4-(4-Cyclopentyl-4-oxo-butyrylamino)-piperidine-1-carboxylic acid tert-butyl ester

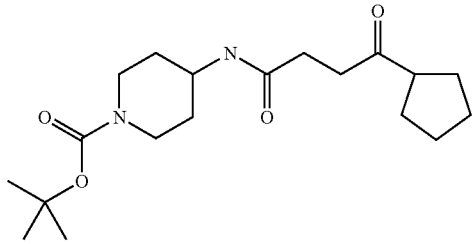

To a stirred solution of 4-Amino-piperidine-1-carboxylic acid tert-butyl ester (0.3 g, 1.49 mmol) in anhydrous CH$_2$Cl$_2$ under argon and cooled to 0° C., were added 4-Cyclopentyl-4-oxo-butyric acid (0.31 g, 1.79 mmol), EDC.HCl (0.35 g, 1.79 mmol), HOBt (0.24 g, 1.79 mmol), and TEA (0.25 mL, 1.79 mmol). The resulting solution was stirred at 25° C. overnight. CH$_2$Cl$_2$ was evaporate and the residue was partitioned between EtOAc and 1N HCl. The organic layer was washed with H$_2$O, brine and dried over Na$_2$SO$_4$. The solvent was removed in vacuo and the residue was purified by flash column chromatography (80% EtOAc in hexanes) to provide the desired product (0.37 g, 71%) as a white solid. $^1$H NMR (400 MHz, CDCl$_3$): δ 1.24–1.32 (m, 2H), 1.45 (s, 9H), 1.60–1.85 (m, 11H), 2.41 (t, J=6.4 Hz, 2H), 2.79–3.04 (m, 5H), 3.85–4.13 (m, 2H), 5.65 (s, 1H). MS(ESI):351 (MH–).

Example B(110)

6-Cyclopentyl-6-[2-(3-ethyl-4-hydroxy-phenyl)-ethyl]-4-hydroxy-3-(5-methyl-1H-imidazol-4-ylmethyl)-5,6-dihydro-pyran-2-one

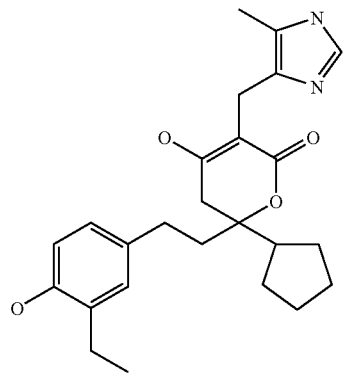

The title compound was prepared analogously to Example A(126), where 4-methyl-5-imidazol carboxaldehyde was substituted in place of 6-Methyl-[1,2,4]triazolo[1,5-a]pyrimidine-2-carbaldehyde of that example. $^1$H NMR (400 MHz, DMSO-d$_6$): δ 1.09 (t, J=7.4 Hz, 3H), 1.30–1.60 (m, 8H), 1.80–1.85 (m, 2H), 2.09 (s, 3H), 2.22–2.31 (m, 1H), 2.38–2.57 (m, 5H), 2.71 (d, J=16 Hz, 1H), 3.46 (m, 2H), 6.64–6.72 (m, 3H), 6.79 (s, 1H), 8.43 (s, 1H). Anal. Calcd. For C$_{25}$H$_{32}$N$_2$O$_4$.1 HCl.0.25H$_2$O: C, 64.51; H, 7.25; N, 6.02. Found: C, 64.22; H, 7.31; N, 5.91. MS(ESI):425.2 (M+H)$^+$.

Example B(111)

6-Cyclopentyl-6-[2-(3-ethyl-4-hydroxy-phenyl)-ethyl]-3-(2-ethyl-5-methyl-1H-imidazol-4-ylmethyl)-4-hydroxy-5,6-dihydro-pyran-2-one

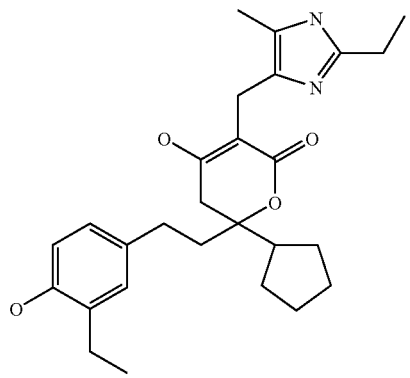

The title compound was prepared analogously to Example A(30), where 2-ethyl-5-formyl-4-methylimidazole carboxaldehyde was substituted in place of 6-Methyl-[1,2,4]triazolo[1,5-a]pyrimidine-2-carbaldehyde of that example. $^1$H NMR (400 MHz, DMSO-d$_6$): δ 1.15 (t, J=7.4 Hz, 3H), 1.25 (t, J=7.6 Hz, 3H), 1.40–1.75 (m, 8H), 1.80–1.9 (m, 2H), 2.17 (s, 3H), 2.25–2.35 (m, 1H), 2.44–2.64 (m, 6H), 2.74 (q, J=7.4 Hz, 2H), 3.46 (d, J=4.5 Hz, 2H), 6.70–6.81 (m, 3H), 6.87 (s, 1H). Anal. Calcd. For C$_{27}$H$_{36}$N$_2$O$_4$.1 H$_2$O: C, 68.91; H, 8.14; N, 5.95. Found: C, 69.89; H, 7.91; N, 6.05. MS(ESI): 453.2 (MH+).

Example B(112)

6-Cyclopentyl-3-(5,7-dimethyl-[1,2,4]triazolo[1,5-a]pyrimidin-2-ylmethyl)-4-hydroxy-6-{2-[4-(1-hydroxy-ethyl)-phenyl]-ethyl}-5,6-dihydro-pyran-2-one

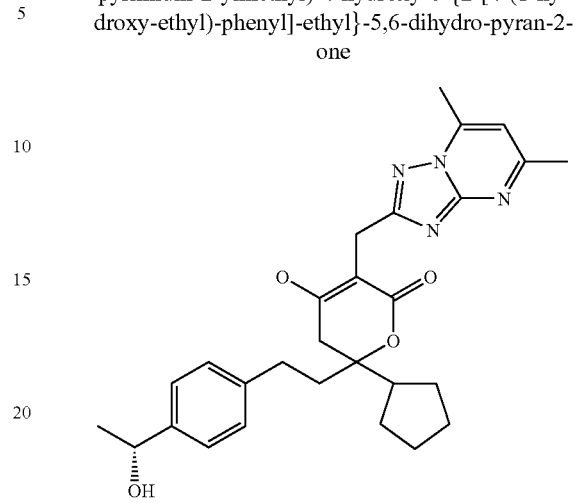

The title compound was prepared analogously to Example B(97), where 6-Cyclopentyl-6-{2-[4-(1-hydroxy-ethyl)-phenyl]-ethyl}-dihydro-pyran-2,4-dione (from step 2 below) was substituted in place of 6-[2-(3-Chloro-5-ethyl-4-methoxy-phenyl)-ethyl]6-cyclopentyl-dihydro-pyran-2,4-dione of that example. $^1$H NMR (400 MHz, DMSO-d$_6$): δ 1.17 (d, J=6.4 Hz, 3H), 1.37–1.56 (m, 8H), 1.96–2 (m, 2H), 2.35–2.44 (m, 10H), 2.67 (d, J=17 Hz, 1H), 3.59 (d, J=16 Hz, 1H), 3.71 (d, J=16 Hz, 1H), 4.50 4.55 (m, 1H), 4.93 (d, J=4.1 Hz, 1H), 6.92 (s, 1H), 7.03 (d, J=8.1 Hz, 2H), 7.10 (d, J=8.1 Hz, 2H), 10.73 (brs, 1H). Anal. Calcd. For C$_{28}$H$_{34}$N$_4$O$_4$: C, 68.55; H, 6.99; N, 11.42. Found: C, 68.70; H, 7.10; N, 11.52. MS(ESI): 491.2 (M+H)$^+$.

Step 2

6-Cyclopentyl-6-{2-[4-(1-hydroxy-ethyl)-phenyl]-ethyl}-dihydro-pyran-2,4-dione

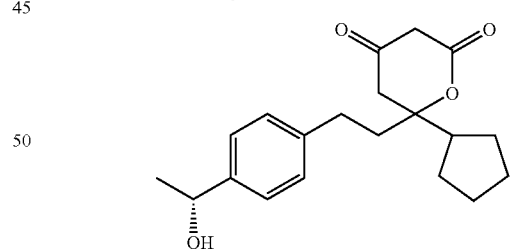

The title compound was prepared analogously to step 4 from Example B(97), where (R)1-(4-Bromo-phenyl)-ethanol (described in step 1 below) was substituted in place of 5-bromo-1-chloro-3-ethyl-2-methoxy-benzene in step 3 of that example. $^1$H NMR (400 MHz, CDCl$_3$): δ 1.48 (d, J=6.4 Hz, 3H), 1.52–1.79 (m, 8H), 1.95 (q, J=17, 8.5 Hz, 2H), 2.26–2.32 (m, 1H), 2.68 (t, J=8.5 Hz, 2H), 2.78 (s, 2H), 3.42 (s, 2H), 4.88 (q, J=13, 6.4 Hz, 1H), 7.13 (d, J=8.1 Hz, 2H), 7.31 (d, J=8.1 Hz, 2H). Anal. Calcd. For C$_{20}$H$_{26}$O$_4$.0.5H$_2$O: C, 70.77; H, 8.02. Found: C, 70.37; H, 7.95. ESIMS (MH−): 329.

Step 1

(R)1-(4-Bromo-phenyl)-ethanol

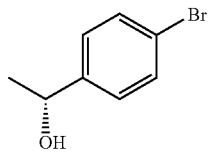

The title compound was prepared as described in the following reference: *Tetrahedron* 2001, 57, 5027–5038.

Example B(113)

6-[2-(4-Chloro-3-ethyl-phenyl)-ethyl]-6-cyclopentyl-3-(5,7-dimethyl-[1,2,4]triazolo[1,5-a]pyrimidin-2-ylmethyl)-4-hydroxy-5,6-dihydro-pyran-2-one

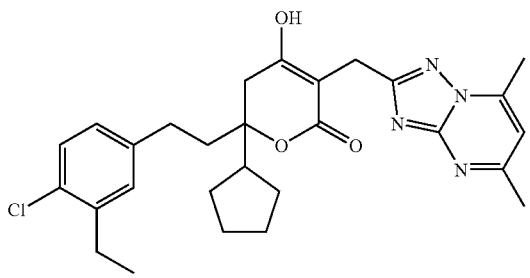

The title compound was prepared analogously to Example B(97) where 4-bromo-1-chloro-2-ethyl-benzene (from step 4 below) was substituted in place of 5-bromo-1-chloro-3-ethyl-2-methoxy-benzene in step 3 of that example. $^1$H NMR (400 MHz, DMSO-$d_6$): δ 1.21 (t, J=7.3 Hz, 3 H), 1.49–1.80 (br m, 8 H), 2.22 (m, 2 H), 2.54–2.77 (m, 12 H), 2.87 (d, J=17.7 Hz, 1 H), 3.80 (d, J=16.0 Hz, 1 H), 3.93 (d, J=16.1 Hz, 1 H), 7.15 (s, 1 H), 7.22 (dd, J=8.1, 2.0 Hz, 1 H), 7.27 (s, 1 H), 7.38 (d, J=8.1 Hz, 1 H). Anal. Calcd. For $C_{28}H_{33}N_4O_3 \cdot 0.5H_2O$: C, 64.91; H, 6.62; N, 10.82. Found: C, 64.93; H, 6.59; N, 10.50.

Step 4

4-Bromo-1-chloro-2-ethyl-benzene

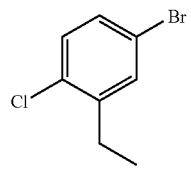

Sodium hydroxide (0.39 g, 9.6 mmol) and hydrazine monohydrate (0.56 mL, 11.5 mmol) were added to a solution of 1-(5-Bromo-2-chloro-phenyl)-ethanone (0.9 g, 3.85 mmol) dissolved in triethylene glycol (5 mL). The reaction mixture was heated to 170° C. for 24 hours and then partitioned between 1N HCl and EtOAc. The organic layer was washed with brine, dried over $Na_2SO_4$ and concentrated. The residue was purified by flash silica gel chromatography (0% to 5% EtOAc in hexanes) to give the title compound (0.52 g, 62%). $^1$H NMR (400 MHz, CDCl$_3$): δ 1.23 (t, J=7.6 Hz, 3 H), 2.72 (q, J=7.6 Hz, 2 H), 7.19 (d, J=8.6 Hz, 1 H), 7.25 (dd, J=8.3, 2.3 Hz, 1 H), 7.36 (d, J=2.5 Hz, 1 H).

Step 3

1-(5-Bromo-2-chloro-phenyl)-ethanone

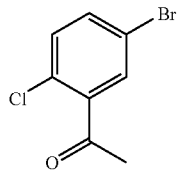

Pyridinium dichromate (2.6 g, 6.94 mmol) was added to a solution of 1-(5-bromo-2-chloro-phenyl)-ethanol (1.09 g, 4.6 mmol) in $CH_2Cl_2$ (20 mL). The reaction was stirred for 15 hours and then more pyridinium dichromate (2.6 g, 6.94 mmol) was added. After another 24 hours celite was added and the mixture was stirred for 20 mins. The reaction mixture was filtered through a pad of celite washing with ether. The filtrate was concentrated to a brown oil. The residue was purified by flash silica gel chromatography (0% to 10% EtOAc in hexanes) to give the title compound as a clear oil (0.92 g, 85%). $^1$H NMR (400 MHz, CDCl$_3$): δ 2.64 (s, 3H), 7.29 (d, J=8.6 Hz, 1 H), 7.51 (dd, J=8.6, 2.3 Hz, 1 H), 7.66 (d, J=2.3 Hz, 1 H).

Step 2

1-(5-Bromo-2-chloro-phenyl)-ethanol

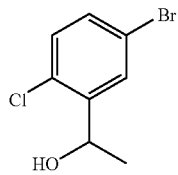

Methyl lithium (11.6 mL, 16.3 mmol, 1.4M in ether) was added to a cooled −78° C. solution of 5-bromo-2-chloro-benzaldehyde (2.75 g, 12.5 mmol) dissolved in THF (40 mL). The reaction mixture was stirred for 15 hours and then quenched with saturated $NH_4Cl$ and extracted with EtOAc. The organic extracts were washed with 1N HCl, brine, dried over $Na_2SO_4$ and concentrated to an oil. The oil was purified by flash column chromatography (0% to 10% EtOAc in hexanes) to give the title compound as a solid (2.63 g, 91%). $^1$H NMR (400 MHz, CDCl$_3$): δ 6.32 (d, J=6.3 Hz, 3 H), 2.00 (d, J=3.8 Hz, 1 H), 5.24 (m, 1 H), 7.19 (d, J=8.6 Hz, 1 H), 7.33 (dd, J=8.6, 2.5 Hz, 1 H), 7.75 (d, J=2.5 Hz, 1 H).

Step 1

5-Bromo-2-chloro-benzaldehyde

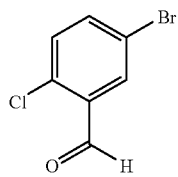

Pyridinium dichromate (3.82 g, 10.2 mmol) was added to a solution of 5-bromo-2-chlorobenzylalcohol (1.5 g, 6.8 mmol) in $CH_2Cl_2$ (30 mL). The reaction was stirred for 5 hours and then celite was added. The mixture was stirred for 20 mins and then filtered through a pad of celite washing with ether. The filtrate was concentrated to a brown oil. The residue was purified by flash silica gel chromatography (0% to 10% EtOAc in hexanes) to give the title compound as a clear oil (1.28 g, 86%). $^1$H NMR (400 MHz, CDCl$_3$): δ 7.35 (d, J=8.6 Hz, 1 H), 7.65 (dd, J=8.3, 2.5 Hz, 1 H), 8.04 (d, J=2.5 Hz, 1 H), 10.41 (s, 1 H).

Example B(114)

6-Cyclopentyl-3-(5,7-dimethyl-[1,2,4]triazolo[1,5-a]pyrimidin-2-ylmethyl)-6-{2-[3-fluoro-4-(1-hydroxy-ethyl)-phenyl]-ethyl}-4-hydroxy-5,6-dihydro-pyran-2-one

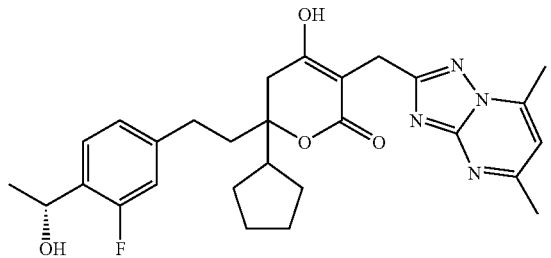

The title compound was prepared analogously to Example B(97) where 6-Cyclopentyl-6-{2-[3-fluoro-4-(1-hydroxy-ethyl)-phenyl]-ethyl}-dihydro-pyran-2,4-dione (from step 4 below) was substituted in place of 6-[2-(3-Chloro-5-ethyl-4-methoxy-phenyl)-ethyl]6-cyclopentyl-dihydro-pyran-2,4-dione of that example. $^1$H NMR (400 MHz, DMSO-d$_6$): δ 1.41 (d, J=6.4 Hz, 3H), 1.57–1.8 (m, 8H), 2.20–2.25 (m, 2H), 2.58–2.74 (m, 10H), 2.90 (d, J=17 Hz, 1H), 3.82 (d, J=16 Hz, 1H), 3.94 (d, J=16 Hz, 1H), 5.0–5.08 (m, 1H), 5.29–5.33 (m, 1H), 7.06 (d, J=11.5 Hz, 1H), 7.16 (s, 1H), 7.19 (d, J=7.70 Hz, 1H), 7.50–7.56 (m, 1H), 11.0 (s, 1H). Anal. Calcd. For C$_{28}$H$_{33}$N$_4$O$_4$F.0.25H$_2$O: C, 65.54; H, 6.58; N, 10.92. Found: C, 65.47; H, 6.56; N, 10.73. MS(ESI): 508.2 (M+H)$^+$.

Example B(115)

6-Cyclopentyl-6-{2-[3-fluoro-4-(1-hydroxy-ethyl)-phenyl]-ethyl}-dihydro-pyran-2,4-dione(

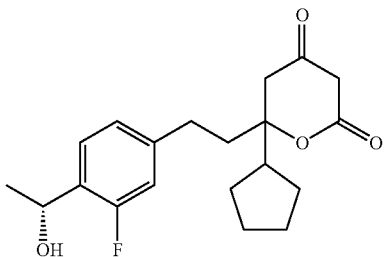

The title compound was prepared analogously to step 4 from Example B(97), where (R) 1-(4-Bromo-2-fluoro-phenyl)-ethanol (described in step 3 below) was substituted in place of 5-bromo-1-chloro-3-ethyl-2-methoxy-benzene in step 3 of that example. $^1$H NMR (400 MHz, CDCl$_3$): δ 1.50 (d, J=6.4 Hz, 3H), 1.52–1.88 (m, 8H), 1.91–1.98 (m, 2H), 2.22–2.32 (m, 1H), 2.64–2.69 (m, 2H), 2.77 (s, 2H), 3.43 (s, 2H), 5.16 (q, J=13, 6.4 Hz, 1H), 6.82 (dd, J=11, 1.5 Hz, 1H), 6.94 (dd, J=7.9, 1.5 Hz, 1H), 7.4 (t, J=7.9 Hz, 1H). Anal. Calcd. For C$_{20}$H$_{25}$FO$_4$.0.5H$_2$O: C, 67.21; H, 7.33. Found: C, 67.15; H, 7.14. ESIMS (MH−): 349.

Step 3

(R) 1-(4-Bromo-2-fluoro-phenyl)-ethanol

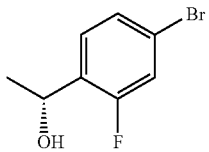

An oven dried 500 mL flask, was charged under nitrogen with (S)-2-methyl-CBS-oxazaborolidine 1M in toluene (5.02 mL) and dissolved in CH$_2$Cl$_2$ (250 mL). Me$_2$-BH$_3$ (30 mL, 60.27 mmol) was then added and cooled to −30° C. and reaction stirred for 15 minutes. (1-(4-Bromo-2-fluoro-phenyl)-ethanone (10.9 g, 50.23 mmol) from step 2 below was dissolved in CH$_2$Cl$_2$ (10 mL) and slowly added via addition funnel to the previous solution. The resulting reaction was stirred at 25° C. overnight. The solution was carefully quenched with MeOH, the solvent was removed in vacuo and the residue was purified by flash column chromatography (20% EtOAc in hexanes) to provide the desired product (9 37 g, 90%) as a clear oil. $^1$H NMR (400 MHz, CDCl$_3$): δ 1.49 (d, J=6.6 Hz, 3H), 5.15 (q, J=12, 6.4 Hz, 1H), 7.15–7.45 (m, 3H).

Step 2

1-(4-Bromo-2-fluoro-phenyl)-ethanone

4-Bromo-2-fluoro-thiobenzoic acid S-pyridin-2-yl ester (39 g, 124.94 mmol) from step 1 below was dissolved in THF (500 mL) and cooled to −78° C. MeMgBr 3.0 M solution (45 mL, 137.43 mmol) was added and reaction stirred 1 hour at −78° C. The resulting reaction mixture was poured into NaHCO$_3$ (100 mL) and extracted with EtOAC. The combined organics were washed with water (100 mL) and brine (100 mL) then dried over Na$_2$SO$_4$, filtered and concentrated. The crude residue was purified by flash chromatography (10% EtOAc in Hexanes) to yield the intermediate ketone as a colorless oil (20 g, 74%). $^1$H NMR (CDCl$_3$): δ 2.63 (d, 3H, J=5.1 Hz, 3H), 7.37 (dd, J=8.8, 1.9 Hz, 1H), 7.37 (s, 1H), 7.77 (7, J=8.8 Hz, 1H). ESIMS (MH+): 218.2.

Step 1

Bromo-2-fluoro-thiobenzoic acid S-pyridin-2-yl ester

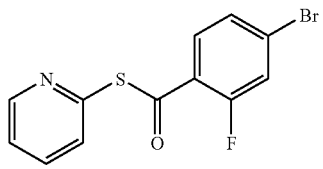

Aldrithiol-2 (30.18 g, 137 mmol followed by triphenylphosphine (36 g, 137 mmol were added to a solution of 4-bromo-2-fluorobenzoic acid (25 g, 114.16 mmol in $CH_2CL_2$ (570 mL) cooled to 0° C. The resulting mixture was stirred 4 hours at room temperature. The $CH_2Cl_2$ was then evaporated and residue was purified by flash column chromatography (20% EtOAc in hexanes) to give the product (35 g, 100%) as a pale yellow oil). $^1H$ NMR (CDCl$_3$) δ 7.33–7.44 (m, 3H), 7.71–7.83 (m, 3H), 8.67–8.71 (m, 1H). ESIMS (MH+): 313.1.

Example B(116)

3-(6-Chloro-[1,2,4]triazolo[1,5-a]pyrimidin-2-ylmethyl)-6-cyclopentyl-6-{2-[3-fluoro-4-(1-hydroxy-ethyl)-phenyl]-ethyl}-4-hydroxy-5,6-dihydro-pyran-2-one

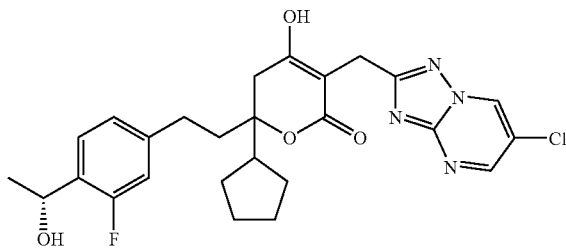

The title compound was prepared analogously to Example B(97) where where 6-Chloro-[1,2,4]triazolo[1,5-a]pyrimidine-2-carbaldehyde was substituted in place of 5,7-Dimethyl-[1,2,4]triazolo[1,5-a]pyrimidine-2-carbaldehyde and 6-Cyclopentyl-6-{2-[3-fluoro-4-(1-hydroxy-ethyl)-phenyl]-ethyl}-dihydro-pyran-2,4-dione (Example B(115) (was substituted in place of 6-[2-(3-Chloro-5-ethyl-4-methoxy-phenyl)-ethyl]6-cyclopentyl-dihydro-pyran-2,4-dione of that example.

$^1H$ NMR (400 MHz, DMSO-d$_6$): δ 1.13 (d, J=6.4 Hz, 3H), 1.23–1.60 (m, 8H), 1.81–1.91 (m, 2H), 2.21–2.25 (m, 1H), 2.40–2.46 (m 3H), 2.6 (d, J=16 Hz, 1H), 3.14 (s, 1H), 3.58 (d, J=16 Hz, 1H), 3.68 (d, J=16 Hz, 1H), 4.78–4.80 (m, 1H), 5.02 (d, J=5 Hz, 1H), 6.75 (d, J=10 Hz, 1H), 6.85 (d, J=7.7 Hz, 1H), 7.23 (t, J=7.70 Hz, 1H), 8.70 (d, J=2.5 Hz, 1H), 9.4 (d, J=2.5 Hz, 1H). Anal. Calcd. For $C_{26}H_{28}ClFN_4O_4 \cdot 0.5H_2O$: C, 59.60; H, 5.58; N, 10.69. Found: C, 59.67; H, 5.44; N, 10.65. MS (ESI): 515.2 (M+H)$^+$.

Example B(117)

6-Cyclopentyl-6-[2-(2,4-dimethoxy-phenyl)-ethyl]-3-(5,7-dimethyl-[1,2,4]triazolo[1,5-a]pyrimidin-2-ylmethyl)-4-hydroxy-5,6-dihydro-pyran-2-one

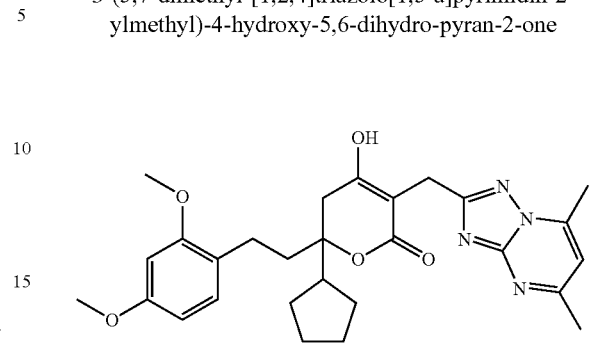

The title compound was prepared analogously to Example B(97) where 1-Bromo-2,4-dimethoxy-benzene was substituted in place of 5-bromo-1-chloro-3-ethyl-2-methoxy-benzene in step 3 of that example. $^1H$ NMR (400 MHz, DMSO-d$_6$): δ 1.52–1.89 (m, 8H), 2.06–2.26 (m, 3H), 2.59–2.70 (m, 9H), 2.95 (d, J=16 Hz, 1H), 3.49 (s, 2H), 3.82 (s, 3H), 3.88 (s, 3H), 6.55–6.62 (m, 2H), 7.18–7.21 (m, 2H), 11 (s, 1H). Anal. Calcd. For $C_{28}H_{34}N_4O_5$: C, 66.39; H, 6.76; N, 11.06. Found: C, 66.18; H, 6.76; N, 10.74. MS (ESI): 507 (M+H)$^+$.

Example B(118)

6-Cyclopentyl-6-[2-(2,4-dimethoxy-phenyl)-ethyl]-4-hydroxy-3-(6-methyl-[1,2,4]triazolo[1,5-a]pyrimidin-2-ylmethyl)-5,6-dihydro-pyran-2-one

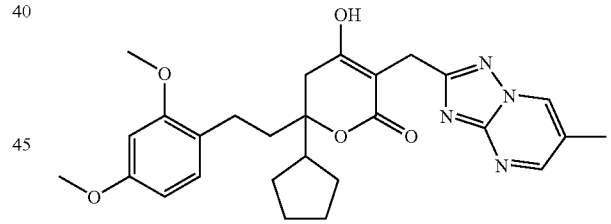

The title compound was prepared analogously to Example B(97) where 6-Methyl-[1,2,4]triazolo[1,5-a]pyrimidine-2-carbaldehyde was substituted in place of 5,7-Dimethyl-[1,2,4]triazolo[1,5-a]pyrimidine-2-carbaldehyde and 6-Cyclopentyl-6-[2-(2,4-dimethoxy-phenyl)-ethyl]-4-hydroxy-5,6-dihydro-pyran-2-one was substituted in place of 6-[2-(3-Chloro-5-ethyl-4-methoxy-phenyl)-ethyl]6-cyclopentyl-dihydro-pyran-2,4-dione of that example. $^1H$ NMR (400 MHz, DMSO-d$_6$): δ 1.36–1.72 (m, 8H), 1.93–2.02 (m, 2H), 2.35 (s, 3H), 2.42–2.58 (m, 2H), 2.76 (d, J=16 Hz, 1H), 3.34 (s, 6H), 3.69 (s, 2H), 3.73 (s, 2H), 6.46 (dd, J=8, 2.5 Hz, 1H), 6.49 (d, J=2.5 Hz, 1H), 7.03 (d, J=8.3 Hz, 1H), 6.70 (d, J=2.5 Hz, 1H), 8.85–8.87 (m, 1H), 10.8 (s, 1H). Anal. Calcd. For $C_{27}H_{32}N_4O_5$: 0.1H$_2$O: C, 63.51; H, 6.71; N, 10.97. Found: C, 63.50; H, 6.70; N, 10.87. MS (ESI): 493 (M+H)$^+$.

Example B(119)

3-(6-Chloro-[1,2,4]triazolo[1,5-a]pyrimidin-2-ylmethyl)-6-cyclopentyl-6-[2-(2,4-dimethoxy-phenyl)-ethyl]-4-hydroxy-5,6-dihydro-pyran-2-one

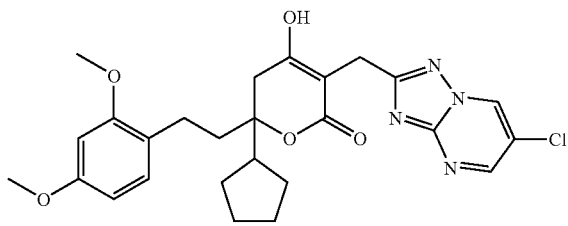

The title compound was prepared analogously to Example B(97), where 6-Chloro-[1,2,4]triazolo[1,5-a]pyrimidine-2-carbaldehyde was substituted in place of 5,7-Dimethyl-[1,2,4]triazolo[1,5-a]pyrimidine-2-carbaldehyde and 6-Cyclopentyl-6-[2-(2,4-dimethoxy-phenyl)-ethyl]4-hydroxy-5,6-dihydro-pyran-2-one was substituted in place of 6-[2-(3-Chloro-5-ethyl-4-methoxy-phenyl)-ethyl]6-cyclopentyl-dihydro-pyran-2,4-dione of that example. $^1$H NMR (400 MHz, DMSO-d$_6$): δ 1.51–1.73 (m, 9H), 1.92–1.98 (m, 2H), 2.38–2.58 (m, 3H), 2.79 (d, J=16 Hz, 1H), 3.71 (s, 2H), 3.73 (s, 6H), 6.40–6.5 (m, 2H), 7.03 (d, J=8 Hz, 1H), 8.89 (d, J=2.6 Hz, 1H), 9.52 (d, J=2.6 Hz, 1H), 10.9 (s, 1H). Anal. Calcd. For C$_{26}$H$_{29}$ClN$_4$O$_5$.0.25H$_2$O: C, 60.35; H, 5.75; N, 10.83. Found: C, 60.40; H, 5.65; N, 10.74. MS (ESI): 513 (M+H)$^+$.

Example B(120)

6-Cyclopentyl-3-(5,7-dimethyl-[1,2,4]triazolo[1,5-a]pyrimidin-2-ylmethyl)-4-hydroxy-6-{2-[3-(1-hydroxy-ethyl)-4-methoxy-phenyl]-ethyl}-5,6-dihydro-pyran-2-one

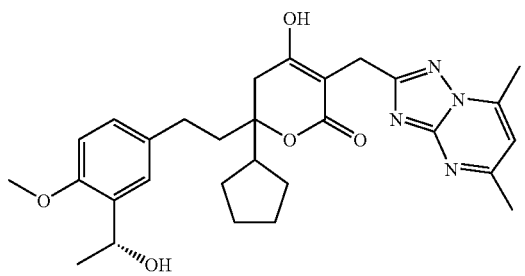

The title compound was prepared analogously to Example B(97) where 6-Cyclopentyl-6-{2-[3-(1-hydroxy-ethyl)-4-methoxy-phenyl]-ethyl}-dihydro-pyran-2,4-dione (from step 2 below) was substituted in place of 6-[2-(3-Chloro-5-ethyl-4-methoxy-phenyl)-ethyl]6-cyclopentyl-dihydro-pyran-2,4-dione of that example. $^1$H NMR (400 MHz, DMSO-d$_6$): δ 1.18–1.24 (m, 3H), 1.37–1.74 (m, 8H), 2.00–2.2 (m, 2H), 2.4–2.83 (m, 9H), 3.75 (s, 3H), 3.75–3.85 (m, 2H), 4.63 (d, J=6 Hz, 1H), 4.93 9 (s, 2H), 6.82 (d, J=8.3 Hz, 1H), 7.05–7.07 (m, 3H), 7.25 (s, 1H), 16.9 (s, 1H). MS (ESI): 521.2 (M+H)$^+$.

Example B(121)

6-Cyclopentyl-6{2-[3-(1-hydroxy-ethyl)-4-methoxy-phenyl]-ethyl}-dihydro-pyran-2,4-dione(

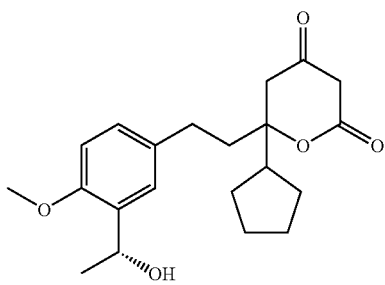

The title compound was prepared analogously to step 4 from Example B(97) where (R) 1-(5-Bromo-2-methoxy-phenyl)-ethanol (described in step 1 below) was substituted in place of 5-bromo-1-chloro-3-ethyl-2-methoxy-benzene in step 3 of that example. $^1$H NMR (400 MHz, CDCl$_3$): δ 1.6–2.28 (m, 16H), 2.6–2.69 (m, 2H), 2.74 (d, J=7.6 Hz, 2H), 3.41 (d, J=4.8 Hz, 2H), 3.70–3.71 (m, 1H), 3.84 (s, 2H), 6.80 (d, J=8.9, 1H), 7.01 (d, J=8.0 Hz, 1H), 7.12 (s, 1H). ESIMS (MH−): 361.2.

Step 1

(R) 1-(5-Bromo-2-methoxy-phenyl)-ethanol

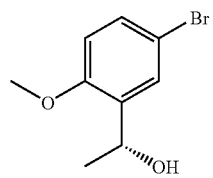

An oven dried 500 mL flask, was charged under nitrogen with (S)-2-methyl-CBS-oxazaborolidine 1M in toluene (2.18 mL) and dissolved in CH$_2$Cl$_2$ (100 mL). Me$_2$-BH$_3$ (13.10 mL, 26.20 mmol) was then added and cooled reaction to −30° C. then stirred for 15 minutes. 5-Bromo-2-methoxyacetophenone (5 g, 21.83 mmol) was dissolved in CH$_2$Cl$_2$ (10 mL) and slowly added via addition funnel to the previous solution. The resulting reaction was stirred at −30° C. for 1 hour. The solution was carefully quenched with MeOH, the solvent was removed in vacuo and the residue was purified by flash column chromatography (20% EtOAc in hexanes) to provide the desired product (5 g, 100%) as a clear oil. $^1$H NMR (400 MHz, CDCl$_3$): δ 1.47 (d, J=6.41 Hz, 3H), 2.44 (d, J=5 Hz, 1H), 3.84 (s, 3H), 5.03–5.11 (m, 1H), 6.74 (d, J=8.7 Hz, 1H), 7.33 (dd, J=8.7, 2.5 Hz, 1H), 7.48 (d, J=2.5 Hz, 1H).

Example B(122)

6-{2-[3-Chloro-4-(2-methyl-[1,3]dioxolan-2-yl)-phenyl]-ethyl}-6-cyclopentyl-3-(5,7-dimethyl-[1,2,4]triazolo[1,5-a]pyrimidin-2-ylmethyl)-4-hydroxy-5,6-dihydro-pyran-2-one

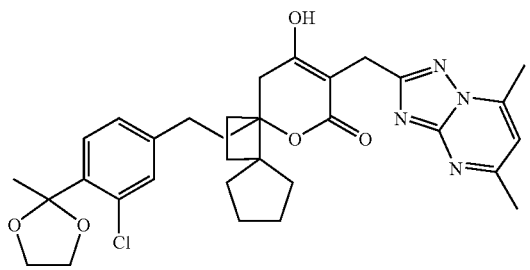

The title compound was prepared analogously to Example B(97) where Example B(123) (6-Cyclopentyl-6-{2-[3-fluoro-4-(1-hydroxy-ethyl)-phenyl]-ethyl}-dihydro-pyran-2,4-dione (below) was substituted in place of 6-[2-(3-Chloro-5-ethyl-4-methoxy-phenyl)-ethyl]6-cyclopentyl-dihydro-pyran-2,4-dione of that example. $^1$H NMR (400 MHz, DMSO-$d_6$): δ 1.5–1.7 (m, 9H) 2.20–2.22 (m, 2H), 2.49–2.90 (m, 10H), 3.39 (s, 3H), 3.70–3.74 (m, 2H), 3.78 (d, J=16 Hz, 1H), 3.90 (d, J=16 Hz, 1H), 4.04–4.07 (m, 2H), 7.13 (s, 1H), 7.32 (s, 1H), 7.36 (d, J=8 Hz, 1H), 7.61 (d, J=8 Hz, 1H), 10.9 (s, 1H). Anal. Calcd. For $C_{30}H_{35}ClN_4O_5$: C, 63.54; H, 6.22; N, 9.88. Found: C, 63.27; H, 6.27; N, 9.56. MS (ESI): 567.2 (M+H)$^+$.

Example B(123)

6-{2-[3-Chloro-4-(2-methyl-[1,3]dioxolan-2-yl)-phenyl]-ethyl}-6-cyclopentyl-dihydro-pyran-2,4-dione(

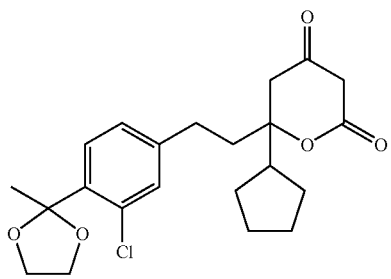

The title compound was prepared analogously to step 4 from Example B(97) where 2-(4-Bromo-2-chloro-phenyl)-2-methyl-[1,3]dioxolane (described in step 3 below) was substituted in place of 5-bromo-1-chloro-3-ethyl-2-methoxy-benzene in step 3 of that example. $^1$H NMR (CDCl$_3$-$d_6$): δ 1.57–1.73 (m, 8H), 1.78 (s, 3H), 1.91–1.98 (m, 2H), 2.2–2.3 (m, 1H), 2.62–2.68 (m, 2H), 2.77 (d, J=2.2 Hz, 2H), 3.43 (s, 2H), 3.75–3.79 (m, 2H), 4.04,4.09 (m, 2H), 7.01 (dd, J=7.9, 1.8 Hz, 1H), 7.17 (d, J=1.8 Hz, 1H), 7.55 (d, J=7.9 Hz, 1H). ESIMS (MNa+): 429.1.

Step 3

2-(4-Bromo-2-chloro-phenyl)-2-methyl-[1,3]dioxolane

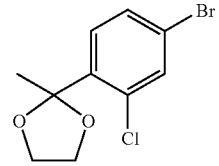

1-(4-Bromo-2-chloro-phenyl)-ethanone (from step 2 below) (1.86 g, 5.66 mmol), below was dissolved in ethylene glycol (5 mL). Triethylorthoformate (0.71 g, 4.79 mmol), and tosic acid (0.02 g) were added and reaction was stirred under nitrogen for 24 hours at room temperature. The resulting reaction mixture was poured into NaHCO$_3$ (10 mL) and extracted with EtOAC. The combined organics were washed with water (10 mL) and brine (10 mL) then dried over Na$_2$SO$_4$, filtered and concentrated. The crude residue was purified by flash chromatography (5% EtOAc in Hexanes) to yield the intermediate ether as a colorless oil (0.69 g, 58%). $^1$H NMR (CDCl$_3$): δ 1.77 (s, 3H), 3.74–3.79 (m, 2H), 4.04–4.09 (m, 2H), 7.37 (dd, J=8.5, 1.9 Hz, 1H), 7.52 (d, J=8.5 Hz, 1H), 7.55 (d, J=1.9 Hz, 1H). ESIMS (MH+): 278.2.

Step 2

1-(4-Bromo-2-chloro-phenyl)-ethanone

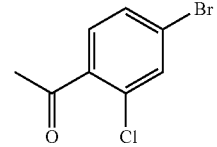

The title compound was prepared analogously to Step 2 from Example X(X): 6-Cyclopentyl-3-(5,7-dimethyl-[1,2,4]triazolo[1,5-a]pyrimidin-2-ylmethyl)-6-{2-[3-fluoro-4-(1-hydroxy-ethyl)-phenyl]-ethyl}-4-hydroxy-5,6-dihydro-pyran-2-one where 4-Bromo-2-chloro-thiobenzoic acid S-pyridin-2-yl ester (described in step 1 below) was substituted in place of 4-Bromo-2-fluoro-thiobenzoic acid S-pyridin-2-yl ester. $^1$H NMR (CDCl$_3$) δ 2.64 (s, 3H), 7.46–7.48 (m,2H), 7.61 (s, 1H). ESIMS (MH+): 234.1.

Step 1

4-Bromo-2-chloro-thiobenzoic Acid S-pyridin-2-yl ester

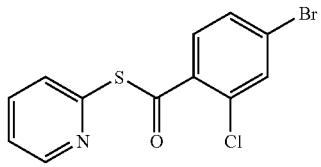

The title compound was prepared analogously to Step 1 from Example X(X): 6-Cyclopentyl-3-(5,7-dimethyl-[1,2,4]triazolo[1,5-a]pyrimidin-2-ylmethyl)-6-{2-[3-fluoro-4-(1-hydroxy-ethyl)-phenyl]-ethyl}4-hydroxy-5,6-dihydro-pyran-2-one where 4-bromo-2-chlorobenzoic acid was substituted in place of 4-bromo-2-fluorobenzoic acid of that example. $^1$H NMR (CDCl$_3$) δ7.34–7.38 (m, 1H), 7.53 (dd, J=8.3, 1.7 Hz, 1H), 7.67–7.85 (m,4H), 8.68 (d, J=5.6 Hz, 1H). ESIMS (MH+): 329.1.

Example B(124)

6-[2-(4-Acetyl-3-chloro-phenyl)-ethyl]-6-cyclopentyl-3-(5,7-dimethyl-[1,2,4]triazolo[1,5-a]pyrimidin-2-ylmethyl)-4-hydroxy-5,6-dihydro-pyran-2-one

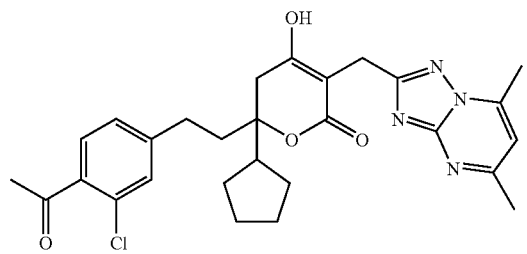

The title compound was prepared in the following way: Example B(122) 6-{2-[3-Chloro-4-(2-methyl-[1,3]dioxolan-2-yl)-phenyl]-ethyl}-6-cyclopentyl-3-(5,7-dimethyl-[1,2,4]triazolo[1,5-a]pyrimidin-2-ylmethyl)-4-hydroxy-5,6-dihydro-pyran-2-one (0.138 g, 0.24 mmol), was dissolved in acetone (8 mL). Amberlyst-13 (0.23 g) was added from top and reaction was stirred under nitrogen for 72 hours at room temperature. The resulting reaction mixture was filtered through fritted funnel to remove the amberlyst and the resultant filtrate was diluted with EtOAC and washed with water (10 mL) and brine (10 mL) then dried over $Na_2SO_4$, filtered and concentrated. The resultant solid was recrystallized from MeOH to yield the product as a white solid (0.05 g, 41%). $^1$H NMR (400 MHz, DMSO-$d_6$): δ 1.5–1.7 (m, 9H) 2.20–2.22 (m, 2H), 2.49–2.90 (m, 10H), 3.39 (s, 3H), 3.78 (d, J=16 Hz, 1H), 3.90 (d, J=16 Hz, 1H), 7.13 (s, 1H), 7.32 (s, 1H), 7.36 (d, J=8 Hz, 1H), 7.61 (d, J=8 Hz, 1H), 10.9 (s, 1H). MS (ESI): 523 (M+H)$^+$.

Example B(125)

1-(2-Chloro-4-{2-[2-cyclopentyl-4-hydroxy-5-(6-methyl-[1,2,4]triazolo[1,5-a]pyrimidin-2-ylmethyl)-6-oxo-3,6-dihydro-2H-pyran-2-yl]-ethyl}-phenyl)-cyclopropanecarbonitrile

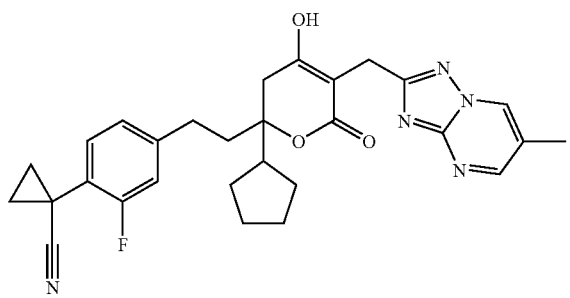

The title compound was prepared analogously to Example B(97) (where 1-(2-Chloro-4-{2-[2-cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-phenyl)-cyclopropanecarbonitrile was substituted in place of 6-[2-(3-Chloro-5-ethyl-4-methoxy-phenyl)-ethyl]-6-cyclopentyl-dihydro-pyran-2,4-dione in that example and 6-Chloro-[1,2,4]triazolo[1,5-a]pyrimidine-2-carbaldehyde in place of the 5,7-Dimethyl-[1,2,4]triazolo[1,5-a]pyrimidine-2-carbaldehyde in that example. $^1$H NMR (400 MHz, CDCl$_3$) δ: 1.38–1.42 (m, 2H), 1.47–1.73 (m, 8H), 1.73–1.77 (m, 2H), 2.01–2.21 (m, 2H)), 2.39–2.50 (m, 1H), 2.56 (d, J=16 Hz, 1H), 2.63–2.69 (m, 2H), 2.80 (d, J=16 Hz, 1H), 3.3 (s, 3H), 3.75 (d, J=16 Hz, 1H), 3.85 (d, J=16 Hz, 1H), 7.29 (dd, J=8, 1.6 Hz, 1H), 7.43–7.45 (m, 2H), 8.74 (d, J=2.3 Hz, 1H), 9.01 (dd, J=2.3, 1.1 Hz, 1H), 10.9 (s, 1H). $C_{29}H_{30}ClN_5O_3$.0.25: C, 64.68; H, 6.08; N, 13.00. Found: C, 64.78; H, 5.74; N, 12.65. MS (ESI): 532.2(M+H$^+$).

Example B(126)

1-(2-Chloro-4-{2-[5-(6-chloro-[1,2,4]triazolo[1,5-a]pyrimidin-2-ylmethyl)-2-cyclopentyl-4-hydroxy-6-oxo-3,6-dihydro-2H-pyran-2-yl]-ethyl}-phenyl)-cyclopropanecarbonitrile

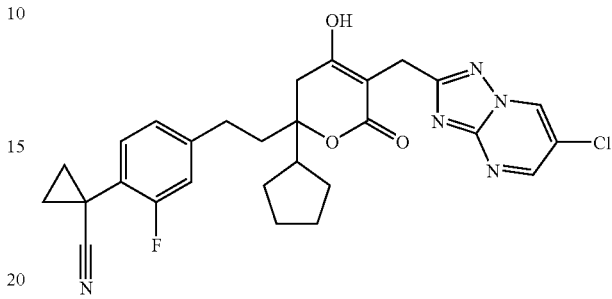

The title compound was prepared analogously to Example B(97), 1-(2-Chloro-4-{2-[2-cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-phenyl)-cyclopropanecarbonitrile was substituted in place of 6-[2-(3-Chloro-5-ethyl-4-methoxy-phenyl)-ethyl]-6-cyclopentyl-dihydro-pyran-2,4-dione in that example and 6-Methyl-[1,2,4]triazolo[1,5-a]pyrimidine-2-carbaldehyde in place of the 5,7-Dimethyl-[1,2,4]triazolo[1,5-a]pyrimidine-2-carbaldehyde in that example. $^1$H NMR (400 MHz, CDCl$_3$) δ: 1.16–1.18 (m, 2H), 1.19–1.5 (m, 8H), 1.51–1.53 (m, 2H), 1.86–1.89 (m, 2H)), 2.16–2.29 (m, 1H), 2.35–2.47 (m, 3H), 2.59 (d, J=17 Hz, 1H), 3.56 (d, J=16 Hz, 1H), 3.65 (d, J=16 Hz, 1H), 7.08 (d, J=7.8, 1 Hz, 1H), 7.20–7.23 (m, 2H), 8.70 (d, J=2.5 Hz, 1H), 9.41 (d, J=2.5, 1.1 Hz, 1H), 10.7 (s, 1H). $C_{28}H_{27}Cl_2N_5O_3$.0.25: C, 60.38; H, 4.98; N, 12.57. Found: C, 60.30; H, 4.80; N, 12.53. MS (ESI): 552.2(M+H$^+$).

Example C(1)

6-Cyclopentyl-6-[2-(3-fluoro-4-isopropoxy-phenyl)-ethyl]-4-hydroxy-3-(quinolin-8-ylsulfanyl)-5,6-dihydro-pyran-2-one

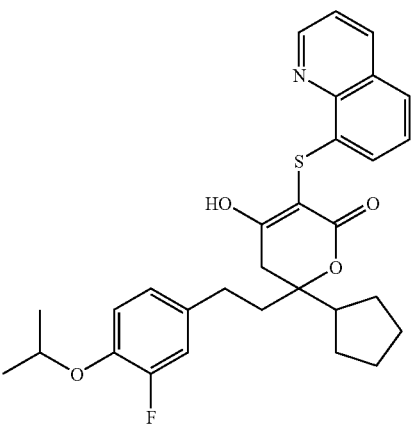

The title compound was prepared analogously to Example C(4), where Quinoline-8-thiol was substituted in place of 5-Pyridin-4-yl-4H-[1,2,4]triazole-3-thiol.

$^1$H NMR (CDCl$_3$): δ 1.33 (d, J=6.1 Hz, 6H)1.39–1.74 (brm, 8H), 1.88 (m, 2H), 2.36 (m, 1H), 2.53 (m, 2H), 2.74 (d, J=18 Hz 1H), 2.92 (m, 2H), 4.42 (m, 1H), 6.81 (d, J=8.4 Hz 1H), 6.93 (d, J=7.8 Hz 1H), 7.01 (s, 1H), 7.54–7.60 (m, 2H), 7.92 (d, J=8.1 Hz 1H), 8.33 (d, J=8.1 Hz 1H), 8.51 (d, J=7.8 Hz 1H), 8.97 (s, 1H). Anal. Calcd. For $C_{30}H_{32}FNO_4S$: C, 69.07; H, 6.18; N, 2.69. Found: C, 69.22; H, 6.08; N, 2.86.

Example C(2)

3-(5-Chloro-1-isopropyl-1-benzoimidazol-2-ylsulfanyl)-6-cyclopentyl-6-[2-(3-fluoro-4-isopropoxyphenyl)-ethyl]-4-hydroxy-5,6-dihydro-pyran-2-one

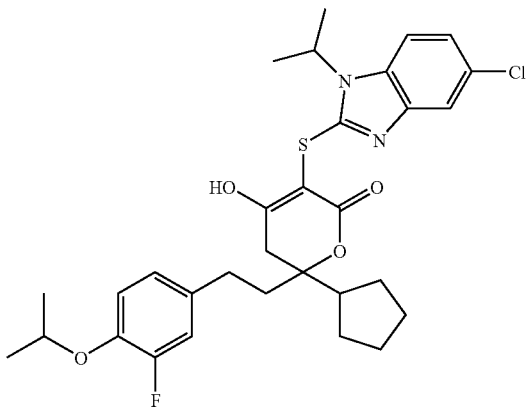

The title compound was prepared analogously to Example C(4), where 5-Chloro-1-isopropyl-1H-benzoimidazole-2-thiol was substituted in place of 5-Pyridin-4-yl-4H-[1,2,4]triazole-3-thiol.

ESIMS (MH+): 588.3.

Example C(3)

6-[2-(3-Chloro-4-methoxy-phenyl)-ethyl]-6-cyclopentyl-4-hydroxy-3-(quinolin-8-ylsulfanyl)-5,6-dihydro-pyran-2-one

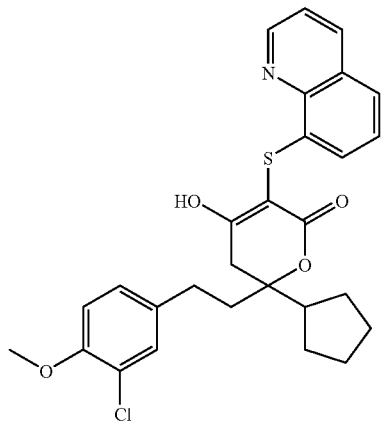

The title compound was prepared analogously to Example C(4), where Quinoline-8-thiol was substituted in place of 5-Pyridin-4-yl-4H-[1,2,4]triazole-3-thiol.

$^1$H NMR (CDCl$_3$): δ 1.25–1.74 (brm, 8H), 1.88 (m, 2H), 2.36 (m, 1H), 2.53 (m, 2H), 2.74 (d, J=18 Hz 1H), 2.92 (m, 2H), 3.86 (s, 3H), 6.79 (d, J=8.4 Hz 1H), 6.91 (d, J=7.8 Hz 1H), 7.01 (s, 1H), 7.56–7.61 (m, 2H), 7.90 (d, J=8.1 Hz 1H), 8.33 (d, J=8.1 Hz 1H), 8.47 (d, J=7.8 Hz 1H), 8.97 (s, 1H). Anal. Calcd. For $C_{28}H_{28}ClNO_4S$: C, 65.94; H, 5.53; N, 2.75. Found: C, 65.68; H, 5.22; N, 2.85.

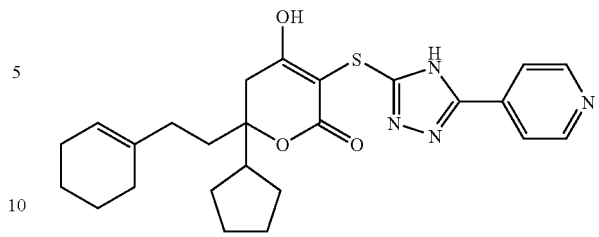

Example C(4)

6-(2-Cyclohex-1-enyl-ethyl)-6-cyclopentyl-4-hydroxy-3-(5-pyridin-4-yl-4H-[1,2,4]triazol-3-ylsulfanyl)-5,6-dihydro-pyran-2-one A solution of 3-Chloro-6-(2-cyclohex-1-enyl-ethyl)-6-cyclopentyl-4-hydroxy-5,6-dihydro-pyran-2-one (150 mg, 0.46 mmol, from Step 1 below), 5-Pyridin-4-yl-4H-[1,2,4]triazole-3-thiol (82 mg, 0.46 mmol), and triethylamine (64 □L, 0.46 mmol) dissolved in DMF (5 mL) was heated to 55° C. under N$_2$ for 8 h. The resulting mixture was concentrated and purified by Prep HPLC to give the title compound (58 mg, 27%) as a pale yellow solid.

$^1$H NMR (DMSO-d$_6$): δ 1.62–1.82 (m, 12H), 2.03–2.11 (m, 8H), 2.51 (m, 1H), 2.87 (d, 1H, J=17.5 Hz), 3.11 (d, 1H, J=17.5 Hz), 5.55 (s, 1H), 8.01 (d, 2H, J=5.8 Hz), 8.84 (d, 2H, J=5.8 Hz). ESIMS: MH$^+$ 467.15

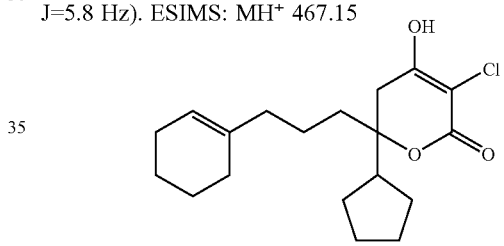

Step 1

3-Chloro-6-(2-cyclohex-1-enyl-ethyl)-6-cyclopentyl-4-hydroxy-5,6-dihydro-pyran-2-one Methyl-2-chloroacetoacetate (1.12 g, 7.42 mmol) was added to a cooled −40° C. suspension of NaH (0.3 g, 7.42 mmol, 60% dispersion in mineral oil) in THF (15 ml). After 20 min n-BuLi (3.0 mL, 7.42 mmol, 2.5M in hexanes) was added. The resulting dianion was stirred for an additional 30 min and then treated with a solution of 3-Cyclohex-1-enyl-1-cyclopentyl-propan-1-one (0.51 g, 2.47 mmol,) in THF (10 ml). After stirring for 2 h at −40° C., the reaction mixture was quenched with saturated NH$_4$Cl and extracted with EtOAc. The organic layers were washed with brine, dried with Na$_2$SO$_4$ and concentrated to a yellow oil that was used without further purification.

The oil was dissolved in toluene (8 mL), treated with bis(dibutylchlorotin)oxide (0.61 g, 1.1 mmol), and heated to 100° C. under N$_2$ for 1 h. The resulting mixture was concentrated and purified by silica gel chromatography to give the title compound (0.31 g, 38% yield).

$^1$H NMR (CDCl$_3$): δ 1.41–1.72 (m, 12H), 1.75–2.0 (m, 8H), 2.31 (m, 1H), 2.63 (d, 1H, J=17.8 Hz), 2.85 (d, 1H, J=17.8 Hz), 5.40 (s, 1H), 6.47 (br s, 1H). ESIMS: MH$^+$ 325.20.

Example C(5)

3-(5-Chloro-1-isopropyl-1H-benzoimidazol-2-ylsulfanyl)-6-(2-cyclohex-1-enyl-ethyl)-6-cyclopentyl-4-hydroxy-5,6-dihydro-pyran-2-one

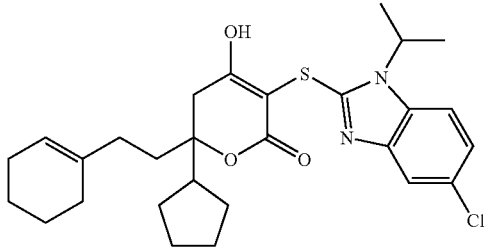

The title compound was prepared analogously to example C(4), where 5-Chloro-1-isopropyl-1H-benzoimidazole-2-thiol was substituted in place of 5-Pyridin-4-yl-4H-[1,2,4]triazole-3-thiol.

$^1$HNMR(DMSO-d$_6$): δ 1.50–1.67 (m, 18H), 1.91–1.98 (m, 7H), 2.16 (m, 1H), 2.37 (m, 1H), 2.59 (d, 1H, J=17.5 Hz), 2.92 (d, 1H, J=17.5 Hz), 4.14 (m, 1H), 5.43 (s, 1H), 8.67 (d, 1H, J=8.7 Hz), 7.32 (s, 1H), 7.66 (d, 1H, J=8.7 Hz). Anal. Calcd. For C$_{28}$H$_{35}$N$_2$O$_3$SCl.0.3 H$_2$O: C, 64.61; H, 6.89; N, 5.38. Found: C, 64.57; H, 6.97; N, 5.18.

Example C(6)

6-[2-(3-Chloro-4-methoxy-phenyl)-ethyl]-6-cyclopentyl-4-hydroxy-3-(5-hydroxy-4-isopropyl-4H-[1,2,4]triazol-3-ylsulfanyl)-5,6-dihydro-pyran-2-one The title compound was prepared analogously to example C(40), where 4-Isopropyl-5-mercapto-4H-[1,2,4]triazol-3-ol was substituted in place of 5-chloro-1-isopropyl-1H-benzoimidazole-2-thiol.

$^1$H NMR (DMSO-d$_6$): δ 1.50 (d, 6H, J=6.8 Hz) 1.42–1.67 (br m, 9H), 1.96 (m, 2H), 2.40 (m, 1H), 2.51 (m, 1H), 2.73 (d, 1H, J=17.7 Hz), 2.90 (d, 1H, J=17.7 Hz), 3.82 (s, 3H), 4.33 (m, 1H), 7.08 (m, 2H), 7.26 (s, 1H), 11.60 (s, 1H), 12.31 (br s, 1H). Anal. Calcd. For C$_{24}$H$_{28}$N$_3$O$_6$ClS: C, 55.22; H, 5.41; N, 8.05. Found: C, 55.02; H, 5.42; N, 8.17.

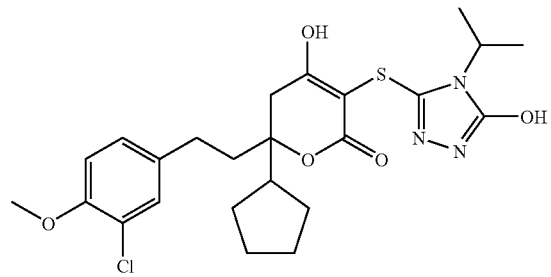

Example C(7)

6-Cyclopentyl-3-(5,7-dimethyl-[1,2,4]triazolo[1,5-a]pyrimidin-2-ylsulfanyl)-6-[2-(3-fluoro-4-isopropoxy-phenyl)-ethyl]-4-hydroxy-5,6-dihydro-pyran-2-one

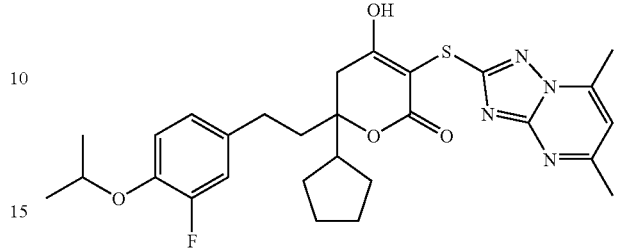

The title compound was prepared analogously to example C(64), where 5,7-Dimethyl-[1,2,4]triazolo[1,5-a]pyrimidine-2-thiol was substituted in place of 5-chloro-1-methyl-1H-benzimidazole-2-thiol.

$^1$H NMR (DMSO-d$_6$): δ 1.26 (d, 6H, J=6.0 Hz), 1.44–1.73 (br m, 9H), 2.21 (m, 2H), 2.39 (s, 3H), 2.53 (s, 3H), 2.58 (m, 2H), 2.71 (d, 1H, J=17.6 Hz), 2.90 (d, 1H, J=17.6 Hz), 4.53 (s, 1H), 7.04–7.13 (m, 4H). Anal. Calcd. For C$_{28}$H$_{33}$N$_4$O$_4$FS.0.4 AcOH: C, 61.26; H, 6.18; N, 9.92. Found: C, 61.33; H, 6.40; N, 9.70.

Example C(8)

6-Cyclopentyl-6-[2-(3-fluoro-4-isopropoxy-phenyl)-ethyl]-4-hydroxy-3-(4-hydroxy-phenylsulfanyl)-5,6-dihydro-pyran-2-one

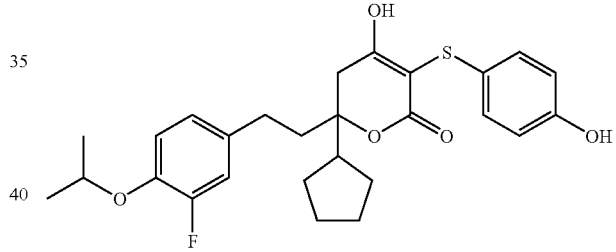

The title compound was prepared analogously to example C(64), where 4-Mercapto-phenol was substituted in place of 5-chloro-1-methyl-1H-benzimidazole-2-thiol.

$^1$H NMR (DMSO-d$_6$): δ 1.34(d, 6H, J=6.0 Hz) 1.43–1.76 (br m, 8H), 1.97 (m, 2H), 2.38 (m, 1H), 2.59 (m, 3H), 2.90 (d, 1H, J=17.9 Hz), 4.48 (m, 1H), 6.70 (d, 2H, J=7.8 Hz), 6.80 (m, 3H), 7.25 (d, 2H, J=7.8 Hz). Anal. Calcd. For C$_{27}$H$_{31}$O$_5$FS.0.8H$_2$O: C, 64.73; H, 6.56. Found: C, 64.54; H, 6.46.

Example C(9)

6-Cyclopentyl-6-[2-(3-fluoro-4-isopropoxy-phenyl)-ethyl]-4-hydroxy-3-(5-methyl-[1,3,4]thiadiazol-2-ylsulfanyl)-5,6-dihydro-pyran-2-one

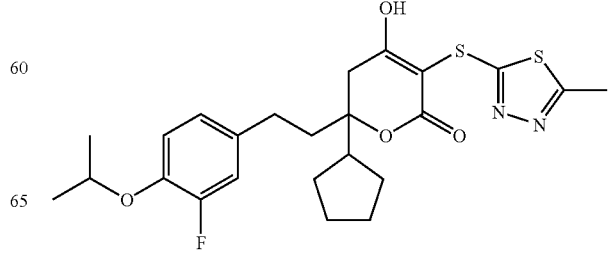

Example C(10)

5-{6-Cyclopentyl-6-[2-(3-fluoro-4-isopropoxy-phenyl)-ethyl]-4-hydroxy-2-oxo-5,6-dihydro-2H-pyran-3-ylsulfanyl}-4-methyl-4H-[1,2,4]triazole-3-carboxylic acid methyl ester

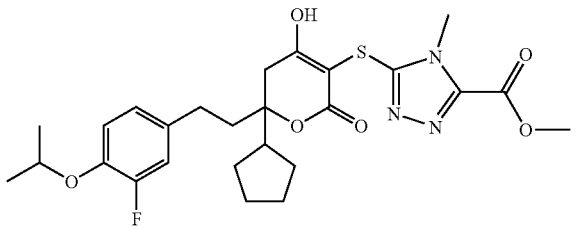

The title compound was prepared analogously to example C(64), where 5-Mercapto-4-methyl-4H-[1,2,4]triazole-3-carboxylic acid methyl ester was substituted in place of 5-chloro-1-methyl-1H-benzimidazole-2-thiol.

$^1$H NMR (DMSO-$d_6$): δ 1.31 (d, 6H, J=6.0 Hz) 1.37–1.74 (br m, 9H), 2.05 (m, 2H), 2.46 (m, 1H), 2.59 (m, 1H), 2.74 (d, 1H, J=17.6 Hz), 2.97 (d, 1H, J=17.7 Hz), 3.85 (s, 3H), 3.94 (s, 3H), 4.58 (m, 1H), 6.99–7.15 (m, 3H). Anal. Calcd. For $C_{26}H_{32}N_3O_6FS$·0.3$H_2O$: C, 57.93; H, 6.10; N, 7.80. Found: C, 57.89; H, 6.08; N, 7.64.

Example C(11)

6-Cyclopentyl-6-[2-(3-fluoro-4-isopropoxy-phenyl)-ethyl]-4-hydroxy-3-(pyrimidin-2-ylsulfanyl)-5,6-dihydro-pyran-2-one

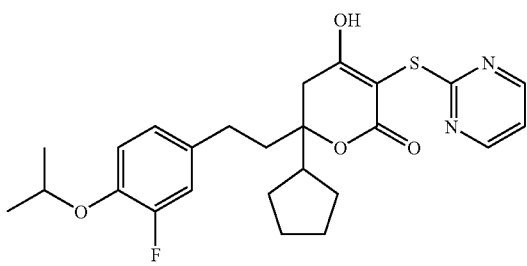

The title compound was prepared analogously to example C(64), where Pyrimidine-2-thiol was substituted in place of 5-chloro-1-methyl-1H-benzimidazole-2-thiol.

$^1$H NMR (DMSO-$d_6$): δ 1.27 (d, 6H, J=6.0 Hz) 1.37–1.74 (br m, 9H), 2.20 (m, 2H), 2.60 (m, 2H), 2.73 (d, 1H, J=17.6 Hz), 2.94 (d, 1H, J=17.6 Hz), 4.56 (m, 1H), 6.95 (d, 1H, J=8.3 Hz), 7.06 (m, 2H), 7.14 (t, 1H, J=4.7 Hz), 8.40 (d, 2H, J=4.8 Hz). Anal. Calcd. For $C_{25}H_{29}N_2O_4FS$·0.3$H_2O$: C, 62.82; H, 6.24; N, 5.86. Found: C, 62.76; H, 6.25; N, 5.75.

Example C(12)

6-Cyclopentyl-6-[2-(3-fluoro-4-isopropoxy-phenyl)-ethyl]-4-hydroxy-3-(5-hydroxy-4-isopropyl-4H-[1,2,4]triazol-3-ylsulfanyl)-5,6-dihydro-pyran-2-one

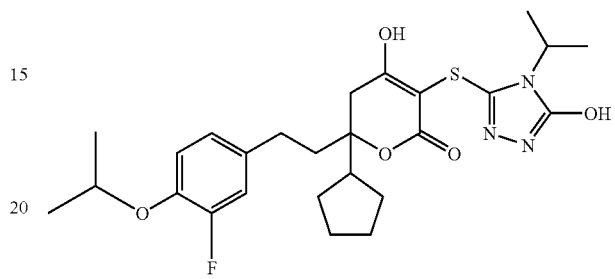

The title compound was prepared analogously to example C(64), where 4-Isopropyl-5-mercapto-4H-[1,2,4]triazol-3-ol was substituted in place of 5-chloro-1-methyl-1H-benzimidazole-2-thiol.

$^1$H NMR (DMSO-$d_6$): δ 1.27 (d, 6H, J=6.0 Hz), 1.39 (d, 6H, J=7.0 Hz), 1.45–1.66 (br m, 9H), 1.96 (m, 2H), 2.4 (m, 1H), 2.54 (1H), 2.73 (d, 1H, J=17.8 Hz), 2.88 (d, 1H, J=17.7 Hz), 4.33 (m, 1H), 4.54 (m, 1H), 6.90 (d, 1H, J=8.3 Hz), 7.02–7.11 (m, 2H). Anal. Calcd. For $C_{26}H_{34}N_3O_5FS$·0.3$H_2O$: C, 59.48; H, 6.64; N, 8.00. Found: C, 59.58; H, 6.64; N, 7.99.

Example C(13)

6-Cyclopentyl-6-{2-[4-(3,5-dimethyl-isoxazol-4-yl)-phenyl]-ethyl}-3-(5,7-dimethyl-[1,2,4]triazolo[1,5-a]pyrimidin-2-ylsulfanyl)-4-hydroxy-5,6-dihydro-pyran-2-one

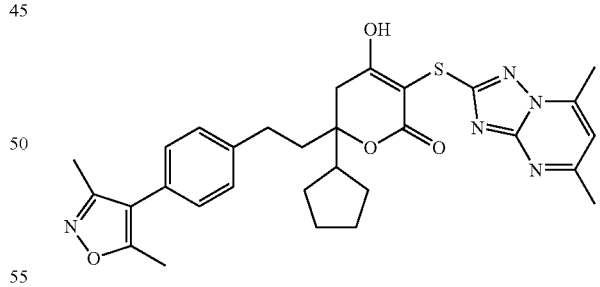

The title compound was prepared from 3-Chloro-6-cyclopentyl-6{2-[4-(3,5-dimethyl-isoxazol-4-yl)-phenyl]-ethyl}4-hydroxy-5,6-dihydro-pyran-2-one from Step 2 and 5,7-Dimethyl-[1,2,4]triazolo[1,5-a]pyrimidine-2-thiol using the coupling method described in Example C(4).

$^1$H NMR (DMSO-$d_6$): δ 1.44–1.75 (br m, 9H), 2.21 (s, 3H), 2.34 (s, 3H), 2.38 (s, 3H), 2.59 (s, 3H), 2.65–2.79 (m, 3H), 2.97 (d, 1H, J=17.0 Hz), 3.17 (s, 2H), 7.02 (s, 10H), 7.29 (d, 2H, J=8.1 Hz), 7.40 (d, 2H, J=8.1 Hz). Anal. Calcd. For $C_{30}H_{33}N_5O_4S$·0.75 AcOH: C, 62.56; H, 6.00; N, 11.58. Found: C, 62.66; H, 5.98; N, 11.56.

Step 1

1-Cyclopentyl-3-[4-(3,5-dimethyl-isoxazol-4-yl)-phenyl]-propan-1-one

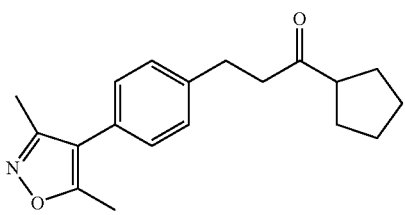

The title compound was prepared as described in Step 1 of Example A(82), where 4-(4-Bromo-phenyl)-3,5-dimethyl-isoxazole from Step 1 of Example A(18), was substituted for 2-Bromopyridine.

Step 2

3-Chloro-6-cyclopentyl-6-{2-[4-(3,5-dimethyl-isoxazol-4-yl)-phenyl]-ethyl}-4-hydroxy-5,6-dihydro-pyran-2-one

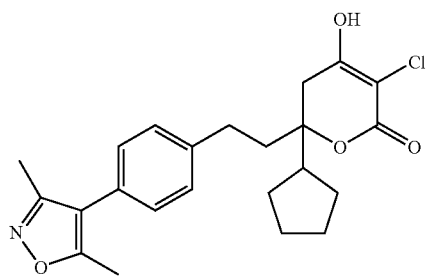

The title compound was prepared as described in Step 1 of Example C(4), where 1-Cyclopentyl-3-[4-(3,5-dimethyl-isoxazol-4-yl)-phenyl]-propan-1-one was substituted for 3-Cyclohex-1-enyl-1-cyclopentyl-propan-1-one).

Example C(14)

3-(5-Chloro-1-methyl-1H-benzoimidazol-2-ylsulfanyl)-6-cyclopentyl-6-{2-[4-(3,5-dimethyl-isoxazol-4-yl)-phenyl]-ethyl}-4-hydroxy-5,6-dihydro-pyran-2-one

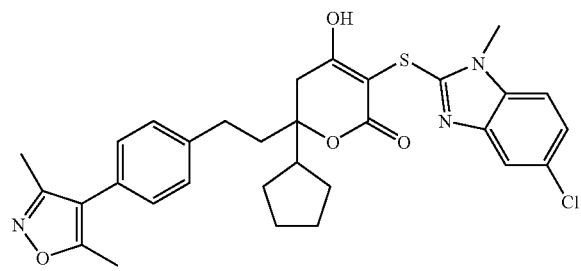

The title compound was prepared analogously to example C(13) where 5-Chloro-1-methyl-1H-benzoimidazole-2-thiol was substituted in place of 5,7-Dimethyl-[1,2,4]triazolo[1,5-a]pyrimidine-2-thiol.

$^1$H NMR (CDCl$_3$): δ 1.27–1.74 (br m, 9H), 2.09 (m, 2H), 2.25 (s, 3H), 2.38 (s, 3H), 2.39 (m, 1H), 2.70 (m, 3H), 3.93 (s, 3H), 7.14 (d, 2H, J=8.1 Hz), 7.21 (d, 2H, J=8.1 Hz), 7.26–7.34 (m, 2H), 7.55 (s, 1H). Anal. Calcd. For C$_{31}$H$_{32}$N$_3$O$_4$SCl.0.7H$_2$O: C, 63.03; H, 5.70; N, 7.11. Found: C, 63.01; H, 5.75; N, 6.97.

Example C(15)

3-(5-Chloro-1-isopropyl-1H-benzoimidazol-2-ylsulfanyl)-6-ethyl-4-hydroxy-6-[2-(4-methoxy-phenyl)-ethyl]-5,6-dihydro-pyran-2-one

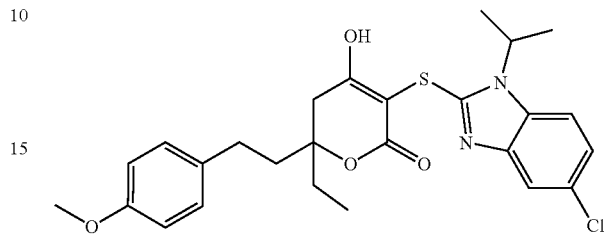

The title compound was prepared from 3-Chloro-6-ethyl-4-hydroxy-6-[2-(4-methoxy-phenyl)-ethyl]-5,6-dihydro-pyran-2-one from Step 1 and 5-Chloro-1-isopropyl-1H-benzoimidazole-2-thiol using the coupling method described in Example C(4), $^1$H NMR (CDCl$_3$): δ 0.96 (t, 3H, J=7.5 Hz), 1.69 (d, 6H, J=7.0 Hz), 1.85 (m, 2H), 1.98 (m, 2H), 2.59 (m, 2H), 2.71 (s, 2H), 3.78 (s, 3H), 5.16 (m, 1H), 6.81 (d, 2H, J=8.5 Hz), 7.06 (d, 2H, J=8.5 Hz), 7.28 (d, 2H, J=8.9 Hz), 7.48 (d, 1H, J=8.9 Hz), 7.59 (s, 1H). ESIMS: MH$^+$501.10, 503.10, MH$^-$4.99.10, 501.10.

Step 1

3-Chloro-6-ethyl-4-hydroxy-6-[2-(4-methoxy-phenyl)-ethyl]-5,6-dihydro-pyran-2-one

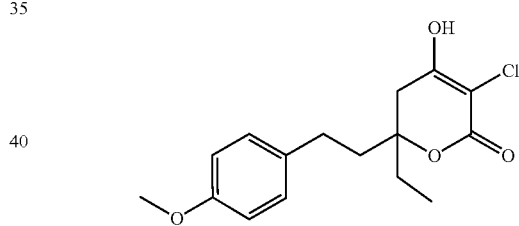

The title compound was prepared as described in Step 1 of Example C(4), where 1-(4-Methoxy-phenyl)-pentan-3-one (from Step 2 of Example A(23)) was substituted in place of cyclohex-1-enyl-1-cyclopentyl-propan-1-one.

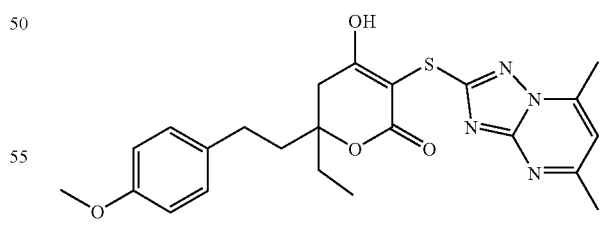

Example C(16): 3-(5,7-Dimethyl-[1,2,4]triazolo[1,5-a]pyrimidin-2-ylsulfanyl)-6-ethyl-4-hydroxy-6-[2-(4-methoxy-phenyl)-ethyl]-5,6-dihydro-pyran-2-one The title compound was prepared analogously to Example C(15) where 5,7-Dimethyl-[1,2,4]triazolo[1,5-a]pyrimidine-2-thiol was substituted in place of 5-Chloro-1-isopropyl-1H-benzoimidazole-2-thiol.

$^1$H NMR (CDCl$_3$): δ 1.01 (t, 3H, J=7.4 Hz), 1.97 (m, 2H), 2.10 (m, 2H), 2.62 (s, 3H), 2.63 (s, 3H), 2.68 (m, 2H), 2.83 (s, 2H), 3.78 (s, 3H), 6.76 (s, 1H), 6.82 (d, 2H, J=8.5 Hz), 7.12 (d, 2H, J=8.5 Hz). Anal. Calcd. For C$_{23}$H$_{26}$N$_4$O$_4$S.0.6H$_2$O: C, 59.36; H, 5.89; N, 12.04. Found: C, 59.26; H, 5.76; N, 11.52.

Example C(17)

6-Cyclopentyl-3-(5,7-dimethyl-[1,2,4]triazolo[1,5-apyrimidin-2-ylsulfanyl)-4-hydroxy-6-methyl-5,6-dihydro-pyran-2-one

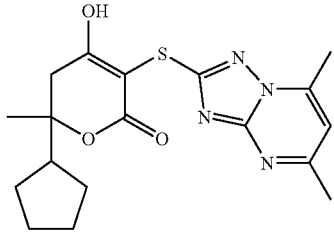

The title compound was prepared from 3-Chloro-6-cyclopentyl-4-hydroxy-6-methyl-5,6-dihydro-pyran-2-one (described in Step 2 below) and 5,7-Dimethyl-[1,2,4]triazolo[1,5-a]pyrimidine-2-thiol using the coupling method described in Example C(4). $^1$H NMR (CDCl$_3$): δ 1.54 (s, 3H), 1.55–2.32 (br m, 9H), 2.59 (m 1H), 2.64 (s, 3H), 2.71 (s, 3H), 2.96 (m, 1H), 6.77 (s, 1H). ESIMS: MH$^+$375.10, MH$^-$373.10.

Step 1

1-Cyclopentyl-ethanone

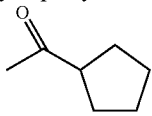

Cyclopentylmagnesium bromide (5 mL, 10 mmol, 2M soln in THF) was added to a cooled −78° C. solution of acetic anhydride (0.8 mL, 8.33 mmol) dissolved in THF (20 mL). The reaction mixture was stirred for 60 min. The reaction was quenched with saturated NH$_4$Cl and extracted with EtOAc. The organic layers were washed with brine, dried over Na$_2$SO$_4$ and concentrated to a yellow oil. The residue was purified by silica gel chromatography (hexanes) to give the title compound as an oil (0.5 g, 54%).

$^1$H NMR (CDCl$_3$): δ 1.55–1.84 (br m, 8H), 2.16 (s, 3H), 2.87 (m, 1H).

Step 2

3-Chloro-6-cyclopentyl-4-hydroxy-6-methyl-5,6-dihydro-pyran-2-one

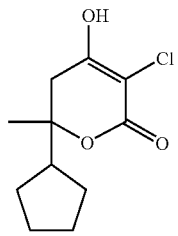

The title compound was prepared as described in Step 1 of Example C(4), where 1-Cyclopentyl-ethanone (from Step 1) was substituted in place of cyclohex-1-enyl-1-cyclopentyl-propan-1-one.
ESIMS: MH$^+$ 231.10, MH$^-$ 230.10.

Example C(18)

3-(5,7-Dimethyl-[1,2,4]triazolo[1,5-a]pyrimidin-2-ylsulfanyl)-6,6-diethyl-4-hydroxy-5,6-dihydro-pyran-2-one

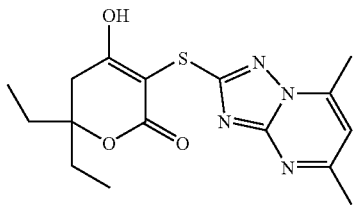

The title compound was prepared from 3-Chloro-6,6-diethyl-4-hydroxy-5,6-dihydro-pyran-2-one (from Step 1) and 5,7-Dimethyl-[1,2,4]triazolo[1,5-a]pyrimidine-2-thiol using the coupling method described in Example C(4). $^1$H NMR (CDCl$_3$): δ 0.97 (t, 6H, J=7.5 Hz), 1.85 (m, 2H), 1.94 (m, 2H), 2.63 (s, 3H), 2.71 (s, 3H), 2.78 (s, 2H), 6.78 (s, 1H). Anal. Calcd. For C$_{16}$H$_{20}$N$_4$O$_3$S.0.5H$_2$O: C, 53.76; H, 5.92; N, 15.68. Found: C, 53.96; H, 5.84; N, 15.37.

Step 1

3-Chloro-6,6-diethyl-4-hydroxy-5,6-dihydro-pyran-2-one

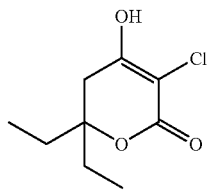

The title compound was prepared as described in Step 1 of Example C(4), where 3-pentanone was substituted in place of cyclohex-1-enyl-1-cyclopentyl-propan-1-one.

Example C(19)

3-(5-Chloro-1-isopropyl-1H-benzoimidazol-2-ylsulfanyl)-6,6-diethyl-4-hydroxy-5,6-dihydro-pyran-2-one

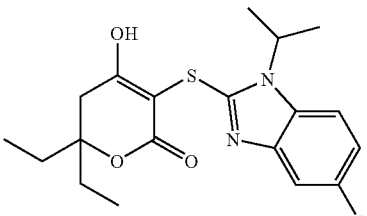

The title compound was prepared analogously to Example C(18) where 5-Chloro-1-isopropyl-1H-benzoimidazole-2- thiol was substituted in place of 5,7-Dimethyl-[1,2,4]triazolo[1,5-a]pyrimidine-2-thiol. $^1$H NMR (CDCl$_3$): δ 0.91 (t, 6H, J=7.4 Hz), 1.68 (d, 6H, J=7.0 Hz), 1.69–1.85 (m, 4H), 2.64 (s, 2H), 5.16 (m, 1H), 6.34 (br s, 1H), 7.28 (d, 1H, J=8.9 Hz), 7.48 (d, 1H, J=8.9 Hz), 7.59 (s, 1H). Anal. Calcd. For C$_{19}$H$_{23}$N$_2$O$_3$SCl.0.2H$_2$O: C, 57.26; H, 5.92; N, 7.03. Found: C, 57.31; H, 5.89; N, 7.02.

Example C(20)

3-(5-Chloro-1-isopropyl-1H-benzoimidazol-2-ylsulfanyl)-6-ethyl-4-hydroxy-6-methyl-5,6-dihydro-pyran-2-one

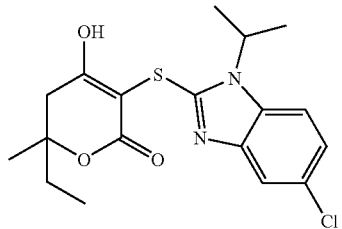

The title compound was prepared from 3-Chloro-6-ethyl-4-hydroxy-6-methyl-5,6-dihydro-pyran-2-one (from Step 1) and 5-Chloro-1-isopropyl-1H-benzoimidazole-2-thiol using the coupling method described in Example C(4).

$^1$H NMR (CDCl$_3$): δ 0.95 (t, 3H, J=7.5 Hz), 1.41 (s, 3H), 1.68 (d, 6H, J=7.0 Hz), 1.75 (m, 2H), 2.52 (d, 1H, J=17.1 Hz), 2.74 (d, 1H, J=17.1 Hz), 6.97 (m, 1H), 6.56 (br s, 1H), 7.28 (d, 1H, J=8.9 Hz), 7.48 (d, 1H, J=8.9 Hz), 7.60 (s, 1H). Anal. Calcd. For C$_{18}$H$_{21}$N$_2$O$_3$SCl.0.1H$_2$O: C, 56.49; H, 5.58; N, 7.32. Found: C, 56.32; H, 5.56; N, 7.17.

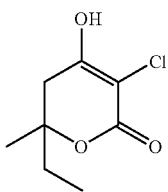

Step 1: 3-Chloro-6-ethyl-4-hydroxy-6-methyl-5,6-dihydro-pyran-2-one.

The title compound was prepared as described in Step 1 of Example C(4), where 2-butanone was substituted in place of cyclohex-1-enyl-1-cyclopentyl-propan-1-one.

Example C(21)

3-(5,7-Dimethyl-[1,2,4]triazolo[1,5-a]pyrimidin-2-ylsulfanyl)-6-ethyl-4-hydroxy-6-methyl-5,6-dihydro-pyran-2-one

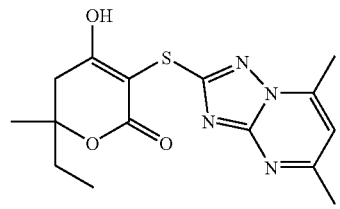

The title compound was prepared analogously to Example C(20) where 5,7-Dimethyl-[1,2,4]triazolo[1,5-a]pyrimidine-2-thiol was substituted in place of 5-Chloro-1-isopropyl-1H-benzoimidazole-2-thiol.

$^1$H NMR (CDCl$_3$): δ 1.01 (t, 3H, J=7.4 Hz), 1.54 (s, 3H), 1.87 (m, 2H), 2.63 (s, 3H), 2.68 (d, 1H, J=17.5 Hz), 2.71 (s, 3H), 2.90 (d, 1H, J=17.5 Hz), 6.78 (m, 1H). Anal. Calcd. For C$_{15}$H$_{18}$N$_4$O$_3$S.0.4AcOH: C, 52.94; H, 5.51; N, 15.63. Found: C, 52.63; H, 5.43; N, 15.92.

Example C(22)

6-[2-(3-Chloro-4-methoxy-phenyl)-ethyl]-6-cyclopentyl-3-(5-phenyl-4H-[1,2,4]triazol-3-ylsulfanyl)-dihydro-pyran-2,4-dione

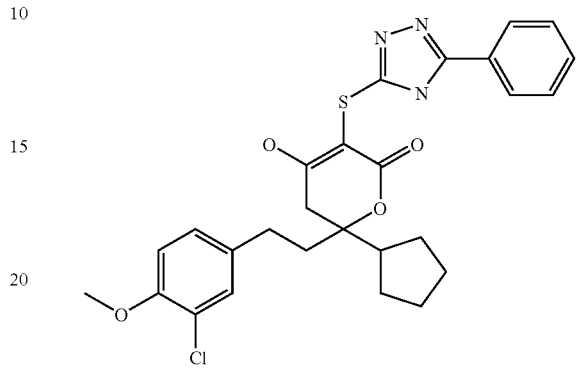

The title compound was prepared analogously to Example C(4), where 3-Chloro-6-[2-(3-chloro-4-methoxy-phenyl)-ethyl]-6-cyclopentyl-4-hydroxy-5,6-dihydro-pyran-2-one Step 1 of example C(40), was substituted in place of 3-Chloro-6-(2-cyclohex-1-enyl-ethyl)-6-cyclopentyl-4-hydroxy-5,6-dihydro-pyran-2-one and 5-Phenyl-1H-1,2,4-triazole-3-thiol was substituted in place of 5-Pyridin-4-yl-4H-[1,2,4]triazole-3-thiol of that example.

$^1$H NMR (DMSO-d$_6$): δ 1.53–1.85 (m, 10H), 2.17–2.34 (m, 1H), 2.69–2.75 (m 2H), 2.95 (d, J=17.0, 1H), 3.08 (d, J=17.0 Hz, 1H), 3.90 (s, 3H), 7.08 (d, J=8.4 Hz, 1H) 7.22–7.26 (m, 1H), 7.40 (d, J=2.0 Hz, 1H), 7.40–7.53 (m, 4H), 7.91–7.94 (m, 2H), 12.0 (brs, 1H); Anal. Calcd. For C$_{27}$H$_{28}$ClN$_3$O$_4$S.1.0 HCl.1.0 H$_2$O: C, 55.86; H, 5.38; N, 7.24. Found: C, 55.75; H, 5.17; N, 7.17. ESIMS (MH+): 527.

Example C(23)

6-[2-(3-Chloro-4-methoxy-phenyl)-ethyl]-6-cyclopentyl-3-[5-(4-hydroxy-phenyl)-4H-[1,2,4]triazol-3-ylsulfanyl]-dihydro-pyran-2,4-dione

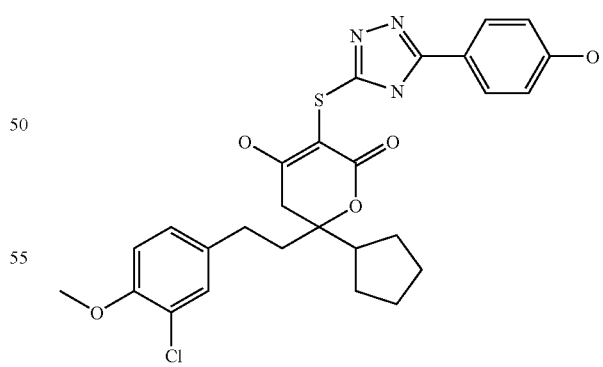

The title compound was prepared analogously to Example C(4), where 3-Chloro-6-[2-(3-chloro-4-methoxy-phenyl)-ethyl]-6-cyclopentyl-4-hydroxy-5,6-dihydro-pyran-2-one example C(40), was substituted in place of 3-Chloro-6-(2-cyclohex-1-enyl-ethyl)-6-cyclopentyl-4-hydroxy-5,6-dihydro-pyran-2-one and 4H-3-mercapto-5-(4-hydroxyphenyl)[1,2,4]-triazole was substituted in place of 5-Pyridin-4-yl-4H-[1,2,4]triazole-3-thiol of that example.

¹H NMR (DMSO-d₆): δ 1.47–1.76 (m, 10H), 2.04–2.23 (m, 1H), 2.58–2.64 (m 2H), 2.83 (d, J=17.0, 1H), 2.94 (d, J=17.0 Hz, 1H), 3.81 (s, 3H), 6.76 (d, J=8.7 Hz, 1H) 6.98 (d, J=8.5 Hz, 2H), 7.13 (dd, J=8.5, 2.0 Hz, 1H), 7.29 (d, J=2.0 Hz, 1H), 7.65 (d, J=8.7 Hz, 2H), 9.88 (s, 1H), 12.0 (brs, 1H); Anal. Calcd. For $C_{27}H_{28}ClN_3O_5S \cdot 1.0$ $HCl \cdot 1.0H_2O$: C, 54.36; H, 5.24; N, 7.04. Found: C, 54.38; H, 5.02; N, 7.24. ESIMS (MH+): 543.

Example C(24)

6-Cyclopentyl-6-[2-(3-fluoro-4-isopropoxy-phenyl)-ethyl]-4-hydroxy-3-(5-phenyl-4H-[1,2,4]triazol-3-ylsulfanyl)-5,6-dihydro-pyran-2-one

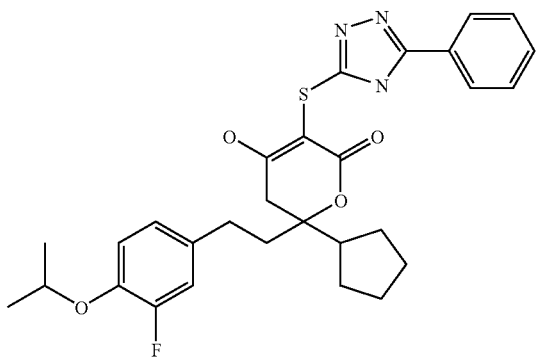

The title compound was prepared analogously to Example C(4), where 3-Chloro-6-[2-(3-chloro-4-isopropoxy-phenyl)-ethyl]-6-cyclopentyl-4-hydroxy-5,6-dihydro-pyran-2-one (from Step 1 below) was substituted in place of 3-Chloro-6-(2-cyclohex-1-enyl-ethyl)-6-cyclopentyl-4-hydroxy-5,6-dihydro-pyran-2-one and 5-Chloro-1-isopropyl-2-mercapto benzimidazole was substituted in place of 5-Pyridin-4-yl-4H-[1,2,4]triazole-3-thiol of that example.

¹H NMR (DMSO-d₆): δ 1.24 (d, J=6.0 Hz, 6H), 1.39–1.73 (m, 10H), 1.97–2.00 (m, 1H), 2.58–2.62 (m 2H), 2.81 (d, J=17.0, 1H), 2.96 (d, J=17.0 Hz, 1H), 4.46–4.54 (m, 1H), 6.91–7.09 (m, 3H), 7.38–7.41 (m, 3H), 7.82–7.84 (m, 2H), 14.2 (brs, 1H); Anal. Calcd. For $C_{29}H_{32}FN_3O_4S$: C, 64.79; H, 6.0; N, 7.82. Found: C, 64.52; H, 6.16; N, 7.75. ESIMS (MH+): 538.

Example C(25)

6-[2-(3-Chloro-4-isopropoxy-phenyl)-ethyl]-3-(5-chloro-1-isopropyl-1H-benzoimidazol-2-ylsulfanyl)-6-yclopentyl-4-hydroxy-5,6-dihydro-pyran-2-one

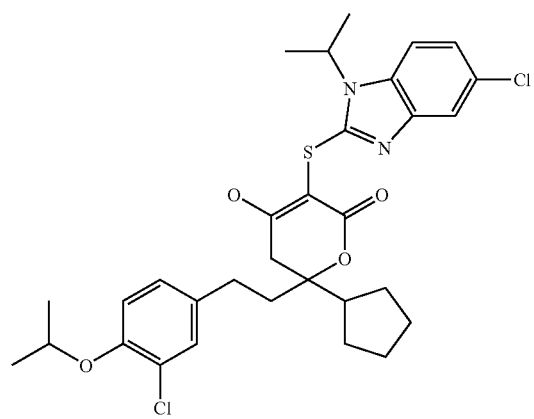

The title compound was prepared analogously to Example C(4), where 3-Chloro-6-[2-(3-chloro-4-isopropoxy-phenyl)-ethyl]-6-cyclopentyl-4-hydroxy-5,6-dihydro-pyran-2-one (from Step 1 below) was substituted in place of 3-Chloro-6-(2-cyclohex-1-enyl-ethyl)-6-cyclopentyl-4-hydroxy-5,6-dihydro-pyran-2-one and 5-Chloro-1-isopropyl-2-mercapto benzimidazole was substituted in place of 5-Pyridin-4-yl-4H-[1,2,4]triazole-3-thiol of that example.

¹H NMR (DMSO-d₆): δ 1.13 (d, J=6.1 Hz, 6H), 1.41 (d, J=7.1 Hz, 6H), 1.42–1.8 (m, 10H), 2.08–2.13 (m, 1H), 2.43–2.54 (m 3H), 2.79 (d, J=17.0, 1H), 4.44–4.48 (m, 1H), 4.63–4.69 (m, 1H), 6.89–6.91 (m, 2H), 6.95–7.00 (m, 2H), 7.14 (s, 1H), 7.49 (d, J=8.6 Hz, 1H), 12.0 (brs, 1H); Anal. Calcd. For $C_{31}H_{36}Cl_2N_2O_4S \cdot 1.0$ AcOH: C, 59.72; H, 6.07; N, 4.22. Found: C, 59.50; H, 6.16; N, 4.33. ESIMS (MH+): 604.

Step 1

3-Chloro-6-[2-(3-chloro 4-isopropoxy-phenyl)-ethyl]-6-cyclopentyl-4-hydroxy-5,6-dihydro-pyran-2-one

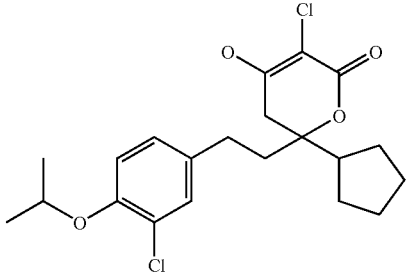

The pyrone intermediate, was prepared analogously to Example C(4), where 3-(3-Chloro-4-isopropoxy-phenyl)-1-cyclopentyl-propan-1-one (from Step 2 below) was substituted in place of 3-Cyclohex-1-enyl-1-cyclopentyl-propan-1-one in Step 1 of that example.

Step 2

3-(3-Chloro-4-isopropoxy-phenyl)-1-cyclopentyl-propan-1-one

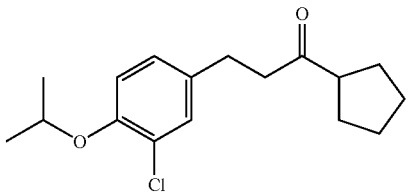

The ketone intermediate, was prepared analogously to Example A(27), where 4-Bromo-2-chloro-1-isopropoxy-benzene (from Step 3 below) was substituted in place of 3-Cyclohex-1-enyl-1-cyclopentyl-propan-1-one in Step 1 of that example.

Step 3

4-Bromo-2-chloro-1-isopropoxy-benzene

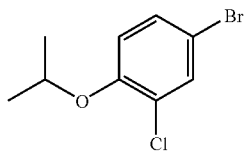

The intermediate bromide, was prepared analogously to Step 1 in Example A(52), where 4-Bromo-2-chloro-phenol was substituted in place of 4-bromo-2-fluorophenol and 2-iodopropane instead of methyl □-bromobutyrate of that example.

Example C(26)

3-(5-Chloro-1H-benzoimidazol-2-ylsulfanyl)-6-[2-(3-chloro-4-isopropoxy-phenyl)-ethyl]-6-cyclopentyl-4-hydroxy-5,6-dihydro-pyran-2-one

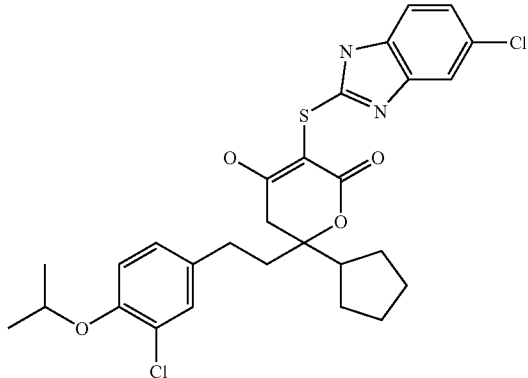

The title compound was prepared analogously to Example C(4), where 3-Chloro-6-[2-(3-chloro-4-isopropoxy-phenyl)-ethyl]-6-cyclopentyl-4-hydroxy-5,6-dihydro-pyran-2-one was substituted in place of 3-Chloro-6-(2-cyclohex-1-enyl-ethyl)-6-cyclopentyl-4-hydroxy-5,6-dihydro-pyran-2-one and 5-Chloro-benzimidazole-2-thiol was substituted in place of 5-Pyridin-4-yl-4H-[1,2,4]triazole-3-thiol of that example.

$^1$H NMR (DMSO-d$_6$): δ 1.34 (d, J=6.1 Hz, 6H), 1.41–1.82 (m, 10H), 2.07–2.14 (m, 1H), 2.55–2.88 (m, 4H), 3.4 (brs, 1H), 4.44–4.48 (m, 1H), 6.81–6.91 (m, 2H), 7.13–7.39 (m, 4H), 12.0 (brs, 1H); ESIMS (MH+) (C$_{28}$H$_{30}$Cl$_2$N$_2$O$_4$S): 562.

Example C(27)

6-(2-Cyclohexyl-ethyl)-6-cyclopentyl-4-hydroxy-3-(5-pyridin-4-yl-4H-1,2,4]triazol-3-ylsulfanyl)-5,6-dihydro-pyran-2-one

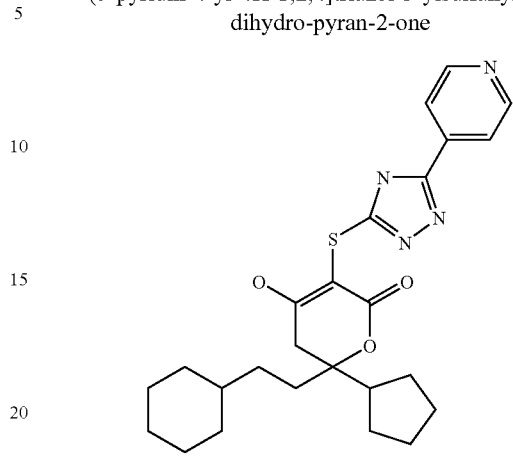

The title compound was prepared analogously to Example C(4), where 3-Cyclohexyl-1-cyclopentyl-propan-1-one from Step 2 of Example A(44), was substituted in place of 3-Cyclohex-1-enyl-1-cyclopentyl-propan-1-one in Step 1 of that example.

$^1$H NMR (CDCl3): δ 0.5–3.4 (m, 28H), 7.84 (d, J=6.0, 2H), 8.66 (d, J=6.0, 2H); Anal. Calcd. For C$_{25}$H$_{32}$N$_4$O$_3$S: C, 64.08; H, 6.88; N, 11.96. Found: C, 64.30; H, 6.68; N=11.90. ESIMS (MH+): 345.

Example C(28)

6-Cyclopentyl-6-(2-cyclopentyl-ethyl)-4-hydroxy-3-(5-pyridin-4-yl-4H-[1,2,4]triazol-3-ylsulfanyl)-5,6-dihydro-pyran-2-one

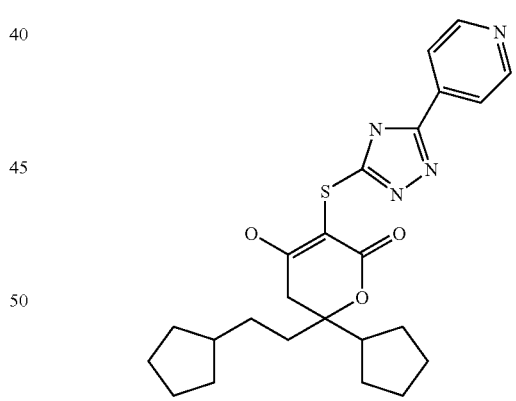

The title compound was prepared analogously to Example C(4), where 3-Chloro-6-cyclopentyl-6-(2-cyclopentyl-ethyl)-4-hydroxy-5,6-dihydro-pyran-2-one (from Step 2 below) was substituted in place of 3-Chloro-6-(2-cyclohex-1-enyl-ethyl)-6-cyclopentyl-4-hydroxy-5,6-dihydro-pyran-2-one of that example.

$^1$H NMR (DMSO-d$_6$): 60.96–1.86 (m, 21H), 2.24–2.26 (m, 1H), 2.61 (d, J=17.0, 1H), 2.90 (d, J=17.0, 1H), 3.31 (brs, 1H), 7.80–7.88 (m, 2H), 8.61–8.71 (m, 2H), 14.0 (brs, 1H); Anal. Calcd. For C$_{24}$H$_{30}$N$_4$O$_3$S: C, 63.41; H, 6.65; N, 12.32. Found: C, 63.20; H, 6.90; N, 12.60. ESIMS (MH+): 454.

Step: 1

4-Cyclopentyl-1-cyclopentyl-butan-1-one

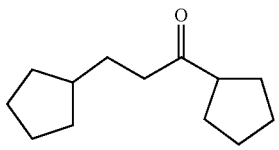

The title compound was prepared analogously to Example A(44), where 3-cyclopentyl propionic acid was substituted in place of 3-cyclohexylpropionic acid in Step 1 of that example.

$^1$H NMR (DMSO-d$_6$):δ 0.79–0.91 (m, 2H), 1.11–1.24 (m, 5H), 1.55–1.88 (m, 12H), 2.41 (t, J=7.4, 2H), 2.81–2.91 (m, 1H).

Step 2

2-Chloro-5-cyclopentyl-5-(2-cyclopentyl-ethyl)-3-hydroxy-cyclohex-2-enone

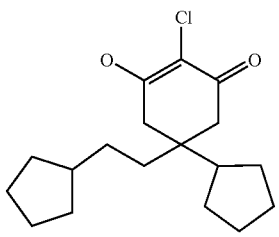

The title compound was prepared analogously to Example C(4), where 4-Cyclopentyl-1-cyclopentyl-butan-1-one from Step 1 above was substituted in place of 3-Cyclohex-1-enyl-1-cyclopentyl-propan-1-one of that example.

$^1$H NMR (CDCl$_3$): δ 0.86–1.73 (m, 23H), 2.24–2.31 (m, 1H), 2.62 (d, J=17, 1H), 2.83 (d, J=17, 1H). ESIMS (MH+): 311.

Example C(29)

3-(5-Chloro-1-isopropyl-1H-benzoimidazol-2-ylsulfanyl)-6-cyclopentyl-4-(2-cyclopentyl-ethyl)-4-hydroxy-5,6-dihydro-pyran-2-one

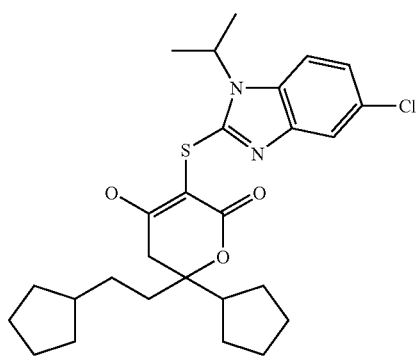

The title compound was prepared analogously to Example C(4), where 3-Chloro-6-cyclopentyl-6-(2-cyclopentyl-ethyl)-4-hydroxy-5,6-dihydro-pyran-2-one from Step 2 of example C(28) was substituted in place of 3-Chloro-6-(2-cyclohex-1-enyl-ethyl)-6-cyclopentyl-4-hydroxy-5,6-dihydro-pyran-2-one and 5-Chloro-1-isopropyl-2-mercapto benzimidazole was substituted in place of 5-Pyridin-4-yl-4H-[1,2,4]triazole-3-thiol of that example.

$^1$H NMR (DMSO-d$_6$): δ 0.84–2.28 (m, 28H), 2.31 (d, J=17.0, 1H), 2.66 (d, J=17.0, 1H), 3.96 (brs, 1H), 4.55–4.67 (m, 1H), 6.93 (d, J=8.5, 1H), 7.12 (s, 1H), 7.46 (d, J=8.5, 1H); Anal. Calcd. For C$_{27}$H$_{35}$ClN$_2$O$_3$S: C, 64.46; H, 7.01; N, 5.57. Found: C, 64.85; H, 7.30; N, 5.76. ESIMS (MH+): 504.

Example C(30)

6-(3-Cyclohexyl-propyl)-6-cyclopentyl-4-hydroxy-3-(5-pyridin-4-yl-4H-[1,2,4]triazol-3-ylsulfanyl)-5,6-dihydro-pyran-2-one

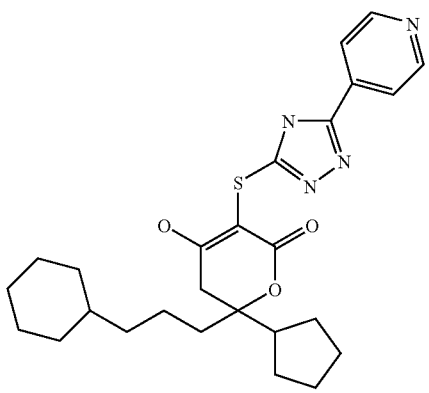

The title compound was prepared analogously to Example C(4), where 3-Chloro-6-(3-cyclohexyl-propyl)-6-cyclopentyl-4-hydroxy-5,6-dihydro-pyran-2-one (described in Step 2 below) was substituted in place of 3-Chloro-6-(2-cyclohex-1-enyl-ethyl)-6-cyclopentyl-4-hydroxy-5,6-dihydro-pyran-2-one of that example.

$^1$HNMR(DMSO-d$_6$): δ 0.5–1.86 (m, 25H), 2.08–2.10 (m, 1H), 2.42 (d, J=17.0, 1H), 2.71 (d, J=17.0, 1H), 3.11 (brs, 1H), 7.61 (d, J=5.8, 2H), 8.43 (d, J=4.5, 2H), 11.71 (brs, 1H); Anal. Calcd. For C$_{26}$H$_{34}$N$_4$O$_3$S.0.5 AcOH-0.75H$_2$O: C, 61.63; H, 7.18; N, 10.65. Found: C, 61.55; H, 7.06; N, 10.98. ESIMS (MH+): 483.

Step 1

4-Cyclohexyl-1-cyclopentyl-butan-1-one

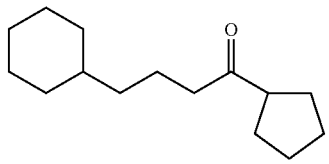

The title compound was prepared analogously to Example A(44), where cyclohexanebutyric acid was substituted in place of 3-cyclohexylpropionic acid in Step 1 of that example.

$^1$H NMR (DMSO-d$_6$): δ 0.79–0.91 (m, 2H), 1.11–1.27 (m, 7H), 1.55–1.85 (m, 14H), 2.41 (t, J=7.4, 2H), 2.81–2.91 (m, 1H).

Step 2

3-Chloro-6-(3-cyclohexyl-propyl)-6-cyclopentyl-4-hydroxy-5,6-dihydro-pyran-2-on

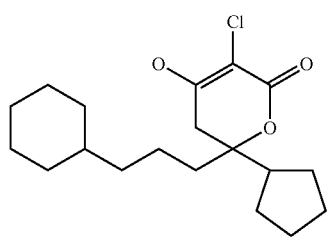

The title compound was prepared analogously to Example C(4), where 4-Cyclohexyl-1-cyclopentyl-butan-1-one from Step 1 above was substituted in place of 3-Cyclohex-1-enyl-1-cyclopentyl-propan-1-one of that example.

$^1$H NMR (CDCl$_3$): δ 0.86–1.75 (m, 26H), 2.27–2.32 (m, 1H), 2.61 (d, J=17, 1H), 2.83 (d, J=17, 1H). ESIMS (MH+): 341.

Example C(31)

3-(5-Chloro-1-isopropyl-1H-benzoimidazol-2-ylsulfanyl)-6-(3-cyclohexyl-propyl)-6-cyclopentyl-4-hydroxy-5,6-dihydro-pyran-2-one

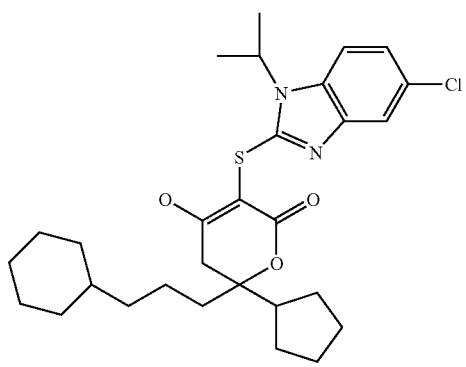

The title compound was prepared analogously to Example C(4), where 3-Chloro-6-(3-cyclohexyl-propyl)-6-cyclopentyl-4-hydroxy-5,6-dihydro-pyran-2-one (described in Step 2 of example C(30) was substituted in place of 3-Chloro-6-(2-cyclohex-1-enyl-ethyl)-6-cyclopentyl-4-hydroxy-5,6-dihydro-pyran-2-one and 5-Chloro-1-isopropyl-2-mercapto benzimidazole was substituted in place of 5-Pyridin-4-yl-4H-[1,2,4]triazole-3-thiol of that example.

$^1$H NMR (DMSO-d$_6$): δ 0.63–1.39 (m, 23H), 1.38 (d, J=6.9, 6H), 1.70–1.73 (m, 2H), 2.14–2.20 (m, 1H), 2.39 (d, J=17.0, 1H), 2.71 (d, J=17.0, 1H), 4.58–4.67 (m, 1H), 6.96 (dd, J=8.6, 2.1, 1H), 7.17 (d, J=2.1, 1H), 7.49 (d, J=8.6, 1H) 12.9 (brs, 1H); Anal. Calcd. For C$_{29}$H$_{39}$ClN$_2$O$_3$S.0.5H$_2$O: C, 64.48; H, 7.46; N, 5.19. Found: C, 64.69; H, 7.30; N, 5.15. ESIMS (MH+): 532.

Example C(32)

6-(4-Cyclohexyl-butyl)-6-cyclopentyl-4-hydroxy-3-(5-pyridin-4-yl-4H-[1,2,4]triazol-3-ylsulfanyl)-5,6-dihydro-pyran-2-one

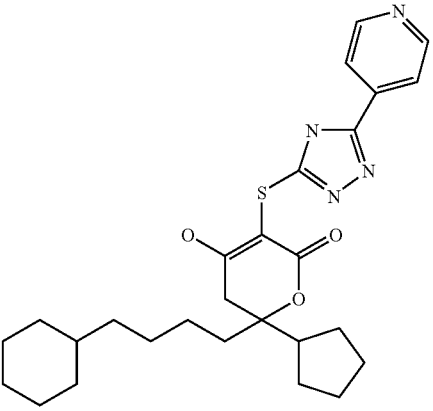

The title compound was prepared analogously to Example C(4), where 3-Chloro-6-(4-cyclohexyl-butyl)-6-cyclopentyl-4-hydroxy-5,6-dihydro-pyran-2-one (from Step 2 below) was substituted in place of 3-Chloro-6-(2-cyclohex-1-enyl-ethyl)-6-cyclopentyl-4-hydroxy-5,6-dihydro-pyran-2-one of that example.

$^1$H NMR (DMSO-d$_6$): δ 0.87–1.75 (m, 27H), 2.13–2.16 (m, 1H), 2.49 (d, J=17.0, 1H), 2.78 (d, J=17.0, 1H), 3.27 (brs, 1H), 7.70 (d, J=6.0, 2H), 8.50 (d, J=5.3, 2H), 13.9 (brs, 1H); Anal. Calcd. For C$_{27}$H$_{36}$N$_4$O$_3$S.1.5H$_2$O: C, 61.93; H, 7.51; N, 10.70. Found: C, 62.22; H, 7.30; N, 10.87. ESIMS (MH+): 497.

Step 1

5-Cyclohexyl-1-cyclopentyl-pentan-1-one

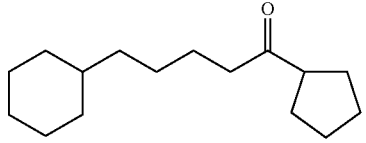

The title compound was prepared analogously to Example A(44), where cyclohexanepentanoic acid was substituted in place of 3-cyclohexylpropionic acid in Step 1 of that example.

$^1$H NMR (DMSO-d$_6$): δ 0.79–0.91 (m, 2H), 1.11–1.85 (m, 23H), 2.40 (t, J=7, 2H), 2.8–2.90 (m, 1H).

Step 2

3-Chloro-6-(3-cyclohexyl-propyl)-6-cyclopentyl-4-hydroxy-5,6-dihydro-pyran-2-one

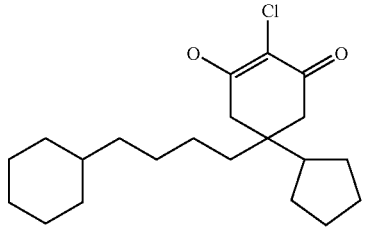

The title compound was prepared analogously to Example C(4), where 5-Cyclohexyl-1-cyclopentyl-pentan-1-one from Step 1 above was substituted in place of 3-Cyclohex-1-enyl-1-cyclopentyl-propan-1-one of that example.

¹H NMR (CDCl₃): δ 0.86–1.80 (m, 28H), 2.25–2.31 (m, 1H), 2.6 (d, J=17, 1H), 2.85 (d, J=17, 1H). ESIMS (MH+): 355.

Example C(33)

6-(4-Cyclohexyl-butyl)-6-cyclopentyl-4-hydroxy-3-(5-pyridin-4-yl-4H-[1,2,4]triazol-3-ylsulfanyl)-5,6-dihydro-pyran-2-one

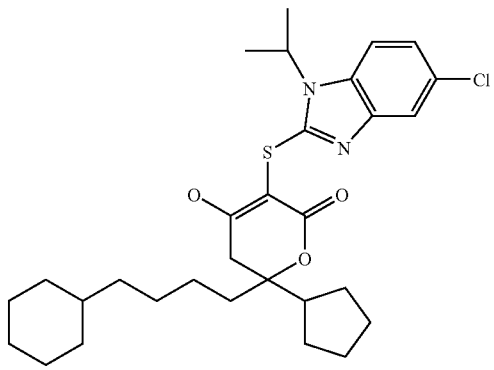

The title compound was prepared analogously to Example C(4), where 3-Chloro-6-(4-cyclohexyl-butyl)-6-cyclopentyl-4-hydroxy-5,6-dihydro-pyran-2-one (described in Step 2 of example C(32) was substituted in place of 3-Chloro-6-(2-cyclohex-1-enyl-ethyl)₆-cyclopentyl-4-hydroxy-5,6-dihydro-pyran-2-one and 5-Chloro-1-isopropyl-2-mercapto benzimidazole was substituted in place of 5-Pyridin-4-yl-4H-[1,2,4]triazole-3-thiol of that example.

¹H NMR (DMSO-d₆): δ 0.73–1.36 (m, 23H), 1.43 (d, J=7.4, 6H), 1.49–1.55 (m, 2H), 1.84–1.88 (m, 2H), 2.18–2.23 (m 1H), 2.41 (d, J=17.0, 1H), 2.77 (d, J=17.0, 1H), 4.65–4.74 (m, 1H), 7.02 (dd, J=8.6, 1.9, 1H), 7.22 (d, J=1.9, 1H), 7.54 (d, J=8.6, 1H), 12.9 (brs, 1H); Anal. Calcd. For C₃₀H₄₁ClN₂O₃S.1.25H₂O: C, 63.47; H, 7.72; N, 4.93. Found: C, 63.27; H, 7.44; N, 4.80. ESIMS (MH+): 546.

Example C(34)

3-[(4-tert-butyl-4H-1,2,4-triazol-3-yl)thio]-6-[2-(3-chloro-4-methoxyphenyl)ethyl]-6-cyclopentyl-4-hydroxy-5,6-dihydro-2H-pyran-2-one

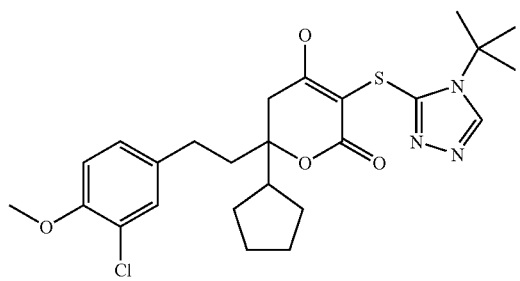

The title compound was prepared analogously to Example C(40), , where 4-tert-butyl-4H-1,2,4-triazole-3-thiol was substituted in place of 5-chloro-1-isopropyl-1H-benzimidazole-2-thiol.

¹H NMR (300 MHz, DMSO-d₆) δ ppm 1.58 (m, 1 H), 1.79 (m, 6 H), 1.89 (s, 9 H), 1.90 (m, 2 H), 2.24 (m, 1 H), 2.38 (m, 1 H), 2.68 (m, 1 H), 2.80 (m, 2 H), 2.84 (d, J=17.3 Hz, 1 H), 3.13 (d, J=17.3 Hz, 1 H), 4.05 (s, 3 H), 7.26 (d, J=8.4 Hz, 1 H), 7.51 (dd, J=8.4, 2.1 Hz, 1 H), 7.58 (d, J=2.1 Hz, 1 H), 8.82 (s, 1 H). Anal. Calcd. For C₂₅H₃₂ClN₃O₄S: C, 59.33; H, 6.37; N, 8.30; S, 6.34. Found: C, 59.07; H, 6.46; N, 8.13; S, 6.18.

Example C(35)

6-[2-(3-chloro-4-methoxyphenyl)ethyl]6-cyclopentyl-3-[(4-ethyl-4H-1,2,4-triazol-3-yl)thio]-4-hydroxy-5,6-dihydro-2H-pyran-2-one

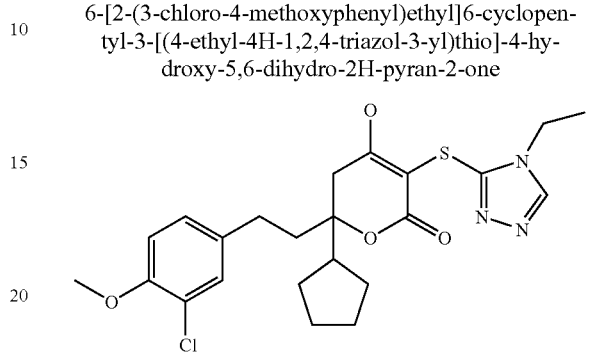

The title compound was prepared analogously to Example C(40), , where 4-ethyl-4H-1,2,4-triazole-3-thiol was substituted in place of 5-chloro-1-isopropyl-1H-benzimidazole-2-thiol.

¹H NMR (300 MHz, DMSO-d₆) δ ppm 1.24 (m, 1 H), 1.26 (t, J=7.3 Hz, 3 H), 1.49 (m, 7 H), 1.90 (m, 2 H), 2.29 (m, 1 H), 2.43 (m, 2 H), 2.56 (d, J=17.5 Hz, 1 H), 2.80 (d, J=17.5 Hz, 1 H), 3.73 (s, 3 H), 3.97 (q, J=7.3 Hz, 2 H), 6.94 (d, J=8.5 Hz, 1 H), 7.11 (dd, J=8.5, 2.1 Hz, 1 H), 7.21 (d, J=2.1 Hz, 1 H), 8.54 (s, 1 H). Anal. Calcd. For C₂₃H₂₈ClN₃O₄S: C, 57.79; H, 5.90; N, 8.79; S, 6.71. Found: C, 57.62; H, 5.93; N, 8.69; S, 6.65.

Example C(36)

6-[2-(3-chloro-4-methoxyphenyl)ethyl]-6-cyclopentyl-4-hydroxy-3-[(4-isopropyl-4H-1,2,4-triazol-3-yl)thio]-5,6-dihydro-2H-pyran-2-one

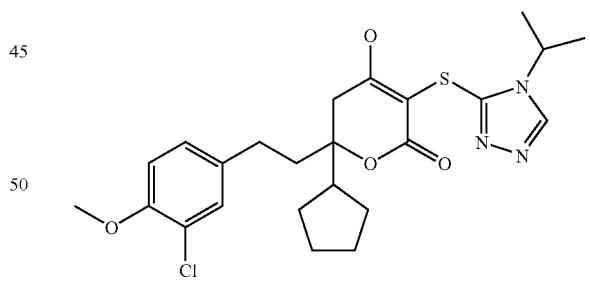

The title compound was prepared analogously to Example C(40), where 4-isopropyl-4H-1,2,4-triazole-3-thiol was substituted in place of 5-chloro-1-isopropyl-1H-benzimidazole-2-thiol.

¹H NMR (300 MHz, DMSO-D₆) δ ppm 1.43 (d, J=6.6 Hz, 3 H), 1.44 (d, J=6.6 Hz, 3 H), 1.48 (m, 8 H), 1.99 (m, 2 H), 2.39 (m, 1 H), 2.53 (m, 2 H), 2.65 (d, J=17.5 Hz, 1 H), 2.89 (d, J=17.5 Hz, 1 H), 3.82 (s, 3 H), 4.59 (dq, J=6.6, 6.6 Hz, 1 H), 6.51 (s, 1 H), 7.03 (d, J=8.4 Hz, 1 H), 7.20 (dd, J=8.4, 2.2 Hz, 1 H), 7.30 (d, J=2.2 Hz, 1 H), 8.76 (s, 1 H). Anal. Calcd. For C₂₄H₃₀ClN₃O₄S: C, 58.59; H, 6.15; N, 8.54; S, 6.52. Found: C, 58.35; H, 6.29; N, 8.29; S, 6.27.

Example C(37)

6-[2-(3-chloro-4-methoxyphenyl)ethyl]-6-cyclopentyl-4-hydroxy-3-[(4-phenyl-4H-1,2,4-triazol-3-yl)thio]-5,6-dihydro-2H-pyran-2-one

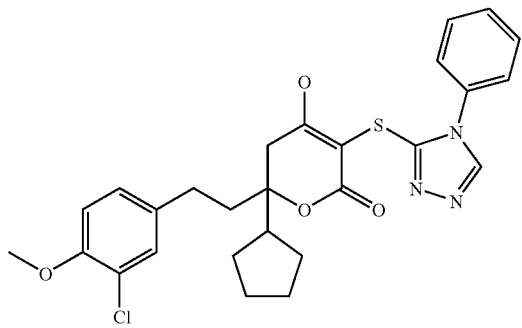

The title compound was prepared analogously to Example C(40), , where 4-phenyl-4H-1,2,4-triazole-3-thiol was substituted in place of 5-chloro-1-isopropyl-1H-benzimidazole-2-thiol.

$^1$H NMR (300 MHz, CDCL$_3$) δ ppm 1.37 (m, 1 H), 1.63 (m, 8 H), 2.00 (m, 2 H), 2.35 (m, 1 H), 2.60 (m, 2 H), 2.91 (d, J=17.8 Hz, 1 H), 3.10 (d, J=17.8 Hz, 1 H), 3.85 (s, 3 H), 6.82 (d, J=8.4 Hz, 1 H), 7.02 (dd, J=8.4, 2.1 Hz, 1 H), 7.15 (d, J=2.1 Hz, 1 H), 7.60 (m, 5 H), 8.27 (s, 1 H). Anal. Calcd. For C$_{27}$H$_{28}$ClN$_3$O$_4$S: C, 61.65; H, 5.36; N, 7.99; S, 6.10. Found: C, 61.53; H, 5.41; N, 7.74; S, 5.92.

Example C(38)

6-[2-(3-chloro-4-methoxyphenyl)ethyl]-6-cyclopentyl-4-hydroxy-3-[(1-methyl-1H-tetrazol-5-yl)thio]-5,6-dihydro-2H-pyran-2-one

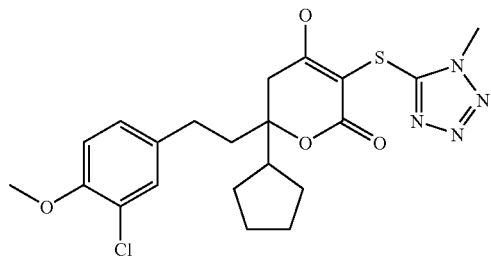

The title compound was prepared analogously to Example C(40), , where 1-methyl-1H-tetrazole-5-thiol was substituted in place of 5-chloro-1-isopropyl-1H-benzimidazole-2-thiol.

$^1$H NMR (300 MHz, CDCL$_3$) δ ppm 1.36 (s, 1 H), 1.59 (m, 8 H), 2.00 (dd, J=11.0, 5.4 Hz, 2 H), 2.35 (s, 1 H), 2.59 (dd, J=11.0, 6.0 Hz, 2 H), 2.90 (d, J=17.9 Hz, 1 H), 3.09 (d, J=17.9 Hz, 1 H), 3.87 (s, 3 H), 4.25 (s, 3 H), 6.83 (d, J=8.5 Hz, 1 H), 6.98 (dd, J=8.5, 2.1 Hz, 1 H), 7.14 (d, J=2.1 Hz, 1 H). Anal. Calcd. For C$_{21}$H$_{25}$ClN$_4$O$_4$S.0.1H$_2$O: C, 54.03; H, 5.44; N, 12.00; S, 6.87. Found: C, 53.90; H, 5.45; N, 11.74; S, 6.75.

Example C(39)

6-[2-(3-chloro-4-methoxyphenyl)ethyl]-6-cyclopentyl-3-[(1-ethyl-1H-tetrazol-5-yl)thio]4-hydroxy-5,6-dihydro-2H-pyran-2-one

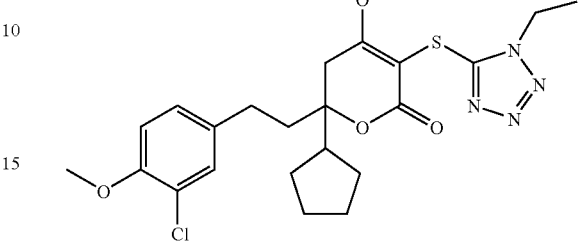

The title compound was prepared analogously to Example C(40), , where 1-ethyl-1H-tetrazole-5-thiol was substituted in place of 5-chloro-1-isopropyl-1H-benzimidazole-2-thiol.

$^1$H NMR (400 MHz, CDCL$_3$) δ ppm 1.34 (m, 1 H), 1.59 (m, 8 H), 1.63 (t, J=7.3 Hz, 3 H), 1.99 (m, 2 H), 2.36 (m, 1 H), 2.59 (m, 2 H), 2.90 (d, J=17.9 Hz, 1 H), 3.10 (d, J=17.9 Hz, 1 H), 3.87 (s, 3 H), 4.65 (q, J=7.3 Hz, 2 H), 6.83 (d, J=8.3 Hz, 1 H), 6.99 (dd, J=8.3, 2.3 Hz, 1 H), 7.14 (d, J=2.3 Hz, 1 H). Anal. Calcd. For C$_{22}$H$_{27}$ClN$_4$O$_4$S: C, 55.16; H, 5.68; N, 11.70; S, 6.69. Found: C, 55.22; H, 5.64; N, 11.48; S, 6.54.

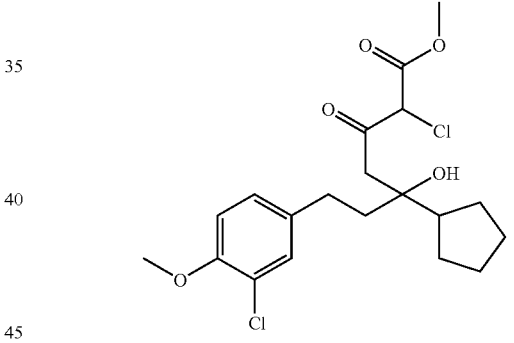

Step 1

2-Chloro-7-(3-chloro-4-methoxy-phenyl)-5-cyclopentyl-5-hydroxy-3-oxo-heptanic acid methyl ester Methyl-2-chloroacetoacetate (2.5 g, 16.9 mmol) was added to a cooled 0° C. suspension of NaH (0.68 g, 16.9 mmol, 60% dispersion in mineral oil) in THF (30 ml). After 15 min the solution was cooled to −40° C. and n-BuLi (10.6 mL, 16.9 mmol, 1.6M in hexanes) was added. The resulting dianion was stirred for an additional 30 min and then treated with a solution of 3-(3-Chloro-4-methoxy-phenyl)-1-cyclopentyl-propan-1-one (1.5 g, 5.6 mmol, compound was prepared analogously to Step 1 of Example A(82), where 4-bromo-2-chloro-1-methoxybenzene was substituted in place of 2-Bromopyridine) in THF (10 ml). After stirring for 1 h at −40° C., the reaction mixture was quenched with saturated NH$_4$Cl and extracted with EtOAc. The organic layers were washed with brine, dried with Na$_2$SO$_4$ and concentrated to an orange oil that was used without further purification.

Step 2

3-Chloro-6-[2-(3-chloro-4-methoxy-phenyl)-ethyl]-6-cyclopentyl-4-hydroxy-5,6-dihydro-pyran-2-one

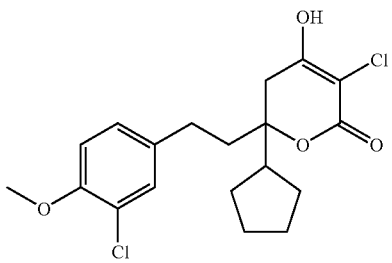

A solution of 2-Chloro-7-(3-chloro-4-methoxy-phenyl)-5-cyclopentyl-5-hydroxy-3-oxo-heptanoic acid methyl ester (2.33 g, 5.6 mmol, from Step 1), and bis(dibutylchlorotin) oxide (1.38 g, 2.5 mmol), dissolved in toluene (18 mL) were heated at reflux for 30 mins. The resulting mixture was concentrated and purified by silica gel chromatography to give the title compound (1.57 g, 75% yield, two Steps).

$^1$H NMR (CDCl$_3$): δ 1.36–1.79 (br m, 8H), 2.02 (m, 2H), 2.41 (m, 1H), 2.65 (m, 3H), 2.89 (d, 1H, J=17.7 Hz), 3.88 (s, 3H), 6.47 (br s, 1H), 6.85 (d, 1H, J=8.4 Hz), 7.01 (dd, 1H, J=8.4, 2.1 Hz), 7.16 (d, 1H, J=2.1 Hz).

Example C(40)

3-[(5-chloro-1-isopropyl-1H-benzimidazol-2-yl)thio]-6-[2-(3-chloro-4-methoxyphenyl)ethyl]-6-cyclopentyl-4-hydroxy-5,6-dihydro-2H-pyran-2-one

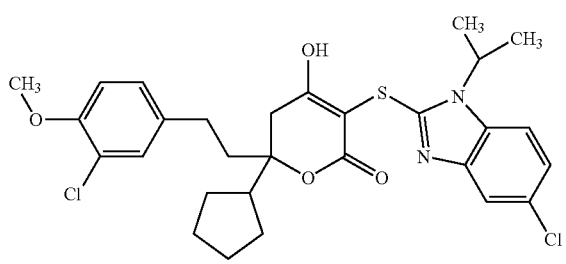

A solution of 3-chloro-6-[2-(3-chloro-4-methoxyphenyl)ethyl]-6-cyclopentyl-4-hydroxy-5,6-dihydro-2H-pyran-2-one (300 mg, 0.78 mmol), 5-chloro-1-isopropyl-1H-benzimidazole-2-thiol (181 mg, 0.80 mmol) and Et$_3$N (0.1 mL, 0.80 mmol) was stirred at 55° C. for 5 hrs. The mixture was concentrated and purified by prep HPLC to obtain 50 mg product (11% yield).

$^1$H NMR (300 MHz, DMSO-D$_6$) δ: 1.49–1.61 (m, 14 H) 2.23–2.30 (m, 2 H) 2.57–2.66 (m, 4 H) 2.91–2.96 (m, 1 H), 3.81 (s, 3 H) 4.73–4.79 (m, 1 H) 6.93 (d, J=2.07 Hz, 1 H), 7.03 (d, J=8.48 Hz, 1 H), 7.09 (dd, J=8.57, 2.17 Hz, 1 H), 7.12–7.16 (m, 1 H), 7.28 (d, J=1.88 Hz, 1 H), 7.62 (d, J=8.67 Hz, 1 H). ESI-MS calcd for C$_{29}$H$_{32}$Cl$_2$N$_2$O$_4$S: 574.1. Found (M+H$^+$): 575.0. Anal. Calcd for C$_{29}$H$_{32}$Cl$_2$N$_2$O$_4$S: C, 60.52; H, 5.60; N, 4.87. Found: C, 60.51; H, 5.74; N, 4.58.

Example C(41)

6-[2-(3-chloro-4-methoxyphenyl)ethyl]-6-cyclopentyl-4-hydroxy-3-[1(1-methyl-1H-benzimidazol-2-yl)thio]-5,6-dihydro-2H-pyran-2-one

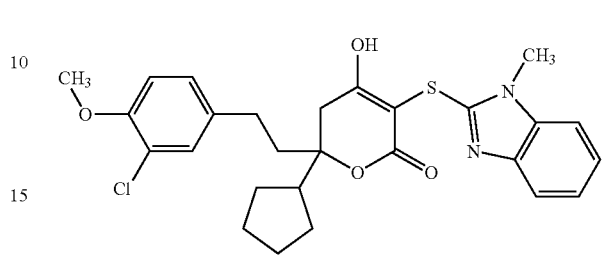

The title compound was prepared analogously to Example C(40), where 1-methyl-1H-benzimidazole-2-thiol was substituted in place of 5-chloro-1-isopropyl-1H-benzimidazole-2-thiol.

$^1$H NMR (300 MHz, DMSO-D$_6$) δ: 1.51–1.70 (m, 8 H), 2.02–2.08 (m, 2 H), 2.35–2.43 (m, 1 H), 2.55–2.60 (m, 3 H), 2.75–2.80 (m, 1 H), 3.81 (s, 6 H), 7.02 (d, J=8.48 Hz, 1 H), 7.10–7.13 (m, 1 H), 7.25–7.34 (m, 4 H), 7.39 (d, J=8.10 Hz, 1 H), 7.62 (d, J=7.35 Hz, 1 H). ESI-MS calcd for C$_{27}$H$_{29}$ClN$_2$O$_4$S: 512.2. Found (M+H$^+$): 513.0. Anal. Calcd for C$_{27}$H$_{29}$ClN$_2$O$_4$S.0.6H$_2$O: C, 61.68; H, 5.76; N, 5.10; S, 5.84. Found: C, 61.71; H, 5.75; N, 5.16; S, 5.85.

Example C(42)

6-[2-(3-chloro-4-methoxyphenyl)ethyl]-6-cyclopentyl-3-{[5-(2-furyl)-4-methyl-4H-1,2,4-triazol-3-yl]thio}-4-hydroxy-5,6-dihydro-2H-pyran-2-one

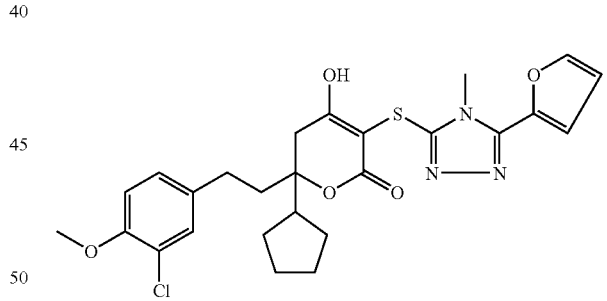

The title compound was prepared analogously to Example C(40), where 5-(2-furyl)-4-methyl-4H-1,2,4-triazole-3-thiol was substituted in place of 5-chloro-1-isopropyl-1H-benzimidazole-2-thiol.

$^1$H NMR (300 MHz, DMSO-D$_6$) δ: 1.17–1.45 (m, 8 H) 1.67–1.74 (m, 2 H), 2.08–2.16 (m, 2 H), 2.29–2.32 (m, 1 H), 2.39–2.45 (m, 1 H), 2.61–2.67 (m, 1 H), 3.54 (s, 3 H), 3.56 (s, 3 H), 6.49 (dd, J=3.39, 1.88 Hz, 1 H), 6.75 (d, J=8.48 Hz, 1 H), 6.83 (d, J=3.39 Hz, 1 H), 6.89 (dd, J=8.48, 2.07 Hz, 1 H), 7.05 (d, J=2.07 Hz, 1 H), 7.70–7.72 (m, 1 H). ESI-MS calcd for C$_{26}$H$_{28}$ClN$_3$O$_5$S: 529.1. Found (M+H$^+$): 530.0. Anal. Calcd for C$_{26}$H$_{28}$ClN$_3$O$_5$S.0.2 HOAc: C, 58.50; H, 5.36; N, 7.75; S, 5.92. Found: C, 58.34; H, 5.32; N, 7.81; S, 5.92.

Example C(43)

6-[2-(3-chloro-4-methoxyphenyl)ethyl]-6-cyclopentyl-4-hydroxy-3-(1H-imidazo[4,5-b]pyridin-2-ylthio)-5,6-dihydro-2H-pyran-2-one

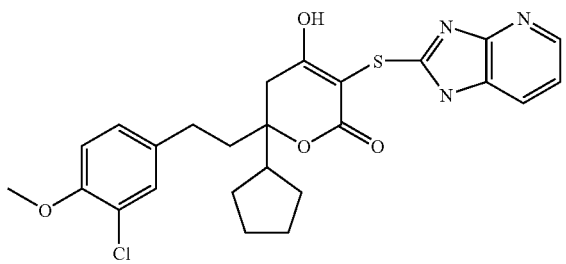

The title compound was prepared analogously to Example C(40), where 1H-imidazo[4,5-b]pyridine-2-thiol was substituted in place of 5-chloro-1-isopropyl-1H-benzimidazole-2-thiol.

$^1$H NMR (300 MHz, DMSO-D$_6$) δ: 1.38–1.75 (m, 8 H), 2.05–2.11 (m, 2 H), 2.40–2.45 (m, 1 H), 2.57–2.63 (m, 2 H), 2.69–2.75 (m, 1 H), 2.93–2.99 (m, 1 H), 3.81 (s, 3 H), 7.05 (d, J=8.48 Hz, 1 H), 7.13 (dd, J=7.91, 4.90 Hz, 1 H), 71.8–7.22 (m, 1 H), 7.31 (d, J=2.07 Hz, 1 H), 7.67 (dd, J=7.82, 1.22 Hz, 1 H), 8.19 (dd, J=4.90, 1.32 Hz, 1 H). ESI-MS calcd for C$_{25}$H$_{26}$ClN$_3$O$_4$S: 499.1. Found (M+H$^+$): 500.00. Anal. Calcd. For C$_{25}$H$_{26}$ClN$_3$O$_4$S.1.0 HOAc: C, 57.90; H, 5.40; N, 7.50; S, 5.73. Found, C, 57.99; H, 5.37; N, 7.29; S, 6.04.

Example C(44)

6-[2-(3-chloro-4-methoxyphenyl)ethyl]-6-cyclopentyl-4-hydroxy-3-[(1-isopropyl-1H-benzimidazol-2-yl)thio]-5,6-dihydro-2H-pyran-2-one

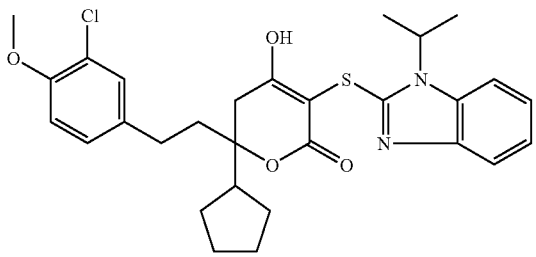

The title compound was prepared analogously to Example C(40), where 1-isopropyl-1H-benzimidazole-2-thiol was substituted in place of 5-chloro-1-isopropyl-1H-benzimidazole-2-thiol.

$^1$H NMR (300 MHz, DMSO-D$_6$) δ: 1.45–1.70 (m, 14 H), 2.04–2.10 (m, 2 H), 2.37–2.43 (m, 1 H), 2.55–2.60 (m, 2 H), 2.71–2.76 (m, 1 H), 3.81 (s, 3 H), 4.89–4.92 (m, 1 H), 7.02 (d, J=8.48 Hz, 1 H), 7.11–7.14 (m, 1 H), 7.19–7.22 (m, 2 H), 7.25 (d, J=1.88 Hz, 1 H), 7.29–7.32 (m, 1 H), 7.71–7.74 (m, 1 H). ESI-MS calcd for C$_{29}$H$_{33}$ClN$_2$O$_4$S: 540.2. Found (M+H$^+$) 541.1. Anal. Calcd. For C$_{29}$H$_{33}$ClN$_2$O$_4$S.1.5HOAc: C, 60.89; H, 6.23; N, 4.44. Found: C, 61.02; H, 6.34; N, 4.82.

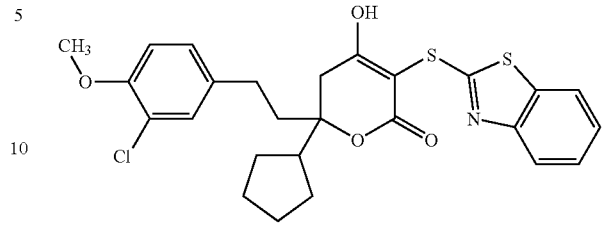

Example C(45)

3-(1,3-benzothiazol-2-ylthio)-6-[2-(3-chloro-4-methoxyphenyl)ethyl]-6-cyclopentyl-4-hydroxy-5,6-dihydro-2H-pyran-2-one The title compound was prepared analogously to Example C(40), where 1,3-benzothiazole-2-thiol was substituted in place of 5-chloro-1-isopropyl-1H-benzimidazole-2-thiol.

$^1$H NMR (300 MHz, DMSO-D$_6$) δ: 1.39–1.73 (m, 8 H), 2.11–2.16 (m, 2 H), 2.43–2.45 (m, 1 H), 2.62–2.67 (m, 2 H), 2.80–2.86 (m, 1 H), 2.99–3.05 (m, 1 H), 3.83 (s, 3 H), 7.07 (d, J=8.48 Hz, 1 H), 7.16–7.19 (m, 1 H), 7.28–7.34 (m, 2 H), 7.37–7.43 (m, 1 H), 7.66 (d, J=7.54 Hz, 1 H), 7.79–7.82 (m, 1 H). ESI-MS calcd for C$_{26}$H$_{26}$ClNO$_4$S$_2$: 515.1. Found (M+H$^+$): 516.2. Anal. Calcd for C$_{26}$H$_{26}$ClNO$_4$S$_2$: C, 60.51; H, 5.08; N, 2.71. Found: C, 60.30; H, 5.24; N, 2.71.

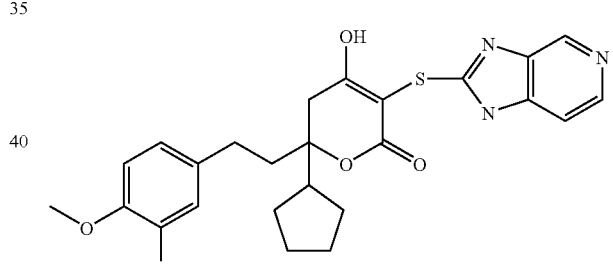

Example C(46)

6-[2-(3-chloro-4-methoxyphenyl)ethyl]-6-cyclopentyl-4-hydroxy-3-(1H-imidazo[4,5-c]pyridin-2-ylthio)-5,6-dihydro-2H-pyran-2-one The title compound was prepared analogously to Example C(40), where 1H-imidazo[4,5-c]pyridine-2-thiol was substituted in place of 5-chloro-1-isopropyl-1H-benzimidazole-2-thiol.

$^1$H NMR (300 MHz, DMSO-D$_6$) δ: 1.45–1.68 (m, 8 H), 1.93–1.99 (m, 2 H), 2.35–2.40 (m, 2 H), 2.54–2.60 (m, 2 H), 2.70–2.72 (m, 1 H), 3.80 (s, 3 H), 7.03 (d, J=8.48 Hz, 1 H), 7.10–7.12 (m, 1 H), 7.22 (d, J=2.07 Hz, 1 H), 7.70 (d, J=6.41 Hz, 1 H), 8.34 (d, J=6.40 Hz, 1 H), 8.83 (s, 1 H). ESI-MS calcd for C$_{25}$H$_{26}$ClN$_3$O$_4$S: 499.1. Found (M+H$^+$): 500.0. Anal. Calcd. For C$_{25}$H$_{26}$ClN$_3$O$_4$S.0.9H$_2$O: C, 58.16; H, 5.43; N, 8.14; S, 6.21. Found: C, 58.29; H, 5.41; N, 8.10; S, 5.94.

Example C(47)

6-[2-(3-chloro-4-methoxyphenyl)ethyl]-6-cyclopentyl-4-hydroxy-3-([1,3]thiazolo[5,4-b]pyridin-2-ylthio)-5,6-dihydro-2H-pyran-2-one

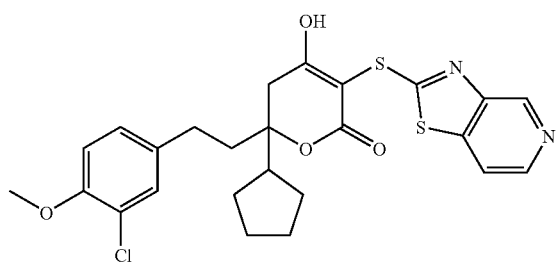

The title compound was prepared analogously to Example C(40), where [1,3]thiazolo[5,4-b]pyridine-2-thiol was substituted in place of 5-chloro-1-isopropyl-1H-benzimidazole-2-thiol.

$^1$H NMR (300 MHz, DMSO-D$_6$) δ: 1.37–1.76 (m, 8 H), 2.04–2.14 (m, 2 H), 2.60–2.65 (m, 2 H), 2.81–3.02 (m, 3 H), 3.82 (s, 3 H), 7.05 (d, J=8.48 Hz, 1 H), 7.16 (m, 1 H), 7.30 (d, J=1.88 Hz, 1 H), 7.45 (dd, J=8.29, 4.71 Hz, 1 H), 8.00 (dd, J=8.29, 1.51 Hz, 1 H), 8.43 (dd, J=4.62, 1.41 Hz, 1 H). ESI-MS calcd for C$_{25}$H$_{25}$ClN$_2$O$_4$S$_2$: 516.1. Found (M+H$^+$): 517.0. Anal. Calcd for C$_{25}$H$_{25}$ClN$_2$O$_4$S$_2$: C, 58.07; H, 4.87; N, 5.42; S, 12.40. Found: C, 57.71; H, 4.87; N, 5.40; S, 12.13.

Example C(48)

6-[2-(3-chloro-4-methoxyphenyl)ethyl]-6-cyclopentyl-4-hydroxy-3-[(1-phenyl-1H-benzimidazol-2-yl)thio]-5,6-dihydro-2H-pyran-2-one

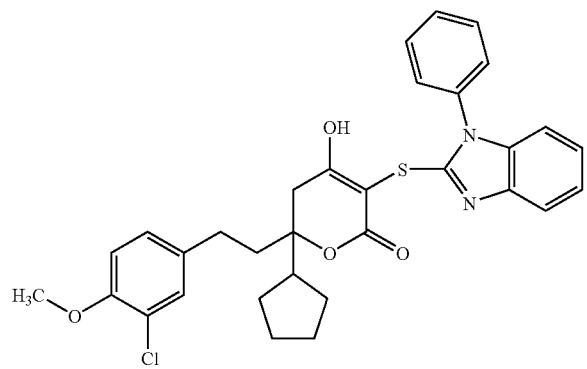

The title compound was prepared analogously to Example C(40), where 1-phenyl-1H-benzimidazole-2-thiol was substituted in place of 5-chloro-1-isopropyl-1H-benzimidazole-2-thiol.

$^1$H NMR (300 MHz, DMSO-D$_6$) δ: 1.41–1.73 (m, 8 H), 2.20–2.29 (m, 2 H), 2.60–2.74 (m, 3 H), 2.89–2.93 (m, 2 H), 3.83 (s, 3 H), 7.06 (d, J=8.59 Hz, 1 H), 7.13–7.21 (m, 6 H), 7.32 (d, J=2.02 Hz, 1 H), 7.59–7.60 (m, 2 H), 7.63–7.68 (m, 2 H). ESI-MS calcd for C$_{32}$H$_{31}$ClN$_2$O$_4$S: 574.2. Found (M+H$^+$): 575.2. Anal. Calcd. For C$_{32}$H$_{31}$ClN$_2$O$_4$S.0.2H$_2$O: C, 66.41; H, 5.47; N, 4.84; S, 5.54. Found: C, 66.34; H, 5.43; N, 4.93; S, 5.44.

Example C(49)

3-[(5-chloro-1H-benzimidazol-2-yl)thio]-6-[2-(3-chloro-4-methoxyphenyl)ethyl]-6-cyclopentyl-4-hydroxy-5,6-dihydro-2H-pyran-2-one

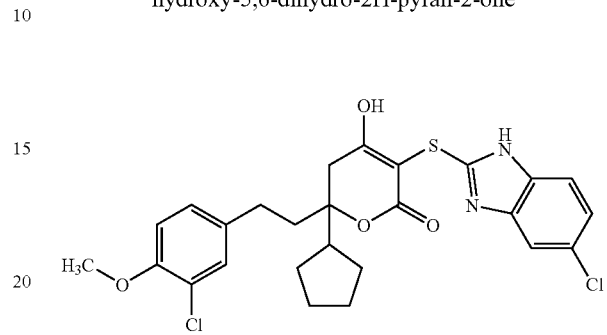

The title compound was prepared analogously to Example C(40), where 5-chloro-1H-benzimidazole-2-thiol was substituted in place of 5-chloro-1-isopropyl-1H-benzimidazole-2-thiol.

$^1$H NMR (300 MHz, DMSO-D$_6$) δ: 1.36–1.71 (s, 8 H), 2.05–2.13 (m, 2 H), 2.38–2.43 (m, 1 H), 2.56–2.72 (m, 3 H), 2.86–2.93 (m, 1 H), 3.81 (s, 3 H), 7.03 (d, J=8.48 Hz, 1 H), 7.10–7.15 (m, 2 H), 7.24–7.35 (m, 3 H). ESI-MS calcd for C$_{26}$H$_{26}$Cl$_2$N$_2$O$_4$S: 532.10. Found (M+H$^+$): 533.00. Anal. Calcd. For C$_{26}$H$_{26}$Cl$_2$N$_2$O$_4$S.1.0H$_2$O: C, 56.62; H, 5.12; N, 5.08; S, 5.81. Found: C, 56.89; H, 5.01; N, 5.35; S, 5.55.

Example C(50)

6-[2-(3-chloro-4-methoxyphenyl)ethyl]-6-cyclopentyl-4-hydroxy-3-[(5-pyridin-4-yl-4H-1,2,4-triazol-3-yl)thio]-5,6-dihydro-2H-pyran-2-one

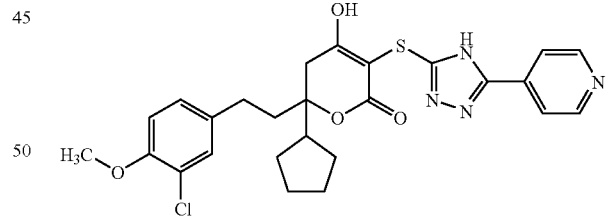

The title compound was prepared analogously to Example C(40), where 5-pyridin-4-yl-4H-1,2,4-triazole-3-thiol was substituted in place of 5-chloro-1-isopropyl-1H-benzimidazole-2-thiol.

$^1$H NMR (300 MHz, DMSO-D$_6$) δ: 1.30–1.68 (m, 8 H), 1.82–2.10 (s, 2 H), 2.31–2.40 (m, 1 H), 2.47–2.52 (m, 2 H), 2.69–2.75 (m, 1 H), 2.86–2.93 (m, 1 H), 3.71 (s, 3 H), 6.90 (d, J=8.48 Hz, 1 H), 7.02–7.06 (m, 1 H), 7.19 (d, J=1.88 Hz, 1 H), 7.64 (d, J=4.71 Hz, 2 H), 8.48 (d, J=4.71 Hz, 2 H). ESI-MS calcd for C$_{26}$H$_{27}$ClN$_4$O$_4$S: 526.1. Found (M+H$^+$): 517.2. Anal. Calcd. For C$_{26}$H$_{27}$ClN$_4$O$_4$S.0.4HOAc: C, 58.41; H, 5.23; N, 10.17; S, 5.82. Found: C, 58.33; H, 5.57; N, 10.02; S, 5.76.

Example C(51)

6-[2-(3-chloro-4-methoxyphenyl)ethyl]-6-cyclopentyl-4-hydroxy-3-[(5-pyridin-4-yl-1,3,4-oxadiazol-2-yl)thio]-5,6-dihydro-2H-pyran-2-one

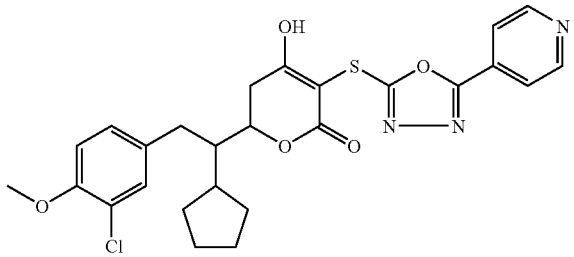

The title compound was prepared analogously to Example C(40), where 5-pyridin-4-yl-1,3,4-oxadiazole-2-thiol was substituted in place of 5-chloro-1-isopropyl-1H-benzimidazole-2-thiol.

$^1$H NMR (300 MHz, DMSO-D$_6$) δ: 1.26–1.62 (m, 8 H), 1.92–1.98 (m, 2 H), 2.26–2.31 (m, 1 H), 2.41–2.50 (m, 2 H), 2.64–2.70 (m, 1 H), 2.84–2.90 (m, 1 H), 3.65 (s, 3 H), 6.85 (d, J=8.48 Hz, 1 H), 7.02 (dd, J=8.48, 2.07 Hz, 1 H), 7.15 (d, J=2.07 Hz, 1 H), 7.60 (d, J=5.84 Hz, 2 H), 8.58 (s, 2 H). ESI-MS calcd for C$_{26}$H$_{26}$ClN$_3$O$_5$S: 527.1. Found (M+H$^+$): 528.1. Anal. Calcd. For C$_{26}$H$_{26}$ClN$_3$O$_5$S: C, 59.14; H, 4.96; N, 7.96; S, 6.07. Found: C, 59.13; H, 5.22; N, 7.62; S, 5.79.

Example C(52)

6-[2-(3-chloro-4-methoxyphenyl)ethyl]-6-cyclopentyl-3-[(5-fluoro-1H-benzimidazol-2-yl)thio]4-hydroxy-5,6-dihydro-2H-pyran-2-one

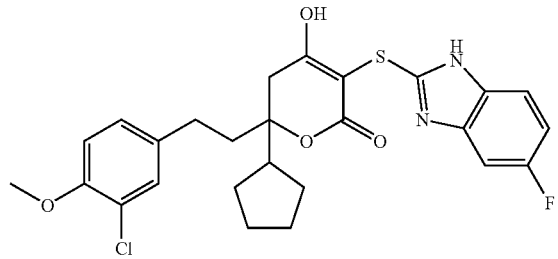

The title compound was prepared analogously to Example C(40), where 5-fluoro-1H-benzimidazole-2-thiol was substituted in place of 5-chloro-1-isopropyl-1H-benzimidazole-2-thiol.

$^1$H NMR (300 MHz, DMSO-D$_6$) δ: 1.41–1.70 (m, 8 H), 2.05–2.09 (m, 2 H), 2.39–2.44 (m, 1 H), 2.56–2.61 (m, 2 H), 2.63–2.67 (m, 1 H), 2.87–2.91 (m, 1 H), 3.75–3.83 (m, 3 H), 6.95–7.01 (m, 1 H), 7.03 (d, J=8.59 Hz, 1 H), 7.10–7.15 (m, 2 H), 7.27–7.28 (m, 1 H), 7.31–7.35 (m, 1 H). ESI-MS calcd for C$_{26}$H$_{26}$ClFN$_2$O$_4$S: 516.1. Found (M+H$^+$): 517.1. Anal. Calcd. For C$_{26}$H$_{26}$ClFN$_2$O$_4$S.0.9H$_2$O: C, 58.47; H, 5.22; N, 4.91; S, 5.61. Found: C, 58.84; H, 5.01; N, 4.64; S, 5.27.

Example C(53)

6-[2-(3-chloro-4-methoxyphenyl)ethyl]-6-cyclopentyl-4-hydroxy-3-[(5-methyl-1H-benzimidazol-2-yl)thio]-5,6-dihydro-2H-pyran-2-one

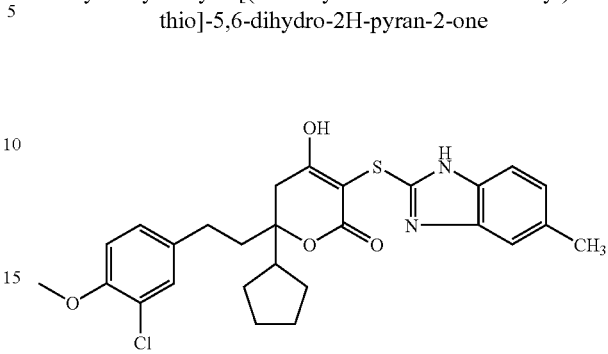

The title compound was prepared analogously to Example C(40), where 5-methyl-1H-benzimidazole-2-thiol was substituted in place of 5-chloro-1-isopropyl-1H-benzimidazole-2-thiol.

$^1$H NMR (300 MHz, DMSO-D$_6$) δ: 1.43–1.69 (m, 8 H), 1.94–1.99 (m, 2 H), 2.35–2.37 (m, 1 H), 2.40 (s, 3 H), 2.52–2.60 (m, 3 H), 2.70–2.76 (m, 1 H), 3.80 (s, 3 H), 7.02 (d, J=8.67 Hz, 1 H), 7.09 (d, J=1.88 Hz, 1 H), 7.12 (brs, 1 H), 7.24 (d, J=2.07 Hz, 1 H), 7.26 (brs, 1 H), 7.36 (d, J=8.29 Hz, 1 H). ESI-MS calcd for C$_{27}$H$_{29}$ClN$_2$O$_4$S: 512.2. Found (M+H$^+$): 513.0. Anal. Calcd. For C$_{27}$H$_{29}$ClN$_2$O$_4$S.0.9HOAc: C, 60.99; H, 5.79; N, 4.94; S, 5.65. Found: C, 61.13; H, 5.81; N, 4.88; S, 5.59.

Example C(54)

6-[2-(3-chloro-4-methoxyphenyl)ethyl]-6-cyclopentyl-4-hydroxy-3-[(4-methyl-1H-benzimidazol-2-yl)thiol]-5,6-dihydro-2H-pyran-2-one

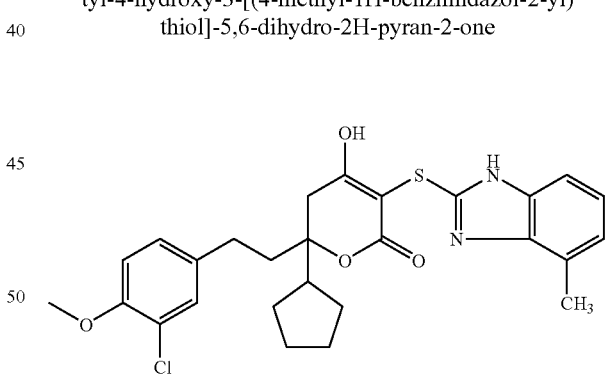

The title compound was prepared analogously to Example C(40), where 4-methyl-1H-benzimidazole-2-thiol was substituted in place of 5-chloro-1-isopropyl-1H-benzimidazole-2-thiol.

$^1$H NMR (300 MHz, DMSO-D$_6$) δ: 1.44–1.68 (m, 8 H), 1.95–2.00 (m, 2 H), 2.36–2.39 (m, 1 H), 2.42 (s, 3 H), 2.45–2.47 (m, 1 H), 2.53–2.59 (m, 2 H), 2.71–2.75 (m, 1 H), 3.80 (s, 3 H), 7.00–7.06 (m, 2 H), 7.09–7.15 (m, 2 H), 7.24–7.27 (m, 2 H). ESI-MS calcd for C$_{27}$H$_{29}$ClN$_2$O$_4$S: 512.2. Found (M+H$^+$): 513.1. Anal. Calcd. For C$_{27}$H$_{29}$ClN$_2$O$_4$S.1.0H$_2$O: C, 61.06; H, 5.88; N, 5.28; S, 6.04. Found: C, 60.89; H, 5.71; N, 5.17; S, 5.86.

Example C(55)

2-({6-[2-(3-chloro-4-methoxyphenyl)ethyl]-6-cyclopentyl-4-hydroxy-2-oxo-5,6-dihydro-2H-pyran-3-yl}thio)-1H-benzimidazole-5-carbonitrile

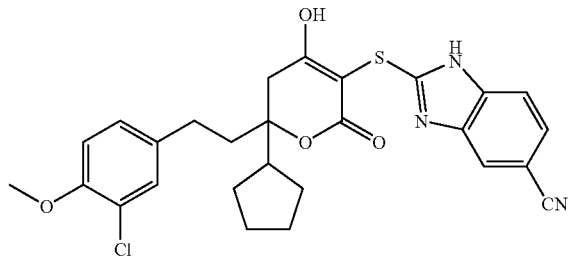

The title compound was prepared analogously to Example C(40), where 2-mercapto-1H-benzimidazole-5-carbonitrile was substituted in place of 5-chloro-1-isopropyl-1H-benzimidazole-2-thiol.

$^1$H NMR (300 MHz, DMSO-D$_6$) δ: 1.54–1.74 (m, 8 H), 2.11–2.17 (m, 2 H), 2.42–2.45 (m, 1 H), 2.57–2.63 (m, 2 H), 2.70–2.76 (m, 1 H), 2.94–3.00 (m, 1 H), 3.82 (s, 3 H), 7.04 (d, J=8.48 Hz, 1 H), 7.14–7.17 (m, 1 H), 7.29 (d, J=2.07 Hz, 1 H), 7.42–7.49 (m, 2 H), 7.69 (s, 1 H). ESI-MS calcd for C$_{27}$H$_{26}$ClN$_3$O$_4$S: 523.1. Found (M+H$^+$): 524.1. Anal. Calcd. For C$_{27}$H$_{26}$ClN$_3$O$_4$S.0.4H$_2$O: C, 61.04; H, 5.09; N, 7.91. Found: C, 61.27; H, 5.42; N, 7.90.

Example C(56)

2-({-6-[2-(3-chloro-4-methoxyphenyl)ethyl]-6-cyclopentyl-4-hydroxy-2-oxo-5,6-dihydro-2H-pyran-3-yl}thio)nicotinonitrile

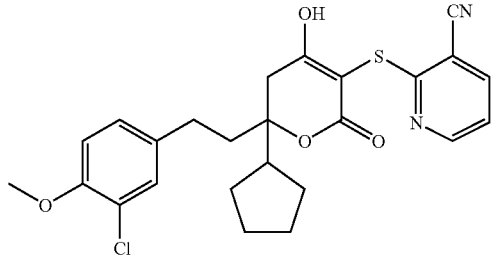

The title compound was prepared analogously to Example C(40), where 2-mercaptonicotinonitrile was substituted in place of 5-chloro-1-isopropyl-1H-benzimidazole-2-thiol.

$^1$H NMR (300 MHz, DMSO-D$_6$) δ: 1.43–1.78 (m, 8 H), 2.04–2.10 (m, 2 H), 2.40–2.45 (m, 1 H), 2.63–2.69 (m, 2 H), 2.78–3.00 (m, 2 H), 3.81 (s, 3 H), 7.06 (d, J=8.48 Hz, 1 H), 7.15–7.19 (m, 1 H), 7.31 (d, J=1.88 Hz, 1 H), 7.52 (dd, J=8.19, 4.43 Hz, 1 H), 8.18 (dd, J=8.19, 1.41 Hz, 1 H), 8.82 (dd, J=4.43, 1.41 Hz, 1 H). ESI-MS calcd for C$_{25}$H$_{25}$ClN$_2$O$_4$S: 484.1. Found (M+H$^+$): 485.0. Anal. Calcd. For C$_{25}$H$_{25}$ClN$_2$O$_4$S.0.4H$_2$O: C, 61.00; H, 5.28; N, 5.69; S, 6.51. Found: C, 60.90; H, 5.15; N, 5.87; S, 6.66.

Example C(57)

6-[2-(3-chloro-4-methoxyphenyl)ethyl]-3-[(5-Chloro-1-methyl-1H-benzimidazol-2-yl)thio]-6-cyclopentyl-4-hydroxy-5,6-dihydro-2H-pyran-2-one

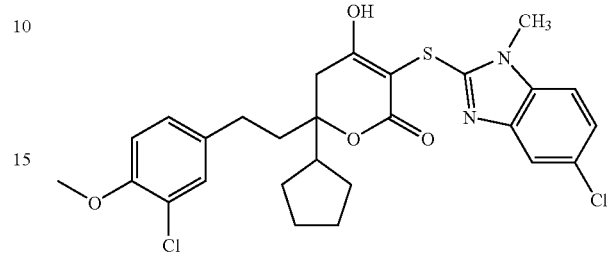

The title compound was prepared analogously to Example C(40), where 5-chloro-1-methyl-1H-benzimidazole-2-thiol was substituted in place of 5-chloro-1-isopropyl-1H-benzimidazole-2-thiol.

$^1$H NMR (300 MHz, DMSO-D$_6$) δ: 1.39–1.70 (m, 8 H), 2.21–2.27 (m, 2 H), 2.42–2.46 (m, 1 H), 2.55–2.70 (m, 3 H), 2.93–2.99 (m, 1 H), 3.73 (s, 3 H), 3.82 (s, 3 H), 7.01–7.04 (m, 2 H), 7.13–7.20 (m, 2 H), 7.29 (d, J=2.07 Hz, 1 H), 7.49 (d, J=8.48 Hz, 1 H). ESI-MS calcd for C$_{27}$H$_{28}$Cl$_2$N$_2$O$_4$S: 546.1. Found (M+H$^+$): 547.0. Anal. Calcd. For C$_{27}$H$_{28}$Cl$_2$N$_2$O$_4$S.0.4HOAc: C, 58.42; H, 5.22; N, 4.90; S, 5.61. Found: 58.25; H, 5.12; N, 4.88; S, 5.46.

Example C(58)

6-[2-(3-chloro-4-methoxyphenyl)ethyl]-6-cyclopentyl-4-hydroxy-3-[(4-hydroxy-1H-benzimidazol-2-yl)thio]-5,6-dihydro-2H-pyran-2-one

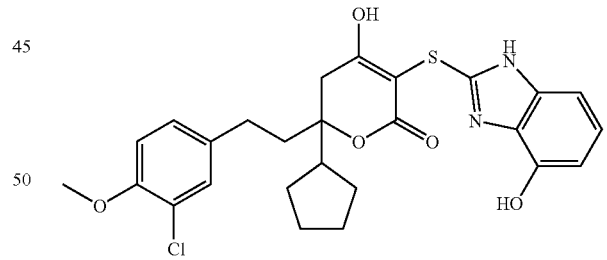

The title compound was prepared analogously to Example C(40), where 2-mercapto-1H-benzimidazol-4-ol was substituted in place of 5-chloro-1-isopropyl-1H-benzimidazole-2-thiol.

$^1$H NMR (300 MHz, DMSO-D$_6$) δ: 1.26–1.55 (m, 8 H), 1.77–1.80 (m, 2 H), 2.19–2.27 (m, 1 H), 2.39–2.45 (m, 3 H), 2.54–2.60 (m, 1 H), 3.66 (s, 3 H), 6.54 (d, J=7.35 Hz, 1 H), 6.77 (d, J=7.91 Hz, 1 H), 6.86–6.97 (m, 3 H), 7.09 (d, J=2.07 Hz, 1 H). HRMS calcd. For C$_{26}$H$_{28}$ClN$_2$O$_5$S (M+H$^+$): 515.1402. Found: 515.1381.

Example C(59)

6-[2-(3-chloro-4-methoxyphenyl)ethyl]-6-cyclopentyl-3-[(5-ethoxy-1H-benzimidazol-2-yl)thio]-4-hydroxy-5,6-dihydro-2H-pyran-2-one

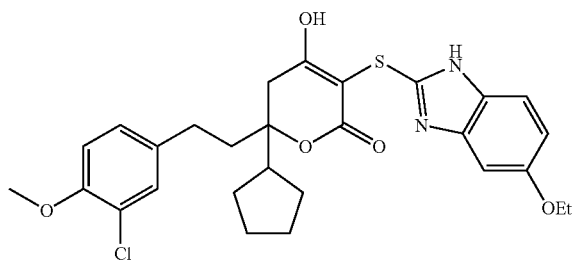

The title compound was prepared analogously to Example C(40), where 5-ethoxy-1H-benzimidazole-2-thiol was substituted in place of 5-chloro-1-isopropyl-1H-benzimidazole-2-thiol.

$^1$H NMR (300 MHz, DMSO-D$_6$) δ: 1.33 (t, J=6.97 Hz, 3 H), 1.41–1.68 (m, 8 H), 1.93–1.99 (m, J=17.33 Hz, 2 H), 2.34–2.44 (m, 2 H), 2.54–2.60 (m, 2 H), 2.71–2.77 (m, 1 H), 3.80 (s, 3 H), 4.02 (q, J=6.91 Hz, 2 H), 6.88 (dd, J=8.76, 2.35 Hz, 1 H), 6.94 (d, J=2.26 Hz, 1 H), 7.02 (d, J=8.48 Hz, 1 H), 7.09–7.12 (m, 1 H), 7.24 (d, J=1.88 Hz, 1 H), 7.36 (d, J=8.67 Hz, 1 H). ESI-MS calcd for C$_{28}$H$_{31}$ClN$_2$O$_5$S: 542.2. Found (M+H$^+$): 543.1. Anal. Calcd. For C$_{28}$H$_{31}$ClN$_2$O$_5$S.0.4HOAc: C, 60.99; H, 5.79; N, 4.94; S, 5.65. Found: C, 61.05; H, 5.82; N, 4.62; S, 5.41.

Example C(60)

6-[2-(3-chloro-4-methoxyphenyl)ethyl]-6-cyclopentyl-3-[(5,6-dichloro-1-methyl-1H-benzimidazol-2-yl)thio]-4-hydroxy-5,6-dihydro-2H-pyran-2-one

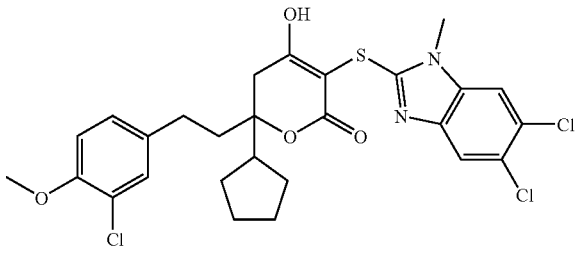

The title compound was prepared analogously to Example C(40), where 5,6-dichloro-1-methyl-1H-benzimidazole-2-thiol was substituted in place of 5-chloro-1-isopropyl-1H-benzimidazole-2-thiol.

$^1$H NMR (300 MHz, DMSO-D$_6$) δ: 1.37–1.74 (m, 8 H), 2.26–2.32 (m, 2 H), 2.41–2.45 (m, 1 H), 2.57–2.63 (m, 2 H), 2.67–2.73 (m, 1 H), 2.98–3.03 (m, 1 H), 3.73 (s, 3 H), 3.82 (s, 3 H), 7.03 (d, J=8.48 Hz, 1 H), 7.08 (s, 1 H), 7.15 (d, J=8.48 Hz, 1 H), 7.28 (d, J=1.70 Hz, 1 H), 7.85 (s, 1 H). ESI-MS calcd for C$_{27}$H$_{27}$Cl$_3$N$_2$O$_4$S: 580.1. Found (M+H$^+$): 581.0. Anal. Calcd. For C$_{27}$H$_{27}$Cl$_3$N$_2$O$_4$S.0.3H$_2$O: C, 55.21; H, 4.74; N, 4.77; S, 5.46. Found: C, 55.22; H, 4.76; N, 4.89; S, 5.20.

Example C(61)

3-[(5-chloro-6-fluoro-1H-benzimidazol-2-yl)thiol]-6-[2-(3-chloro-4-methoxyphenyl)ethyl]-6-cyclopentyl-4-hydroxy-5,6-dihydro-2H-pyran-2-one

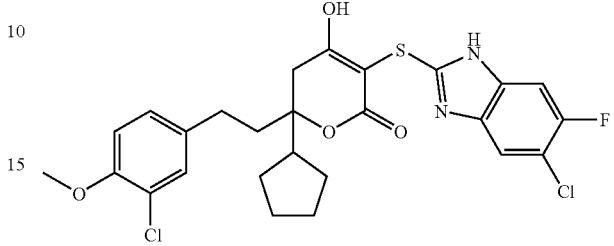

The title compound was prepared analogously to Example C(40), where 5-chloro-6-fluoro-1H-benzimidazole-2-thiol was substituted in place of 5-chloro-1-isopropyl-1H-benzimidazole-2-thiol.

$^1$H NMR (300 MHz, DMSO-D$_6$) δ: 1.40–1.71 (m, 8 H), 2.13–2.18 (m, 2 H), 2.40–2.45 (m, 1 H), 2.56–2.62 (m, 2 H), 2.70–2.76 (m, 1 H), 2.95–3.01 (m, 1 H), 3.81 (s, 3 H), 7.04 (d, J=8.48 Hz, 1 H), 7.13–7.16 (m, 1 H), 7.25 (d, J=9.61 Hz, 1 H), 7.29 (d, J=1.88 Hz, 1 H), 7.37 (d, J=6.78 Hz, 1 H). ESI-MS calcd for C$_{26}$H$_{25}$Cl$_2$FN$_2$O$_4$S: 550.1. Found (M+H$^+$): 551.0. Anal. Calcd. For C$_{26}$H$_{25}$Cl$_2$FN$_2$O$_4$S.0.3H$_2$O: C, 56.08; H, 4.63; N, 5.03; S, 5.76. Found: C, 56.08; H, 4.86; N, 5.17; S, 5.80.

Example C(62)

6-[2-(3-chloro-4-methoxyphenyl)ethyl]-3-{[7-chloro-5-(trifluoromethyl)-1H-benzimidazol-2-yl]thio}-6-cyclopentyl-4-hydroxy-5,6-dihydro-2H-pyran-2-one

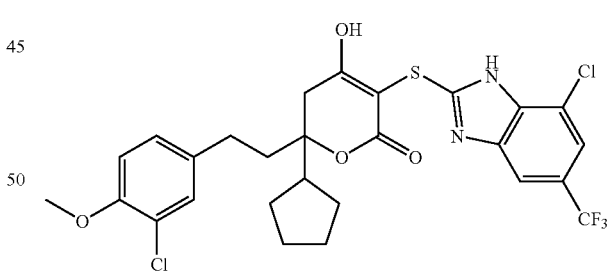

The title compound was prepared analogously to Example C(40), where 7-chloro-5-(trifluoromethyl)-1H-benzimidazole-2-thiol was substituted in place of 5-chloro-1-isopropyl-1H-benzimidazole-2-thiol.

$^1$H NMR (300 MHz, DMSO-D$_6$) δ:1.42–1.68 (m, 8 H), 1.92–1.96 (m, 2 H), 2.32–2.37 (m, 1 H), 2.53–2.66 (m, 3 H), 3.07–3.15 (m, 1 H), 3.79 (s, 3 H), 7.00 (d, J=8.48 Hz, 1 H), 7.07–7.11 (m, 1 H), 7.22 (d, J=2.07 Hz, 1 H), 7.42 (d, J=1.13 Hz, 1 H), 7.56 (s, 1 H). ESI-MS calcd for C$_{27}$H$_{25}$Cl$_2$F$_3$N$_2$O$_4$S: 600.1. Found (M+H$^+$): 610.0. Anal. Calcd. For C$_{27}$H$_{25}$Cl$_2$F$_3$N$_2$O$_4$S.1.0H$_2$O: C, 52.35; H, 4.39; N, 4.52; S, 5.18. Found: C, 52.06; H, 4.64; N, 4.80; S, 4.82.

Example C(63)

6-[2-(5-chloro-2,4-dimethoxyphenyl)ethyl]-3-[(5-chloro-1-methyl-1H-benzimidazol-2-yl)thio]-6-cyclopentyl-4-hydroxy-5,6-dihydro-2H-pyran-2-one

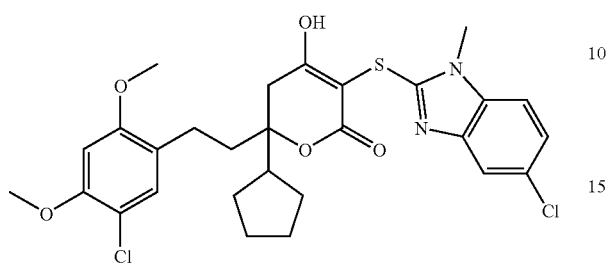

The title compound was prepared analogously to Example C(40), where 3-chloro-6-[2-(5-chloro-2,4-dimethoxyphenyl)ethyl]-6-cyclopentyl-4-hydroxy-5,6-dihydro-2H-pyran-2-one was substituted in place of 3-chloro-6-[2-(3-chloro-4-methoxyphenyl)ethyl]6-cyclopentyl-4-hydroxy-5,6-dihydro-2H-pyran-2-one and 5-chloro-1-methyl-1H-benzimidazole-2-thiol was substituted in place of 5-chloro-1-isopropyl-1H-benzimidazole-2-thiol.

$^1$H NMR (300 MHz, DMSO-D$_6$) δ: 1.37–1.71 (m, 8 H), 2.07–2.19 (m, 2 H), 2.35–2.42 (m, 1 H), 2.57–2.72 (m, 3 H), 2.83–2.88 (m, 1 H), 3.71 (s, 3 H), 3.75 (s, 3 H), 3.86 (s, 3 H), 6.71 (s, 1 H), 7.01 (d, J=1.70 Hz, 1 H), 7.13 (s, 1 H), 7.16 (d, J=2.07 Hz, 1 H), 7.45 (d, J=8.67 Hz, 1 H). ESI-MS calcd for C$_{28}$H$_{30}$Cl$_2$N$_2$O$_5$S: 576.1. Found (M+H$^+$): 577.1. Anal. Calcd. For C$_{28}$H$_{30}$Cl$_2$N$_2$O$_5$S.1.0H$_2$O: C, 56.47; H, 5.42; N, 4.70; S, 5.38. Found: C, 56.86; H, 5.24; N, 5.05; S, 5.20.

Example C(64)

6-[2-(3-chloro-4-isopropoxyphenyl)ethyl]-3-[(5-chloro-1-methyl-1H-benzimidazol-2-yl)thio]-6-cyclopentyl-4-hydroxy-5,6-dihydro-2H-pyran-2-one

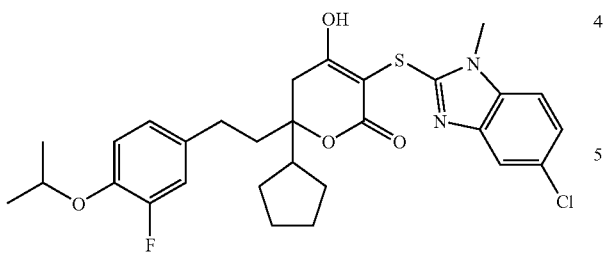

The title compound was prepared analogously to Example C(40), where 3-chloro-6-cyclopentyl-6-[2-(3-fluoro-4-isopropoxyphenyl)ethyl]-4-hydroxy-5,6-dihydro-2H-pyran-2-one, where 4-bromo-2-fluoro-1-isopropoxybenzene was) was substituted in place of 3-chloro-6-[2-(3-chloro-4-methoxyphenyl)ethyl]-6-cyclopentyl-4-hydroxy-5,6-dihydro-2H-pyran-2-one and 7-chloro-5-(trifluoromethyl)-1H-benzimidazole-2-thiol was substituted in place of 5-chloro-1-isopropyl-1H-benzimidazole-2-thiol.

$^1$H NMR (300 MHz, DMSO-D$_6$) δ: 1.26 (d, J=6.03 Hz, 6 H), 1.43–1.71 (m, 8 H), 2.16–2.22 (m, 2 H), 2.39–2.42 (m, 1 H), 2.53–2.69 (m, 3 H), 2.70–2.75 (m, 1 H), 3.70 (s, 3 H), 4.50–4.58 (m, 1 H), 6.93–6.96 (m, 1 H), 7.02–7.08 (m, 2 H), 7.11–7.15 (m, 2 H), 7.41–7.44 (m, 1 H). ESI-MS calcd for C$_{29}$H$_{32}$Cl$_2$N$_2$O$_4$S: 558.2. Found (M+H$^+$): 559.1. Anal. Calcd. For C$_{29}$H$_{32}$Cl$_2$N$_2$O$_4$S.1.0H$_2$O: C, 60.35; H, 5.94; N, 4.85; S, 5.56. Found: C, 60.46; H, 5.95; N, 4.74; S, 5.52.

Step 1

Methyl 2-chloro-5-cyclopentyl-7-(3-fluoro-4-isopropoxyphenyl)-5-hydroxy-3-oxoheptanoate

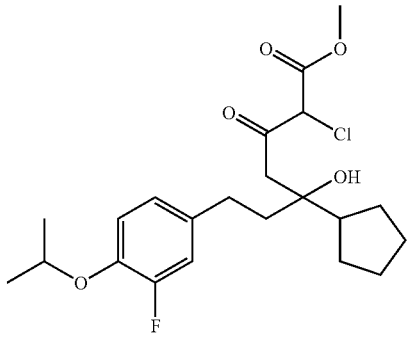

Methyl-2-chloroacetoacetate (2.0 mL, 16.2 mmol) was added to a cooled 0° C. suspension of NaH (0.65 g, 16.2 mmol, 60% dispersion in mineral oil) in THF (54 mL). After 15 min the solution was cooled to −40° C. and n-BuLi (10.0 mL, 16.2 mmol, 1.6M in hexanes) was added. The resulting dianion was stirred for an additional 30 min and then treated with a solution of 1-cyclopentyl-3-(3-fluoro-4-isopropoxyphenyl)propan-1-one (1.5 g, 5.4 mmol, compound was prepared analogously to Step 1 of Example A(82), where 4-(bromo)-2-fluoro-1-isopropoxybenzene was substituted in place of 2-Bromopyridine) in THF (10 ml). After stirring for 1 h at −40° C., the reaction mixture was quenched with saturated NH$_4$Cl and extracted with EtOAc. The organic layers were washed with brine, dried with Na$_2$SO$_4$ and concentrated to an orange oil that was used without further purification.

Step 2

3-chloro-6-cyclopentyl-6-[2-(3-fluoro-4-isopropoxyphenyl)ethyl]-4-hydroxy-5,6-dihydro-2H-pyran-2-one

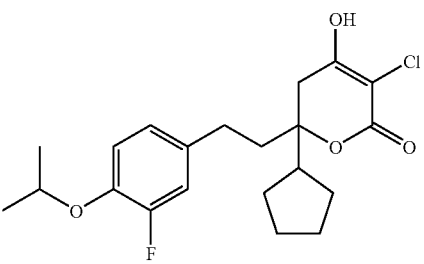

A solution of methyl 2-chloro-5-cyclopentyl-7-(3-fluoro-4-isopropoxyphenyl)-5-hydroxy-3-oxoheptanoate (1.74 g, 4.1 mmol), and bis(dibutylchlorotin)oxide (1.38 g, 2.5 mmol), dissolved in toluene (20 mL) were heated at reflux for 30 mins. The resulting mixture was concentrated and purified by silica gel chromatography to give the title compound (0.80 g, 50% yield, two Steps).

¹H NMR (300 MHz, CDCl₃): δ 1.33 (d, J=6.03 Hz, 6 H), 1.45–1.80 (m, 10 H), 1.99–2.05 (m, 2 H), 2.34–2.44 (m, 1 H), 2.59–2.66 (m, 2 H), 4.44–4.52 (m, 1 H), 6.78–6.91 (m, 3 H).

Example C(65)

6-[2-(3-chloro-4-methoxyphenyl)ethyl]-6-cyclopentyl-4-hydroxy-3-(9H-purin-8-ylthio)-5,6-dihydro-2H-pyran-2-one

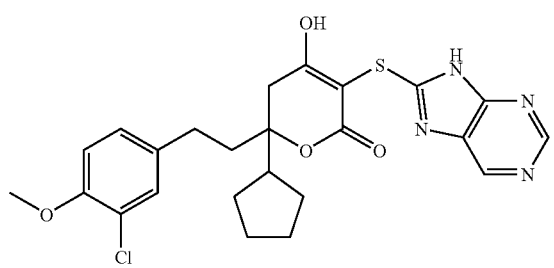

The title compound was prepared analogously to Example C(40), where 9H-purine-8-thiol was substituted in place of 5-chloro-1-isopropyl-1H-benzimidazole-2-thiol.

¹H NMR (300 MHz, DMSO-D₆) δ: 1.37–1.68 (m, 8 H), 2.04–2.10 (m, 2 H), 2.38–2.43 (m, 1 H), 2.55–2.60 (m, 2 H), 2.69–2.75 (m, 1 H), 2.93–2.98 (m, 1 H), 3.78 (s, 3 H), 7.03 (d, J=8.48 Hz, 1 H), 7.15–7.19 (m, 1 H), 7.28 (d, J=1.88 Hz, 1 H), 8.62 (s, 1 H), 8.72 (s, 1 H). ESI-MS calcd for C₂₄H₂₅ClN₄O₄S: 500.1. Found (M+H⁺): 501.1. Anal. Calcd. For C₂₄H₂₅ClN₄O₄S.1.2H₂O: C, 55.15; H, 5.28; N, 10.72; S, 6.14. Found: C, 54.92; H, 5.28; N, 11.16; S, 6.01.

Example C(66)

6-[2-(3-chloro-4-methoxyphenyl)ethyl]-6-cyclopentyl-4-hydroxy-3-(quinolin-2-ylthio)-5,6-dihydro-2H-pyran-2-one

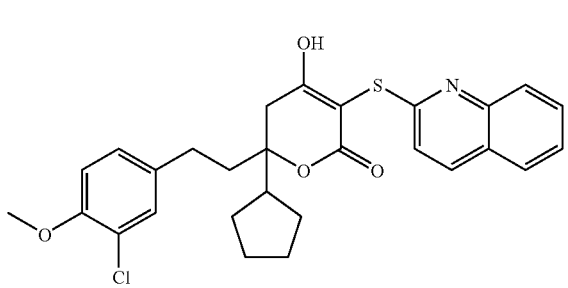

The title compound was prepared analogously to Example C(40), where quinoline-2-thiol was substituted in place of 5-chloro-1-isopropyl-1H-benzimidazole-2-thiol.

¹H NMR (300 MHz, DMSO-D₆) δ: 1.33–1.64 (m, 8 H), 1.91–2.03 (m, 2 H), 2.13–2.20 (m, 1 H), 2.38–2.49 (m, 2 H), 2.55–2.61 (m, 2 H), 2.73–2.79 (m, 1 H), 3.59 (s, 3 H), 6.81 (d, J=8.48 Hz, 1 H), 6.92–6.95 (m, 1 H), 7.02–7.08 (m, 3 H), 7.19–7.22 (m, 2 H), 7.59–7.62 (m, 1 H), 7.87 (d, J=8.85 Hz, 1 H). ESI-MS calcd for C₂₈H₂₈ClNO₄S: 509.1. Found (M+H⁺): 510.1. Anal. Calcd. For C₂₈H₂₈ClNO₄S.0.5H₂O: C, 64.79; H, 5.63; N, 2.70; S, 6.18. Found: C, 64.52; H, 5.66; N, 2.68; S, 6.07.

Example C(67)

6-[2-(3-chloro-4-methoxyphenyl)ethyl]-6-cyclopentyl-4-hydroxy-3-(7H-purin-2-ylthio)-5,6-dihydro-2H-pyran-2-one

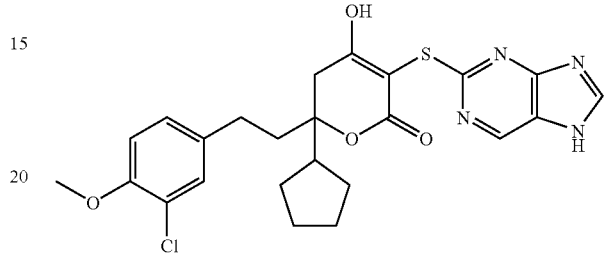

The title compound was prepared analogously to Example C(40), where 7H-purine-2-thiol was substituted in place of 5-chloro-1-isopropyl-1H-benzimidazole-2-thiol.

¹H NMR (300 MHz, DMSO-D₆) δ: 1.43–1.71 (m, 8 H), 2.18–2.29 (m, 2 H), 2.60–2.76 (m, 4 H), 2.88–2.94 (m, 1 H), 3.82 (m, 3 H), 7.03–7.36 (m, 3 H), 8.39–8.74 (m, 2 H). ESI-MS calcd for C₂₄H₂₅ClN₄O₄S: 500.1. Found (M+H⁺): 501.1. Anal. Calcd. For C₂₄H₂₅ClN₄O₄S.0.7H₂O: C, 56.12; H, 5.18; N, 10.91; S, 6.24. Found: C, 55.87; H, 5.26; N, 10.73; S, 6.14.

Example C(68)

6-[2-(3-chloro-4-methoxyphenyl)ethyl]-6-cyclopentyl-4-hydroxy-3-(quinazolin-4-ylthio)-5,6-dihydro-2H-pyran-2-one

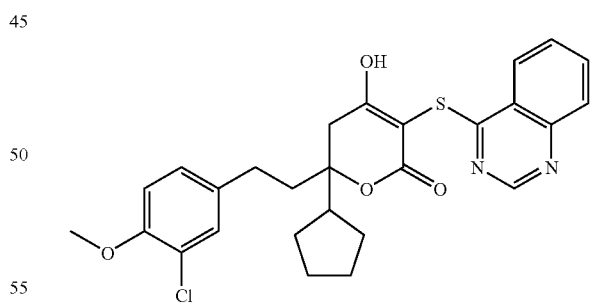

The title compound was prepared analogously to Example C(40), where quinazoline-4-thiol was substituted in place of 5-chloro-1-isopropyl-1H-benzimidazole-2-thiol.

¹H NMR (300 MHz, DMSO-D₆) δ: 1.42–1.77 (m, 8 H), 2.25–2.35 (m, 2 H), 2.61–2.77 (m, 4 H), 2.96–3.02 (m, 1 H), 3.83 (m, 3 H), 7.07–7.10 (m, 1 H), 7.16–7.20 (m, 1 H), 7.30 (s, 1 H), 7.71–7.76 (m, 1 H), 7.90–7.99 (m, 1 H), 8.21 (d, J=8.29 Hz, 1 H), 8.49 (s, 1 H). HRMS calcd. For C₂₇H₂₈ClN₂O₄S (M+H⁺): 511.1453. Found: 511.1443.

Example C(69)

6-Cyclopentyl-6-{2-[4-(difluoromethyl)-3-fluorophenyl]ethyl}-3-[(5,7-dimethyl[1,2,4]triazolo[1,5-a]pyrimidin-2-yl)thio]4-hydroxy-5,6-dihydro-2H-pyran-2-one

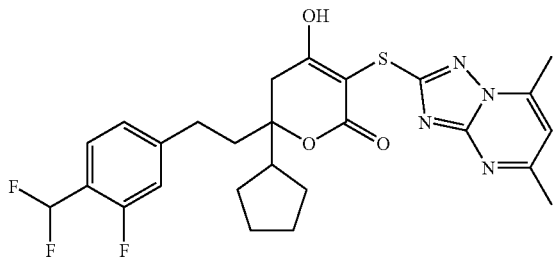

A mixture of 3-chloro-6-cyclopentyl-6-{-[4-(difluoromethyl)-3-fluorophenyl]ethyl}dihydro-2H-pyran-2,4(3H)-dione (200 mg, 0.514 mmol), from Step 1, below, and 5,7-dimethyl[1,2,4]triazolo[1,5-a]pyrimidine-2-thiol (93 mg, 0.514 mmol) in DMF (4 mL) was treated with triethylamine (52 mg, 0.514 mmol, 1 equiv). The mixture stirred and heated at 55° C. for 4 h. The reaction was cooled to room temperature, and the DMF removed in vacuo. Water and ethyl acetate were added to the resinous material, resulting in the precipitation of a solid. This was filtered, washed with ether, and allowed to air dry, affording 186 mg (68%) of the title product.

$^1$H NMR (DMF-d$_7$) δ 1.81–2.00 (m, 8H) 2.56–2.62 (m, 2H) 2.71 (s, 3H) 2.76 (s, 3H) 2.80 (m, 1H) 3.07(m, 2H) 3.14 (d, J=6 Hz, 1H) 3.32 (d, J=18 Hz, 1H) 7.40 (t, J=57 Hz, 1H), 7.24 (s, 1H) 7.66 (m, 2H) 7.84 (m, 1H,). MS (APCI) calcd for C$_{26}$H$_{27}$F$_3$O$_3$S: 532.58; MS found; (M+H$^+$) 533.1. Anal. Calc'd for C$_{26}$H$_{27}$F$_3$O$_3$S: C, 58.64; H, 5.11; N, 10.52; S, 6.02. Found: C, 58.26, 58.33; H, 5.25, 5.14; N, 10.69, 10.61; S, 5.78, 5.79.

Step 1

3-chloro-6-cyclopentyl-6-{-[4-(difluoromethyl)-3-fluorophenyl]ethyl}dihydro-2H-pyran-2,4(3 H)-dione

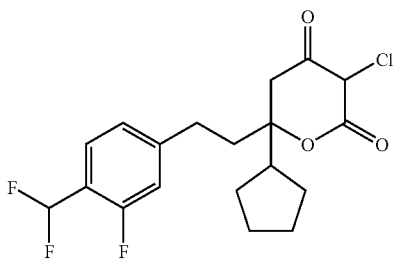

To a slurry of NaH (450 mg, 18.65 mmol) in dry THF (6 mL) at –40° C. under nitrogen was added a cold solution of methyl 2-chloroacetoacetate (2.67 g, 17.76 mmol) in 20 mL dry THF (20 mL) at such a rate that the temperature was maintained within 5° C. of –40° C. When the addition was complete, the mixture was stirred at this temperature for an additional 30 min, then cooled to –70° C. with a dry ice/acetone bath. Cold n-BuLi (9 mL, 2.08 M, 18.65 mmol) was slowly added via syringe, maintaining the temperature at –70° C. The mixture was stirred for an additional 45 min at this temperature. A solution of 1-cyclopentyl-3-[4-(difluoromethyl)-3-fluorophenyl]propan-1-one (4 g, 14.8 mmol) in dry THF (20 mL) was added slowly via an addition funnel. The reaction was allowed to stir at –70° C. for 45 min, then warmed to room temperature. After stirring for 2 h, the mixture was quenched with 4M aqueous NH$_4$Cl (9.35 mL, 37.3 mmol), stirred for 5 min, then concentrated in vacuo. The oily residue was treated with water and extracted with CH$_2$Cl$_2$ (3×50 mL). The extract was dried over Na$_2$SO$_4$, filtered and concentrated to a orange resin. Purification by column chromatography on silica gel and a gradient of 10% ethyl acetate/hexanes to 100% ethyl acetate afforded 3.5 g (8.32 mmol, 56%) of methyl 2-chloro-5-cyclopentyl-7-[4-(difluoromethyl)-3-fluorophenyl]-5-hydroxy-3-oxoheptanoate. This hydroxyester intermediate was dissolved in toluene (20 mL), treated with bis(dibutylchlorotin)oxide (2.07 g, 3.75 mmol, 0.45 equiv), and the mixture refluxed for 1 h. The solution was cooled to room temperature, the solvent removed in vacuo, and the resin filtered through a plug of silica gel, eluting with 5% MeOH/ethyl acetate. The fractions containing the product were evaporated and recrystallized from ethyl ether, affording 437 mg (13.5% yield) of the title product.

Example C(70)

8-({6-[2-(5-chloro-2,4-dimethoxyphenyl)ethyl]-6-cyclopentyl-4-hydroxy-2-oxo-5,6-dihydro-2H-pyran-3-yl}thio)-1,7-dihydro-6H-purin-6-one

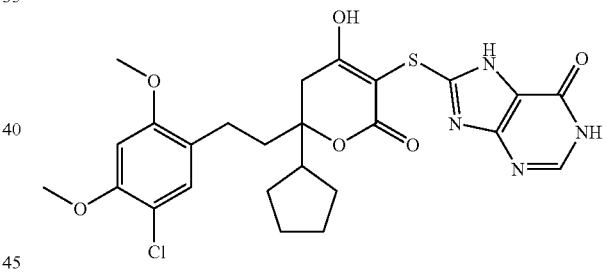

A solution of 3-chloro-6-[2-(5-chloro-2,4-dimethoxyphenyl)ethyl]6-cyclopentyldihydro-2H-pyran-2,4(3 H)-dione in anhydrous DMF (0.5 M, 160 μL, 0.08 mmol) was delivered by electronic pipette to a reaction vessel. To this was added a solution of 6-hydroxy-8-mercaptopurine monohydrate in anhydrous DMF (0.5M, 160 μL, 0.08 mmol, 1 equiv), and a solution of triethylamine in DMF (1M, 80 μL, 0.08 mmol, 1 equiv). The reaction mixture was heated at 55+/–5° C. for 16 h. The solvent was evaporated and the residue dissolved in DMSO to make a final concentration of 0.0572 M, and the product purified by HPLC using a Pecke Hi-Q 5 μm, 20×100 mm column with a 5–90% CH$_3$CN/0.05% TFA gradient. A run time of 8.1 min, a flow rate of 30.0 mL/min, and a monitoring wavelength at 260 nm were used.

$^1$H NMR (500 MHz, DMSO-d$_6$, WET suppression of DMSO [2.5 ppm] and H$_2$O [3.35 ppm]) δ 1.55–1.70 (m, 8 H) 1.91 (m, 2 H) 2.35 (m, 1 H) 2.63 (m, 1 H) 2.50–2.60 (m, 2H) 2.75 (d, J=17.6 Hz, 1H) 2.98 (d, J=17.6 Hz, 1 H) 3.80 (s, 3 H) 3.84 (s, 3 H) 6.71 (s, 1 H) 7.20 (s, 1 H) 7.88 (s, 1H) 12.14 (s, 1 H). MS (APCI) calcd for C$_{25}$H$_{27}$ClN$_4$O$_6$S: 546.13. found [M+1]: 547.1.

Example C(71)

6-[2-(5-Chloro-2,4-dimethoxyphenyl)ethyl]-6-cyclopentyl-4-hydroxy-3-[(5-phenyl-1H-1,2,4-triazol-3-yl)thio]-5,6-dihydro-2H-pyran-2-one

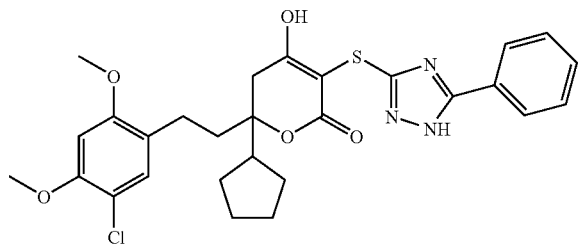

The title compound was prepared as described in Example C(70), where 3-phenyl-1,2,4-triazole-5-thiol was used in place of 6-hydroxy-8-mercaptopurine monohydrate.

$^1$H NMR (500 MHz, DMSO-$d_6$, WET suppression of DMSO [2.5 ppm] and H$_2$O [3.35 ppm]) δ 1.55–1.74 (m, 8 H) 1.90 (m, 1H) 2.35 (s, 1 H) 2.62 (m, 1 H) 2.70 (d, J=17.9 Hz, 1 H) 2.80 (d, J=17.6 Hz, 2 H) 2.89 (d, J=17.9 Hz, 1 H) 3.70 (s, 3 H) 3.78 (s, 3 H) 6.64 (s, 1 H) 7.15 (s, 2 H) 7.32 (d, J=5 Hz, 1H) 7.70 (s 1) 7.78 (s, 1H). MS (APCI) calcd for C$_{28}$H$_{30}$ClN$_3$O$_5$S: 556.08. found M: 556.

Example C(72)

6-[2-(5-Chloro-2,4-dimethoxyphenyl)ethyl]-6-cyclopentyl-4-hydroxy-3-[(1-methyl-1H-tetrazol-5-yl)thio]-5,6-dihydro-2H-pyran-2-one

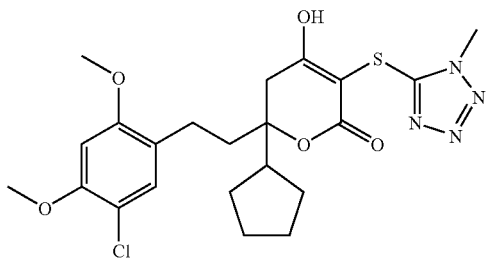

The title compound was prepared as described in Example C(70), where 5-mercapto-1-methyltetrazole was used in place of 6-hydroxy-8-mercaptopurine monohydrate.

$^1$H NMR (500 MHz, DMSO-$d_6$, WET suppression of DMSO [2.5 ppm] and H$_2$O [3.35 ppm]) δ 1.50–1.69 (m, 8 H) 1.92 (m, 2 H) 2.37 (m, 1 H) 2.50 (m, 1H) 2.63 (m, 1 H) 2.72 (d, J=17.9 Hz, 1 H) 2.93 (d, J=17.9 Hz, 1 H) 3.77 (s, 3 H) 3.84 (s, 3 H) 3.97 (s, 3 H) 6.71 (s, 1 H) 7.18 (s, 1 H). MS (APCI) calcd for C$_{22}$H$_{27}$ClN$_4$O$_5$S: 494.99. found M=495.1.

Example C(73)

6-[2-(5-Chloro-2,4-dimethoxyphenyl)ethyl]-3-[(5-chloro-1-isopropyl-1H-benzimidazol-2-yl)thio]-6-cyclopentyl-4-hydroxy-5,6-dihydro-2H-pyran-2-one

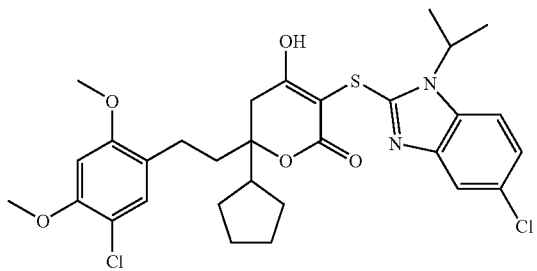

The title compound was prepared as described in Example C(70), where 5-chloro-1-isopropyl-2-mercaptobenzimidazole was used in place of 6-hydroxy-8-mercaptopurine monohydrate.

$^1$H NMR (500 MHz, DMSO-$d_6$, WET suppression of DMSO [2.5 ppm] and H$_2$O [3.35 ppm]) δ 1.56 (s, 3H) 1.57 (s, 3 H) 1.60–1.74 (m, 8 H) 2.13 (m, 1 H) 2.29 (m, 1 H) 2.35 (m, 1 H) 2.50 (m, 1H) 2.63 (m, 1 H) 2.74 (d, J=17.3 Hz, 1 H) 2.97 (d, J=17.3 Hz, 1H) 3.74 (s, 3 H) 3.86 (s, 3 H) 4.80 (m, 1 H) 6.71 (s, 1 H) 6.91 (s, 1 H) 7.11 (dd, J=8.65, 2.06 Hz, 1 H) 7.16 (s, 1 H) 7.63 (d, J=8.79 Hz, 1 H). MS (APCI) calcd for C$_{30}$H$_{34}$Cl$_2$N$_2$O$_5$S: 605.58. found M=605.0.

Example C(74)

6-[2-(5-chloro-2,4-dimethoxyphenyl)ethyl]-6-cyclopentyl-4-hydroxy-3-{[4-hydroxy-6-(trifluoromethyl)pyrimidin-2-yl]thio}-5, 6-dihydro-2H-pyran-2-one

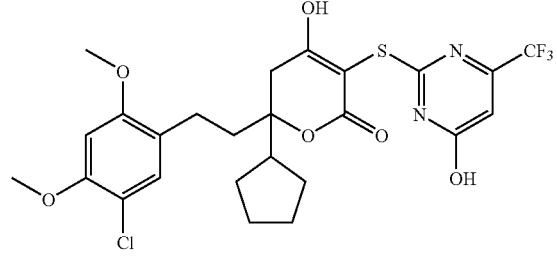

The title compound was prepared as described in Example C(70), where 4-hydroxy-6-(trifluoromethyl)pyrimidine-2-thiol was used in place of 6-hydroxy-8-mercaptopurine monohydrate.

$^1$H NMR (500 MHz, DMSO-$d_6$, WET suppression of DMSO [2.5 ppm] and H$_2$O [3.35 ppm]) δ 1.52–1.68 (m, 8 H) 1.84 (m, 1 H) 2.02 (m, 1 H) 2.35 (s, 1 H) 2.50 (m, 1H, overlap with dmso) 2.63 (s, 1 H) 2.80–2.88 (m, 2 H) 3.77 (s, 3 H) 3.83 (s, 3 H) 6.52 (s, 1 H) 6.70 (s, 1 H) 7.12 (s, 1 H). MS (APCI) calcd for C$_{25}$H$_{26}$ClF$_3$N$_2$O$_6$S: 575.00. found M=575.0.

Example C(75)

6-[2-(5-chloro-2,4-dimethoxyphenyl)ethyl]-6-cyclopentyl-4-hydroxy-3-[(5-pyridin-3-yl-4H-1,2,4-triazol-3-yl)thio]-5,6-dihydro-2H-pyran-2-one

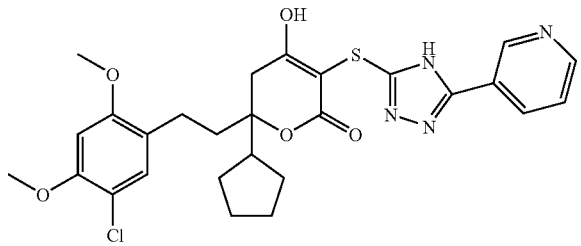

The title compound was prepared as described in Example C(70), where 5-(3-pyridinyl)-4H-1,2,4-triazole-3-thiol was used in place of 6-hydroxy-8-mercaptopurine monohydrate.

$^1$H NMR (500 MHz, DMSO-$d_6$, WET suppression of DMSO [2.5 ppm] and H$_2$O [3.35 ppm]) δ 1.55–1.73 (m, 8 H) 1.92 (m, 1 H) 2.11 (m, 1 H) 2.35 (m, 1 H) 2.50 (m, 1H, buried under dmso peak) 2.81 (d, J=17.6 Hz, 1 H) 3.46 (m, 2 H) 3.71 (s, 3 H) 3.78 (s, 3 H) 6.61 (s, 1 H) 7.12 (s, 1 H) 7.38 (m, 1 H) 8.08 (m, 1 H) 8.59 (d, J=5.2 Hz, 1 H) 9.02 (s, 1 H). MS (APCI) calcd for $C_{27}H_{29}ClN_4O_5S$: 557.07. found M=557.0.

Example C(76)

3-[(5-amino-1-methyl-1H-benzimidazol-2-yl)thio]-6-[2-(5-chloro-2,4-dimethoxyphenyl)ethyl]-6-cyclopentyl-4-hydroxy-5,6-dihydro-2H-pyran-2-one

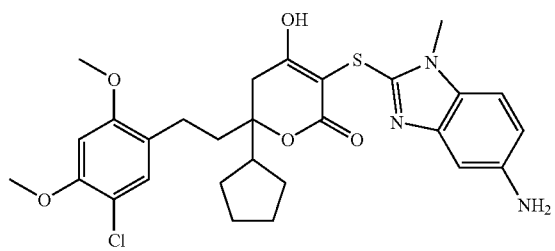

The title compound was prepared as described in Example C(70), where 5-Amino-1-methyl-1H-benzimidazole-2-thiol was used in place of 6-hydroxy-8-mercaptopurine monohydrate.

$^1$H NMR (500 MHz, DMSO-$d_6$, WET suppression of DMSO [2.5 ppm] and H$_2$O [3.35 ppm]) δ 1.60 (m, 8 H) 1.88 (m, 2 H) 2.62 (m, 1 H) 2.79 (d, J=17.86 Hz, 1 H) 3.78 (m, 1 H) 6.71 (s, 1 H) 6.88 (m, 1 H) 7.12 (s, 1 H) 7.48 (d, J=8.79 Hz, 1 H). MS (APCI) calcd for $C_{28}H_{32}ClN_3O_5S$: 558.09. found M=558.1.

Step 1

6-amino-1H-benzimidazole-2-thiol

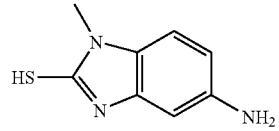

$N^1$-methylbenzene-1,2,4-triamine (Le Bris, M. T. *Bull. Soc. Chim Fr* 1976, 5, 921) (10.91 g, 40 mmol) in EtOH (75 mL) and H$_2$O (12 mL) and potassium o-ethyl dithiocarbonate (10.47 g, 64.01 mmol) were placed in a 250 mL 3-necked round bottomed flask, outfitted with a mechanical overhead stirrer and N2 flow. The resulting suspension was stirred for 15 min at room temperature. K2CO3 (8.36 g, 60.50 mmol) was added to the pot and the reaction mixture refluxed for 18 h. Warm water (150 mL, 80° C.) was added to the reaction mixture along with an 8:5 acetic acid/water solution (27 mL) to bring the pH to 5. The reaction mixture was allowed to cool to room temperature over 2 h and then was suction filtered. The filtrate (filtrate A) was concentrated to half the volume (250 mL to 125 mL) by heating, then allowed to cool to room temperature over the weekend.

The solid obtained from the filtration was dissolved in 8% NaOH (50 mL) and filtered to remove any undissolved solids. This filtrate was brought to pH 5 by the addition of glacial acetic acid and stirred for 1.5 h at room temperature. The solution was filtered and washed with water to give Filtrate B.

Filtrate A formed a sticky black solid on the bottom and sides of the flask. The liquid (Filtrate A) was decanted off and the solid was dissolved in 8% NaOH (150 mL) and filtered to remove any undissolved solids. The filtrate (Filtrate C) was acidified to pH 5 using glacial acetic acid (25 mL) and stirred at room temperature for 2 h. It was filtered again and washed with water, then concentrated to half its volume (225 mL to 115 mL). Filtrates A, B and C were combined and concentrated by heating. The solution was suction filtered and washed with H$_2$O (30 mL). A dark violet solid was obtained and dried in a vacuum oven affording 1.25 g (15.8%) of the desired product.

$^1$H NMR (DMSO-$d_6$) d 3.53 (s, 3H); 5.03 (broad s, 2H); 6.94 (s, 1H); 6.43–6.46 (d, J=9 Hz, 1H); 6.98–7.01 (d, J=9 Hz, 1H); 12.23 (broad s, 1H). MS (APCI) calcd for $C_8H_9N_3S$: 179.2. found (M+H$^+$) 180.0.

Example C(77)

6-[2-(5-chloro-2,4-dimethoxyphenyl)ethyl]-6–6cyclopentyl-4-hydroxy-3-[(5-pyridin-3-yl-1H-imidazol-2-yl)thio]-5,6-2H-pyran-2-one

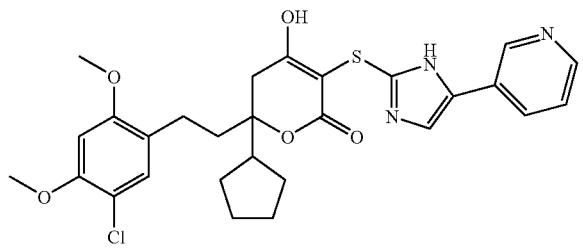

The title compound was prepared as described in Example C(70), where 5-pyridin-3-yl-1H-imidazole-2-thiol was used in place of 6-hydroxy-8-mercaptopurine monohydrate.

$^1$H NMR (500 MHz, DMSO-d$_6$, WET suppression of DMSO-h$_6$ (2.5 ppm) and H$_2$O (3.35 ppm) peak areas) δ 1.40–1.71 (m, 8 H) 1.91 (m, 1H)) 2.02 (m, 1 H) 2.36 (m, 1 H) 2.49 (m, 1H, overlap with dmso) 2.62 (m, 1 H) 2.72 (d, J=17.6 Hz, 1 H) 2.94 (d, J=17.9 Hz, 1 H) 3.72 (s, 3 H) 3.79 (s, 3 H) 6.61 (s, 1 H) 7.08 (s, 1 H) 7.58 (m, 1 H) 7.95 (s, 1 H) 8.23 (m., 1 H) 8.54 (d, J=4.67 Hz, 1 H) 8.92 (s, 1 H). MS (APCI) calcd for C$_{28}$H$_{30}$ClN$_3$O$_5$S: 556.08. found M=556.1.

Example C(78)

6-[2-(5-chloro-2,4-dimethoxyphenyl)ethyl]-6-cyclopentyl-4-hydroxy-3-[(3-methylpyrazin-2-yl)thio]-5,6-dihydro-2H-pyran-2-one

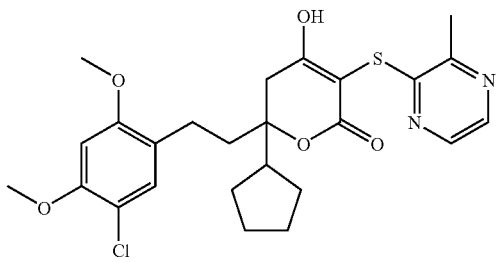

The title compound was prepared as described in Example C(70), where 3-methylpyrazine-2-thiol was used in place of 6-hydroxy-8-mercaptopurine monohydrate.

$^1$H NMR (500 MHz, DMSO-d$_6$, WET suppression of DMSO-h$_6$ (2.5 ppm) and H$_2$O (3.35 ppm) peak areas) d 1.54–1.71 (m, 8 H) 2.05 (m, 1 H) 2.18 (m, 1 H) 2.35 (m, 1 H) 2.50 (m, 1H, overlap with dmso) 2.63 (m, 1 H) 2.75 (d, J=17.6 Hz, 1 H) 2.95 (d, J=17.3 Hz, 1 H) 3.30 (s, 3H, overlap with H$_2$O) 3.74 (s, 3 H) 3.86 (s, 3 H) 6.72 (s, 1 H) 7.10 (s, 1 H) 7.84 (d, J=2.20 Hz, 1 H) 8.11 (d, J=2.75 Hz, 1 H). MS (APCI) calcd for C$_{25}$H$_{29}$ClN$_2$O$_5$S: 505.03. found M=505.0.

Step 1

3-methylpyrazine-2-thiol

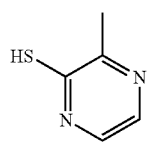

Sodium hydrogen sulfide dihydrate (139.7 g, 1.58 mol), 2-chloro-3,(5),(6)-methylpyrazine (with 80% of 3-methyl isomer) (65.0 g, 0.51 mol) and 1,3-propanediol (300 mL) were added to a 3-L round bottomed flask, which was equipped with a magnetic stir bar, a condenser and a thermometer. The reaction mixture was heated for 1.5 h at 110–130° C. After cooling to room temperature, the inorganic salt was filtered and washed with methanol (200 mL). The combined filtrate was concentrated in vacuo, (10–20 mmHg/140–120° C.). Water (200 mL) was added to the residue and aqueous NaOH was used to adjust from pH 1 to pH 14. Insoluble material was filtered and the filtrate was adjusted to pH 5–6. The yellow solid was filtered, washed with water (2×100 mL) and lyophilized to yield 44 of a mixture of isomers of the desired product, of which contained 80% of the 3-methyl isomer. The mixture was dissolved in 4 L of hot isopropanol/ethanol (1:1). Upon cooling to room temperature, the yellow crystallized impurity was filtered. After evaporating the filtrate under reduced pressure, the desired product was obtained as a yellow solid. (25.0 g, 39% yield, 85% pure).

$^1$H NMR (DMSO-d$_6$): d 2.5 (s, 3H) 7.54 (s, 1H) 7.71 (d, J=3.0 Hz, 1H) 14.15 (broad s, 1H). MS (APCI) calcd for C$_5$H$_6$N$_2$S: 126.03. found (M+H$^+$): 127.0.

Example C(79)

6-[2-(5-chloro-2,4-dimethoxyphenyl)ethyl]-6-cyclopentyl-4-hydroxy-3-{[5-(3-methoxyphenyl)-4-methyl-4H-1,2,4-triazol-3-yl]thio}-5,6-dihydro-2H-pyran-2-one

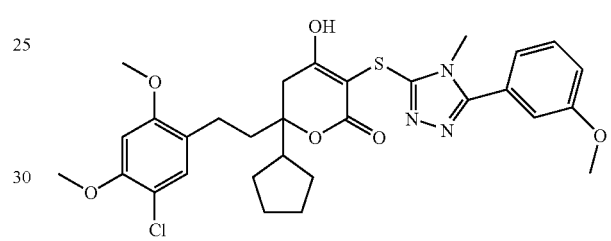

The title compound was prepared as described in Example C(70), where 5-(3-methoxyphenyl)-4-methyl-4H-1,2,4-triazole-3-thiol was used in place of 6-hydroxy-8-mercaptopurine monohydrate.

$^1$H NMR (500 MHz, DMSO-d$_6$, WET suppression of DMSO-h$_6$ (2.5 ppm) and H$_2$O (3.35 ppm) peak areas) δ 1.53–1.74 (m, 8 H) 1.91 (m,Hz, 2 H) 2.35 (m, 1 H) 2.50 (m, 1H, overlap with dmso) 2.63 (m, 1 H) 2.70 (d, J=17.9 Hz, 1 H) 2.92 (d, J=17.6 Hz, 1 H) 3.67 (s, 3 H) 3.77 (s, 3 H) 3.80 (s, 3 H) 3.83 (s, 3 H) 6.69 (s, 1 H) 7.11 (m, 1 H) 7.20 (s, 2 H) 7.45 (t, J=8.2 Hz, 1 H). MS (APCI) calcd for C$_{30}$H$_{34}$ClN$_3$O$_6$S: 600.13. found M=600.1.

Example C(80)

6-[2-(5-chloro-2,4-dimethoxyphenyl)ethyl]-6-cyclopentyl-4-hydroxy-3-[(5-hydroxy-4-isopropyl-4H-1,2,4-triazol-3-yl)thiol-5,6-dihydro-2H-pyran-2-one

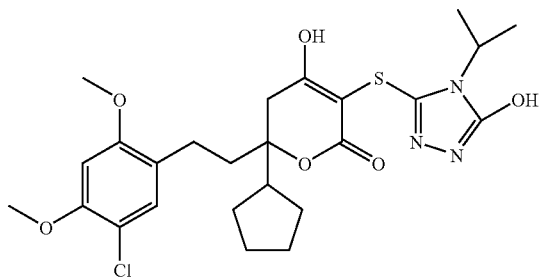

The title compound was prepared as described in Example C(70), where 4-isopropyl-5-mercapto-4H-1,2,4-triazol-3-ol was used in place of 6-hydroxy-8-mercaptopurine monohydrate.

$^1$H NMR (500 MHz, DMSO-d$_6$, WET suppression of DMSO-h$_6$ (2.5 ppm) and H$_2$O (3.35 ppm) peak areas) δ 1.35 (s, 3 H) 1.37 (s, 3 H) 1.54–1.69 (m, 8 H) 1.80 (m, 1 H) 1.91 (m, 1 H) 2.06 2.34 (m, 1 H) 2.50 (m, 1H, overlap with dmso) 2.63 (m, 1 H) 2.74 (d, J=15.0 Hz, 1 H) 2.85 (d, J=15.0 Hz, 1 H) 3.77 (s, 3 H) 3.84 (s, 3 H) 4.31 (m, 1 H) 6.70 (s, 1 H) 7.13 (s, 1 H) 11.52 (s, 2 H). MS (APCI) calcd for C$_{25}$H$_{32}$ClN$_3$O$_6$S: 538.06. found M=538.1.

Example C(81)

6-[2-(5-chloro-2,4-dimethoxyphenyl)ethyl]-6-cyclopentyl-4-hydroxy-3{[5-(4-hydroxyphenyl)-4H-1,2,4-triazol-3-yl]thio}-5,6-dihydro-2H-pyran-2-one

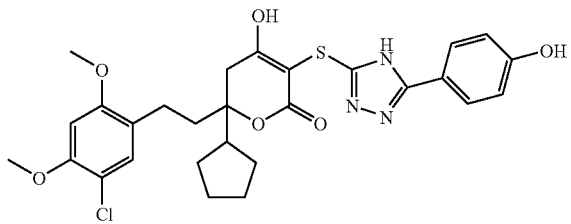

The title compound was prepared as described in Example C(70), where 4H-mercapto-5(4-hydroxyphenyl)-[1,2,4]triazole was used in place of 6-hydroxy-8-mercaptopurine monohydrate.

$^1$H NMR (500 MHz, DMSO-d$_6$, WET suppression of DMSO-h$_6$ (2.5 ppm) and H$_2$O (3.35 ppm) peak areas) δ 1.50–1.72 (m, 8 H) 1.89 (m, 2 H) 2.35 (m, 1 H) 2.50 (m, 1H, overlap with dmso) 2.63 (m, 1 H) 2.79 (d, J=17.9 Hz, 1 H) 3.73 (s, 3 H) 3.81 (s, 3 H) 6.66 (s, 1 H) 6.70 (s, 1 H) 6.72 (s, 1 H) 7.14 (s, 1 H) 7.56 (s, 2 H). MS (APCI) calcd for C$_{28}$H$_{30}$ClN$_3$O$_6$S: 572.08. found M=572.2

Example C(82)

6-[2-(5-chloro-2,4-dimethoxyphenyl)ethyl]-6-cyclopentyl-4-hydroxy-3-[(5-methyl[1,2,4]triazolo[1,5-a]pyrimidin-2-yl)thio]-5,6-dihydro-2H-pyran-2-one

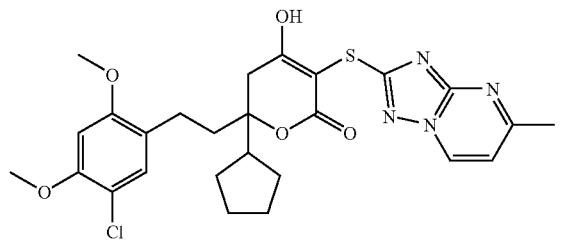

The title compound was prepared as described in Example C(70), where 5-methyl[1,2,4]triazolo[1,5-a]pyrimidine-2-thiol was used in place of 6-hydroxy-8-mercaptopurine monohydrate.

$^1$H NMR (500 MHz, DMSO-d$_8$, WET suppression of DMSO-h$_6$ (2.5 ppm) and H$_2$O (3.35 ppm) peak areas) δ 1.55–1.73 (m, 8 H) 2.03 (m, 1 H) 2.11 (m, 1 H) 2.35 (m, 1 H) 2.56 (m, 1 H) 2.62 (m, 1 H) 2.75 (d, J=17.6 Hz, 1 H) 2.95 (d, J=17.6 Hz, 1 H) 3.75 (s, 2 H) 3.84 (s, 3 H) 6.69 (s, 1 H) 7.10 (d, J=6.9 Hz, 1 H) 7.19 (s, 1 H) 8.69 (d, J=6.9 Hz, 1 H). MS (APCI) calcd for C$_{26}$H$_{29}$ClN$_4$O$_5$S: 545.06. found M=545.2.

Step 1

4-methyl-2-methylsulfanyl-pyrimidine

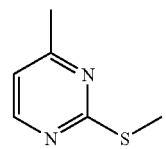

Based on a reported procedure (Ishizumi, K.; Kojima, A.; Antoku, F. *Chem Pharm Bull* 1991, 39, 2288). Sodium hydroxide (92.5 g, 2.31 mol) was added to a suspension of 2-mercapto-4-methyl pyrimidine hydrochloride (150 g, 0.93 mol) in water (1.5 L). Methyl iodide (78.9 ml, 1.39 mol) was rapidly added to the clear solution (solution temp. <20° C.). After overnight stirring, diethyl ether (400 mL), the organic layer was separated and the aqueous layer was extracted with diethyl ether (4×200 ml) all organic layers were combined, washed with 5% aq. NaOH solution (100 ml), brine (200 ml, 2 times), and dried (MgSO$_4$), concentrated in vacuo to afford 119.3 g of crude material (95% pure by NMR) which was used in the next step without purification.

$^1$H NMR (CDCl$_3$, 300 MHz) δ, ppm: 2.46 (s, 3H), 2.56 (s, 3H), 6.82 (d, J=5 Hz, 1H,), 8.37 (d, J=5 Hz 1H).

Step 2

(4-methyl-pyrimidin-2-yl)-hydrazine

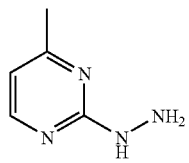

Based on a reported procedure (Vanderhaeghe, Claesen, *Bull. Soc. Chim. Belg.* 1959, 68, 30). Hydrazine monohydrate (334.7 ml, 6.90 mmol) was added in one portion to a solution of 4-Methyl-2-methylsulfanyl-pyrimidine (357.9 g, 2.55 mol) in abs. EtOH (890 ml). The resulting mixture was refluxed for 50 h, then hydrazine monohydrate (200 ml) was added and refluxing was continued for 50 h (the reaction was monitored by $^1$H NMR). Then it was cooled to 0° C. to crystallize and 213 g of crude product was isolated by filtration. Recrystallization from ethanol gave the title compound (184.7 g, 59%) as a white solid.

$^1$H NMR (CDCl$_3$, 300 MHz) δ, ppm: 2.40 (s, 3H), 4.00 (broad, 2H), 6.512 (d, 1H, 5 Hz), 7.03 (broad, 1H), 8.24 (d, 1H, 5 Hz).

Step 3

Sodium 7-methyl-1H-[1,2,4]triazolo[4,3-a]pyrimidine-3-thiolate

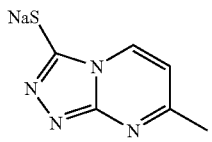

The title compound was prepared by a modification or a reported procedure (Shirakawa, K. *Yakugaku Zasshi* 1960, 80, 1542. A solution of (4-Methyl-pyrimidin-2-yl)-hydrazine (140 g, 1.13 mol), sodium hydroxide (45 g, 1.13 mol) and carbon disulfide (67.7 ml, 1.13 mol) in 50% aqueous ethanol (900 ml) was refluxed for 6 hours. The resulting mixture was cooled to ambient temperature and 54.7 g the yellow solid formed was isolated (54.7 g). It was recrystallized from 50% aqueous ethanol and dried at 40° C./1 Torr for 10 hours to give 44 g (18%) of sodium 5-methyl-1H-[1,2,4]triazolo[4,3-a]pyrimidine-3-thiolate, 85% pure by ELSD and $^1$H NMR.

The initial mother liquid was kept at 0° C. for 2 days. The crystallized orange solid was isolated by filtration, dried for 10 h at 40° C./1 Torr to give 68.1 g (27%) of the title compound, sodium 7-methyl-1H-[1,2,4]triazolo[4,3-a]pyrimidine-3-thiolate, used in Step 4, below. $^1$H NMR (DMSO-d$_6$, 300 MHz) δ, ppm: 2.44 (s, 3H), 6.60 (d, 1H, 7 Hz), 8.29 (d, 1H, 7 Hz).

Step 4

5-methyl[1,2,4]triazolo[1,5-a]pyrimidine-2-thiol

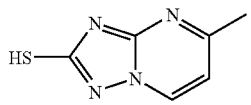

The title compound was synthesized from 7-methyl-1H-[1,2,4]triazolo[4,3-a]pyrimidine-3-thiolate (from Step 3, above) using the procedure described for the synthesis of 7-methyl[1,2,4]triazolo[1,5-a]pyrimidine-2-thio][Step 2 in the AG-101578 example], to give the crude product in 77% yield. Two recrystallizations from 50% aqueous ethanol provided 99% pure ($^1$H NMR and ELSD) material in 46% yield. $^1$H NMR (DMSO-d$_6$, 300 MHz) δ, ppm: 2.58 s, 3H), 7.34 (d, 1H, 7 Hz), 8.99 (d, 1H, 7 Hz), 14.10 (broad, 1H)."

Example C(83)

6-[2-(5-chloro-2,4-dimethoxyphenyl)ethyl]-6-cyclopentyl-3-({5-[(dimethylamino)methyl]-4-methyl-4H-1,2,4-triazol-3-yl}thio)-4-hydroxy-5,6-dihydro-2H-pyran-2-one

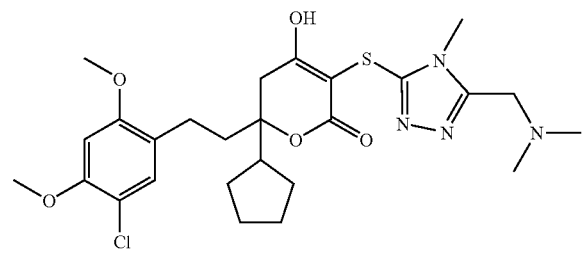

The title compound was prepared as described in Example C(70), where 5-[(dimethylamino)methyl]-4-methyl-4H-1,2,4-triazole-3-thiol was used in place of 6-hydroxy-8-mercaptopurine monohydrate. $^1$H NMR (500 MHz, DMSO-d$_6$, WET suppression of DMSO-h$_6$ (2.5 ppm) and H$_2$O (3.35 ppm) peak areas) d ppm 1.59 (m, 8 H) 1.91 (m, 2 H) 2.36 (m, 1 H) 2.62 (m, 1 H) 2.73 (d, J=17.58 Hz, 1 H) 2.86 (s, 9 H) 2.91 (d, J=17.86 Hz, 1 H) 3.63 (s, 1 H) 3.80 (d, J=3.02 Hz, 1 H) 3.84 (s, 1 H) 4.52 (s, 3 H) 6.71 (s, 1 H) 7.20 (s, 1 H). MS (APCI) calcd for C$_{26}$H$_{35}$ClN$_4$O$_5$S: 551.10. found M=551.2.

Step 1

5-[(dimethylamino)methyl]-4-methyl-4H-1,2,4-triazole-3-thiol

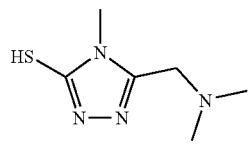

N,N-dimethylglycine hydrazide hydrochloride (50 g, 0.263 mol) was stirred for 5 min in EtOH (525 mL). To this suspension was added Cs2CO3 (62.5 g, 0.192 mol) and the mixture was stirred at room temperature for 15 min. Methyl isothiocyanate (19.25 g, 0.263 mol) in EtOH (270 mL) was added to the pot and the reaction mixture was brought to reflux. The reflux condenser was removed and the EtOH was allowed to evaporate under atmospheric pressure (oil bath temperature 105–110° C.) over 3 h to give a purple paste. The reaction was removed from heat and allowed to sit at room temperature overnight (18 h), during which time the paste became a solid. The solid was mixed with CH$_2$Cl$_2$ (1.5 L) and filtered. The organic filtrate was concentrated under reduced pressure to give 31 g of a crude yellow oil. The oil was purified by column chromatography through silica gel, eluting with 4:1 CH$_2$Cl$_2$/MeOH to afford 15.3 g (34.9%) of the desired product.

$^1$H NMR (DMSO-d$_6$) d 2.17 (s, 6H) 3.46 (s, 5H) 13.57 (s, 1H). MS (APCI) calcd for C$_6$H$_{12}$N$_4$S: 172.25. found (M−H+) 171.1.

Example C(84)

6-[2-(5-chloro-2,4-dimethoxyphenyl)ethyl]-6-cyclopentyl-4-hydroxy-3-([1,2,4]triazolo[1,5-a]pyrimidin-2-ylthio-5,6-dihydro-2H-pyran-2-one

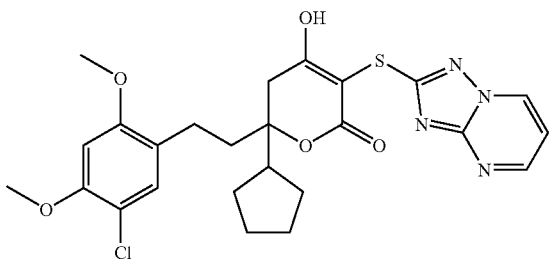

The title compound was prepared as described in Example C(70), where [1,2,4]triazolo[1,5-a]pyrimidine-2-thiol was used in place of 6-hydroxy-8-mercaptopurine monohydrate.

$^1$H NMR (500 MHz, DMSO-d$_6$, WET suppression of DMSO-h$_6$ (2.5 ppm) and H$_2$O (3.35 ppm) peak areas) δ 1.55–1.72 (m, 8 H) 2.08 (m, 2 H) 2.35 (m, 1 H) 2.50 (m, 1H, overlap with dmso) 2.63 (m, 1 H) 2.78 (d, J=17.9 Hz, 1 H) 2.96 (d, J=17.6 Hz, 1 H) 3.76 (s, 3 H) 3.85 (s, 3 H) 6.70 (s, 1 H) 7.20 (m, 1H, overlap) 7.21 (s, 1 H) 7.22 (m, 1 H, overlap) 8.75 (dd, J=4.4, 1.7 Hz, 1 H) 8.87 (dd, J=6.9, 1.7 Hz, 1 H). MS (APCI) calcd for C$_{25}$H$_{27}$ClN$_4$O$_5$S: 531.03. found M=531.1.

Step 1: [1,2,4]triazolo[1,5-a]pyrimidine-2-thiol

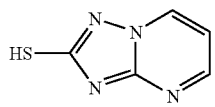

The title compound was prepared from malonodialdehyde bis(dimethylacetal) and 3-amino-5-mercapto-1,2,4-triazole as previously described by M. Künstlinger and E. Breitmaier in *Synthesis*, 1983, 4447.

$^1$H NMR (DMSO-d$_6$) d 7.07 (dd, J=6.8, J=3.8, 1 H) 8.63 (d, J=6.8, 1 H) 8.76 (s, 1 H). MS (APCI) calcd for C$_5$H$_4$N$_4$S: 152.18. found (M=H$^+$) 153.0.

Example C(85)

6-[-(5-chloro-2,4-dimethoxyphenyl)ethyl]-6-cyclopentyl-4-hydroxy-3-[(4-methyl-5-pyridin-3-yl-4H-1,2,4-triazol-3-yl)thio]-5,6-dihy

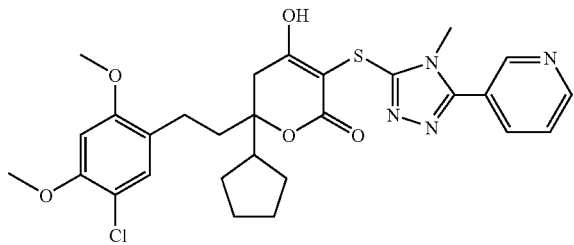

The title compound was prepared as described in Example C(70), where 4-methyl-5-(3-pyridyl)-4H-1,2,4-triazole-3-thiol was used in place of 6-hydroxy-8-mercaptopurine monohydrate.

$^1$H NMR (500 MHz, DMSO-d$_6$, WET suppression of DMSO-h$_6$ (2.5 ppm) and H$_2$O (3.35 ppm) peak areas) d ppm 1.52–1.69 (m, 8 H) 1.92 (m,2 H) 2.37 (m, 1 H) 2.5 (m, 1 H, overlap with dmso) 2.62 (m, 1 H) 2.73 (d, J=17.6 Hz, 1 H) 2.94 (d, J=17.9 Hz, 2 H) 3.70 (s, attenuation due to proximity to H$_2$O peak) 3.8 (s, attenuation due to proximity to H$_2$O peak) 6.70 (s, 1 H) 7.21 (s, 1 H) 7.59 (dd, J=7.7, 4.7 Hz, 1 H) 8.12 (d, J=8.5 Hz, 1 H) 8.73 (d, J=4.1 Hz, 1 H) 8.89 (s, 1 H). MS (APCI) calcd for C$_{28}$H$_{31}$ClN$_4$O$_5$S: 571.09. found M=571.1.

Example C(86)

6-[2-(5-chloro-2,4-dimethoxyphenyl)ethyl]-6-cyclopentyl-4-hydroxy-3-{[5-methyl-4-(2-morpholin-4-ylethyl)-4H-1,2,4-triazol-3-yl]thio}-5,6-dihydro-2H-pyran-2-one

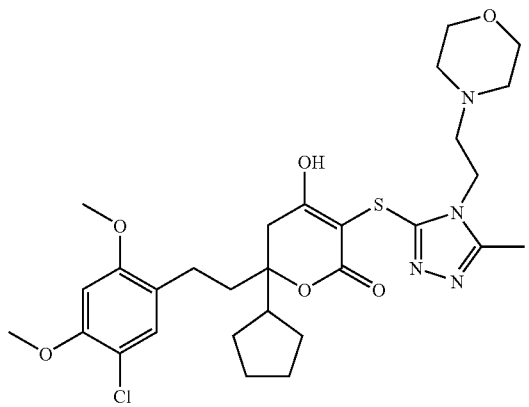

The title compound was prepared as described in Example C(70), where 5-methyl-4-(2-morpholin-4-ylethyl)-4H-1,2,4-triazole-3-thiol was used in place of 6-hydroxy-8-mercaptopurine monohydrate.

$^1$H NMR (500 MHz, DMSO-d$_6$, WET suppression of DMSO-h$_6$ (2.5 ppm) and H$_2$O (3.35 ppm) peak areas) d ppm 1.50 (m, 9 H) 1.83 (m, 2 H) 2.33 (m, 2 H) 2.42 (m, 1 H) 2.63 (m, 1 H) 2.78 (d, J=16.5 Hz, 1 H) 3.27 (s, 4 H) 3.42 (s, 3 H) 3.53 (m, 3 H) 3.82 (d, J=15.0 Hz, 1 H) 4.45 (m, 2 H) 6.71 (s, 2 H) 7.13 (s, 1 H). MS (APCI) calcd for C$_{29}$H$_{39}$ClN$_4$O$_6$S: 607.17. found M=607.1.

Step 1

5-methyl-4-(2-morpholin-4-ylethyl)-4H-1,2,4-triazole-3-thiol

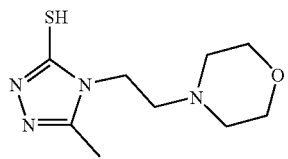

The title compound was prepared by a modification of a procedure reported for related compounds: Henichart, J. P.; Bernier, J. L. *Synthesis* 1980, 4, 311. Acetic hydrazide (3.7 g, 50 mmol) in ethanol (50 mL) was placed in a 200 mL 3-necked round bottomed flask outfitted with a magnetic stir bar and a reflux condenser. 2-morpholinoethyl isothiocyanate (8.61 g, 500 mmol) in ethanol (50 mL) was added to the pot. The mixture was refluxed, under N$_2$, for 6 h. The reaction was cooled to room temperature and the solvent removed on the rotovap. The resulting resin was dissolved in minimal ethanol and ether. A white solid precipitated out, was filtered and washed with cold ether. The filtrate, containing uncyclized intermediate, was concentrated and dissolved in xylenes. The mixture was refluxed under N2 for 8 h, then allowed to sit at room temperature, under N2. for 48 h. A white solid formed, was filtered and washed with cold ether. The first and second batches of white solid were combined to yield 7.33 g (64%) of the desired product.

$^1$H NMR (DMSO-d$_6$): d 2.33 (s, 3H) 2.41 (m, 4H) 2.55 (m, 2H) 3.52 (m, 4H) 3.99 (t, 2H, J=6) 13.41 (s, 1H). MS (APCI) calcd for C$_9$H$_{16}$N$_4$OS: 228.32. found (M+H$^+$) 229.1.

Example C(87)

6-[2-(5-chloro-2,4-dimethoxyphenyl)ethyl]-6-cyclopentyl-4-hydroxy-3-[(6-methyl[1,2,4]triazolo[1,5-a]pyrimidin-2-yl)thio]-5,6-dihydro-2H-pyran-2-one

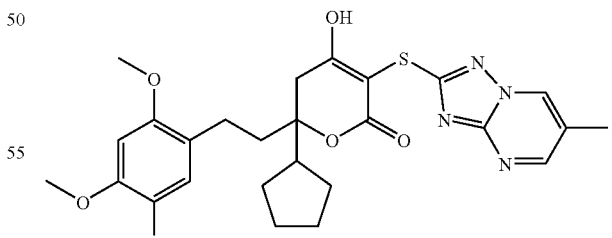

The title compound was prepared as described in Example C(70), where 6-methyl[1,2,4]triazolo[1,5-a]pyrimidine-2-thiol in place of 6-hydroxy-8-mercaptopurine monohydrate.

$^1$H NMR (500 MHz, DMSO-d$_6$, WET suppression of DMSO-h$_6$ (2.5 ppm) and H$_2$O (3.35 ppm) peak areas) d 1.40–1.74 (m, 8 H) 2.09 (m, 1 H) 2.18 (m, 1 H) 2.29 (s, 3 H) 2.35 (m, 1 H) 2.63 (m, 1 H) 2.69 (m, 1 H) 2.75 (d, J=17.6

Hz, 1 H) 2.86 (m, 1 H) 2.98 (d, J=17.9 Hz, 1 H) 3.75 (s, 2 H) 3.85 (m, 3 H) 6.70 (s, 1 H) 7.19 (s, 1 H) 8.48 (s, 1 H) 8.64 (d, J=2.2 Hz, 1 H). MS (APCI) calcd for $C_{26}H_{29}ClN_4O_5S$: 545.06. found M=545.2.

Step 1

6-methyl[1,2,4]triazolo[1,5-a]pyrimidine-2-thiol

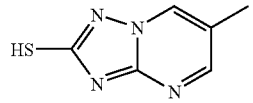

The title compound was prepared from 3-ethoxymethacrolein and 3-amino-5-mercapto-1,2,4-triazole as previously described by M. Künstlinger and E. Breitmaier in *Synthesis*, 1983, 44–47.

$^1$H NMR (DMSO-$d_6$) d 2.31 (s, 1 H) 8.45 (s, 1 H) 8.68 (s, 1 H). MS (APCI) calcd for $C_6H_6N_4S$: 166.21. found (M+H$^+$) 167.0.

Example C(88)

6-[2-(5-chloro-2,4-dimethoxyphenyl)ethyl]-6-cyclopentyl-3-[(4,5-dimethyl-4H-1,2,4-triazol-3-yl)thio]-4-hydroxy-5,6-dihydro-2H-pyran-2-one

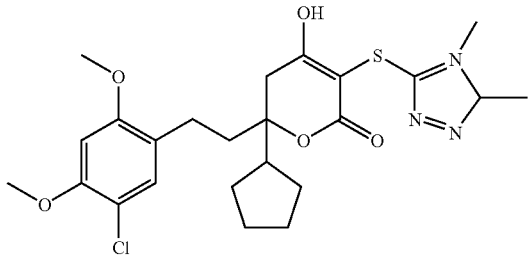

The title compound was prepared as described in Example C(70), where 4,5-dimethyl-4H-1,2,4-triazole-3-thiol was used in place of 6-hydroxy-8-mercaptopurine monohydrate.

$^1$H NMR (500 MHz, DMSO-$d_6$, WET suppression of DMSO-$h_6$ (2.5 ppm) and H$_2$O (3.35 ppm) peak areas) δ 1.48–1.65 (m, 8 H) 1.84 (m, 3 H) 2.18 (m, 1 H) 2.32 (m, 2H) 2.38 (s, 3 H) 2.61 (d, J=17.9 Hz, 1 H) 2.82 (d, J=17.3 Hz, 1H) 3.56 (s, attenuation due to proximity to H$_2$O peak) 3.78 (s, attenuation due to proximity to H$_2$O peak) 3.84 (s, 3H) 6.71 (s, 1H) 7.12 (s, 1H). MS (APCI) calcd for $C_{24}H_{30}ClN_3O_5S$: 508.04. found M=508.1.

Step 1

4,5-dimethyl-4H-1,2,4-triazole-3-thiol

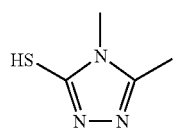

Acetic hydrazide (7.4 g, 100 mmol) in ethanol (75 mL) was placed in a 200 mL 3-necked round bottomed flask outfitted with a magnetic stir bar and a reflux condenser. Methyl isothiocyanate (7.3 g, 100 mmol) in ethanol (75 mL) was added to the pot. The mixture was refluxed, under N$_2$, for 6 h. The reaction was cooled to room temperature and the solvent removed on the rotovap. The resulting wet solid was triturated with ether and filtered to give a sticky, yellow solid. This solid was triturated with hot CH$_2$Cl$_2$/ethyl acetate (1:1), which afforded a white solid of the uncyclized intermediate. The solid and all liquids associated with the reaction were combined, dissolved in ethanol. Aqueous NaOH (1 M, 50 mL) was added and the mixture refluxed under N$_2$ for 1 h. Acetic acid was used to acidify to a pH of 4–5. The mixture was then cooled on an ice bath to facilitate precipitation. White solid formed, was filtered and washed with ether. (repeated the crystallization process three times with mother liquors). Combined all solids collected and chromatographed through silica gel, eluting with 1–4% MeOH/ ethyl acetate. The collected fractions were concentrated, washed with ether and filtered to yield 5.02 g (38.9%) of the desired product.

$^1$H NMR (DMSO-$d_6$): d 2.27 (s, 3H) 3.37 (s, 3H) 13.36 (broad s, 1H). MS (APCI) calcd for $C_4H_7N_3S$: 129.18. found (M+H$^+$) 130.0.

Example C(89)

Methyl 5-({6-[2-(5-chloro-2,4-dimethoxyphenyl) ethyl]-6-cyclopentyl-4-hydroxy-2-oxo-5,6-dihydro-2H-pyran-3-yl}thio)-4-methyl-4H-1,2,4-triazole-3-carboxylate

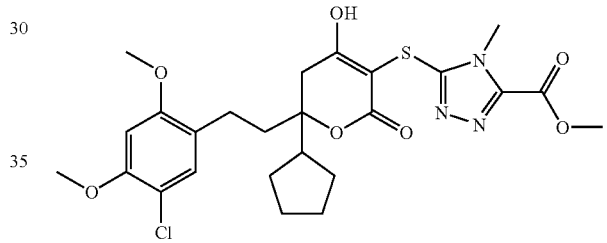

The title compound was prepared as described in Example C(70), where methyl 5-mercapto-4-methyl-4H-1,2,4-triazole-3-carboxylate was used in place of 6-hydroxy-8-mercaptopurine monohydrate.

$^1$H NMR (500 MHz, DMSO-$d_6$, WET suppression of DMSO-$h_6$ (2.5 ppm) and H$_2$O (3.35 ppm) peak areas) d 1.51–1.67 (m, 8 H) 1.88 (m, 2 H) 2.36 (m, 1 H) 2.5 (m, 1H, overlap with dmso) 2.63 (m, 1 H) 2.73 (d, J=17.6 Hz, 1 H) 2.90 (d, J=17.6 Hz, 1 H) 3.77 (s, 3 H) 3.81 (s, 3 H) 3.85 (s, 3 H) 3.87 (s, 3 H) 6.70 (s, 1 H) 7.16 (s, 1 H). MS (APCI) calcd for $C_{25}H_{30}ClN_3O_7S$: 552.05. found M=552.1.

Step 1 methyl hydrazino(oxo)acetate

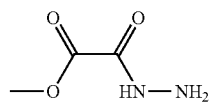

This compound was prepared as described: Smuszkovicz, J.; Greig, M. E. *J. Med Pharm. Chem.* 1961, 4, 259). From 1.08 mol of dimethyl oxalate, 51.7 g (44%) of the title product was obtained.

$^1$H NMR (DMSO-d$_6$) d 3.75 (s, 3H) 4.63 (broad s, 2H) 10.24 (broad s, 1H). MS (APCI) calcd for C$_3$H$_6$N$_2$O$_3$: 118.09. found (M+H$^+$) 119.1.

Step 2 methyl 5-mercapto-4-methyl-4H-1,2,4-triazole-3-carboxylate

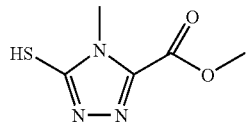

Methyl isothiocyanate (24 g, 0.328 mol) in MeOH (100 mL) was added to a stirred solution of methyl hydrazino(oxo)acetate (35 g, 0.296 mol) in MeOH (350 mL) and the reaction mixture refluxed for 24 h. TLC (MeOH/CH$_2$Cl$_2$, 1:9) indicated no starting material present, intermediate product appeared on TLC as a single spot, Rf=0.44. Cs$_2$CO$_3$ (24 g, 0.74 mol) was added to the hot reaction mixture, cautiously, as the reaction was exothermic. The reaction mixture was cooled down to room temperature and then filtered. The filtrate was concentrated to wet yellow paste. The paste was triturated with CH$_2$Cl$_2$ and filtered. The solid material was dried in the vacuum oven at 30° C. to afford 43.1 g of product. The mother liquor was concentrated, then triturated with cold CH$_2$Cl$_2$ and filtered and dried in the vacuum oven at 30° C. to give an additional 6 g of product. The two batches were combined to yield 49.1 g (95.8%) of desired product. $^1$H NMR (DMSO-d$_6$) d 3.63 (s, 3H) 3.84 (s, 3H) 13.83 (broad s, 1H). MS (APCI) calcd for C$_5$H$_7$N$_3$O$_2$S: 173.19. found (M+H$^+$) 174.0.

Example C(90)

6-[2-(5-chloro-2,4-dimethoxyphenyl)ethyl]-6-cyclopentyl-4-hydroxy-3-{[4-methyl-5-(2-morpholin-4-ylethyl)-4H-1,2,4-triazol-3-yl]thio}-5,6-dihydro-2H-pyran-2-one

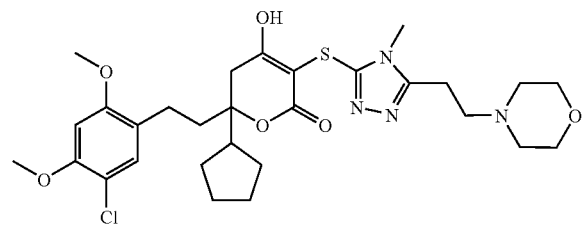

The title compound was prepared as described in Example C(70), where methyl-5-(2-morpholin-4-ylethyl)-4H-1,2,4-triazole-3-thiol was used in place of 6-hydroxy-8-mercaptopurine monohydrate.

$^1$H NMR (500 MHz, DMSO-d$_6$, WET suppression of DMSO-h$_6$ (2.5 ppm) and H$_2$O (3.35 ppm) peak areas) d 1.46–1.66 (m, 12 H) 1.88 (dd, J=9.8, 6.7 Hz, 4 H) 2.34 (m, 1 H) 2.50 (m, 1H, overlap with dmso) 2.63 (m, 1 H) 2.69 (d, J=17.9 Hz, 2 H) 2.87 (d, J=17.6 Hz, 2 H) 3.16 (t, J=7.55 Hz, 2 H) 3.80 (s, attenuation due to proximity to H$_2$O peak) 3.82 (m, 2 H) 3.84 (s, 6 H) 6.71 (s, 1 H) 7.19 (s, 1 H). MS (APCI) calcd for C$_{29}$H$_{39}$ClN$_4$O$_6$S: 607.17. found M=607.1.

Step 1

3-morpholin-4-ylpropanohydrazide

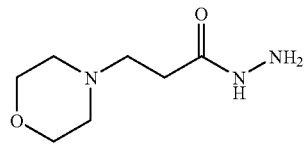

Hydrazine (64.1 g, 2 mol) was added dropwise, over 8–10 min, to methyl 3-morpholinopropionate (35 g, 0.202 mol) and the reaction mixture was refluxed for 16 h. The excess hydrazine was removed under reduced pressure and the material was dried in vacuo at room temperature for 16 h to give the crude product as an oil. The $^1$H NMR showed the presence of hydrazine, so the crude material was dried using a lyophilizer. Then the oil was refluxed in benzene/water (using a Dean-Stark distilling receiver). The benzene was then removed under reduced pressure, and the product was triturated with petroleum ether. After sitting in petroleum ether at room temperature for 16 h, the oil solidified. The petroleum ether was decanted and the solid was dried under house vacuum at room temperature to give the desired product (21.5 g, 61.4%), which was used without further purification.

Step 2

4-methyl-5-(2-morpholin-4-ylethyl)-4H-1,2,4-triazole-3-thiol

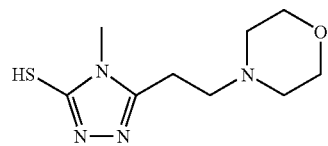

Prepared according to a procedure reported for related compounds: Henichart, J. P. et al. J. Het Chem. 1977, 14, 615. Methyl isothiocyanate (9.08 g, 0.124 mol) in EtOH (50 mL) was added at room temperature to a stirred solution of 3-morpholin-4-ylpropanohydrazide (21.5 g, 0.124 mol) in EtOH (200 mL). The mixture was refluxed for 8 h, then removed from heat and stirred at room temperature for 16 h. The EtOh was removed under reduced pressure to give the crude material as a yellow oil. The oil was purified by column chromatography through silica gel, eluting with CH$_2$Cl$_2$/MeOH to afford the title compound. (6 g, 21.2%).

$^1$H NMR (DMSO-d$_6$) d 2.42 (m, 4H) 2.64 (m, 2 H) 2.85 (m, 2H; 3.43 (s, 3H) 3.55 (m, 4H) 13.47 (s, 1H). MS (APCI) calcd for C$_9$H$_{16}$N$_4$OS: 228.32. found (M–H+) 227.1.

Example C(91)

3 6-[2-(3-chlor-4-methoxyphenyl)ethyl]-6-cyclopentyl-4-hydroxy-3-[(6-hydroxy-7H-purin-8-yl)thio]-5,6-dihydro-2H-pyran-2-one

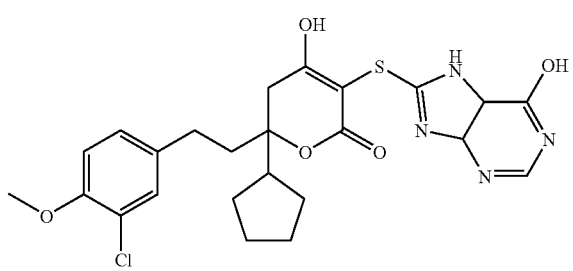

The title compound was prepared as described in Example C(70), where 3-chloro-6-[2-(3-chloro-4-methoxyphenyl)ethyl]-6-cyclopentyldihydro-2H-pyran-2,4(3 H)-dione was used in place of 3-chloro-6-[2-(5-chloro-2,4-dimethoxyphenyl)ethyl]6-cyclopentyldihydro-2H-pyran-2,4(3 H)-dione.

$^1$H NMR (500 MHz, DMSO-$d_6$, WET suppression of DMSO-$h_6$ (2.5 ppm) and H$_2$O (3.35 ppm) peak areas) δ 1.54–1.69 (m, 9 H) 2.03 (m, 2 H) 2.35 (m, 1 H) 2.58 (m, 1 H) 2.63 (m, Hz, 1 H) 2.76 (d, J=17.6 Hz, 1 H) 2.96 (d, J=15.0 Hz, 1 H) 3.80 (s, 3 H) 7.05 (d, J=8.5 Hz, 1 H) 7.24 (dd, J=8.5, 17 Hz, 1 H) 7.30 (d, J=1.7 Hz, 1 H) 7.90 (d, J=3.6 Hz, 1 H) 12.15 (broad s, 2H). MS (APCI) calcd for C$_{24}$H$_{25}$ClN$_4$O$_5$S: 517.00. found M=517.1.

Example C(92)

6-[2-(3-chloro-4-methoxyphenyl)ethyl]-6-cyclopentyl-4-hydroxy-3-[(5-pyridin-3-yl-4H-1,2,4-triazol-3-yl)thio]-5,6-dihydro-2H-pyran-2-one

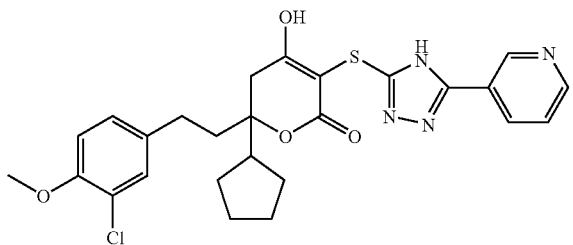

The title compound was prepared as described in Example C(70), where 3-chloro-6-[2-(3-chloro-4-methoxyphenyl)ethyl]-6-cyclopentyldihydro-2H-pyran-2,4(3 H)-dione was used in place of 3-chloro-6-[2-(5-chloro-2,4-dimethoxyphenyl)ethyl]6-cyclopentyldihydro-2H-pyran-2,4(3 H)-dione and 5-(3-pyridinyl)-4H-1,2,4-triazole-3-thiol was used in place of 6-hydroxy-8-mercaptopurine monohydrate.

$^1$H NMR (500 MHz, DMSO-$d_6$, WET suppression of DMSO-$h_6$ (2.5 ppm) and H$_2$O (3.35 ppm) peak areas) δ 1.53–1.69 (m, 8 H) 2.03 (m, 1 H) 2.11 (m, 1 H) 2.35 (m, 1 H) 2.57 (m, 1 H) 2.63 (m, 1 H) 2.82 (d, J=17.6 Hz, 1 H) 2.96 (d, J=15.0 Hz, 1 H) 3.77 (s, 3 H) 6.95 (d, J=8.5 Hz, 1 H) 7.09 (d, J=8.5 Hz, 1 H) 7.23 (d, J=1.4 Hz, 1 H) 7.41 (m, 1 H) 8.13 (s, 1 H) 8.60 (d, J=4.1 Hz, 1 H) 9.03 (s, 1 H). MS (APCI) calcd for C$_{26}$H$_{27}$ClN$_4$O$_4$S: 527.04. found M=527.0.

Example C(93)

Ethyl 2-({6-[2-(5-chloro-2,4-dimethoxyphenyl)ethyl]-6-cyclopentyl-4-hydroxy-2-oxo-5,6-dihydro-2H-pyran-3-yl}thio)[1,2,4]triazolo[1,5-a]pyrimidine-6-carboxylate

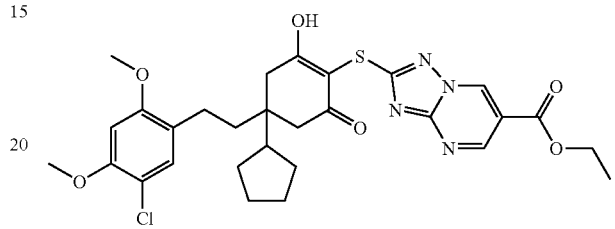

The title compound was prepared as described in Example C(70), where ethyl 2-mercapto[1,2,4]triazolo-[1,5-a]pyrimidine-6-carboxylate was used in place of 6-hydroxy-8-mercaptopurine monohydrate.

$^1$H NMR (500 MHz, DMSO-$d_6$, WET suppression of DMSO-$h_6$ (2.5 ppm) and H$_2$O (3.35 ppm) peak areas) d 1.34 (t, J=7.14 Hz, 3 H) 1.55–1.74 (m, 8 H) 2.07 (m, 1 H) 2.16 (m, 1 H) 2.35 (m, 1 H) 2.5 (m, 1H, overlap with dmso) 2.63 (m, 1 H) 2.78 (d, J=17.6 Hz, 1 H) 2.98 (d, J=17.6 Hz, 1 H) 3.72 (s, 3 H) 3.82 (s, 3 H) 4.37 (q, J=7.1 Hz, 2 H) 6.67 (s, 1 H) 7.19 (s, 1 H) 9.09 (d, J=2.2 Hz, 1 H) 9.22 (d, J=2.2 Hz, 1 H). MS (APCI) calcd for C$_{28}$H$_{31}$ClN$_4$O$_7$S: 603.09. found M=603.1.

Step 1 ethyl 2-mercapto[1,2,4]triazolo-[1,5-a]pyrimidine-6-carboxylate

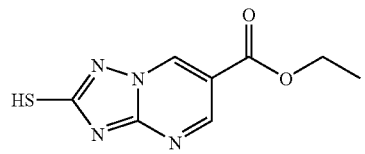

The title compound was prepared by reaction of (ethoxycarbonyl)malonialdehyde with 3-amino-5-mercapto-1,2,4-triazole as previously described by M. Künstlinger and E. Breitmaier in *Synthesis*, 1983, 44–47. $^1$H NMR (DMSO-$d_6$) d 1.35 (t, J=6.99, 1 H) 4.39 (q, J=6.80, 1 H) 9.10 (s, 1 H) 9.55 (s, 1H). MS (APCI) calcd for C$_8$H$_8$N$_4$O$_2$S: 224.24. found (M+H$^+$) 225.0.

Example C(94)

Ethyl 2-({6-[2-(3-chloro-4-methoxyphenyl)ethyl]-6-cyclopentyl-4-hydroxy-2-oxo-5,6-dihydro-2H-pyran-3-yl}thio)[1,2,4]triazolo[1,5-a]pyrimidine-6-carboxylate

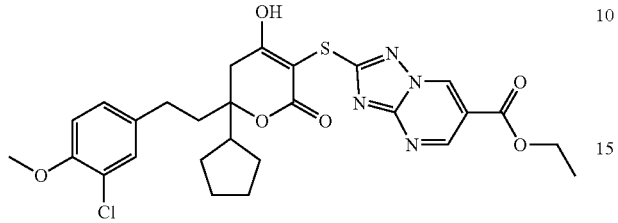

The title compound was prepared as described in Example C(70), where 3-chloro-6-[2-(3-chloro-4-methoxyphenyl)ethyl]-6-cyclopentyldihydro-2H-pyran-2,4(3 H)-dione was used in place of 3-chloro-6-[2-(5-chloro-2,4-dimethoxyphenyl)ethyl]6-cyclopentyldihydro-2H-pyran-2,4(3H)-dione and ethyl 2-mercapto[1,2,4]triazolo-[1,5-a]pyrimidine-6-carboxylate was used in place of 6-hydroxy-8-mercaptopurine monohydrate.

$^1$H NMR (500 MHz, DMSO-$d_6$, WET suppression of DMSO-$h_6$ (2.5 ppm) and H$_2$O (3.35 ppm) peak areas) δ 1.34 (t, J=7.1 Hz, 3H) 1.55–1.74 (m, 8 H) 2.07 (m, 1 H) 2.22 (m, 2 H) 2.63 (d, J=8.2 Hz, 2 H) 2.75 (d, J=17.6 Hz, 2 H) 3.00 (d, J=15.0 Hz, 1 H) 3.81 (s 3 H) 4.38 (m, 2 H) 7.06 (t, J=8.8 Hz, 1 H) 7.25 (s, 1 H) 7.27 (s, 1 H) 7.30 (m, 1 H) 9.13 (s, 1 H) 9.26 (s, 1 H). MS (APCI) calcd for $C_{27}H_{29}ClN_4O_6S$: 573.07. found M=573.1.

Example C(95)

6-[2-(3-chloro-4-methoxyphenyl)ethyl]-6-cyclopentyl-4-hydroxy-3-[(7-methyl[1,2,4]triazolo[1,5-a]pyrimidin-2-yl)thio]-5,6-dihydro-2H-pyran-2-one

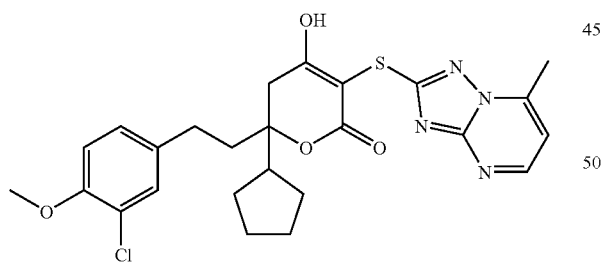

The title compound was prepared as described in Example C(70), where 3-chloro-6-[2-(3-chloro-4-methoxyphenyl)ethyl]-6-cyclopentyldihydro-2H-pyran-2,4(3H)-dione was used in place of 3-chloro-6-[2-(5-chloro-2,4-dimethoxyphenyl)ethyl]6-cyclopentyldihydro-2H-pyran-2,4(3H)-dione and 7-methyl[1,2,4]triazolo[1,5-a]pyrimidine-2-thiol was used in place of 6-hydroxy-8-mercaptopurine monohydrate.

1H NMR (500 MHz, DMSO-$d_6$, WET suppression of DMSO-$h_6$ (2.5 ppm) and H$_2$O (3.35 ppm) peak areas) d 1.53–1.73 (m, 8 H) 2.14 (m, 1 H) 2.24 (m, 1 H) 2.35 (m, 1H) 2.50 (m, 1 H, overlap with dmso) 2.62 (m, 1 H) 2.80 (d, J=17.9 Hz, 1 H) 2.96 (d, J=20.0 Hz, 1 H) 3.80 (s, 3 H) 7.03 (d, J=8.2 Hz, 1 H) 7.15 (d, J=4.7 Hz, 1 H) 7.22 (dd, J=8.4, 2.06 Hz, 1 H) 7.29 (d, J=1.9 Hz, 1 H) 8.63 (d, J=4.7 Hz, 1 H). MS (APCI) calcd for $C_{25}H_{27}ClN_4O_4S$; 515.03. found M=515.0.

Step 1

Sodium 5-methyl-1H-[1,2,4]triazolo[4,3-a]pyrimidine-3-thiolate

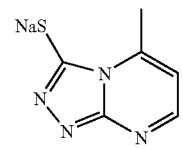

The title compound was prepared by a modification or a reported procedure (Shirakawa, K. *Yakugaku Zasshi* 1960, 80, 1542. A solution of (4-Methyl-pyrimidin-2-yl)-hydrazine (140 g, 1.13 mol), sodium hydroxide (45 g, 1.13 mol) and carbon disulfide (67.7 ml, 1.13 mol) in 50% aqueous ethanol (900 ml) was refluxed for 6 hours. The resulting mixture was cooled to ambient temperature and 54.7 g the yellow solid formed was isolated (54.7 g). It was recrystallized from 50% aqueous ethanol and dried at 40° C./1 Torr for 10 hours to give 44 g (18%) of sodium 5-methyl-1H-[1,2,4]triazolo[4,3-a]pyrimidine-3-thiolate, 85% pure by ELSD and $^1$H NMR.

The initial mother liquid was kept at 0° C. for 2 days. The crystallized orange solid was isolated by filtration, dried for 10 h at 40° C./1 Torr to give 68.1 g (27%) of the title compound, sodium 7-methyl-1H-[1,2,4]triazolo[4,3-a]pyrimidine-3-thiolate. $^1$H NMR (DMSO-$d_6$, 300 MHz) δ, ppm: 2.44 (s, 3H), 6.60 (d, 1H, 7 Hz), 8.29 (d, 1H, 7 Hz).

Step 2

7-methyl[1,2,4]triazolo[1,5-a]pyrimidine-2-thiol

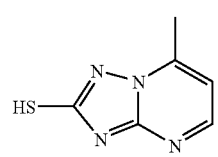

A solution of sodium 5-methyl-1H-[1,2,4]triazolo[4,3-a]pyrimidine-3-thiolate from Step 3 (56 g, 0.25 mol) and pyridine (50 ml) in water (169 ml) was heated at reflux for 60 hours (the reaction was monitored by $^1$H NMR). After the disappearance of starting material the reaction mixture was evaporated to dryness, dissolved in water (100 ml) and acidified with acetic acid (23 ml). The solid was filtered, washed with water and dried for 4 h at 40° C./1 Torr to give 42 g (84%) of desired product, 95% pure by $^1$H NMR and ELSD. $^1$H NMR (DMSO-$d_6$, 300 MHz) δ, ppm: 2.68 (s, 3H), 7.34 (d, 1H, 3 Hz), 8.56 (d, 1H. 3 Hz).

Example C(96)

6-[2-(3-chloro-4-methoxyphenyl)ethyl]-6-cyclopentyl-4-hydroxy-3-[(4-methyl-5-pyridin-3-yl-4H-1,2,4-triazol-3-yl)thio-5,6-dihydro-2H-pyran-2-one

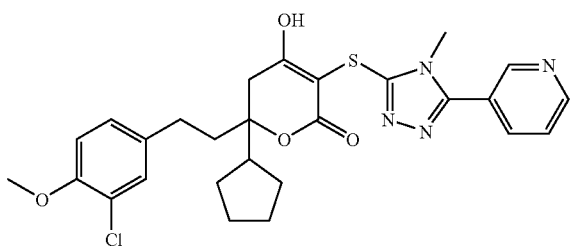

The title compound was prepared as described in Example C(70), where 3-chloro-6-[2-(3-chloro-4-methoxyphenyl)ethyl]-6-cyclopentyldihydro-2H-pyran-2,4(3H)-dione was used in place of 3-chloro-6-[2-(5-chloro-2,4-dimethoxyphenyl)ethyl]6-cyclopentyldihydro-2H-pyran-2,4(3H)-dione and 4-methyl-5-(3-pyridyl)-4H-1,2,4-triazole-3-thiol was used in place of 6-hydroxy-8-mercaptopurine monohydrate.

1H NMR (500 MHz, DMSO-d$_6$, WET suppression of DMSO-h$_6$ (2.5 ppm) and H$_2$O (3.35 ppm) peak areas) δ 1.52–1.69 (m, 8 H) 2.03 (m, 1 H) 2.09 (m, 1 H) 2.36 (m, 1 H) 2.50 (m, 1H, overlap with dmso) 2.63 (m, 1 H) 2.73 (d, J=17.6 Hz, 1 H) 2.95 (d, J=17.6 Hz, 1 H) 3.71 (s, 3 H) 3.80 (s, 3 H) 7.01 (d, J=8.5 Hz, 1 H) 7.18 (dd, J=8.2, 1.9 Hz, 1 H) 7.32 (d, J=1.9 Hz, 1 H) 7.61 (dd, J=7.6, 4.8 Hz, 1 H) 8.14 (d, J=8.2 Hz, 1 H) 8.74 (d, J=5.00 Hz, 1 H) 8.91 (s, 1 H). MS (APCI) calcd for C$_{27}$H$_{29}$ClN$_4$O$_4$S: 541.07. found M=541.1.

Example C(97)

6-[2-(3-chloro-4-methoxyphenyl)ethyl]-6-cyclopentyl-3-({5-[(dimethylamino)methyl]-4-methyl-4H-1,2,4-triazol-3-yl}thio)-4-hydroxy-5,6-dihydro-2H-pyran-2-one

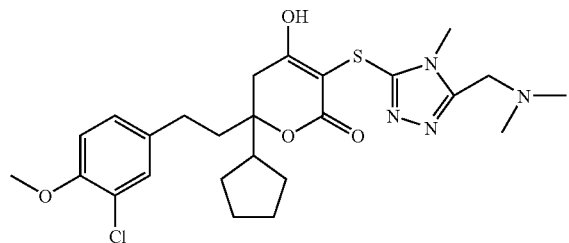

The title compound was prepared as described in Example C(70), where 3-chloro-6-[2-(3-chloro-4-methoxyphenyl)ethyl]-6-cyclopentyldihydro-2H-pyran-2,4(3H)-dione was used in place of 3-chloro-6-[2-(5-chloro-2,4-dimethoxyphenyl)ethyl]6-cyclopentyldihydro-2H-pyran-2,4(3H)-dione and 5-[(dimethylamino)methyl]-4-methyl-4H-1,2,4-triazole-3-thiol, as described in Step 1 of Example C(83), was used in place of 6-hydroxy-8-mercaptopurine monohydrate.

$^1$H NMR (500 MHz, DMSO-d$_6$, WET suppression of DMSO-h$_6$ (2.5 ppm) and H$_2$O (3.35 ppm) peak areas) δ 1.50–1.69 (m, 8 H) 2.02 (m, 2 H) 2.35 (m, 1H) 2.50 (m, 1H, overlap with dmso) 2.63 (m, 1 H) 2.72 (d, J=18.1 Hz, 1 H) 2.87 (s, 6 H) 2.92 (d, J=15.0 Hz, 1 H) 3.63 (s, 3 H) 3.80 (s, 3 H) 4.53 (s, 2 H) 7.01 (d, J=8.5 Hz, 1 H) 7.18 (dd, J=8.4, 2.1 Hz, 1 H) 7.31 (d, J=1.9 Hz, 1 H). MS (APCI) calcd for C$_{25}$H$_{33}$ClN$_4$O$_4$S: 521.08. found M=521.2.

Example C(98)

6-[2-(3-chloro-4-methoxyphenyl)ethyl]-6-cyclopentyl-4-hydroxy-3-[(6-methyl[1,2,4]triazolo[1,5-a]pyrimidin-2-yl)thio]-5,6-dihydro-2H-pyran-2-one

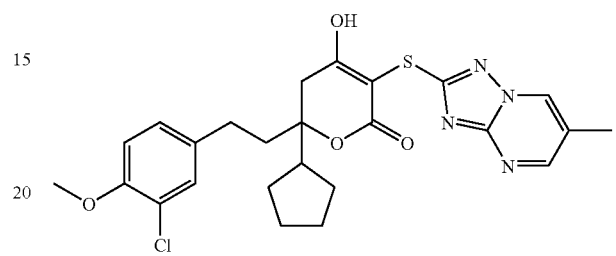

The title compound was prepared as described in Example C(70), where 3-chloro-6-[2-(3-chloro-4-methoxyphenyl)ethyl]-6-cyclopentyldihydro-2H-pyran-2,4(3H)-dione was used in place of 3-chloro-6-[2-(5-chloro-2,4-dimethoxyphenyl)ethyl]6-cyclopentyldihydro-2H-pyran-2,4(3H)-dione and 6-methyl[1,2,4]triazolo[1,5-a]pyrimidine-2-thiol was used in place of 6-hydroxy-8-mercaptopurine monohydrate.

$^1$H NMR (500 MHz, DMSO-d$_6$, WET suppression of DMSO-h$_6$ (2.5 ppm) and H$_2$O (3.35 ppm) peak areas) δ 1.52–1.69 (m, 8 H) 2.22 (m, 2 H) 2.30 (s, 3 H) 2.35 (m, 1H) 2.50 (m, 1 H, overlap with dmso) 2.62 (m, 1 H) 2.73 (d, J=17.6 Hz, 1 H) 2.98 (d, J=17.9 Hz, 1 H) 3.81 (s, 3 H) 7.06 (d, J=8.2 Hz, 1 H) 7.24 (dd, J=8.5, 1.9 Hz, 1 H) 7.30 (d, J=1.9 Hz, 1 H) 8.55 (d, J=1.1 Hz, 1 H) 8.67 (d, J=2.2 Hz, 1 H). MS (APCI) calcd for C$_{25}$H$_{27}$ClN$_4$O$_4$S: 515.03. found M=515.0.

Example C(99)

6-[2-(3-chloro-4-methoxyphenyl)ethyl]-6-cyclopentyl-3-[(4,5-dimethyl-4H-1,2,4-triazol-3-yl)thio]-4-hydroxy-5,6-dihydro-2H-pyran-2-one

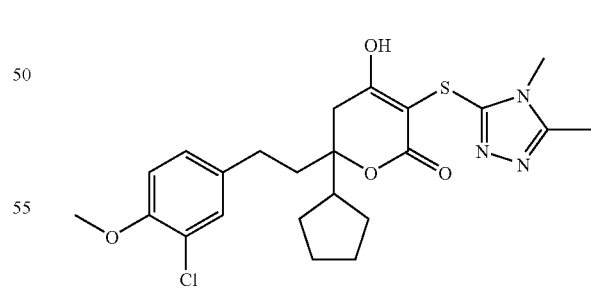

The title compound was prepared as described in Example C(70), where 3-chloro-6-[2-(3-chloro-4-methoxyphenyl)ethyl]-6-cyclopentyldihydro-2H-pyran-2,4(3H)-dione was used in place of 3-chloro-6-[2-(5-chloro-2,4-dimethoxyphenyl)ethyl]6-cyclopentyldihydro-2H-pyran-2,4(3H)-dione and 4,5-dimethyl-4H-1,2,4-triazole-3-thiol, as shown in Example C(88), Step 1, was used in place of 6-hydroxy-8-mercaptopurine monohydrate.

$^1$H NMR (500 MHz, DMSO-d$_6$, WET suppression of DMSO-h$_6$ (2.5 ppm) and H$_2$O (3.35 ppm) peak areas) δ 1.49–1.64 (m, 8 H) 1.92 (m, 2 H) 2.33 (m, 1 H) 2.37 (s, 3 H) 2.50 (m, 2H, overlap with dmso) 2.62 (d, J=15 Hz, 1 H) 2.80 (d, J=17.6 Hz, 1 H) 3.55 (s, attenuation due to proximity to H$_2$O peak) 3.80 (s, 3 H) 7.02 (d, J=8.5 Hz, 1 H) 7.12 (dd, J=8.5, 1.9 Hz, 1 H) 7.24 (d, J=1.9 Hz, 1 H). MS (APCI) calcd for C$_{23}$H$_{28}$ClN$_3$O$_4$S: 478.01. found M=478.1.

Example C(100)

Methyl 5-({6-[2-(3-chloro-4-methoxyphenyl)ethyl]-6-cyclopentyl-4-hydroxy-2-oxo-5,6-dihydro-2H-pyran-3-yl}thio)-4-methyl-4H-1,2,4-triazole-3-carboxylate

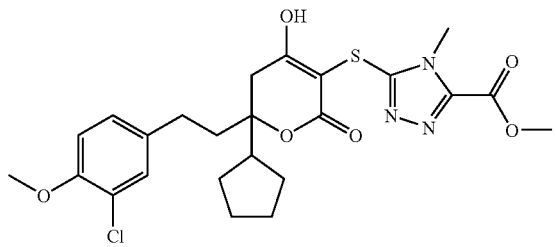

The title compound was prepared as described in Example C(70), where 3-chloro-6-[2-(3-chloro-4-methoxyphenyl)ethyl]-6-cyclopentyldihydro-2H-pyran-2,4(3H)-dione was used in place of 3-chloro-6-[2-(5-chloro-2,4-dimethoxyphenyl)ethyl]6-cyclopentyldihydro-2H-pyran-2,4(3H)-dione and methyl 5-mercapto-4-methyl-4H-1,2,4-triazole-3-carboxylate, as shown in Example 21, Step 2, was used in place of 6-hydroxy-8-mercaptopurine monohydrate.

$^1$H NMR (500 MHz, DMSO-d$_6$, WET suppression of DMSO-h$_6$ (2.5 ppm) and H$_2$O (3.35 ppm) peak areas) δ 1.50–1.70 (s, 8 H) 1.98 (m, 2 H) 2.35 (m, 1 H) 2.50 (m, 1H, overlap with dmso) 2.63 (m, 1 H) 2.71 (d, J=18.1 Hz, 1 H) 2.90 (d, J=17.6 Hz, 1 H) 3.81 (s, 3 H) 3.81 (s, 3 H) 3.88 (s, 3 H) 7.02 (d, J=8.2 Hz, 1 H) 7.15 (dd, J=8.2, 1.9 Hz, 1 H) 7.27 (d, J=10.9 Hz, 1 H). MS (APCI) calcd for C$_{24}$H$_{28}$ClN$_3$O$_6$S: 522.02. found M=522.1.

Example C(101)

6-[2-(3-chloro-4-methoxyphenyl)ethyl]-6-cyclopentyl-4-hydroxy-3-[(1-methyl-1H-imidazol-2-yl)thio]-5,6-dihydro-2H-pyran-2-one

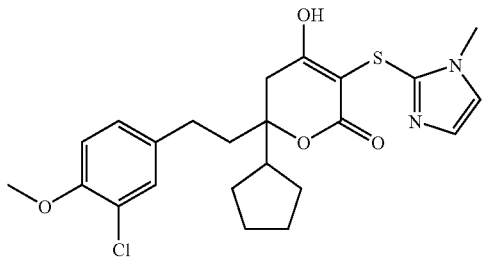

The title compound was prepared as described in Example C(70), where 3-chloro-6-[2-(3-chloro-4-methoxyphenyl)ethyl]-6-cyclopentyldihydro-2H-pyran-2,4(3 H)-dione was used in place of 3-chloro-6-[2-(5-chloro-2,4-dimethoxyphenyl)ethyl]6-cyclopentyldihydro-2H-pyran-2,4(3H)-dione and 2-mercapto-1-methylimidazole was used in place of 6-hydroxy-8-mercaptopurine monohydrate.

$^1$H NMR (500 MHz, DMSO-d$_6$, WET suppression of DMSO-h$_6$ (2.5 ppm) and H$_2$O (3.35 ppm) peak areas) δ 1.48–1.65 (m, 8 H) 1.86 (m, 2 H) 3.72 (s, 3 H) 3.80 (s, 3 H) 7.04 (m, 2 H) 7.19 (d, J=1.7 Hz, 1 H) 7.46 (s, 1 H) 7.58 (s, 1 H). MS (APCI) calcd for C$_{23}$H$_{27}$ClN$_2$O$_4$S: 462.99. found 463.1.

Example C(102)

6-[2-(3-chloro-4-methoxyphenyl)ethyl]-6-cyclopentyl-4-hydroxy-3-[(4-methyl-4H-1,2,4-triazol-3-yl)thio]-5,6-dihydro-2H-pyran-2-one

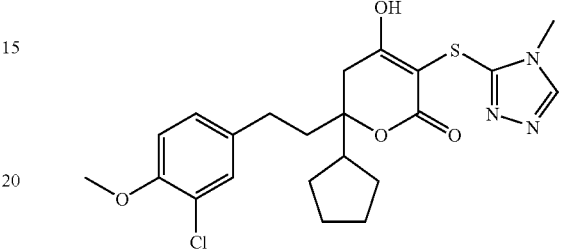

The title compound was prepared as described in Example C(70) where 3-chloro-6-[2-(3-chloro-4-methoxyphenyl)ethyl]-6-cyclopentyldihydro-2H-pyran-2,4(3 H)-dione was used in place of 3-chloro-6-[2-(5-chloro-2,4-dimethoxyphenyl)ethyl]6-cyclopentyldihydro-2H-pyran-2,4(3H)-dione and 4-methyl-4H-1,2,4-triazole-3-thiol was used in place of 6-hydroxy-8-mercaptopurine monohydrate.

$^1$H NMR (500 MHz, DMSO-d$_6$, WET suppression of DMSO-h$_6$ (2.5 ppm) and H$_2$O (3.35 ppm) peak areas) δ 1.48–1.65 (m, 8 H) 1.96 (m, 2 H) 2.65 (d, J=15.1 Hz, 1 H) 2.87 (d, J=17.7 Hz, 1 H) 3.16 (s, 1 H) 3.64 (s, 3 H) 3.80 (s, 3 H) 7.02 (d, J=8.8 Hz, 1 H) 7.16 (dd, J=8.5, 2.20 Hz, 1 H) 7.27 (d, J=1.9 Hz, 1 H) 8.56 (s, 1 H). MS (APCI) calcd for C$_{22}$H$_{26}$ClN$_3$O$_4$S: 463.98. found M=464.9.

Example C(103)

6-[2-(3-chloro-4-methoxyphenyl)ethyl]-6-cyclopentyl-4-hydroxy-3-(1H-imidazol-2-ylthio)-5,6-dihydro-2H-pyran-2-one

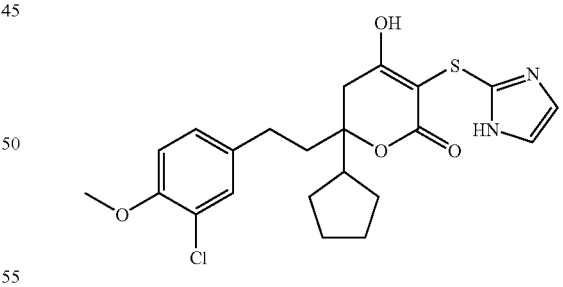

The title compound was prepared as described in Example C(70), where 3-chloro-6-[2-(3-chloro-4-methoxyphenyl)ethyl]-6-cyclopentyldihydro-2H-pyran-2,4(3H)-dione was used in place of 3-chloro-6-[2-(5-chloro-2,4-dimethoxyphenyl)ethyl]6-cyclopentyldihydro-2H-pyran-2,4(3H)-dione and 2-mercaptoimidazole was used in place of 6-hydroxy-8-mercaptopurine monohydrate.

$^1$H NMR (500 MHz, DMSO-d$_6$, WET suppression of DMSO-h$_6$ (2.5 ppm) and H$_2$O (3.35 ppm) peak areas) δ 1.50–1.64 (m, 8 H) 1.89 (m, 2 H) 2.71 (d, J=15.0 Hz, 1 H) 3.80 (s, 3 H) 7.03 (d, J=8.5 Hz, 1 H) 7.08 (d, J=5.0 Hz, 1 H)

7.21 (d, J=1.9 Hz, 1 H) 7.46 (s, 2 H). MS (APCI) calcd for C$_{22}$H$_{25}$ClN$_2$O$_4$S: 448.97. found M=449.0.

Example C(104)

6-[2-(3-chloro-4-methoxyphenyl)ethyl]-6-cyclopentyl-4-hydroxy-3-[(5-pyridin-4-yl-1,3,4-oxadiazol-2-yl)thio]-5,6-dihydro-2H-pyran-2-one

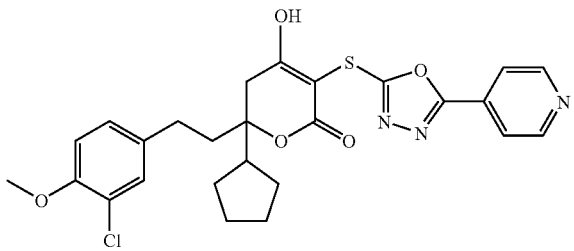

The title compound was prepared as described in Example C(70), where 3-chloro-6-[2-(3-chloro-4-methoxyphenyl)ethyl]-6-cyclopentyldihydro-2H-pyran-2,4(3H)-dione was used in place of 3-chloro-6-[2-(5-chloro-2,4-dimethoxyphenyl)ethyl]6-cyclopentyldihydro-2H-pyran-2,4(3H)-dione and 5-(4-pyridyl)-1,3,4-oxadiazole-2-thiol was used in place of 6-hydroxy-8-mercaptopurine monohydrate.

$^1$H NMR (500 MHz, DMSO-d$_6$, WET suppression of DMSO-h$_6$ (2.5 ppm) and H$_2$O (3.35 ppm) peak areas) δ 1.53–1.70 (m, 8 H) 2.09 (m, 2 H, overlap) 2.82 (d, J=18.1 Hz, 1 H) 3.00 (d, J=18.1 Hz, 1 H) 3.78 (s, 3 H) 6.97 (d, J=8.5 Hz, 1 H) 7.13 (dd, J=8.4, 2.1 Hz, 1 H) 7.27 (d, J=1.9 Hz, 1 H) 7.73 (d, J=5.5 Hz, 2 H) 8.71 (d, J=5.8 Hz, 2 H). MS (APCI) calcd C$_{26}$H$_{26}$ClN$_3$O$_5$S: 528.03. found M=528.1.

Example C(105)

2-({6-[2-(3-chloro-4-methoxyphenyl)ethyl]-6-cyclopentyl-4-hydroxy-2-oxo-5,6-dihydro-2H-pyran-3-yl}thio)-4,6-dimethylnicotinonitrile

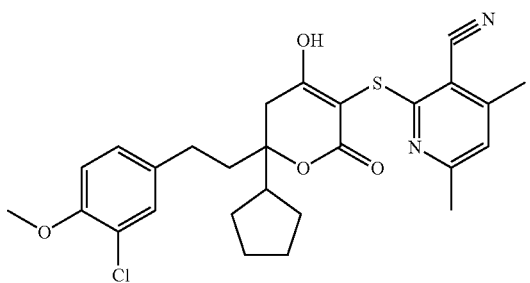

The title compound was prepared as described in Example C(70), where 3-chloro-6-[2-(3-chloro-4-methoxyphenyl)ethyl]-6-cyclopentyldihydro-2H-pyran-2,4(3H)-dione was used in place of 3-chloro-6-[2-(5-chloro-2,4-dimethoxyphenyl)ethyl]6-cyclopentyldihydro-2H-pyran-2,4(3H)-dione and 4,6-dimethyl-2-mercaptonicotinonitrile was used in place of 6-hydroxy-8-mercaptopurine monohydrate.

$^1$H NMR (500 MHz, DMSO-d$_6$, WET suppression of DMSO-h$_6$ (2.5 ppm) and H$_2$O (3.35 ppm) peak areas) δ 1.53–1.71 (m, 8 H) 2.01 (s, 3 H) 2.06 (m, 2 H) 2.34 (m, 1 H) 2.37 (s, 3 H) 2.58 (m, 2 H) 2.83 (d, J=17.9 Hz, 1 H) 2.93 (d, J=15.0 Hz, 1 H) 3.80 (s, attenuation due to proximity to H$_2$O peak) 6.98 (s, 1 H) 7.02 (d, J=8.2 Hz, 1 H) 7.11 (d, J=5.0 Hz, 1 H) 7.23 (d, J=1.9 Hz, 1 H). MS (APCI) calcd for C$_{27}$H$_{29}$ClN$_2$O$_4$S: 513.06. found M=513.1.

Example C(106)

6-[2-(3-chloro-4-methoxyphenyl)ethyl]-6-cyclopentyl-4-hydroxy-3-[(4-phenyl-1,3-thiazol-2-yl)thio]-5,6-dihydro-2H-pyran-2-one

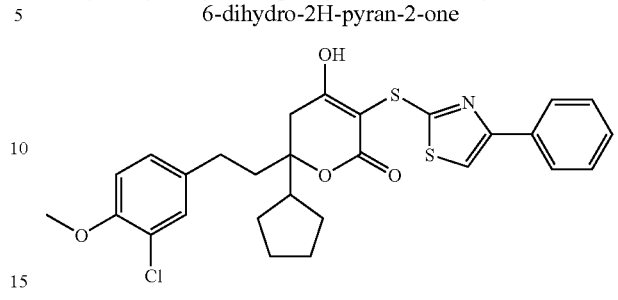

The title compound was prepared as described in Example C(70), where 3-chloro-6-[2-(3-chloro-4-methoxyphenyl)ethyl]-6-cyclopentyldihydro-2H-pyran-2,4(3H)-dione was used in place of 3-chloro-6-[2-(5-chloro-2,4-dimethoxyphenyl)ethyl]6-cyclopentyldihydro-2H-pyran-2,4(3H)-dione and 2-mercapto-4-phenylthiazole was used in place of 6-hydroxy-8-mercaptopurine monohydrate.

$^1$H NMR (500 MHz, DMSO-d$_6$, WET suppression of DMSO-h$_6$ (2.5 ppm) and H$_2$O (3.35 ppm) peak areas) δ 1.53–1.71 (m, 8 H) 2.05 (m, 2 H, overlap) 2.35 (m, 1 H) 2.50 (m, 1 H, overlap with dmso) 2.61 (m, 1 H) 2.84 (d, J=17.3 Hz, 1 H) 2.95 (d, J=20.0 Hz, 1 H) 3.80 (s, 3 H) 7.03 (d, J=8.5 Hz, 1 H) 7.13 (dd, J=8.4, 2.1 Hz, 1 H) 7.28 (d, J=1.9 Hz, 1 H) 7.32 (d, J=7.1 Hz, 1 H) 7.38 (t, J=7.4 Hz, 2 H) 7.85 (d, J=7.7 Hz, 3 H).

MS (APCI) calcd for C$_{28}$H$_{28}$ClNO$_4$S$_2$: 542.12. found M=542.0.

Example C(107)

6-[2-(3-chloro-4-methoxyphenyl)ethyl]-6-cyclorpentyl-4-hydroxy-3-[(pyridin-2-ylmethyl)thiol]-5,6-dihydro-2H-pyran-2-one

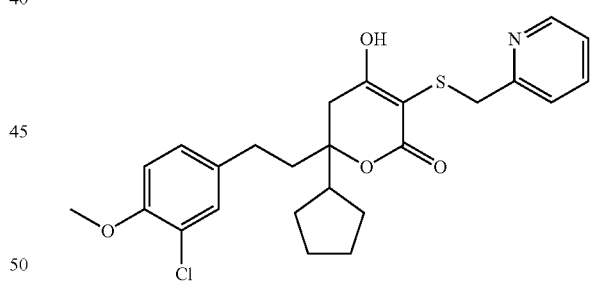

The title compound was prepared as described in Example C(70), where 3-chloro-6-[2-(3-chloro-4-methoxyphenyl)ethyl]-6-cyclopentyldihydro-2H-pyran-2,4(3H)-dione was used in place of 3-chloro-6-[2-(5-chloro-2,4-dimethoxyphenyl)ethyl]6-cyclopentyldihydro-2H-pyran-2,4(3H)-dione and pyridine-2-methanethiol was used in place of 6-hydroxy-8-mercaptopurine monohydrate.

$^1$H NMR (500 MHz, DMSO-d$_6$, WET suppression of DMSO-h$_6$ (2.5 ppm) and H$_2$O (3.35 ppm) peak areas) δ 1.47–1.58 (m, 8 H) 1.80 (m, 2 H) 2.23 (m, 1 H) 2.66 (d, J=20.6 Hz, 1 H) 3.80 (s, 3 H) 3.96 (m, 2 H) 7.03 (d, J=8.2 Hz, 1 H) 7.07 (d, J=5.0 Hz, 1 H) 7.21 (d, J=1.9 Hz, 1 H) 7.34 (s, 1 H) 7.49 (d, J=7.1 Hz, 1 H) 7.84 (s, 1 H) 8.44 (s, 1 H). MS (APCI) calcd for C$_{25}$H$_{28}$ClNO$_4$S: 474.02. found M=474.1.

Example C(108)

6-[2-(3-chloro-4-methoxyphenyl)ethyl]6-cyclopentyl-3-[(2,3-dichlorophenyl)thio]4-hydroxy-5,6-dihydro-2H-pyran-2-one

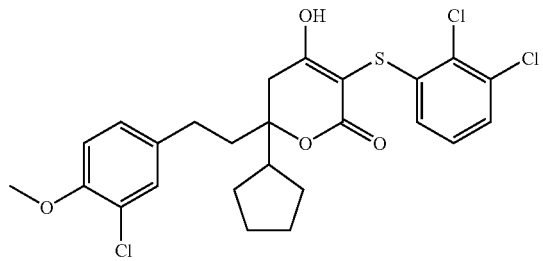

The title compound was prepared as described in Example C(70), where 3-chloro-6-[2-(3-chloro-4-methoxyphenyl)ethyl]-6-cyclopentyldihydro-2H-pyran-2,4(3H)-dione was used in place of 3-chloro-6-[2-(5-chloro-2,4-dimethoxyphenyl)ethyl]6-cyclopentyldihydro-2H-pyran-2,4(3H)-dione and 2,3-dichlorothiophenol was used in place of 6-hydroxy-8-mercaptopurine monohydrate.

MS (APCI) calcd for $C_{25}H_{25}Cl_3O_4S$: 527.89. found M=529.0.

Example C(109)

6-[2-(3-Chloro-4-methoxy-phenyl)-ethyl]-6-cyclopentyl-4-hydroxy-3-(2-pyridin-2-yl-ethylsulfanyl)-5,6-dihydro-pyran-2-one

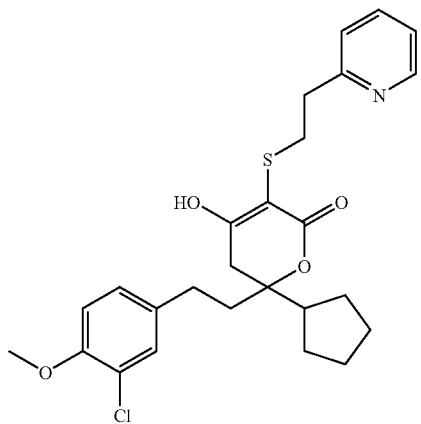

The title compound was prepared analogously to Example F(7), Step 6, substituting 3-chloro-6-[2-(3-chloro-4-methoxy-phenyl)-ethyl]-6-cyclopentyl-dihydro-pyran-2,4-dione (0.201 g, 0.52 mmol, described below) in place of 3-chloro-6-cyclopentyl-6-[4-(3-hydroxy-phenyl)-but-3-ynyl]-dihydro-pyran-2,4-dione, and 2-Pyridin-2-yl-ethanethiol in place of 2-mercaptothiazole.

Yield: 12.6 mg, 5% yield. $^1$HNMR(CDCl$_3$) δ: 1.48–1.73 (m, 8H), 1.92–1.98 (m, 2H), 2.34 (p, J=8.32 Hz, 1H), 2.56–2.62 (m, 4H), 2.80–3.01 (m, 4H), 3.80 (s, 3H), 6.76 (d, J=8.32 Hz, 1H), 6.95 (dd, J1=8.48 Hz, J2=2.08 Hz, 1H), 7.09 (d, J=2.24 Hz, 1H), 7.41–7.48 (m, 2H), 7.93 (t, J=7.52 Hz, 1H), 8.52 (d, J=5.12 Hz, 1H).

Step 1

2-Chloro-7-(3-chloro-4-methoxy-phenyl)-5-cyclopentyl-5-hydroxy-3-oxo-heptanoic acid methyl ester

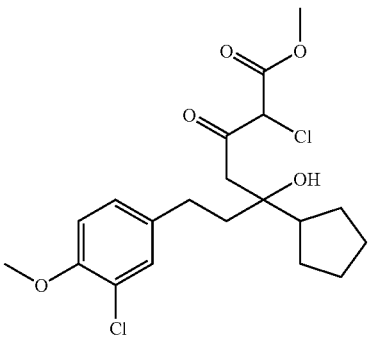

Methyl-2-chloroacetoacetate (2.5 g, 16.9 mmol) was added to a cooled 0° C. suspension of NaH (0.68 g, 16.9 mmol, 60% dispersion in mineral oil) in THF (30 ml). After 15 min the solution was cooled to −40° C. and n-BuLi (10.6 mL, 16.9 mmol, 1.6M in hexanes) was added. The resulting dianion was stirred for an additional 30 min and then treated with a solution of 3-(3-Chloro-4-methoxy-phenyl)-1-cyclopentyl-propan-1-one (1.5 g, 5.6 mmol, prepared from Heck route) in THF (10 ml). After stirring for 1 h at −40° C., the reaction mixture was quenched with saturated NH$_4$Cl and extracted with EtOAc. The organic layers were washed with brine, dried with Na$_2$SO$_4$ and concentrated to an orange oil that was used without further purification.

Step 2

3-Chloro-6-[2-(3-chloro-4-methoxy-phenyl)-ethyl]-6-cyclopentyl-4-hydroxy-5,6-dihydro-pyran-2-one

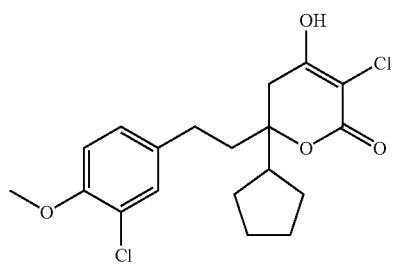

A solution of 2-Chloro-7-(3-chloro-4-methoxy-phenyl)-5-cyclopentyl-5-hydroxy-3-oxo-heptanoic acid methyl ester (2.33 g, 5.6 mmol, from Step 1 below), and bis(dibutylchlorotin)oxide (1.38 g, 2.5 mmol), dissolved in toluene (18 mL) were heated at reflux for 30 mins. The resulting mixture was concentrated and purified by silica gel chromatography to give the title compound (1.57 g, 75% yield, two Steps).

$^1$H NMR (CDCl$_3$): δ 1.36–1.79 (br m, 8H), 2.02 (m, 2H), 2.41 (m, 1H), 2.65 (m, 3H), 2.89 (d, 1H, J=17.7 Hz), 3.88 (s, 3H), 6.47 (br s, 1H), 6.85 (d, 1H, J=8.4 Hz), 7.01 (dd, 1H, J=8.4, 2.1 Hz), 7.16 (d, 1H, J=2.1 Hz).

Section C: Compounds with Oxygen

Scheme 3

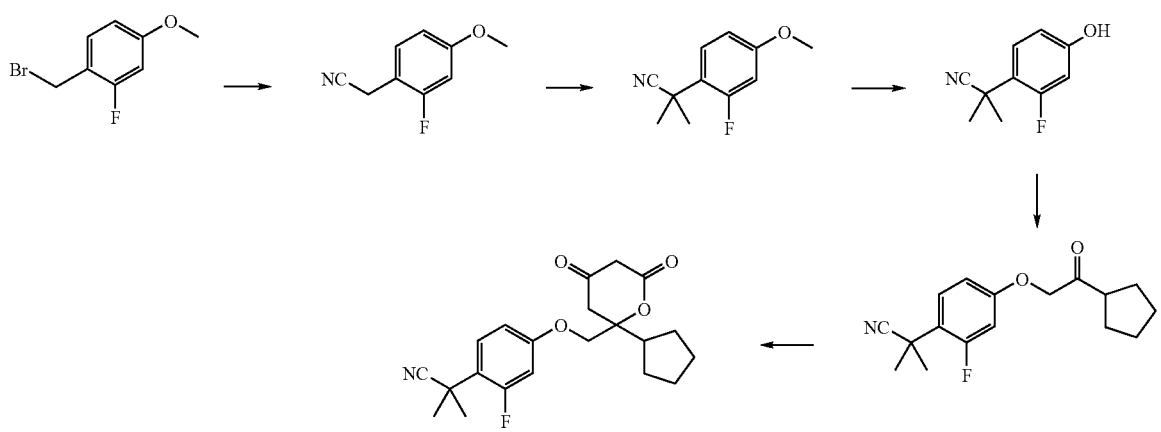

Example C(110)

2-[4-(2-Cyclopentyl-4,6-dioxo-tetrahydro-pyran-2-ylmethoxy)-2-fluor-phenyl]-2-methyl-propionitrile

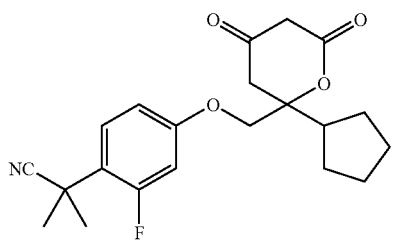

Sodium hydride (60%) (0.49 g, 12.3 mmol) was magnetically stirred in dry THF (33 mL) and cooled to 0° C. The mixture was then treated with Methyl acetoacetate (1.34 mL, 12.3 mmol) dropwise over 15 min. The reaction was allowed to stir for 30 min at 0° C. To the resulting clear solution was added nBuLi (1.6M in Hexanes) (7.71 mL, 12.3 mmol). The reaction was then allowed to stir for 30 min at 0° C. To the yellow solution was added 2-[4-(2-Cyclopentyl-2-oxo-ethoxy)-2-fluoro-phenyl]-2-methyl-propionitrile (1.19 g, 4.1 mmol) as a solution in dry THF (15 mL). The result was stirred at 0° C. for 15 min and then at room temperature for 90 min. The solution was next poured into 0.5N HCl (100 mL) and extracted with EtOAc (2×50 mL). The organics were concentrated and the residue dissolved in MeOH (33 mL) and treated with $K_2CO_3$ (1.5 g). The mixture was heated to 65° C. and maintained for 1 hr. The reaction was cooled and poured into 0.5N HCl (100 mL) and extracted with EtOAc (2×50 mL). The organics were dried over $Na_2SO_4$, filtered and concentrated. The residue was purified by flash chromatography (silica gel) eluting with $CH_2Cl_2$ through 1% MeOH in $CH_2Cl_2$ to yield the title compound as a white solid (1.21 g, 79%). $^1$H NMR (300 MHz, DMSO-$d_6$) δ: 1.55 (m, 8 H), 1.69 (s, 6 H), 2.37 (m, 1 H), 2.62 (s, 2 H), 3.33 (s, 2 H), 4.10 (m, 2 H), 6.87 (m 2 H), 7.34 (m 1 H).

Step 4

Preparation of Compound 2-[4-(2-Cyclopentyl-2-oxo-ethoxy)-2-fluoro-phenyl]-2-methyl-propionitrile

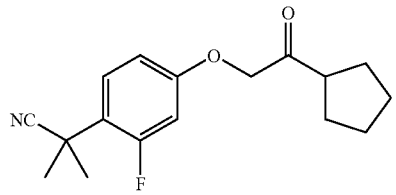

Potassium carbonate (3.1 g, 22 mmol) was added to a solution of 2-(2-Fluoro-4-hydroxy-phenyl)-2-methyl-propionitrile (1.0 g, 6.0 mmol) and 2-Chloro-1-cyclopentyl-ethanone (3.3 g, 22 mmol) in DMF (20 mL). The mixture was stirred at room temperature for 16 hours. The mixture was poured into water (100 mL) and extracted with EtOAc (2×50 mL). The organics were washed with brine (100 mL), dried over $Na_2SO_4$, filtered and concentrated. The residue was purified by flash column chromatography (0–15% EtOAc in hexanes) to give the product (1.2 g, 75% yield) as a clear oil. $^1$H NMR (300 MHz, CDCl$_3$) δ: 1.57–1.93 (m, 14 H), 3.10 (m, 1 H), 4.64 (s, 2 H), 6.65 (d, J=9.6 Hz, 2 H), 7.37 (t, J=8.9 Hz, 1 H).

Step 3

Preparation of Compound 2-(2-Fluoro-4-hydroxy-phenyl)-2-methyl-propionitrile

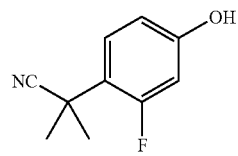

To a solution of 2-(2-Fluoro-4-methoxy-phenyl)-2-methyl-propionitrile (1.5 g, 7.8 mmol) in $CH_2Cl_2$ (75 mL) at −78° C. was added Boron tribromide (1M solution in CH₂Cl₂) (16 mL, 16 mmol). The solution was allowed to warm to room temperature and stir for 48 hours. The reaction was quenched with 0.5N HCl (50 mL) and poured into water (100 mL). The organic layer was separated and the aqueous was extracted with CH₂Cl₂ (50 mL). The combined organics were washed with water (100 mL), dried over Na₂SO₄, filtered and concentrated. The resulting oil was used without further purification.

Step 2

Preparation of Compound 2-(2-Fluoro-4-methoxy-phenyl)-2-methyl-propionitrile

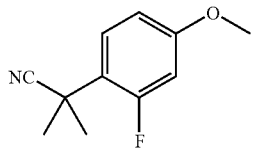

A solution of (2-Fluoro-4-methoxy-phenyl)-acetonitrile (5 g, 30 mmol) and Iodomethane (6.03 mL, 97 mmol) in DMSO (30 mL) was added dropwise over 2 hours to a stirring solution of KOH (7.47 g, 133 mmol) in water (4 mL) and DMSO (20 mL) at 0° C. The solution was allowed to warm to room temperature and stirred for 4 hours. The reaction was poured into water (100 mL) and extracted with EtOAc (2×50 mL). The organics were washed with water (100 mL) and brine (100 mL), dried over Na₂SO₄, filtered and concentrated. The residue was purified by flash column chromatography (0–10% EtOAc in hexanes) to give the product (4.76 g, 82% yield) as a clear oil.

$^1$H NMR (300 MHz, CDCl₃) δ: 1.82 (s, 6 H), 3.85 (s, 3 H), 6.64 (d, J=9.6 Hz, 2 H), 7.42 (m, 1 H).

Step 1

Preparation of Compound (2-Fluoro-4-methoxy-phenyl)-acetonitrile

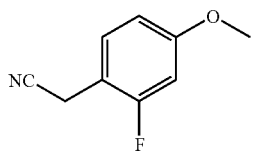

To a mixture of 1-Bromomethyl-2-fluoro-4-methoxy-benzene (4.5 g, 21 mmol) and Tetrabutylammonium iodide (0.66 g, 2.1 mmol) in CH₂Cl₂ (50 mL) was added a solution potassium cyanide (4.0 g, 60 mmol) in water (50 mL). The resulting biphasic mixture was stirred vigorously for 8 hours. The reaction was poured into water (100 mL) and extracted with CH₂Cl₂ (2×50 mL). The organics were washed with water (100 mL) and brine (100 mL), dried over Na₂SO₄, filtered and concentrated. The residue was purified by flash column chromatography (10–30% EtOAc in hexanes) to give the product (2.6 g, 75% yield) as a clear oil. $^1$H NMR (300 MHz, CDCl₃) δ: 3.66 (s, 2 H), 3.82 (s, 3 H), 6.69 (m, 2 H), 7.31 (m, 1 H).

Example C(111)

2-{4-[2-Cyclopentyl-4-hydroxy-5-(6-methyl-[1,2,4]triazolo[1,5-a]pyrimidin-2-ylmethyl)-6-oxo-3,6-dihydro-2H-pyran-2-ylmethoxy]-2-fluoro-phenyl}-2-methyl-propionitrile

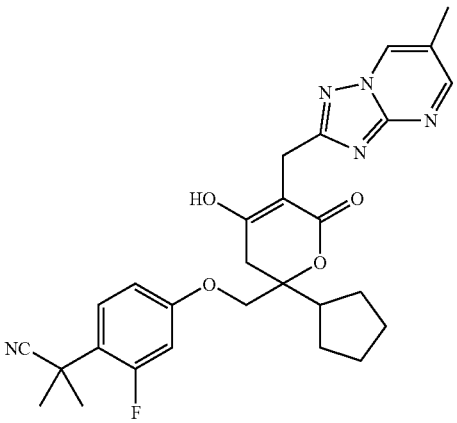

A solution of 2-[4-(2-Cyclopentyl-4,6-dioxo-tetrahydro-pyran-2-ylmethoxy)-2-fluoro-phenyl]-2-methyl-propionitrile (200 mg, 0.54 mmol) in anhydrous MeOH (4.0 mL) was treated with 6-Methyl-[1,2,4]triazolo[1,5-a]pyrimidine-2-carbaldehyde (140 mg, 0.86 mmol), followed by borane-dimethylamine complex (47 mg, 0.8 mmol) at room temperature. The reaction was stirred for 5 hours before it was quenched by the addition of 0.5N HCl (25 mL). The mixture was extracted with 10% MeOH in CH₂Cl₂ (3×10 mL) and the combined organic layers were washed with brine, dried over Na₂SO₄, filtered and concentrated. The residue was purified by crystallization from EtOAc/Hexanes to give the product as a white solid (91 mg, 32% yield). $^1$H NMR (300 MHz, DMSO-d₆) δ: 1.67 (m, 8 H), 1.70 (s, 6 H), 2.38 (s, 3 H), 2.55 (m, 1 H), 2.77 (m, 2 H), 3.77 (m, 2 H), 4.12 (m, 1 H), 4.44 (m, 1 H), 6.97 (m 2 H), 7.35 (m, 1 H), 8.69 (s, 1 H), 9.03 (s, 1 H), 10.98 (brs, 1 H).

Example C(112)

2-{4-[2-Cyclopentyl-5-(5,7-dimethyl-[1,2,4]triazolo[1,5-a]pyrimidin-2-ylmethyl)-4-hydroxy-6-oxo-3,6-dihydro-2H-pyran-2-ylmethoxy]-2-fluoro-phenyl}-2-methyl-propionitrile

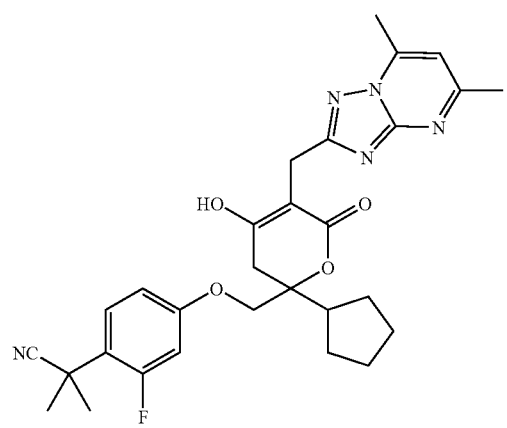

This compound was prepared analogously to example C (111), except that 5,7-Dimethyl-[1,2,4]triazolo[1,5-a]pyrimidine-2-carbaldehyde was used in place of 6-Methyl-[1,2,4]triazolo[1,5-a]pyrimidine-2-carbaldehyde. The result was a white solid. ¹H NMR (300 MHz, DMSO-d₆) δ: 1.64 (m, 8 H), 1.70 (s, 6 H), 2.50 (1, 1 H), 2.57 (s, 3 H), 2.63 (s, 3 H), 2.79 (m, 2 H), 3.77 (m, 2 H), 4.12 (brs, 1 H), 4.50 (m, 1 H), 6.95 (m 3 H), 7.35 (m, 1 H), 10.95 (brs, 1 H).

Example D(1)

6-[2-(3-Chloro-4-methoxy-phenyl)-ethyl]-6-cyclopentyl-4-hydroxy-3-(methyl-phenyl-amino)-5,6-dihydro-pyran-2-one

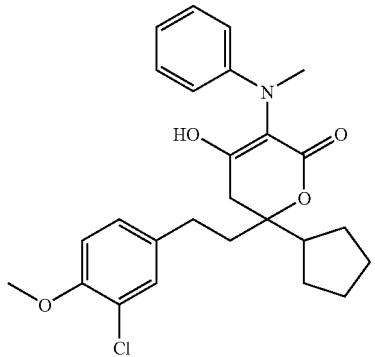

To a refluxing solution of N-methylaniline (0.115 mL, 1.1 mmol) and rhodium (II) acetate (9.4 mg) in toluene (1.6 mL) was added 6-[2-(3-chloro-4-methoxy-phenyl)-ethyl]-6-cyclopentyl-3-diazo-dihydro-pyran-2,4-dione (0.080 g, 0.213 mmol) from Step 1 below over 1 hour. The reaction was stirred at reflux for three more hours. The reaction was concentrated by rotary evaporation, and then purified by preparatory HPLC to give the desired product (28 mg, 29% yield).

¹H NMR (CDCl₃) δ: 1.48–1.78 (m, 8H), 1.92–2.07 (m, 2H), 2.38 (p, J=8.10 Hz, 1H), 2.51–2.63 (m, 3H), 2.90 (d, J=17.90 Hz, 1H), 3.10 (s, 3H), 3.82 (s, 3H), 6.77–6.81 (m, 2H), 6.86 (t, J=7.44 Hz, 1H), 6.94 (dd, J1=8.38 Hz, J2=1.98 Hz, 1H), 7.10 (d, J=2.07 Hz), 7.18–7.23 (m, 2H), 7.29 (s, 1H).

Step 1

6-[2-(3-Chloro-4-methoxy-phenyl)-ethyl]-6-cyclopentyl-3-diazo-dihydro-pyran-2,4-dione

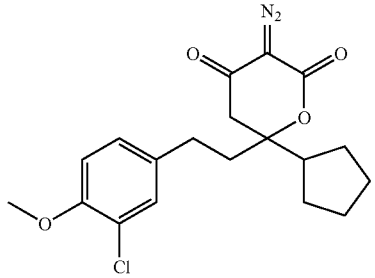

le;.5qTo a solution of 6-[2-(3-chloro-4-methoxy-phenyl)-ethyl]-6-cyclopentyl-dihydro-pyran-2,4-dione (0.500 g, 1.44 mmol) from Example B(87), and sodium dihydrogen phosphate (0.26 g, 2.16 mmol) in DMF (6 mL) was added 4-acetamidobenzenesulfonyl azide (0.52 g, 2.16 mmol). The reaction was stirred for 4 hours, and then concentrated by rotary evaporation. The crude material was purified by flash chromatography to yield the desired compound (0.537 g, 100% yield).

MS (ESI): 373 (M+H).

Example D(2)

6-[2-(3-Chloro-4-methoxy-phenyl)-ethyl]-6-cyclopentyl-4-hydroxy-3-phenoxy-5,6-dihydro-pyran-2-one

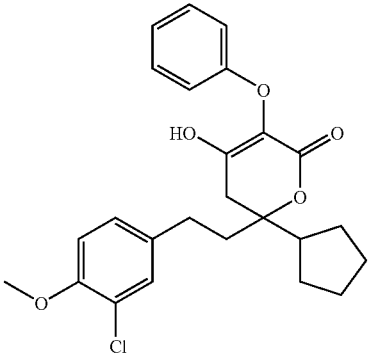

The target compound was synthesized analogously to Example D(1), substituting phenol (56 mg, 0.598 mmol) in place of N-methylaniline. Yield 12.3 mg, 23% yield.

¹H NMR (CDCl₃) δ: 1.49–1.79 (m, 8H), 1.96–2.18 (m, 2H), 2.46)ₚ, J=8.32 Hz, 1H), 2.54 (d, J=17.91 Hz, 1H), 2.63 (t, J=8.32 Hz, 2H), 2.92 (d, J=17.59 Hz, 1H), 3.82 (s, 3H), 6.79 (d, J=8.32 Hz, 1H), 6.88 (d, J=8.00 Hz, 2H), 6.95–7.02 (m, 2H), 7.13 (d, J=1.92 Hz, 1H), 7.21–7.29 (m, 2H).

Example D(3)

6-Cyclopentyl-6-{2-[5-ethyl-4-(2-methoxy-ethoxymethoxy)-2-methyl-phenyl]-ethyl}-dihydro-pyran-2,4-dione

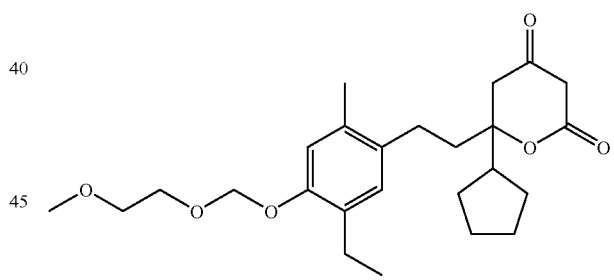

Methyl acetoacetate (0.36 mL, 3.4 mmol) was added to a cooled −40° C. solution of LDA (prepared from n-BuLi (4.2 ml, 6.71 mmol, 1.6 M in hexanes) and diisoproplyamine (0.94 mL, 6.71 mmol)) in THF (6 mL). The mixture was stirred for 30 mins and then treated with a solution of 1-cyclopentyl-3-[5-ethyl-4-(2-methoxy-ethoxymethoxy)-2-methyl-phenyl]-propan-1-one (0.39 g, 1.1 mmol) in THF (3 ml). After stirring for 6 h, the reaction mixture was partitioned between 1N HCl and EtOAc. The organic layers were washed with brine, dried over Na₂SO₄ and concentrated to a yellow oil that was purified by flash column chromatography (10–25% EtOAc in hexanes) to give a clear oil (0.33 g, 65%).

The oil (0.33 g, 0.71 mmol) was dissolved in methanol (5 mL), treated with potassium carbonate (0.29 g, 2.1 mmol), and refluxed under N₂ for 60 min. The reaction mixture was partitioned between 1N HCl and EtOAc. The organic layers were washed with brine, dried over Na₂SO₄ and concentrated to a yellow oil that was purified by silica gel chromatography (20% to 40% EtOAc in hexanes) to give the title compound as an oil (0.21 g, 69% yield). $^1$H NMR (400 MHz, CDCl$_3$): δ 1.16 (t, J=7.6 Hz, 3 H), 1.51–1.91 (br m, 10 H), 2.23 (s, 3 H), 2.32 (m, 1 H), 2.57 (m, 4 H), 2.79 (s, 2 H), 3.39 (s, 3 H), 3.42 (s, 2 H), 3.57 (m, 2 H), 3.82 (m, 2 H), 5.25 (s, 2 H), 6.83 (s, 1 H), 6.91 (s, 1 H). C$_{25}$H$_{36}$O$_6$ (M+H)$^+$ 433.30.

Step 5

1-Cyclopentyl-3-[5-ethyl-4-(2-methoxy-ethoxymethoxy)-2-methyl-phenyl]-propan-1-one

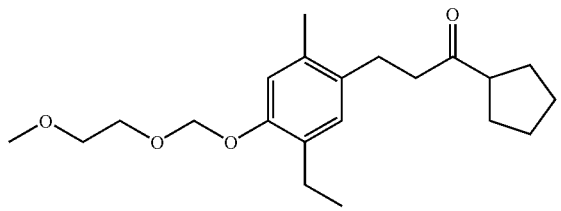

A mixture of 1-cyclopentyl-3-[5-ethyl-4-(2-methoxy-ethoxymethoxy)-2-methyl-phenyl]-propenone (0.75 g, 2.2 mmol) and 5% wt Pd/BaSO$_4$ (0.15 g) in THF (10 mL) was stirred under a balloon of H$_2$ for 30 mins. The reaction mixture was filtered through a pad of celite washing with EtOAc. The filtrate was concentrated and purified by flash column chromatography (0% to 15% EtOAc in hexanes) to give the title compound as an oil (0.39 g, 52%). $^1$H NMR (400 MHz, CDCl$_3$): δ 1.16 (t, J=7.6 Hz, 3 H), 1.54–1.84 (br m, 8 H), 2.25 (s, 3 H), 2.58 (q, J=7.6 Hz, 2 H), 2.68 (m, 2H), 2.82 (m, 3 H), 3.39 (s, 3 H), 3.57 (m, 2 H), 3.83 (m, 2 H), 5.26 (s, 2 H), 6.89 (s, 1 H), 6.91 (s, 1H).

Step 4

1-Cyclopentyl-3-[5-ethyl-4-(2-methoxy-ethoxymethoxy)-2-methyl-phenyl]-propenone

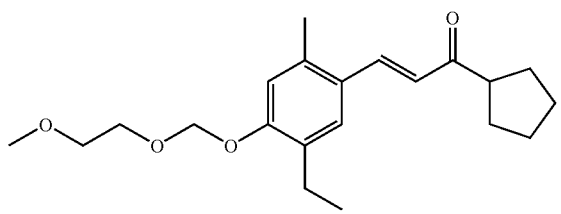

Ba(OH)$_2$ (0.18 g, 1.1 mmol) was added to a solution of 5-ethyl-4-(2-methoxy-ethoxymethoxy)-2-methyl-benzaldehyde (0.87 g, 3.5 mmol) and 1-cyclopentyl-ethanone (0.59 g, 5.3 mmol) dissolved in EtOH (7 mL). The reaction mixture was stirred together for 24 hours and then partitioned between 1N HCl and EtOAc. The organic layer was washed with saturated NaHCO$_3$, brine, dried over Na$_2$SO$_4$ and concentrated to an oil. Flash column chromatography (0% to 10% EtOAc in hexanes) gave the title compound as a clear oil (0.78 g, 65%). $^1$H NMR (400 MHz, CDCl$_3$): δ 1.20 (t, J=7.6 Hz, 3 H), 1.54–1.91 (br m, 8 H), 2.41 (s, 3 H), 2.62 (q, J=7.6 Hz, 2 H), 3.18 (m, 1 H), 3.39 (s, 3 H), 3.57 (m, 2 H), 3.83 (m, 2 H), 5.30 (s, 2 H), 6.65 (d, J=15.9 Hz, 1 H), 6.94 (s, 1 H), 7.41 (s, 1 H), 7.84 (d, J=15.9 Hz, 1 H).

Step 3

5-Ethyl-4-(2-methoxy-ethoxymethoxy)-2-methyl-benzaldehyde

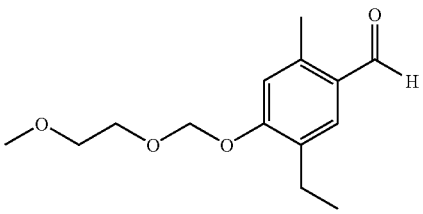

A solution of 5-ethyl-4-hydroxy-2-methyl-benzaldehyde (0.9 g, 5.5 mmol) dissolved in THF (10 mL) was added to a cooled 0° C. suspension of NaH (0.29 g, 7.2 mmol, 60% dispersion in mineral oil) in THF (5 ml). After the addition was complete the reaction mixture was warmed up to room temperature and stirred for 30 mins. 2-Methoxyethoxymethyl chloride (0.82 mL, 7.1 mmol) was added and the reaction was stirred for 4 hours. The reaction mixture was quenched with 1N HCl and extracted with EtOAc. The organic layers were washed with brine, dried over Na$_2$SO$_4$ and concentrated to a yellow oil. Purification by flash column chromatography (10% to 20% EtOAc in hexanes) gave the title compound as a clear oil (0.89 g, 65%). $^1$H NMR (400 MHz, CDCl$_3$): δ 1.21 (t, J=7.3 Hz, 3 H), 2.63 (m, 5 H), 3.39 (s, 3 H), 3.57 (m, 2 H), 3.84 (m, 2 H), 5.37 (s, 2 H), 6.95 (s, 1 H), 7.62 (s, 1 H), 10.15 (s, 1 H).

Step 2

5-Ethyl-4-hydroxy-2-methyl-benzaldehyde

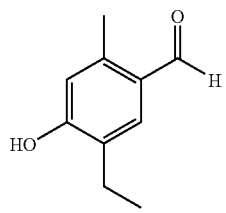

Titanium(IV) chloride (11 mL, 11 mmol, 1M in CH$_2$Cl$_2$) followed by dichloromethyl methyl ether (1.04 g, 9.1 mmol) was added to a cooled 0° C. solution of 2-ethyl-5-methyl-phenol (0.75 g, 5.5 mmol) The reaction mixture was stirred for 30 mins and then warmed up to rt and stirred for another 30 mins. The mixture was poured into ice and extracted with EtOAc. The organic layers were washed with satd NaHCO$_3$, brine, dried over Na$_2$SO$_4$ and concentrated to a purple oil. Purification by flash column chromatography (0% to 10% EtOAc in hexanes) gave the title compound as an oil (0.45 g, 50%). $^1$H NMR (400 MHz, CDCl$_3$): δ 1.26 (t, J=7.6 Hz, 3 H), 2.60 (s, 3 H), 2.65 (q, J=7.6 Hz, 2 H), 5.37 (s, 1 H), 6.62 (s, 1 H), 7.62 (s, 1 H), 10.11 (s, 1 H).

Step 1

2-Ethyl-5-methyl-phenol

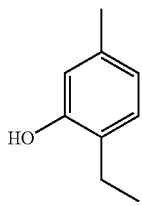

A mixture of 1-(2-hydroxy-4-methyl-phenyl)-ethanone (5 g, 33.3 mmol) and 10 wt % Pd/C (2 g, Degussa type) in MeOH (50 mL) was stirred under a balloon of $H_2$ for 24 hours. The reaction mixture was filtered through a pad of celite washing with EtOAc. The filtrate was concentrated to a clear oil (4.5 g, 99%). $^1$H NMR (400 MHz, CDCl$_3$): δ 1.23 (t, J=7.6 Hz, 3 H), 2.27 (s, 3 H), 2.59 (q, J=7.6 Hz, 2 H), 4.68 (s, 1 H), 6.59 (s, 1 H), 6.71 (d, J=7.7 Hz, 1 H), 7.01 (d, J=7.7 Hz, 1 H).

Example D(4)

6-Cyclopentyl-6-[2-(2,3-dihydro-benzofuran-5-yl)-ethyl]-3-(5,7-dimethyl-[1,2,4]triazolo[1,5-a]pyrimidin-2-ylmethyl)-4-hydroxy-5,6-dihydro-pyran-2-one

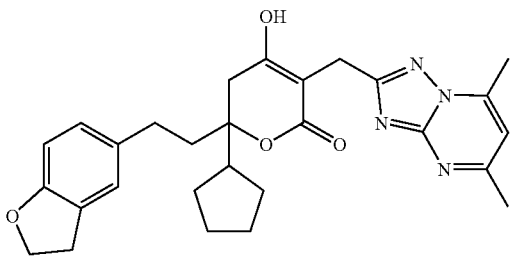

The title compound was prepared analogously to Example A(123) where 6-cyclopentyl-6-[2-(2,3-dihydro-benzofuran-5-yl)-ethyl]-dihydro-pyran-2,4-dione (Example D(5)) was substituted in place of 6-cyclopentyl-6-[2-(3-ethyl-5-fluoro-4-hydroxy-phenyl)-ethyl]-dihydro-pyran-2,4-dione. $^1$H NMR (400 MHz, DMSO-d$_6$): δ 1.39–1.69 (br m, 8 H), 2.05–2.11 (m, 2 H), 2.39 (m, 1 H), 2.49–2.55 (m, 9 H), 2.75 (d, J=17.6 Hz, 1 H), 3.11 (t, J=8.8 Hz, 2 H), 3.70 (d, J=16.2 Hz, 1 H), 3.82 (d, J=16.2 Hz, 1 H), 4.48 (t, J=8.8 Hz, 2 H), 6.62 (d, J=8.1 Hz, 1 H), 6.92 (d, J=6.6 Hz, 1 H), 7.04 (s, 1 H), 7.07 (s, 1 H). Anal. Calcd. For $C_{28}H_{32}N_4O_4 \cdot 0.4H_2O$: C, 67.83; H, 6.67; N, 11.30. Found: C, 67.86; H, 6.74; N, 11.40.

Example D(5)

6-Cyclopentyl-6-[2-(2,3-dihydro-benzofuran-5-yl)-ethyl]-dihydro-pyran-2,4-dione

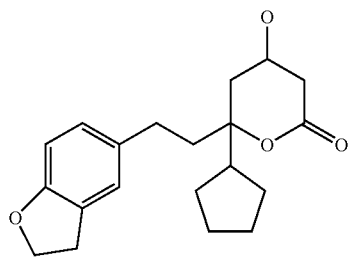

The title compound was prepared analogously to Example D(1) where 2,3-dihydro-benzofuran-5-carbaldehyde was substituted in place of 5-ethyl-4-(2-methoxy-ethoxymethoxy)-2-methyl-benzaldehyde in step 4 of that example. $^1$H NMR (400 MHz, CDCl$_3$) δ: 1.51–180 (br m, 8 H), 1.76–2.01 (m, 2 H), 2.28 (m, 1 H), 2.60 (t, J=8.6 Hz, 2 H), 2.76 (s, 2 H), 3.17 (t, J=8.6 Hz, 2 H), 3.42 (s, 2 H), 4.55 (t, J=8.8 Hz, 2 H), 6.70 (d, J=8.1 Hz, 1 H), 6.87 (d, J=9.6 Hz, 1 H), 6.97 (s, 1 H). Anal. Calcd. For $C_{20}H_{24}O_4$: C, 73.15; H, 7.37. Found: C, 72.88; H, 7.35.

Example D(6)

6-Cyclopentyl-6-{2-[5-ethyl-2-fluoro-4-(2-methoxy-ethoxymethoxy)-phenyl]-ethyl}-dihydro-pyran-2,4-dione

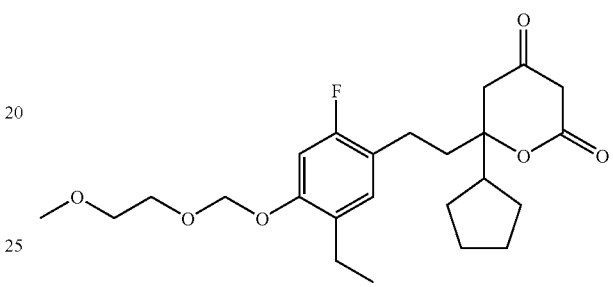

The title compound was prepared analogously to Example D(1) where 1-(4-fluoro-2-hydroxy-phenyl)-ethanone was substituted in place of 1-(2-hydroxy-4-methyl-phenyl)-ethanone in step 1 of that example. $^1$H NMR (400 MHz, CDCl$_3$): δ 1.15 (t, J=7.6 Hz, 3 H), 1.44–1.96 (br m, 10 H), 2.31 (m, 1 H), 2.53–2.67 (m, 4 H), 2.77 (s, 2 H), 3.39 (s, 3 H), 3.43 (s, 2 H), 3.56 (m, 2 H), 3.81 (m, 2 H), 5.24 (s, 2 H), 6.06 (m, 2 H).

Example D(7)

6-Cyclopentyl-6-{2-[5-ethyl-2-(2-methoxy-ethoxymethoxy)-phenyl]-ethyl}-dihydro-pyran-2,4-dione

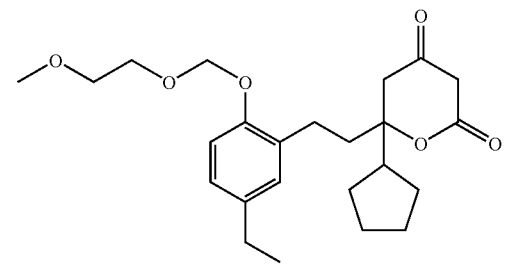

The title compound was prepared analogously to Example D(1) where 5-ethyl-2-(2-methoxy-ethoxymethoxy)-benzaldehyde (from step 1 below) was substituted in place of 5-ethyl-4-(2-methoxy-ethoxymethoxy)-2-methyl-benzaldehyde in step 4 of that example. $^1$H NMR (400 MHz, CDCl$_3$): δ 1.15 (t, J=7.6 Hz, 3 H), 1.44–1.98 (br m, 10 H), 2.35 (m, 1 H), 2.56 (q, J=7.6 Hz, 2 H), 2.56–2.70 (m, 2H), 2.74 (d, J=16.2 Hz, 1 H), 2.56 (d, J=16.2 Hz, 1 H), 3.38 (s, 3 H), 3.43 (s, 2H), 3.56 (m, 2H), 3.80 (m, 2 H), 5.25 (s, 2H), 6.91 (d, J=2.1 Hz, 1 H), 6.99 (dd, J=8.4, 2.1 Hz, 1 H), 7.04 (d, J=8.4 Hz, 1 H).

421

Step 1

5-Ethyl-2-(2-methoxy-ethoxymethoxy)-benzaldehyde

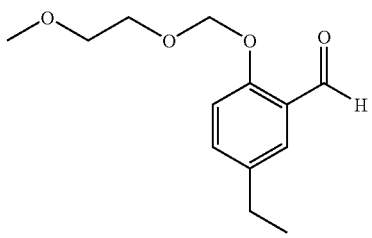

CHCl$_3$ (10 mL) was slowly added to a suspension of 4-ethyl phenol (30 g, 0.25 mol) in 10N NaOH (150 mL). After the vigorous reaction died down, the mixture was stirred for 20 mins and then additional CHCl$_3$ (20 mL) was added very slowly. The reaction was cooled to 0° C. and let stand for 2 hrs. The reaction mixture was acidified with 12 N HCl, diluted with water and then extracted with CH$_2$Cl$_2$ The organics were concentrated to a brown oil (17.3 g).

The oil was dissolved in THF (50 mL) and added to a cooled 0° C. suspension of NaH (5.76 g, 0.14 mol, 60% dispersion in mineral oil) in THF (100 ml). After the addition was complete the reaction mixture was warmed up to room temperature and stirred for 1 hr. Methoxyethoxymethyl chloride (17.1 mL, 0.15 mmol) was added and the reaction was stirred for 20 hours. The reaction mixture was quenched with 1N HCl and extracted with EtOAc. The organic layers were washed with 1N NaOH, brine, dried over Na$_2$SO$_4$ and concentrated to a brown oil. Purification by flash column chromatography (0% to 10% EtOAc in hexanes) gave the title compound as a yellow oil (10.8 g, 18%). $^1$H NMR (400 MHz, CDCl$_3$): δ 1.22 (t, J=7.6 Hz, 3 H), 2.63 (q, J=7.6 Hz, 2 H), 3.38 (s, 3H), 3.57 (m, 2H), 3.87 (m, 2H), 5.38 (s, 2H), 7.19 (d, J=8.5 Hz, 1 H), 7.37 (dd, J=8.3, 2.3 Hz, 1 H), 7.67 (d, J=2.5 Hz, 1 H), 10.47 (s, 1 H).

Example D(8)

6-[2-(2-Benzyloxy-5-ethyl-phenyl)-ethyl]-6-cyclopentyl-dihydro-pyran-2,4-dione

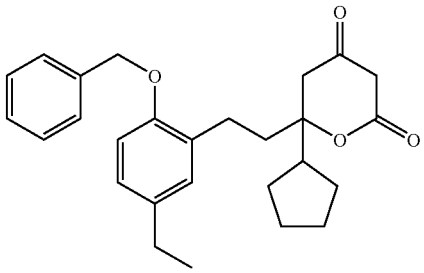

The title compound was prepared analogously to Example D(1) where 2-benzyloxy-5-ethyl-benzaldehyde (from step 2 below) was substituted in place of 5-ethyl-4-(2-methoxyethoxymethoxy)-2-methyl-benzaldehyde in step 4 of that example. $^1$H NMR (400 MHz, CDCl$_3$): δ 1.20 (t, J=7.8 Hz, 3 H), 1.33–1.70 (br m, 8 H), 1.87 (m, 1 H), 1.99 (m, 1 H), 2.27 (m, 1 H), 2.54–2.74 (m, 6 H), 3.27 (s, 2 H), 5.01 (s, 2 H), 6.83 (d, J=8.1 Hz, 1 H), 6.93 (s, 1 H), 7.01 (d, J=8.1 Hz, 1 H), 7.34–7.40 (m, 5 H). MS (ESI): 421.10 (M+H$^+$).

422

Step 2

2-Benzyloxy-5-ethyl-benzaldehyde

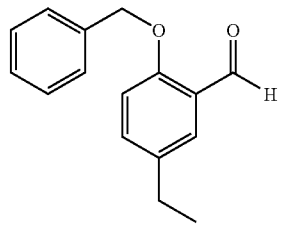

n-BuLi (7.56 mL, 18.9 mmol, 2.5M in hexanes) followed by DMF (5.5 mL) were added to a cooled −78° C. solution of 1-benzyloxy-2-bromo-4-ethyl-benzene (5 g, 17.2 mmol) in THF (40 mL). The reaction was stirred at −78° C. for 1 hr and then warmed up to rt. After 2 hrs the reaction was quenched with 1N HCl and extracted with EtOAc. The organic layers were washed with brine, dried over Na$_2$SO$_4$ and concentrated to a yellow oil. Purification by flash column chromatography (0% to 5% EtOAc in hexanes) gave the title compound as a clear oil (3.6 g, 87%). $^1$H NMR (400 MHz, CDCl$_3$): δ 1.22 (t, J=7.8 Hz, 3 H), 2.62 (q, J=7.8 Hz, 2 H), 5.17 (s, 2 H), 6.97 (d, J=8.6 Hz, 1 H), 7.33–7.45 (m, 6 H), 7.69 (s, 1 H), 10.54 (s, 1 H).

Step 1

1-Benzyloxy-2-bromo-4-ethyl-benzene

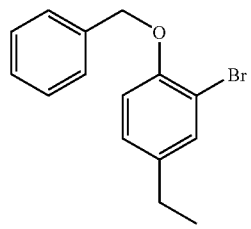

Potassium carbonate (21.6 g, 0.16 mol) followed by benzyl bromide (6.2 mL, 52 mmol) were added to a solution of 4-bromo-2-ethyl-phenol (1.6 g, 7.9 mmol, from step 1 of Example B(98)) in DMF (75 mL). The mixture was stirred for 20 hours and then partitioned between 1N HCl and EtOAc. The organic layers were washed with brine, dried over Na$_2$SO$_4$ and concentrated. The crude yellow oil was purified by flash column chromatography (hexanes) to give the desired product (13.1 g, 87%). $^1$H NMR (400 MHz, CDCl$_3$): δ 1.20 (t, J=7.6 Hz, 3 H), 2.56 (q, J=7.8 Hz, 2 H), 5.13 (s, 2 H), 6.84 (d, J=8.3 Hz, 1 H), 7.04 (dd, J=8.3, 2.3 Hz, 1 H), 7.32 (m, 1 H), 7.38 (m, 3 H), 7.47 (d, J=7.9 Hz, 2 H).

Example E(1)

3-[4-(2-Cyclopentyl-4,6-dioxo-tetrahydro-pyran-2-ylethynyl)-phenyl]-3-oxo-propionitrile

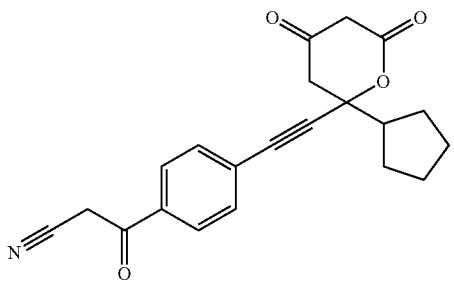

The title compound was prepared analogously to example A(75), where the hydrogenation of the triple bond Step was omitted. Yield 48 mg, 32%.

$^1$H NMR (CDCl$_3$): δ 1.35 to 1.71 (bm, 8H), 2.34 (m, 1H), 2.66 (d, J=17.8 Hz, 1H), 2.87 (d, J=17.4 Hz, 1H), 3.36 (d, J=20.2 Hz, 1H), 3.75 (d, J=19.8 Hz, 1H), 3.93 (s, 2H), 7.41 (d, J=8.3 Hz, 2H), 7.76 (d, J=8.6 Hz, 2H). ESIMS (M+Na$^+$): 372.13.

Example E(2)

3-[5-(2-Cyclopentyl-4,6-dioxo-tetrahydro-pyran-2-ylethynyl)-thiophen-2-yl]-3-oxo-propionitrile

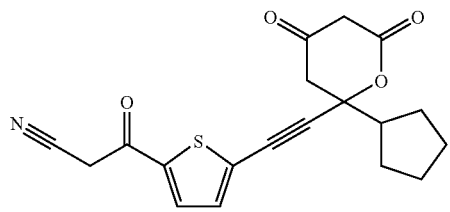

The title compound was prepared analogously to Example A(86), , where 3-(5-Bromo-thiophen-2-yl)-isoxazole was substituted in place of. 1-(4-Bromo-phenyl)-cyclopropanecarboxylic acid methyl ester in Step 3 of that example, and the hydrogenation of the triple bond Step was omitted (Note that the isoxazole opens to the cyanomethyl ketone during the Sonogashira coupling Step). Yield 30 mg, 35%.

$^1$H NMR (CDCl$_3$): δ 1.35 to 1.68 (bm, 8H), 2.33 (m, 1H), 2.65 (d, J=17.7 Hz, 1H), 2.87 (d, J=17.4 Hz, 1H), 3.37 (d, J=20.2 Hz, 1H), 3.70 (d, J=20.0 Hz, 1H), 3.83 (s, 2H), 7.52 (m, 2H). ESIMS (M+Na$^+$): 378.09.

Example E(3)

[3-(2-Cyclopentyl-4,6-dioxo-tetrahydro-pyran-2-ylethynyl)-phenyl]-acetonitrile

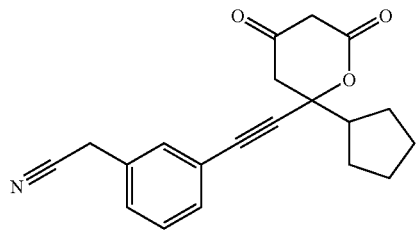

The title compound was prepared analogously to example A(86), , where (3-Bromo-phenyl)-acetonitrile was substituted in place of. 1-(4-Bromo-phenyl)-cyclopropanecarboxylic acid methyl ester in Step 3 of that example, and the hydrogenation of the triple bond Step was omitted.

$^1$H NMR (CDCl$_3$): δ 1.44 to 1.72 (bm, 8H), 2.82 (m, 1H), 3.79 (d, J=17.4 Hz, 1H), 2.87 (d, J=17.4 Hz, 1H), 3.35 (d, J=20.0 Hz, 1H), 3.61 (s, 2H), 3.81 (d, J=20.2 Hz, 1H), 7.13 (s, 1H), 7.24 (bm, 4 H). ESIMS (M+Na$^+$): 344.14.

Example F(1)

6-Cyclopentyl-6-[4-(4-hydroxy-2,6-dimethyl-phenyl)-but-3-ynyl]-dihydro-pyran-2,4-dione

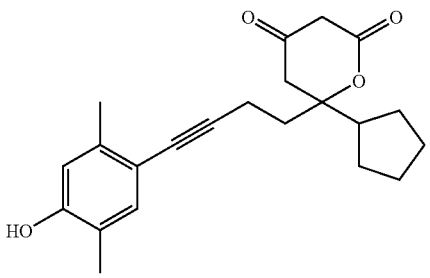

To 5-cyclopentyl-5-hydroxy-9-(4-hydroxy-2,5-dimethyl-phenyl)-3-oxo-non-8-ynoic acid methyl ester (60 mg, 0.155 mmol) from Step 2 below was added NaOH (0.3 M in MeOH, 1 mL, 0.31 mmol). The solution was stirred overnight, and then quenched with 1 N HCl (5 mL). The solution was extracted with 4×10 mL CH$_2$Cl$_2$. The organic layer was dried over Na$_2$SO$_4$, and then the solids were removed by filtration. After concentrating the mother liquor, the resulting oil was purified by flash chromatography to yield the desired product (54 mg, 98% yield).

$^1$H NMR (CDCl$_3$) δ: 1.35–1.75 (m, 8H), 1.93–1.99 (m, 3H), 2.10 (s, 3H), 2.23 (s, 3H), 2.51 (t, J=7.33 Hz, 2H), 2.69 (d, J=16.17 Hz, 1H), 2.83 (d, J=16.18 Hz, 1H), 3.37 (s, 2H), 4.66 (s, 1H), 6.52 (s, 1H), 7.05 (s, 1H). MS (ESI): 353 (M−H).

Step 1

1-Cyclopentyl-5-(4-hydroxy-2,5-dimethyl-phenyl)-pent-4-yn-1-one

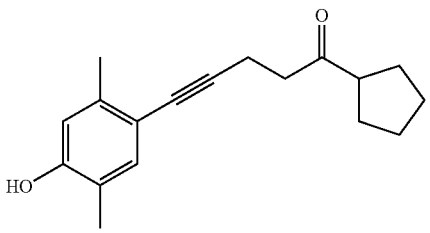

A solution of 1-cyclopentyl-pent-4-yn-1-one (0.33 g, 2.2 mmol) from example F(7), Step 2,4-iodo-2,5-dimethyl-phenol (0.54 g, 2.2 mmol), copper (I) iodide (33 mg, 0.18 mmol), trans-dichlorobis(triphenylphosphine)palladium (II) (63 mg, 0.09 mmol), and diisopropylamine (2.2 mL) in DMF (2.2 mL) was heated to 100° C. for 30 minutes. The reaction was cooled to room temperature and diluted with 10 mL of EtOAc. The resulting slurry was filtered, and the mother liquor was concentrated to a black oil. The oil was then purified by flash chromatography to give the desired product (112 mg, 19% yield).

¹H NMR (CDCl₃) δ: 1.58–1.84 (m, 8H), 2.15 (s, 3H), 2.29 (s, 3H), 2.68–2.70 (m, 2H), 2.75–2.79 (m, 2H), 2.90 (p, J=8.08 Hz, 1H), 6.57 (s, 1H), 7.10 (s, 1H).

Step 2

5-Cyclopentyl-5-hydroxy-9-(4-hydroxy-2,5-dimethyl-phenyl)-3-oxo-non-8-ynoic acid methyl ester

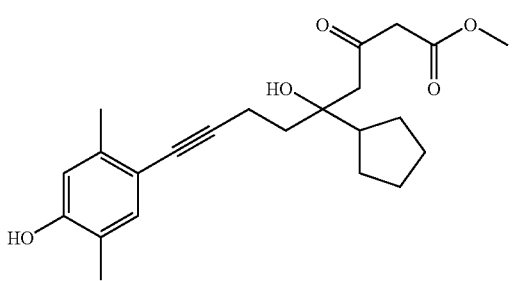

To a freshly prepared solution of LDA (1 M, 2.2 mL, 2.2 mmol) cooled to 0° C. was added methyl acetoacetate (0.12 mL, 1.1 mmol) dissolved in THF (1 mL). After stirring for 30 minutes, 1-cyclopentyl-5-(4-hydroxy-2,5-dimethyl-phenyl)-pent-4-yn-1-one (0.10 g, 0.37 mmol) from Step 1 above dissolved in THF (1 mL) was added. The reaction was stirred for 1 hour, and then warmed to room temperature. After quenching with 10 mL saturated ammonium chloride, the layers were separated. The aqueous layer was extracted with 2×15 mL CH₂Cl₂, and the organic layers were combined. After drying over Na₂SO₄, and filtering to remove the solids, the mother liquor was concentrated to an oil. Flash chromatography of the oil gave the desired product (69 mg, 48% yield).

MS (ESI): 385 (M–H).

Example F(2)

3-[4-(2-Cyclopentyl-4,6-dioxo-tetrahydro-pyran-2-yl)-but-1-ynyl]-benzenesulfonamide

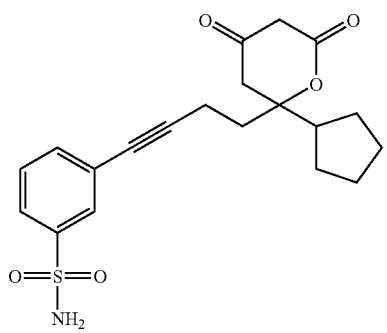

The desired product was prepared analogously to example F(1), substituting 5-cyclopentyl-5-hydroxy-3-oxo-9-(3-sulfamoyl-phenyl)-non-8-ynoic acid methyl ester (80 mg, 0.19 mmol) from Step 2 below in place of 5-cyclopentyl-5-hydroxy-9-(4-hydroxy-2,5-dimethyl-phenyl)-3-oxo-non-8-ynoic acid methyl ester. Yield: 17 mg, 23%.

¹H NMR (CDCl₃) δ: 1.43–1.74 (m, 8H), 1.93–2.05 (m, 2H), 2.20 (p, J=8.59 Hz, 1H), 2.52 (t, J=7.45 Hz, 2H), 2.70 (d, J=16.17 Hz, 1H), 2.80 (d, J=16.17 Hz, 1H), 3.39 (s, 2H), 4.82 (s, 2H), 7.38 (t, J=7.83 Hz, 1H), 7.50 (d, J=8.84 Hz, 1H), 7.76 (d, J=7.83 Hz, 1H), 7.90 (t, J=1.52 Hz, 1H). MS (ESI): 388 (M–H).

Step 1

3-(5-Cyclopentyl-5-oxo-pent-1-ynyl)-benzenesulfonamide

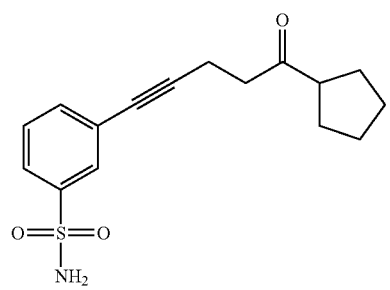

The desired product was prepared analogously to example F(1), Step 1 substituting 3-bromo-benzenesulfonamide (400 mg, 2.7 mmol) in place of 4-iodo-2,5-dimethyl-phenol. Yield: 0.556 g, 67%.

¹H NMR (CDCl₃) δ: 1.66–1.96 (m, 8H), 2.77 (t, J=6.82 Hz, 2H), 2.88 (t, J=6.82 Hz, 2H), 2.99 (p, J=7.96 Hz, 1H), 5.01 (s, 1H), 5.09 (s, 1H), 7.52 (t, J=7.83 Hz, 1H), 7.79–7.82 (m, 1H), 7.94–7.97 (m, 1H), 8.17 (t, J=1.89 Hz, 1H).

Step 2

5-Cyclopentyl-5-hydroxy-3-oxo-9-(3-sulfamoyl-phenyl)-non-8-ynoic acid methyl ester

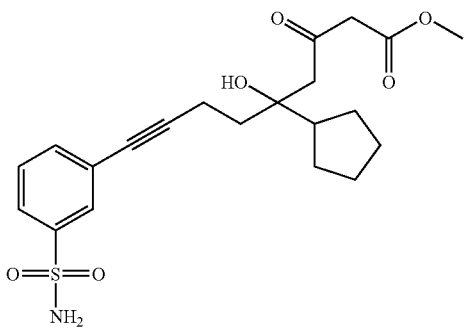

The desired product was prepared analogously to example A(86), Step 2, substituting 3-(5-cyclopentyl-5-oxo-pent-1-ynyl)-benzenesulfonamide (200 mg, 0.66 mmol) from Step 1 above in place of 1-cyclopentyl-5-(4-hydroxy-2,5-dimethyl-phenyl)-pent-4-yn-1-one. Yield: 89 mg, 32%.

MS (ESI): 420 (M–H).

Example F(3)

6-Cyclopentyl-6-[4-(2-methylsulfanyl-phenyl)-but-3-ynyl]-dihydro-pyran-2,4-dione

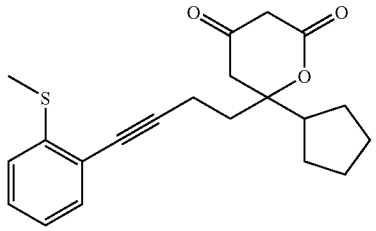

The desired product was prepared analogously to example F(1), substituting 5-cyclopentyl-5-hydroxy-9-(2-methylsulfanyl-phenyl)-3-oxo-non-8-ynoic acid methyl ester (43 mg, 0.11 mmol) from Step 2 below in place of 5-cyclopentyl-5-hydroxy-9-(4-hydroxy-2,5-dimethyl-phenyl)-3-oxo-non-8-ynoic acid methyl ester. Yield: 38 mg, 97%.

$^1$H NMR (CDCl$_3$) δ: 1.41–1.69 (m, 8H), 1.94–2.01 (m, 2H), 2.13–2.18 (m, 1H), 2.36 (s, 3H), 2.55 (t, J=7.45 Hz, 2H), 2.67 (d, J=16.17 Hz, 1H), 2.87 (d, J=16.17 Hz, 1H), 3.34 (d, J=8.84 Hz, 2H), 6.93–7.01 (m, 2H), 7.14–7.16 (m, 1H), 7.24 (d, J=6.32 Hz, 1H). MS (ESI): 355 (M–H).

Step 1

1-Cyclopentyl-5-(2-methylsulfanyl-phenyl)-pent-4-yn-1-one

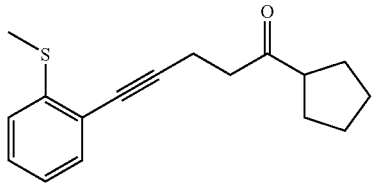

The desired product was prepared analogously to example F(1), Step 1, substituting 2-bromothioanisole (0.58 g, 2.8 mmol) in place of 4-iodo-2,5-dimethyl-phenol. Yield: 63 mg, 8.3%.

MS (APCI): 273 (M+H).

Step 2

5-Cyclopentyl-5-hydroxy-9-(2-methylsulfanyl-phenyl)-3-oxo-non-8-ynoic acid

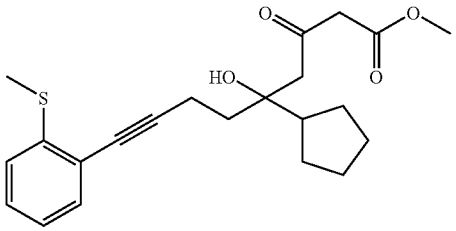

The desired product was prepared analogously to example F(1), Step 2, substituting 1-Cyclopentyl-5-(2-methylsulfanyl-phenyl)-pent-4-yn-1-one (60 mg, 0.22 mmol) from Step 1 above in place of 1-cyclopentyl-5-(4-hydroxy-2,5-dimethyl-phenyl)-pent-4-yn-1-one. Yield: 43 mg, 50%.

MS (ESI): 387 (M–H).

Example F(4)

6-Cyclopentyl-6-[4-(2-trifluoromethoxy-phenyl)-but-3-ynyl]-dihydro-pyran-2,4-dione

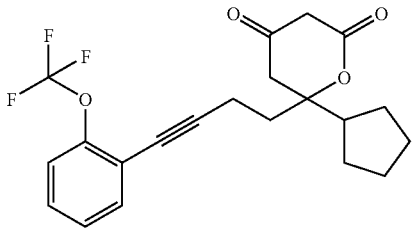

The desired product was prepared analogously to example F(1), substituting 5-cyclopentyl-5-hydroxy-3-oxo-9-(2-trifluoromethoxy-phenyl)-non-8-ynoic acid methyl ester (72 mg, 0.17 mmol) from Step 2 below in place of 5-cyclopentyl-5-hydroxy-9-(4-hydroxy-2,5-dimethyl-phenyl)-3-oxo-non-8-ynoic acid methyl ester. Yield: 25 mg, 37%.

$^1$H NMR (CDCl$_3$) δ: 1.33–1.73 (m, 8H), 1.89–2.06 (m, 2H), 2.14–2.23 (m, 1H), 2.55 (t, J=7.58 Hz, 2H), 2.69 (d, J=16.17 Hz, 1H), 2.84 (d, J=16.17 Hz, 1H), 3.37 (s, 2H), 7.15–7.21 (m, 2H), 7.23–7.27 (m, 1H), 7.38–7.44 (m, 1H). MS (ESI): 393 (M–H).

Step 1

1-cyclopentyl-5-(2-trifluoromethoxy-phenyl)-pent-4-yn-1-one

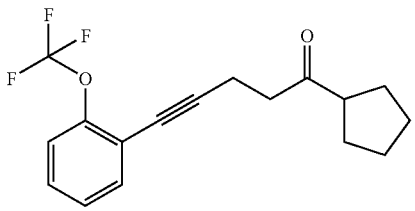

The desired product was prepared analogously to example F(1), Step 1, substituting 1-Iodo-2-trifluoromethoxy-benzene (0.80 g, 2.8 mmol) in place of 4-iodo-2,5-dimethyl-phenol. Yield: 0.247 g, 28%.

$^1$H NMR (CDCl$_3$) δ: 1.80–2.05 (m, 8H), 2.70–3.12 (m, 5H), 7.40–7.45 (m, 2H), 7.49–7.53 (m, 1H), 7.64–7.69 (m, 1H).

Step 2

5-cyclopentyl-5-hydroxy-3-oxo-9-(2-trifluoromethoxy-phenyl)-non-8-ynoic acid methyl ester

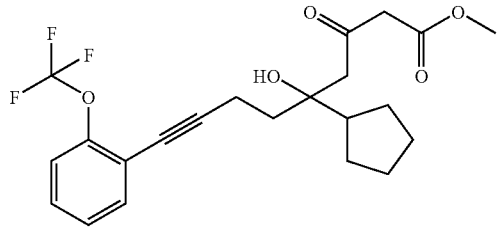

The desired product was prepared analogously to example F(1), Step 2, substituting 1-cyclopentyl-5-(2-trifluoromethoxy-phenyl)-pent-4-yn-1-one (200 mg, 0.65 mmol) from Step 1 above in place of 1-cyclopentyl-5-(4-hydroxy-2,5-dimethyl-phenyl)-pent-4-yn-1-one. Yield: 72 mg, 26%.

MS (ESI): 425 (M–H).

Example F(5)

6-Cyclopentyl-6-[4-(4-fluoro-phenyl)-but-3-ynyl]-dihydro-pyran-2,4-dione

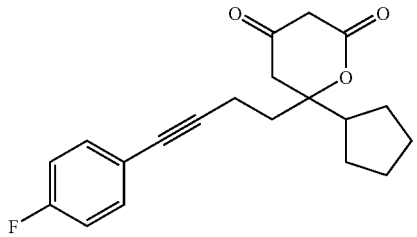

The desired product was prepared analogously to example F(1), substituting 5-cyclopentyl-9-(4-fluoro-phenyl)-5-hydroxy-3-oxo-non-8-ynoic acid methyl ester (400 mg, 1.1 mmol) from Step 2 below in place of 5-cyclopentyl-5-hydroxy-9-(4-hydroxy-2,5-dimethyl-phenyl)-3-oxo-non-8-ynoic acid methyl ester. Yield: 190 mg, 53%. MS (ESI): 327 (M–H).

Step 1

1-Cyclopentyl-5-(4-fluoro-phenyl)-pent-4-yn-1-one

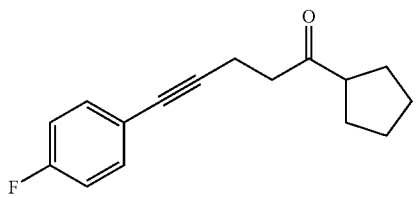

The desired product was prepared analogously to example F(1), Step 1, substituting 1-fluoro-4-iodo-benzene (0.38 mL, 3.3 mmol) in place of 4-iodo-2,5-dimethyl-phenol. Yield: 0.415 g, 51%.

$^1$H NMR (CDCl$_3$) δ: 1.44–1.74 (m, 8H), 2.52–2.58 (m, 2H), 2.66 (t, J=6.95 Hz, 2H), 2.79 (p, J=7.96 Hz, 1H), 6.85 (t, J=8.84 Hz, 2H), 7.22 (ddd, J1=11.81 Hz, J2=5.24 Hz, J3=2.65 Hz, 2H).

Step 2

5-Cyclopentyl-9-(4-fluoro-phenyl)-5-hydroxy-3-oxo-non-8-ynoic acid methyl ester

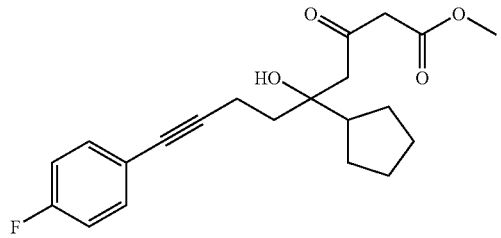

The desired product was prepared analogously to example F(1), Step 2, substituting 1-cyclopentyl-5-(4-fluoro-phenyl)-pent-4-yn-1-one (300 mg, 1.23 mmol) from Step 1 above in place of 1-cyclopentyl-5-(4-hydroxy-2,5-dimethyl-phenyl)-pent-4-yn-1-one. The crude product was used directly without purification.

MS (ESI): 359 (M–H).

Example F(6)

6-Cyclopentyl-6-(4-p-tolyl-but-3-ynyl)-dihydro-pyran-2,4-dione

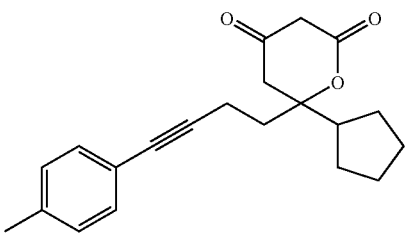

The desired product was prepared analogously to example F(1), substituting 5-cyclopentyl-5-hydroxy-3-oxo-9-p-tolyl-non-8-ynoic acid methyl ester (400 mg, 1.1 mmol) from Step 2 below in place of 5-cyclopentyl-5-hydroxy-9-(4-hydroxy-2,5-dimethyl-phenyl)-3-oxo-non-8-ynoic acid methyl ester. Yield: 180 mg, 50%.

MS (ESI): 323 (M–H).

Step 1

1-Cyclopentyl-5-p-tolyl-pent-4-yn-1-one

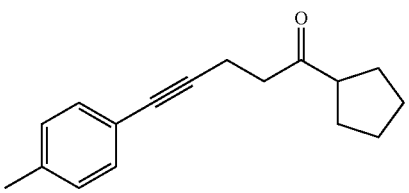

The desired product was prepared analogously to example F(1), Step 1, substituting 4-iodotoluene (0.727 g, 3.3 mmol) in place of 4-iodo-2,5-dimethyl-phenol. Yield: 0.412 g, 52%.

$^1$H NMR (CDCl$_3$) δ: 1.49–1.79 (m, 8H), 2.26 (s, 3H), 2.57–2.61 (m, 2H), 2.69–2.73 (m, 2H), 2.84 (p, J=8.08 Hz, 1H), 7.01 (d, J=7.83 Hz, 2H), 7.19 (d, J=8.34 Hz, 2H).

Step 2

5-Cyclopentyl-5-hydroxy-3-oxo-9-p-tolyl-non-8-ynoic acid methyl ester

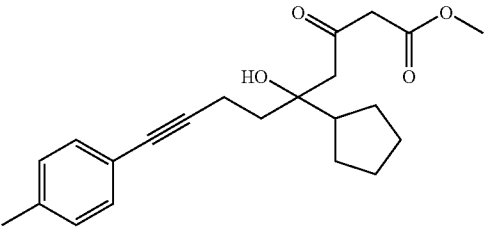

The desired product was prepared analogously to example F(1), Step 2, above substituting 1-cyclopentyl-5-p-tolyl-pent-4-yn-1-one (300 mg, 1.23 mmol) from Step 1 above in place of 1-cyclopentyl-5-(4-hydroxy-2,5-dimethyl-phenyl)-pent-4-yn-1-one. The crude product was used directly without purification.

MS (ESI): 355 (M–H).

Example F(7)

6-Cyclopentyl-4-hydroxy-6-[4-(3-hydroxy-phenyl)-but-3-ynyl]-3-(thiazol-2-ylsulfanyl)-5,6-dihydro-pyran-2-one

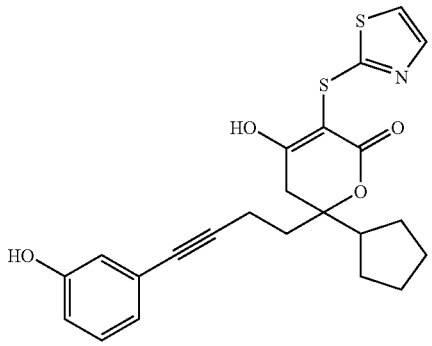

To a solution of 3-chloro-6-cyclopentyl-6-[4-(3-hydroxy-phenyl)-but-3-ynyl]-dihydro-pyran-2,4-dione (216 mg, 0.6 mmol) from Step 5 below and 2-mercaptothiazole (141 mg, 1.2 mmol) in DMF (6 mL) was added triethylamine (0.15 mL, 1.2 mmol). The reaction was stirred at 50° C. for 2.5 hours and then quenched with 10 mL of saturated ammonium chloride. The mixture was further acidified to a pH of 1–2 with 1 N HCl. To this mixture was added 10 mL CH$_2$Cl$_2$ and the layers were separated. The aqueous was extracted with 2×10 mL CH$_2$Cl$_2$, and the organic layers were combined. After drying the organic layer over MgSO$_4$, the solids were filtered away and the liquid was concentrated to an oil. The oil was chromatographed on silica to yield the desired product (28 mg, 11% yield).

$^1$H NMR (CDCl$_3$) δ: 1.09–1.58 (m, 8H), 1.93–2.05 (m, 3H), 2.58–2.82 (m, 4H), 6.59 (d, J=6.82 Hz, 2H), 6.65 (d, J=7.58 Hz, 1H), 6.96–7.00 (m, 1H), 7.32 (d, J=3.28 Hz, 1H), 7.46 (d, J=3.28 Hz, 1H). MS (ESI): 440 (M−H).

Step 1

Pent-4-ynethioic acid S-pyridin-2-yl ester

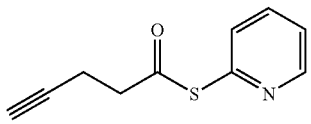

To a solution of 4-pentynoic acid (9.27 g, 94.5 mmol) dissolved in CH$_2$Cl$_2$ (125 mL) was added triphenylphosphine (32.2 g, 123 mmol) and 2,2'-dithiodipyridine (26 g, 118 mmol) and stirred at room temperature for 2 hours. The reaction was concentrated by rotary evaporation, and then chromatographed to yield the desired product (17.9 g, 99% yield).
MS (ESI): 192 (M+H).

Step 2

1-cyclopentyl-pent-4-yn-1-one

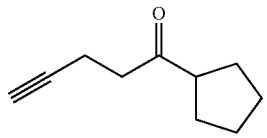

To a solution of pent-4-ynethioic acid S-pyridin-2-yl ester (17.9 g, 94 mmol), dissolved in THF (900 mL) cooled to −78° C. was added cyclopentylmagnesium bromide (2.0 M, 94 mL, 188.5 mmol). The reaction was stirred for 15 minutes, and then warmed to −50° C. The reaction was poured into 500 mL 1 N HCl and the layers were separated. The aqueous layer was extracted with 2×200 mL diethyl ether and the organic layers were combined. The organics were then washed with 300 mL of 1 N NaOH. The organic layer was dried over Mg SO$_4$, and the solids were removed by filtration. The solvent was removed by rotary evaporation to give the desired compound (14.0 g, 99% yield).

$^1$H NMR (CDCl$_3$) δ: 1.54–1.87 (m, 8H), 1.94 (t, J=2.65 Hz, 1H), 2.45 (dt, J1=7.33 Hz, J2=2.78 Hz, 2H), 2.71 (t, J=7.58 Hz, 2H), 2.87 (p, J=7.96 Hz, 1H).

Step 3

2-Chloro-5-cyclopentyl-5-hydroxy-3-oxo-non-8-ynoic acid methyl ester

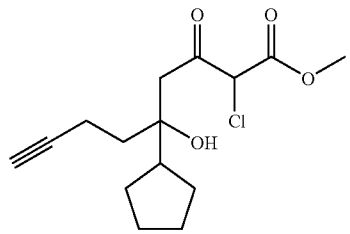

A slurry of NaH (3.2 g, 60% suspension in mineral oil, 80 mmol) in dry THF (250 mL) was cooled to −40° C. Methyl-2-chloroacetoacetate (9.74 mL, 80 mmol) was added slowly. The reaction was stirred until all gas evolution had ceased, and then butyl lithium (2.5 M, 32 mL, 80 mmol) was added. The reaction was stirred for 10 minutes, and then 1-cyclopentyl-pent-4-yn-1-one (4.0 g, 27 mmol) from Step 2 above, was added as a solution in 20 mL THF. The reaction was stirred 1 hour, and then warmed to room temperature. The reaction was quenched with 1 N HCl (200 mL) and the layers were separated. The aqueous layer was extracted with CH$_2$Cl$_2$ and the organic layers were combined. The organic layer was washed with water, and then concentrated by rotary evaporation. The crude product was purified by chromatography to yield the pure product (6.345 g, 78% yield).
MS (ESI): 298 (M−H), 300 (M+2−H).

Step 4

6-But-3-ynyl-3-chloro-6-cyclopentyl-dihydro-pyran-2,4-dione

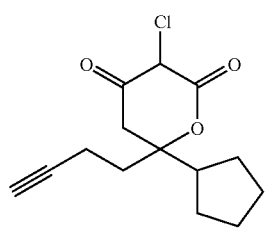

A slurry of 2-chloro-5-cyclopentyl-5-hydroxy-3-oxo-non-8-ynoic acid methyl ester (6.0 g, 20 mmol) from Step 3 above and K$_2$CO$_3$ (11 g, 80 mmol) in methanol (100 mL) was stirred at 50° C. for 1.5 hours. The reaction was concentrated by rotary evaporation, and then re-dissolved in ethyl acetate. The solution was washed with water, and then saturated Na$_2$CO$_3$. The organic layer was dried over sodium

Step 5

3-Chloro-6-cyclopentyl-6-[4-(3-hydroxy-phenyl)-but-3-ynyl]-dihydro-pyran-2,4-dione

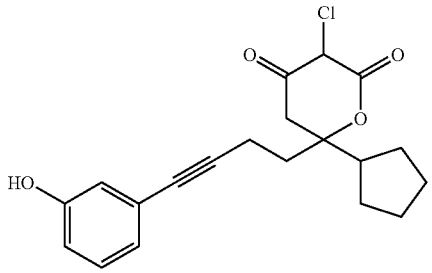

A solution of 6-but-3-ynyl-3-chloro-6-cyclopentyl-dihydro-pyran-2,4-dione (200 mg, 0.66 mmol) from Step 4 above, 3-iodophenol (145 mg, 0.66 mmol), bis(triphenylphosphine)palladium (II) dichloride (18 mg, 0.026 mmol), and copper (I) iodide (10 mg, 0.052 mmol) in DMF (0.66 mL) and diisopropylamine (0.66 mL) was sonicated for 1 minute and then heated to 90° C. for 20 minutes. The reaction was cooled to room temperature, and then diluted with 10 mL CH$_2$Cl$_2$. The reaction was then neutralized to a pH of 4 with 6 N HCl and the layers were separated. The aqueous layer was extracted with 3×10 mL CH$_2$Cl$_2$ and the organic layers were combined, and then dried over sodium sulfate. After filtering the solids, the organic layer was concentrated to a dark oil, which was used without further purification.

MS (ESI): 359 (M−H), 361 (M+2−H).

Example G(1)

6-[2-(3-chloro-4-methoxyphenyl)ethyl]-6-cyclopentyl-4-(pyridin-3-ylmethoxy)-5,6-dihydro-2H-pyran-2-one

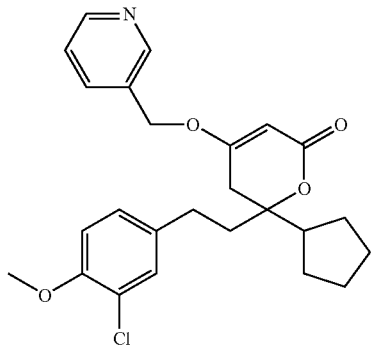

The title compound was prepared analogously to Example B(78), where 3-(chloromethyl)pyridine hydrochloride was substituted in place of benzyl bromide in that example.

$^1$H NMR (CDCl$_3$): δ 1.41–1.70 (bm, 8H), 2.02 (m, 3H), 2.44 (m, 2H), 2.63 (m, 2H), 3.87 (s, 3H), 4.96 (s, 2H), 5.30 (s, 1H), 6.83 (d, J=8.64 Hz, 1H), 7.02 (d, J=8.64 Hz, 1H), 7.17 (s, 1H), 7.36 (t, J=4.80 Hz, 1H), 7.72 (d, J=7.68 Hz, 1H), 8.65 (s, 2H).

Example G(2)

6-[2-(3-Chloro-4-methoxy-phenyl)-ethyl]-6-cyclopentyl-4-(pyridin-2-ylmethoxy)-5,6-dihydro-pyran-2-one

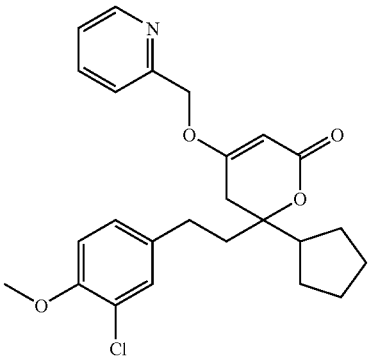

The target compound was isolated out of the same reaction that was used for Example B(81).

$^1$H NMR (CDCl$_3$) ?: 1.57–1.80 (m, 8H), 1.89–20.4 (m, 2H), 2.39–2.50 (m, 2H), 2.60–2.66 (m, 2H), 2.74–2.80 (d, J=17.27 Hz, 1H), 3.87 (s, 3H), 5.28 (s, 1H), 6.84 (d, J=8.32 Hz, 1H), 6.99–7.03 (m, 1H), 7.24–7.30 (m, 1H), 7.38 (d, J=8.00 Hz, 1H), 7.74 (tt, J1=7.26 Hz, J2=7.26 Hz, J3=1.76 Hz, 1H), 8.61 (d, J=3.84 Hz, 1H).

Example G(3): 6-[2-(3-Chloro-4-methoxy-phenyl)-ethyl]-6-cyclopentyl-4-methoxy-5,6-dihydro-pyran-2-one

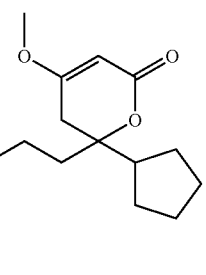

To a solution of 6-[2-(3-Chloro-4-methoxy-phenyl)-ethyl]-6-cyclopentyl-dihydro-pyran-2,4-dione (60 mg, 0.17 mmol) from Example B(87), dissolved in DMF (1.5 mL), were added DBU (0.028 mL, 0.188 mmol) and iodomethane (0.011 mL, 0.17 mmol). The reaction was stirred at room temperature overnight, and then was quenched with water. The reaction was extracted with EtOAc, and the organic layers were combined. After washing with saturated NaCl, the organic layer was dried over Na$_2$SO$_4$. The solids were removed by filtration, and the liquid was concentrated by rotary evaporation. Purification by preparatory HPLC gave the desired product (8.2 mg, 13% yield).

$^1$H NMR (CDCl$_3$) δ: 1.47–1.69 (m, 8H), 1.89–1.95 (m, 2H), 2.25–2.35 (m, 2H), 2.52–2.63 (m, 3H), 3.67 (s, 3H), 3.80 (s, 3H), 6.77 (d, J=8.32 Hz, 1H), 6.94 (dd, J1=8.32 Hz, J2=2.24 Hz, 1H), 7.09 (d, J=1.92 Hz, 1H).

Example H(1)

N-[2-(2-Cyclopentyl-4,6-dioxo-tetrahydro-pyran-2-yl)-ethyl]-3-furan-2-yl-propionamide

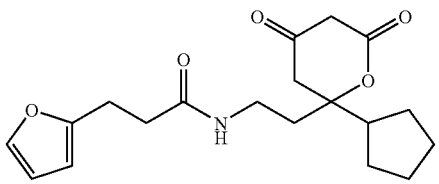

A solution of 6-(2-Amino-ethyl)-6-cyclopentyl-dihydro-pyran-2,4-dione (90 mg, 0.4 mmol) from Step 5 below, TEA (0.22 mL, 1.6 mmol), 3-furan-2-yl-propionic acid (67 mg, 0.48 mmol) and HATU (182 mg, 0.48 mmol) in DMF (2 mL) was stirred at room temperature overnight. The reaction was purified directly by preparatory HPLC to yield the desired product (26 mg, 19% yield).

$^1$H NMR (CDCl$_3$) δ: 1.27–3.47 (m, 21H), 6.94 (s, 1H), 6.19 (s, 1H), 7.22 (s, 1H). MS (ESI): 346 (M–H).

Step 1

(3-Chloro-1-cyclopentyl-propan-1-one

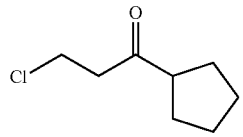

A solution of cyclopentanecarbonyl chloride (10 g, 75 mmol) and AlCl$_3$ (11.1 g, 83 mmol) in CH$_2$Cl$_2$ (100 mL) was cooled to −10° C. A solution of vinyltrimethylsilane (12 mL, 75 mmol) in CH$_2$Cl$_2$ (50 mL) was added drop wise over 30 minutes. The reaction was stirred for 20 additional minutes, and then poured over 200 g of ice. The layers were separated, and the aqueous layer was extracted with CH$_2$Cl$_2$. The organic layers were combined and washed with saturated NaHCO$_3$. The organic was then dried over Na$_2$SO$_4$, the solids were filtered away, and the product was purified by distillation (7.17 g, 60%).

$^1$H NMR (CDCl$_3$) δ: 1.43–1.70 (m, 8H), 2.69–2.80 (m, 3H), 3.61 (t, J=6.57 Hz, 2H).

Step 2

(3-Cyclopentyl-3-oxo-propyl)-carbamic acid tert-butyl ester

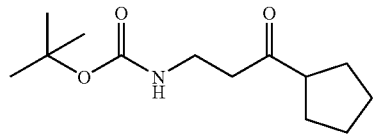

To a solution of 3-chloro-1-cyclopentyl-propan-1-one (2.913 g, 18.1 mmol) from Step 1 above in DMF (40 mL) was added sodium azide (1.77 g, 27.2 mmol). The reaction was heated to 70° C. for 3 hours. The reaction was cooled to room temperature, and then diluted with 100 mL of ethyl acetate and 100 mL of water. The layers were separated, and the aqueous was extracted with 2×50 mL of ethyl acetate. The organic layer was then washed with 2×50 mL of water. The organic layer was dried over sodium sulfate, filtered, and concentrated to an oil. The oil was then dissolved in ethanol (75 mL) and TFA was added (3 mL). To this solution was added 10% Pd/C (300 mg). The slurry was stirred under a hydrogen atmosphere for 2 hours. The solids were removed by filtration, and the organic was concentrated by rotary evaporation to a black oil. The black oil was dissolved in THF (100 mL) and TEA (7.5 mL) and di-tert-butyl pyrocarbonate (1 M in THF, 40 mL, 40 mmol) were added. The reaction was stirred at room temperature for 18 hours, and then concentrated by rotary evaporation. The crude oil was purified by flash chromatography to yield the product (1.677 g, 38%).

$^1$H NMR (CDCl$_3$) δ: 1.43 (s, 9H), 1.56–1.84 (m, 8H), 2.68 (t, J=5.65 Hz, 2H), 2.85 (p, J=5.65 Hz, 1H), 3.36 (q, J=6.03, 2H).

Step 3

7-tert-Butoxycarbonylamino-5-cyclopentyl-5-hydroxy-3-oxo-heptanoic acid methyl ester

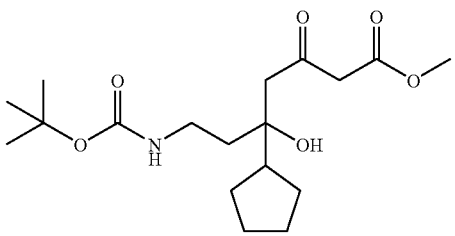

The desired product was prepared analogously to example F(1), Step 2 replacing 1-cyclopentyl-5-(4-hydroxy-2,5-dimethyl-phenyl)-pent-4-yn-1-one, from Step 2 above with (3-cyclopentyl-3-oxo-propyl)-carbamic acid tert-butyl ester (1,6 g, 6.6 mmol) described in Step 2 above. Yield: 1.36 g, 58%.

MS (ESI): 356 (M–H).

Step 4

[2-(2-Cyclopentyl-4,6-dioxo-tetrahydro-pyran-2-yl)-ethyl]-carbamic acid tert-butyl ester

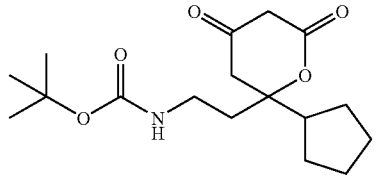

To 7-tert-butoxycarbonylamino-5-cyclopentyl-5-hydroxy-3-oxo-heptanoic acid methyl ester (1.36 g, 3.8 mmol) from Step 3 above dissolved in MeOH (50 mL) was added a NaOH solution (2.8 M, 2.7 mL, 7.6 mmol). The reaction was stirred at room temperature for 18 hours. The reaction was then quenched with acetic acid (0.44 mL, 7.7 mmol) and concentrated by rotary evaporation to an oil. The oil was dissolved in CH$_2$Cl$_2$ and washed with water. The organic layer was separated, and dried over Na$_2$SO$_4$. The solids were removed by filtration, and the liquid was concentrated to yield the product (1.061 g, 86% yield).

MS (ESI): 324 (M–H).

Step 5

6-(2-Amino-ethyl)-6-cyclopentyl-dihydro-pyran-2,4-dione

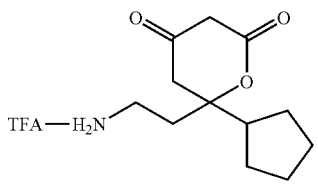

A solution of [2-(2-cyclopentyl-4,6-dioxo-tetrahydro-pyran-2-yl)-ethyl]-carbamic acid tert-butyl ester (1.0 g, 2.8 mmol) from Step 4 above in 10% TFA/CH$_2$Cl$_2$ was stirred at room temperature for 20 minutes. The reaction was concentrated by rotary evaporation and used as is without further purification.

MS (ESI): 224 (M–H).

Example H(2)

Furan-2-carboxylic acid [2-(2-cyclopentyl-4,6-dioxo-tetrahydro-pyran-2-yl)-ethyl]-amide

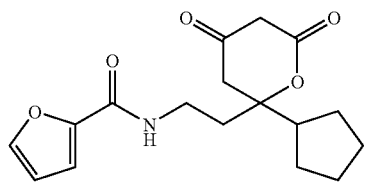

The desired product was prepared analogously to Example H(1), substituting 2-furanoic acid (54 mg, 0.48 mmol) in place of 3-furan-2-yl-propionic acid. Yield: 28 mg, 22%.

$^1$H NMR (CDCl$_3$) δ: 1.46–3.29 (m, 21H), 6.62 (s, 1H), 7.20 (s, 1H), 7.58 (s, 1H). MS (ESI): 318 (M–H).

Example H(3)

} N-[3-(2-Cyclopentyl-4,6-dioxo-tetrahydro-pyran-2-yl)-propyl]-3-furan-2-yl-propionamide

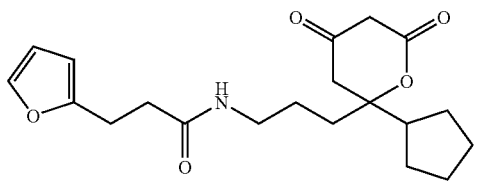

The desired product was prepared analogously to example H(1) substituting 6-(3-Amino-propyl)-6-cyclopentyl-dihydro-pyran-2,4-dione (62 mg, 0.26 mmol) in place of 36-(2-Amino-ethyl)-6-cyclopentyl-dihydro-pyran-2,4-dione. Yield: 12 mg, 13%.

$^1$H NMR (CDCl$_3$) δ: 1.10–1.47 (m, 8H), 2.09–2.39 (m, 8H), 2.55–2.66 (m, 3H), 2.74–2.94 (m, 4H), 5.68 (s, 1H), 5.93 (s, 1H), 6.96 (s, 1H). MS (ESI): 360 (M–H).

Example H(4)

N-{2-[2-Cyclopentyl-5-(5,7-dimethyl-[1,2,4]triazolo[1,5-a]pyrimidin-2-ylsulfanyl)-4-hydroxy-6-oxo-3,6-dihydro-2H-pyran-2-yl]-ethyl}-3-furan-2-yl-propionamide

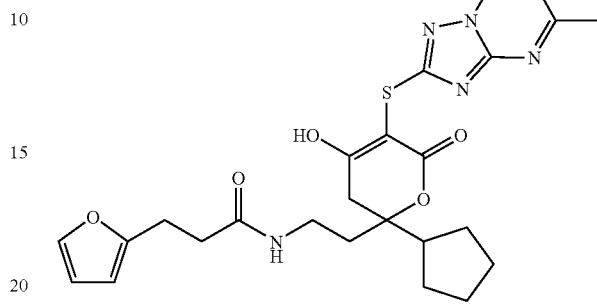

The desired product was prepared analogously to example F(7), substituting N-[2-(5-chloro-2-cyclopentyl-4,6-dioxo-tetrahydro-pyran-2-yl)-ethyl]-3-furan-2-yl-propionamide from Step 3 below in place of 3-chloro-6-cyclopentyl-6-[4-(3-hydroxy-phenyl)-but-3-ynyl]-dihydro-pyran-2,4-dione and 5,7-dimethyl-[1,2,4]triazolo[1,5-a]pyrimidine-2-thiol in place of 2-mercaptothiazole. Yield: 11 mg, 8%. MS (ESI): 524 (M–H).

Step 1

3-Amino-1-cyclopentyl-propan-1-one

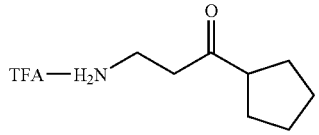

The desired product was prepared analogously to example H(1), Step 5, substituting (3-Cyclopentyl-3-oxo-propyl)-carbamic acid tert-butyl ester (described in Step 2 of example H(1)) in place of [2-(2-cyclopentyl-4,6-dioxo-tetrahydro-pyran-2-yl)-ethyl]-carbamic acid tert-butyl ester.

MS (ESI): 142 (M+H).

Step 2

N-(3-Cyclopentyl-3-oxo-propyl)-3-furan-2-yl-propionamide

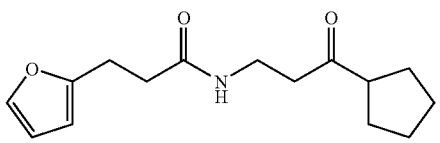

The desired product was prepared analogously to example H(1), substituting 3-amino-1-cyclopentyl-propan-1-one (0.874 g, 6.2 mmol) from Step 1 above in place of 6-(2-Amino-ethyl)-6-cyclopentyl-dihydro-pyran-2,4-dione. Yield: 0.901 g, 55%.

¹H NMR (CDCl₃) δ: 1.33–1.60 (m, 8H), 2.24 (t, J=7.58 Hz, 2H), 2.42–2.48 (m, 3H), 2.73 (t, J=7.45 Hz, 2H), 3.24 (q, J=6.06 Hz, 2H), 5.78 (d, J=3.79 Hz, 1H), 6.03 (d, J=6.03 Hz, 1H), 7.06 (d, J=2.53 Hz, 1H).

Step 3

N-[2-(5-Chloro-2-cyclopentyl-4,6-dioxo-tetrahydro-pyran-2-yl)-ethyl]-3-furan-2-yl-propionamide

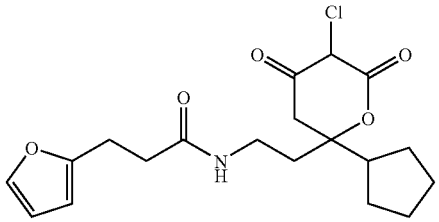

The desired product was prepared analogously to example F(1), Step 2, substituting N-(3-cyclopentyl-3-oxo-propyl)-3-furan-2-yl-propionamide (300 mg, 1.1 mmol) from Step 2 above in place of 1-cyclopentyl-5-(4-hydroxy-2,5-dimethyl-phenyl)-pent-4-yn-1-one and methyl 2-chloroacetoacetate (0.7 mL, 5.7 mmol) in place of methyl acetoacetate. Yield: 103 mg, 14%.

MS (ESI): 380 (M−H), 382 (M+2−H).

Example H(5)

3-Cyclopentyl-5-(3-furan-2-yl-propionylamino)-3-hydroxy-pentanoic acid

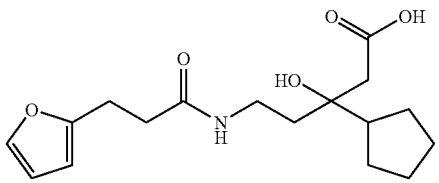

A solution of NaOH (0.3 M, 1.6 mL, 0.49 mmol) was added to 3-cyclopentyl-5-(3-furan-2-yl-propionylamino)-3-hydroxy-pentanoic acid ethyl ester (86 mg, 0.245 mmol) from Step 1 below and stirred at room temperature until complete by HPLC. The reaction was diluted with 10 mL CH₂Cl₂, and washed with 10 mL saturated NH₄Cl. The aqueous layer was extracted with 2×10 mL CH₂Cl₂, and the organic layers were combined. After concentrating by rotary evaporation, the residue was purified by flash chromatography to give the desired compound (29 mg, 37% yield).

¹H NMR (CDCl₃) δ: 1.39–1.75 (m, 8H), 2.00–2.09 (m, 2H), 2.39–2.52 (m, 5H), 2.90 (t, J=7.45 Hz, 2H), 3.29–3.40 (m, 2H), 5.96 (s, 1H), 6.2 (s, 1H), 6.31 (br, 1H), 7.23 (s, 1H). MS (ESI): 322 (M−H).

Step 1

3-Cyclopentyl-5-(3-furan-2-yl-propionylamino)-3-hydroxy-pentanoic acid ethyl ester

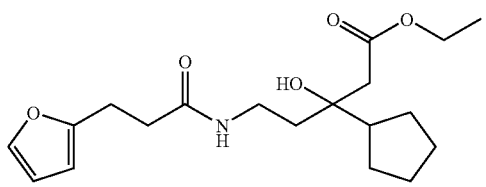

To a solution of LDA (1.0 M, 1.1 mL, 1.1 mmol) cooled to −78° C. was added EtOAc (0.1 mL, 1.1 mmol). After stirring for 30 minutes, a solution of N-(3-cyclopentyl-3-oxo-propyl)-3-furan-2-yl-propionamide (100 mg, 0.38 mmol; described in Step 2 of example H(4)) dissolved in 3 mL THF was added. The reaction was stirred for 2 hours and then allowed to warm to −40° C. The reaction was quenched with 10 mL saturated NH₄Cl, and the layers were separated. The aqueous layer was extracted with 3×10 mL CH₂Cl₂, and the organic layers were combined. After concentrating the organic layers by rotary evaporation, the product was purified by flash chromatography (86 mg, 64% yield). MS (ESI): 350 (M−H).

Example I(1)

6-cyclopentyl-6-[(pyrimidin-2-ylthio)methyl]dihydro-2H-pyran-2,4(3H)-dion

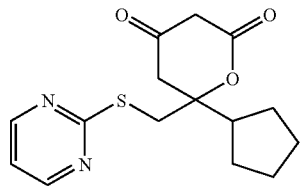

The title compound was prepared analogously to Example A(6), where pyrimidine-2-thiol was substituted in place of p-methoxythiophenol in Step 2 of that example.

¹H NMR (CDCl₃): δ 1.6–2.0 (brm, 8H), 2.48 (m, 1H), 2.66 (s, 1H), 2.86 (s, 1H), 3.66 (s, 1H), 3.43 (s, 2H), 3.70–3.74 (m, 2H), 3.78 (d, J=7.54 Hz, 1H), 7.03 (t, J=4.90 Hz, 1H), 8.50, (d, J=4.71 Hz, 2H). Anal. Calcd. For C₁₅H₁₈N₂O₃S: C, 58.80; H, 5.92; N, 9.14. Found: C, 58.95; H, 6.04; N, 9.20.

Example I(2)

6-cyclopentyl-6-{[(2-furylmethyl)thio]methyl}dihydro-2H-pyran-2,4(3H)-dione

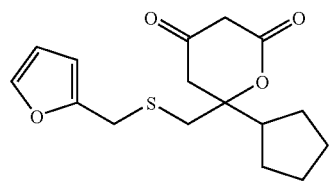

The title compound was prepared analogously to Example A(6), where 2-furylmethanethiol was substituted in place of p-methoxythiophenol in Step 2 of that example.

¹H NMR (CDCl₃): δ 1.31–175 (brm, 8H), 2.25 (m, 1H), 2.68 (m, 2H), 2.86–2.88 (m, 2H), 3.72 (s, 1H), 3.75 (s, 1H), 6.22 (d, J=1.88 Hz, 1H), 6.32 (t, J=1.88 Hz, 1H), 7.38, (s, 1H). Anal. Calcd. For C₁₆H₂₀O₄S: C, 62.31; H, 6.54. Found: C, 62.54; H, 6.37.

Example I(3)

6-cyclopentyl-6-{[(6-ethoxy-1,3-benzothiazol-2-yl)thio]methyl}dihydro-2H-pyran-2,4(3H)-dione

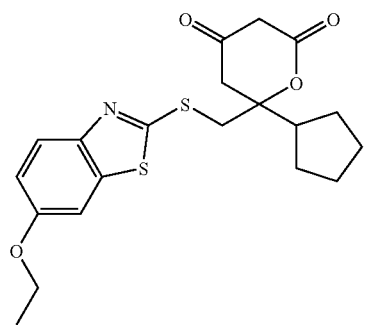

The title compound was prepared analogously to Example A(6), where 6-ethoxy-1,3-benzothiazole-2-thiol was substituted in place of p-methoxythiophenol in Step 2 of that example. LCMS: 404, M-ve on APCI. Rf: 0.3; 98:2, DCM: MeOH, developed with anisaldehyde. Anal. Calcd. For $C_{20}H_{23}S_2O_4N$: C, 59.24; H, 5.72; N, 3.45. Found: C, 56.50; H, 6.04; N, 3.63.

Example I(4)

6-cyclopentyl-6{[(4-isopropylphenyl)thio]methyl}dihydro-2H-pyran-2,4(3H)-dione

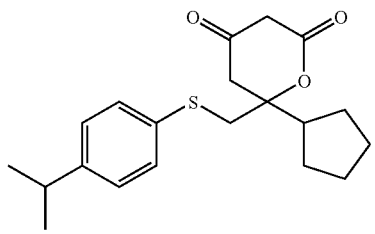

The title compound was prepared analogously to Example A(6), where 4-isopropylbenzenethiol was substituted in place of p-methoxythiophenol in Step 2 of that example.

$^1$H NMR (CDCl$_3$): δ 1.00 (m, 1H), 1.23 (d, J=6.97 Hz), 6H), 1.44–1.70 (brm, 8H), 1.94 (m, 1H), 2.67 (m, 2H), 2.77 (s, 2H), 3.42 (s, 2H), 7.07, (d, J=8.10 Hz, 2H), 7.15 (d, J=8.10 Hz, 2H). Anal. Calcd. For $C_{20}H_{26}O_3S$: C, 69.33; H, 7.56. Found: C, 69.55; H, 7.70.

General Scheme for Resolution of 6-(2-cyclopentyl-2-hydroxybut-3-ynyl)-2,2-dimethyl-4H-1,3-dioxin-4-one Precursors

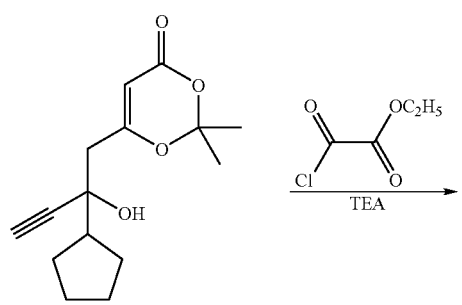

-continued

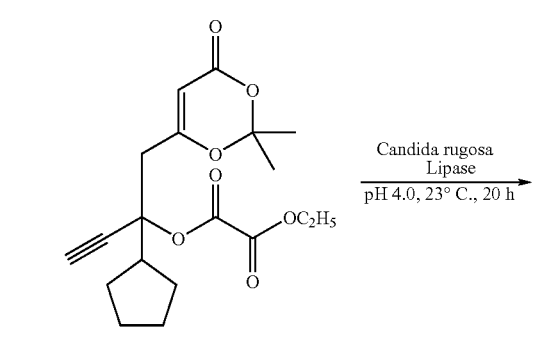

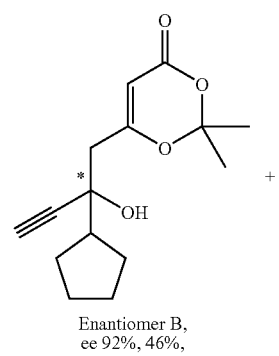

Enantiomer B,
ee 92%, 46%,

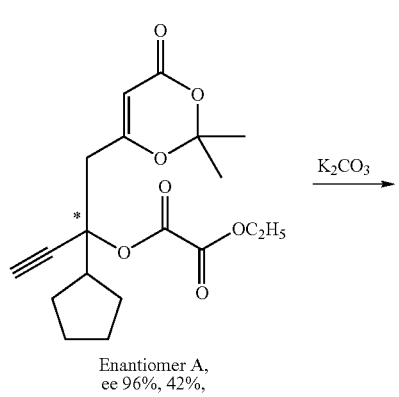

Enantiomer A,
ee 96%, 42%,

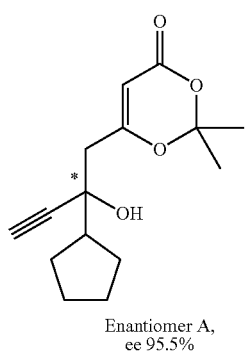

Enantiomer A,
ee 95.5%

Enantiomers A and B of 6-(2-cyclopentyl-2-hydroxybut-3-ynyl)-2,2-dimethyl-4H-1,3-dioxin-4-one (Absolute Stereochemistry Not Known)

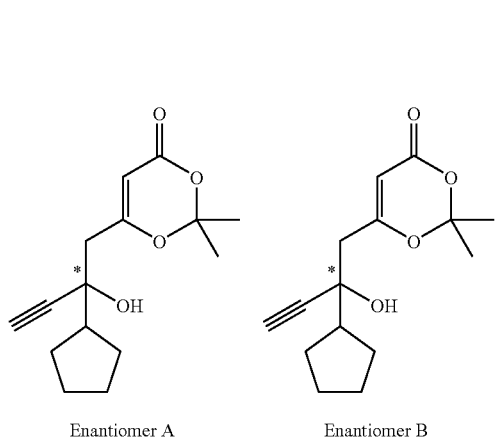

Enantiomer A          Enantiomer B

Step 1

1-cyclopentyl-1-[(2,2-dimethyl-4-oxo-4H-1,3-dioxin-6-yl)methyl]prop-2-ynyl ethyl oxalate

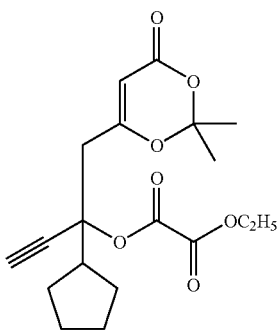

To a solution of racemic 6-(2-cyclopentyl-2-hydroxybut-3-ynyl)-2,2-dimethyl-4H-1,3-dioxin-4-one (10 g, 37.9 mmol) in $CH_2Cl_2$ (200 ml) was added triethylamine (3.0 eqv, 113.7 mmol) at 0° C. Then ethyl chlorooxoacetate (3.0 eqv, 113.7 mmol) in $CH_2Cl_2$ (10 ml) was added dropwise over a 30-minute period under argon. The solution was allowed to stir overnight at room temperature. After removal of solvent, the crude product was purified using a flash column (heptane: EtOAc, 3:1) to afford the desired oxalate (13.5 g, >95%). API-MS: [M+Na$^+$]: 387;

$^1$H NMR (CDCl$_3$, 300 MHz) δ: 5.27 (s, 1H), 4.33 (dq, J=2.5 and 7.5 Hz, 2H), 2.67 (s, 2H), 2.64 (m, 1H), 1.65 (s, 6H), 1.40–1.80 (m, 6H), 1.36 (dt, J=3.0 and 7.2 Hz, 3H). $^{13}$C NMR (CDCl$_3$, 75 MHz) δ: 171.47, 165.83, 163.62, 161.84, 107.31, 97.74, 83.33, 79.21, 77.58, 63.48, 46.65, 42.82, 28.62, 28.62, 28.44, 25.28, 14.54, 14.44, 12.89.

Step 2

Enantiomer B of 6-(2-cyclopentyl-2-hydroxybut-3-ynyl)-2,2-dimethyl-4H-1,3-dioxin-4-one

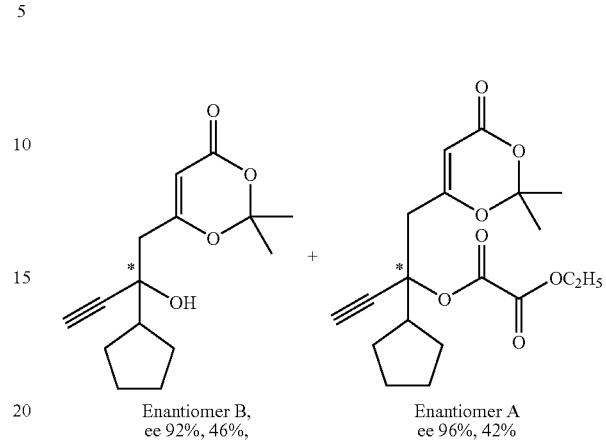

Enantiomer B,          Enantiomer A
ee 92%, 46%,           ee 96%, 42%

To a 250 ml three-necked flask equipped with a pH electrode was added 72 ml of phosphate buffer (pH 4.0, 0.5M) and *Candida rugosa* lipase (5 g, Amano A Y). The mixture was stirred vigorously and then the oxalate (6 g) in 18 ml of acetonitrile was added. The reaction mixture was allowed to stir at 23° C. and the pH was kept at 4.0 using a pH titrator. The reaction was monitored with HPLC and stopped after 50% conversion (<20 hrs). The mixture was extracted by MTBE (×3) and the combined organic layer was dried over MgSO4. After removal of the solvent, the crude product was separated carefully by silica-gel chromatography, using heptane/EtOAC (5:1, 2:1), which afforded 2.6 g of the oxalate (43% yield, 96% ee) and 2.0 g of product (enantiomer B: 46% yield, 92% ee).

$^1$H NMR (300 MHz, CDCl$_3$) δ: 1.45–1.80 (m, 8 H), 1,72 (s, 3 H), 1.74 (s, 3 H), 2.13–2.18 (m, 1 H), 2.49 (s, 1 H), 2.56 (s, 1 H), 2.58 (s, 2 H), 5.43 (s, 1 H).

Step 3

Enantiomer A of 6-(2-cyclopentyl-2-hydroxybut-3-ynyl)-2,2-dimethyl-4H-1,3-dioxin-4-one

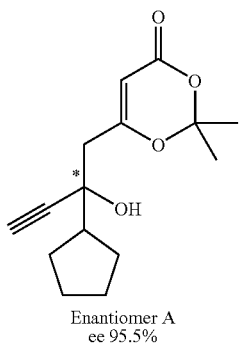

Enantiomer A
ee 95.5%

To the optically pure oxalate (2.5 g, 15.1 mmol) in 50 ml of MeOH was added $K_2CO_3$ (2.0 g). The mixture was stirred at 23° C. for 8 h. After complete conversion, the mixture was neutralized with 1N HCl at cold temperature. The aqueous solution was extracted with MTBE (×3) and the organic layer was washed with brine and dry over MgSO$_4$. After removal of MTBE, 1.75 g of the desired product (enantiomer A) was produced with 95.5% ee and 96% yield.

$^1$H NMR (300 MHz, CDCl$_3$) δ: 1.45–1.80 (m, 8 H), 1,72 (s, 3 H), 1.74 (s, 3 H), 2.13–2.18 (m, 1 H), 2.49 (s, 1 H), 2.56 (s, 1 H), 2.58 (s, 2 H), 5.43 (s, 1 H).

Example J(1)

6-cyclopentyl-6-[2-(3-fluoro-4-isopropoxyphenyl)ethyl]dihydro-2H-pyran-2,4(3H)-dione (Enantiomer A)

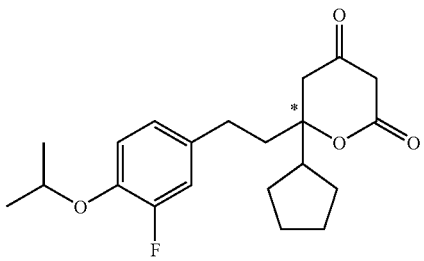

The title compound was prepared analogously to Example A(64), , where Enantiomer A (described above) of 6-(2-cyclopentyl-2-hydroxybut-3-ynyl)-2,2-dimethyl-4H-1,3-dioxin-4-one was substituted in place of the racemic material.

$^1$H NMR (300 MHz, CDCl$_3$) δ: ?1.34 (d, J=6.03 Hz, 6 H), 1.61–1.77 (m, 8 H), 1.89–1.97 (m, 2 H), 2.24–2.29 (m, 1 H), 2.61 (t, J=8.38 Hz, 2 H), 2.76 (s, 2 H), 3.43 (s, 2 H), 4.44–4.52 (m, 1 H), 6.79–6.92 (m, 3 H). HRMS calcd for C$_{21}$H$_{28}$O$_4$F (M+H$^+$): 363.1966. Found: 363.1980.

Example J(2)

6-cyclopentyl-6-[2-(3-fluoro-4-isopropoxyphenyl)ethyl]dihydro-2H-pyran-2,4(3 H)-dione (Enantiomer B)

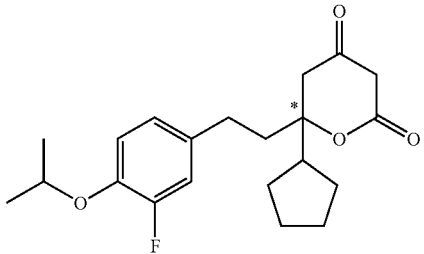

The title compound was prepared analogously to Example A(64), where Enantiomer B (described above) of 6-(2-cyclopentyl-2-hydroxybut-3-ynyl)-2,2-dimethyl-4H-1,3-dioxin-4-one was substituted in place of the racemic material.

$^1$H NMR (300 MHz, CDCl$_3$) δ: 1.34 (d, J=6.03 Hz, 6 H), 1.61–1.77 (m, 8 H), 1.89–1.97 (m, 2 H), 2.24–2.29 (m, 1 H), 2.61 (t, J=8.38 Hz, 2 H), 2.76 (s, 2 H), 3.43 (s, 2 H), 4.44–4.52 (m, 1 H), 6.79–6.92 (m, 3 H). ESI-MS calcd for C$_{21}$H$_{27}$O$_4$F: 362.2. Found (M+Na$^+$): 385.1.

Example J(3)

6-cyclopentyl-3-[(5,7-dimethyl[1,2,4]triazolo[1,5-a]pyrimidin-2-yl)methyl]-6-[2-(3-fluoro-4-isopropoxyphenyl)ethyl]-4-hydroxy-5,6-dihydro-2H-pyran-2-one (Enantiomer A)

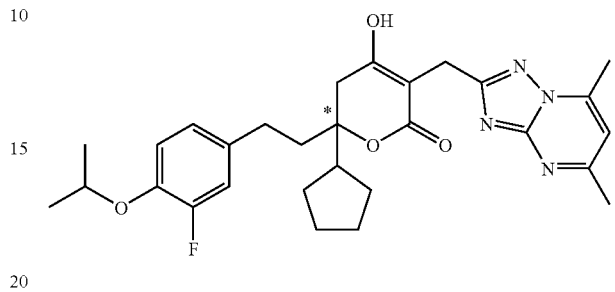

The title compound was prepared analogously to Example B(31), where Enantiomer A of 6-cyclopentyl-6-[2-(3-fluoro-4-isopropoxyphenyl)ethyl]dihydro-2H-pyran-2,4(3H)-dione was substituted in place of 6-[2-(3-chloro-4-isopropoxyphenyl)ethyl]-6-cyclopentyldihydro-2H-pyran-2,4(3H)-dione.

$^1$H NMR (300 MHz, CDCl$_3$) δ: ?1.32 (d, J=6.03 Hz, 6 H), 1.50–1.80 (m, 8 H), 1.95–2.01 (m, 2 H), 2.33–2.41 (m, 1 H), 2.56–2.62 (m, 3 H), 2.66 (s, 3 H), 2.71–2.73 (m, 1 H), 2.79 (s, 3 H), 4.09 (s, 2 H), 4.41–4.50 (m, 1 H), 6.78–6.88 (m, 4 H). HRMS calcd for C$_{29}$H$_{36}$N$_4$O$_4$F (M+H$^+$): 523.2715. Found: 523.2708.

Example J(4)

6-cyclopentyl-3-[(5,7-dimethyl[1,2,4]triazolo[1,5-a]pyrimidin-2-yl)methyl]-6-[2-(3-fluoro-4-isopropoxyphenyl)ethyl]-4-hydroxy-5,6-dihydro-2H-pyran-2-one (Enantiomer B)

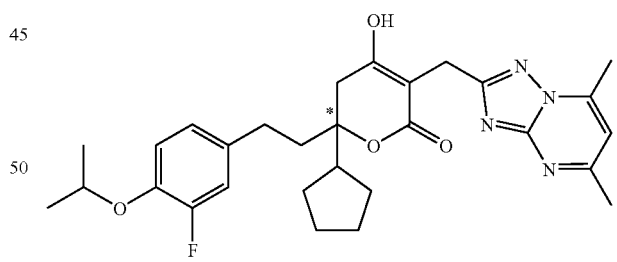

The title compound was prepared analogously to Example B(31), where Enantiomer B of 6-cyclopentyl-6-[2-(3-fluoro-4-isopropoxyphenyl)ethyl]dihydro-2H-pyran-2,4(3H)-dione was substituted in place of 6-[2-(3-chloro-4-isopropoxyphenyl)ethyl]-6-cyclopentyldihydro-2H-pyran-2,4(3H)-dione.

$^1$H NMR (300 MHz, CDCl$_3$) δ: ?1.32 (d, J=6.03 Hz, 6 H), 1.50–1.80 (m, 8 H), 1.95–2.01 (m, 2 H), 2.33–2.41 (m, 1 H), 2.56–2.62 (m, 3 H), 2.66 (s, 3 H), 2.71–2.73 (m, 1 H), 2.79 (s, 3 H), 4.09 (s, 2 H), 4.41–4.50 (m, 1 H), 6.78–6.88 (m, 4 H). HRMS calcd for C$_{29}$H$_{36}$N$_4$O$_4$F (M+H$^+$): 523.2715. Found: 523.2699.

Example J(5)

6-Cyclopentyl-6-[2-(3-ethyl-phenyl)-ethyl]-dihydro-pyran-2,4-dione (Enantiomer A)

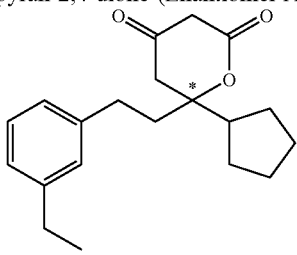

The title compound was prepared analogously to Example A(64), where 1-Bromo-3-ethyl-benzene was substituted in place of 4-bromo-2-fluoro-1-isopropylbenzene in that example, and Enantiomer A of 6-(2-cyclopentyl-2-hydroxy-but-3-ynyl)-2,2-dimethyl-4H-1,3-dioxin-4-one was used in place of the racemic alkyne.

$^1$H NMR (CDCl$_3$): δ 1.23 (t, 3H, J=7.6 Hz), 1.50–1.83 (br m, 8H), 1.91–2.05 (m, 2H), 2.29 (m, 1H), 2.59–2.68 (m, 4H) 2.27, (s, 2H), 3.42 (s, 2H), 6.96 (m, 2H), 7.06 (d, 1H, J=7.01 Hz), 7.21 (t, 1H, J=8.0 Hz). ESIMS: MH$^+$315.20, MH$^-$313.20.

Example J(6)

6-Cyclopentyl-6-[2-(3-ethyl-phenyl)-ethyl]-dihydro-pyran-2,4-dione (Enantiomer B)

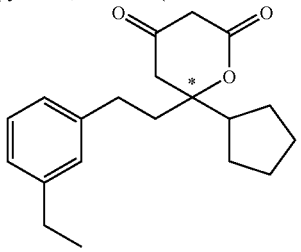

The title compound was prepared analogously to Example A(64), where 1-Bromo-3-ethyl-benzene was substituted in place of 4-bromo-2-fluoro-1-isopropylbenzene of that example and Enantiomer B of 6-(2-cyclopentyl-2-hydroxy-but-3-ynyl)-2,2-dimethyl-4H-1,3-dioxin-4-one was used in place of the racemic alkyne.

$^1$H NMR (CDCl$_3$): δ 1.23 (t, 3H, J=7.6 Hz), 1.50–1.83 (br m, 8H), 1.91–2.05 (m, 2H), 2.29 (m, 1H), 2.59–2.68 (m, 4H) 2.27, (s, 2H), 3.42 (s, 2H), 6.96 (m, 2H), 7.06 (d, 1H, J=7.01 Hz), 7.21 (t, 1H, J=8.0 Hz). ESIMS: MH$^+$315.20, MH$^-$313.20.

Example J(7)

6-Cyclopentyl-3-(5,7-dimethyl-[1,2,4]triazolo[1,5-a]pyrimidin-2-ylmethyl)-6-[2-(3-ethyl-phenyl)-ethyl]-4-hydroxy-5,6-dihydro-pyran-2-one (Enantiomer A)

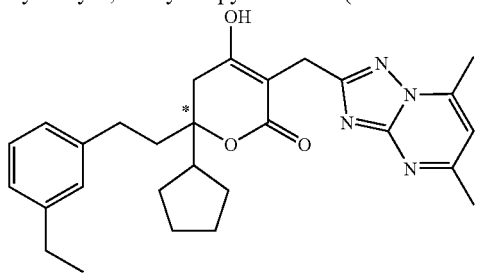

The title compound was prepared by coupling 6-Cyclopentyl-6-[2-(3-ethyl-phenyl)-ethyl]-dihydro-pyran-2,4-dione (Enantiomer A) (Example J(6)) to 5,7-Dimethyl-[1,2,4]triazolo[1,5-?]pyrimidine-2-carbaldehyde using the Me$_2$NHBH$_3$ method described in the synthesis of Example B(31).

$^1$H NMR (DMSO-d$_6$): δ 1.18 (t, 3H, J=7.6 Hz), 1.46–1.76 (br m, 8H), 2.18 (m, 2H), 2.48–2.67 (m, 12H), 2.85 (d, 1H, J=17.4 Hz), 3.78 (d, 1H, J=16.3 Hz), 3.91 (d, 1H, J=16.3 Hz), 7.08 (m, 4H), 7.22 (t, 1H, J=7.6 Hz), 10.91 (s, 1H). C$_{28}$H$_{34}$N$_4$O$_3$ (M+H)$^+$ 475.20.

Example J(8)

6-Cyclopentyl-3-(5,7-dimethyl-[1,2,4]triazolo[1,5-a]pyrimidin-2-ylmethyl)-6-[2-(3-ethyl-phenyl)-ethyl]-4-hydroxy-5,6-dihydro-pyran-2-one (Enantiomer B)

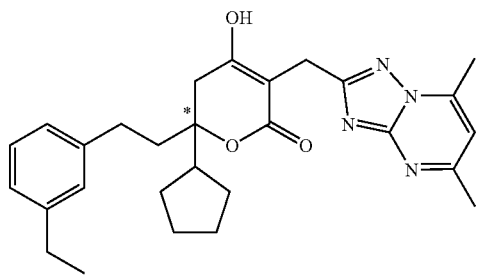

$^1$H NMR (DMSO-d$_6$): δ 1.18 (t, 3H, J=7.6 Hz), 1.46–1.76 (br m, 8H), 2.18 (m, 2H), 2.48–2.67 (m, 12H), 2.85 (d, 1H, J=17.4 Hz), 3.78 (d, 1H, J=16.3 Hz), 3.91 (d, 1H, J=16.3 Hz), 7.08 (m, 4H), 7.22 (t, 1H, J=7.6 Hz), 10.91 (s, 1H). C$_{28}$H$_{34}$N$_4$O$_3$ (M+H)$^+$ 475.20.

The title compound was prepared by coupling 6-Cyclopentyl-6-[2-(3-ethyl-phenyl)-ethyl]-dihydro-pyran-2,4-dione (Enantiomer B) (Example J(7)) to 5,7-Dimethyl-[1,2,4]triazolo[1,5-?]pyrimidine-2-carbaldehyde using the Me$_2$NHBH$_3$ method described in the synthesis of Example B(31).

The compounds of the present invention are potent inhibitors of Hepatitis C virus, in particular HCV replication, and even in more particular, HCV RNA-dependent RNA-polymerase.

The compounds are all adapted to therapeutic use as anti-HCV agents in mammals, particularly in humans.

The active compound may be applied as a sole therapy or may involve one or more other antiviral substances, for example those selected from, for example, HCV inhibitors such as interferon alphacon-1, natural interferon, interferon beta-1a, interferon omega, interferon gamma-1b, interleukin-10, BILN 2061 (serine protease), amantadine (Symmetrel), thymozine alpha-1, viramidine; HIV inhibitors such as nelfinavir, delavirdine, indinavir, nevirapine, ritonavir, saquinavir, and tenofovir. Such conjoint treatment may be achieved by way of the simultaneous, sequential or separate dosing of the individual components of the treatment. The in vitro activity of the compounds of formula 1 may be determined by the following procedure.

The compounds described herein were tested for activity with HCV polymerase. Recombinant HCV polymerase was tested for its ability to perform primer/template-directed transcription in assays that contained 30 mM tris-HCl pH 7.2, 10 mM MgCl$_2$, 20 mM NaCl, 1 mM Dithiothreitol (DTT), 0.05% Tween-20, 1% glycerol, 5 pmoles biotin-dG$_{12}$ (primer), 0.5 pmoles poly(rC)$_{300}$ (template), 1 μM GTP, 0.1–0.3 uCi α-$^{32}$P-GTP, and 2.5 pmoles (0.15 μg) HCV polymerase protein in a final volume of 75 μL. Reactions were initiated by addition of enzyme and incubated 30 minutes at 30° C. Reactions were stopped by addition of 33 mM EDTA, and polynucleotide products were collected by filtration through Diethylaminoethyl (DE) Filtermat papers (Wallac). Unincorporated triphosphate was removed by washing the filters with 5% dibasic sodium phosphate. The filters were counted in a Packard Tri-Lux Microbeta scintillation counter (Packard Bioscience, Meriden, Conn.). Compounds to be tested were added at various concentrations, e.g., 1 µm to 50 µm, from stocks in 10% DMSO-water (final DMSO is 1% in reaction).

$IC_{50}$ values were estimated from the primary cpm data (collected in triplicate) using the formula: cpm (I)=cpm (no inhibitor)(1−([I]/([I]+$IC_{50}$))). An $IC_{50}$ value represents the concentration (in µM) of a compound that provides 50% inhibition of polymerase-directed transcription in the above assay. A percent inhibition value is expressed for a compound where it was impractical to calculate an $IC_{50}$ value with available data. If the $IC_{50}$ estimated by the above equation was less than 200 nM, it was recalculated using the following equation, which takes into account the enzyme concentration (30 nM) in the assay: cpm(I)=cpm(no inhibitor)(1−((((I+$IC_{50}$+30e−9)−sqrt(((I+$IC_{50}$+30e−9)$^2$)−4×30e−9×I)))/((2) (30e−9))). Curve fitting was performed using the program KaleidaGraph (Synergy Software, Reading, Pa.).

Inhibition concentration ($IC_{50}$) data as determined for exemplary compounds of the invention are presented in Table 1 below.

TABLE 1

| Example ( ) | IC50 (µM) |
| --- | --- |
| Example A(01) | 38.3 |
| Example A(02) | 2.4 |
| Example A(03) | 4.3 |
| Example A(04) | 5.6 |
| Example A(05) | 5.1 |
| Example A(06) | 23.5 |
| Example A(07) | 13.4 |
| Example A(08) | 6 |
| Example A(09) | 5.5 |
| Example A(10) | 8.1 |
| Example A(11) | 16.7 |
| Example A(12) | 18.3 |
| Example A(13) | 63 |
| Example A(14) | 35% @ 50 uM |
| Example A(15) | 4.4 |
| Example A(16) | 14.4 |
| Example A(17) | 23 |
| Example A(18) | 3.1 |
| Example A(19) | 37% @ 50 uM |
| Example A(20) | 32 |
| Example A(21) | 12.3 |
| Example A(22) | 0.3 |
| Example A(23) | 1% @ 50 uM |
| Example A(24) | 29% @ 50 uM |
| Example A(25) | 73.9 |
| Example A(26) | 20% @ 50 uM |
| Example A(27) | 0.125 |
| Example A(28) | 3.9 |
| Example A(29) | 1.5 |
| Example A(30) | 0.84 |
| Example A(31) | 0.4 |
| Example A(32) | 5.2 |
| Example A(33) | 5 |
| Example A(34) | 10 |
| Example A(35) | 4.1 |
| Example A(36) | 8.4 |
| Example A(37) | 8.7 |
| Example A(38) | 12 |
| Example A(39) | 14% @ 50 uM |
| Example A(40) | 2 |
| Example A(41) | 13 |
| Example A(42) | 8 |
| Example A(43) | 20 |
| Example A(44) | 68.3 |
| Example A(45) | 30 |
| Example A(46) | 73 |
| Example A(47) | 7 |
| Example A(48) | 33.2 |
| Example A(49) | 9 |

TABLE 1-continued

| Example ( ) | IC50 (µM) |
| --- | --- |
| Example A(50) | 5.9 |
| Example A(51) | 3.9 |
| Example A(52) | 1.5 |
| Example A(53) | 3.3 |
| Example A(54) | 2.9 |
| Example A(55) | 11.2 |
| Example A(56) | 39 |
| Example A(57) | 6.3 |
| Example A(58) | 6.5 |
| Example A(59) | 3.2 |
| Example A(60) | 8.7 |
| Example A(61) | 40% @ 50 uM |
| Example A(62) | 8.3 |
| Example A(63) | 11 |
| Example A(64) | 4 |
| Example A(65) | 1.3 |
| Example A(66) | 3.6 |
| Example A(67) | 24% @ 20 uM |
| Example A(68) | 3.4 |
| Example A(69) | 9.9 |
| Example A(70) | 9.4 |
| Example A(71) | 1.9 |
| Example A(72) | 1.5 |
| Example A(73) | 3.3 |
| Example A(74) | 1.2 |
| Example A(75) | 7.1 |
| Example A(76) | 5.8 |
| Example A(77) | 24 |
| Example A(78) | 21 |
| Example A(79) | 1 |
| Example A(80) | 20 |
| Example A(81) | 0.14 |
| Example A(82) | 11% @ 20 uM |
| Example A(83) | 5.4 |
| Example A(84) | 6.8 |
| Example A(85) | 12.4 |
| Example A(86) | 0.4 |
| Example A(87) | 0.89 |
| Example A(88) | 2.3 |
| Example A(89) | 2.8 |
| Example A(90) | 0.77 |
| Example A(91) | 0.5 |
| Example A(92) | 1 |
| Example A(93) | 0.7 |
| Example A(94) | 4 |
| Example A(95) | 2.1 |
| Example A(96) | 3.2 |
| Example A(97) | 0.29 |
| Example A(98) | 0.01 |
| Example A(99) | 0.017 |
| Example A(100) | 0.088 |
| Example A(101) | 0.066 |
| Example A(102) | 0.005 |
| Example A(103) | 0.18 |
| Example A(104) | 0.008 |
| Example A(105) | NA |
| Example A(106) | NA |
| Example A(107) | 0.36 |
| Example A(108) | 0.003 |
| Example A(109) | 0.004 |
| Example A(110) | 0.001 |
| Example A(111) | 0.002 |
| Example A(112) | 0.006 |
| Example A(113) | 0.008 |
| Example A(114) | 0.01 |
| Example A(115) | 0.005 |
| Example A(116) | NA |
| Example A(117) | NA |
| Example A(118) | 3.2 |
| Example A(119) | 1.2 |
| Example A(120) | 13 |
| Example A(121) | 1.3 |
| Example A(122) | 31 |
| Example A(123) | 0.012 |
| Example A(124) | 0.35 |
| Example A(125) | 0.011 |
| Example A(126) | 0.009 |

TABLE 1-continued

| Example ( ) | IC50 (µM) |
|---|---|
| Example A(127) | 0.005 |
| Example A(128) | 0.49 |
| Example A(129) | 8.9 |
| Example A(130) | 1.3 |
| Example A(131) | 0.137 |
| Example A(132) | 13 |
| Example A(133) | 0.072 |
| Example A(134) | 38 |
| Example A(135) | 0.015 |
| Example A(136) | 0.002 |
| Example A(137) | 0.007 |
| Example A(138) | 0.008 |
| Example A(139) | 0.002 |
| Example A(140) | NA |
| Example A(141) | NA |
| Example A(142) | 0.004 |
| Example A(143) | 0.009 |
| Example A(144) | 0.011 |
| Example A(145) | 3.9 |
| Example A(146) | 0.002 |
| Example A(147) | 1.4 |
| Example A(148) | 0.005 |
| Example A(149) | 3.9 |
| Example A(150) | 0.007 |
| Example A(151) | 0.3 |
| Example A(152) | 0.001 |
| Example A(153) | 0.003 |
| Example A(154) | 0.005 |
| Example A(155) | 0.003 |
| Example A(156) | 0.021 |
| Example A(157) | 0.065 |
| Example A(158) | NA |
| Example A(159) | NA |
| Example A(160) | 0.029 |
| Example A(161) | 0.008 |
| Example A(162) | 0.01 |
| Example A(163) | 1.9 |
| Example A(164) | 0.042 |
| Example A(165) | NA |
| Example A(166) | 0.001 |
| Example A(167) | 0.004 |
| Example A(168) | 0.009 |
| Example A(169) | 0.4 |
| Example A(170) | 0.01 |
| Example A(171) | 0.004 |
| Example A(172) | 0.006 |
| Example A(173) | 0.004 |
| Example A(174) | 0.006 |
| Example A(175) | 0.009 |
| Example A(176) | 0.006 |
| Example A(177) | 0.014 |
| Example A(178) | 1.3 |
| Example A(179) | 0.005 |
| Example A(180) | 0.01 |
| Example A(181) | 0.6 |
| Example A(182) | 0.004 |
| Example A(183) | 0.007 |
| Example A(184) | 0.52 |
| Example A(185) | 0.008 |
| Example A(186) | 0.04 |
| Example A(187) | 0.004 |
| Example A(188) | 0.006 |
| Example A(189) | 2.9 |
| Example A(190) | 0.011 |
| Example A(191) | 0.017 |
| Example A(192) | 0.028 |
| Example A(193) | 0.098 |
| Example A(194) | 6.9 |
| Example A(195) | 11 |
| Example A(196) | 0.007 |
| Example A(197) | 0.006 |
| Example A(198) | 0.016 |
| Example A(199) | 0.01 |
| Example A(200) | 0.005 |
| Example A(201) | 0.012 |
| Example A(202) | 0.012 |
| Example A(203) | 0.02 |

TABLE 1-continued

| Example ( ) | IC50 (µM) |
|---|---|
| Example A(204) | 0.017 |
| Example A(205) | 0.001 |
| Example A(206) | |
| Example A(207) | 0.004 |
| Example A(208) | 0.007 |
| Example A(209) | 0.05 |
| Example A(210) | 0.002 |
| Example A(211) | 0.004 |
| Example A(212) | 0.004 |
| Example A(213) | 0.0045 |
| Example A(214) | 0.038 |
| Example A(215) | 4.9 |
| Example A(216) | 0.045 |
| Example A(217) | 0.014 |
| Example A(218) | 0.061 |
| Example A(219) | 0.088 |
| Example A(220) | 0.172 |
| Example A(221) | 0.014 |
| Example A(222) | 0.12 |
| Example A(223) | 0.005 |
| Example A(224) | 0.004 |
| Example A(225) | 0.003 |
| Example A(226) | 0.0.0039 |
| Example A(227) | 0.01 |
| Example A(228) | 0.47 |
| Example A(229) | 0.01 |
| Example A(230) | 0.011 |
| Example A(231) | 0.006 |
| Example A(232) | 0.004 |
| Example A(233) | 0.011 |
| Example A(234) | 0.011 |
| Example A(235) | 0.89 |
| Example A(236) | 0.003 |
| Example A(237) | 1.0 |
| Example A(238) | 0.01 |
| Example A(239) | 0.003 |
| Example A(240) | 0.009 |
| Example A(241) | 0.8 |
| Example A(242) | NA |
| Example A(243) | NA |
| Example A(244) | NA |
| Example A(245) | NA |
| Example A(246) | NA |
| Example A(247) | NA |
| Example A(248) | 0.016 |
| Example A(249) | 0.019 |
| Example A(250) | NA |
| Example A(251) | NA |
| Example A(252) | 0.01 |
| Example A(253) | 0.006 |
| Example A(254) | 0.012 |
| Example A(255) | 1.9 |
| Example A(256) | NA |
| Example A(257) | 0.04 |
| Example A(258) | 0.002 |
| Example A(259) | 0.006 |
| Example A(260) | 0.007 |
| Example A(261) | 0.004 |
| Example A(262) | 0.006 |
| Example A(263) | 0.007 |
| Example A(264) | 0.004 |
| Example A(265) | 0.004 |
| Example A(266) | 0.019 |
| Example A(267) | 0.004 |
| Example A(268) | 0.68 |
| Example A(269) | 0.026 |
| Example A(270) | 0.037 |
| Example A(271) | 0.006 |
| Example A(272) | 0.006 |
| Example B(01) | 0.015 |
| Example B(02) | 0.027 |
| Example B(03) | 0.005 |
| Example B(04) | 0.024 |
| Example B(05) | 0.13 |
| Example B(06) | 0.15 |
| Example B(07) | 0.001 |
| Example B(08) | 0.013 |

TABLE 1-continued

| Example ( ) | IC50 (μM) |
|---|---|
| Example B(09) | 0.054 |
| Example B(10) | 0.053 |
| Example B(11) | 0.019 |
| Example B(12) | 0.026 |
| Example B(13) | 0.02 |
| Example B(14) | 0.63 |
| Example B(16) | 0.9 |
| Example B(17) | 1.1 |
| Example B(18) | 0.021 |
| Example B(19) | 0.06 |
| Example B(20) | 0.004 |
| Example B(21) | 0.4 |
| Example B(22) | 1.2 |
| Example B(23) | 0.87 |
| Example B(24) | 0.14 |
| Example B(25) | 0.24 |
| Example B(26) | 2.3 |
| Example B(27) | 47% @ 20 uM |
| Example B(28) | 0.011 |
| Example B(29) | 0.22 |
| Example B(30) | 2 |
| Example B(31) | 0.003 |
| Example B(32) | 0.07 |
| Example B(33) | 0.136 |
| Example B(34) | 0.03 |
| Example B(35) | 0.07 |
| Example B(36) | 0.042 |
| Example B(37) | 0.008 |
| Example B(38) | 0.021 |
| Example B(39) | 0.029 |
| Example B(40) | 0.014 |
| Example B(41) | 0.12 |
| Example B(42) | 0.21 |
| Example B(43) | 0.36 |
| Example B(44) | 0.053 |
| Example B(45) | 0.053 |
| Example B(46) | 0.02 |
| Example B(47) | 0.8 |
| Example B(48) | 0.7 |
| Example B(49) | 0.01 |
| Example B(50) | 0.09 |
| Example B(51) | 0.072 |
| Example B(52) | 0.17 |
| Example B(53) | 0.35 |
| Example B(54) | 0.3 |
| Example B(55) | 0.15 |
| Example B(56) | 0.1 |
| Example B(57) | 0.05 |
| Example B(58) | 6.2 |
| Example B(59) | 0.006 |
| Example B(60) | 0.54 |
| Example B(61) | 0.12 |
| Example B(62) | 0.2 |
| Example B(63) | 0.016 |
| Example B(64) | 0.033 |
| Example B(65) | 0.11 |
| Example B(66) | 0.22 |
| Example B(67) | 3.2 |
| Example B(68) | 0.1 |
| Example B(69) | 0.8 |
| Example B(70) | 0.24 |
| Example B(71) | 0.08 |
| Example B(72) | 1.4 |
| Example B(73) | 0.062 |
| Example B(74) | 3.4 |
| Example B(75) | 0.003 |
| Example B(76) | 0.001 |
| Example B(77) | 5.5 |
| Example B(78) | 1 |
| Example B(79) | 2.4 |
| Example B(80) | 0.56 |
| Example B(81) | ~0.24 uM |
| Example B(82) | 0.68 |
| Example B(83) | 0.36 |
| Example B(84) | 0.11 |
| Example B(85) | 0.74 |
| Example B(86) | 22.1 |
| Example B(87) | 1.8 |
| Example B(88) | 5.1 |
| Example B(89) | 0.185 |
| Example B(90) | 0.006 |
| Example B(91) | 0.01 |
| Example B(92) | 0.008 |
| Example B(93) | 0.09 |
| Example B(94) | 1% |
| Example B(95) | 0.013 |
| Example B(96) | 0.005 |
| Example B(97) | 0.009 |
| Example B(98) | 0.006 |
| Example B(99) | 0.35 |
| Example B(100) | 0.003 |
| Example B(101) | 0.61 |
| Example B(102) | 0.5 |
| Example B(103) | 0.107 |
| Example B(104) | 0.003 |
| Example B(105) | 0.046 |
| Example B(106) | NA |
| Example B(107) | 0.006 |
| Example B(108) | NA |
| Example B(109) | 23% @ 50 uM |
| Example B(110) | 0.107 |
| Example B(111) | 0.321 |
| Example B(112) | 0.097 |
| Example B(113) | 0.019 |
| Example B(114) | 0.016 |
| Example B(115) | 3.3 |
| Example B(116) | 0.011 |
| Example B(117) | 0.111 |
| Example B(118) | 0.2 |
| Example B(119) | 0.07 |
| Example B(120) | 0.012 |
| Example B(121) | 6 |
| Example B(122) | 0.007 |
| Example B(123) | 0.58 |
| Example B(124) | 0.09 |
| Example B(125) | 0.004 |
| Example B(126) | 0.023 |
| Example C(01) | 0.337 |
| Example C(02) | 0.014 |
| Example C(03) | 0.5 |
| Example C(04) | 1.8 |
| Example C(06) | 0.25 |
| Example C(07) | 0.019 |
| Example C(08) | 0.31 |
| Example C(09) | 0.326 |
| Example C(10) | 0.016 |
| Example C(11) | 0.19 |
| Example C(12) | 0.082 |
| Example C(13) | 0.016 |
| Example C(14) | 0.014 |
| Example C(15) | 22% @ 20 uM |
| Example C(16) | 8% @ 20 uM |
| Example C(17) | 2% @ 50 uM |
| Example C(18) | 2% @ 50 uM |
| Example C(19) | 22% @ 50 uM |
| Example C(20) | 11% @ 50 uM |
| Example C(21) | 12% @ 50 uM |
| Example C(22) | 0.068 |
| Example C(23) | 0.05 |
| Example C(24) | 0.051 |
| Example C(25) | 0.02 |
| Example C(26) | 0.13 |
| Example C(27) | 2.5 |
| Example C(28) | 8 |
| Example C(29) | 9.3 |
| Example C(30) | 0.55 |
| Example C(31) | 0.51 |
| Example C(32) | 0.27 |
| Example C(33) | 0.26 |
| Example C(34) | 0.053 |
| Example C(35) | 0.07 |
| Example C(36) | 0.079 |
| Example C(37) | 0.13 |
| Example C(38) | 0.28 |

TABLE 1-continued

| Example ( ) | IC50 (μM) |
|---|---|
| Example C(39) | 0.22 |
| Example C(40) | 0.025 |
| Example C(41) | 0.17 |
| Example C(42) | 0.013 |
| Example C(43) | 0.035 |
| Example C(44) | 0.18 |
| Example C(45) | 3.2 |
| Example C(46) | 0.037 |
| Example C(47) | 0.24 |
| Example C(48) | 0.14 |
| Example C(49) | 0.08 |
| Example C(50) | 0.01 |
| Example C(51) | 0.256 |
| Example C(52) | 0.14 |
| Example C(53) | 0.067 |
| Example C(54) | 0.22 |
| Example C(55) | 0.03 |
| Example C(56) | 1.3 |
| Example C(57) | 0.002 |
| Example C(58) | 0.14 |
| Example C(59) | 0.2 |
| Example C(60) | 0.015 |
| Example C(61) | 0.14 |
| Example C(62) | 0.5 |
| Example C(63) | 0.008 |
| Example C(64) | 0.012 |
| Example C(65) | 0.054 |
| Example C(66) | 0.9 |
| Example C(67) | 0.05 |
| Example C(68) | 0.2 |
| Example C(69) | 0.13 |
| Example C(70) | 0.0074 |
| Example C(71) | 0.058 |
| Example C(72) | 0.078 |
| Example C(73) | 0.035 |
| Example C(74) | 0.099 |
| Example C(75) | 0.044 |
| Example C(76) | 0.053 |
| Example C(77) | 0.062 |
| Example C(78) | 0.047 |
| Example C(79) | 0.063 |
| Example C(80) | 0.031 |
| Example C(81) | 0.014 |
| Example C(82) | 0.027 |
| Example C(83) | 0.04 |
| Example C(84) | 0.033 |
| Example C(85) | 0.035 |
| Example C(86) | 0.048 |
| Example C(87) | 0.028 |
| Example C(88) | 0.022 |
| Example C(89) | 0.02 |
| Example C(90) | 0.04 |
| Example C(91) | 0.04 |
| Example C(92) | 0.082 |
| Example C(93) | 0.014 |
| Example C(94) | 0.087 |
| Example C(95) | 0.074 |
| Example C(96) | 0.075 |
| Example C(97) | 0.12 |
| Example C(98) | 0.068 |
| Example C(99) | 0.079 |
| Example C(100) | 0.032 |
| Example C(101) | 0.14 |
| Example C(102) | 0.038 |
| Example C(103) | 0.24 |
| Example C(104) | 0.31 |
| Example C(105) | 0.2 |
| Example C(106) | 0.24 |
| Example C(107) | 0.16 |
| Example C(108) | 0.21 |
| Example C(109) | 0.9 |
| Example C(110) | 7.6 |
| Example C(111) | 0.395 |
| Example C(112) | 0.064 |
| Example D(01) | 0.41 |
| Example D(02) | 0.54 |
| Example D(03) | 1.5 |

TABLE 1-continued

| Example ( ) | IC50 (μM) |
|---|---|
| Example D(04) | 0.054 |
| Example D(05) | 6.8 |
| Example D(06) | 1.3 |
| Example D(07) | 0.32 |
| Example D(08) | 2.3 |
| Example E(1) | 22 |
| Example E(2) | 8.2 |
| Example E(3) | 65 |
| Example F(1) | 7.2 |
| Example F(2) | 7.2 |
| Example F(3) | 8.4 |
| Example F(4) | 5.8 |
| Example F(5) | 25 |
| Example F(6) | 83 |
| Example F(7) | 7.5 |
| Example G(1) | 16% @ 20 uM |
| Example G(2) | 3% @ 20 uM |
| Example G(3) | 29 |
| Example H(1) | 1 |
| Example H(2) | 51 |
| Example H(3) | 1.2 |
| Example H(4) | 60 |
| Example H(5) | 7% @ 50 uM |
| Example I(1) | 27% @ 50 uM |
| Example I(2) | 22% @ 50 uM |
| Example I(3) | −2% @ 50 uM |
| Example I(4) | 44% @ 50 uM |
| Example J(1) | 4.4 |
| Example J(2) | 3.9 |
| Example J(3) | 0.005 |
| Example J(4) | 0.019 |
| Example J(5) | 1.9 |
| Example J(6) | 1.2 |
| Example J(7) | 0.01 |
| Example J(8) | 0.014 |

The examples and preparations provided above further illustrate and exemplify the compounds of the present invention and methods of preparing such compounds. It is to be understood that the scope of the present invention is not limited in any way by the scope of the following examples and preparations.

We claim:

1. Compounds of formula (4),

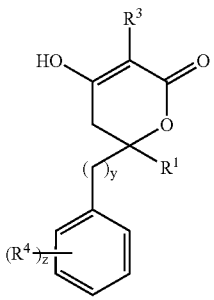

(4)

wherein:
$R^1$ is cyclopentyl;
$R^3$ is —$(CR^8R^9)_t$(4–10 membered heterocyclic), wherein t is an integer from 0 to 5, and the heterocyclic moiety is optionally substituted by 1 to 5 $R^4$ groups;
each $R^4$ is independently chosen from halo, $C_1$–$C_{10}$ alkyl, and $R^6$—O—, and each $C_1$–$C_{10}$ alkyl may be optionally substituted by at least one substituent chosen from halo, trifluoromethyl, trifluoromethoxy, $C_1$–$C_{10}$ alkyl, and cyano; or
when two adjacent $R^4$ groups are both $C_1$–$C_{10}$ alkyl, they, together with the atoms to which they are attached, form a 3- to 7-membered ring, wherein in said ring any carbon atom may be replaced by a heteroatom chosen from N, O, and S, provided that two adjacent carbons are not both replaced by heteroatoms;

$R^8$ is hydrogen or $C_1$–$C_{10}$ alkyl;

$R^8$ and $R^9$ are hydrogen;

z is an integer from 1 to 5; and y is an integer from 0 to 5.

2. Compounds according to claim 1, wherein:

$R^3$ is —$(CH_2)_t$([1,2,4]triazolo[1,5-a]pyrimidinyl), optionally substituted by 1 to 3 $R^4$ groups;

t is an integer from 1–3; and y is an integer from 1 to 3.

3. Compounds according to claim 2, wherein:

$R^3$ is —$(CH_2)$([1,2,4]triazolo[1,5-a]pyrimidinyl), substituted by 1 to 3 $R^4$ groups;

each $R^4$ is independently chosen from halo and $C_1$–$C_{10}$ alkyl optionally substituted with cyano; or two adjacent $R^4$ groups are both $C_1$–$C_{10}$ alkyl and, together with the atoms to which they are attached, form a 3- to 7-membered ring, wherein a carbon atom is replaced by a heteroatom chosen from N, O, and S;

z is an integer from 2 to 3; and y is 2.

4. Compounds according to claim 3, wherein:

$R^3$ is —$(CH_2)$([1,2,4]triazolo[1,5-a]pyrimidinyl), substituted by 2 $R^4$ groups; and each $R^4$ is independently chosen from halo, —$CH_3$, and —$C(CH_3)_2CN$.

5. Compounds according to claim 3, wherein two adjacent $R^4$ groups are both $C_1$–$C_{10}$ alkyl and, together with the atoms to which they are attached, form a 3- to 7-membered ring, wherein a carbon atom is replaced by a heteroatom chosen from N, O, and S.

6. Compounds according to claim 5, wherein:

$R^3$ is —$(CH_2)$([1,2,4]triazolo[1,5-a]pyrimidinyl), substituted by at least one substituent chosen from halo and methyl; and two adjacent $R^4$ groups, together with the atoms to which they are attached form a 5-membered ring, wherein in said ring one carbon atom is replaced by O.

7. Compounds of formula (4b),

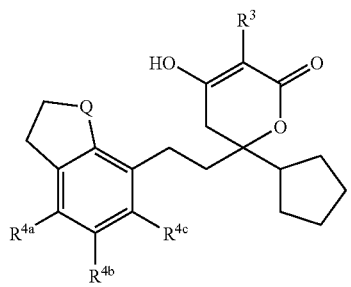

(4b)

wherein:

$R^3$ is —$(CH_2)$([1,2,4]triazolo[1,5-a]pyrimidinyl), substituted by at least one substituent chosen from halo and methyl;

Q is chosen from N, O, and S;

$R^{4a}$, $R^{4b}$, and $R^{4c}$ are independently chosen from hydrogen, halo, $C_1$–$C_{10}$ alkyl, and $R^5$—O—; and $R^6$ is chosen from hydrogen and $C_1$–$C_{10}$ alkyl.

8. Compounds of formula (5),

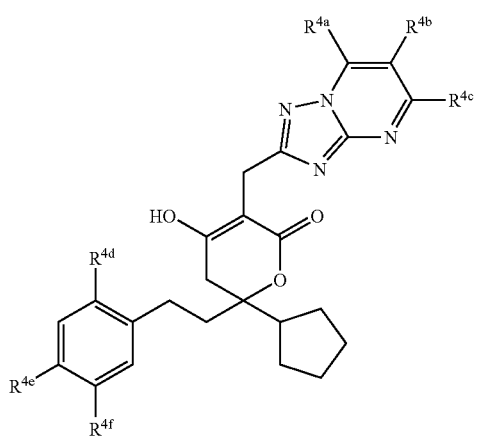

(5)

wherein:

$R^{4a}$, $R^{4b}$, and $R^{4c}$ are independently chosen from halo and $C_1$–$C_{10}$ alkyl;

$R^{4d}$, $R^{4e}$, and $R^{4f}$ are independently chosen from halo, $R^6$—O—, and $C_1$–$C_{10}$ alkyl, wherein said $C_1$–$C_{10}$ alkyl is optionally substituted with at least one substituent chosen from halo and cyano; and $R^5$ is $C_1$–$C_{10}$ alkyl or hydrogen.

9. Compounds of formula (6),

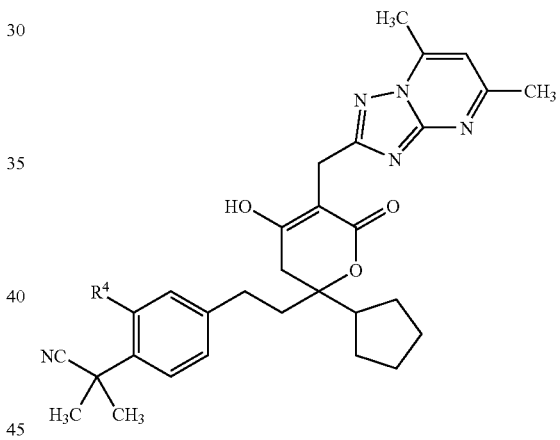

(6)

wherein $R^4$ is halo.

10. Compounds according to claim 9, wherein $R^4$ is chosen from fluorine and chlorine.

11. Compounds of formula (7),

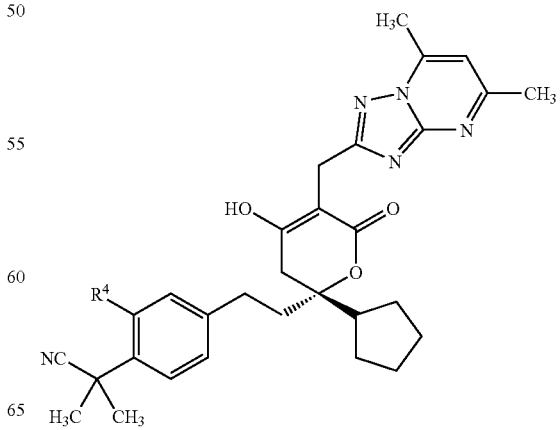

(7)

wherein $R^4$ is halo.

12. Compounds according to claim 11, wherein $R^4$ is chosen from fluorine and chlorine.

13. Compounds of formula (8),

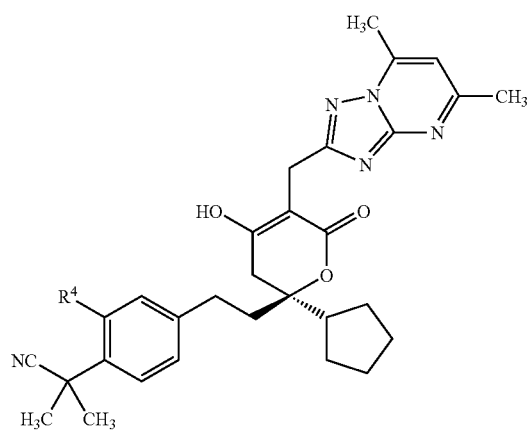

(8)

wherein $R^4$ is halo.

14. Compounds according to claim 13, wherein $R^4$ is chosen from fluorine and chlorine.

15. Compounds according to claim 2, wherein:
$R^3$ is —$(CH_2)$([1,2,4]triazolo[1,5-a]pyrimidinyl), optionally substituted by 1 to 3 $R^4$ groups,
each $R^4$ is independently chosen from halo, $C_1$–$C_{10}$ alkyl, and $R^8$—O—, and each $C_1$–$C_{10}$ alkyl may be optionally substituted by at least one substituent chosen from halo, trifluoromethyl, trifluoromethoxy, $C_1$–$C_{10}$ alkyl, and cyano;
z is an integer from 1 to 3; and
y is 2.

16. Compounds according to claim 15, wherein:
$R^6$ is hydrogen or methyl; and
z is an integer from 2–3.

17. Compounds of formula (9),

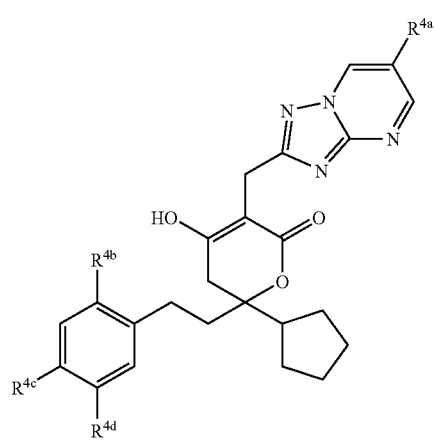

(9)

wherein:
$R^{4a}$ is halo or $C_1$–$C_{10}$ alkyl;
$R^{4b}$, $R^{4c}$, and $R^{4d}$ are independently chosen from $C_1$–$C_{10}$ alkyl and $R^6$—O—; and
$R^6$ hydrogen or methyl.

18. Compounds according to claim 17, wherein:
$R^{4a}$ is halo;
$R^{4b}$ and $R^{4c}$ are each $R^6$—O—; and
$R^{4d}$ is $C_1$–$C_{10}$ alkyl.

19. Compounds according to claim 18, wherein:
$R^{4a}$ is fluorine or chlorine;
$R^{4b}$ is —$OCH_3$;
$R^{4c}$ is —OH; and
$R^{4d}$ is —$CH_2CH_3$.

20. Compounds according to claim 19, wherein $R^{4a}$ is chlorine.

21. A compound of formula (10),

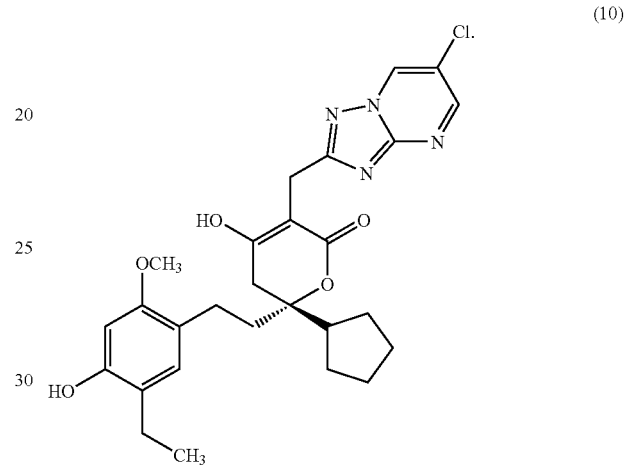

(10)

22. A compound of formula (11),

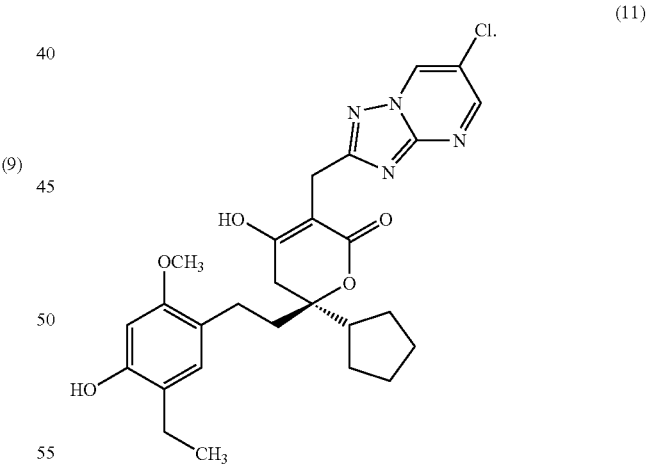

(11)

23. A compound chosen from;
6-Cyclopentyl-3-(5,7-dimethyl-[1,2,4]triazolo[1,5-a-pyrimidin-2-ylmethyl)-6-[2-(3-fluoro-4-methoxy-phenyl)-ethyl]-4-hydroxy-5,6-dihydro-pyran-2-one;

6-[2-(3-tert-Butyl-phenyl)-ethyl]-6-cyclopentyl-3-(5,7-dymethyl-[1,2,4]triazolo[1,5-a]pyrimidin-2-ylmethyl)-4-hydroxy-5,6-dihydro-pyran-2-one;

6-Cyclopentyl-3-(5,7-dimethyl-[1,2,4]triazolo[1,5-a]pyrimidin-2-ylmethyl)-6-[2-(3-ethyl-4-hydroxy-phenyl)-ethyl]4-hydroxy-5,6-dihydro-pyran-2-one;

6-[2-(3-tert-Butyl-4-hydroxy-phenyl)-ethyl]-6-cyclopentyl-3-(5,7-dimethyl-[1,2,4]triazolo(1,5-a]pyrimidin-2-ylmethyl)-4-hydroxy-5,6-dihydro-pyran-2-one;
6-[2-(3-Chloro-4-isopropoxy-phenyl)-ethyl]-6-cyclopentyl-3-(5,7-dimethyl-[1,2,4]triazolo-[1,5-a]pyrimidin-2-ylmethyl)-4-hydroxy-5,6-dihydro-pyran-2-one;
6-Cyclopentyl-6-[2-(3,5-dichloro-4-ethoxy-phenyl)-ethyl]-3-(5,7-dimethyl-[1,2,4]triazolo[1,5-a]pyrimidin-2-ylmethyl)-4-hydroxy-5,6-dihydro-pyran-2-one;
6-cyclopentyl-3-[(5,7-dimethyl[1,2,4]triazolo[1,5a]-pyrimidin-2-yl)methyl]-6-[2-(3-isopropylphenyl)ethyl]dihydro-2H-pyran-2,4(3H)-dione;
7-({6-[2-(5-Chloro-2,4-dimethoxyphenyl)ethyl]-6-cyclopentyl-4-hydroxy-2-oxo-5,6-dihydro-2H-pyran-3-yl}methyl)-3-methyl-5H-[1,3]thiazolo[3,2-a]pyrimidin-5-one;
2-(4-{2-[2-Cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-2-fluoro-phenyl)-2-methyl-propionitrile;
1-(4-{2-[2-Cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-2-fluoro-phenyl)-cyclopropanecarbonitrile;
6-[2-(5-chloro-2,4-dimethoxyphenyl)ethyl]-6-cyclopentyl-4-hydroxy-3-(imidazo[1,2-a]pyrimidin-2-ylmethyl)-5,6-dihydro-2H-pyran-2-one;
6N-[4-(2-{2-cyclopentyl-5-[(5,7-dimethyl[1,2,4]triazolo[1,5-a]pyrimidin-2-yl)methyl]-4,6-dioxotetrahydro-2H-pyran-2-yl}ethyl)-2-ethylphenyl]-N-methylmethanesulfonamide;
2-[4-(2-{2-cyclopentyl-4-hydroxy-5-[(1-methyl-1H-indol-5-yl)methyl]-6-oxo-3,6-dihydro-2H-pyran-2-yl}ethyl)-2-fluorophenyl]-2-methylpropanenitrile;
6-[2-(3-Chloro-4-hydroxy-phenyl)-ethyl]-6-cyclopentyl-3-(5,7-dimethyl-[1,2,4]trlazolo[1,5-a]pyrimidin-2-ylmethyl)-4-hydroxy-5,6-dihydro-pyran-2-one;
6-Cyclopentyl-3-(5,7-dimethyl-[1,2,4]triazolo[1,5-a]pyrimidin-2-ylmethyl)-6-[2-(3-ethyl-4-methoxy-phenyl)-ethhyl]-4-hydroxy-5,6-dihydro-pyran-2-one;
3-(5-Chloro-1-isopropyl-1-benzoimidazol-2-ylsulfanyl)-6-cyclopentyl-6-[2-(3-fluoro-4-isopropoxy-phenyl)-ethyl]-4-hydroxy-5,6-dihydro-pyran-2-one;
5-{6-Cyclopentyl-6-[2-(3-fluoro-4-isopropoxy-phenyl)-ethyl]-hydroxy-2-oxo-5,6-dihydro-2H-pyran-3-ylsulfanyl}-4-methyl-4H-[1,2,4]triazole-3-carboxylic acid methyl ester;
3-(5-Chloro-1-methyl-1H-benzoimidazol-2-ylsulfanyl)-6-cyclopentyl-6-[2-[4-(3,5-dimethyl-isoxazol-4-yl)-phenyl]-ethyl]-4-hydroxy-5,6-dihydro-pyran-2-one;
6-[2-(3-chloro-4-methoxyphenyl)ethyl]-6-cyclopentyl-3-{[5-(2-furyl)-4-methyl-4H-1,2,4-triazol-3-yl]thio}-4-hydroxy-5,6-dihydro-2H-pyran-2-one;
6-[2-(3-chloro-4-methoxyphenyl)ethyl]-6-cyclopentyl-4-hydroxy-3-[(5-pyridin-4-yl-4H-1,2,4-triazol-3-yl)thio]-5,6-dihydro-2H-pyran-2-one;
6-[2-(3-chloro-4-methoxyphenyl)ethy)]-3-[(5-chloro-1-methyl-1H-benzimidazol-2-yl)thio]-6-cyclopentyl-4-hydroxy-5,6-dihydro-2H-pyran-2-one;
6-[2-(5-chloro-2,4-dimethoxyphenyl)ethyl]-3-[(5-chloro-1-methyl-1H-benzimidazol-2-yl)thio]-6-cyclopentyl-4-hydroxy-5,6-dihydro-2H-pyran-2-one;
6-[2-(3-chloro-4-isopropoxyphenyl)ethyl]-3-[(5-chloro-1-methyl-1H-benzimidazol-2-yl)thio]-6-cyclopentyl-4-hydroxy-5,6-dihydro-2H-pyran-2-one;
8-({6-[2-(5-chloro-2,4-dimethoxyphenyl)ethyl]-6-cyclopentyl-4-hydroxy-2-oxo-5,6-dihydro-2H-pyran-3-yl}thio)-1,7-dihydro-6H-purin-6-one;
6-[2-(5-chlor-2,4-dimethoxyphenyl)ethyl]-6-cyclopentyl-4-hydroxy-3-{[5-(4-hydroxyphenyl)-4H-1,2,4-triazol-3-yl]thio}-5,6-dihydro-2H-pyran-2-one;
ethyl 2-({6-[2-(5-chloro-2,4-dimethoxyphenyl)ethyl]-6-cyclopentyl-4-hydroxy-2-oxo-5,6-dihydro-2H-pyran-3-yl}thio)[1,2,4]triazolo[1,5-a]pyrimidine-6-carboxylate;
6-cyclopentyl-3-[(5,7-dimethyl[1,2,4]triazolo[1,5-a]pyrimidin-2-yl)methyl]-6-[2-(3-fluoro-4-isopropoxyphenyl)ethyl]4-hydroxy-5,6-dihydro-2H-pyran-2-one;
6-Cyclopenty-3-(5,7-dimethyl-[1,2,4]triazolo[1,5-a]pyrimidin-2-ylmethyl)-6-[2-(3-ethyl-phenyl)-ethyl]-4-hydroxy-5,6-dihydro-pyran-2-one;
6-Cyclopentyl-3-(5,7-dimethyl-[1,2,4]triazolo[1,5-a]pyrimidin-2-ylmethyl)-6-[2-(3-ethyl-phenyl)-elhyl]4-hydroxy-5,6-dihydro-pyran-2-one;
2-[4-(2-{5-[(4-chloro-1-methyl-1H-pyrazol-3-yl)methyl]-2-cyclopentyl-4-hydroxy-6-oxo-3,6-dihydro-2H-pyran-2-yl}ethyl)-2-fluorophenyl]-2-methylpropanenitrile;
2-{4-[2-(2-Cyclopentyl-4,6-dioxo-5-[1,2,4]triazolo[1,5-a]pyrimidin-2-ylmethyl-tetrahydro-pyran-2-yl)-ethyl]-2-fluoro-phenyl}-2-methyl-propionitrile;
2-(4-{2-[2-Cyclopentyl-5-(6-methyl-[1,2,4]triazolo[1,5-a]pyrimidin-2-ylmethyl)-4,6-dioxo-tetrahydro-pyran-2-yl]-ethyl}-2-fluoro-phenyl)-2-methyl-propionitrile;
(+)-2-(4-{2-[2-Cyclopentyl-5-(6-methyl-[1,2,4]triazolo[1,5-a]pyrimidin-2-ylmethyl)-4,6-dioxo-tetrahydro-pyran-2-yl]-ethyl}-2-fluoro-phenyl)-2-methyl-propionitrile;
(−)-2-(4-{2-[2-Cyclopentyl-5-(6-methyl-[1,2,4]triazolo[1,5-a]pyrimidin-2-ylmethyl)-4,6-dioxo-tetrahydro-pyran-2-yl]-ethyl}-2-fluoro-phenyl)-2-methyl-propionitrile;
2-(4-{2-[5-(6-Chloro-[1,2,4]triazolo[1,5-a]pyrimidin-2-ylmethyl)-2-cyclophenyl-4,6-dioxo-tetrahydro-pyran-2-yl]-ethyl}-2-fluoro-phenyl)-2-methyl-propionitrile;
2-(4-{2-[2-Cyclopentyl-5-(5,7-dimethyl-[1,2,4]triazolo[1,5-a]pyrimidin-2-ylmethyl)-4,6-dioxo-tetrahydro-pyran-2-yl]-ethyl}-2-fluoro-phenyl)-2-ethyl-butyronitrile;
1-(4-{2-[2-Cyclopentyl-5-(6-methyl-[1,2,4]triazolo[1,5-a]pyrimidin-2-ylmethyl)-4,6-dioxo-tetrahydro-pyran-2-yl]-ethyl}-2-fluoro-phenyl)-cyclopropanecarbonitrile;
1-(4-{2-[5-(6-Chloro-[1,2,4]triazolo[1,5-a]pyrimidin-2-ylmethyl)-2-cyclopentyl-4,6-dioxo-tetrahydro-pyran-2-yl]-ethyl}-2-fluoro-phenyl)-cyclopropanecarbonitrile;
6-Cyclopentyl-6-[2-(3ethyl-4-hydroxy-phenyl)-ethyl]-4-hydroxy-3-(6-methyl-[1,2,4]triazolo[1,5-a]pyrimidin-2-ylmethyl)-5,6-dihydro-pyran-2-one;
3-(6-Chloro-[1,2,4]triazolo[1,5-a]pyrimidin-2-ylmethyl)-6-cyclopentyl-6-[2-(3-ethyl-4-hydroxy-phenyl)-ethyl]4-hydroxy-5,6-dihydro-pyran-2-one;
6-cyclopentyl-3-[(5,7-diethyl[1,2,4]triazolo[1,5-a]pyrimidin-2-yl)methyl]-4-hydroxy-6-[2-(4-hydroxy-3-propylphenyl)ethyl]-5,6-dihydro-2H-pyran-2-one;
6-cyclopentyl-3-[(5,7-diethyl[1,2,4]triazolo[1,5-a]pyrimidin-2-yl)methyl]-6-[2-(3-ethyl-4-hydroxyphenyl)ethyl]-4-hydroxy-5,6-dihydro-2H-pyran-2-one;
N-{2-[4-(2-{2-cyclopentyl-5-[(5,7-dimethyl[1,2,4]triazolo[1,5,-a]pyrimidin-2-yl)methyl]-hydroxy-6-oxo-3,6-dehydro-2H-pyran-2-yl}ethyl)-2-ethylphenoxy]ethyl}acetamide;
2-(4-{2-[2-Cyclopentyl-5-5,7-dimethyl-[1,2,4]triazolo[1,5-a]pyrimidin-2-ylmethyl]-4-hydroxy-6-oxo-3,6-dihydro-2H-pyran-2-yl]-ethyl}-2,6-difluoro-phenyl)-2-methyl-propionitrile;

2-(4-{2-[2-Cyclopentyl-4-hydroxy-5-(6-methyl-[1,2,4]
triazolo[1,5-a]pyrimidin-2-ylmethyl)-6-oxo-3,6-dihydro-2H-pyran-2-yl]-ethyl}-2,6-difluoro-phenyl)-2-methyl-propionitrile;

2-(2-Chloro-4-{2-[2-cyclopentyl-5-(5,7-dimethyl-[1,2,4]
triazolo[1,5-a]pyrimidin-2-ylmethyl)-4-hydroxy-6-oxo-3,6-dihydro-2H-pyran-2-yl]-ethyl}-phenyl)-2-methyl-propionitrile;

1-(2-Chloro-4-{2-[2-cyclopentyl-5-(5,7-dimethyl-[1,2,4]
triazolo[1,5-a]pyrimidin-2-ylmethyl)-4-hydroxy-6-oxo-3,6-dihydro-2H-pyran-2-yl]-ethyl}-phenyl)-cyclopropanecarbonitrile;

6-Cyclopentyl-3-(5,7-dimethyl-[1,2,4]triazolo[1,5-a]pyrimidin-2-ylmethyl)-6-[2-(5-ethyl-4-hydroxy-2-mothoxy-phenyl)-ethyl]-4-hydroxy-5,6-dihydro-pyran-2-one;

(+)-2-(2-chloro-4-{2-[2-cyclopentyl-5-(5,7-dimethyl-[1,2,4]triazolo[1,5-a]pyrimidin-2-ylmethyl)-4-hydroxy-6-oxo-3,6-dihydro-2H-pyran-2yl]-ethyl}-phenyl)-methyl-propionitrile;

(−)-2-(2-chloro-4-{2-[2-cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-phenyl)-2-methyl-propionitrile;

(+)-2-4-{-2-[2-Cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-2-fluorophenyl)-2-methylpropionitrile;

(−)-2-(4-{2-[2-Cyclopentyl-5-(5,7-dimethyl-[1,2,4]triazolo[1,5-a]pyrimidin-2-ylmethyl)-4-hydroxy-6-oxo-3,6-hydro-2H-pyran-2-yl]-ethyl}-2-fluorophenyl)-2-methylpropionitrile;

(+)-3-[(6-chloro[1,2,4]triazolo[1,5-a]pyrimidin-2-yl)methyl]-6-cyclopentyl-6-[2-(5-ethyl-4-hydroxy-2-methoxyphenyl)ethyl]-4-hydroxy-5,6-dihydro-2H-pyran-2-one;

(−)-3-[(6-chloro[1,2,4]triazolo[1,5-a]pyrimidin-2-yl)methyl]-6-cyclopentyl-6-[2-(5-ethyl-4-hydroxy-2-melhoxyphenyl)ethyl]-hydroxy-5,6-dihydro-2H-pyran-2-one;

6-Cyclopentyl-3-(5,7-dimethyl-[1,2,4,]triazolo[1,5-a]pyrimidin-2-ylmethyl)-6-[2-(5-ethyl-4-hydroxy-2-methoxy-phenyl)-ethyl]-4-hydroxy-5,6-dihydro-pyran-2-one;

(−)-6-Cyclopentyl-3-(5,7-dimethyl-[1,2,4]triazolo[1,5-a]pyrimidin-2-ylmethyl)-6-[2-(5-ethyl-4-hydroxy-2-methoxy-phenyl)-ethyl]-4-hydroxy-5,6-dihydro-pyran-2-one;

6-[2-(3-Chloro-5-ethyl-4-methoxy-phenyl)-ethyl]-6-cyclopentyl-3-(5,7-dimethyl-[1,2,4]triazolo[1,5-a]pyrimidin-2-ylmethyl)-4-hydroxy-5,6-dihydro-pyran-2-one;

6-Cyclopentyl-3-(5,7-dimethyl-[1,2,4]triazolo[1,5-a]pyrimidin-2-ylmethyl)-6-[2-(5-ethyl-2-methoxy-phenyl)-ethyl]4-hydroxy-5,6-dihydro-pyran-2-one;

6-[2-(3-Chloro-5-ethyl-4-hydroxy-phenyl)-ethyl)-6-cyclopentyl-3-(5,7-dimethyl-[1,2,4]triazolo[1,5-a]pyrimidin-2-ylmethyl)-4-hydroxy-5,6-dihydro-pyran-2-one;

6-Cyclopentyl-3-(5,7-dimethyl-[1,2,4]triazolo[1,5-a]pyrimidin-2-ylmethyl)-6-{2-[3-ethyl-4-(2-hydroxy-ethoxy)-phenyl]-ethyl}-4-hydroxy-5,6-dihydro-pyran-2-one;

6-Cyclopentyl-6-[2-(3-cyclopropyl-4-methoxy-phenyl)-ethyl]-3-(5,7-dimethyl-[1,2,4]triazolo(1,5-a]pyrimidin-2-ylmethyl)-4-hydroxy-5,6-dihydro-pyran-2-one;

6-Cyclopentyl-3-(5,7-dimethyl-[1,2,4]triazolo[1,5-a]pyrimidin-2-ylmethyl)-6-[2-(5-ethyl-4-hydroxy-2,3-dihydro-benzofuran-7-yl)-ethyl]-4-hydroxy-5,6-dihydro-pyran-2-one;

(+)-6-Cyclopentyl-3-(5,7-dimethyl-[1,2,4]triazolo[1,5-a]pyrimidin-2-ylmethyl)-6-[2-(5-ethyl-4-hydroxy-2,3-dihydro-benzofuran-7-yl)-ethyl]-4-hydroxy-5,6-dihydro-pyran-2-one;

(−)-6-Cyclopentyl-3-(5,7-dimethyl-[1,2,4]triazolo[1,5-a]pyrimidin-2-ylmethyl)-6-[2-(5-ethyl-4-hydroxy-2,3-dihydro-benzofuran-7-yl)-ethyl]-4-hydroxy-5,6-dihydro-pyran-2-one;

6-Cyclopentyl-3-(5,7-dimethyl-[1,2,4]triazolo[1,5-a]pyrimidin-2-ylmethyl)-6-[2-(5-ethyl-pyridin-3-yl)-ethyl]-4-hydroxy-5,6-dihydro-pyran-2-one; and pharmaceutically acceptable salts, solvates and prodrugs of the foregoing compounds.

24. A compound chosen from:

2-[4-(2-{5-[((4-chloro-1-methyl-1H-pyrazol-3-yl)methyl]-2-cyclopentyl-4-hydroxy-6-oxo-3,6-dihydro-2H-pyran-2-yl}ethyl)-2-fluorophenyl]-2-methylpropanenitrile;

2-(4-{2-[2-Cyclopentyl-5-(6-methyl-[1,2,4]triazolo[1,5-a]pyrimidin-2-ylmethyl)4,6-dioxo-tetrahydro-pyran-2-yl]-ethyl}-2-fluoro-phenyl)-2-methyl-propionitrile;

(+)-2-(4-{2-[2-Cyclopentyl-5-(6-methyl-[1,2,4]triazolo[1,5-a]pyrimidin-2-ylmethyl)4,6-dioxo-tetrahydro-pyran-2-yl]-ethyl}-2-fluoro-phenyl)-2-methyl-propionitrile;

(−)-2-(4-{2-[2-Cyclopentyl-5-(6-methyl-[1,2,4]triazolo[1,5-a]pyrimidin-2-ylmethyl)-4,6-dioxo-tetrahydro-pyran-2-yl]-ethyl}-2-fluoro-phenyl)-2-methyl-propionitrile;

2-(4-{2-[5-(6-Chloro-[1,2,4]triazolo[1,5-a]pyrimidin-2-ylmethyl)-2-cyclopentyl-4,6-dioxo-tetrahydro-pyran-2-yl]-ethyl}-2-fluoro-phenyl)-2-methyl-propionitrile;

3-(6-Chloro-[1,2,4]triazolo[1,5-a]pyrimidin-2-ylmethyl)-6-cyclopentyl-6-[2-(3-ethyl-4-hydroxy-phenyl)-ethyl]-4-hydroxy-5,6-dihydro-pyran-2-one;

N-{2-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylphenoxy]ethyl}acetamide;

2-(4-{2-[2-Cyclopentyl-5-5,7-dimethyl-[1,2,4]triazolo[1,5-a]pyrimidin-2-ylmethyl]-4-hydroxy-6-oxo-3,6-dihydro-2H-pyran-2-yl}-ethyl)-2,6-difluoro-phenyl)-2-methyl-propionitrile;

(+)-2-(2-chloro-4-{2-[2-cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-phenyl)-2-methyl-propionitrile;

(−)-2-(2-chloro-4-{2-[2-cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-phenyl)-2-methyl-propionitrile;

(+)-2-(4-{2-[2-Cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-2-fluorophenyl)-2-methylpropionitrile;

(−)-2-(4-{2-[2-Cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-2-fluorophenyl-2-methylpropionitrile;

(+)-3-[(6-chloro[1,2,4]triazolo[1,5-a]pyrimidin-2-yl)methyl]-6-cyclopentyl-6-[2-(5-ethyl-4-hydroxy-2-methoxyphenyl)ethyl]-4-hydroxy-5,6-dihydro-2H-pyran-2-one;

(−)-3-[(6-chloro[1,2,4]triazolo[1,5-a]pyrimidin-2-yl)methyl]-6-cyclopentyl-6-[2-(5-ethyl-4-hydroxy-2-methoxyphenyl)ethyl]-4-hydroxy-5,6-dihydro-2H-pyran-2-one;

1-(2-Chloro-4-{2-[2-cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-phenyl)-cyclopropanecarbonitrile;

6-Cyclopentyl-3-(5,7-dimethyl-[1,2,4]triazolo[1,5-a]pyrimidin-2-ylmethyl)-6-[2-(5-ethyl-4-hydroxy-2-methoxy-phenyl)-ethyl]-4-hydroxy-5,6-dihydro-pyran-2-one;

(−)-6-Cyclopentyl-3-(5,7-dimethyl-[1,2,4]triazolo[1,5-a]pyrimidin-2-ylmethyl)-6-[2-(5-ethyl-4-hydroxy-2-methoxy-phenyl)-ethyl]-4-hydroxy-5,6-dihydro-pyran-2-one;

6-[2-(3-Chloro-5-ethyl-4-hydroxy-phenyl)-ethyl]-6-cyclopentyl-3-(5,7-dimethyl-[1,2,4]triazolo[1,5-a]pyrimidin-2-ylmethyl)-4-hydroxy-5,6-dihydro-pyran-2-one;

6-Cyclopentyl-3-(5,7-dimethyl-[1,2,4]triazolo[1,5-a]pyrimidin-2-ylmethyl)-6-{2-[3-ethyl-4-(2-hydroxy-ethoxy)-phenyl]-ethyl}4-hydroxy-5,6-dihydro-pyran-2-one;

6-Cyclopentyl-3-(5,7-dimethyl-[1,2,4]triazolo[1,5-a]pyrimidin-2-ylmethyl)-6-[2-(5-ethyl-4-hydroxy-2,3-dihydro-benzofuran-7-yl)-ethyl]-4-hydroxy-5,6-dihydro-pyran-2-one;

(+)-6-Cyclopentyl-3-(5,7-dimethyl-[1,2,4]triazolo[1,5-a]pyrimidin-2-ylmethyl)-6-[2-(5-ethyl-4-hydroxy-2,3-dihydro-benzofuran-7-yl)-ethyl]-4-hydroxy-5,6-dihydro-pyran-2-one;

(−)-6-Cyclopentyl-3-(5,7-dimethyl-[1,2,4]triazolo[1,5-a]pyrimidin-2-ylmethyl)-6-[2-(5-ethyl-4-hydroxy-2,3-dihydro-benzofuran-7-yl)-ethyl]-4-hydroxy-5,6-dihydro-pyran-2-one;

6-Cyclopentyl-3-(5,7-dimethyl-[1,2,4]triazolo[1,5-a]pyrimidin-2-ylmethyl)-6-[2-(5-ethyl-pyridin-3-yl)-ethyl]-4-hydroxy-5,6-dihydro-pyran-2-one; and pharmaceutically acceptable salts, solvates and prodrugs of the foregoing compounds.

25. A compound chosen from:

(+)-2-(4-{2-[2-Cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-2-fluorophenyl-2-methylpropionitrile;

(−)-2-(4-{2-[2-Cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-2-fluorophenyl-2-methylpropionitrile;

(+)-2-(2-chloro-4-{2-[2-cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-phenyl)-2-methyl-propionitrile;

(−)-2-(2-chloro-4-{2-[2-cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-phenyl)-2-methyl-propionitrile;

(+)-3-[(6-chloro[1,2,4]triazolo[1,5-a]pyrimidin-2-yl)methyl]-6-cyclopentyl-6-[2-(5-ethyl-4-hydroxy-2-methoxyphenyl)ethyl]-4-hydroxy-5,6-dihydro-2H-pyran-2-one;

(−)-3-[(6-chloro[1,2,4]triazolo[1,5-a]pyrimidin-2-yl)methyl]-6-cyclopentyl-6-[2-(5-ethyl-4-hydroxy-2-methoxyphenyl)ethyl]-4-hydroxy-5,6-dihydro-2H-pyran-2-one;

6-Cyclopentyl-3-(5,7-dimethyl-[1,2,4]triazolo[1,5-a]pyrimidin-2-ylmethyl)-6-[2-(5-ethyl-4-hydroxy-2,3-dihydro-benzofuran-7-yl)-ethyl]-4-hydroxy-5,6-dihydro-pyran-2-one;

(+)-6-Cyclopentyl-3-(5,7-dimethyl-[1,2,4]triazolo[1,5-a]pyrimidin-2-ylmethyl)-6-[2-(5-ethyl-4-hydroxy-2,3-dihydro-benzofuran-7-yl)-ethyl]-4-hydroxy-5,6-dihydro-pyran-2-one;

(−)-6-Cyclopentyl-3-(5,7-dimethyl-[1,2,4]triazolo[1,5-a]pyrimidin-2-ylmethyl)-6-[2-(5-ethyl-4-hydroxy-2,3-dihydro-benzofuran-7-yl)-ethyl]-4-hydroxy-5,6-dihydro-pyran-2-one;

6-Cyclopentyl-3-(5,7-dimethyl-[1,2,4]triazolo[1,5-a]pyrimidin-2-ylmethyl)-6-[2-(5-ethyl-pyridin-3-yl)-ethyl]-4-hydroxy-5,6-dihydro-pyran-2-one; and pharmaceutically acceptable salts, solvates and prodrugs of the foregoing compounds.

26. A method of treating Hepatitis C virus in a mammal comprising administering to said mammal an amount of a compound according to claim 1 that is effective in treating HCV.

27. A method of inhibiting Hepatitis C virus polymerase, comprising contacting said polymerase with a polymerase-inhibiting amount of a compound according to claim 1.

28. A pharmaceutical composition for the treatment of Hepatitis C virus in a mammal, comprising an amount of a compound according to claim 1 that is effective in treating Hepatitis C virus, and a pharmaceutically acceptable carrier.

* * * * *

UNITED STATES PATENT AND TRADEMARK OFFICE
CERTIFICATE OF CORRECTION

PATENT NO. : 7,148,226 B2
APPLICATION NO. : 10/718337
DATED : December 12, 2006
INVENTOR(S) : Allen Borchardt et al.

It is certified that error appears in the above-identified patent and that said Letters Patent is hereby corrected as shown below:

In the Claims, Claim 1, Column 457, Line 3:

Please delete "$R^8$" and insert -- $R^6$ --

In the Claims, Claim 7, Column 457, Line 66:
Please delete "$R^5$-O-" and insert --$R^6$-O- --

In the Claims, Claim 8, Column 458, Line 28:
Please delete "$R^5$" and insert -- $R^6$ --

In the Claims, Claim 15, Column 459, Line 32:
Please delete "$R^8$-O-" and insert -- $R^6$-O- --

In the Claims, Claim 23, Column 460, Lines 65 – 67:
Please delete "6-Cyclopentyl-3-(5,7-dimethyl-[1,2,4]triazolo[1,5-a]pyrimidin-2-ylmethyl)-6-[2-(3-ethyl-4-hydroxy-phenyl)-ethyl]4-hydroxy-5,6-dihydro-pyran-2-one" and insert -- 6-Cyclopentyl-3-(5,7-dimethyl-[1,2,4]triazolo[1,5-a]pyrimidin-2-ylmethyl)-6-[2-(3-ethyl-4-hydroxy-phenyl)-ethyl]-4-hydroxy-5,6-dihydro-pyran-2-one --

In the Claims, Claim 23, Column 461, Lines 1 – 3:
Please delete "6-[2-(3-tert-Butyl-4-hydroxy-phenyl)-ethyl]-6-cyclopentyl-3-(5,7-dimethyl-[1,2,4]triazolo(1,5-a]pyrimidin-2-ylmethyl)-4-hydroxy-5,6-dihydro-pyran-2-one" and insert -- 6-[2-(3-tert-Butyl-4-hydroxy-phenyl)-ethyl]-6-cyclopentyl-3-(5,7-dimethyl-[1,2,4]triazolo[1,5-a]pyrimidin-2-ylmethyl)-4-hydroxy-5,6-dihydro-pyran-2-one --

In the Claims, Claim 23, Column 461, Lines 4 – 6:
Please delete "6-[2-(3-Chloro-4-isopropoxy-phenyl)-ethyl]-6-cyclopentyl-3-(5,7-dimethyl-[1,2,4]triazolo(1,5-*a*]pyrimidin-2-ylmethyl)-4-hydroxy-5,6-dihydro-pyran-2-one" and insert -- 6-[2-(3-Chloro-4-isopropoxy-phenyl)-ethyl]-6-cyclopentyl-3-(5,7-dimethyl-[1,2,4]triazolo[1,5-*a*]pyrimidin-2-ylmethyl)-4-hydroxy-5,6-dihydro-pyran-2-one --

In the Claims, Claim 23, Column 461, Lines 10 – 12:
Please delete "6-cyclopentyl-3-[(5,7-dimethyl [1,2,4]triazolo[1,5*a*]pyrimidin-2-yl)methyl]-6-[2-(3-isopropylphenyl)ethyl]dihydro-2*H*-pyran-2,4(3*H*)-dione" and insert -- 6-cyclopentyl-3-[(5,7-dimethyl[1,2,4]triazolo[1,5-*a*]pyrimidin-2-yl)methyl]-6-[2-(3-isopropylphenyl)ethyl]dihydro-2*H*-pyran-2,4(3*H*)-dione --

UNITED STATES PATENT AND TRADEMARK OFFICE
CERTIFICATE OF CORRECTION

PATENT NO. : 7,148,226 B2
APPLICATION NO. : 10/718337
DATED : December 12, 2006
INVENTOR(S) : Allen Borchardt et al.

It is certified that error appears in the above-identified patent and that said Letters Patent is hereby corrected as shown below:

In the Claims, Claim 23, Column 461, Lines 34 – 36:
Please delete "6-[2-(3-Chloro-4-hydroxy-phenyl)-ethyl]-6-cyclopentyl-3-(5,7-dimethyl-[1,2,4]triazolo[1,5-a]pyrimidin-2-ylmethyl)-4-hydroxy-5,6-dihydro-pyran-2-one" and insert -- 6-[2-(3-Chloro-4-hydroxy-phenyl)-ethyl]-6-cyclopentyl-3-(5,7-dimethyl-[1,2,4]triazolo[1,5-a]pyrimidin-2-ylmethyl)-4-hydroxy-5,6-dihydro-pyran-2-one --

In the Claims, Claim 23, Column 461, Lines 37 – 39:
Please delete "6-Cyclopentyl-3-(5,7-dimethyl-[1,2,4]triazolo[1,5-a]pyrimidin-2-ylmethyl)-6-[2-(3-ethyl-4-methoxy-phenyl)-ethhyl]-4-hydroxy-5,6-dihydro-pyran-2-one" and insert -- 6-Cyclopentyl-3-(5,7-dimethyl-[1,2,4]triazolo[1,5-a]pyrimidin-2-ylmethyl)-6-[2-(3-ethyl-4-methoxy-phenyl)-ethyl]-4-hydroxy-5,6-dihydro-pyran-2-one --

In the Claims, Claim 23, Column 461, Lines 56 – 58:
Please delete "6-[2-(3-chloro-4-methoxyphenyl)ethy)]-3-[(5-chloro-1-methyl-1$H$-benzimidazol-2-yl)thio]-6-cyclopentyl-4-hydroxy-5,6-dihydro-2$H$-pyran-2-one" and insert -- 6-[2-(3-chloro-4-methoxyphenyl)ethyl]-3-[(5-chloro-1-methyl-1$H$-benzimidazol-2-yl)thio]-6-cyclopentyl-4-hydroxy-5,6-dihydro-2$H$-pyran-2-one --

In the Claims, Claim 23, Column 462, Lines 8 – 10:
Please delete "6-cyclopentyl-3-[(5,7-dimethyl[1,2,4]triazolo[1,5-$a$]pyrimidin-2-yl)methyl]-6-[2-(3-fluoro-4-isopropoxyphenyl)ethyl]4-hydroxy-5,6-dihydro-2$H$-pyran-2-one" and insert -- 6-cyclopentyl-3-[(5,7-dimethyl[1,2,4]triazolo[1,5-$a$]pyrimidin-2-yl)methyl]-6-[2-(3-fluoro-4-isopropoxyphenyl)ethyl]-4-hydroxy-5,6-dihydro-2$H$-pyran-2-one --

In the Claims, Claim 23, Column 462, Lines 14 – 16:
Please delete "6-Cyclopentyl-3-(5,7-dimethyl-[1,2,4]triazolo[1,5-a]pyrimidin-2-ylmethyl)-6-[2-(3-ethyl-phenyl)-ethyl]4-hydroxy-5,6-dihydro-pyran-2-one" and insert -- 6-Cyclopentyl-3-(5,7-dimethyl-[1,2,4]triazolo[1,5-a]pyrimidin-2-ylmethyl)-6-[2-(3-ethyl-phenyl)-ethyl]-4-hydroxy-5,6-dihydro-pyran-2-one --

In the Claims, Claim 23, Column 462, Lines 48 – 50:
Please delete "6-Cyclopentyl-6-[2-(3ethyl-4-hydroxy-phenyl)-ethyl]-4-hydroxy-3-(6-methyl-[1,2,4]triazolo[1,5-a]pyrimidin-2-ylmethyl)-5,6-dihydro-pyran-2-one" and insert -- 6-Cyclopentyl-6-[2-(3-ethyl-4-hydroxy-phenyl)-ethyl]-4-hydroxy-3-(6-methyl-[1,2,4]triazolo[1,5-a]pyrimidin-2-ylmethyl)-5,6-dihydro-pyran-2-one --

UNITED STATES PATENT AND TRADEMARK OFFICE
CERTIFICATE OF CORRECTION

PATENT NO. : 7,148,226 B2
APPLICATION NO. : 10/718337
DATED : December 12, 2006
INVENTOR(S) : Allen Borchardt et al.

It is certified that error appears in the above-identified patent and that said Letters Patent is hereby corrected as shown below:

In the Claims, Claim 23, Column 462, Lines 60 – 63:
    Please delete "N-{2-[4-(2-{2-cyclopentyl-5-[(5,7-dimethyl[1,2,4]triazolo[1,5-a]pyrimidin-2-yl)methyl]-hydroxy-6-oxo-3,6-dehydro-2H-pyran-2-yl}ethyl)-2-ethylphenoxy]ethyl}acetamide" and insert -- N-{2-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylphenoxy]ethyl}acetamide --

In the Claims, Claim 23, Column 463, Lines 12 – 15:
    Please delete "6-Cyclopentyl-3-(5,7-dimethyl-[1,2,4]triazolo[1,5-a]pyrimidin-2-ylmethyl)-6-[2-(5-ethyl-4-hydroxy-2-mothoxy-phenyl)-ethyl]-4-hydroxy-5,6-dihydro-pyran-2-one" and insert -- 6-Cyclopentyl-3-(5,7-dimethyl-[1,2,4]triazolo[1,5-a]pyrimidin-2-ylmethyl)-6-[2-(5-ethyl-4-hydroxy-2-methoxy-phenyl)-ethyl]-4-hydroxy-5,6-dihydro-pyran-2-one --

In the Claims, Claim 23, Column 463, Lines 16 – 19:
    Please delete "(+)-2-(2-chloro-4-{2-[2-cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-phenyl)-methyl-propionitrile" and insert -- (+)-2-(2-chloro-4-{2-[2-cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-phenyl)-2-methyl-propionitrile --

In the Claims, Claim 23, Column 463, Lines 24 – 27:
    Please delete "(+)-2-4-{2-[2-Cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-2-fluorophenyl)-2-methylpropionitrile" and insert -- (+)-2-(4-{2-[2-Cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-2-fluorophenyl)-2-methylpropionitrile --

In the Claims, Claim 23, Column 463, Lines 28 – 31:
    Please delete "(-)-2-(4-{2-[2-Cyclopentyl-5-(5,7-dimethyl-[1,2,4]triazolo[1,5-a]pyrimidin-2-ylmethyl)-4-hydroxy-6-oxo-3,6-hydro-2H-pyran-2-yl]-ethyl}-2-fluorophenyl)-2-methylpropionitrile" and insert -- (-)-2-(4-{2-[2-Cyclopentyl-5-(5,7-dimethyl-[1,2,4]triazolo[1,5-a]pyrimidin-2-ylmethyl)-4-hydroxy-6-oxo-3,6-dihydro-2H-pyran-2-yl]-ethyl}-2-fluorophenyl)-2-methylpropionitrile --

In the Claims, Claim 23, Column 463, Lines 35 – 38:
    Please delete "(-)-3-[(6-chloro[1,2,4]triazolo[1,5-a]pyrimidin-2-yl)methyl]-6-cyclopentyl-6-[2-(5-ethyl-4-hydroxy-2-melhoxyphenyl)ethyl]-hydroxy-5,6-dihydro-2H-pyran-2-one"

UNITED STATES PATENT AND TRADEMARK OFFICE
CERTIFICATE OF CORRECTION

PATENT NO. : 7,148,226 B2
APPLICATION NO. : 10/718337
DATED : December 12, 2006
INVENTOR(S) : Allen Borchardt et al.

It is certified that error appears in the above-identified patent and that said Letters Patent is hereby corrected as shown below:

and insert -- (-)-3-[(6-chloro[1,2,4]triazolo[1,5-*a*]pyrimidin-2-yl)methyl]-6-cyclopentyl-6-[2-(5-ethyl-4-hydroxy-2-methoxyphenyl)ethyl]-4-hydroxy-5,6-dihydro-2*H*-pyran-2-one --

In the Claims, Claim 23, Column 463, Lines 51 – 53:
Please delete "6-Cyclopentyl-3-(5,7-dimethyl-[1,2,4]triazolo[1,5-a]pyrimidin-2-ylmethyl)-6-[2-(5-ethyl-2-methoxy-phenyl)-ethyl]4-hydroxy-5,6-dihydro-pyran-2-one" and insert -- 6-Cyclopentyl-3-(5,7-dimethyl-[1,2,4]triazolo[1,5-a]pyrimidin-2-ylmethyl)-6-[2-(5-ethyl-2-methoxy-phenyl)-ethyl]-4-hydroxy-5,6-dihydro-pyran-2-one --

In the Claims, Claim 23, Column 463, Lines 61 – 63:
Please delete "6-Cyclopentyl-6-[2-(3-cyclopropyl-4-methoxy-phenyl)-ethyl]-3-(5,7-dimethyl-[1,2,4]triazolo(1,5-a]pyrimidin-2-ylmethyl)-4-hydroxy-5,6-dihydro-pyran-2-one" and insert -- 6-Cyclopentyl-6-[2-(3-cyclopropyl-4-methoxy-phenyl)-ethyl]-3-(5,7-dimethyl-[1,2,4]triazolo[1,5-a]pyrimidin-2-ylmethyl)-4-hydroxy-5,6-dihydro-pyran-2-one --

In the Claims, Claim 24, Column 464, Lines 22 – 25:
Please delete "(+)-2-(4-{2-[2-Cyclopentyl-5-(6-methyl-[1,2,4]triazolo[1,5-a]pyrimidin-2-ylmethyl)4,6-dioxo-tetrahydro-pyran-2-yl]-ethyl}-2-fluoro-phenyl)-2-methyl-propionitrile" and insert -- (+)-2-(4-{2-[2-Cyclopentyl-5-(6-methyl-[1,2,4]triazolo[1,5-a]pyrimidin-2-ylmethyl)-4,6-dioxo-tetrahydro-pyran-2-yl]-ethyl}-2-fluoro-phenyl)-2-methyl-propionitrile --

Signed and Sealed this

Twentieth Day of February, 2007

JON W. DUDAS
*Director of the United States Patent and Trademark Office*